(12) United States Patent
Balasubramanian et al.

(10) Patent No.: US 11,180,504 B2
(45) Date of Patent: Nov. 23, 2021

(54) SUBSTITUTED CARBAPENEMS FOR THE TREATMENT OF BACTERIAL INFECTIONS

(71) Applicants: ORCHID PHARMA LTD., Tamilnadu (IN); MERCK SHARP & DOHME CORP., Rahway, NJ (US)

(72) Inventors: Gopalan Balasubramanian, Chennai (IN); Maneesh Paul-Satyaseela, Bengaluru (IN); Chidambaram Venkateswaran Srinivasan, Chennai (IN); Sridhar Ramanathan Iyer, Chennai (IN); Hariharan Periasamy, Chennai (IN); Venkatesan Parameswaran, Chennai (IN); Bharani Thirunavukkarasu, Chennai (IN); Prabhakar Rao Gunturu, Chennai (IN); Manjula Devi Deshkumar, Chennai (IN); Venkateshwarlu Jakkala, Chennai (IN); Michael Miller, Scotch Plains, NJ (US); Ravi P. Nargund, East Brunswick, NJ (US); Sheo Singh, Edison, NJ (US); Shuzhi Dong, Kenilworth, NJ (US); Hongwu Wang, Kenilworth, NJ (US); Katherine Young, Kenilworth, NJ (US)

(73) Assignees: ORCHID PHARMA LTD., Tamilnadu (IN); MERCK SHARP & DOHME CORP., Rahway, NJ (US)

( * ) Notice: Subject to any disclaimer, the term of this patent is extended or adjusted under 35 U.S.C. 154(b) by 334 days.

(21) Appl. No.: 16/083,980

(22) PCT Filed: Mar. 15, 2017

(86) PCT No.: PCT/IN2017/000060
§ 371 (c)(1),
(2) Date: Sep. 11, 2018

(87) PCT Pub. No.: WO2017/158616
PCT Pub. Date: Sep. 21, 2017

(65) Prior Publication Data
US 2020/0291029 A1     Sep. 17, 2020

(30) Foreign Application Priority Data

Mar. 16, 2016  (IN) ............................. 201641009127

(51) Int. Cl.
*A61K 31/407*  (2006.01)
*C07D 487/04*  (2006.01)
*C07D 519/00*  (2006.01)

(52) U.S. Cl.
CPC ......... *C07D 487/04* (2013.01); *C07D 519/00* (2013.01)

(58) Field of Classification Search
CPC .................. A61K 31/407; C07D 487/04

USPC ........................................ 514/413; 548/453
See application file for complete search history.

(56) References Cited

U.S. PATENT DOCUMENTS

| 4,194,047 A | 3/1980 | Christensen et al. |
| 4,413,000 A | 11/1983 | Eglington |

FOREIGN PATENT DOCUMENTS

| EP | 0017992 | 10/1980 |
| EP | 0059554 | 9/1982 |
| EP | 0 372 582 A2 | 6/1990 |
| EP | 0518558 | 12/1992 |
| EP | 0 126 587 B1 | 4/1995 |
| EP | 0 579 826 B1 | 11/1998 |
| EP | 0 528 678 B1 | 5/2001 |
| JP | S565478 | 1/1981 |
| JP | S57158785 | 9/1982 |
| JP | H07048375 | 2/1995 |
| RU | 2130457 C1 | 5/1999 |

OTHER PUBLICATIONS

Corbett, David F. et al., "Chemical Modification of the Olivanic Acids: Synthesis of Substituted 6-[1-(1,2,3-Triazol-1-yl)Ethyl] Carbapenem Derivative", Tetrahedron Letters, 1983, vol. 24 (49), p. 5543-5546.
RU Official Action dated Apr. 15, 2020 (English translation).
RU Search Report dated Apr. 15, 2020 (English translation).
International Search Report and Written Opinion EP ISA dated Aug. 9, 2017 (PCT/IN2017/000060).

(Continued)

*Primary Examiner* — Douglas M Willis
(74) *Attorney, Agent, or Firm* — Morgan, Lewis & Bockius LLP; Todd Esker

(57) ABSTRACT

This invention relates to carbapenem compounds of the following formula:

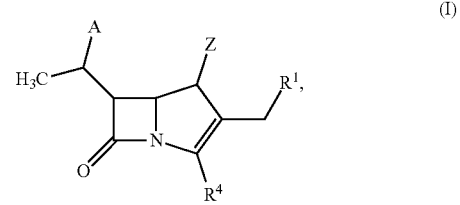

(I)

wherein A, Z, X, $R^1$, and $R^4$ are as described herein, as well as stereoisomers, pharmaceutically acceptable salts or N-oxides thereof, which may be useful for the treatment of bacterial infections, particularly drug-resistant bacterial infections, as well as the processes for the preparation of compounds, the pharmaceutical compositions of these compounds and their use in the treatment of bacterial infection.

32 Claims, No Drawings

(56) References Cited

OTHER PUBLICATIONS

Chaudhary et al., Indian Journal of Medical Microbiology, 2004, 22(2), 75-80.
Falagas et al., Journal of Antimicrobial Chemotherapy, 2007, 60, 1124-1130.
Sumita, Y et al., Journal of Antibiotics, 1995, 48(2), 188-190.
Sunagawa M et al., Journal of Antibiotics, 1997, 50(7), 621-627.
Bassetti et al., Current Medicinal Chemistry, vol. 16, No. 5, Abstract (2009).
Bassetti et al., "Current Status of Newer Carbapenems" Current Medicinal Chemistry, vol. 16, No. 5, (2009) (pp. 564-575).

SUBSTITUTED CARBAPENEMS FOR THE TREATMENT OF BACTERIAL INFECTIONS

CROSS-REFERENCE TO RELATED APPLICATIONS

This application is a 371 U.S. National Stage Entry of PCT/IN17/00060 filed Mar. 15, 2017 which claims priority to IN Application No. 201641009127 filed Mar. 16, 2016.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

INCORPORATION-BY-REFERENCE OF MATERIAL SUBMITTED ON A COMPACT DISK

Not Applicable

BACKGROUND OF THE INVENTION

Field of the Invention

Described herein are carbapenem compounds, their stereoisomers, pharmaceutically acceptable salts or V-oxides thereof, which may be useful for the treatment of bacterial infections, particularly drug-resistant bacterial infections. Also described herein are the processes for the preparation of compounds, the pharmaceutical compositions of these compounds and their use in the treatment of bacterial infection.

DESCRIPTION OF RELATED ART

Antimicrobial resistance is the most important crisis in the antibacterial therapy. One of the mechanisms of resistance development is due to enzymes, which deactivate certain class of antibiotics by hydrolysis, e.g. β-lactam ring of β-lactam antibiotics. In the mid 1980's, it was found that the enzymes which are responsible for the deactivation of the β-lactams are β-lactamases, particularly Extended Spectrum β-Lactamase (ESBL). ESBL is produced mainly by Enterobacteriaceae group (Chaudhary et al., *Indian Journal of Medical Microbiology*, 2004, 22(2), 75-80, Extended Spectrum β-Lactamases (ESBL)—An Emerging Threat to Clinical Therapeutics).

The risk factors involved in the expression of ESBL are increased length of hospitalization or ICU stay, increased severity of illness, use of a central venous or arterial catheter or urinary catheter, ventilatory support, hemodialysis, emergency abdominal surgery, gastrostomy or jejunostomy, gut colonization, prior administration of antibiotics, particularly of oxyimino-β-lactams (Falagas et al., *Journal of Antimicrobial Chemotherapy*, 2007, 60, 1124-1130, Risk factors of carbapenem-resistant *Klebsiella pneumoniae* infections: a matched case—control study).

The antibiotics which are used as a last resort because of their broad spectrum of antimicrobial activity are carbapenems. Carbapenems such as Imipenem (U.S. Pat. No. 4,194,047 A), Meropenem (European Pat. No. EP0126587 B1), Ertapenem (European Pat. No. EP0579826 B1) and Doripenem (European Pat. No. EP0528678 B1) are ultrabroad spectrum injectable antibiotics. These antibiotics give rise to cell death by binding to penicillin-binding proteins (PBPs) and inhibiting cell wall biosynthesis. The emergence of carbapenemases belonging to class A and class D β-lactamases threatens their clinical utility.

It has been reported that the presence of a hydroxyethyl side chain in carbapenems provides stability to these compounds. (Sumita, Y et al., *Journal of Antibiotics*, 1995, 48(2), 188-190).

Sunagawa M et al., *Journal of Antibiotics*, 1997, 50(7), 621-627, discloses carbapenem compounds having antimicrobial activity.

Carbapenem compounds with potency against carbapenem-resistant gram negative bacteria have not been reported. Therefore, the development of a novel carbapenem compound with broad antibacterial spectrum, preferably a compound possessing potent activity against resistant bacteria which produce β-lactamase is desirable.

Still there remains a huge unmet medical need for new antimicrobial agents due to the emerging bacterial resistance over the current therapies.

OBJECTIVE

The objective of the present invention is to provide carbapenem compounds, their stereoisomers, pharmaceutically acceptable salts or N-oxides thereof.

Yet another objective of the present invention is to provide processes for the preparation of Carbapenem compounds and pharmaceutical compositions containing these compounds.

A further objective of the present invention is to provide a method for preventing or treating bacterial infection and to provide carbapenem compounds as broad spectrum antibacterial agents.

BRIEF SUMMARY OF THE INVENTION

The present invention relates to novel carbapenems. In particular, the present invention relates to a compound of formula ((I), (Ia) or (Ib), or a stereoisomer, internal salt, N-oxide, or pharmaceutically acceptable salt thereof. The compounds of formula (I), (Ia) or (Ib), or a stereoisomer, internal salt, N-oxide, or pharmaceutically acceptable salt thereof can be useful in the treatment of bacterial infections. The present invention relates to compounds of formula (I)

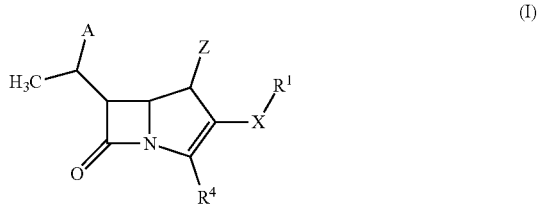

or a stereoisomer, internal salt, N-oxide, prodrug, or pharmaceutically acceptable salt thereof:
wherein:
A represents —NR⁰R or —OR$^z$;
Z represents —H or —CH$_3$;
X represents —S— or —CH$_2$—;
R$^z$ represents isoxazolyl;
R⁰ is hydrogen or C$_{1-6}$alkyl which is optionally substituted with one or two substituents selected from halogen, hydroxyl, cyano, carbamoyl, —SO$_2$NH$_2$ and C$_{1-6}$alkoxy;
R is:
1) —(CH$_2$)$_n$C(=O)R$^2$,
2) —(CH$_2$)$_n$C(=S)R$^2$,
3) —(CH$_2$)$_n$SO$_2$R$^2$,
4) —C$_{1-6}$alkyl optionally substituted with —C$_{3-6}$cycloalkyl, or
5) —CH(=NH), or
R and R⁰ together with the N to which they are attached form a substituted or unsubstituted 5-6 membered cyclic ring with 0, 1, 2, 3 or 4 additional heteroatom ring atoms independently selected from N, O and S;
n is an integer selected from 0, 1, 2, 3, 4, 5 and 6;
R$^1$ is:
1) —(CH$_2$)$_{0-6}$-AryC,
2) —(CH$_2$)$_{1-6}$-HetC,
3) —(CH$_2$)$_{1-6}$NH(C=NH)NH$_2$, or
4) C$_{2-6}$aminoalkyl optionally substituted with
  a) —C(=O)C$_{1-6}$alkoxy,
  b) —C(=O)-pyrrolidinyl substituted with —NR$^x$R$^y$,
  c) —CR$^x$=NR$^x$, or
  d) —COO-phenyl;
R$^2$ is:
1) H,
2) C$_{1-6}$alkyl optionally substituted with 1, 2 or 3 substitutents independently selected from halogen, —OH, —CN,
  C$_{3-8}$cycloalkyl, —(CH$_2$)$_{0-1}$C(=O)NR$^x$R$^y$, —NR$^a$R$^b$, C$_{1-6}$alkoxy, —OC(=O)C$_{1-6}$alkyl, —P(=O)(C$_{1-6}$alkoxy)$_2$, —COOH, —COOC$_{1-6}$alkyl, —SO$_2$C$_{1-6}$alkyl, —S(=O)C$_{1-6}$haloalkyl, —SCHF$_2$, Het A, Ary A, —S-AryA, azetidine and azetidinone optionally substituted with C$_{1-6}$hydroxy alkyl,
3) C$_{3-8}$cycloalkyl substituted with C$_{1-6}$haloalkyl or —NR$^x$R$^y$,
4) —(CH$_2$)$_{0-3}$—CR$^k$=NOC$_{1-6}$alkyl optionally substituted with —COOR$^x$,
5) —C(=O)NR$^x$R$^y$,
6) —C(=O)C$_{1-6}$alkoxy,
7) —NR$^x$R$^y$,
8) —OH,
9) —COOH,
10) C$_{1-6}$alkoxy,
11) C$_{1-6}$haloalkyl,
12) C$_{1-6}$haloalkoxy,
13) Ary A, or
14) HetA;
R$^4$ is —COO⁻ or —COOR$^5$;
R$^5$ is hydrogen, a carboxylic acid protecting group or an ester prodrug moiety;
AryA is 1) a substituted or unsubstituted 5- or 6-membered aromatic ring with 0, 1, 2, 3 or 4 heteroatom ring atoms independently selected from N, O and S, or
  2) a substituted or unsubstituted 9- or 10-membered bicyclic aromatic ring with 1, 2, 3, 4, 5 or 6 heteroatom ring atoms independently selected from N, O and S;
HetA is a substituted or unsubstituted 5- to 10-membered saturated ring with 1, 2, 3 or 4 heteroatom ring atoms independently selected from N, O and S, wherein any S atom in the ring is optionally oxidized;
AryC is 1) a substituted or unsubstituted 5- or 6-membered aromatic ring with 0, 1, 2 or 3 heteroatom ring atoms independently selected from N, O and S, wherein the N atom is optionally quaternized with —CH$_3$, or
  2) a substituted or unsubstituted 7- to 10-membered bicyclic aromatic ring with 0, 1, 2 or 3 heteroatom ring atoms selected from N, S, and O;
HetC is a substituted or unsubstituted 4- to 8-membered saturated ring with 1 or 2 heteroatom ring atoms selected from N, O or S;
R$^a$ is hydrogen, C$_{1-6}$alkyl, C$_{3-8}$cycloalkyl, —CR$^x$(=NR$^x$), —C(=NR$^x$)N(R$^x$)$_2$, —CH$_2$C(=O)N(R$^x$)$_2$, —(CH$_2$)$_{1-6}$ OR$^x$ or —SO$_2$C$_{1-6}$alkyl;
R$^b$ is hydrogen or C$_{1-3}$alkyl;
R$^c$ is
1) H,
2) —C$_{1-6}$alkyl optionally substituted with —NR$^h$R$^j$, —CN or —OH,
3) —(CH$_2$)$_{1-3}$C(=O)NR$^x$R$^y$,
4) —(CH$_2$)$_{1-3}$C(=O)NHCH$_2$CH$_2$OH,
5) —(CH$_2$)$_{1-3}$C(=O)NHOCH$_3$,
6) —(CH$_2$)$_{1-3}$C(=O)NHOBn,
7) —C$_{1-6}$alkoxy,
8) pyridinyl,
9) —(CH$_2$)$_{1-3}$-pyrrolidinyl optionally substituted with —C(=O)NR$^x$R$^y$,
10) tetrahydro-2H-pyran-4-yl,
11) —(CH$_2$)$_{1-3}$C(=O)-diazepanyl,
12) —(CH$_2$)$_{1-3}$C(=O)-pyrrolidin-1-yl substituted with NR$^x$R$^y$,
13) —C(=NH)-pyrrolidin-1-yl optionally substituted with NR$^x$R$^y$,
14) —(CH$_2$)$_{1-3}$-pyranyl optionally substituted with 1 or 2 substituents selected from oxo and methoxy,
15) —(CH$_2$)$_{1-3}$-pyridinyl optionally substituted with one or more groups selected from —CH$_3$, —OH, and oxo,
16) -phenyl-C(=O)-pyrrolidinyl-NR$^x$R$^y$
17) -phenyl-C(=O)-piperazinyl, or
18) -phenyl-(CH$_2$)$_{1-3}$—NR$^x$R$^y$;
R$^d$ is hydrogen, C$_{1-3}$alkyl, C$_{1-3}$hydroxyalkyl or C$_{1-3}$cyanoalkyl, or
R$^c$ and R$^d$ are taken together, with the N to which they are attached, to form a substituted or unsubstituted 4- to 12-membered heterocyclic ring or ring system with 0, 1, or 2 additional heteroatom ring atoms independently selected from N, O, and S, wherein the rings in the heterocyclic ring system can be bridged, fused, spiro-linked or any combination of two thereof; wherein any nitrogen ring atom of the heterocyclic ring or ring system is optionally quadricovalent; and wherein the heterocyclic ring or ring system is optionally substituted with 1, 2, 3 or 4 substituents independently selected from
1) —(CH$_2$)$_{0-3}$halogen,
2) oxo,
3) =NH,
4) —(CH$_2$)$_{0-3}$OH,
5) —C$_{1-6}$alkyl optionally substituted with halogen, —CN and —OH,
6) —OC$_{1-6}$alkyl,
7) —CH$_2$CH(OH)CH$_2$NH$_2$,
8) —CH$_2$CH(F)CH$_2$NH$_2$,
9) —C(=O)OH,
10) —(CH$_2$)$_{0-3}$NR$^h$R$^j$ optionally substituted with 1 or 2 of —CH$_3$, —NH$_2$ or halogen,
11) —NHCH$_2$CN, 12) —NHCH=NH,
13) —NHC(=O)R$^i$,
14) —NHC(=O)CH$_2$NHC(=NH)NH$_2$,
15) —C(=NH)NH$_2$,
16) —C(=O)C$_{1-6}$aminoalkyl optionally substituted with —OH,
17) —(CH$_2$)$_{0-2}$C(=O)(CH$_2$)$_{0-2}$NR$^h$R$^j$ optionally substituted with —NH$_2$ or —OH,
18) —(CH$_2$)$_{0-2}$C(=O)CH(NH$_2$)(CH$_2$)$_{0-2}$OH,
19) —C(=O)NH(CH$_2$)$_{1-3}$NH$_2$ optionally substituted with —OH,
20) —C(=O)(CH$_2$)$_{1-3}$NH$_2$ optionally substituted with —NH$_2$,
21) —C(=O)(CH$_2$)$_{0-3}$NHC(=NH)NH$_2$,
22) —(CH$_2$)$_{0-1}$NHCH$_2$CH$_2$NR$^h$R$^j$,
23) —(CH$_2$)$_{0-3}$NHC(=NH)NH$_2$,
24) —(CH$_2$)$_{0-1}$NH(CH$_2$)$_{0-1}$C(=O)(CH$_2$)$_{0-1}$NR$^h$R$^j$,
25) —(CH$_2$)$_{0-1}$NHSO$_2$(CH$_2$)$_{0-2}$NR$^h$R$^j$,
26) —(CH$_2$)$_{0-2}$NHSO$_2$CH$_3$,
27) —ONH$_2$,
28) —ONHC(=O)CH$_2$NHCH$_3$,
29) —C(=O)NH-pyridinyl,
30) —C(=O)-diazepinyl optionally substituted with —C(=N)NH$_2$,
31) —C(=O)-piperazinyl,
32) —(CH$_2$)$_{0-1}$C(=O)-pyrrolidinyl optionally substituted with —NH$_2$,
33) —NHCH$_2$-pyridinyl optionally substituted with one or more groups selected from —CH$_3$, —OH, and oxo,
34) —NH-pyrimidinyl,
35) —(CH$_2$)$_{0-1}$-phenyl,
36) —(CH$_2$)$_{0-2}$-piperazinyl,
37) —(CH$_2$)$_{0-2}$azetidinyl optionally substituted with —NH$_2$, —CH$_2$NH$_2$, or —OH,
38) —(CH$_2$)$_{0-2}$pyrrolidinyl optionally substituted with —NH$_2$,
39) —(CH$_2$)$_{0-2}$triazolyl optionally substituted with —CH$_2$NH$_2$, and
40) —(CH$_2$)$_{0-2}$tetrazolyl;

R$^f$ is H, —C(=O)N(C$_{1-6}$alkyl)$_2$, —SO$_2$C$_{1-6}$alkyl, —SO$_2$N(R$^x$)$_2$, —C(=O)-cyclopentyl-N(R$^x$)$_2$, —C(=O)-pyridinyl optionally substituted with one or more groups selected from oxo, —C$_{1-3}$alkyl and —OH, —C(=O)-pyrrolidinyl substituted with —NR$^a$R$^b$ or halogen, —C(=O)-thiazolidinyl, —SO$_2$-piperazine, or —SO$_2$-pyrrolidinyl-N(R$^x$)$_2$;

R$^g$ is hydrogen or C$_{1-3}$alkyl, or

R$^f$ and R$^g$ are taken together, with the N to which they are attached, to form morpholinyl; piperazinyl; pyrrolidinyl optionally substituted with —CH$_3$; piperidinyl or thiomorpholinyl optionally substituted with —C$_{1-6}$alkyl or —N(R$^x$)$_2$; or triazolyl substituted with —CH$_2$NH$_2$;

R$^h$ and R$^j$ is independently H, C$_{1-6}$alkyl, or C$_{3-8}$cycloalkyl;

R$^i$ is —C$_{1-5}$ amino alkyl, —OC$_{1-6}$alkyl, —C$_{1-3}$cyanoalkyl, or —C$_{1-6}$haloalkyl optionally substituted with —NR$^x$R$^y$;

R$^k$ is C$_{1-6}$alkyl, or thiazole substituted with —NH$_2$;

each R$^x$ and R$^y$ is independently hydrogen or C$_{1-3}$alkyl; and wherein when HetA, AryA, AryC, HetC, or the rings formed by combining R and R$^0$ are substituted, the substituents are 1 to 4 members selected from
1) halogen,
2) —OH,
3) oxo,
4) —COOH,
5) —COOC$_{1-6}$ alkyl,
6) C$_{1-6}$alkyl,
7) C$_{1-6}$alkoxy,
8) —(CH$_2$)$_{0-3}$O—C$_{1-3}$alkyl,
9) C$_{1-6}$haloalkyl,
10) C$_{1-6}$hydroxy alkyl,
11) C$_3$-C$_8$cycloalkyl,
12) —C(=O)C$_{1-6}$ alkyl,
13) —C(=O)C$_{1-6}$aminoalkyl,
14) —C(=O)NR$^c$R$^d$,
15) —(CH$_2$)$_{0-1}$NR$^x$R$^y$,
16) —(CH$_2$)$_{0-3}$NR$^f$R$^g$,
17) —(CH$_2$)$_{1-3}$—C(=O)NR$^x$R$^y$,
18) —NHCH$_2$CN,
19) —NHC(=O)R$^i$,
20) —(CH$_2$)$_{0-1}$NHSO$_2$NR$^x$R$^y$,
21) —SO$_2$NR$^c$R$^d$,
22) —CH=NH,
23) —(CH$_2$)$_{0-3}$C(=NH)NH$_2$,
24) —(CH$_2$)$_{0-3}$NHC(=NH)NH$_2$,
25) —(CH$_2$)$_{0-2}$-thienyl,
26) —(CH$_2$)$_{0-2}$-tetrazolyl,
27) —(CH$_2$)$_{0-2}$-thiazolyl,
28) —(CH$_2$)$_{0-2}$-pyridinyl optionally substituted with —CH$_3$ or quaternized with —CH$_3$ or CH$_2$CONH$_2$,
29) —(CH$_2$)$_{0-2}$-triazolyl,
30) —(CH$_2$)$_{0-2}$-piperidinyl optionally substituted with —CH$_3$ or quaternized with —CH$_3$ or —(CH$_2$)$_{0-3}$NH$_2$,
31) —(CH$_2$)$_{0-2}$-pyrazolyl optionally substituted with one or more of —(CH$_2$)$_{0-3}$NH$_2$ and further optionally quaternized with —CH$_3$,
32) —(CH$_2$)$_{1-3}$—C(=O)-pyrolidinyl optionally substituted with —NR$^x$R$^y$,
33) —(CH$_2$)$_{0-2}$-pyrolidinyl optionally substituted with —NR$^x$R$^y$,
34) —C(=NH)-pyrolidinyl optionally substituted with —NR$^x$R$^y$, and
35) 4,5-dihydrothiazol-2-yl.

The present invention also relates to compounds of formula (Ib)

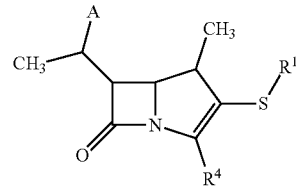

(Ib)

or a stereoisomer, internal salt, N-oxide, prodrug, or pharmaceutically acceptable salt thereof:
wherein:
A represents —NR$^0$R or —OR$^z$;
R$^z$ represents isoxazolyl;
R$^0$ is hydrogen or C$_{1-6}$alkyl which is optionally substituted with one or two substituents selected from halogen, hydroxyl, cyano, carbamoyl, —SO$_2$NH$_2$ and C$_{1-6}$alkoxy;
R is:
—(CH$_2$)$_n$C(=O)R$^2$;
—(CH$_2$)$_n$C(=S)R$^2$;
—(CH$_2$)$_n$SO$_2$R$^2$;
—C$_{1-6}$alkyl optionally substituted with —C$_{3-6}$cycloalkyl; or
—CH(=NH); or R and $R^o$ together with the N to which they are attached form a substituted or unsubstituted 5-6 membered cyclic ring with 0, 1, 2, 3 or 4 additional heteroatom ring atoms independently selected from N, O and S;

n is an integer selected from 0, 1, 2, 3, 4, 5 and 6;

$R^1$ is:
1) —$(CH_2)_{0-6}$-AryC;
2) —$(CH_2)_{0-6}$-HetC; or
3) $C_{2-6}$aminoalkyl optionally substituted with
  a) —C(=O)$C_{1-6}$alkoxy,
  b) —C(=O)-pyrrolidinyl substituted with —$NR^xR^y$,
  c) —$CR^x$=$NR^x$, or
  d) —COO-phenyl;

$R^2$ is:
H;
$C_{1-6}$alkyl optionally substituted with 1, 2 or 3 substitutents independently selected from halogen, —OH, —CN,
  $C_{3-8}$cycloalkyl, —$(CH_2)_{0-1}$C(=O)$NR^xR^y$, —$NR^aR^b$, $C_{1-6}$alkoxy, —OC(=O)$C_{1-6}$alkyl, —P(=O)($C_{1-6}$alkoxy)$_2$, —COOH, —COO$C_{1-6}$alkyl, —$SO_2C_{1-6}$alkyl, —S(=O)$C_{1-6}$haloalkyl, Ary A, —S-AryA and azetidinone optionally substituted with $C_{1-6}$hydroxy alkyl;
$C_{3-8}$cycloalkyl substituted with $C_{1-6}$haloalkyl or —$NR^xR^y$;
—$CR^k$=$NOC_{1-6}$alkyl optionally substituted with —$COOR^x$;
—C(=O)$NR^xR^y$;
—C(=O)$C_{1-6}$alkoxy;
—$NR^xR^y$;
—OH;
—COOH;
$C_{1-6}$alkoxy;
$C_{1-6}$haloalkyl;
$C_{1-6}$haloalkoxy;
Ary A; or
HetA;

$R^4$ is —COO$^-$ or —COO$R^5$;

$R^5$ is hydrogen, a carboxylic acid protecting group or an ester prodrug moiety;

Ary A is 1) a substituted or unsubstituted 5- or 6-membered aromatic ring with 0, 1, 2, 3 or 4 heteroatom ring atoms independently selected from N, O and S, or
2) a substituted or unsubstituted 9- or 10-membered bicyclic aromatic ring with 1, 2, 3, 4, 5 or 6 heteroatom ring atoms independently selected from N, O and S;

HetA is a substituted or unsubstituted 5- to 10-membered saturated ring with 1, 2, 3 or 4 heteroatom ring atoms independently selected from N, O and S, wherein any S atom in the ring is optionally oxidized;

AryC is 1) a substituted or unsubstituted 5- or 6-membered aromatic ring with 1, 2 or 3 heteroatom ring atoms independently selected from N, O and S, or
2) a substituted or unsubstituted 7- to 10-membered bicyclic aromatic ring with 0, 1, 2 or 3 heteroatom ring atoms selected from N, S, and O;

HetC is a substituted or unsubstituted 4- to 6-membered saturated ring with 1 or 2 heteroatom ring atoms selected from N, O or S;

$R^a$ is hydrogen, $C_{1-6}$alkyl, $C_{3-8}$cycloalkyl, —$CR^x$(=$NR^x$), —C(=$NR^x$)N($R^x$)$_2$, —$CH_2$C(=O)N($R^x$)$_2$, or —$SO_2C_{1-6}$alkyl;

$R^b$ is hydrogen or $C_{1-3}$alkyl;

$R^c$ is H; —$C_{1-6}$alkyl optionally substituted with —$NR^hR^j$, —CN or —OH;
—$(CH_2)_{1-3}$C(=O)$NR^xR^y$; —$(CH_2)_{1-3}$C(=O)$NHCH_2CH_2OH$; —$(CH_2)_{1-3}$C(=O)$NHOCH_3$;
—$(CH_2)_{1-3}$C(=O)NHOBn; —$C_{1-6}$alkoxy; pyridinyl; pyrrodinyl optionally substituted with —C(=O)$NR^xR^y$; tetrahydro-2H-pyran-4-yl; —$(CH_2)_{1-3}$C(=O)-diazepanyl;
—$(CH_2)_{1-3}$C(=O)-pyrrodinyl-1-yl substituted with $NR^xR^y$;
—$(CH_2)_{1-3}$-pyranyl optionally substituted with 1 or 2 substituents selected from oxo and methoxy;
—$(CH_2)_{1-3}$-pyridinyl optionally substituted with one or more groups selected from —$CH_3$, —OH, and oxo; or
-phenyl-C(=O)-pyrrodinyl-$NR^xR^y$;

$R^d$ is hydrogen, $C_{1-3}$alkyl, $C_{1-3}$hydroxyalkyl or $C_{1-3}$cyanoalkyl; or $R^c$ and $R^d$ are taken together, with the N to which they are attached, to form a substituted or unsubstituted 4- to 12-membered heterocyclic ring or ring system with 0, 1, or 2 additional heteroatom ring atoms independently selected from N, O, and S, wherein the rings in the heterocyclic ring system can be bridged, fused, spiro-linked or any combination of two thereof; wherein any nitrogen ring atom of the heterocyclic ring or ring system is optionally quadricovalent; and wherein the heterocyclic ring or ring system is optionally substituted with 1, 2, 3 or 4 substituents independently selected from
halogen;
oxo;
—OH;
—$C_{1-6}$alkyl optionally substituted with —OH, halogen, or cyano;
—$CH_2CH(OH)CH_2NH_2$;
—C(=O)OH;
—$(CH_2)_{0-3}NR^hR^j$ optionally substituted with —$NH_2$ or halogen;
—$NHCH_2CN$;
—NHCH=NH;
—NHC(=)$R^i$;
—NHC(=O)$CH_2NHC$(=NH)$NH_2$;
—C(=NH)$NH_2$;
—C(=O)$C_{1-6}$aminoalkyl optionally substituted with —OH;
—$(CH_2)_{0-2}$C(=O)$(CH_2)_{0-2}NR^hR^j$;
—$(CH_2)_{0-2}$C(=O)CH($NH_2$)$(CH_2)_{0-2}$OH;
—C(=O)$(CH_2)_{0-3}$NHC(=NH)$NH_2$;
—$(CH_2)_{0-1}NHCH_2CH_2NR^hR^j$;
—$(CH_2)_{0-3}$NHC(=NH)$NH_2$;
—$(CH_2)_{0-1}$NH$(CH_2)_{0-1}$C(=O)$(CH_2)_{0-1}NR^hR^j$;
—$(CH_2)_{0-1}NHSO_2(CH_2)_{0-2}NR^hR^j$;
—$(CH_2)_{0-2}NHSO_2CH_3$;
—$ONH_2$;
—ONHC(=O)$CH_2NHCH_3$;
—C(=O)NH-pyridinyl;
—C(=O)-piperazinyl;
—C(=O)-pyrrolidinyl optionally substituted with —$NH_2$;
—$NHCH_2$-pyridinyl optionally substituted with one or more groups selected from
—$CH_3$, —OH, and oxo;
—NH-pyrimidinyl;
—$(CH_2)_{0-1}$-phenyl;
—$(CH_2)_{0-2}$-piperazinyl;
—$(CH_2)_{0-2}$azetidinyl optionally substituted with —$NH_2$, —$CH_2NH_2$, or —OH;
—$(CH_2)_{0-2}$pyrrolidinyl optionally substituted with —$NH_2$;
—$(CH_2)_{0-2}$triazolyl optionally substituted with —$CH_2NH_2$; and
—$(CH_2)_{0-2}$tetrazolyl;

$R^f$ is H; —C(=O)N(C$_{1-6}$alkyl)$_2$; —SO$_2$C$_{1-6}$alkyl; —SO$_2$N(R$^x$)$_2$; —C(=O)-cyclopentyl-N(R$^x$)$_2$; —C(=O)-pyridinyl optionally substituted with one or more groups selected from oxo, —C$_{1-3}$alkyl and —OH; —C(=O)-pyrrolidinyl substituted with —NR$^a$R$^b$ or halogen; —C(=O)-thiazolidinyl; —SO$_2$-piperazine; or —SO$_2$-pyrrolidinyl-N(R$^x$)$_2$;

$R^g$ is hydrogen or C$_{1-3}$alkyl; or $R^f$ and $R^g$ are taken together, with the N to which they are attached, to form morpholinyl; piperazinyl; pyrrolidinyl optionally substituted with —CH$_3$; piperidinyl or thiomorpholinyl optionally substituted with —C$_{1-6}$alkyl or —N(R$^x$)$_2$; or triazolyl substituted with —CH$_2$NH$_2$;

$R^h$ and $R^j$ is independently H, C$_{1-6}$alkyl, or C$_{3-8}$cycloalkyl;

$R^i$ is —C$_{1-5}$ amino alkyl; —OC$_{1-6}$alkyl; —C$_{1-3}$cyanoalkyl; or —C$_{1-6}$haloalkyl optionally substituted with —NR$^x$R$^y$;

$R^k$ is C$_{1-6}$alkyl; or thiazole substituted with —NH$_2$;

each R$^x$ and R$^y$ is independently hydrogen or C$_{1-3}$alkyl;

wherein when HetA, Ary A, AryC, HetC or the rings formed by combining R and R$^0$ are substituted, the substituents are 1 to 4 members selected from halogen;
—OH;
oxo;
—COOH;
—COOC$_{1-6}$alkyl;
C$_{1-6}$ alkyl;
C$_{1-6}$alkoxy;
—(CH$_2$)$_{0-3}$O—C$_{1-3}$alkyl;
C$_{1-6}$haloalkyl;
C$_{1-6}$hydroxyalkyl;
C$_3$-C$_8$cycloalkyl;
—C(=O)C$_{1-6}$ alkyl;
—C(=O)C$_{1-6}$aminoalkyl;
—C(=O)NR$^c$R$^d$;
—(CH$_2$)$_{0-3}$NR$^f$R$^g$;
—NHCH$_2$CN;
—NHC(=O)R$^i$;
—(CH$_2$)$_{0-1}$NHSO$_2$NR$^x$R$^y$;
—SO$_2$NR$^c$R$^d$; —CH=NH;
—(CH$_2$)$_{0-2}$-thienyl;
—(CH$_2$)$_{0-2}$-tetrazolyl;
—(CH$_2$)$_{0-2}$-thiazolyl;
—(CH$_2$)$_{0-2}$-pyridinyl optionally substituted with —CH$_3$ or quaternized with —CH$_3$;
—(CH$_2$)$_{0-2}$-triazolyl; and
4,5-dihydrothiazol-2-yl.

The present invention also relates to a compound of formula (Ia), or a stereoisomer, internal salt N-oxide, or pharmaceutically acceptable salt thereof, wherein

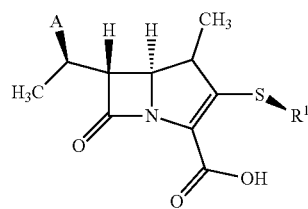

(Ia)

wherein:
A is NR$^0$R or -triazolyl substituted with —CH$_2$OH;
R is:
—C(=O)—C$_{1-6}$alkyl-NR$^a$R$^b$;

—C(=O)CHF$_2$;
—C(=O)CH$_2$SCHF$_2$,
—C(=O)CH$_2$NH(CH$_2$)$_2$OMe,
—C(=O)CH$_2$pyrrolidine,
—C(=O)CH$_2$azetidine,
—C(=O)CH$_2$piperazine,
—C(=O)CH$_2$ pyrrolidine optionally substituted with 1 or 2 substituents selected from fluorine and —CH$_2$NHMe,
—C(=O)CH$_2$-tetrazole optionally substituted with —C(CH$_3$)$_3$, —CF$_3$, —CHF$_2$, —CH$_3$, —NH$_2$—COOC$_{1-6}$alkyl, thienyl, —CH$_2$NHCH$_3$, —NH$_2$, or —COOCH$_2$CH$_3$; or —SO$_2$CH$_3$;

R$^0$ is H;

R$^1$ is pyrrolidinyl substituted with 1 or 2 of —CONR$^c$R$^d$; —CH$_2$NHSO$_2$NH$_2$ or —CH$_2$-pyrrolidinyl optionally substituted with —NH$_2$;

R$^a$ and R$^b$ are independently H, —C$_{1-6}$alkyl, —C$_{3-8}$cycloalkyl, —SO$_2$CH$_3$, —CH(=NH), —C(=NH)NH$_2$ or —CH$_2$C(=O)NH$_2$;

R$^c$ and R$^d$ are independently H, —C$_{1-3}$alkyl, —C(=NH)-pyrrolidinyl optionally substituted with —NH$_2$ or R$^c$ and R$^d$ are taken together, with the N to which they are attached, to form a 4- to 12-membered heterocyclic ring or ring system with 0, 1, 2 or 3 additional heteroatom ring atoms selected from N and O;

wherein any nitrogen ring atom of the heterocyclic ring or ring system is optionally quadricovalent; the ring system is a bridged, fused or spiro ring system; and the 4- to 12-membered heterocyclic ring or ring system is optionally substituted with 1, 2 or 3 substituents selected from (=NH)
—C(=O)(CH$_2$)$_{1-2}$NH$_2$,
—C(=O)CH$_2$NHCH$_3$,
—CH$_2$CH(NH$_2$)CH$_2$NH$_2$,
—C(=O)CH(NH$_2$)CH$_2$NH$_2$,
—C(=O)CH(F)CH$_2$NH$_2$,
—C(=O)CH(NH$_2$)CH$_2$OH,
—CH$_2$CH(OH)CH$_2$NH$_2$,
—C(=O)NH CH$_2$CH(OH)CH$_2$NH$_2$,
—C(=NH)NH$_2$,
—COOH,
—CH$_3$,
—CH$_2$C(=O)NH$_2$,
—CH$_2$NH CH$_2$C(=O)NH$_2$,
—CH$_2$NR$^h$R$^j$,
—CH$_2$CH$_2$NH$_2$,
—CH$_2$CH$_2$NH—C(=NH)—NH$_2$,
—CH$_2$NHSO$_2$NH$_2$,
—CH$_2$OH,
—C(CH$_3$)$_2$NH$_2$,
—CH$_2$F,
—OH,
-OMe,
—F,
—NR$^h$R$^j$,
—NHCH=NH,
—NH—C(=NH)—NH$_2$,
—NHCOCH$_2$—NH—C(=NH)—NH$_2$,
—NHCOCH$_2$NH$_2$;
—(CH$_2$)$_{0-3}$NR$^h$R$^j$ optionally substituted with —NH$_2$ or halogens;
azetidinyl optionally substituted with —OH,
piperazinyl, and
triazolyl substituted with CH$_2$NH$_2$; and $R^h$ and $R^j$ are independently H, $C_{1-6}$alkyl, or $C_{3-8}$cycloalkyl.

Any of the combinations of A, X, Z, $R^1$, and $R^4$ are encompassed by this disclosure and specifically provided by the invention.

In another aspect, described herein is also a pharmaceutical composition comprising a compound of formula (I), (Ia) or (Ib), or a stereoisomer, pharmaceutically acceptable salt or N-oxide thereof.

In another aspect, the compounds described herein can also be combined with appropriate β-lactamase inhibitors to increase the antibiotic spectrum. In another aspect, the compounds described herein can also be combined with appropriate dehydropeptidase inhibitors.

In another aspect, described herein is a process for preparation of a compound of formula (I), (Ia) or (Ib), or a stereoisomer, pharmaceutically acceptable salt or N-oxide thereof.

In another aspect, described herein is also a method for preventing or treating a bacterial infection comprising administering a therapeutically effective amount of a compound of formula (I), (Ia) or (Ib), or a stereoisomer, pharmaceutically acceptable salt, pharmaceutical composition or N-oxide thereof.

In another aspect, described herein is also a method for preventing or treating a gram negative and/or gram positive bacterial infection comprising administering a therapeutically effective amount of a compound of formula (I), (Ia) or (Ib), or a stereoisomer, pharmaceutically acceptable salt, pharmaceutical composition or N-oxide thereof.

In another aspect, described herein is also a method for preventing or treating a bacterial infection comprising administering a therapeutically effective amount of a compound of formula (I), (Ia) or (Ib), in combination or alternation with one or more other antimicrobial agents.

Embodiments, sub-embodiments, aspects and features of the present invention are either further described in or will be apparent from the ensuing description, examples and appended claims.

BRIEF DESCRIPTION OF THE SEVERAL VIEWS OF THE DRAWING(S)

Not Applicable

DETAILED DESCRIPTION OF THE INVENTION

The present invention is based, in part, on the discovery of carbapenem derivatives that are bacteriocidal against a broad spectrum of bacteria.

In a first embodiment, the present invention relates to compound of formula (I), (Ia) or (Ib), as described above, or a stereoisomer, internal salt, N-oxide, or pharmaceutically acceptable salt thereof.

In a second embodiment, the present invention relates to a compound of formula (I), (Ia) or (Ib), or a stereoisomer, internal salt N-oxide, or pharmaceutically acceptable salt thereof, wherein A represents —$NR^0R$, and the other groups are as provided in the general formula for formula (I), (Ia) or (Ib).

In another embodiment, A represents —$NR^0R$. In another embodiment X is —S—. In another embodiment Z is —$CH_3$.

In a third embodiment, the present invention relates to a compound of formula (I), (Ia) or (Ib), or a stereoisomer, internal salt N-oxide, or pharmaceutically acceptable salt thereof, wherein $R^0$ is hydrogen or methyl;
R is
—$(CH_2)_nC(\!=\!O)R^2$; or
—$(CH_2)_nSO_2R^2$; or
R and $R^0$ together with the N to which they are attached form
1) [1,2,3-]triazolyl substituted with $C_{1-6}$alkyl, wherein the $C_{1-6}$alkyl is substituted with halo, —$NR^aR^b$, —OH, or $C_{1-3}$alkoxy; or
2) tetrazolyl optionally substituted with —$NR^aR^b$;
and the other groups are as provided in the general formula for formula (I), (Ia) or (Ib), above or in the embodiments.

In another embodiment, $R^0$ is hydrogen or methyl;
R is
—$(CH_2)_nC(\!=\!O)R^2$; or
—$(CH_2)_nSO_2R^2$; or
R and $R^0$ together with the N to which they are attached form
1) [1,2,3-]triazolyl substituted with $C_{1-6}$alkyl, wherein the $C_{1-6}$alkyl is substituted with halo, —$NR^aR^b$, —OH, or $C_{1-3}$alkoxy; or
2) tetrazolyl optionally substituted with —$NR^aR^b$.

In a fourth embodiment, the present invention relates to a compound of formula (I), (Ia) or (Ib), or a stereoisomer, internal salt N-oxide, or pharmaceutically acceptable salt thereof, wherein n is 0 or 1, and the other groups are as provided in the general formula for formula (I), (Ia) or (Ib), above or in the embodiments. In one aspect of this embodiment, n is 0.

In another embodiment, n is 0 or 1. In one aspect of this embodiment, n is 0.

In a fifth embodiment, the present invention relates to a compound of formula (I), (Ia) or (Ib), or a stereoisomer, internal salt N-oxide, or pharmaceutically acceptable salt thereof, wherein $R^1$ is: —$(CH_2)_{0-2}$-AryC or —$(CH_2)_{0-1}$-HetC, and the other groups are as provided in the general formula for formula (I), (Ia) or (Ib), above or any of the embodiments.

In another embodiment, $R^1$ is —$(CH_2)_{0-2}$-AryC or —$(CH_2)_{0-1}$-HetC.

In another embodiment, $R^4$ is —COOH.

In a sixth embodiment, the present invention relates to a compound of formula (I), (Ia) or (Ib), or a stereoisomer, internal salt, N-oxide, or pharmaceutically acceptable salt thereof, wherein Ary A is 1) a 5- to 6-membered aromatic ring with 0, 1, 2, 3 or 4 heteroatom ring atoms independently selected from N, O and S, optionally substituted with 1 or 2 substituents independently selected from halogen, $C_{1-6}$alkyl, $C_{1-6}$haloalkyl, —$(CH_2)_{0-1}NR^xR^y$, $C_3$-$C_8$cycloalkyl, —COOH, —$COOC_{1-6}$ alkyl, $C_{1-6}$alkoxy, thienyl, and tetrazolyl, or
2) a 9- to 10-membered bicyclic aromatic ring with 1 to 6 heteroatom ring atoms independently selected from N, O and S, optionally substituted with 1 or 2 substituents selected from halogen, $C_{1-6}$alkyl, and $C_{1-6}$haloalkyl;

HetA is a 5- to 10-membered saturated ring with 1 or 2 heteroatom ring atoms independently selected from N, O and S, optionally substituted with 1 or 2 substituents independently selected from halogen, —$NR^xR^y$, —$CH_2NR^xR^y$, —OH, and oxo;

AryC is 1) a 5- or 6-membered aromatic ring with 0, 1 or 2 heteroatom ring atoms independently selected from N and S, optionally quaternized with $CH_3$ and optionally substituted 1 to 3 substituents independently selected from —CH$_2$NR$^x$R$^y$, —CH$_2$-pyrrolidinyl, —OH, oxo, pyridinyl which is optionally quaternized with methyl or —CH$_2$CONH$_2$, or
2) a 7- to 10-membered bi cyclic aromatic ring with 3 heteroatom ring atoms selected from N; and HetC is a 4- to 8-membered saturated ring with 1 or 2 N or O ring atoms, optionally substituted with 1 or 2 substituents independently selected from halogen, —OH, —C$_{1-6}$alkyl, —(CH$_2$)$_{0-3}$NR$^f$R$^g$, —CH=NH, —C(=O)C$_{1-6}$alkyl, —C(=NH)—NH$_2$, —CH$_2$—(C=O)-pyrrolidinyl optionally substituted with —NR$^x$R$^y$, —NH—C(=NH)—NH$_2$, —CH$_2$—NH—C(=NH)—NH$_2$, —C(=O)C$_{1-6}$aminoalkyl, —C(=O)NR$^c$R$^d$, —NR$^x$R$^y$, —NHSO$_2$NR$^x$R$^y$, —SO$_2$NR$^c$R$^d$, thiazolyl, and 4,5-dihydrothiazol-2-yl; and the other groups are as provided in the general formula for formula (I), (Ia) or (Ib), above or any of the embodiments.

In another embodiment, AryA is 1) a 5- to 6-membered aromatic ring with 0, 1, 2, 3 or 4 heteroatom ring atoms independently selected from N, O and S, optionally substituted with 1 or 2 substituents independently selected from halo, C$_{1-6}$alkyl, C$_{1-6}$haloalkyl, —(CH$_2$)$_{0-1}$NRxRy, C$_1$-C$_6$cycloalkyl, —COOH, —COOC$_{1-6}$alkyl, C$_{1-6}$alkoxy, thienyl, and tetrazolyl; or
2) a 9- to 10-membered bi cyclic aromatic ring with 1 to 6 heteroatom ring atoms independently selected from N, O and S, optionally substituted with 1 or 2 substituents selected from halo, C$_{1-6}$alkyl, and C$_{1-6}$haloalkyl;

HetA is a 5- or 6-membered saturated ring with 1 or 2 heteroatom ring atoms independently selected from N, O and S, optionally substituted with 1 or 2 substituents independently selected from halo, —NR$^x$R$^y$, —OH, and oxo;

AryC is 1) a 5- or 6-membered aromatic ring with 1 or 2 heteroatom ring atoms independently selected from N and S, optionally substituted 1 to 3 substituents independently selected from —CH$_2$NR$^x$R$^y$, —OH, oxo, pyridinyl which is optionally quaternized with methyl; or
2) a 8-membered bicyclic aromatic ring with 3 heteroatom ring atoms selected from N; and HetC is a 4- to 6-membered saturated ring with 1 or 2 N ring atoms, optionally substituted with 1 or 2 substituents independently selected from halo; —C$_{1-6}$alkyl optionally substituted with —NR$^f$R$^g$; —CH=NH; —C(=O)C$_{1-6}$alkyl; —C(=O)C$_{1-6}$aminoalkyl; —C(=O)NR$^c$R$^d$; —NR$^x$R$^y$; —NHSO$_2$NR$^x$R$^y$; —SO$_2$NR$^c$R$^d$; thiazolyl and 4,5-dihydrothiazol-2-yl.

In a seventh embodiment, the present invention relates to a compound of formula (I), (Ia) or (Ib), or a stereoisomer, internal salt N-oxide, or pharmaceutically acceptable salt thereof,
wherein:
R$^c$ is
1) H,
2) —CH$_2$CN,
3) —C$_{1-6}$alkyl optionally substituted with —NR$^h$R$^j$, pyrrolidinyl or —OH,
4) —CH$_2$CH$_2$C(=O)NR$^x$R$^y$,
5) —CH$_2$CH$_2$C(=O)NHCH$_2$CH$_2$OH,
6) —CH$_2$CH$_2$C(=O)NHOCH$_3$,
7) —CH$_2$CH$_2$C(=O)NHOBn,
8) —C$_{1-6}$alkoxy,
9) pyridinyl,
10) pyrrolidinyl optionally substituted with —C(=O)NR$^x$R$^y$,
11) —C(=NH)-pyrrolidin-1-yl optionally substituted with NR$^x$R$^y$,
12) tetrahydro-2H-pyran-4-yl,
13) —CH$_2$CH$_2$C(=O)-diazepanyl,
14) —CH$_2$CH$_2$C(=O)-pyrrolidin-1-yl substituted with NR$^x$R$^y$,
15) —CH$_2$-pyranyl optionally substituted with 1 or 2 substituents selected from oxo and methoxy,
16) —CH$_2$-pyridinyl optionally substituted with —CH$_3$, —OH, and oxo,
17) -phenyl-C(=O)-piperazinyl,
18) -phenyl-CH$_2$—NR$^x$R$^y$, or
19) -phenyl-C(=O)-pyrrolidinyl-NR$^x$R$^y$;
R$^d$ is hydrogen, or C$_{1-3}$alkyl; or
R$^c$ and R$^d$ are taken together, with the N to which they are attached, to form
a) a 4- to 8-membered heterocyclic ring with 0, 1, or 2 additional heteroatom ring atoms independently selected from N, O, and S, or
b) a 6- to 12-membered heterocyclic bi- or tricyclic ring with 0, 1, or 2 additional heteroatom ring atoms independently selected from N, O, and S, wherein the bicyclic ring is optionally bridged, fused, spirocyclic or any combination of two thereof, and wherein any nitrogen ring atom of the heterocyclic ring or heterocyclic bicyclic ring is optionally quadricovalent; and wherein the heterocyclic ring or heterocyclic bicyclic ring is optionally substituted with 1, 2 or 3 substituents independently selected from
1) halogen,
2) —C$_{1-6}$alkyl optionally substituted with 1 or 2 substituents selected from halogen, —CN and —OH,
3) —C(=NH)NH$_2$,
4) —(CH$_2$)$_{0-2}$C(=O)(CH$_2$)$_{0-2}$NR$^h$R$^j$ optionally substituted with —NH$_2$ or —OH,
5) —(CH$_2$)$_{0-3}$NR$^h$R$^j$ optionally substituted with —NH$_2$ or halogens,
6) —C(=O)C$_{1-6}$aminoalkyl optionally substituted with —OH,
7) —C(=O)OH,
8) —C(=O)(CH$_2$)$_{0-3}$NHC(=NH)NH$_2$,
9) —(CH$_2$)$_{0-1}$NHCH$_2$CH$_2$NR$^h$R$^j$,
10) —(CH$_2$)$_{0-3}$NHC(=NH)NH$_2$,
11) —(CH$_2$)$_{0-1}$NH(CH$_2$)$_{0-1}$C(=O)(CH$_2$)$_{0-1}$NR$^h$R$^j$,
12) —(CH$_2$)$_{0-1}$NHSO$_2$NH$_2$,
13) —(CH$_2$)$_{0-1}$NHSO$_2$(CH$_2$)$_{0-2}$NH$_2$,
14) —(CH$_2$)$_{0-2}$NHSO$_2$CH$_3$,
15) —NR$^h$R$^j$,
16) —NHCH$_2$CN,
17) —NHCH=NH,
18) —NHC(=O)R$^i$;
19) —NHSO$_2$N(CH$_3$)$_2$,
20) —NHC(=O)(CH$_2$)$_{0-2}$NH(=NH)NH$_2$,
21) —OH,
22) —OC$_{1-6}$alkyl,
23) —ONH$_2$,
24) —ONHC(=O)CH$_2$NHCH$_3$,
25) oxo,
26) =NH,
27) —(CH$_2$)$_{0-1}$-phenyl,
28) —(CH$_2$)$_{0-2}$-piperazinyl,
29) —C(=O)NH-pyridinyl,
30) —C(=O)-piperazinyl,
31) —C(=O)-pyrrolidinyl optionally substituted with —NH$_2$,
32) azetidinyl optionally substituted with —CH$_2$NH$_2$, —NH$_2$, or —OH,
33) pyrrolidinyl optionally substituted with —NH$_2$,
34) —NHCH$_2$-pyridinyl substituted with oxo, —CH$_3$, and —OH,
35) —NH-pyrimidinyl, 36) triazolyl optionally substituted with —CH$_2$NH$_2$, and
37) tetrazolyl;
and the other groups are as provided in the general formula for formula (I), (Ia) or (Ib), above or any of the embodiments.

In another embodiment, R$^c$ is H; —CH$_2$CN; —C$_{1-6}$alkyl optionally substituted with —NR$^h$R$^j$ or —OH; —CH$_2$CH$_2$C(=O)NR$^x$R$^y$; —CH$_2$CH$_2$C(=O)NHCH$_2$CH$_2$OH; —CH$_2$CH$_2$C(=O)NHOCH$_3$; —CH$_2$CH$_2$C(=O)NHOBn; —C$_{1-6}$alkoxy; pyridinyl; pyrrolidinyl optionally substituted with —C(=O)NR$^x$R$^y$;
tetrahydro-2H-pyran-4-yl; —CH$_2$CH$_2$C(=O)-diazepanyl; —CH$_2$CH$_2$C(=O)-pyrrolidin-1-yl substituted with NR$^x$R$^y$; —CH$_2$-pyranyl optionally substituted with 1 or 2 substituents selected from oxo and methoxy;
—CH$_2$-pyridinyl optionally substituted with —CH$_3$, —OH, and oxo; or
-phenyl-C(=O)-pyrrobdinyl-NR$^x$R$^y$;

R$^d$ is hydrogen or C$_{1-3}$alkyl; or

R$^c$ and R$^d$ are taken together, with the N to which they are attached, to form
  a) a 4- to 8-membered heterocyclic ring with 0, 1, or 2 additional heteroatom ring atoms independently selected from N, O, and S; or
  b) a 6- to 12-membered heterocyclic bicyclic ring with 0, 1, or 2 additional heteroatom ring atoms independently selected from N, O, and S, wherein the bicyclic ring is optionally bridged, fused, spirocyclic or any combination of two thereof;
and wherein any nitrogen ring atom of the heterocyclic ring or heterocyclic bicyclic ring is optionally quadricovalent; and wherein the heterocyclic ring or heterocyclic bicyclic ring is optionally substituted with 1 or 2 substituents independently selected from
halo;
—C$_{1-6}$alkyl optionally substituted with 1 or 2 substituents selected from halo, —CN, —NR$^h$R$^j$, and —OH;
—C(=NH)NH$_2$;
—(CH$_2$)$_{0-2}$C(=O)(CH$_2$)$_{0-2}$NR$^h$R$^j$;
—(CH$_2$)$_{0-3}$NR$^h$R$^j$ optionally substituted with —NH$_2$ or halogens;
—C(=O)C$_{1-6}$aminoalkyl optionally substituted with —OH;
—C(=O)OH;
—C(=O)(CH$_2$)$_{0-3}$NHC(=NH)NH$_2$;
—(CH$_2$)$_{0-1}$NHCH$_2$CH$_2$NR$^h$R$^j$;
—(CH$_2$)$_{0-3}$NHC(=NH)NH$_2$;
—(CH$_2$)$_{0-1}$NH(CH$_2$)$_{0-1}$C(=O)(CH$_2$)$_{0-1}$NR$^h$R$^j$;
—(CH$_2$)$_{0-1}$NHSO$_2$NH$_2$;
—(CH$_2$)$_{0-1}$NHSO$_2$(CH$_2$)$_{0-2}$NH$_2$;
—(CH$_2$)$_{0-2}$NHSO$_2$CH$_3$;
—NR$^h$R$^j$;
—NHCH$_2$CN;
—NHCH=NH;
—NHC(=O)R$^i$;
—NHSO$_2$N(CH$_3$)$_2$;
—OH;
—ONH$_2$;
—ONHC(=O)CH$_2$NHCH$_3$;
oxo;
—(CH$_2$)$_{0-1}$-phenyl;
—(CH$_2$)$_{0-2}$-piperazinyl;
—C(=O)NH-pyridinyl;
—C(=O)-piperazinyl;
—C(=O)-pyrrolidinyl optionally substituted with —NH$_2$;

azetidinyl optionally substituted with —CH$_2$NH$_2$, —NH$_2$, or —OH;
pyrrolidinyl optionally substituted with —NH$_2$;
—NHCH$_2$-pyridinyl substituted with oxo, —CH$_3$ and —OH;
—NH-pyrimidinyl;
triazolyl optionally substituted with —CH$_2$NH$_2$; and
tetrazolyl.

In an eighth embodiment, the present invention relates to a compound of formula (I), (Ia) or (Ib), or a stereoisomer, internal salt N-oxide, or pharmaceutically acceptable salt thereof, wherein:

R$^o$ is hydrogen and R is:
1) —C(=O)CHF$_2$,
2) —C(=O)CF$_3$,
3) —C(=O)CH$_2$CF$_3$,
4) —C(=O)CF$_2$CF$_3$,
5) —C(=O)CF$_2$—C$_{1-6}$ alkyl,
6) —C(=O)CHFCH$_3$,
7) —C(=O)CF$_2$CH$_2$NH$_2$,
8) —C(=O)CF$_2$CH$_2$OH,
9) —C(=O)CH$_2$OH,
10) —C(=O)CH$_2$OCOCH$_3$,
11) —C(=O)CH$_2$CN,
12) —C(=O)CH$_2$SO$_2$C$_{1-6}$alkyl,
13) —C(=O)CH$_2$SCHF$_2$,
14) —C(=O)CH$_2$S(=O)CHF$_2$,
15) —C(=O)CH$_2$P(=O)(OCH$_3$)$_2$,
16) —C(=O)CH$_2$S-tetrazole optionally substituted with —CH$_3$,
17) —C(=O)CH$_2$-thienyl,
18) —C(=O)CH(NH$_2$)CH$_2$-tetrazole,
19) —C(=O)CH(NH$_2$)CH$_2$-pyrazole,
20) —C(=O)CH$_2$-tetrazole optionally substituted with —C(CH$_3$)$_3$, —CF$_3$, —CHF$_2$, —CH$_3$, NH$_2$—COOC$_{1-6}$ alkyl, thienyl, —CH$_2$NHCH$_3$, —NH$_2$, or —COOEt,
21) —C(=O)CH$_2$-triazole optionally substituted with —CH$_2$NR$^a$R$^b$, or —CH$_3$ and —CF$_3$, or —CF$_3$ and —NH$_2$,
22) —C(=O)CH$_2$-oxadiazole-CH$_2$NR$^a$R$^b$,
23) —C(=O)C(CH$_3$)$_2$-tetrazole,
24) —C(=O)CH$_2$-azetidine,
25) —C(=O)CH(CH$_3$)-azetidine optionally substituted with oxo, hydroxyethyl, or both,
26) —C(=O)CH$_2$-pyrrolidinyl optionally substituted with one or more —F or —CH$_2$NHCH$_3$,
27) —C(=O)CF$_2$-thienyl,
28) —C(=O)—C$_{1-6}$alkyl-NR$^a$R$^b$,
29) —C(=O)-pyrrolidinyl optionally substituted with F or NH$_2$,
30) —C(=O)-tetrahydrofuran,
31) —C(=O)—(CH$_2$)$_{0-1}$piperazine,
32) —C(=O)-pyrazine,
33) —C(=O)-thiazolidine optionally substituted with one or more oxo,
34) —C(=O)-pyrazole optionally substituted with CH$_3$ and CF$_3$,
35) —C(=O)CH(NH$_2$)C$_{1-6}$alkyl optionally substituted with —OH or phenyl,
36) —C(=O)CHFC$_{1-6}$ alkyl,
37) —C(=O)CH(OH)C$_{1-6}$alkyl,
38) —C(=O)CR$^k$=NOC(CH$_3$)$_2$COOH,
39) —C(=O)CR$^k$=NOCH$_3$,
40) —C(=S)OC$_{1-6}$ alkyl,
41) —C(=O)C(=O)OH,
42) —C(=O)C(=O)NR$^a$R$^b$,
43) —C(=O)(CH$_2$)$_{1-6}$C(=O)NR$^a$R$^b$, 44) —C(=O)C(=O)ONR$^a$R$^b$,
45) —C(=O)C(=O)OC$_{1-6}$ alkyl,
46) —(CH$_2$)$_{0-6}$C(=O)OH,
47) —(CH$_2$)$_{0-6}$C(=O)OC$_{1-6}$alky,
48) —(CH$_2$)$_{0-6}$C(=O)(CH$_2$)$_{1-6}$OH,
49) —(CH$_2$)$_{0-6}$C(=O)(CH$_2$)$_{1-6}$OC$_{1-6}$ alkyl,
50) —C(=O)OCH$_2$CHF$_2$,
51) —C(=O)OCH$_2$CF$_3$,
52) —C(=O)—C$_{3-6}$cycloalkyl substituted with CF$_3$ or NH$_2$,
53) —C$_{1-6}$alkyl-NR$^a$R$^b$,
54) —C$_{1-6}$alkyl-C$_{3-6}$cycloalkyl,
55) —(CH$_2$)$_{0-6}$SO$_2$(CH$_2$)$_{0-4}$R$^e$,
56) —CH(=NH), or
57) —C$_{1-6}$alkyl, or R and R$^0$ together with the N to which they are attached form a [1,2,3-]triazole optionally substituted with —CH$_2$OH, —CH$_2$OCH$_3$, —CH$_2$F, —CH$_2$NH$_2$, —CH$_2$NHCH$_3$, —C(=O)OCH$_3$, or a tetrazole optionally substituted with —NH$_2$; and the other groups are as provided in the general formula for formula (I), (Ia) or (Ib).

In another embodiment, R$^0$ is hydrogen and R is:
—C(=O)CHF$_2$;
—C(=O)CF$_3$;
—C(=O)CH$_2$CF$_3$;
—C(=O)CF$_2$CF$_3$;
—C(=O)CF$_2$—C$_{1-6}$ alkyl;
—C(=O)CHF CH$_3$;
—C(=O)CF$_2$CH$_2$NH$_2$;
—C(=O)CF$_2$CH$_2$OH;
—C(=O)CH$_2$OH;
—C(=O)CH$_2$OCOCH$_3$;
—C(=O)CH$_2$CN;
—C(=O)CH$_2$SO$_2$C$_{1-6}$alkyl;
—C(=O)CH$_2$S(=O)CHF$_2$;
—C(=O)CH$_2$P(=O)(OCH$_3$)$_2$;
—C(=O)CH$_2$S-tetrazole optionally substituted with —CH$_3$;
—C(=O)CH$_2$-thienyl;
—C(=O)CH(NH$_2$)CH$_2$-tetrazole;
—C(=O)CH(NH$_2$)CH$_2$-pyrazole;
—C(=O)CH$_2$-tetrazole optionally substituted with —C(CH$_3$)$_3$, —CF$_3$, —CHF$_2$, —CH$_3$, NH$_2$—COOC$_{1-6}$alkyl, thienyl, —CH$_2$NHCH$_3$, —NH$_2$, or —COOEt;
—C(=O)CH$_2$-triazole optionally substituted with —CH$_2$NR$^a$R$^b$, or —CH$_3$ and —CF$_3$, or —CF$_3$ and —NH$_2$;
—C(=O)CH$_2$-oxadiazole-CH$_2$NR$^a$R$^b$;
—C(=O)C(CH$_3$)$_2$-tetrazole;
—C(=O)CH(CH$_3$)-azetidine optionally substituted with oxo, hydroxy ethyl, or both;
—C(=O)CF$_2$-thienyl;
—C(=O)—C$_{1-6}$alkyl-NR$^a$R$^b$;
—C(=O)-pyrrolidinyl optionally substituted with F or NH$_2$;
—C(=O)-tetrahydrofuran;
—C(=O)-piperazine;
—C(=O)-pyrazine;
—C(=O)-thiazolidine optionally substituted with one or more oxo;
—C(=O)-pyrazole optionally substituted with CH$_3$ and CF$_3$;
—C(=O)CH(NH$_2$)C$_{1-6}$alkyl optionally substituted with —OH or phenyl;
—C(=O)CHF C$_{1-6}$alkyl;
—C(=O)CH(OH)C$_{1-6}$ alkyl;
—C(=O)CR$^k$=NOC(CH$_3$)$_2$COOH;
—C(=O)CR$^k$=NOCH$_3$;
—C(=S)OC$_{1-6}$ alkyl;
—C(=O)C(=O)OH;
—C(=O)C(=O)NR$^a$R$^b$;
—C(=O)(CH$_2$)$_{1-6}$C(=O)NR$^a$R$^b$;
—C(=O)C(=O)ONR$^a$R$^b$;
—C(=O)C(=O)OC$_{1-6}$ alkyl;
—(CH$_2$)$_{0-6}$C(=O)OH;
—(CH$_2$)$_{0-6}$C(=O)OC$_{1-6}$alkyl;
—(CH$_2$)$_{0-6}$C(=O)(CH$_2$)$_{1-6}$OH;
—(CH$_2$)$_{0-6}$C(=O)(CH$_2$)$_{1-6}$OC$_{1-6}$ alkyl;
—C(=O)OCH$_2$CHF$_2$;
—C(=O)OCH$_2$CF$_3$;
—C(=O)—C$_{3-6}$cycloalkyl substituted with CF$_3$ or NH$_2$;
—C$_{1-6}$alkyl-NR$^a$R$^b$;
—C$_{1-6}$alkyl-C$_{3-6}$cycloalkyl;
—(CH$_2$)$_{0-6}$SO$_2$(CH$_2$)$_{0-4}$R$^e$;
—CH(=NH); or
—C$_{1-6}$alkyl; or R and R$^0$ together with the N to which they are attached form a [1,2,3-]triazole optionally substituted with —CH$_2$OH, —CH$_2$OCH$_3$, —CH$_2$F, —CH$_2$NH$_2$, —CH$_2$NHCH$_3$, or —C(=O)OCH$_3$; or a tetrazole optionally substituted with —NH$_2$.

In another embodiment, R$^0$ is hydrogen or C$_{1-6}$alkyl which is optionally substituted with one or two substituents selected from halogen, hydroxyl, cyano, carbamoyl, —SO$_2$NH$_2$ and C$_{1-6}$alkoxy;

R is:
1) —(CH$_2$)$_n$C(=O)R$^2$, or
2) —(CH$_2$)$_n$SO$_2$R$^2$, or

R and R$^0$ together with the N to which they are attached form a substituted or unsubstituted 5-6 membered cyclic ring with 0, 1, 2, 3 or 4 additional heteroatom ring atoms independently selected from N, O and S.

In another embodiment, R$^0$ is hydrogen or C$_{1-6}$alkyl which is optionally substituted with one or two substituents selected from halogen, hydroxyl, cyano, carbamoyl, —SO$_2$NH$_2$ and C$_{1-6}$alkoxy;

R is:
1) —(CH$_2$)$_n$C(=S)R$^2$,
2) —C$_{1-6}$alkyl optionally substituted with —C$_{3-6}$cycloalkyl, or
3) —CH(=NH), or R and R$^0$ together with the N to which they are attached form a substituted or unsubstituted 5-6 membered cyclic ring with 0, 1, 2, 3 or 4 additional heteroatom ring atoms independently selected from N, O and S.

In a ninth embodiment, the present invention relates to a compound of formula (I), (Ia) or (Ib), or a stereoisomer, internal salt N-oxide, or pharmaceutically acceptable salt thereof, wherein R$^0$ is hydrogen and R is:
1) —C(=O)CHF$_2$,
2) —C(=O)CH$_2$NH$_2$,
3) —C(=O)CH$_2$NHCH$_3$,
4) —C(=O)CH$_2$NHC(=NH)NH$_2$,
5) —C(=O)CH$_2$-tetrazolyl, or
6) —SO$_2$CH$_3$, or R and R$^0$ combine together to form -triazolyl optionally substituted with —CH$_2$—OH; and the other groups are as provided in the general formula for formula (I), (Ia) or (Ib), above.

In another embodiment, R$^0$ is hydrogen and R is:
—C(=O)CHF$_2$;
—C(=O)CH$_2$NH$_2$;
—C(=O)CH$_2$NHCH$_3$;
—C(=O)CH$_2$NHC(=NH)NH$_2$;

—C(=O)CH$_2$-tetrazolyl; or
—SO$_2$CH$_3$; or
R and R$^0$ combine together to form -triazolyl optionally substituted with —CH$_2$—OH.

In other embodiment, the present invention relates to a compound of formula (I), (Ia) or (Ib), or a stereoisomer, internal salt N-oxide, or pharmaceutically acceptable salt thereof, wherein R$^1$ is:
1) pyrrolidinyl substituted with 1 or 2 of
   a) —CONR$^c$R$^d$,
   b) —CON(CH$_3$)CH$_2$CH$_2$C(=O)-pyrrolidin-1-yl substituted with NH$_2$ or diazepanyl,
   c) —CH$_2$NR$^f$R$^g$,
   d) —CH=NH,
   e) F,
   f) —(CH$_2$)$_{0-1}$NHC(=NH)NH$_2$,
   g) —CH$_2$NHSO$_2$-pyrrolidinyl-NH$_2$,
   h) —CH$_2$NH(C=O)-pyrrolidinyl substituted NH$_2$ or F,
   i) —CH$_2$NH(C=O)-pyridinyl substituted with oxo, CH$_3$ and OH,
   j) —CH$_2$NH(C=O)-cyclopentyl-NH$_2$,
   k) —CH$_2$NHSO$_2$-piperazine,
   l) —CH$_3$, or
   m) OH, 2) 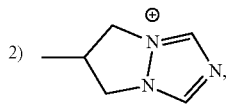

3) —CH$_2$-pyridinyl,
4) thiazole substituted with pyridinyl wherein the pyridinyl is optionally substituted with —CH$_3$ or —CH$_2$C(=O)NH$_2$,
5) azetidinyl substituted with —C(=NH)NH$_2$, —SO$_2$NH$_2$, thiazolyl or 4,5-dihydrothiazol-2-yl,
6) —CH$_2$CH$_2$-pyridinyl substituted with oxo, CH$_2$NH$_2$ and OH,
7) —CH$_2$-pyrrolidinyl substituted with acetyl and —NH$_2$, or —NHSO$_2$NH$_2$,
8) —CH$_2$-piperazine,
9) —CH$_2$CH$_2$—NH(=NH)NH$_2$, 10) 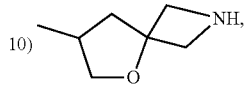

11) pyrazole optionally quaternized with —CH$_3$ and optionally substituted with —CH$_2$ pyrrolidine, or CH$_2$ piperidine optionally quaternized with —CH$_3$ and optionally substituted with —CH$_2$CH$_2$NH$_2$,
12) —CH$_2$-phenyl substituted with pyrazole optionally quaternized with —CH$_3$ and substituted with —(CH$_2$)$_3$NH$_2$, or
13) —CH$_2$CH$_2$NHCO$_2$-tert-butyl;
and the other groups are as provided in the general formula for formula (I), (Ia) or (Ib), above or the seventh or eighth embodiments.

In another embodiment, R$^1$ is:
1) pyrrolidinyl substituted with 1 or 2 of
   —CONR$^c$R$^d$;
   —CON(CH$_3$)CH$_2$CH$_2$C(=O)-pyrrolidin-1-yl substituted with NH$_2$ or diazepanyl;
   —CH$_2$NR$^f$R$^g$;
   —CH=NH;
   F;
   —CH$_2$NHSO$_2$-pyrrolidinyl-NH$_2$;
   —CH$_2$NH(C=O)-pyrrolidinyl substituted NH$_2$ or F;
   —CH$_2$NH(C=O)-pyridinyl substituted with oxo, CH$_3$ and OH;
   —CH$_2$NH(C=O)-cyclopentyl-NH$_2$;
   —CH$_2$NHSO$_2$-piperazine; or
   —CH$_3$;

2) 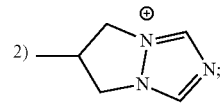

3) —CH$_2$-pyridinyl;
4) thiazole substituted with pyridinyl wherein the pyridinyl is optionally substituted with CH$_3$;
5) azetidinyl substituted with thiazolyl or 4,5-dihydrothiazol-2-yl;
6) —CH$_2$CH$_2$-pyridinyl substituted with oxo, CH$_2$NH$_2$ and OH;
7) —CH$_2$-pyrrolidinyl substituted with acetyl and —NH$_2$, or —NHSO$_2$NH$_2$; or
8) —CH$_2$-piperazine.

In a tenth embodiment, the present invention relates to a compound of formula (I), (Ia) or (Ib), or a stereoisomer, internal salt N-oxide, or pharmaceutically acceptable salt thereof, wherein R$^1$ is pyrrolidinyl substituted with
1) —C(=O)NR$^c$R$^d$;
2) —CH$_2$NHSO$_2$NH$_2$, or
3) —CH$_2$-pyrrolidinyl-NH$_2$, or
4) —CH$_2$—CO-pyrrolidinyl-NH$_2$;
wherein
R$^c$ is —CH$_3$,
R$^d$ is —CH$_3$;
R$^c$ and R$^d$ are taken together, with the N to which they are attached, to form
1) azetidinyl optionally substituted with —NHC(=NH)NH$_2$,
2) pyrrolidinyl substituted with
   a. one or two —NH$_2$,
   b. —NHCH$_3$,
   c. —C(Me)$_2$NH$_2$,
   d. one or two —OH,
   e. —CH$_2$NH$_2$,
   f. —NHC(=O)CH$_2$NH$_2$,
   g. —NHC(=O)CH$_2$CH$_2$NH$_2$,
   h. —NHC(=O)CH$_2$NH(=NH)NH$_2$,
   i. —NHCH=NH,
   j. —F and —NH$_2$,
   k. —NH$_2$ and —OH,
   l. —NH$_2$ and —CH$_3$,
   m. —NH$_2$ and —CH$_2$OH,
   n. —NH$_2$ and —CH$_2$NH$_2$,
   o. —NH$_2$ and -OMe,
   p. —OH and —CH$_2$NH$_2$,
   q. —CH$_2$OH and —CH$_2$NH$_2$,
   r. —NH$_2$ and —COOH,
   s. —NHC(=NH)NH$_2$,
   t. —NHC(=NH)NH$_2$ and —OH,
   u. —NHC(=NH)NH$_2$ and —CH$_2$OH,
   v. —NHC(=NH)NH$_2$ and —NH$_2$,
   w. —NH$_2$ and —CH$_2$NHSO$_2$NH$_2$,
   x. —CH$_2$F and NH$_2$, y. —OH, —NH$_2$ and —CH$_2$NH$_2$,
z. —OH, —NH$_2$ and —CH$_2$OH, or
aa. triazolyl substituted with —CH$_2$NH$_2$,
3) piperidinyl substituted with —(CH$_2$)$_{0-2}$NH$_2$, —CH$_2$NHCH$_2$C(=O)NH$_2$, —CH$_2$CH$_2$NH$_2$, —CH$_3$ and —NH$_2$, —CH$_2$OH and —CH$_2$NH$_2$, —F and —NH$_2$, —OH and —NH$_2$, —CONHCH$_2$CH(OH)CH$_2$NH$_2$, or azetidinyl substituted with —OH or piperazinyl,
4) piperazinyl optionally substituted with one or two —CH$_3$, —CH$_2$NH$_2$, —CH$_2$CH$_2$NH$_2$, —C(=NH)NH$_2$, —CH$_2$CH$_2$NHC(=NH)NH$_2$, —C(=O)(CH$_2$)$_{1-2}$NH$_2$, —C(=O)CH(NH$_2$)NH$_2$, —CH$_2$CH(NH$_2$)CH$_2$NH$_2$, —CH$_2$CH(F)CH$_2$NH$_2$, —C(=O)CH$_2$NHCH$_3$, —C(=O)CH(NH$_2$)CH$_2$OH, or —CH$_3$ and —CH$_2$C(=O)NH$_2$;
5) morpholinyl optionally substituted with —CH$_2$NH$_2$;
6) 1,4-diazepane optionally substituted with —C(=NH)NH$_2$;
7) octahydro-1H-pyrrolo[3,2-c]pyridine optionally substituted with —CH$_2$CH$_2$NH$_2$, —CH$_2$CH(OH)NH$_2$, or —C(=NH)NH$_2$,
8) octahydrocyclopenta[c]pyrrole optionally substituted with
a. one or two —NH$_2$,
b. —NH$_2$ and —CH$_2$OH,
c. —NH$_2$ and —CH$_2$NH$_2$,
d. —NH$_2$,
e. —NHC(=NH)NH$_2$,
f. —NHC(=NH)NH$_2$ and —CH$_2$OH, or
g. s-OH, —NH$_2$ and —CH$_2$OH,
9) octahydro-1H-pyrrolo[2,3-c]pyridine,
10) octahydro-1H-pyrrolo[3,2-c]pyridine optionally substituted with —CH$_2$CH(OH)CH$_2$NH$_2$,
11) octahydro-1H-pyrrolo[3,4-b]pyridine optionally substituted with —CH$_2$OH,
12) octahydropyrrolo[3,4-b]pyrrole optionally substituted with —CH$_2$OH, —CH$_2$CH$_2$NH$_2$, or —C(=NH)NH$_2$;
13) octahydro-1H-pyrrolo[3,4-c]pyridine optionally substituted with —CH$_2$OH, or —COOH;
14) 5,5-dimethyloctahydro-1H-pyrrolo[3,2-c]pyridin-1-5-ium,
15) octahydropyrrolo[3,4-c]pyrrole optionally substituted with —CH$_2$OH,
16) octahydropyrrolo[3,4-d]imidazole optionally substituted with =NH,
17) octahydro-1H-pyrrolo[3,2-b]pyridine,
18) octahydropyrrolo[3,4-b][1,4]oxazine,
19) 3,6-diazabicyclo [3.2.0]heptane,
20) 1,9-diazaspiro[5.5]undecane,
21) decahydro-1,6-naphthyridine,
22) 5,6,7,8-tetrahydroimidazo[1,5-a]pyrazine optimally substituted with —NH$_2$,
23) 2,7-diazaspiro[4.4]nonane,
24) 2,8-diazaspiro[4.5]decane,
25) 2,6-diazaspiro[3.4]octane,
26) 1,7-diazaspiro[3.5]nonane,
27) 2,7-diazaspiro[3.5]nonane,
28) 1,8-diazaspiro[4.5]decane,
29) 1,7-diazaspiro[4.5]decane,
30) 5-oxa-2-azaspiro[3.4]octane optionally substituted with —NH$_2$,
31) 3,8-diaza-tricyclo[5.2.1.0$^{1,5}$]decane, or
32) 8-azaspiro[bicyclo[3.2.1]octane-3,3'-pyrrolidine;
and the other groups are as provided in the general formula for formula (I), (Ia) or (Ib), above, or the embodiments.

In another embodiment, R$^1$ is pyrrolidinyl substituted with
—C(=O)NR$^c$R$^d$;
—CH$_2$NHSO$_2$NH$_2$; or
—CH$_2$-pyrrolidinyl-NH$_2$;
wherein
R$^c$ is —CH$_3$,
R$^d$ is —CH$_3$;
R$^c$ and R$^d$ are taken together, with the N to which they are attached, to form pyrrolidinyl substituted with
one or two —NH$_2$,
—NHCH$_3$,
two —OH,
—CH$_2$NH$_2$,
—NHC(=O)CH$_2$NH$_2$,
—NHCH=NH,
—NH$_2$ and —OH,
—NH$_2$ and —CH$_3$,
—NH$_2$ and —CH$_2$OH,
—NHC(=NH)NH$_2$ and —OH, or
triazolyl substituted with —CH$_2$NH$_2$;
piperidinyl substituted with
—(CH$_2$)$_{0-2}$NH$_2$,
—CH$_2$NHCH$_2$C(=O)NH$_2$,
—CH$_3$ and —NH$_2$,
F and —NH$_2$, or
azetidinyl substituted with —OH or piperazinyl;
piperazinyl optionally substituted with
one or two —CH$_3$,
—CH$_2$CH$_2$NH$_2$,
—C(=NH)NH$_2$,
—CH$_2$CH$_2$NHC(=NH)NH$_2$,
—C(=O)(CH$_2$)$_{1-2}$NH$_2$,
—C(=O)CH$_2$NHCH$_3$,
—C(=O)CH(NH$_2$)CH$_2$OH, or
—CH$_3$ and —CH$_2$C(=O)NH$_2$;
octahydro-1H-pyrrolo[3,2-c]pyridine;
1.7-diazaspiro[3.5]nonane;
2.7-diazaspiro[3.5]nonane;
1.8-diazaspiro[4.5]decane; or
8-azaspiro[bicyclo[3.2.1]octane-3,3'-pyrrolidine].

In an eleventh embodiment, the present invention relates to a compound of formula (Ia), or a stereoisomer, internal salt N-oxide, or pharmaceutically acceptable salt thereof,

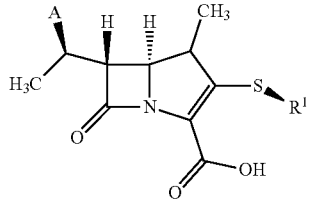

(Ia)

wherein:
A is NR$^0$R or -triazolyl substituted with —CH$_2$OH;
R is:
1) —C(=O)—C$_{1-6}$alkyl-NR$^a$R$^b$;
2) —C(=O)CHF$_2$,
3) —C(=O)CH$_2$SCHF$_2$,
4) —C(=O)CH$_2$NH(CH$_2$)$_2$OMe,
5) —C(=O)CH$_2$pyrrolidin,
6) —C(=O)CH$_2$azetidine,
7) —C(=O)CH$_2$piperazine, 8) —C(=O)CH₂ pyrrolidine optionally substituted with 1 or 2 substituents selected from fluorine and —CH₂NHMe,
9) —C(=O)CH₂-tetrazole optionally substituted with —C(CH₃)₃, —CF₃, —CHF₂, —CH₃, —NH₂—COOC₁₋₆alkyl, thienyl, —CH₂NHCH₃, —NH₂, or —COOCH₂CH₃, or
10) —SO₂CH₃;
R⁰ is H;
R¹ is
1) pyrrolidinyl substituted with 1 or 2 of —CONR^cR^d,
2) —CH₂NHSO₂NH₂, or
3) —CH₂-pyrrolidinyl optionally substituted with —NH₂;
R^a and R^b are independently H, —C₁₋₆alkyl, —C₃₋₈cycloalkyl, —SO₂CH₃, —CH(=NH), —C(=NH)NH₂, or —CH₂C(=O)NH₂;
R^c and R^d are independently H, C₁₋₃alkyl, —C(=NH)-pyrrolidinyl optionally substituted with —NH₂, or
R^c and R^d are taken together, with the N to which they are attached, to form a 4- to 12-membered heterocyclic ring or ring system with 0, 1, 2 or 3 additional heteroatom ring atoms selected from N and O;
wherein any nitrogen ring atom of the heterocyclic ring or ring system is optionally quadricovalent; the ring system is a bridged, fused or spiro ring system; and the 4- to 12-membered heterocyclic ring or ring system is optionally substituted with 1, 2 or 3 substituents selected from
1) =NH,
2) —C(=O)(CH₂)₁₋₂NH₂,
3) —C(=O)CH₂NHCH₃,
4) —CH₂CH(NH₂)CH₂NH₂,
5) —C(=O)CH(NH₂)CH₂NH₂,
6) —C(=O)CH(F)CH₂NH₂,
7) —C(=O)CH(NH₂)CH₂OH,
8) —CH₂CH(OH)CH₂NH₂,
9) —C(=O)NH CH₂CH(OH)CH₂NH₂,
10) —C(=NH)NH₂,
11) —COOH,
12) —CH₃,
13) —CH₂C(=O)NH₂,
14) —CH₂NH CH₂C(=O)NH₂,
15) —CH₂NR^hR^j,
16) —CH₂CH₂NH₂,
17) —CH₂CH₂NH—C(=NH)—NH₂,
18) —CH₂NHSO₂NH₂,
19) —CH₂OH,
20) —C(CH₃)₂NH₂,
21) —CH₂F,
22) —OH,
23) -OMe,
24) —F,
25) —NR^hR^j,
26) —NHCH=NH,
27) —NH—C(=NH)—NH₂,
28) —NHCOCH₂—NH—C(=NH)—NH₂,
29) —NHCOCH₂NH₂;
30) —(CH₂)₀₋₃NR^hR^j optionally substituted with —NH₂ or halogens,
31) azetidinyl optionally substituted with —OH,
32) piperazinyl, and
33) triazolyl substituted with CH₂NH₂; and
R^h and R^j are independently H, C₁₋₆alkyl, or C₃₋₅cycloalkyl; and the other groups are as provided in the general formula for formula (I), (Ia) or (Ib), above, or the embodiments.

In another embodiment, the compound has a structure according to formula Ia:

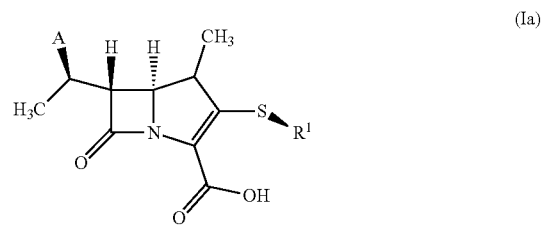

wherein:
A is NR⁰R or -triazolyl substituted with —CH₂OH;
R is:
—C(=O)—C₁₋₆alkyl-NR^aR^b;
—C(=O)CHF₂;
—C(=O)CH₂-tetrazole optionally substituted with —C(CH₃)₃, —CF₃, —CHF₂, —CH₃, —NH₂—COOC₁₋₆alkyl, thienyl, —CH₂NHCH₃, —NH₂, or —COOCH₂CH₃; or
—SO₂CH₃;
R⁰ is H;
R¹ is pyrrolidinyl substituted with 1 or 2 of —CONR^cR^d; —CH₂NHSO₂NH₂ or —CH₂— pyrrolidinyl optionally substituted with —NH₂;
R^a and R^b are independently H, —C₁₋₆alkyl, —C₃₋₈cycloalkyl, —SO₂CH₃, —CH(=NH), —C(=NH)NH₂ or —CH₂C(=O)NH₂;
R^c and R^d are independently C₁₋₃alkyl, or
R^c and R^d are taken together, with the N to which they are attached, to form a 4- to 10-membered heterocyclic ring or ring system with 0, 1, or 2 additional heteroatom ring atoms selected from N and O;
wherein any nitrogen ring atom of the heterocyclic ring or ring system is optionally quadricovalent; the ring system is a bridged, fused or spiro ring system; and the 4- to 12-membered heterocyclic ring or ring system is optionally substituted with 1 or 2 substituents selected from
—C(=O)(CH₂)₁₋₂NH₂,
—C(=O)CH₂NHCH₃,
—C(=O)CH(NH₂)CH₂OH,
—C(=NH)NH₂,
—CH₃,
—CH₂C(=O)NH₂,
—CH₂NH CH₂C(=O)NH₂,
—CH₂NR^hR^j,
—CH₂CH₂NH₂,
—CH₂CH₂NH—C(=NH)—NH₂,
—CH₂OH,
—OH,
—F,
—NR^hR^j,
—NHCH=NH,
—NH—C(=NH)—NH₂,
—NHCOCH₂NH₂;
—(CH₂)₀₋₃NR^hR^j optionally substituted with —NH₂ or halogens;
azetidinyl optionally substituted with —OH, piperazinyl, and
triazolyl substituted with CH₂NH₂; and
R^h and R^j are independently H, C₁₋₆alkyl, or C₃₋₈cycloalkyl.

In another embodiment the present invention relates to a compound of formula (I), (Ia) or (Ib), or a stereoisomer, internal salt N-oxide, or pharmaceutically acceptable salt thereof, wherein $R^0$ is hydrogen or $C_{1-6}$alkyl which is optionally substituted with one or two substituents selected from halogen, hydroxyl, cyano, carbamoyl, —$SO_2NH_2$ and $C_{1-6}$alkoxy;

R is:
1) —$(CH_2)_nC(=O)R^2$,
2) —$(CH_2)_nC(=S)R^2$,
3) —$(CH_2)_nSO_2R^2$,
4) —$C_{1-6}$alkyl optionally substituted with —$C_{3-6}$cycloalkyl, or
5) —CH(=NH), or R and $R^0$ together with the N to which they are attached form a substituted or unsubstituted 5-6 membered cyclic ring with 0, 1, 2, 3 or 4 additional heteroatom ring atoms independently selected from N, O and S, provided that when R and $R^0$ together with the N to which they are attached form triazole, then Z is not H.

In another embodiment the present invention relates to a compound of formula (I), (Ia) or (Ib), or a stereoisomer, internal salt N-oxide, or pharmaceutically acceptable salt thereof,
wherein $R^0$ is hydrogen or $C_{1-6}$alkyl which is optionally substituted with one or two substituents selected from halogen, hydroxyl, cyano, carbamoyl, —$SO_2NH_2$ and $C_{1-6}$alkoxy;

R is:
1) —$(CH_2)_nC(=O)R^2$,
2) —$(CH_2)_nC(=S)R^2$,
3) —$(CH_2)_nSO_2R^2$,
4) —$C_{1-6}$alkyl optionally substituted with —$C_{3-6}$cycloalkyl, or
5) —CH(=NH), or R and $R^0$ together with the N to which they are attached form a substituted or unsubstituted 5-6 membered cyclic ring with 0, 1, 2, 3 or 4 additional heteroatom ring atoms independently selected from N, O and S, provided that when R and $R^0$ together with the N to which they are attached form triazole or tetrazole, then Z is not H.

In another embodiment the present invention relates to a compound of formula (I), (Ia) or (Ib), or a stereoisomer, internal salt N-oxide, or pharmaceutically acceptable salt thereof, wherein R is —$(CH_2)_nC(=O)R^2$, —$(CH_2)_nC(=S)R^2$, —$(CH_2)_nSO_2R^2$, or —CH(=NH); or R and $R^0$ together with N to which they are attached form a substituted or unsubstituted 5-6 membered cyclic ring with 0, 1, 2, 3 or 4 additional heteroatom ring atoms independently selected from N, O and S;
with the provisos that
when R is —$(CH_2)_nC(=O)R^2$, n is 0 and $R^0$ is H, then $R^2$ is not unsubstituted $C_{1-6}$alkyl;
when R is —$(CH_2)_nC(=O)R^2$ and n is not 0, $R^2$ is not OH or $NH_2$;
when R is —$(CH_2)_nSO_2R^2$ and n is not 0, $R^2$ is not OH or $NH_2$; and
when R and $R^0$ combine together to form triazole then Z is not H.

In another embodiment the present invention relates to a compound of formula (I), (Ia) or (Ib), or a stereoisomer, internal salt N-oxide, or pharmaceutically acceptable salt thereof, wherein R and $R^0$ together with N to which they are attached form a substituted or unsubstituted 5-6 membered cyclic ring with 0, 1, 2, 3 or 4 additional heteroatom ring atoms independently selected from N, O and S;
with the provisos that
when R is —$(CH_2)_nC(=O)R^2$, n is 0 and $R^0$ is H, then $R^2$ is not unsubstituted $C_{1-6}$alkyl;
when R is —$(CH_2)_nC(=O)R^2$ and n is not 0, $R^2$ is not OH or $NH_2$;
when R is —$(CH_2)_nSO_2R^2$ and n is not 0, $R^2$ is not OH or $NH_2$; and
when R and $R^0$ combine together to form triazole or tetrazole then Z is not H.

In another embodiment the present invention relates to a compound of formula (I), (Ia) or (Ib), or a stereoisomer, internal salt N-oxide, or pharmaceutically acceptable salt thereof, wherein R is —$(CH_2)_nC(=O)R^2$, —$(CH_2)_nC(=S)R^2$, —$(CH_2)_nSO_2R^2$, or —CH(=NH); or R and $R^0$ together with N to which they are attached form a substituted or unsubstituted 5-6 membered cyclic ring with 0, 1, 2, 3 or 4 additional heteroatom ring atoms independently selected from N, O and S;
provided that
when R is —$(CH_2)_nC(=O)R^2$, n is 0 and $R^0$ is H, then $R^2$ is not unsubstituted $C_{1-6}$alkyl; and/or
when R is —$(CH_2)_nC(=O)R^2$ and n is not 0, $R^2$ is not OH or $NH_2$; and/or
when R is —$(CH_2)_nSO_2R^2$ and n is not 0, $R^2$ is not OH or $NH_2$; and/or
when R and $R^0$ combine together to form triazole or tetrazole then Z is not H.

In another embodiment the present invention relates to a compound of formula (I), (Ia) or (Ib), or a stereoisomer, internal salt N-oxide, or pharmaceutically acceptable salt thereof, wherein R is —$(CH_2)_nC(=O)R^2$, —$(CH_2)_nC(=S)R^2$, —$(CH_2)_nSO_2R^2$, or —CH(=NH); or R and $R^0$ together with N to which they are attached form a substituted or unsubstituted 5-6 membered cyclic ring with 0, 1, 2, 3 or 4 additional heteroatom ring atoms independently selected from N, O and S;
with the provisos that
when R is —$(CH_2)_nC(=O)R^2$, n is 0 and $R^0$ is H, then $R^2$ is not unsubstituted $C_{1-6}$alkyl;
when R is —$(CH_2)_nC(=O)R^2$ and n is not 0, $R^2$ is not OH or $NH_2$;
when R is —$(CH_2)_nSO_2R^2$ and n is not 0, $R^2$ is not OH; and
when R and $R^0$ combine together to form triazole or tetrazole, then Z is not H.

In another embodiment the present invention relates to a compound of formula (I), (Ia) or (Ib), or a stereoisomer, internal salt N-oxide, or pharmaceutically acceptable salt thereof, wherein R is —$(CH_2)_nC(=O)R^2$, —$(CH_2)_nC(=S)R^2$, —$(CH_2)_nSO_2R^2$, or —CH(=NH); or R and $R^0$ together with N to which they are attached form a substituted or unsubstituted 5-6 membered cyclic ring with 0, 1, 2, 3 or 4 additional heteroatom ring atoms independently selected from N, O and S;
with the provisos that
when R is —$(CH_2)_nC(=O)R^2$, n is 0 and $R^0$ is H, then $R^2$ is not unsubstituted $C_{1-6}$alkyl;
when R is —$(CH_2)_nC(=O)R^2$ and n is not 0, $R^2$ is not OH or $NH_2$;
when R is —$(CH_2)_nSO_2R^2$ and n is 0, $R^0$ is not H;
when R is —$(CH_2)_nSO_2R^2$ and n is not 0, $R^2$ is not OH; and when R and $R^o$ combine together to form triazole then Z is not H.

In another embodiment the present invention relates to a compound of formula (I), (Ia) or (Ib), or a stereoisomer, internal salt N-oxide, or pharmaceutically acceptable salt thereof, wherein R is —$(CH_2)_nC(=O)R^2$, —$(CH_2)_nC(=S)R^2$, —$(CH_2)_nSO_2R^2$, or —CH(=NH); or R and $R^o$ together with N to which they are attached form a substituted or unsubstituted 5-6 membered cyclic ring with 0, 1, 2, 3 or 4 additional heteroatom ring atoms independently selected from N, O and S;

with the provisos that when R is —$(CH_2)_nC(=O)R^2$, n is 0 and $R^o$ is H, then $R^2$ is not unsubstituted $C_{1-6}$alkyl;

when R is —$(CH_2)_nC(=O)R^2$ and n is not 0, $R^2$ is not OH or $NH_2$;

when R is —$(CH_2)_nSO_2R^2$ and n is 0, $R^o$ is not H;

when R is —$(CH_2)_nSO_2R^2$ and n is not 0, $R^2$ is not OH; and when R and $R^o$ combine together to form triazole or tetrazole then Z is not H.

In another embodiment the present invention relates to a compound of formula (I), (Ia) or (Ib), or a stereoisomer, internal salt N-oxide, or pharmaceutically acceptable salt thereof, wherein R is —$(CH_2)_nC(=O)R^2$, —$(CH_2)_nC(=S)R^2$, —$(CH_2)_nSO_2R^2$, or —CH(=NH); or R and $R^o$ together with N to which they are attached form a substituted or unsubstituted 5-6 membered cyclic ring with 0, 1, 2, 3 or 4 additional heteroatom ring atoms independently selected from N, O and S;

with the provisos that when R is —$(CH_2)_nC(=O)R^2$, n is 0 and $R^o$ is H, then $R^2$ is not unsubstituted $C_{1-6}$alkyl;

when R is —$(CH_2)_nC(=O)R^2$ and n is not 0, $R^2$ is not OH or $NH_2$;

when R is —$(CH_2)_nSO_2R^2$ and n is 0, $R^o$ is not H; and when R is —$(CH_2)_nSO_2R^2$ and n is not 0, $R^2$ is not OH.

In another embodiment of the present invention,

R is —$(CH_2)_nC(=O)R^2$, —$(CH_2)_nC(=S)R^2$, —$(CH_2)_nSO_2R^2$, or —CH(=NH); or

R and $R^o$ together with N to which they are attached form a substituted or unsubstituted 5-6 membered cyclic ring with 0, 1, 2, 3 or 4 additional heteroatom ring atoms independently selected from N, O and S;

with the provisos that when R is —$(CH_2)_nC(=O)R^2$ and n is 0, $R^o$ is not H;

when R is —$(CH_2)_nC(=O)R^2$ and n is not 0, $R^2$ is not OH or $NH_2$;

when R is —$(CH_2)_nSO_2R^2$ and n is 0, $R^o$ is not H; and when R is —$(CH_2)_nSO_2R^2$ and n is not 0, $R^2$ is not OH.

In another embodiment of the present invention, $R^1$ is $C_{2-6}$aminoalkyl optionally substituted with —$CR^x=NR^x$.

In another embodiment, A represents —$NR^OR$. In another embodiment, A represents —$OR^z$.

In another embodiment, Z represents —H. In another embodiment, Z represents —$CH_3$.

In another embodiment, X represents —S—. In another embodiment, X represents —$CH_2$—.

In another embodiment, $R^o$ is hydrogen.

In another embodiment, R is —$(CH_2)_nC(=O)R^2$.

In another embodiment, $R^1$ is —$(CH_2)_{0-6}$-HetC or —$(CH_2)_{1-6}NH(C=NH)NH_2$. In another embodiment, $R^1$ is HetC or —$(CH_2)_2$—NH(C=NH)NH_2$.

In another embodiment, $R^1$ is —$(CH_2)_{0-6}$-HetC. In another embodiment, $R^1$ is -HetC.

In another embodiment, $R^1$ is —$(CH_2)_{1-6}NH(C=NH)NH_2$. In another embodiment, $R^1$ is —$(CH_2)_2$—NH(C=NH)NH_2$.

In another embodiment, $R^2$ is AryA. In another embodiment, $R^2$ is tetrazole.

In another embodiment, $R^4$ is —$CO_2H$.

In one embodiment, HetC is a substituted or unsubstituted pyrrolidine.

In one embodiment, $R^c$ is —C(=NH)-pyrrobdin-1-yl substituted with $NH_2$.

In another embodiment, $R^d$ is hydrogen.

In another embodiment, $R^c$ and $R^d$ are taken together, with the N to which they are attached, to form a a heterocyclic ring or ring system selected from: azetidine, pyrrolidine, piperazine, octahydropyrrolo[3,4-b]pyrrole, octahydro-1H-pyrrolo[3,2-c]pyridine, 2,7-diazaspiro[4,4]-nonane, octahydropyrrolo[3,4-d]imidazole, and 3,8-diaza-tricyclo[5.2.1.01,5]decane, wherein the heterocyclic ring or ring system is optionally substituted with 1, 2, 3 or 4 substituents independently selected from: =NH, —$(CH_2)_{0-3}OH$, —$CH_2CH(OH)CH_2NH_2$, —$(CH_2)_{0-3}NR^hR^j$ optionally substituted with —$NH_2$, —$NHC(=O)CH_2NHC(=NH)NH_2$, —$C(=NH)NH_2$, and —$(CH_2)_{0-3}NHC(=NH)NH_2$.

In another embodiment, $R^c$ and $R^d$ are taken together, with the N to which they are attached, to form a heterocyclic ring or ring system selected from: azetidine, pyrrolidine, piperazine, octahydropyrrolo[3,4-b]pyrrole, octahydro-1H-pyrrolo[3,2-c]pyridine, 2,7-diazaspiro[4,4]-nonane, octahydropyrrolo[3,4-d]imidazole, and 3,8-diaza-tricyclo[5.2.1.01,5]decane, wherein the heterocyclic ring or ring system is optionally substituted with 1, 2, 3 or 4 substituents independently selected from: =NH, —$CH_2OH$, OH, —$CH_2CH(OH)CH_2NH_2$, —$(CH_2)_3NH_2$ optionally substituted with —$NH_2$, —$CH_2CH(NH_2)CH_2NH_2$, —$NHC(=O)CH_2NHC(=NH)NH_2$, —$C(=NH)NH_2$, and —$NHC(=NH)NH_2$.

In another embodiment, each $R^x$ and $R^y$ is independently hydrogen.

In another embodiment, HetC is substituted with one substituent selected from —$C(=O)NR^cR^d$.

In another embodiment of the present invention, the pharmaceutically acceptable salt is selected from sodium, potassium, calcium, magnesium and ammonium salts.

In a twelfth embodiment of the invention, the compound of the invention is selected from the exemplary species depicted in EXAMPLES 1 to 601 shown below, and pharmaceutically acceptable salts thereof.

In a thirteenth embodiment of the invention, the compound of the invention is selected from the exemplary species depicted in EXAMPLES 32, 44, 95, 103, 106, 112, 120, 121, 124, 129, 132, 135, 146, 149, 157, 158, 159, 161, 168, 169, 176, 178, 184, 186, 218, 219, 221, 242, 264, 278, 283, 298, 314, 324, 352, 360, 361, 362, 363, 364, 365, 366, 367, 368, 391, 395, 396, 397, 398, 400, 404, 411, 412, 413, 414, 419, 420, 425, 426, 427, 429, 431, 432, 433, 435, 437, 438, 439. 457, 481, 493, 505, 521, 523, 544, 545, 560, 566, 567, 571, 575, 576, 580, 584, 585, 593 shown below, and pharmaceutically acceptable salts thereof Reference to different embodiments with respect to Formula I or (I) compounds, specifically includes different embodiments of Formula I, such as Formulas Ia and Ib, sub-embodiments of Formulas Ia and Ib, other embodiments provided herein, and individual compounds described herein.

Other embodiments of the present invention include the following:

(a) A pharmaceutical composition comprising a compound of Formula I or Ia or Ib, as defined herein, or a pharmaceutically acceptable salt thereof, and a pharmaceutically acceptable carrier.

(b) The pharmaceutical composition of (a), further comprising a beta-lactamase inhibitor.

(c) The pharmaceutical composition of (b), wherein the beta lactamase inhibitor is clinically approved Clavulanic acid and its salts, Sulbactam and its salts, Tazobactam and its salts, Avibactam and its salts, and Cilastatin and its salts. Other beta lactamase inhibitors include Relebactam, RPX 7009 and BAL 30072.

(d) A pharmaceutical composition which comprises (i) a compound of formula (I), (Ia) or (Ib), or a pharmaceutically acceptable salt thereof, and (ii) a beta lactamase inhibitor, wherein the compound of formula I or Ia or Ib, and the beta lactamase inhibitor are each employed in an amount that renders the combination effective for overcoming drug resistance in a bacterial infection.

(e) The combination of (d), wherein the beta lactamase inhibitor is clinically approved Clavulanic acid and its salts, Sulbactam and its salts, Tazobactam and its salts, Avibactam and its salts, and Cilastatin and its salts. Other beta lactamase inhibitors include Relebactam, RPX 7009 and BAL 30072

(f) A method for inhibiting bacterial peptidoglycan synthesis which comprises administering to a subject in need of treatment an effective amount of a compound of Formula I or Ia or Ib, or a pharmaceutically acceptable salt thereof.

(g) A method for preventing and/or treating a bacterial infection which comprises administering to a subject in need of such treatment an effective amount of a compound of Formula I or Ia or Ib, or a pharmaceutically acceptable salt thereof.

(h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to *Escherichia* spp., or *Pseudomonas* spp., *Staphylococcus* spp., or *Streptococcus* spp.

The present invention also includes a compound of Formula I or Ia or Ib, or a pharmaceutically acceptable salt thereof, (1) for use in, (2) for use as a medicament for, or (3) for use in the preparation (or manufacture) of a medicament for, medicine or inhibiting bacterial peptidoglycan synthesis or treating bacterial infection. In these uses, the compounds of the present invention can optionally be employed in combination with one or more beta-lactamase inhibitors.

Additional embodiments of the invention include the pharmaceutical compositions, combinations and methods set forth in (a)-(i) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (i) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se; i.e., the purity of the active ingredient in the composition.

Definitions

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent.

"About", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±1%, 2%, 3%, 4%, 5%, 10%, or 20%.

"Aromatic ring system", as exemplified herein, by Ary A, AryB and AryC, means monocyclic, bicyclic or tricyclic aromatic ring or ring system containing 5-14 ring atoms, wherein at least one of the rings is aromatic. Aromatic ring systems, as used herein, encompass aryls and heteroaryls. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In another example, a heteromonocyclic ring is fused through two ring atoms to a phenyl or 5-6-membered heteroaryl containing 1, 2, or 3 heteroatoms selected from N, O, and S.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, and the like.

"Drug resistant" means, a bacterium which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

"Halogen" includes fluorine, chlorine, and bromine.

"Heteroaryl" means monocyclic, bicyclic or tricyclic ring or ring system containing 5-14 carbon atoms and containing at least one ring heteroatom selected from N, NH, a N as a quaternary salt, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothienyl (including S-oxide and dioxide), benzotriazolyl, furo(2,3-b)pyridyl, quinolyl, indolyl, isoquinolyl, quinazolinyl, dibenzofuranyl, and the like.

"Heterocycle" means monocyclic, bicyclic or tricyclic saturated or monounsaturated ring or ring system containing 3-14 carbon atoms and containing at least one ring heteroatom selected from N, NH, a N as a quaternary salt, S (including SO and $SO_2$) and O. When a heterocycle contains two rings, the rings may be fused, bridged or spiro-linked. Examples of monocyclic heterocycle rings include piperazine, piperidine, and morpholine. When a heterocycle contains two or more rings, the rings may be fused, bridged and/or spiro-linked. Examples of monocyclic heterocycle rings include piperazine, piperidine, and morpholine. Examples of tricyclic ring systems include 8-azaspiro[bicyclo[3.2.1]octane-3,3'-pyrrolidine "Oxo" means an oxygen atom connected to another atom by a double bond and is can be represented "=O".

Another embodiment of the present invention is a compound of Formula I, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to about 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer. All isomeric forms of these compounds, whether individually or in mixtures, are within the scope of the present invention.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When a group, e.g., $C_{1-8}$alkyl, is indicated as being substituted, such substitutions can also be occur where such group is part of a larger substituent, e.g., —$C_{1-8}$alkyl-$C_{3-7}$cycloalkyl and —$C_{1-8}$alkyl-aryl.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the EXAMPLES herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_{1-6}$ when used with a chain, for example an alkyl chain, means that the chain can contain 1, 2, 3, 4, 5 or 6 carbon atoms. It also includes all ranges contained therein including $C_{1-5}$, CM, $C_{1-3}$, $C_{1-2}$, $C_{2-6}$, $C_{3-6}$, $C_{4-6}$, $C_{5-6}$, and all other possible combinations.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). A pharmaceutically acceptable salt can be formed, for example, by treating the compound of the invention (e.g., a compound of Formula I) with one molar equivalent of a mild base (e.g., sodium carbonate, sodium bicarbonate, potassium bicarbonate, or sodium acetate). In this case, M is a cation, such as $Na^+$ in the event of treatment with a sodium base.

Described herein are also prodrugs of a compound of the invention, which on administration undergo chemical conversion by metabolic processes before becoming active pharmacological substances. In general, such prodrugs will be functional derivatives of a compound of the invention that are readily convertible in vivo into compound of formula (I).

As set forth above, the present invention includes pharmaceutical compositions comprising a compound of Formula I of the present invention, optionally one or more other active components, and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, or a pharmaceutically acceptable salt thereof. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I mean providing the compound, or a pharmaceutically acceptable salt thereof, to the individual in need of treatment. When a compound or a salt thereof is provided in combination with one or more other active agents, "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein with respect to a nargenicin compound means the amount of active compound sufficient to inhibit DnaE and/or cause a bacteriocidal or bacteriostatic effect. In one embodiment, the effective amount is a "therapeutically effective amount" meaning the amount of active compound that can overcome bacterial drug resistance and which is sufficient to inhibit bacterial replication and/or result in bacterial killing. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, $21^{st}$ edition, 2006. In one embodiment, compounds of the invention are administered intravenously in a hospital setting. In another embodiment, administration is oral in the form of a tablet or capsule or the like. The dosage of the compounds of the invention and of their pharmaceutically acceptable salts may vary within wide limits and should naturally be adjusted, in each particular case, to the individual conditions and to the pathogenic agent to be controlled. In general, for a use in the treatment of bacterial infections, the daily dose may be between 0.005 mg/kg to 100 mg/kg, 0.01 mg/kg to 10 mg/kg, 0.05 mg/kg to 5 mg/kg, 0.05 mg/kg to 1 mg/kg. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

In some embodiments, the compound in the invention is provided in a pharmaceutical formulation for oral, intravenous, intramuscular, nasal, or topical administration. Thus, in some embodiments, the formulation can be prepared in a dosages form, such as but not limited to, a tablet, capsule, liquid (solution or suspension), suppository, ointment, cream, or aerosol. In some embodiments, the presently disclosed subject matter provides such compounds and/or formulations that have been lyophilized and that can be reconstituted to form pharmaceutically acceptable formulations for administration, for example, as by intravenous or intramuscular injection.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Infections that may be treatable by the compounds of the invention can be caused by a variety of microbes, including fungi, algae, protozoa, bacteria, and viruses. In some embodiments, the infection is a bacterial infection. Exemplary microbial infections that may be treated by the methods of the invention include, but are not limited to, infections caused by one or more of *Staphylococcus aureaus. Enterococcus faecalis. Bacillus anthracis*, a *Streptococcus* species (e.g., *Streptococcus pyogenes* and *Streptococcus pneumoniae*), *Escherichia coli, Pseudomonas aeruginosa, Burkholderia cepacia*, a *Proteus* species (e.g., *Proteus mirabilis* and *Proteus vulgaris*), *Klebsiella pneumoniae, Acinetobacter baumannii*, and *Strenotrophomonas maltophillia*.

In certain embodiments, the infection is an infection of a bacterium selected from *Pseudomonas* spp., *Klebsiella* spp., *Enterobacter* spp., *Escherichia* spp., *Morganella* spp., *Citrobacter* spp., *Serratia* spp. or *Acintetobacter* spp.

In some embodiments, the compound of Formula (I), (Ia) or (Ib), is administered prophylactically to prevent or reduce the incidence of one of: (a) a bacterial infection in a subject at risk of infection; (b) a recurrence of a bacterial infection; and (c) combinations thereof. In some embodiments, the compound of Formula (I), (Ia) or (Ib), is administered to treat an existing bacterial infection. In some embodiments, the compound of Formula ((I), (Ia) or (Ib), is administered to treat an infection of a multi-drug resistant strain of bacterial (i.e., a strain that is resistant to two or more previously known anti-bacterial drugs, such as i) Carbapenemase producing Enterobacteriaceae that are resistant to Cephalosporins and certain carbapenems; ii) Extended spectrum β-lactamase (ESBL) producing Enterobacteriaceae that are resistant to cephalosporins and penicillins; iii) Aminoglycoside and Fluoroquinolone resistant Enterobacteriaceae; iv) Extended spectrum β-lactamase (ESBL) producing *P. aeruginosa* and v) Aminoglycoside and Fluoroquinolone resistant *P. aeruginosa*. In some embodiments, the compound of Formula (I), (Ia) or (Ib), has a minimum inhibitory concentration (MIC) against one or bacterial species of 25 µg/mL or less. In some embodiments, the compound of Formula (I), (Ia) or (Ib), is administered to treat an infection of a multi-drug resistant strain.

In some embodiments, the compound of Formula I, Ia, has a minimum inhibitory concentration (MIC) against one or more bacterial species of 25 µg/mL or less. MICs can be determined via methods known in the art, for example, as described in Hurdle et al., 2008, *J. Antimicrob. Chemother.* 62:1037-1045.

In some embodiments, the methods of the invention further comprise administering to the subject an additional therapeutic compound. In some embodiments, the compound of the invention is administered to the subject before, after, or at the same time as one or more additional therapeutic compounds. In some embodiments, the additional therapeutic compound is an antibiotic.

The invention thus provides in a further aspect, a combination comprising a compound of Formula I, or a pharmaceutically acceptable salt thereof, together with one or more additional therapeutic agents. Examples of such one or more additional therapeutic agents include, but not limited to, β-lactams, aminoglycosides, tetracyclines, macrocycles, oxazolidinones, glycopeptides, lipopeptides, quinolones, etc., Thus, the other antibiotic which may be combined with the compounds of formula I or Ia or Ib are, for example, Vancomycin, Linezolid, Tedizolid, Ceftaroline, Ceftobiprole, Ceftalozane, Daptomycin, Dalbavancin, Televancin, Oritavancin, Aztreonam, Delafloxacin, GSK2140944, Plazomicin, Tigecycline, Solithromycin etc., Abbreviations employed herein include the following: ACN=acetonitrile; aq.=aqueous; Bn=benzyl; Boc=tert-butoxy carbonyl; CDCl$_3$=deuterated chloroform; CDI=carbodiimidazole; DCE=1,2-dichloroethane; DCM=dichloromethane; DIAD=diisopropyl azodicarboxylate; DIPEA=diisopropylethylamine; DMAP=4-dimethylaminopyridine or N,N-dimethylaminopyridine; DMF=N,N-dimethylformamide; DMSO=dimethyl sulfoxide; Et=ethyl; EtOAc=ethyl acetate; H$_2$=hydrogen gas, HPLC=high-performance liquid chromatography; LC-MS=liquid chromatography/mass spectrometry; Me=methyl; MeCN=acetonitrile; MeOH=methanol; MIC=minimum inhibitory concentration; MW=molecular weight; MS=mass spectrometry; Pd/C=palladium on carbon; PNB—p-nitrobenzyl; PNZ=]p-nitrobenzyl carbamate; PPh₃=triphenylphosphine; RB=round bottom flask; RT=room temperature; TBDMS=tert-butyl dimethylsilyl; TBTU=N,N,N',N'-tetramethyl-O-(benzotriazol-1-yl) uronium tetrafluoroborate; TEA=triethylamine; TFA=trifluoroacetic acid; THF=tetrahydrofuran; TLC=thin layer chromatography.

The compounds disclosed herein can be prepared according to the following reaction schemes and EXAMPLES, or modifications thereof, using readily available starting materials, reagents and conventional synthesis procedures. In these reactions, it is also possible to make use of variations which are themselves known to those of ordinary skill in this art, but are not mentioned in greater detail. Furthermore, other methods for preparing compounds disclosed herein will be readily apparent to the person of ordinary skill in the art in light of the following reaction schemes and EXAMPLES.

Described below are processes for the preparation of a compound of formula ((I), (Ia) or (Ib) as shown in the general schemes 1, 2, 2a and 3, wherein all the groups are as defined earlier.

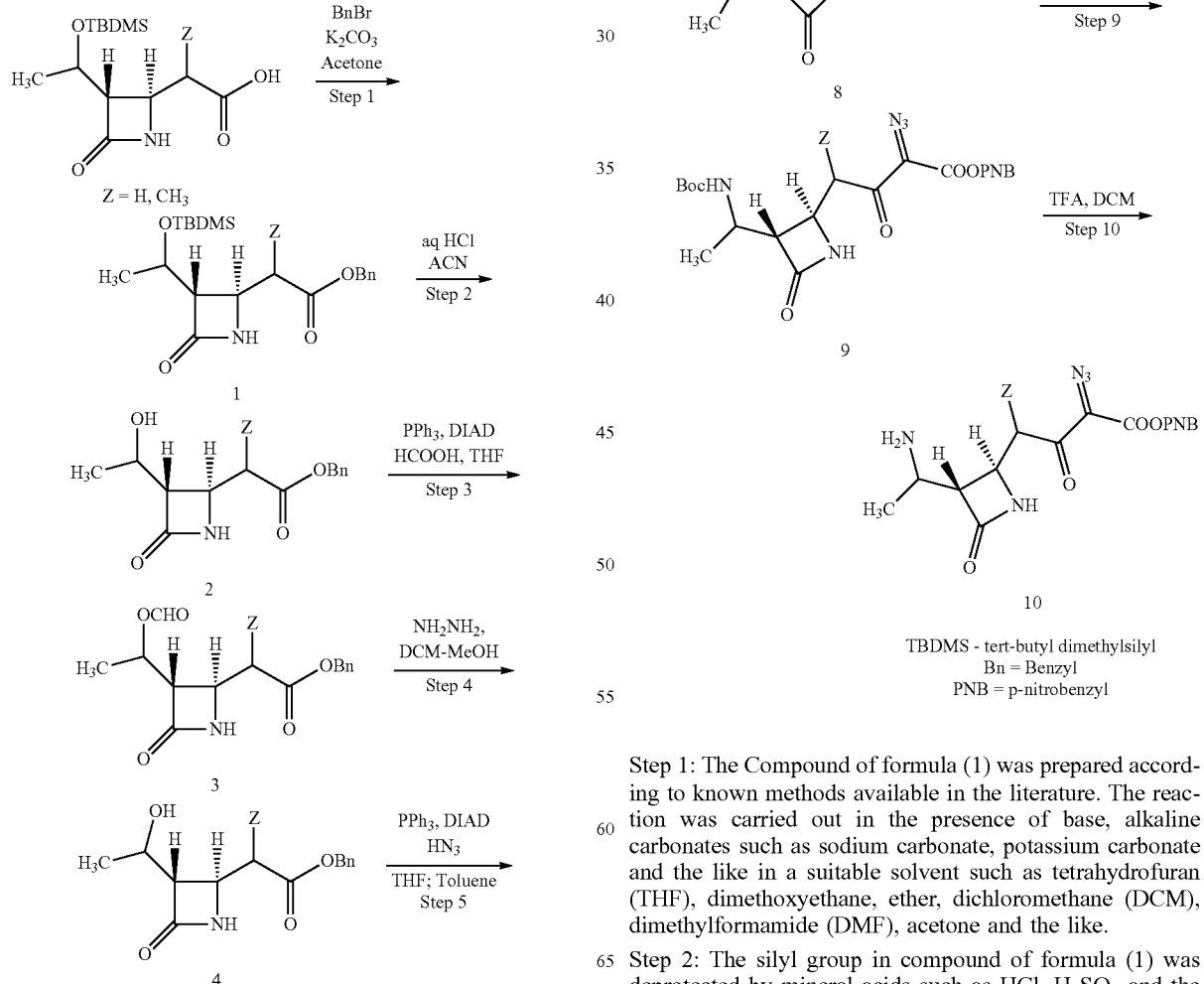

Step 1: The Compound of formula (1) was prepared according to known methods available in the literature. The reaction was carried out in the presence of base, alkaline carbonates such as sodium carbonate, potassium carbonate and the like in a suitable solvent such as tetrahydrofuran (THF), dimethoxyethane, ether, dichloromethane (DCM), dimethylformamide (DMF), acetone and the like.

Step 2: The silyl group in compound of formula (1) was deprotected by mineral acids such as HCl, H₂SO₄ and the like in presence of solvent such as tetrahydrofuran, dioxane, acetonitrile (ACN), dimethylformamide and the like to yield the compound of formula (2).

Step 3: The compound of formula (3) was obtained by reacting a compound of formula (2) with triphenylphosphine (PPh$_3$), formic acid and Diisopropyl azodicarboxylate (DIAD) in the presence of THF.

Step 4: The compound of formula (3) was hydrolyzed according to the procedure given in *Bull Chem Soc Japan,* 1976, 49, 510 to yield the compound of formula (4).

Step 5: The compound of formula (4) was reacted with triphenylphosphine, hydrazoic acid and DIAD according to the procedure given in *Tetrahedron Letters,* 1983, 49, 554, to yield the compound of formula (5).

Step 6: Reducing the Compound of formula (5) using reducing reagents such as triphenylphosphine, trimethylphosphine, triethylphosphine, tributylphosphine, methyl diphenylphosphinite or ethyldiphenylphosphinite and the like in presence of aqueous organic solvents such as tetrahydrofuran (THF), dioxane, acetonitrile (ACN), acetone, or dimethylformamide (DMF) containing about 1% to 50% water, preferably about 5% to 10% water and the like according to known Staudinger reaction gave the compound of formula (6).

Step 7: The compound of formula (7) was synthesized by reacting a compound of formula (6) with amino protecting group in presence of organic base such as sodium bicarbonate and the like and water soluble solvents such as THF, dioxane and acetone followed by hydrolyzing using base such as LiOH and the like. Suitable amino-protecting groups include, for example, acyl groups such as formyl, acetyl and substituted acetyl (e.g., halogenated acetyl), benzoyl and substituted benzoyl, alkoxycarbonyl, halogenated alkoxycarbonyl, alkenyloxycarbonyl, aralkoxycarbonyl, halogenated aralkoxycarbonyl, benzyl and benzyl derivatives, trityl and trityl derivatives, sulfenyl derivatives, sulfonyl derivatives, diacyl derivatives such as phthalimido or succinimido or derivatives thereof and Schiff bases formed with aldehydes or ketones. Carbamate protection was done by using di-tert-butoxycarbonylanhydride (BOC anhydride) and inorganic base such as sodium bicarbonate in water soluble solvent such as tetrahydrofuran, dioxan and acetone.

Step 8: The Compound of formula (7) was reacted with carbodiimidazole and magnesium mono p-nitrobenzyl malonate ester by a known method given in D. G. Melillo et al., *Tetrahedron Letters,* 1980, 21, 2783 to yield the compound of formula (8). The reaction of a magnesium malonate with the activated carboxy moiety was carried out in organic solvent such as tetrahydrofuran, dioxane, dichloromethane, acetonitrile, benzene, toluene and the like.

Step 9: The compound of formula (8) was subjected to a diazo-transfer reaction to yield compound of formula (9). The compound of formula (8) was treated with an azide such as dodecabenzenesulfonylazide, 4-carboxybenzenesulfonylazide, p-toluenesulfonylazide, methanesulfonylazide and the like in presence of a base such as triethylamine (TEA), diethylamine, pyridine or lutidine and the like and solvent such as acetonitrile, dichloromethane, toluene, benzene and the like to yield the Compound of formula (9).

Step 10: The compound of formula (10) was synthesized by treating the compound of formula (9) with acids such as trifluoroacetic acid (TFA) or HCl and the like in presence of solvents such as dioxane or ether and the like.

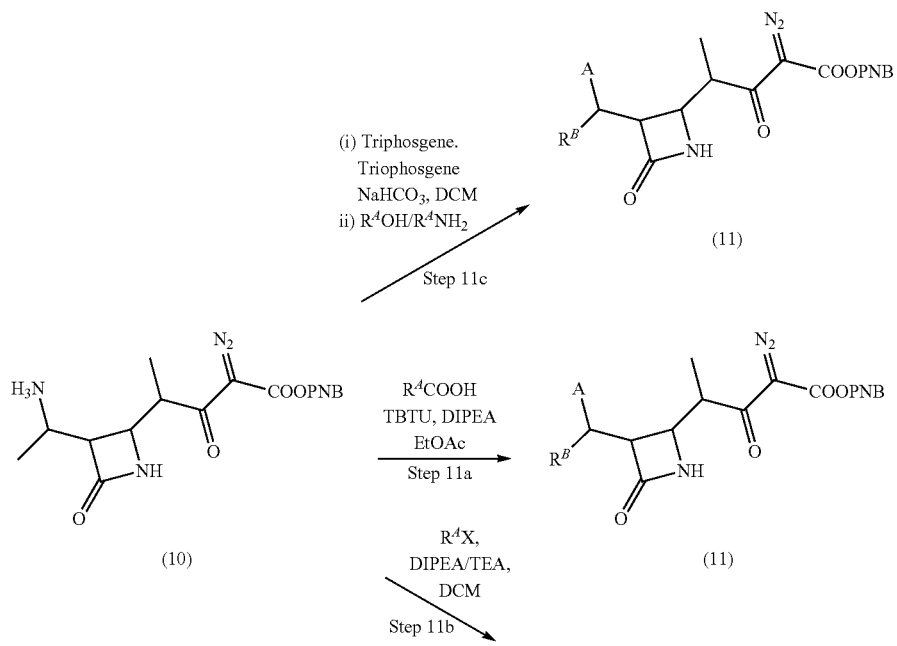

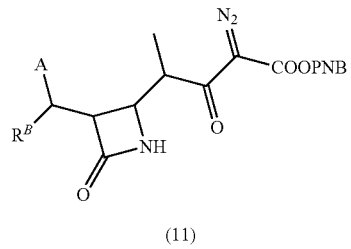

(11)

Step 11a: Reacting compound of formula (10) with R⁴COOH in the presence of coupling agents such as carbodiimides, phosphonium, uronium, guanidinium salts and the like and solvents such as ethyl acetate (EtOAc) and the like gave the compound of formula (11).

Step 11b: Reacting compound of formula (10) with R⁴X (X is Cl, Br, F, I) in the presence of acid binding agents such as alkali acetate, alkali hydroxide, calcium oxide, calcium carbonate, magnesium carbonate or organic bases such as pyridine, N-methyl morpholine, diisopropylethylamine (DIPEA), TEA and the like and solvents such as DCM, dioxane, toluene and the like gave the compound of formula (11).

Step 11c: The compound of formula (10) was reacted with carbonylating agent such as phosgene, diphosgene, triphosgene, N,N'-carbonyldiimidazole (CDI), thiophosgene, thiocarbonyldiimidazole and the like in presence of bases such as pyridine, N-methyl morpholine, DIPEA, TEA and the like in solvents such as DCM, 1,2-dichloromethane, toluene, ACN and the like and successively treated with R⁴OH/R⁴NH₂ to yield the compound of formula (11).

SCHEME 2a

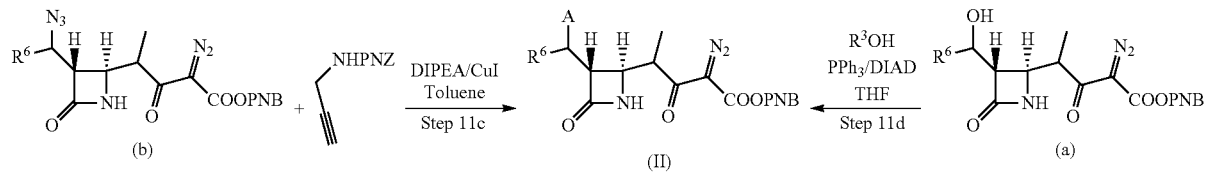

Step 11d: The compound of formula (a) was reacted with R³OH in presence of triphenylphosphine and DIAD in solvents such as THF and the like to obtain a compound of formula (11).

Step 11e: The compound of formula (b) was reacted with compound (c) in presence of copper iodide and DIPEA in solvents such as toluene and the like to obtain a compound of formula (11).

SCHEME 3

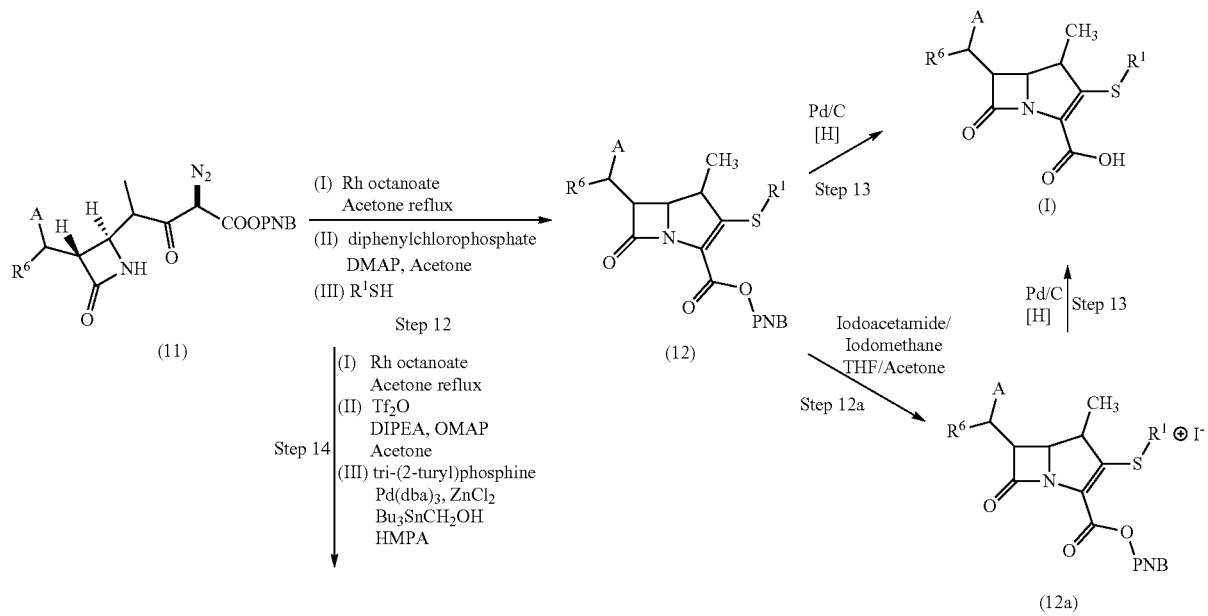

-continued

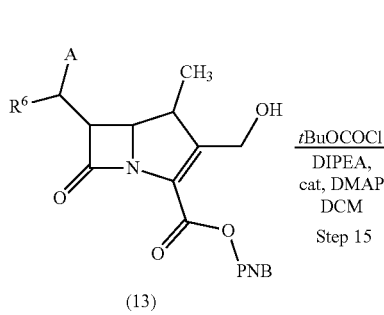
(13)

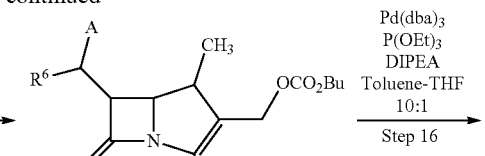

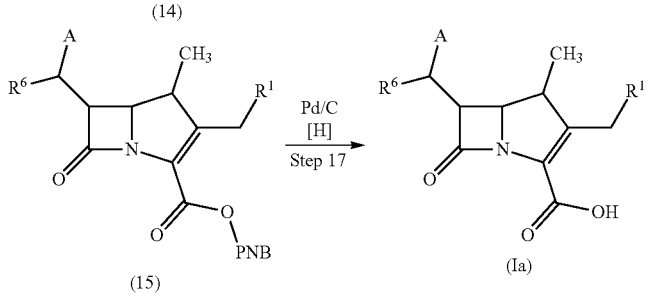
(15)          (Ia)

Step 12: The compound of formula (12) was prepared by reacting a compound of formula (11) with the compound of general formula H—SR$^1$, wherein the R$^1$ is as defined earlier in presence of activating agent such as diphenyl chlorophosphate, dimethylaminopyridine (DMAP) and the like and catalyst such as bis(acetylacetonate)Cu(II), copper sulfate, copper powder, rhodium acetate [Rh$_2$(OAc)$_4$], rhodium(II) octanoate, Pd(OAc)$_2$, Pb(OAc)$_4$ and the like and solvents such as tetrahydrofuran, ethyl acetate, benzene, toluene, hexane, cyclohexane and the like.

Step 12a: Reacting the compound of formula (12) with 2-iodoacetamide or iodomethane and the like in presence of solvents such as THF-acetone and the like gave the compound of formula (I), (Ia) or (Ib).

Step 13: The compound of formula (I), (Ia) or (Ib), was prepared by reducing the compound of formula (12) or the compound of formula (12a) with Pd/C in presence of solvents such as THF-water and the like under pressure.

Step 14: Hydroxymethylation by a cross coupling reaction between carbapenem-2-triflate and Bu$_3$SnCH$_2$OH.

Step 15: Allylic carbonate (14) was prepared by isobutyl-chloroformate in presence of DIPEA, DMAP and in solvents like dichloromethane and tetrahydrofuran.

Step 16: Allylic amine (15) was prepared by reaction of allylic carbonate (14) and amine in presence of Palladium catalyst.

Step 17: Formula (Ia) was prepared by reducing the compound of formula (15) with Pt/C in presence of solvents such as THF-water and the like under pressure.

The examples below are provided by way of illustration only and should not be considered to limit the scope of the invention.

EXAMPLES

Preparation 1: (R)-Benzyl 2-((2S',3S)-3-((R)-1-(t-butyldimethylsilyloxy)ethyl)-4-oxoazetidin-2-yl) propanoate

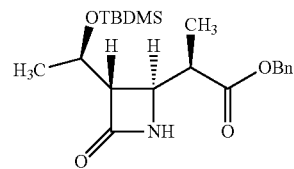 [SMILES: C[C@@H](O[Si](C)(C)C(C)(C)C)[C@H]1C(=O)N[C@@H]1[C@@H](C)C(=O)OCc1ccccc1]

To a mixture of (R)-2-((2S',3S)-3-((R)-1-(t-butyldimethylsilyloxy)ethyl)-4-oxoazetidin-2-yl)propanoic acid (1 g, 3.32 mmoles), potassium carbonate (0.68 g, 4.95 mmoles) and acetone (10 mL), benzyl bromide (0.63 g, 3.67 mmoles) was added and heated to reflux for 5 hours. The reaction mixture was filtered and the residue was washed with ethyl acetate (25 mL). The organic layer was washed with water and brine. After drying over sodium sulphate, the organic layer was concentrated to afford the title compound as oil. (1.2 g, 92.3%). $^1$H NMR (DMSO-d$_6$) δ ppm: 0.01 (d, 6H), 0.79 (s, 9H), 1.04 (d, 6H), 2.37-2.46 (m, 1H), 2.84 (t, 1H), 3.63-3.65 (d, 1H), 4.02-4.07 (m, 1H), 4.83-4.84 (m, 2H), 7.30-7.38 (m, 5H), 8.06 (s, 1H).

Preparation 2: (R)-Benzyl-2-((2S,3S)-3-((R)-1-hydroxyethyl)-4-oxoazetidin-2-yl) propanoate

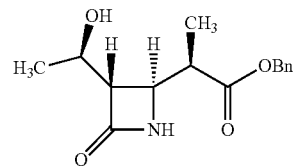 [SMILES: C[C@@H](O)[C@H]1C(=O)N[C@@H]1[C@@H](C)C(=O)OCc1ccccc1]

Aqueous hydrochloric acid (2 N, 10 mL) was added to 10 g of (R)-benzyl-2-((2S',3S)-3-((R)-1-(t-butyldimethylsilyloxy)ethyl)-4-oxoazetidin-2-yl)propanoate (10 g) dissolved in acetonitrile (100 mL) and stirred at room temperature for 3 hours. Reaction mixture was concentrated to obtain crude oil, which was dissolved in ethyl acetate (250 mL). The organic layer was washed with water and brine. After drying over sodium sulphate, the organic layer was concentrated under vacuum. The residue thus obtained was triturated with hexane (100 mL), filtered and dried to give the product as a white solid (6.2 g, 87.5%). $^1$H NMR (DMSO-$d_6$) δ ppm: 1.08-1.09 (d, 3H), 1.17-1.18 (d, 3H), 2.66-2.73 (m, 1H), 2.86-2.87 (d, 1H), 3.63-3.65 (d, 1H), 3.86-3.91 (m, 1H), 4.85-4.86 (d, 1H), 5.08-5.31 (m, 2H), 7.35-7.42 (m, 5H), 8.17 (s, 1H).

Preparation 3: (R)-Benzyl 2-((2S',3S)-3-((R)-1-(formyloxy)ethyl)-4-oxoazetidin-2-yl) propanoate

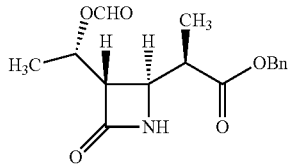

To a solution of (R)-benzyl 2-((2S,3S)-3-((R)-1-hydroxyethyl)-4-oxoazetidin-2-yl) propanoate (10 g, 36.05 mmoles) in tetrahydrofuran (100 mL), was added triphenylphosphine (15.2 g, 57.95 mmoles) and 98% formic acid (3.33 g, 72.34 mmoles) at ice-cold condition. Diisopropylazodicarboxylate (11.7 g, 57.86 mmoles) was then added to the reaction mixture, slowly over a period of 15 minutes. The reaction mixture was further stirred at ice-cold condition for a period of 30 minutes. Subsequently, water (50 mL) was added and the reaction mixture was extracted with ethyl acetate (100 mL). The organic layer was washed with water and brine. After drying over sodium sulphate, the organic layer was concentrated under vacuum. The residue thus obtained was stirred with toluene (100 mL) and filtered. The filtrate was concentrated to yield oily crude. The crude thus obtained was purified by column chromatography to yield the product as an oily substance. (3.32 g, 30.2%). $^1$H NMR (DMSO-$d_6$) δ ppm: 1.036 (d, 3H), 1.13 (d, 3H), 2.49-2.5 (q, 1H), 2.65 (t, 1H), 2.81-2.83 (q, 1H), 3.58-3.6 (q, 1H), 3.81-3.85 (q, 1H), 4.80 (br, 1H), 5.03-5.12 (dd, 2H), 7.30-7.38 (m, 5H), 8.12 (s, 1H).

Preparation 4: (R)-Benzyl 2-((2S',3S)-3-((S)-1-hydroxyethyl)-4-oxoazetidin-2-yl) propanoate

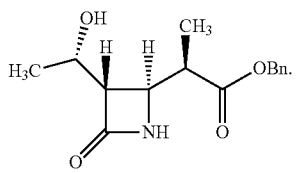

To a solution of (R)-benzyl 2-((2S',3S)-3-((S)-1-(formyloxy)ethyl)-4-oxoazetidin-2-yl)propanoate (10 g, 32.75 mmoles) in tetrahydrofuran (100 mL), lithium hydroxide (0.768 g, 32.07 mmoles) dissolved in 30 mL water was added at ice cold condition. After completion of the reaction, the reaction mixture was concentrated and diluted with ethyl acetate (150 mL). The organic layer was washed with water and brine. After drying over sodium sulphate, the organic layer was concentrated. The crude product thus obtained was purified by column chromatography to yield the product as white color solid. (8 g, 88.1%). $^1$H NMR (DMSO-$d_6$) δ ppm: 1.12 (d, 3H), 1.17 (d, 3H), 2.65-2.70 (q, 1H), 2.84 (q, 1H), 3.48-3.51 (m, 1H), 3.81-3.85 (m, 1H), 5.09 (dd, 2H), 7.35-7.39 (m, 5H), 8.05 (s, 1H).

Preparation 5: (R)-Benzyl 2-((2S,3S)-3-((R)-1-azidoethyl)-4-oxoazetidin-2-yl) propanoate

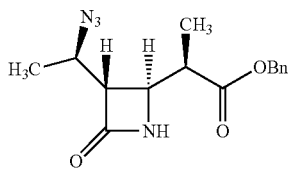 [SMILES: C[C@@H](N=[N+]=[N-])[C@H]1C(=O)N[C@@H]1[C@@H](C)C(=O)OCc1ccccc1]

To a solution of (R)-benzyl 2-((2S',3S)-3-((S)-1-hydroxyethyl)-4-oxoazetidin-2-yl) propanoate (10 g, 36.05 mmoles) in 200 mL of tetrahydrofuran:toluene (1:1) was added triphenylphosphine (15.14 g, 57.72 mmoles) and 85 mL of 0.85 M hydrazoic acid (3.1 g, 72.09 mmoles) at −10° C. under nitrogen atmosphere. To the above, diisopropylazodicarboxylate (11.7 g, 57.86 mmoles) was added slowly over a period of 15 minutes. The mixture was further stirred at ice-cold condition for a period of 30 minutes. To the reaction mixture, water (50 mL) was added and concentrated to half of the volume. Then the reaction mixture was extracted with ethyl acetate (300 mL). The organic layer was washed with water and brine. After drying over sodium sulphate, the organic layer was concentrated. The residue thus obtained was stirred with toluene (100 mL) and filtered. The filtrate was concentrated to obtain the oily crude. The crude thus obtained was purified by column chromatography to yield the product as an oily substance. (7.95 g, 72.9%). $^1$H NMR (DMSO-$d_6$) δ ppm: 1.12-1.19 (m, 6H), 2.65-2.71 (q, 1H), 3.01-3.03 (q, 1H), 3.5-3.53 (m, 1H), 3.89-3.92 (m, 1H), 5.06-5.14 (dd, 2H), 7.33-7.39 (m, 5H), 8.37 (s, 1H).

Preparation 6: (R)-Benzyl 2-((2S,3R)-3-((R)-1-aminoethyl)-4-oxoazetidin-2-yl) propanoate

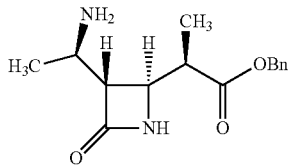 [SMILES: C[C@@H](N)[C@H]1C(=O)N[C@@H]1[C@@H](C)C(=O)OCc1ccccc1]

Triphenylphosphine (6.51 g, 24.8 mmoles) was added to a solution of (R)-benzyl 2-((2S. 3S)-3-((R)-1-azidoethyl)-4-oxoazetidin-2-yl)propanoate (5 g, 16.6 mmoles) in tetrahydrofuran (25 mL) and the mixture was stirred at room temperature for 5 hours under nitrogen atmosphere. To the reaction mixture, water (5 mL) was added and it was stirred at room temperature for a period of 16 hours. Brine solution (50 mL) was added to the reaction mixture and extracted with ethyl acetate (100 mL). The organic layer was washed with water and brine. After drying over sodium sulphate, the organic layer was concentrated. The residue thus obtained was stirred with toluene (100 mL) and filtered. The filtrate was concentrated to obtain oily crude. The crude thus obtained was purified by column chromatography to yield the product as an oily substance. (4 g, 87.5%). ¹H NMR (DMSO-d₆) δ ppm: 0.963-0.98 (d, 3H), 1.00-1.12 (d, 3H), 2.62-2.66 (m, 1H), 2.69-2.72 (m, 1H), 2.96-2.98 (m, 1H), 3.52-3.54 (m, 1H), 5.08-5.09 (dd, 2H), 7.30-7.39 (m, 5H), 8.15 (s, 1H).

Preparation 7: (R)-Benzyl 2-((2S,3R)-3-((R)-1-(t-butoxycarbonylamino)ethyl)-4-oxoazetidin-2-yl)propanoate

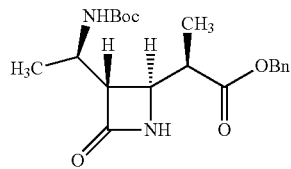 [SMILES: C[C@@H](NC(=O)OC(C)(C)C)[C@H]1C(=O)N[C@@H]1[C@@H](C)C(=O)OCc1ccccc1]

To a mixture of sodium bicarbonate (6.1 g, 72.04 mmoles) and (R)-benzyl 2-((2S,3R)-3-((R)-1-aminoethyl)-4-oxoazetidin-2-yl)propanoate (10 g, 36.18 mmoles) in 150 mL of tetrahydrofuran:water (2:1), di-t-butyldicarbonate (9.5 g, 43.47 mmoles) was added and stirred at room temperature for 6 hours. The reaction mixture was filtered and extracted with ethyl acetate (250 mL). The organic layer was washed with water and brine. After drying over sodium sulphate, the organic layer was concentrated to obtain the product as a white solid, (10 g, 73.4%). ¹H NMR (DMSO-d₆) δ ppm: 1.09-1.112 (m, 6H), 1.36 (s, 9H), 2.65-2.70 (m, 1H), 2.92 (m, 1H), 3.51-3.53 (m, 1H), 3.60-3.74 (m, 1H), 5.10-5.16 (dd, 2H), 6.73-6.75 (d, 1H), 7.32-7.37 (m, 5H), 8.2 (2, 1H).

Preparation 8: (R)-2-((2S,3R)-3-((R)-1-(t-Butoxycarbonylamino)ethyl)-4-oxoazetidin-2-yl)propanoic acid

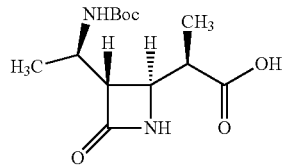

Lithium hydroxide (0.768 g, 32.07 mmoles) was added to the solution of (R)-benzyl 2-((2S,3R)-3-((R)-1-(t-butoxycarbonylamino)ethyl)-4-oxoazetidin-2-yl)propanoate (10 g, 26.56 mmoles) in 50 mL of tetrahydrofuran:methanol:water (1:1:0.5) at ice-cold condition. The reaction mixture was continued to be stirred at room temperature for 1 hour. The reaction mixture was concentrated and diluted with water (150 mL). The aqueous layer was washed with EtOAc (150 mL). The separated aqueous layer was now acidified with citric acid to pH 2 and extracted with ethyl acetate (250 mL). The organic layer was washed with water and brine. After drying over sodium sulphate the organic layer was concentrated to give the product as a white solid. (7.05 g, 92.7%). ¹H NMR (DMSO-d₆) δ ppm: 1.09-1.112 (m, 6H), 1.39 (s, 9H), 2.50-2.51 (m, 1H), 2.88-2.91 (m, 1H), 3.4-3.58 (m, 1H), 3.69-3.75 (m, 1H), 6.7 (d, 1H), 8.15 (s, 1H), 12.35 (s, 1H).

Preparation 9: (R)-4-Nitrobenzyl 4-((2R,3R)-3-((R)-1-(tert-butoxycarbonylamino)ethyl) -4-oxoazetidin-2-yl)-3-oxopentanoate

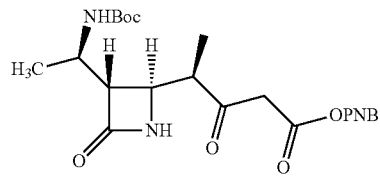

To a solution of (R)-2-((2S,3R)-3-((R)-1-(tert-butoxycarbonylamino)ethyl)-4-oxoazetidin-2-yl)propanoic acid (10 g, 34.93 mmoles) in acetonitrile (100 mL), 1,1'-carbonyldiimidazole (6.52 g, 40.21 mmoles) was added and continued to stir for a period of 1 hour at ice-cold condition under nitrogen atmosphere. The above obtained solution was added slowly to a suspension of magnesium salt of mono-p-nitrobenzylmalonate (20.32 g, 77.26 mmoles) in acetonitrile (100 mL) and stirred for 5 hours at room temperature and heated to 50° C. for a further period of 6 hours under nitrogen atmosphere. The reaction mixture was filtered and the filtrate was concentrated and the obtained crude was diluted with ethyl acetate. The organic layer was washed with water and brine. After drying over sodium sulphate, the organic layer was concentrated to give oily crude. The crude thus obtained was purified by column chromatography to yield the product as a white solid (10 g, 61.78%). ¹H NMR (DMSO-d₆) δ ppm: 1.09-1.112 (m, 6H), 1.39 (s, 9H), 2.87-2.91 (m, 1H), 2.99-3.00 (m, 1H), 3.5-3.52 (m, 1H), 3.73-3.77 (m, 1H), 3.8-3.93 (dd, 2H), 5.29 (s, 2H), 6.7 (d, 1H), 7.60-7.66 (d, 2H), 8.09 (s, 1H), 8.23-8.26 (d, 2H).

Preparation 10: (R)-4-Nitrobenzyl 4-((2R,3R)-3-((R)-1-(tert-butoxycarbonylamino) ethyl)-4-oxoazetidin-2-yl)-2-diazo-3-oxopentanoate

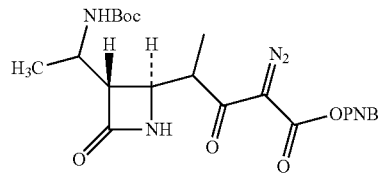

To a solution of (R)-4-nitrobenzyl 4-((2R,3R)-3-((R)-1-(tert-butoxycarbonylamino) ethyl)-4-oxoazetidin-2-yl)-3-oxopentanoate (10 g, 21.57 mmoles) in acetonitrile (50 mL) was added successively dodecabenzenesulfonylazide (70% in toluene, 13 mL, 25.9 mmoles) and triethylamine (12.7 mL, 91.1 mmoles) at ice-cold condition. The reaction mixture was stirred for 1 hour and then it was concentrated and diluted with ethyl acetate (150 mL). The organic layer was washed with water and brine. After drying over sodium sulphate, the organic layer was concentrated to give oily crude. The crude thus obtained was purified by column chromatography to yield the product as a white solid (10 g, 94.69%). ¹H NMR (DMSO-d₆) δ ppm: 1.00-1.02 (d, 3H), 1.06-1.08 (d, 3H), 1.39 (s, 9H), 3.01-3.03 (m, 1H), 3.47-3.49 (m, 1H), 3.63-3.66 (m, 1H), 3.71-3.73 (m, 1H), 5.43 (s, 2H), 6.55 (d, 1H), 7.69-7.72 (d, 2H), 8.15 (s, 1H), 8.25-8.27 (d, 2H).

Preparation 11: (R)-4-Nitrobenzyl 4-((2R,3R)-3-((R)-1-aminoethyl)-4-oxoazetidin-2-yl)-2-diazo-3-oxopentanoate

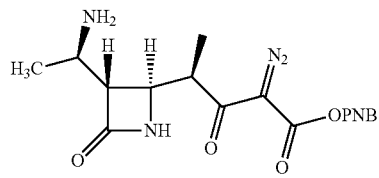

Trifluoroacetic acid (1.40 g, 12.3 mmoles) was added to a solution of (R)-4-nitrobenzyl 4-((2R,3R)-3-((R)-1-(t-butoxycarbonylamino)ethyl)-4-oxoazetidin-2-yl)-2-diazo-3-oxopentanoate (2 g, 4.08 mmoles) in dichloromethane (10 mL) at ice-cold condition and stirred for 2 hours at nitrogen atmosphere. The reaction mixture was concentrated and the residue obtained was triturated with diethyl ether to yield the product as a white solid.

Preparation 12: 2-((Z)-1-((R)-1-((2R,3R)-2-(R)-4-diazo-5-(4-nitrobenzyloxy)-3,5-dioxopentan-2-yl)-4-oxoazetidin-3-yl)ethylamino)-1-oxopropan-2-ylideneaminooxy)-2-methylpropanoic acid

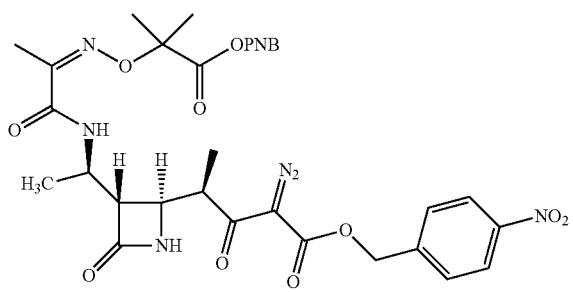

A mixture of (Z)-2-(2-methyl-1-(4-nitrobenzyloxy)-1-oxopropan-2-yloxyimino) propanoic acid (1 g, 3.08 mmoles), N,N,N',N'-tetramethyl-O-(benzotriazol-1-yl) uroniumtetrafluoroborate (TBTU) (1.19 g, 3.7 mmoles), diisopropylethylamine (1.1 mL, 6.32 mmoles) and ethyl acetate (50 mL) was stirred at room temperature for 30 minutes under nitrogen atmosphere. To the reaction mixture (R)-4-nitrobenzyl 4-((2R,3R)-3-((R)-1-aminoethyl)-4-oxoazetidin-2-yl)-2-diazo-3-oxopentanoate (1.2 g, 3.08 mmoles) was added and it was stirred for a further period of 30 minutes. The reaction mixture was treated with water (20 mL) and extracted with EtOAc (50 mL). The separated organic layer was washed with water and brine. After drying over sodium sulphate the organic layer was concentrated to give the product as an off-white solid. $^1$H NMR (DMSO-$d_6$) δ ppm: 1.47-1.49 (m, 9H), 1.55 (s, 3H), 2.06-2.08 (d, 1H), 3.06 (t, 1H), 3.64-3.72 (d, 1H), 4.31-4.34 (q, 1H), 5.43 (s, 4H), 7.29-7.34 (s, 2H), 7.70-7.77 (dd, 4H), 8.25-8.32 (dd, 4H).

Preparation 13: (R)-4-Nitrobenzyl 2-diazo-4-((2R, 3S)-3-(R)-1-(methylsulfonamido) ethyl)-4-oxoazetidin-2-yl)-3-oxopentanoate

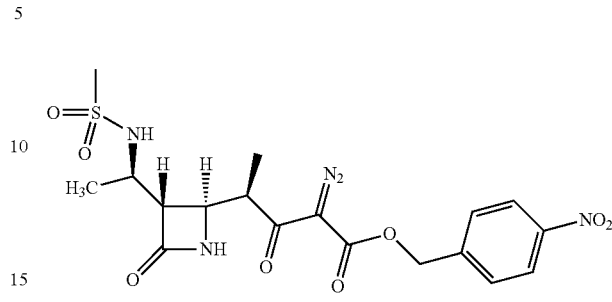

Methane sulfonyl chloride (0.19 mL, 25.7 mmoles) was added to a mixture of (R)-4-nitrobenzyl4-((2R,3R)-3-((R)-1-aminoethyl)-4-oxoazetidin-2-yl)-2-diazo-3-oxopentanoate (1 g, 2.57 mmoles) and diisopropylethylamine (0.92 mL, 51.4 mmoles) in dichloromethane (20 mL) at ice-cold condition under nitrogen atmosphere. The reaction mixture was treated with water (20 mL) and extracted with dichloromethane (50 mL). The separated organic layer was washed with water and brine. After drying over sodium sulphate, the organic layer was concentrated to obtain crude, which on purification by column chromatography yielded the product as an off-white solid. $^1$H NMR (DMSO-$d_6$) δ ppm: 1.14-1.18 (d, 3H), 1.19-1.22 (d, 3H), 2.85-2.89 (d, 1H), 2.91 (s, 3H), 3.52-3.57 (m, 2H), 3.69-3.72 (m, 1H), 5.39-5.47 (dd, 2H), 7.08-7.10 (d, 1H), 7.70-7.72 (d, 2H), 8.25-8.27 (dd, 3H).

Preparation 14: (R)-4-Nitrobenzyl 2-diazo-4-((2R, 3R)-3-((R)-1-(methoxycarbonyl amino) ethyl)-4-oxoazetidin-2-yl)-3-oxopentanoate

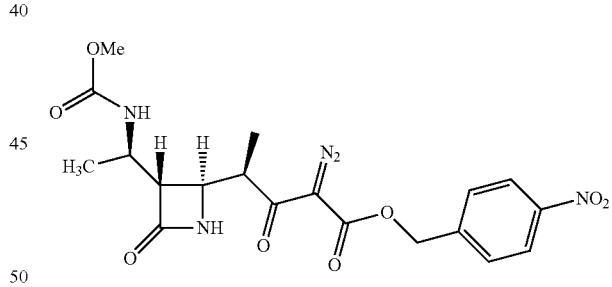

Methyl chloroformate (0.2 mL, 2.58 mmoles) was added to a mixture of (R)-4-nitrobenzyl-4-((2R,3R)-3-((R)-1-aminoethyl)-4-oxoazetidin-2-yl)-2-diazo-3-oxo pentanoate (1 g, 2.57 mmoles) and diisopropylethylamine (0.92 mL, 51.4 mmoles) in dichloromethane (20 mL) at ice-cold condition under nitrogen atmosphere. The reaction mixture was treated with water (20 mL) and extracted with dichloromethane (50 mL). The separated organic layer was washed with water and brine. After drying over sodium sulphate the organic layer was concentrated to obtain crude which on column purification yield an off-white solid. $^1$H NMR (DMSO-$d_6$) δ ppm: 1.01-1.02 (d, 3H), 1.06-1.09 (d, 3H), 2.82-2.85 (d, 1H), 3.44-3.48 (m, 1H), 3.49 (s, 3H), 3.65-3.69 (m, 2H), 5.41-5.44 (m, 2H), 7.10-7.12 (d, 1H), 7.69-7.73 (d, 2H), 8.25-8.27 (m, 3H).

Preparation 15: (R)-4-Nitrobenzyl 2-diazo-4-((2R, 3R)-3-(R)-1-(methoxycarbonothioylamino)ethyl)-4-oxoazetidin-2-yl)-3-oxopentanoate

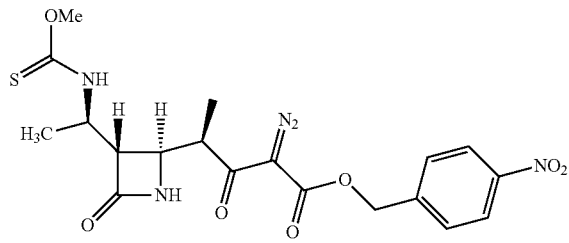

To an ice-cold solution of (R)-4-nitrobenzyl 4-((2R,3R)-3-((R)-1-aminoethyl)-4-oxoazetidin-2-yl)-2-diazo-3-oxo-pentanoate (1 g, 2.57 mmoles) in dichloromethane (10 mL) was added aqueous solution of NaHCO$_3$ (0.6 g in 10 mL, 7.14 mmoles). Thiophosgene (0.25 mL, 3.34 mmoles) was added to the above and stirred for 1 hour. After completion of the reaction, the reaction mixture was filtered. The organic layer was washed with water and evaporated to obtain a crude product. The crude thus obtained was purified by column chromatography. The compound obtained was dissolved in methanol (10 mL) and heated to reflux for 5 hours. The reaction mixture was evaporated and purified by column chromatography to obtain the title compound. $^1$H NMR (DMSO-d$_6$) δ ppm: 1.10-1.15 (d, 3H), 1.21-1.22 (d, 3H), 2.00 (d, 1H), 2.88-2.89 (d, 1H), 3.50-3.51 (m, 1H), 3.61-3.62 (s, 3H), 3.68-3.70 (m, 1H), 5.42 (m, 2H), 6.89-6.90 (d, 1H), 7.70-7.75 (d, 2H), 8.24-8.26 (d, 2H), 8.34 (s, 1H).

Preparation 16: (R)-4-Nitrobenzyl 2-diazo-4-((2R, 3R)-3-((R)-1-(2-methoxy-2-oxo acetamido)ethyl)-4-oxoazetidin-2-yl)-3-oxopentanoate

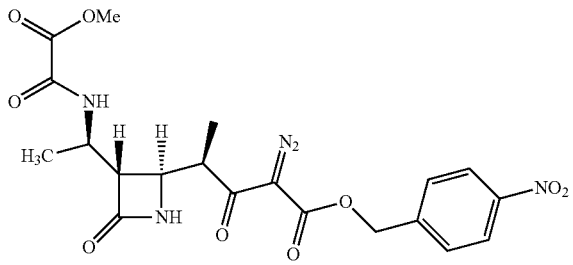

A mixture of 2-methoxy-2-oxoacetic acid (0.14 g, 1.35 mmoles), N,N,N',N'-tetramethyl-O-(benzotriazol-1-yl)uro-niumtetrafluoroborate (TBTU, 0.43 g, 1.35 mmoles) and diisopropyl ethylamine (0.25 mL, 1.46 mmoles) in ethyl acetate (10 mL) was stirred for 30 minutes. To the above reaction mixture a solution of (R)-4-nitrobenzyl 4-((2R,3R)-3-((R)-1-aminoethyl)-4-oxoazetidin-2-yl)-2-diazo-3-oxo-pentanoate (0.6 g, 1.22 mmoles) in ethyl acetate (5 mL) was added and stirred for 2 hours. After completion of the reaction, the reaction mixture was diluted with water. The organic layer was separated and washed with water and brine successively. After drying over sodium sulphate, the organic layer was concentrated to obtain crude which on purification by column chromatography yielded the product as oily substance. (0.25 g-42.8%). $^1$H NMR (DMSO-d$_6$) δ ppm: 1.11-1.18 (d, 3H), 1.20-1.21 (d, 3H), 2.08 (d, 1H), 2.86-2.88 (d, 1H), 3.50-3.51 (m, 1H), 3.61-3.62 (s, 3H), 3.65-3.70 (m, 1H), 5.42 (m, 2H), 6.91-6.96 (d, 1H), 7.70-7.71 (d, 2H), 8.22-8.25 (d, 2H), 8.13 (s, 1H).

Preparation 17: (R)-4-Nitrobenzyl 2-diazo-4-((2R, 3R)-3-(R)-1-(2,2-difluoroacetamido)ethyl)-4-oxoazetidin-2-yl)-3-oxopentanoate

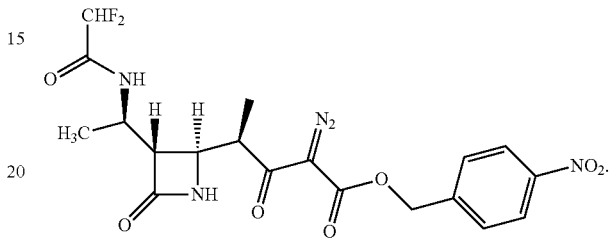

By following the procedure provided in preparation 16, (R)-4-nitrobenzyl 4-((2R,3R)-3-((R)-1-aminoethyl)-4-oxoazetidin-2-yl)-2-diazo-3-oxopentanoate (5 g, 12.84 mmoles) was derivatised with difluoroacetic acid to yield the title product (3.7 g 78.7%). $^1$H NMR (DMSO-d$_6$) δ ppm: 1.10-1.12 (d, 3H), 1.21-1.23 (d, 3H), 2.06 (d, 1H), 2.87-2.91 (d, 1H), 3.51-3.55 (m, 1H), 3.67-3.69 (m, 1H), 5.43 (m, 2H), 6.94-6.96 (t, 1H), 7.70-7.72 (d, 2H), 8.14-8.16 (d, 2H), 8.20 (s, 1H).

Preparation 18: (R)-4-nitrobenzyl 4-((2R,3R)-3-((R)-1-cyanamidoethyl)-4-oxoazetidin-2-yl)-2-diazo-3-oxopentanoate

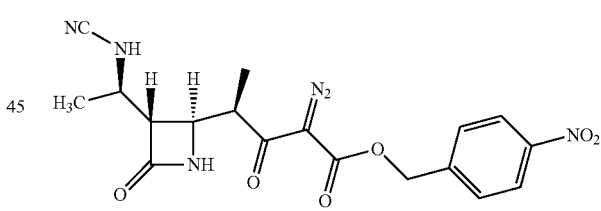

Cyanogen bromide (0.14 g, 1.28 mmol) was added to a solution of (R)-4-nitrobenzyl 4-((2R,3R)-3-((R)-1-amino-ethyl)-4-oxoazetidin-2-yl)-2-diazo-3-oxopentanoate (0.5 g, 1.28 mmol) in dichloromethane (10 mL) at ice cold condition. Triethylamine (0.3 mL, 2.15 mmol) was added to above and stirred at ice-cold condition for 1 hour. After completion of the reaction, the reaction mixture was treated with water. The organic layer was separated and washed with water and brine solution. After drying over sodium sulphate, the organic layer was concentrated to obtain crude which on purification by column chromatography yields the product as a white solid. (0.33 g, 62%). $^1$H NMR (DMSO-d$_6$) δ ppm: 1.11-1.18 (d, 3H), 1.21-1.23 (d, 3H), 2.08 (d, 1H), 2.87-2.89 (d, 1H), 3.51-3.54 (q, 1H), 3.68-3.71 (q, 1H), 5.43 (s, 2H), 6.95-6.96 (d, 1H), 7.69-7.71 (d, 2H), 8.24-8.26 (d, 2H), 8.34 (s, 1H).

Preparation 19: (R)-2-diazo-4-((2R,3S)-3-((R)-1-(isoxazol-3-yloxy)ethyl)-4-oxoazetidin-2-yl)-3-oxopentanoic 4-nitrobenzoic anhydride

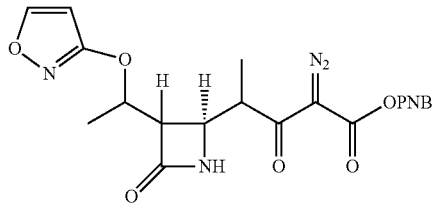

To a solution of (R)-4-nitrobenzyl 2-diazo-4-((2R,3S)-3-((S)-1-hydroxyethyl)-4-oxoazetidin-2-yl)-3-oxopentanoate (2.15 g, 5.34 mmoles) in tetrahydrofuran (10 mL) was added triphenylphosphine (2.24 g, 8.54 mmoles) and isoxazol-3-ol (0.9 g, 10.62 mmoles) at 0° C. Diisopropyl azodicarboxylate (1.73 g, 8.56 mmoles) was added slowly at 0° C. for 10 minutes. The reaction mixture was stirred for 5 hours at room temperature. On completion of reaction (as measured by TLC), the reaction mixture was diluted with ethyl acetate (25 mL) and washed with water (25 mL) and brine (25 mL). The organic layer was dried over sodium sulfate and the solvent was evaporated to obtain the crude as an oily substance. The crude product was treated with toluene (10 mL) and stirred at 0° C. for 30 minutes, filtered and washed with 10 mL of toluene (cold). The filtrate and the washings were mixed together and concentrated to obtain crude product. The crude product on purification by column chromatography (15% EtOAc in hexane) yields the title product (0.9 g, 34.6%).

Preparation 20: (R)-4-nitrobenzyl 2-diazo-4-((2R,3S)-3-((R)-1-(4-(((4-nitrobenzyloxy) carbonylamino)methyl)-1H-1,2,3-triazol-1-yl)ethyl)-4-oxoazetidin-2-yl)-3-oxopentanoate

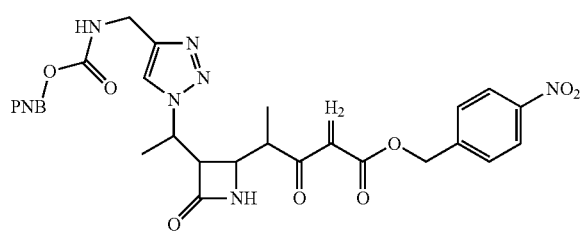

A mixture of (4R)-4-nitrobenzyl 4-(3-((R)-1-azidoethyl)-4-oxoazetidin-2-yl)-2-diazo-3-oxopentanoate (1 g, 2.41 mmoles), 4-nitrobenzyl prop-2-ynylcarbamate (0.56 g, 2.41 mmoles) and copper iodide (0.09 g, 0.48 mmoles) in toluene (10 mL) was stirred for 18 hours. The solvent was evaporated and the obtained crude product was purified by flash chromatography to afford the title compound. (Eluted in 6% acetone-DCM).

Preparation 21: (R)-4-nitrobenzyl 2-diazo-4-((2R,3R)-3-((R)-1-(2-(methyl((4-nitrobenzyloxy)carbonyl)amino)acetamido)ethyl)-4-oxoazetidin-2-yl)-3-oxopentanoate

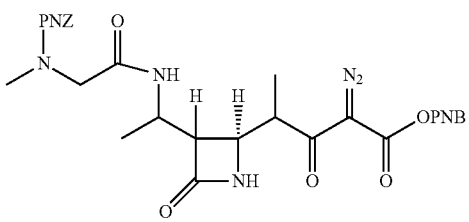

To a mixture of p-nitrobenzyloxycarbonyl-Sarcosine (10 g, 37.28 mmoles) and diisopropylethylamine (9.3 mL, 56.26 mmoles) in ethyl acetate (60 mL) was added TBTU (14.36 g, 44.72 mmoles) and stirred for 0.5 hour at room temperature. A solution of (R)-4-nitrobenzyl 4-((2R,3R)-3-((R)-1-aminoethyl)-4-oxoazetidin-2-yl)-2-diazo-3-oxopentanoate (14.5 g, 37.24 mmoles) in EtOAc (25 mL) was added to the above at 0° C. and the reaction mixture was stirred for 3 hours at room temperature. After completion of the reaction, the reaction mixture was diluted with EtOAC (150 mL) and washed with water and brine. The organic layer was dried over sodium sulfate and the solvent was evaporated under reduced pressure to obtain crude product as an oily substance. The crude product on purification by column chromatography (20% acetone in dichloromethane) yields the title compound as a pale yellow solid. (10.7 g, 65%).

Preparation 22: 1-(2-amino-2-oxoethyl)-1-methyl-4-((2S,4S)-4-((4R,5S,6S)-4-methyl-6-((R)-1-(methylsulfonamido)ethyl)-2-((4-nitrobenzyloxy)carbonyl)-7-oxo-1-azabicyclo[3.2.0]hept-2-en-3-ylthio)-1-((4-nitrobenzyloxy)carbonyl)pyrrolidine-2-carbonyl)piperazin-1-ium iodide

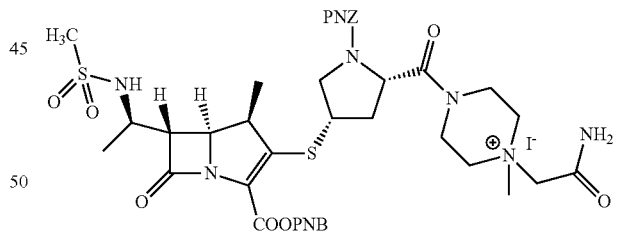

(4R,5S,6S)-4-nitrobenzyl 4-methyl-3-((3S,5S)-5-(4-methylpiperazine-1-carbonyl)-1-((4-nitrobenzyloxy)carbonyl)pyrrolidin-3-ylthio)-6-((R)-1-(methylsulfonamido)ethyl)-7-oxo-1-azabicyclo[3.2.0]hept-2-ene-2-carboxylate (0.5 g, 0.6 mmoles) was dissolved in tetrahydrofuran (2 mL) and acetone (5 mL). 2-Iodoacetamide (0.55 g, 2.97 mmoles) was added to the reaction mixture and heated to reflux for 4 hours. The reaction mixture was concentrated under vacuum and triturated with ethyl acetate (10 mL) to obtain solid. The solid obtained was filtered and dried to obtain the product as an off-white solid. (0.36 g, 60%). $^1$H NMR (DMSO-d$_6$) δ ppm: 1.15-1.19 (d, 3H), 1.24-1.28 (d, 3H), 2.92 (s, 3H), 3.16-3.29 (m, 2H), 3.54-3.57 (s, 2H), 3.61-3.66 (m, 4H), 3.73-3.82 (m, 4H), 3.86-3.91 (m, 3H), 4.0-4.03 (m, 3H), 4.15-4.23 (m, 4H), 5.21-5.47 (m, 4H), 7.33-7.35 (d, 1H), 7.52-7.54 (d, 1H), 7.64-7.66 (d, 1H), 7.69-7.71 (d, 1H), 7.76-7.79 (d, 1H), 8.22-8.24 (4H).

Preparation 23: (R)-4-nitrobenzyl 2-diazo-4-((2R, 3R)-3-((R)-1-(2-ethoxy-2-oxoethylamino)ethyl)-4-oxoazetidin-2-yl)-3-oxopentanoate

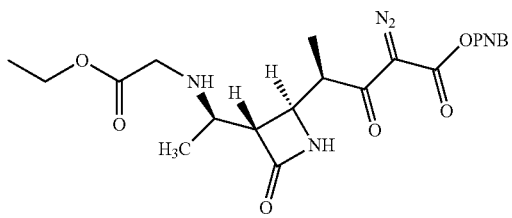

Ethyl bromoacetate (0.342 g 2.05 mmole) was added to a mixture of solution of (R)-4-nitrobenzyl 4-((2R,3R)-3-(R)-1-aminoethyl)-4-oxoazetidin-2-yl)-2-diazo-3-oxopentanoate (1 g, 2.05 mmoles), diisopropylethylamine (0.45 mL, 2.58 mmoles) and catalytic amounts of dimethylaminopyridine in dichloromethane (15 mL) at 0° C. and stirred for 16 hours at room temperature. After regular work up, the crude obtained was purified by chromatography to obtain the title compound (0.37 g, 30%). $^1$HNMR (DMSO-d$_6$) δ ppm: 1.08 (d, 3H), 1.12 (d, 3H), 1.29 (t, 3H), 2.85 (d, 1H), 3.40-3.42 (m, 1H), 3.63-3.66 (m, 1H), 3.77 (s, 2H), 3.99 (m, 1H), 4.13 (q, 2H), 5.44 (s, 2H), 8.25 (m, 2H), 8.32 (s, 2H).

Preparation 24: (R)-4-nitrobenzyl 4-((2R,3S)-3-((R)-1-(butyl((4-nitrobenzyloxy)carbonyl)amino)ethyl)-4-oxoazetidin-2-yl)-2-diazo-3-oxopentanoate

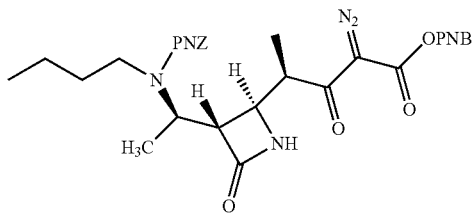

Step (i): A solution of mixture of 1-bromobutane (0.56 g 4.09 mmole) and (R)-4-nitrobenzyl 4-((2R,3R)-3-((R)-1-aminoethyl)-4-oxoazetidin-2-yl)-2-diazo-3-oxopentanoate (1 g, 2.05 mmoles) in dimethylformamide (20 mL) was heated at 50-55° C. for 16 hr. After regular work up, the crude obtained was purified by chromatography to obtain (R)-4-nitrobenzyl 4-((2R,3R)-3-((R)-1-(butylamino)ethyl)-4-oxoazetidin-2-yl)-2-diazo-3-oxopentanoate (0.5 g, 43.7%). $^1$H NMR (CDCl$_3$) δ ppm: 0.93 (t, 3H), 1.27 (m, 6H), 1.42 (m, 3H), 1.60 (m, 3H), 2.88 (d, 1H), 3.42 (m, 1H), 3.74 (m, 1), 3.80 (m, 1H), 5.35 (s, 2H), 6.01 (s, 1H), 7.53 (m, 2H), 8.25 (m, 2H).

Step (ii): 4-nitrobenzylchloroformate (0.42 g, 1.96 mmoles) was added to a mixture of solution of (R)-4-nitrobenzyl 4-((2R,3R)-3-((R)-1-(butylamino)ethyl)-4-oxoazetidin-2-yl)-2-diazo-3-oxopentanoate (0.5 g, 1.12 mmoles), triethylamine (0.34 g, 2.45 mmoles) and catalytic amount of dimethylaminopyridine at 0° C. and stirred at room temperature for 16 hr. After regular work up, the crude obtained was purified by column chromatography to obtain the title compound (0.31 g 44.2%). $^1$HNMR (DMSO-de) δ ppm: 0.84 (t, 3H), 1.1 (d, 3H), 1.26 (m, 6H) 1.50 (m, 3H), 3.08 (m, 1H), 3.47 (m, 1H), 3.56 (m, 1), 4.01 (m, 1H), 5.19 (dd, 2H), 5.34 (s, 2H), 7.60 (m, 2H), 7.67 (m, 2H), 8.24 (m, 4H).

Preparation 25: Ethyl 2-pivalamidoacetate

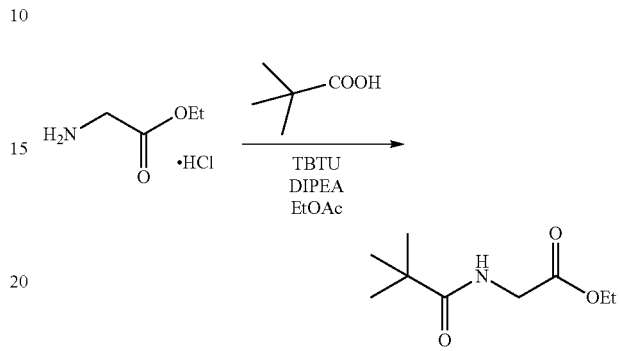

O-(1H-Benzotriazol-1-yl)-N,N,N',N'-tetramethyluronium tetrafluoroborate (TBTU, 70.8 g, 0.22 mol) was added to a mixture of pivalic acid (15 g, 0.147 mol) and triethylamine (35 mL, 0.25 mol) in ethyl acetate (150 mL) and stirred for 0.5 hour at room temperature. Glycine ethyl ester HCl (20.52 g, 0.147 mol) was added to the above at 0° C. and the reaction mixture was stirred for 16 hours at room temperature. After the completion of the reaction, the reaction mixture was diluted with EtOAC (150 mL) and washed with water and brine. After drying over sodium sulphate, the organic layer was evaporated under reduced pressure to obtain crude product as oil. The crude on purification by column chromatography (10% MeOH in dichloromethane) yielded the title compound as an off-white solid. (18.4 g, 67%). $^1$H NMR (CDCl$_3$) δ=1.26 (s, 9H), 1.41 (t, 3H), 4.01 (m, 2H), 4.23 (q, 2H), 6.17 (brs, 1H).

Preparation 26: Ethyl 2-(5-tert-butyl-1H-tetrazol-1-yl)acetate

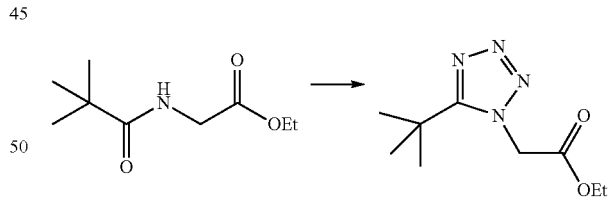

A solution of ethyl 2-pivalamidoacetate (10 g, 0.053 mol) in acetonitrile (200 mL) was treated with sodium azide (14 g, 0.22 mol) and tetrachlorosilane (10 mL, 0.087 mol). The solution was heated to 90° C. under nitrogen for 16 hours. A further amount of sodium azide (7 g, 0.1 mol) and tetrachlorosilane (6 mL, 0.052 mol) were added and continued the reflux for additional 16 hours. The reaction mixture was poured into cold 5% aqueous sodium bicarbonate solution and extracted with ethyl acetate (150 mL×3). The organic layers were combined, dried over sodium sulfate, filtered and concentrated to afford a crude solid (1.68 g). The solid was purified by column chromatography to obtain the product as an oil (9.5 g, 83.8%)$^1$H NMR (CDCl$_3$) δ—1.29 (t, 3H), 1.47 (s, 9H), 4.27 (q, 2H), 5.24 (s, 2H).

Preparation 27:
2-(5-Tert-butyl-1H-tetrazol-1-yl)acetic acid

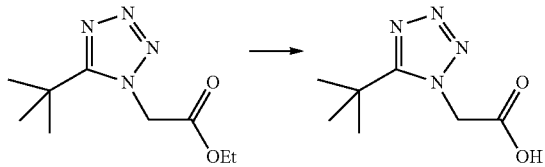

At 0° C., a solution of ethyl 2-(5-tert-butyl-1H-tetrazol-1-yl)acetate (9 g, 0.042 mol) in tetrahydrofuran-MeOH (90 mL:45 mL) was treated with a solution of lithium hydroxide monohydrate (2.68 g 0.064 mol) in 45 mL of water. The reaction mixture was warmed to room temperature and stirred for 3 hours. The reaction mixture was neutralized with 1N HCl to pH=6-7 and concentrated. The crude was treated with aqueous lithium hydroxide (2.6 g in 100 mL) and a washed with ethyl acetate (150 mL). The aqueous layer was acidified with 1N HCl to pH 2 and extracted with ethyl acetate (2×100 mL). The combined organic layers were washed with brine solution (150 mL). The organic layer was evaporated after drying over sodium sulphate to obtain the title product as a white solid (6.8 g, 87%). $^1$H NMR (DMSO-$d_6$) δ=1.39 (s, 9H), 5.46 (s, 2H), 13.78 (brs, 1H).

Example 1: (4R,5S,6S)-3-((3S,5S)-5-(Dimethylcarbamoyl)pyrrolidin-3-ylthio)-4-methyl-6-((R)-1-(methylsulfonamido)ethyl)-7-oxo-1-azabicyclo[3.2.0]hept-2-ene-2-carboxylic acid

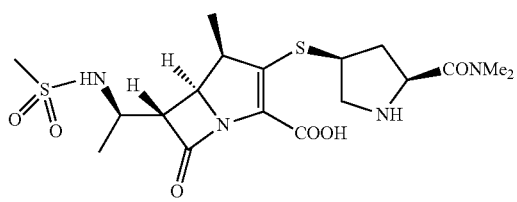

Step 1: (4R,5S,6S)-4-Nitrobenzyl 3-((3S,5S)-5-(dimethylcarbamoyl)-1-((4-nitrobenzyloxy)carbonyl)pyrrolidin-3-ylthio)-4-methyl-6-((R)-1-(methylsullonamido) ethyl)-7-oxo-1-azabicyclo[3.2.0]hept-2-ene-2-carboxylate

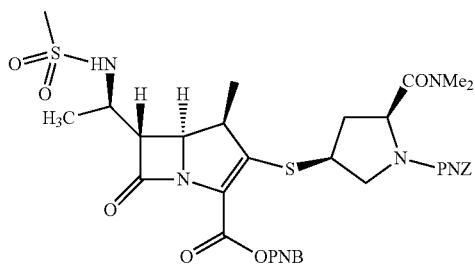

To a solution of (R)-4-nitrobenzyl-2-diazo-4-((2S,3S)-3-((R)-1-(methyl sulfonamido)ethyl)-4-oxoazetidin-2-yl)-3-oxopentanoate (preparation 13) in acetone (10 mL), Rhodium octanoate (0.008 g, 0.01 mmoles) was added and heated to reflux for 1 hour. The reaction mixture was cooled to room temperature and then to -50 to -40° C. using dry ice-acetone bath. Diisopropylethylamine (0.25 mL, 1.43 mmoles), catalytical amount of dimethylaminopyridine and diphenylchlorophosphate (0.26 mL, 1.28 mmoles) were added successively to the reaction mixture and stirred for 30 minutes at -50 to -40° C. (2S,4S)-4-nitrobenzyl-2-(dimethylcarbamoyl)-4-mercaptopyrrolidine-1-carboxylate (0.374 g, 1.06 mmoles) and diisopropylethylamine (0.25 mL, 1.43 mmoles) were added to the reaction mixture and continued stirring at -20° C. for 1 hour. The reaction mixture was then warmed to 0° C. and the stirring was continued for a further period of 3 hours. The reaction mixture was treated with water (20 mL) and extracted with ethyl acetate (50 mL). The separated organic layer was washed with water and brine. After drying over sodium sulphate, the organic layer was concentrated to obtain the crude, which on purification by column chromatography, yielded a white solid 0.4 g-48% (compound eluted with 20-30% acetone in dichloromethane). $^1$H NMR (DMSO-$d_6$) δ ppm: 1.14-1.18 (d, 6H), 1.6-1.8 (m, 1H), 2.83-2.86 (m, 3H), 2.94 (m, 1H), 2.99-3.01 (d, 3H), 3.20 (m, 1H), 3.40-3.43 (m, 1H), 3.59-3.61 (m, 2H), 3.88-4.22 (m, 3H), 4.23-4.27 (m, 2H) 4.78-4.88 (m, 1H), 5.09-5.32 (d, 2H), 5.43-5.47 (d, 1H), 5.47-5.5 (d, 1H), 7.20-7.21 (d, 1H) 7.55-7.57 (d, 1H), 7.66-7.68 (d, 1H), 7.73-7.75 (m, 2H), 8.13-8.15 (d, 1H), 8.25-8.27 (m, 4H).

Step 2: (4R,5S,6S)-3-((3S,5S)-5-(Dimethylcarbamoyl)pyrrolidin-3-ylthio)-4-methyl-6-((R)-1-(methylsulfonamido)ethyl)-7-oxo-1-azabicyclo[3.2.0]hept-2-ene-2-carboxylic acid To a solution of (4R,5S,6S)-nitrobenzyl 3-((3S,5S)-5-(dimethylcarbamoyl)-1-((4-nitrobenzyloxy)carbonyl)pyrrolidin-3-ylthio)-4-methyl-6-((R)-1-(methylsulfonamido) ethyl)-7-oxo-1-azabicyclo[3.2.0]hept-2-ene-2-carboxylate obtained from step 1 (0.2 g, 0.258 mmoles) in THF: water (15 mL, 1:1) was subjected to hydrogenation in the presence of Pd/C. The reaction mixture was filtered over celite. The filtrate was washed with EtOAc (30 mL×6). The aqueous layer was then lyophilised to yield the title compound as a white solid (90 mg, 75%). $^1$H NMR ($D_2O$) δ ppm: 1.21-1.23 (d, 3H), 1.33-1.39 (d, 3H), 1.92-1.96 (m, 1H), 2.99-3.00 (s, 3H), 3.01-3.03 (m, 1H), 3.11 (m, 1H), 3.47 (s, 6H), 3.46-3.48 (m, 2H), 3.97-3.99 (m, 2H), 4.03-4.21 (d, 1H), 4.73-4.75 (d, 1H), 4.8-4.86 (d, 1H). MS m/z: 460.7.

Examples 2-6, 17, 21, 26, 28, 31, 32, 35, 37-38, 40, 42-46, 49-50, 53-56, 58-68, 70-85 and 87-94 were prepared by treating the compound of formula (10) with appropriate $R^4$COOH according to the procedure given in the preparations 12, 16 and 17, followed by the procedure given in Example 1.

Examples 7-16, 18-19, 23-25, 27, 29-30, 33-34, 39, 48, 51, 57 and 86 were prepared by treating the compound of formula (10) with appropriate $R^4$X according to the procedure given in preparation 13 and 14, followed by the procedure given in Example 1.

Examples 20, 22, 36, 41, 47, 52 and 69 were prepared by treating the compound of formula (10) with appropriate carbonylating agents according to the procedure given in the preparation 15 followed by the procedure given in example 1. The quaternization of the heterocyclic rings in Examples 39, 45, 46, 80 and 94 were carried out according to the procedure given in preparation 19.

| Example | Structure | Analytical Data |
|---|---|---|
| 2 | (4R,5S,6R)-3-((3S,5S)-5-(Dimethylcarbamoyl)pyrrolidin-3-ylthio)-4-methyl-7-oxo-6-((S)-1-(2-(thiophen-2-yl)acetamido)ethyl)-1-azabicyclo[3.2.0]hept-2-ene-2-carboxylic acid | $^1$H NMR (D$_2$O) δ ppm: 1.12 (d, 1H), 1.29 (d, 3H), 1.33 (d, 3H), 1.36 (d, 2H), 1.98 (m, 1H), 2.99 (s, 3H), 3.06 (s, 3H), 3.19 (m, 1H), 3.41 (t, 1H), 3.85 (m, 1H), 3.98 (m, 1H), 4.24 (m, 1H), 4.51 (d, 1H), 4.78 (d, 1H), 4.79-4.83 (m, 1H), 7.02-7.03 (q, 1H), 7.16 (d, 1H) 7.42 (d, 1H). MS m/z: 505.1 (M − 1). |
| 3 | (4R,5S,6R)-6-((R)-1-((Z)-2-(2-Carboxypropan-2-yloxyimino)propanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.39 (d, 3H), 1.48 (d, 3H), 1.58 (d, 6H), 2.04 (s, 3H), 2.99 (d, 3H), 3.08 (d, 6H), 3.41-3.45 (m, 2H), 3.61 (d, 1H), 3.73-3.78 (m, 1H), 4.0 (t, 2H), 4.54-4.58 (m, 1H). MS m/z: 552 (M − 1). |
| 4 | (4R,5S,6R)-6-((S)-1-((Z)-2-(2-Aminothiazol-4-yl)-2-(2-carboxypropan-2-yloxyimino)acetamido)ethyl)-3-((3S,5S)-5-(dimethylcarbamoyl)pyrrolidin-3-ylthio)-4-methyl-7-oxo-1-azabicyclo[3.2.0]hept-3-ene-2-carboxylic acid | $^1$H NMR (D$_2$O) δ ppm: 1.25 (d, 3H), 1.34 (d, 3H), 1.36 (s, 3H), 1.50 (s, 3H), 1.92 (m, 1H), 2.23 (m, 1H), 2.97 (s, 3H), 2.99 (d, 1H), 3.02 (s, 3H), 3.36-3.42 (q, 2H), 3.50-3.76 (m, 2H), 4.03-4.23 (m, 2H), 4.82-4.88 (d, 1H), 6.98 (s, 1H). MS m/z: 637.8 |
| 5 | (4S,5S,6R)-3-((3S,5S)-5-(Dimethylcarbamoyl)pyrrolidin-3-ylthio)-4-methyl-7-oxo-6-((R)-1-(2-(thiophen-2-yl)acetamido)ethyl)-1-azabicyclo[3.2.0]hept-2-ene-2-carboxylic acid | $^1$H NMR (D$_2$O) δ ppm: 1.27 (d, 3H), 1.32 (d, 3H), 1.96-2.04 (m, 1H), 2.96 (d, 1H), 3.00 (s, 4H), 3.07 (s, 4H), 3.41-3.45 (m, 2H), 3.71-3.77 (m, 1H), 3.80-3.85 (m, 1H), 3.99-4.03 (m, 1H), 4.36 (s, 2H), 4.54-4.57 (m, 1H), 7.09 (t, 1H), 7.15 (d, 1H), 7.48 (d, 1H). MS m/z: 506.6 |

| Example | Structure | Analytical Data |
| --- | --- | --- |
| 6 | (4R,5S,6R)-6-((R)-1-((Z)-2-(2-Carboxypropan-2-yloxyimino)propanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.40 (d, 3H), 1.45 (d, 3H), 1.58 (d, 6H), 2.05 (s, 3H), 2.99 (d, 3H), 3.08 (s, 3H), 3.10 (s, 3H), 3.42-3.49 (m, 1H), 3.61 (d, 1H), 3.74-3.78 (m, 2H), 3.96-4.07 (dd, 2H), 4.51-4.73 (m, 1H). MS m/z: 553.7 |
| 7 | (4R,5S,6S)-4-Methyl-6-((R)-1-(methylsulfonamido)ethyl)-7-oxo-3-((3S,5S)-5-((sulfamoylamino)methyl)pyrrolidin-3-ylthio)-1-azabicyclo[3.2.0]hept-2-ene-2-carboxylic acid | $^1$H NMR (D$_2$O) δ ppm: 1.22-1.25 (d, 3H), 1.37-1.39 (d, 3H), 1.73-1.76 (m, 1H), 2.71-2.75 (m, 1H), 3.11 (s, 3H), 3.14 (s, 3H), 3.35-3.55 (m, 2H), 3.90-3.91 (d, 1H), 3.99-4.02 (m, 2H), 4.20-4.23 (d, 1H), 4.79-4.85 (d, 1H). MS m/z: 497.6 |
| 8 | (4R,5S,6S)-3-((3S,5S)-5-(Dimethylcarbamoyl)pyrrolidin-3-ylthio)-4-methyl-6-((S)-1-(methylsulfonamido)ethyl)-7-oxo-1-azabicyclo[3.2.0]hept-2-ene-2-carboxylic acid | $^1$H NMR (D$_2$O) δ ppm: 1.24 (d, 3H), 1.36 (d, 3H), 1.94 (m, 1H), 2.96 (s, 3H), 2.97 (m, 1H) 3.07 (m, 1H), 3.14 (m, 1H), 3.36-3.43 (m, 6H), 3.61 (m, 2H), 3.68 (m, 1H), 3.93 (t, 1H), 4.01 (m, 1H), 4.23 (d, 1H). MS m/z: 460.7 |
| 9 | (4R,5S,6S)-6-((R)-1-(3,4-Dimethoxyphenylsulfonamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.13 (m, 6H), 1.92 (m, 1H), 3.01 (s, 3H), 3.02 (m, 1H), 3.08 (s, 3H), 3.08 (m, 1H) 3.34-3.41 (m, 1H), 3.81 (m, 1H), 3.92 (d, 1H), 3.94 (d, 2H), 3.96 (d, 6H), 4.75 (d, 2H), 7.23 (d, 1H), 7.47 (s, 1H) 7.61 (d, 1H). MS m/z: 582.6 |

| Example | Structure | Analytical Data |
|---|---|---|
| 10 | (4R,5S,6S)-3-((3S,5S)-5-(Dimethylcarbamoyl)pyrrolidin-3-ylthio)-6-((R)-1-(ethylsulfonamido)ethyl)-4-methyl-7-oxo-1-azabicyclo[3.2.0]hept-3-ene-2-carboxylic acid | ¹H NMR (D₂O) δ ppm: 1.20-1.21 (t, 3H), 1.37-1.38 (d, 6H), 1.92-1.97 (m, 2H), 2.99-3.00 (s, 3H), 3.23 (s, 3H), 3.21-3.26 (m, 2H), 3.42-3.44 (m, 2H), 3.67-3.74 (d, 1H), 3.76 (d, 1H), 3.92-3.95 (m, 2H), 4.02-4.03 (d, 1H), 4.23-4.25 (d, 1H). MS m/z: 474.6 |
| 11 | (4R,5S,6S)-3-((3S,5S)-5-(Dimethylcarbamoyl)pyrrolidin-3-ylthio)-4-methyl-7-oxo-6-((R)-1-(phenylsulfooamidn)ethyl)-1-azabicyclo[3.2.0]hept-2-ene-2-carboxylic acid | ¹H NMR (D₂O) δ ppm: 1.09-1.14 (m, 6H), 1.93 (d, 1H), 3.00 (s, 3H), 3.13 (s, 3H), 3.15 (d, 1H) 3.41 (d, 2H), 3.68 (t, 1H), 3.87 (t, 1H), 3.99 (d, 2H), 4.71 (d, 1H), 4.94 (d, 1H), 7.65-7.69 (t, 2H) 7.75 (d, 1H), 7.96 (d, 2H). MS m/z: 522.7 |
| 12 | (4R,5S,6S)-3-((3S,5S)-5-(Dimethylcarbamoyl)pyrrolidin-3-ylthio)-6-((R)-1-(4-fluorophenylsulfonamido)ethyl)-4-methyl-7-oxo-1-azabicyclo[3.2.0]hept-2-ene-2-carboxylic acid | ¹H NMR (D₂O) δ ppm: 1.09-1.10 (d, 3H), 1.14-1.16 (d, 3H), 1.92-1.94 (s, 1H), 3.00-3.02 (d, 3H), 3.03 (m, 1H), 3.04-3.07 (s, 3H) 3.08 (m, 1H) 3.20-3.21 (t, 1H), 3.40-3.42 (d, 2H), 3.66-3.69 (m 1H), 3.70-3.85 (m, 1H), 4.10-4.04 (m, 2H), 7.37-7.41 (m, 2H), 7.97-8.00 (m, 2H). MS m/z: 540.7 |
| 13 | (4R,5S,6S)-3-((3S,5S)-5-(Dimethylcarbamoyl)pyrrolidin-3-ylthio)-4-methyl-7-oxo-6-((R)-1-(trifluoromethylsulfonamido)ethyl)-1-azabicyclo[3.2.0]hept-2-eoe-2-carboxylic acid | ¹H NMR (D₂O) δ ppm: 1.22-1.23 (d, 3H), 1.37-1.39 (d, 3H), 1.99-2.01 (m, 2H), 3.00-3.01 (s, 3H), 3.12 (s, 3H), 3.47-3.48 (m, 1H), 3.61-3.63 (d, 1H), 3.72-3.77 (d, 1H), 4.06-4.17 (m, 1H), 4.19-4.20 (m, 1H), 4.47-4.50 (m, 3H). MS m/z: 513.1 (M − 1). |

-continued

| Example | Structure | Analytical Data |
|---|---|---|
| 14 | (4R,5S,6R)-3-((3S,5S)-5-(Dimethylcarbamoyl)pyrrolidin-3-ylthio)-6-((R)-1-(methoxycarbonylamino)ethyl)-4-methyl-7-oxo-1-azabicyclo[3.2.0]hept-2-ene-2-carboxylic acid | $^1$H NMR (D$_2$O) δ ppm: 1.19-1.21 (d, 3H), 1.27-1.29 (d, 3H), 1.96-1.97 (m, 1H), 3.00 (s, 3H), 3.07 (s, 3H), 3.31 (m, 2H), 3.43-3.46 (m, 2H), 3.66 (s, 3H), 4.03 (m, 2H), 4.15-4.17 (m, 2H), 4.53 (m, 1H). MS m/z: 439 (M − 1) |
| 15 | (4R,5S,6R)-3-((3S,5S)-5-(Dimethylcarbamoyl)pyrrolidin-3-ylthio)-6-((R)-1-(ethoxycarbonylamino)ethyl)-4-methyl-7-oxo-1-azabicyclo[3.2.0]hept-2-ene-2-carboxylic acid | $^1$H NMR (D$_2$O) δ ppm: 1.19-1.21 (d, 3H), 1.27-1.29 (d, 3H), 1.96-1.97 (m, 2H), 3.00 (s, 3H), 3.07 (s, 3H), 3.31 (m, 2H), 3.43-3.46 (m, 2H), 3.66 (s, 3H), 4.03 (m, 3H), 4.15-4.17 (m, 2H), 4.53 (m, 1H). MS m/z: 455.7 (M + 1) |
| 16 | (4R,5S,6S)-3-((3S,5S)-5-(Dimethylcarbamoyl)pyrrolidin-3-ylthio)-4-methyl-7-oxo-6-((R)-1-(phenylmethylsulfonamido)ethyl)-1-azabicyclo[3.2.0]hept-2-ene-2-carboxylic acid | $^1$H NMR (D$_2$O) δ ppm: 1.19 (s, 3H), 1.31-1.32 (d, 3H), 1.90-1.93 (m, 1H), 3.00-3.03 (s, 3H), 3.07-3.08 (s, 3H) 3.09 (m, 1H) 3.29-3.33 (m, 2H), 3.33 (m, 1H), 3.64 (m, 1H), 3.66-3.69 (m, 1H), 3.86-3.89 (m, 1H), 3.99-4.00 (m, 1H), 4.13-4.16 (m, 1H), 4.54 (s, 2H), 7.49 (m, 5H). MS m/z: 537.2 (M + 1) |
| 17 | (4R,5S,6R)-3-((3S,5S)-5-(Dimethylcarbamoyl)pyrrolidin-3-ylthio)-4-methyl-7-oxo-6-((R)-1-(1-(trifluoromethyl)cyclopropanecarboxamido)ethyl)-1-azabicyclo[3.2.0]hept-2-ene-2-carboxylic acid | $^1$H NMR (D$_2$O) δ ppm: 1.19 (d, 3H) 1.27 (d, 3H), 1.35 (m, 4H), 2.86 (m, 1H) 2.98 (s, 3H), 3.07 (s, 3H), 3.23 (m 1H), 3.34 (d, 2H), 3.54 (d, 1H), 3.89 (d, 1H), 4.12 (d, 2H), 4.40 (d, 2H). MS m/z: 519.1 (M + 1) |
| 18 | (4R,5S,6S)-6-((R)-1-(Butylsulfonamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 0.8-0.9 (m, 3H), 1.28 (d, 3H) 1.34-1.39 (m, 3H), 1.42 (m, 2H), 1.68 (m, 2H) 1.8 (s, 3H), 2.70 (m, 1H), 2.88 (s, 3H), 2.97 (s, 3H), 3.12-3.18 (m, 4H), 3.37-3.39 (m, 2H), 4.10-4.15 (m, 2H). MS m/z: 503.2 (M + 1) |

| Example | Structure | Analytical Data |
|---|---|---|
| 19 | 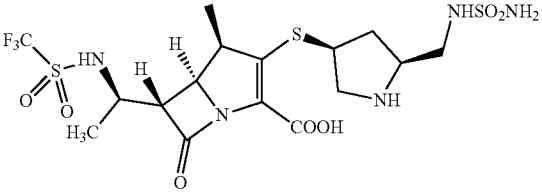<br>(4R,5S,6S)-4-Methyl-7-oxo-3-((3S,5S)-5-((sulfamoylamino)methyl)pyrrolidin-3-ylthio)-6-((R)-1-(trifluoromethylsulfonamido)ethyl)-1-azabicyclo[3.2.0]hept-2-ene-2-carboxylic acid | $^1$H NMR (D$_2$O) δ ppm: 1.25 (s, 3H), 1.39 (s, 3H), 1.62 (m, 1H), 1.92 (m, 1H), 2.62 (m, 1H), 3.2 (d, 1H), 3.40 (m, 2H) 3.50 (m, 1H), 3.60 (m, 1H), 3.7 (m, 1H), 3.90 (m, 1H) 4.10 (d, 1H), 4.20 (m, 1H). MS m/z: 552 (M + 1) |
| 20 | 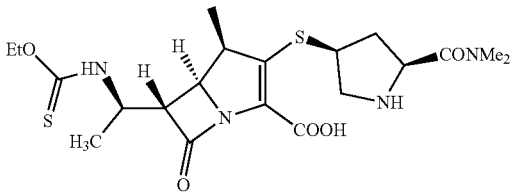<br>(4R,5S,6R)-3-((3S,5S)-5-(Dimethylcarbamoyl)pyrrolidin-3-ylthio)-6-((R)-1-(ethoxycarhonothioylamino)ethyl)-4-methyl-7-oxo-1-azabicyclo[3.2.0]hept-2-ene-2-carboxylic acid | $^1$H NMR (D$_2$O) δ ppm: 1.25-1.42 (m, 9H), 1.96-2.01 (m, 3H), 2.97-3.02 (s, 6H), 3.12-3.17 (m, 1H), 3.34-3.38 (m, 1H), 3.48-3.56 (m, 2H), 3.77 (m, 1H) 4.11 (m, 4H). MS m/z: 471.7 (M + 1). |
| 21 | 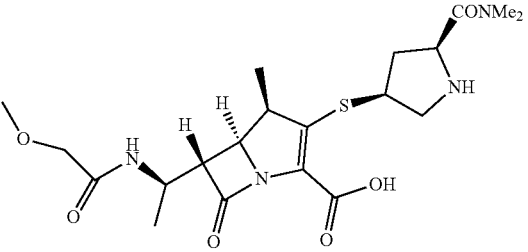<br>(4R,5S,6R)-3-((3S,5S)-5-(Dimethylcarbamoyl)pyrrolidin-3-ylthio)-6-((R)-1-(2-methoxyacetamido)ethyl)-4-methyl-7-oxo-1-azabicyclo[3.2.0]hept-2-ene-2-carboxylic acid | $^1$H NMR (D$_2$O) δ ppm: 1.19-1.21 (d, 3H), 1.27-1.29 (d, 3H), 1.96-1.97 (m, 1H), 2.35-2.6 (m, 2H), 3.00 (s, 3H), 3.07 (s, 3H), 3.30 (s, 3H), 3.4 (m, 1H), 3.43-3.46 (d, 2H), 3.53 (m, 2H), 3.63 (m, 1H) 4.03 (d, 1H), 4.15-4.17 (d, 1H), 4.53 (d, 1H). MS m/z: 455 (M + 1) |
| 22 | 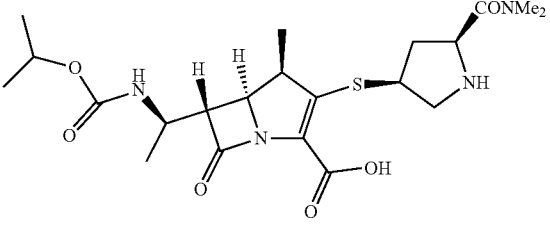<br>(4R,5S,6R)-3-((3S,5S)-5-(Dimethylcarharmoyl)pyrrolidin-3-ylthio)-6-((R)-1-(isopropoxycarhonylamino)ethyl)-4-methyl-7-oxo-1-azabicyclo[3.2.0]hept-2-ene-2-carboxylic acid | $^1$H NMR (D$_2$O) δ ppm: 1.12-1.18 (m, 12H) 2.90 (d, 5H), 2.9 (s, 3H), 3.27 (d, 2H), 3.41 (d, 1H) 3.49 (m, 1H), 3.88 (d, 1H), 4.05 (m, 2H), 4.63 (d, 1H), 4.70 (m, 1H). MS m/z: 469.1 (M + 1) |

| Example | Structure | Analytical Data |
|---|---|---|
| 23 | (4R,5S,6S)-4-Methyl-3-((3S,5S)-5-(4-methylpiperazine-1-carbonyl)pyrrolidin-3-ylthio)-6-((R)-1-(methylsulfonamido)ethyl)-7-oxo-1-azabicyclo[3.2.0]hept-2-ene-2-carboxylic acid | $^1$H NMR (D$_2$O) δ ppm: 1.10-1.12 (d, 3H), 1.21-1.23 (s, 3H), 1.75-1.81 (m, 1H), 2.39-2.50 (s, 3H), 2.84 (m, 4H), 2.88-3.03 (m, 4H), 3.22-3.30 (m, 3H) 3.39-3.45 (m, 3H), 3.45-3.48 (m, 2H), 3.85-3.88 (t, 2H), 4.10-4.45 (d, 1H), 4.50 (m, 1H). MS m/z: 516.1 (M + 1) |
| 24 | (4R,5S,6S)-3-((3S,5S)-5-(4-Hydroxypiperidine-1-carbonyl)pyrrolidin-3-ylthio)-4-methyl-6-((R)-1-(methylsulfonamido)ethyl)-7-oxo-1-azabicyclo[3.2.0]hept-2-ene-2-carboxylic acid | $^1$H NMR (D$_2$O) δ ppm: 1.21-1.23 (d, 3H), 1.33-1.34 (d, 3H), 1.41-1.43 (m, 2H), 1.94-1.98 (m, 4H), 2.92-2.94 (dd, 2H), 3.01 (s, 3H), 3.24 (s, 3H) 3.34-3.36 (d, 2H), 3.41-3.42 (dd, 2H), 3.62-3.65 (dd, 4H), 4.12-4.14 (d, 1H). MS m/z: 517.2 (M + 1) |
| 25 | (4R,5S,6S)-4-Methyl-3-((3S,5S)-5-(4-methylpiperazine-1-carbonyl)pyrrolidin-3-ylthio)-7-oxo-6-((R)-1-(trifluoromethylsulfonamido)ethyl)-1-azabicyclo[3.2.0]hept-2-ene-2-carboxylic acid | $^1$H NMR (D$_2$O) δ ppm: 1.11-1.12 (d, 3H), 1.28-1.30 (d, 3H), 1.82 (m, 1H), 2.53 (s, 3H), 2.85 (s, 3H), 3.25 (d, 1H), 3.50-3.32 (s, 3H) 3.8 (m, 3H), 3.92 (d, 2H), 4.06-4.08 (d, 4H), 4.38 (d, 1H). MS m/z: 568 (M − 1). |
| 26 | (4R,5S,6R)-6-((R)-1-(2-Acetoxyacetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.09-1.11 (d, 3H), 1.22-1.24 (d, 3H), 1.84-1.88 (m, 1H), 2.10 (s, 3H), 2.91 (s, 3H), 2.97 (s, 3H), 2.98 (m, 1H) 3.24 (m, 2H), 3.34-3.36 (m, 1H) 3.44-3.45 (d, 1H), 3.61-3.66 (m, 1H), 3.93-3.98 (m, 1H), 4.02-4.04 (m, 1H), 4.29-4.33 (m, 1H), 4.52 (s, 2H). MS m/z: 483.1 (M + 1). |

-continued

| Example | Structure | Analytical Data |
|---|---|---|
| 27 | (4R,5S,6S)-4-Methyl-6-((R)-1-(methylsulfonamido)ethyl)-3-((3S,5S)-5-(morpholine-4-carbonyl)pyrrolidin-3-ylthio)-7-oxo-1-azabicyclo[3.2.0]hept-2-ene-2-carboxylic acid | $^1$H NMR (D$_2$O) δ ppm: 1.11-1.12 (d, 3H), 1.21-1.23 (d, 3H), 1.81-1.84 (m, 1H), 2.88 (m, 1H), 3.00-3.03 (d, 3H), 3.28 (d, 2H), 3.39-3.41 (d, 2H) 3.54 (m, 2H), 3.67 (m, 3H), 3.85-3.90 (m, 4H), 4.11-4.12 (d, 1H) 4.59 (m, 2H). MS m/z: 503.1 (M + 1). |
| 28 | (4R,5S,6R)-3-((3S,5S)-5-(Dimethylcarbamoyl)pyrrolidin-3-ylthio)-6-((R)-1-(2-ethoxy-2-oxoacetamido)ethyl)-4-methyl-7-oxo-1-azabicyclo[3.2.0]hept-2-ene-2-carboxylic acid | $^1$H NMR (D$_2$O) δ ppm: 1.11-1.15 (d, 3H), 1.23-1.26 (d, 3H), 1.81 (m, 1H), 2.89 (s, 3H), 2.96 (s, 3H), 3.25-3.29 (m 3H), 3.49-3.51 (d, 2H) 3.60-3.62 (d, 1H), 3.68-3.71 (m, 1H), 3.89-3.90 (m, 1H), 4.04-4.06 (m, 1H), 4.25-4.27 (m, 2H), 4.31-4.35 (d, 3H). MS m/z: 483.2 (M + 1). |
| 29 | (4R,5S,6S)-4-Methyl-3-((3S,5S)-5-(morpholine-4-carbonyl)pyrrolidin-3-ylthio)-7-oxo-6-((R)-1-(trifluoromethylsulfonamido)ethyl)-1-azabicyclo[3.2.0]hept-2-ene-2-carboxylic acid | $^1$H NMR (D$_2$O) δ ppm: 1.09-1.11 (d, 3H), 1.20 (s, 3H), 1.81 (s, 1H), 2.87 (s, 1H), 3.32 (m, 2H), 3.5 (m, 3H), 3.60 (s, 3H) 3.70-3.80 (s, 6H), 3.90 (m, 1H), 4.10 (d, 1H), 4.30 (t, 1H) 4.04-4.50 (m, 1H). MS m/z: 555.1 (M − 1). |
| 30 | (4R,5S,6S)-3-((3S,5S)-5-(4-Hydroxypiperidine-1-carbonyl)pyrrolidin-3-ylthio)-4-methyl-7-oxo-6-((R)-1-(trifluoromethylsulfonamido)ethyl)-1-azabicyclo[3.2.0]hept-2-ene-carboxylic acid | $^1$H NMR (D$_2$O) δ ppm: 1.30-1.32 (d, 3H), 1.42-1.45 (d, 3H), 1.79 (m, 2H), 1.81-1.91 (m, 3H), 2.88-2.92 (t, 1H), 3.09-3.13 (t, 1H), 3.27-3.30 (d, 3H), 3.50-3.54 (t, 2H), 3.64-3.67 (d, 2H) 3.91 (s, 1H), 4.01 (m, 3H), 4.10 (d, 1H), 4.40 (t, 1H) 4.42 (s, 1H). MS m/z: 571 (M + 1). |

-continued

| Example | Structure | Analytical Data |
|---|---|---|
| 31 | (4R,5S,6R)-6-((R)-1-((S)-2-Amino-4-methylpentanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.01 (d, 9H), 1.1 (m, 1H), 1.30-1.31 (d, 3H), 1.32-1.35 (m, 3H), 2.88 (s, 3H), 3.00 (s, 3H), 3.08-3.12 (d, 1H), 3.35-3.37 (m, 3H) 3.59-3.60 (d, 1H), 3.74-3.80 (d, 2H), 3.86-3.89 (m, 1H), 4.14-4.17 (d, 1H) 4.30-4.32 (d, 1H) 4.40-4.44 (m, 1H). MS m/z: 496.2 (M + 1). |
| 32 | (4R,5S,6R)-6-((R)-1-(2,2-Difluoroacetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.09-1.1 (d, 3H), 1.25-1.27 (d, 3H), 1.98 (m, 1H), 2.89 (s, 3H), 2.95 (s, 3H), 3.22-3.26 (d, 2H), 3.36-3.37 (d, 2H), 3.48-3.50 (dd, 1H), 3.61 (m, 1H) 3.91-3.93 (d, 1H), 4.07-4.08 (m, 1H), 4.35-4.37 (d, 1H) 6.07-6.25 (m, 1H). MS m/z: 461.1 (M + 1). |
| 33 | (4R,5S,6S)-3-((3S,5S)-5-(Dimethylcarbamoyl)pyrrolidin-3-ylthio)-4-methyl-7-oxo-6-((R)-1-(thiophene-2-sulfonamido)ethyl)-1-azabicyclo[3.2.0]hept-2-ene-2-carboxylic acid | $^1$H NMR (D$_2$O) δ ppm: 1.13 (d, 3H), 1.18 (d, 3H) 1.94 (m, 1H), 3.05 (m, 3H) 3.07 (s, 3H), 3.25 (m, 2H), 3.44 (m, 2H), 3.72 (m, 1H), 3.90 (m, 1H), 4.03 (m, 2H), 4.8 (m, 1H), 7.24 (t, 1H), 7.78 (d, 1H), 7.88 (d, 1H). MS m/z: 529 (M + 1). |
| 34 | (4R,5S,6S)-3-((3S,5S)-5-((R)-3-Hydroxypyrrolidine-1-carbonyl)pyrrolidin-3-ylthio)-4-methyl-7-oxo-6-((R)-1-(trifluoromethylsulfonamido)ethyl)-1-azabicyclo[3.2.0]hept-2-ene-2-carboxylic acid | $^1$H NMR (D$_2$O) δ ppm: 1.2 (d, 3H), 1.4 (s, 3H), 2.1 (m, 4H) 2.98 (m, 1H), 3.35 (q, 2H), 3.60 (m, 5H), 3.77 (m, 1H), 4.17 (d, 1H), 4.46 (m, 1H), 4.54 (m, 2H). MS m/z: 555 (M − 1). |

| Example | Structure | Analytical Data |
|---|---|---|
| 35 | (4R,5S,6R)-6-((R)-1-(2,2-Difluoroacetamido)ethyl)-4-methyl-7-oxo-3-((3S,5S)-5-(thiomorpholine-4-carbonyl)pyrrolidin-3-ylthio)-1-azabicyclo[3.2.0]hept-2-ene-2-carboxylic acid | $^1$H NMR (D$_2$O) δ ppm: 1.19-1.21 (d, 3H), 1.35-1.37 (d, 3H), 1.83-1.85 (m, 1H), 1.91 (d, 1H), 2.69-2.76 (m, 4H), 2.9-2.94 (m, 1H), 3.31-3.36 (q, 2H), 3.52 (d, 1H), 3.36 (d, 1H), 3.78-3.80 (m, 2H) 3.90-3.91 (d, 2H), 4.13-4.14 (d, 1H), 4.43 (t, 1H) 4.47 (t, 1H) 6.02-6.28 (t, 1H). MS m/z: 519.1 (M + 1). |
| 36 | (4R,5S,6R)-3-((3S,5S)-5-(Dimethylcarbamoyl)pyrrolidin-3-ylthio)-6-((R)-1-(methoxycarbonothioylamino)ethyl)-4-methyl-7-oxo-1-azabicyclo[3.2.0]hept-2-ene-2-carboxylic acid | $^1$H NMR (D$_2$O) δ ppm: 1.21-1.29 (d, 6H), 1.99-2.06 (m, 1H), 3.01 (s, 6H), 3.08 (s, 3H), 3.7 (s, 3H), 3.36 (d, 1H), 3.47-3.54 (m, 2H), 3.77 (d, 1H) 4.12 (d, 2H). MS m/z: 457 (M + 1). |
| 37 | (4R,5S,6R)-3-((3S,5S)-5-(4-Carboxypiperidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.07 (d, 3H), 1.35 (d, 3H), 1.74 (m, 3H), 2.07 (m, 4H), 2.55 (m, 1H), 2.91 (m, 1H), 3.24 (m, 1H), 3.35 (d, 1H), 3.44 (m, 1H), 3.58 (m, 1H) 3.66 (m, 1H), 3.81 (m, 2H), 4.02 (m, 1H), 4.17 (m, 1H) 4.32 (m, 1H), 4.47 (m, 1H), 6.02-6.28 (t, 1H). MS m/z: 545.2 (M + 1). |
| 38 | (4R,5S,6R)-6-((R)-1-(2,2-Difluoroacetamido)ethyl)-4-methyl-7-oxo-3-((3S,5S)-5-((sulfamoylamino)methyl)pyrrolidin-3-ylthio)-1-azabicyclo[3.2.0]hept-2-ene-2-carboxylic acid | $^1$H NMR (D$_2$O) δ ppm- 1.20-1.21 (d, 3H), 1.35-1.35 (d, 3H), 1.70-1.76 (m, 1H), 1.91 (s, 1H), 2.71-2.73 (m, 1H), 3.34-3.35 (t, 2H), 3.38-3.40 (d, 1H), 3.39-3.40 (d, 1H), 3.41-3.43 (m, 1H), 3.64-3.67 (d, 1H) 3.86-3.88 (m, 1H), 3.90 (d, 1H), 4.14-4.16 (d, 1H), 4.43-4.46 (d, 1H) 4.45-4.46 (m, 1H). MS m/z: 498.1 (M + 1). |

| Example | Structure | Analytical Data |
| --- | --- | --- |
| 39 | 1-(2-Amino-2-oxoethyl)-4-((2S,4S)-4-((4R,5S,6S)-2-carboxy-4-methyl-6-((R)-1-(methylsulfonamido)ethyl)-7-oxo-1-azabicyclo[3.2.0]hept-2-ene-3-ylthio)pyrrolidine-2-carbonyl)-1-methylpiperazine-1-ium iodide | $^1$H NMR (D$_2$O) δ ppm: 1.35 (d, 3H), 1.38-1.40 (d, 3H), 1.88-1.93 (m, 1H), 2.93-2.99 (m, 1H), 3.15 (s, 3H), 3.46 (d, 2H), 3.52 (s, 3H), 3.57-3.59 (d, 1H), 3.78-3.93 (m, 4H), 3.99 (d, 1H) 4.00-4.16 (m, 4H), 4.18 (s, 2H), 4.32-4.34 (d, 1H), 4.64-4.69 (d, 2H), 4.81 (m, 1H). MS m/z: 573.2. |
| 40 | (4R,5S,6R)-3-((3S,5S)-5-(Dimethylcarbamoyl)pyrrolidin-3-ylthio)-4-methyl-7-oxo-6-((R)-1-(3,3,3-trifluoropropanamido)ethyl)-1-azabicyclo[3.2.0]hept-2-ene-2-carboxylic acid | $^1$H NMR (D$_2$O) δ ppm: 1.08-1.1 (d, 3H), 1.28 (d, 3H) 1.82 (m, 1H), 2.88-2.89 (s, 2H), 2.97-3.01 (s, 3H), 3.1-3.34 (m, 3H), 3.30-3.33 (d, 2H), 3.43-3.45 (d, 1H), 3.56-3.59 (m, 1H), 3.90-3.92 (d, 1H), 4.03-4.04 (d, 1H), 4.29-4.31 (m, 1H), 4.62-4.66 (m, 2H). MS m/z: 493.1 (M + 1). |
| 41 | (4R,5S,6R)-6-((R)-1-((2,2-Difluoroethoxy)carbonylamino)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.08-1.1 (d, 3H), 1.28 (d, 3H) 1.82 (m, 1H), 2.88-2.89 (s, 2H), 2.97-3.01 (s, 3H), 3.1-3.34 (m, 3H), 3.30-3.33 (d, 2H), 3.43-3.45 (d, 1H), 3.56-3.59 (m, 1H), 3.90-3.92 (d, 1H), 4.03-4.04 (d, 1H), 4.29-4.31 (m, 1H), 4.62-4.66 (m. 2H). MS m/z: 491.1 (M + 1). |
| 42 | (4R,5S,6R)-6-((R)-1-(2,2-Difluoroacetamido)ethyl)-4-methyl-7-oxo-3-((3S,5S)-5-(1-oxothiomorpholine-4-carbonyl)pyrrolidin-3-ylthio)-1-azabicyclo[3.2.0]hept-2-ene-2-carboxylic acid | $^1$H NMR (D$_2$O) δ ppm: 1.12 (s, 3H) 1.26 (s, 3H), 2.97 (m, 6H), 3.25 (t, 1H), 3.35 (d, 1H) 3.50 (d, 1H), 3.64 (m, 1H), 3.70 (d, 1H), 3.95 (m, 2H), 4.07 (m, 2H), 4.36 (m, 2H), 4.8 (m, 1H), 6.06 (t, 1H). MS m/z: 535 (M + 1). |

| Example | Structure | Analytical Data |
|---|---|---|
| 43 | (4R,5S,6R)-6-((R)-1-(2,2-Difluoroacetamido)ethyl)-4-methyl-3-((3S,5S)-5-(4-methylpiperazine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.16 (d, 3H), 1.27 (d, 3H) 2.55 (s, 3H), 2.90-2.99 (s, 3H), 3.01 (m, 2H) 3.31 (m, 2H), 3.54 (m, 3H), 3.64 (m, 4H), 3.90 (m, 2H), 4.07 (m, 1H), 4.37 (m, 1H), 4.70 (m, 1H), 5.92-6.19 (t, 1H). MS m/z: 516.1 (M + 1). |
| 44 | (4R,5S,6R)-6-((R)-1-(2-Aminoacetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.11-1.15 (d, 3H), 1.17-1.19 (d, 3H) 1.82-1.84 (m, 1H), 2.89-2.92 (s, 3H), 2.98-3.01 (s, 3H), 3.23-3.25 (m, 2H), 3.48-3.50 (d, 1H), 3.56-3.58 (d, 1H), 3.61-3.68 (m, 3H), 3.91-3.94 (m, 1H), 4.04-4.06 (d, 1H), 4.60-4.62 (m, 1H), 4.7-4.76 (m, 2H). MS m/z: 440.1 (M + 1). |
| 45 | 4-((2S,4S)-4-((4R,5S,6R)-2-Carboxy-6-((R)-1-(2,2-difluoroacetamido)ethyl)-4-methyl-7-oxo-1-azabicyclo[3.2.0]hept-2-en-3-ylthio)pyrrolidine-2-carbonyl)-1,1-dimethylpiperazin-1-ium iodide | $^1$H NMR (D$_2$O) δ ppm: 1.10 (d, 3H), 1.26 (d, 3H) 1.81 (d, 1H), 2.88 (m, 1H), 3.17 (s, 6H), 3.27 (m, 2H), 3.47 (m, 6H), 3.83-3.88 (m, 5H), 4.06 (d, 1H), 4.32-4.36 (m, 1H), 4.58-4.70 (m, 1H), 5.91-6.18 (t, 1H). MS m/z: 530.2. |

| Example | Structure | Analytical Data |
|---|---|---|
| 46 | 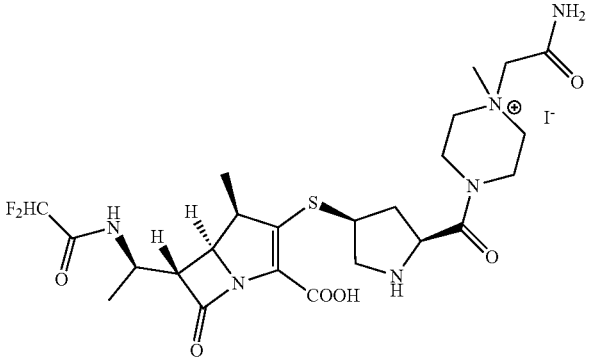<br>1-(2-Amino-2-oxoethyl)-4-((2S,4S)-4-((4R,5S,6R)-2-carboxy-6-((R)-1-(2,2-difluoroacetamido)ethyl)-4-methyl-7-oxo-1-azabicyclo[3.2.0]hept-2-en-3-ylthio)pyrrolidine-2-carbonyl)-1-methylpiperazin-1-ium iodide | $^1$H NMR (D$_2$O) δ ppm: 1.20 (d, 3H), 1.40 (d, 3H) 1.83 (m, 1H), 1.86 (m, 1H), 2.87-2.93 (m, 1H), 3.25 (m, 1H), 3.27 (m, 1H), 3.45 (s, 3H), 3.58-3.60 (m, 1H), 3.82-3.97 (m, 6H), 4.14-4.17 m, 2H), 4.30-4.33 (m, 1H), 4.47-4.51 (m, 2H), 4.64-4.69 (d, 2H), 4.81 (m, 1H) 6.03-6.29 (t, 1H). MS m/z: 573.2. |
| 47 | 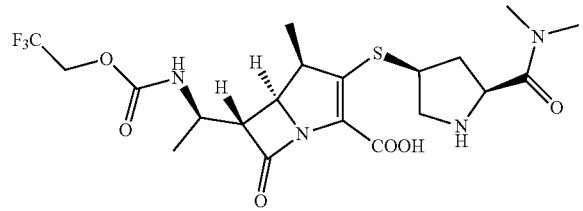<br>(4R,5S,6R)-3-((3S,5S)-5-(Dimethylcarbamoyl)pyrrolidin-3-ylthio)-4-methyl-7-oxo-6-((R)-1-((2,2,2-trifluoroethoxy)carbonylamino)ethyl)-1-azabicyclo[3.2.0]hept-2-ene-2-carboxylic acid | $^1$H NMR (D$_2$O) δ ppm: 1.21 (d, 3H), 1.31 (d, 3H) 1.97 (m, 1H), 2.98 (s, 3H), 3.04 (s, 3H), 3.34 (m, 1H), 3.43 (m, 1H), 3.53-3.54 (dd, 2H), 3.67-3.71 (m, 2H), 4.03 (t, 1H), 4.12-4.18 (m, 2H), 4.56-4.62 (m, 2H). MS m/z: 509 (M + 1) |
| 48 | 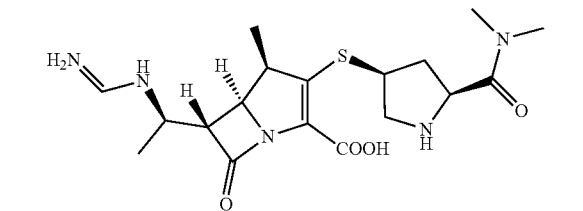<br>(4R,5S,6R)-3-((3S,5S)-5-(Dimethylcarbamoyl)pyrrolidin-3-ylthio)-6-((R)-1-formimidamidoethyl)-4-methyl-7-oxo-1-azabicyclo[3.2.0]hept-2-ene-2-carboxylic acid | $^1$H NMR (D$_2$O) δ ppm: 1.39 (d, 3H), 1.42-1.43 (d, 3H) 1.92-1.96 (m, 1H), 2.99 (s, 3H), 3.05 (s, 3H), 3.24-3.25 (d, 1H), 3.40-3.43 (d, 1H), 3.57-3.67 (m, 3H), 3.97-4.05 (m, 2H), 4.58-4.59 (d, 1H), 4.61-4.68 (m, 1H), 8.81 (s, 1H). MS m/z: 410.1 (M + 1). |
| 49 | 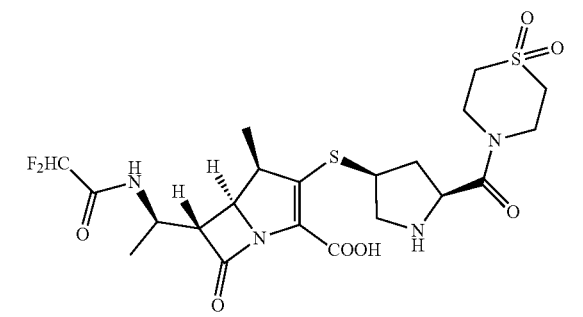<br>(4R,5S,6R)-6-((R)-1-(2,2-Difluoroacetamido)ethyl)-4-methyl-7-oxo-3-((3S,5S)-5-(1,1-dioxothiomorpholine-4-carbonyl)pyrrolidin-3-ylthio)-1-azabicyclo[3.2.0]hept-2-ene-2-carboxylic acid | $^1$H NMR (D$_2$O) δ ppm: 1.20-1.21 (d, 3H), 1.32-1.37 (d, 3H) 1.96-1.98 (m, 1H), 3.00 (m 1H), 3.37 (dd, 6H), 3.53-3.60 (d, 2H), 4.03 (d, 4H), 4.15-4.17 (d, 2H), 4.43-4.47 (m, 2H), 6.02-6.29 (m, 1H). MS m/z: 550.1. |

| Example | Structure | Analytical Data |
|---|---|---|
| 50 | (4R,5S,6R)-6-((R)-1-(2,2-difluoroacetamido)ethyl)-3-(6,7-dihydro-5H-pyrazolo[1,2-a][1,2,4]triazol-4-ium-6-ylthio)-4-methyl-7-oxo-1-azabicyclo[3.2.0]hept-2-ene-2-carboxylate | $^1$H NMR (D$_2$O) δ ppm: 1.05-1.07 (s, 3H), 1.36-1.38 (d, 3H), 3.38 (t, 1H), 3.66 (d, 1H), 4.24 (m, 2H), 4.47 (m, 2H), 4.91-4.94 (d, 1H), 5.07 (d, 2H), 6.02-6.29 (m, 1H), 9.03 (d, 2H). MS m/z: 428.1 (M$^+$). |
| 51 | (4R,5S,6R)-3-((3S,5S)-5-(Dimethylcarbamoyl)pyrrolidin-3-ylthio)-4-methyl-6-((R)-1-((S)-2-(methylsulfonamido)propanamido)ethyl)-7-oxo-1-azabicyclo[3.2.0]hept-2-ene-2-carboxylic acid | $^1$H NMR (D$_2$O) δ ppm: 1.21 (d, 3H), 1.40 (d, 3H), 1.92 (s, 2H), 3.00 (s, 3H), 3.07 (m, 3H), 3.10 (m, 3H), 3.30-3.40 (m, 3H), 3.53-3.55 (d, 1H), 3.6 (m, 1H), 4.00-4.02 (m, 3H), 4.13-4.16 (d, 2H) 4.34-4.38 (m, 1H), 4.68 (m, 1H). MS m/z: 532.1 (M + 1). |
| 52 | (4R,5S,6R)-4-Methyl-7-oxo-3-((3S,5S)-5-((sulfamoylamino)methyl)pyrrolidin-3-ylthio)-6-((R)-1-((2,2,2-trifluoroethoxy)carbonylamino)ethyl)-1-azabicyclo[3.2.0]hept-2-ene-2-carboxylic acid | $^1$H NMR (D$_2$O) δ ppm: 1.25 (d, 3H), 1.31 (d, 3H), 1.58-1.66 (m, 1H), 2.60-2.68 (m, 1H), 3.22-3.26 (m, 1H), 3.41-3.46 (m, 3H), 3.50-3.52 (m, 2H), 3.71-3.79 (m, 1H), 3.94 (t, 1H), 4.13-4.15 (d, 2H), 4.44-4.64 (m, 2H). MS m/z: 546.1 (M + 1). |
| 53 | (4R,5S,6R)-3-((3S,5S)-5-(Dimethylcarbamoyl)pyrrolidin-3-ylthio)-6-((R)-1-((Z)-2-(methoxyimino)propanamido)ethyl)-4-methyl-7-oxo-1-azabicyclo[3.2.0]hept-2-ene-2-carboxylic acid | $^1$H NMR (D$_2$O) δ ppm: 1.21 (d, 3H), 1.36 (d, 3H), 2.97 (s, 3H), 3.02 (s, 3H), 3.07-3.12 (s, 3H), 3.30-3.34 (m, 2H 3.36 (m, 1H), 3.57 (m, 1H), 3.48-3.51 (m, 1H) 3.80 (m, 1H), 4.00 (s, 3H), 4.15 (m, 2H) 4.53 (m, 1H) 4.68 (m, 1H). MS m/z: 482.1 (M + 1). |

| Example | Structure | Analytical Data |
|---|---|---|
| 54 | 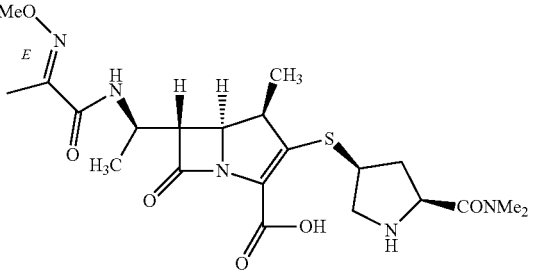<br>(4R,5S,6R)-3-((3S,5S)-5-(Dimethylcarbamoyl)pyrrolidin-3-ylthio)-6-((R)-1-((E)-2-(methoxyimino)propanamido)ethyl)-4-methyl-7-oxo-1-azabicyclo[3.2.0]hept-2-ene-2-carboxylic acid | $^1$H NMR (D$_2$O) δ ppm: 1.30-1.32 (d, 3H), 1.42-1.44 (d, 3H), 2.64 (s, 3H), 2.84 (m, 2H), 2.98 (s, 3H), 3.02 (s, 3H), 3.07 (s, 3H), 3.24 (m, 1H), 3.48-3.51 (m, 1H), 3.86 (m, 1H), 3.98 (m, 3H), 4.26 (m, 1H), 4.53 (m, 1H). MS m/z: 482.1 (M + 1). |
| 55 | 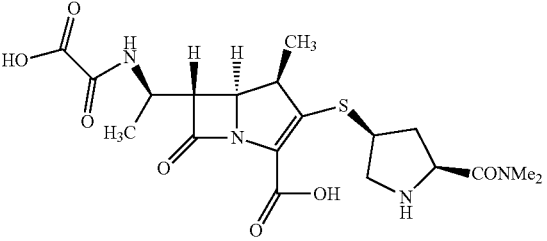<br>(4R,5S,6R)-6-((R)-1-(Carboxyformamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.16 (d, 3H), 1.29 (d, 3H), 1.41 (m, 1H) 2.00 (s, 2H), 2.99 (s, 3H), 3.06 (s, 3H), 3.42 (m, 2H), 3.75 (m, 2H), 3.90 (m, 1H), 4.06 (m, 1H), 4.46 (m, 1H). MS m/z: 410 (M − CO$_2$). |
| 56 | 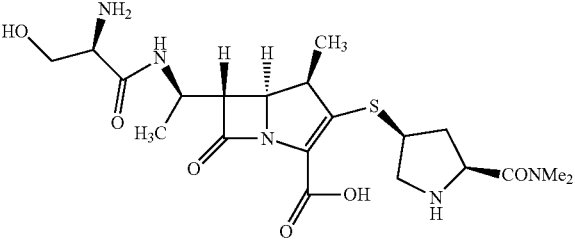<br>(4R,5S,6R)-6-((R)-1-((R)-2-Amino-3-hydroxypropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.21 (d, 3H), 1.32 (d, 3H), 1.41 (m, 1H) 2.69 (m, 1H) 2.99 (s, 3H), 3.07 (s, 3H), 3.34 (m, 2H), 3.55 (m, 1H), 3.72-4.14 (m, 5H), 4.15 (m, 1H), 4.47 (m, 1H) 4.68 (m, 1H). MS m/z: 468.1 (M − 1). |
| 57 | 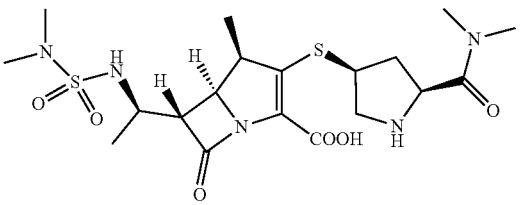<br>(4R,5S,6S)-3-((3S,5S)-5-(Dimethylcarbamoyl)pyrrolidin-3-ylthio)-6-((R)-1-(N,N-dimethylsulfamoylamino)ethyl)-4-methyl-7-oxo-1-azabicyclo[3.2.0]hept-2-ene-2-carboxylic acid | $^1$H NMR (D$_2$O) δ ppm: 1.19 (d, 3H), 1.30-1.32 (d, 3H) 2.70 (s, 6H) 2.87 (s, 3H) 2.95 (s, 3H), 3.23 (m, 2H), 3.37 (m, 1H), 3.45 (m, 1H), 3.77 (m, 1H), 3.80 (m, 2H), 4.13 (m, 1H), 4.40 (m, 1H), 4.63 (m, 1H). MS m/z: 490.1 (M + 1). |

| Example | Structure | Analytical Data |
|---|---|---|
| 58 | (4R,5S,6R)-3-((3S,5S)-5-(Dimethylcarbamoyl)pyrrolidin-3-ylthio)-4-methyl-7-oxo-6-((R)-1-((R)-tetrahydrofuran-2-carboxamido)ethyl)-1-azabicyclo[3.2.0]hept-2-ene-2-carboxylic acid | $^1$H NMR (D$_2$O) δ ppm: 1.19 (d, 3H), 1.35 (d, 3H), 1.97 (m, 4H) 2.16 (m, 1H), 2.25 (m, 1H), 3.00 (s, 3H), 3.06 (s, 3H), 3.21 (d, 2H), 3.39 (m, 3H), 3.45 (m, 2H), 3.70 (m, 2H), 3.90 (m, 2H). MS m/z: 481.1 (M + 1). |
| 59 | (4R,5S,6R)-6-((R)-1-((R)-2-Aminopropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.09-1.11 (d, 3H) 1.19-1.20 (d, 3H), 1.38-1.42 (d, 3H), 1.70 (m, 1H) 2.81 (d, 1H), 2.96 (s, 6H), 3.17-3.20 (d 1H), 3.25-3.27 (m, 1H), 3.35-3.36 (m, 1H), 3.45-3.46 (d, 1H), 3.83-3.87 (d, 1H), 4.03-4.06 (d, 1H), 4.33-4.35 (m, 1H). MS m/z: 454.2 (M + 1). |
| 60 | (4R,5S,6R)-3-((3S,5S)-5-(Dimethylcarbamoyl)pyrrolidin-3-ylthio)-6-((R)-1-(2-hydroxyacetamido)ethyl)-4-methyl-7-oxo-1-azabicyclo[3.2.0]hept-2-ene-2-carboxylic acid | $^1$H NMR (D$_2$O) δ ppm: 1.19-1.21 (d, 3H) 1.39-1.41 (d, 3H), 1.95-1.99 (m, 1H) 2.97 (s, 3H), 3.06 (s, 3H), 3.39-3.47 (m, 2H), 3.68-3.73 (d, 1H), 3.94-3.96 (d, 2H), 4.32-4.34 (d, 1H), 4.46-4.51 (m, 1H), 4.69 (d, 1H). MS m/z: 441.1 (M + 1). |
| 61 | (4R,5S,6R)-6-((R)-1-(2,2-Difluoropropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.22 (d, 3H), 1.27 (d, 3H), 1.87 (s, 3H) 1.97 (m, 1H), 3.00 (s, 3H), 3.02 (m, 1H), 3.07 (s, 3H), 3.09 (m, 1H) 3.35 (m, 1H), 3.45 (m, 1H), 3.60 (t, 1H), 4.02 (m, 1H), 4.16 (d, 1H), 4.42 (d, 1H), 4.47 (d, 1H). MS m/z: 475.1 (M + 1). |
| 62 | (4R,5S,6R)-3-((3S,5S)-5-(Dimethylcarbamoyl)pyrrolidin-3-ylthio)-6-((R)-1-formamidoethyl)-4-methyl-7-oxo-1-azabicyclo[3.2.0]hept-2-ene-2-carboxylic acid | $^1$H NMR (D$_2$O) δ ppm: 1.29 (d, 3H) 1.49 (d, 3H), 1.97-2.06 (m, 2H) 2.97 (s, 3H), 3.04 (s, 3H), 3.45-3.49 (dd, 1H), 3.56 (m, 1H), 3.73-3.78 (m, 1H), 3.89 (m, 1H), 3.91 (m, 1H), 4.04-4.08 (m, 1H), 4.50 (m, 1H), 4.83 (m, 1H), 8.75 (s, 1H). MS m/z: 411.1 (M + 1). |

| Example | Structure | Analytical Data |
|---|---|---|
| 63 | (4R,5S,6R)-3-((3S,5S)-5-(Dimethylcarbamoyl)pyrrolidin-3-ylthio)-6-((R)-1-(2-(ethylsulfonyl)acetamido)ethyl)-4-methyl-7-oxo-1-azabicyclo[3.2.0]hept-2-ene-2-carboxylic acid | $^1$H NMR (D$_2$O) δ ppm: 1.19 (d, 3H) 1.39 (d, 3H), 1.92-1.98 (m, 1H) 2.92 (s, 3H), 3.00 (s, 3H), 3.37 (m, 1H), 3.39-3.43 (dd, 2H), 3.46 (t, 1H), 3.67 (m, 1H), 3.69-3.72 (m, 1H), 4.04 (m, 1H), 4.46-4.49 (m, 1H), 4.81 (m, 1H). MS m/z: 517.1 (M + 1). |
| 64 | (4R,5S,6R)-3-((3S,5S)-5-(Dimethylcarbamoyl)pyrrolidin-3-ylthio)-4-methyl-7-oxo-6-((R)-1-(2,2,2-trifluoroacetamido)ethyl)-1-azabicyclo[3.2.0]hept-2-ene-2-carboxylic acid | $^1$H NMR (D$_2$O) δ ppm: 1.21 (d, 3H) 1.41 (d, 3H), 2.98 (s, 3H), 3.05 (s, 3H), 3.12-3.18 (m, 1H), 3.31 (d, 1H), 3.37-3.41 (m, 2H), 3.78 (m, 3H), 4.03 (d, 1H), 4.10 (t, 1H), 4.53 (t, 1H), 7.33 (s, 1H), 8.11 (d, 1H) 8.25 (d, 1H). MS m/z: 479.1 (M + 1). |
| 65 | (4R,5S,6R)-6-((R)-1-(2,2-Difluoro-2-(thiophen-2-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.21 (d, 3H) 1.41 (d, 3H), 2.98 (s, 3H), 3.05 (s, 3H), 3.12-3.18 (m, 1H), 3.31 (d, 1H), 3.37-3.41 (m, 2H), 3.78 (m, 3H), 4.03 (d, 1H), 4.10 (t, 1H), 4.53 (t, 1H), 7.33 (s, 1H), 8.11 (d, 1H) 8.25 (d, 1H). MS m/z: 543 (M + 1). |
| 66 | (4R,5S,6R)-6-((R)-1-(2-(Dimethylamino)-2-oxoacetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.20-1.22 (d, 3H) 1.34-1.36 (d, 3H), 1.94-1.99 (m, 1H) 2.98-3.00 (s, 6H), 3.10 (s, 6H), 3.35-3.40 (m, 1H), 3.40-3.47 (dd, 1H), 3.610-3.63 (d, 1H), 3.72-3.77 (dd, 1H), 4.01-4.06 (m, 1H), 4.18-4.21 (m, 1H), 4.47-4.50 (m, 1H). MS m/z: 482.1 (M + 1). |

| Example | Structure | Analytical Data |
|---|---|---|
| 67 | (4R,5S,6R)-3-((3S,5S)-5-(Dimethylcarbamoyl)pyrrolidin-3-ylthio)-6-((R)-1-((S)-2-hydroxy-4-methylpentanamido)ethyl)-4-methyl-7-oxo-1-azabicyclo[3.2.0]hept-2-ene-2-carboxylic acid | $^1$H NMR (D$_2$O) δ ppm: 1.26 (d, 6H) 1.33 (d, 3H), 1.39 (d, 3H), 1.56 (m, 1H), 1.68 (m, 2H), 2.94 (m, 1H), 2.98 (s, 3H), 3.05 (s, 3H), 3.19 (m, 1H), 3.48 (d, 1H), 3.57 (dd, 1H), 3.67 (m, 1H), 3.94-3.98 (m, 1H), 4.02 (m, 1H), 4.12-4.17 (m, 1H), 4.38 (t, 1H), 4.49-4.52 (dd, 1H), 5.10 (dd, 1H). MS m/z: 497 (M + 1). |
| 68 | (4R,5S,6R)-6-((R)-1-((S)-2-Aminopropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (DMSO-d$_6$) δ ppm: 1.12 (d, 3H) 1.19 (d, 3H), 1.39 (d, 3H), 1.70 (m, 1H) 2.8 (s, 3H), 2.95 (s, 3H), 3.18-3.24 (dd 3H), 3.38-3.43 (d, 3H), 3.6 (dd, 1H), 3.82-3.87 (m, 4H), 4.02-4.03 (d, 1H), 4.28-4.32 (m, 1H), 4.43 (m, 1H) 4.6 (d, 1H). MS m/z: 454.1 (M + 1). |
| 69 | (4R,5S,6R)-3-((3S,5S)-5-(Dimethylcarbamoyl)pyrrolidin-3-ylthio)-4-methyl-6-((R)-1-(morpholine-4-carboxamido)ethyl)-7-oxo-1-azabicyclo[3.2.0]hept-2-ene-2-carboxylic acid | $^1$H NMR (DMSO-d$_6$) δ ppm: 1.24 (d, 3H) 1.28-1.29 (d, 3H), 1.98 (m, 1H), 2.99 (s, 3H) 3.03 (s, 3H), 3.07-3.12 (dd, 2H), 3.35-3.40 (dd 4H), 3.44-3.46 (d, 1H), 3.70 (dd, 4H), 3.80-3.82 (d, 2H), 3.93-3.95 (d, 1H), 4.15-4.19 (m, 1H), 4.22-4.26 (m, 2H). MS m/z: 496 (M + 1). |
| 70 | (4R,5S,6R)-3-((3S,5S)-5-(Dimethylcarbamoyl)pyrrolidin-3-ylthio)-4-methyl-6-((R)-1-(2-(methylsulfonamido)acetamido)ethyl)-7-oxo-1-azabicyclo[3.2.0]hept-2-ene-2-carboxylic acid | $^1$H NMR (D$_2$O) δ ppm: 1.15 (d, 3H), 1.29 (d, 3H), 2.95 (s, 3H), 3.00 (s, 3H) 3.04 (s, 3H), 3.27 (m, 1H), 3.36 (m, 1H), 3.73 (m, 2H), 3.86 (s, 2H), 4.01 (m, 1H), 4.07-4.11 (m, 1H), 4.47 (m, 2H), 4.61 (m, 2H). MS m/z: 518.1 (M + 1). |

| Example | Structure | Analytical Data |
| --- | --- | --- |
| 71 | (4R,5S,6R)-6-((R)-1-((S)-2-Amino-3-phenylpropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 0.97 (d, 3H), 1.18 (d, 3H), 2.97 (s, 3H), 3.08 (s, 3H) 3.08-3.13 (dd, 2H), 3.20-3.25 (dd, 2H), 3.25 (m, 2H), 3.39-3.44 (dd, 1H), 3.53 (m, 2H), 3.66-3.70 (m, 2H), 4.06-4.13 (m, 1H), 4.29 (m, 1H), 7.23-7.42 (m, 5H). MS m/z: 530.2 (M + 1). |
| 72 | (4R,5S,6R)-6-((R)-1-((R)-2-Amino-3-phenylpropanamido)ethyl)-3-((3S,5S)-5-(dimethylcarbamoyl)pyrrolidin-3-ylthio)-4-methyl-7-oxo-1-azabicyclo[3.2.0]hept-2-eoe-2-carboxylic acid | $^1$H NMR (D$_2$O) δ ppm: 1.06-1.08 (d, 3H) 1.26 (d, 3H), 2.95 (s, 3H), 3.03 (s, 3H), 3.08 (m, 2H), 3.11-3.13 (d, 2H), 3.16-3.20 (m, 2H), 3.21 (d, 1H), 3.40 (m, 2H), 3.51 (d, 2H), 4.21-4.22 (m, 1H), 4.54 (m, 1H), 7.23-7.42 (m, 5H). MS m/z: 530.2 (M + 1). |
| 73 | (4R,5S,6R)-3-((3S,5S)-5-(Dimethylcarhamoyl)pyrrolidin-3-ylthio)-6-((R)-1-(2-isopropoxy-2-oxoacetamido)ethyl)-4-methyl-7-oxo-1-azabicyclo[3.2.0]hept-2-ene-2-carboxylic acid | $^1$H NMR (D$_2$O) δ ppm: 1.21 (d, 3H) 1.34-1.35 (m, 9H), 1.94-1.98 (m, 1H), 3.00 (s, 3H), 3.06 (d, 3H), 3.32-3.34 m, 2H), 3.36 (d, 2H), 3.60-3.62 (d, 1H), 3.70-3.72 (m, 1H), 4.03 (m, 1H), 4.14-4.17 (d, 1H), 4.42-4.22 (m, 1H), 5.13-5.16 (t, 1H). MS m/z: 495.1 (M + 1). |
| 74 | (4R,5S,6R)-3-((3S,5S)-5-(Dimethylcarbamoyl)pyrrolidin-3-ylthio)-6-((R)-1-(2-methoxy-2-oxoacetamido)ethyl)-4-methyl-7-oxo-1-azabicyclo[3.2.0]hept-2-ene-2-carboxylic acid | $^1$H NMR (D$_2$O) δ ppm: 1.19-1.21 (d, 3H) 1.36-1.38 (d, 3H), 1.93-2.0 (d, 1H), 3.00 (s, 1H), 3.08 (s, 3H), 3.32-3.35 (q, 1H), 3.44-3.47 (q, 1H), 3.60-3.62 (d, 1H), 3.72-3.76 (q, 1H), 3.90 (s, 3H), 4.01 (t, 1H), 4.15-4.17 (d, 1H), 4.42-4.46 (t, 1H). MS m/z: 469.1 (M + 1). |

| Example | Structure | Analytical Data |
|---|---|---|
| 75 | (4R,5S,6R)-3-((3S,5S)-5-(Dimethylcarbamoyl)pyrrolidin-3-ylthio)-4-methyl-6-((R)-1-(2-(methylamino)-2-oxoacetamido)ethyl)-7-oxo-1-azabicyclo[3.2.0]hept-2-ene-2-carboxylic acid | $^1$H NMR (D$_2$O) δ ppm: 1.19-1.21 (d, 3H), 1.36-1.37 (d, 3H) 1.92-1.95 (m, 1H), 2.84 (s, 3H), 3.03 (s, 3H), 3.32 (s, 3H), 3.33 (m, 2H), 3.41 (dd, 1H), 3.60-3.62 (d, 1H), 3.68-3.71 (t, 1H), 4.02 (t, 1H), 4.13 (d, 1H), 4.39-4.41 (t, 1H), 4.76-4.81 (d, 1H). MS m/z: 468.1 (M + 1). |
| 76 | (4R,5S,6R)-6-((R)-1-(2,2-Difluoroacetamido)ethyl)-3-((3S,5S)-5-(4,4-difluoropiperidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.19-1.21 (d, 3H), 1.35-1.37 (d, 3H) 2.09-2.13 (m, 3H), 3.02 (m, 1H), 3.35-3.37 (dd, 2H), 3.57-3.60 (d, 2H), 3.64-3.65 (d, 2H), 3.75 (d, 2H), 4.09 (m, 1H), 4.15-4.16 (d, 2H), 4.43-4.47 (m, 2H), 4.74 (m, 1H), 6.02-6.29 (m, 1H). MS m/z: 537.1 (M + 1). |
| 77 | (4R,5S,6R)-6-((R)-1-(2,2-Difluoroacetamido)ethyl)-3-((3S,5S)-5-((S)-3-hydroxypyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.14-1.21 (d, 3H), 1.35-1.37 (d, 3H) 2.01-2.09 (m, 2H), 3.01 (m, 1H), 3.35 (m, 3H), 3.42-3.46 (t, 3H), 3.47-3.70 (dd, 3H), 4.01 (t, 1H), 4.1-4.19 (d, 1H), 4.45-4.47 (t, 1H), 4.70-4.81 (q, 2H), 6.02-6.29 (t, 1H). MS m/z: 503.1 (M + 1). |
| 78 | (4R,5S,6R)-3-((3S,5S)-5-(Dimethylcarbamoyl)pyrrolidin-3-ylthio)-4-methyl-6-((R)-1-(2-(methylsulfonyl)acetamido)ethyl)-7-oxo-1-azabicyclo[3.2.0]hept-2-ene-2-carboxylic acid | $^1$H NMR (D$_2$O) δ ppm: 1.1-1.19 (d, 3H) 1.41-1.43 (d, 3H), 3.00 (s, 3H), 3.08 (s, 3H), 3.25 (s, 2H), 3.33-3.35 (m, 2H), 3.41-3.46 (dd, 2H), 3.54-3.56 (d, 2H), 4.01-4.04 (t, 2H), 4.15-4.19 (d, 2H), 3.22-4.26 (m, 2H), 4.40-4.44 (m, 1H). MS m/z: 503.1 (M + 1). |

| Example | Structure | Analytical Data |
| --- | --- | --- |
| 79 | (4R,5S,6R)-3-(((3S,5S)-5-(Dimethylcarbamoyl)pyrrolidin-3-ylthio)-6-((R)-1-((R)-2-fluoro-4-methylpentanamido)ethyl)-4-methyl-7-oxo-1-azabicyclo[3.2.0]hept-2-ene-2-carboxylic acid | ¹H NMR (D₂O) δ ppm: 1.27 (d, 3H) 1.33 (m, 3H), 1.65-1.74 (m, 6H), 2.99 (s, 3H), 3.09 (d, 3H), 3.31-3.42 (m, 2H), 3.55-3.56 (m, 2H), 3.62-3.63 (dd, 2H), 4.01 (m, 2H), 4.06-4.13 (d, 2H), 4.41-4.44 (m, 2H), 4.68-4.70 (m, 2H). MS m/z: 499.2 (M + 1). |
| 80 | 1-(((4S)-4-((4R,5S,6R)-2-Carboxy-6-((R)-1-(2,2-difluoroacetamido)ethyl)-4-methyl-7-oxo-1-azabicyclo[3.2.0]hept-2-en-3-ylthio)pyrrolidin-2-yl)methyl)-1-methylpyrrolidinium iodide | ¹H NMR (D₂O) δ ppm: 1.11 (d, 3H), 1.20-1.22 (d, 3H), 1.49 (m, 1H), 2.24 (m, 4H), 2.72 (m, 1H), 3.04-3.17 (m, 2H), 3.30 (s, 3H), 3.38 (m, 2H), 3.56-3.61 (m, 5), 3.79 (m, 2H), 4.13-4.15 (m, 1H), 4.43-4.46 (m, 1H), 4.73 (m, 1H), 6.02-6.29 (m, 1H). MS m/z: 487.2. |
| 81 | (4R,5S,6R)-6-((R)-1-(2,2-Difluoroacetamido)ethyl)-4-methyl-7-oxo-3-((3S)-5-(pyrrolidin-1-ylmethyl)pyrrolidin-3-ylthio)-1-azabicyclo[3.2.0]hept-2-ene-2-carboxylic acid | ¹H NMR (D₂O) δ ppm: 1.21 (d, 3H), 1.37 (d, 3H), 1.51 (d, 1H), 2.08 (d, 4H), 2.67 (t, 1H), 3.06-3.13 (d, 1H), 3.40 (m, 8H), 3.73 (d, 1H), 3.83 (d, 2H), 4.15 (t, 1H), 4.17-4.54 (t, 1H), 6.02-6.29 (t, 1H). MS m/z: 473.2 (M + 1). |
| 82 | (4R,5S,6R)-6-((1R)-1-(2-(Difluoromethylsulfinyl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | ¹H NMR (D₂O) δ ppm: 1.05-1.12 (d, 3H), 1.15 (d, 3H), 1.19 (d, 3H), 1.31 (d, 3H), 1.96-1.99 (m, 2H), 2.94-3.07 (s, 1H), 3.27-3.29 (m, 1H), 3.31 (m, 1H), 3.59-3.63 (d, 2H), 3.84-3.85 (d, 2H), 3.93-4.02 (d, 2H), 4.35 (m, 1H), 4.79 (m, 1H). MS m/z: 523.1 (M + 1). |

| Example | Structure | Analytical Data |
|---|---|---|
| 83 | 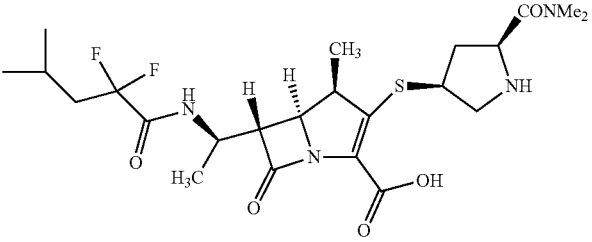<br>(4R,5S,6R)-6-((R)-1-(2,2-Difluoro-4-methylpentanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR ($D_2O$) δ ppm: 0.96-0.98 (d, 6H), 1.19 (d, 3H), 1.38 (d, 3H), 1.90-1.92 (d, 2H), 1.99 (m, 1H), 3.02-3.03 (s, 6H), 3.26-3.29 (m, 1H), 3.31 (d, 1H), 3.57-3.59 (m, 2H), 4.00-4.06 (d, 2H), 4.14 (m, 2H), 4.65-4.67 (m, 1H), 4.80-4.86 (d, 1H). MS m/z: 517.2 (M + 1). |
| 84 | 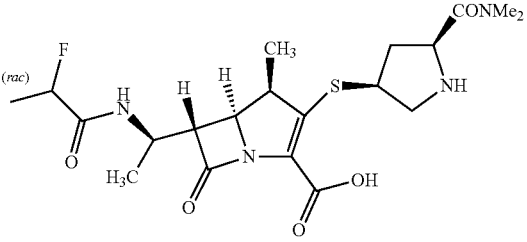<br>(4R,5S,6R)-3-((3S,5S)-5-(Dimethylcarbamoyl)pyrrolidin-3-ylthio)-6-((1R)-1-(2-fluoropropanamido)ethyl)-4-methyl-7-oxo-1-azabicyclo[3.2.0]hept-2-ene-2-carboxylic acid | $^1$H NMR ($D_2O$) δ ppm: 1.21-1.28 (d, 3H) 1.33-1.35 (d, 3H), 1.50-1.52 (d, 3H), 3.00 (s, 3H), 3.07 (s, 3H), 3.39-3.42 (m, 2H), 3.56-3.58 (d, 2H), 3.65-3.66 (m, 2H), 4.00 (d, 2H), 4.14 (t, 2H), 4.42 (d, 1H). MS m/z: 457.2 (M + 1). |
| 85 | 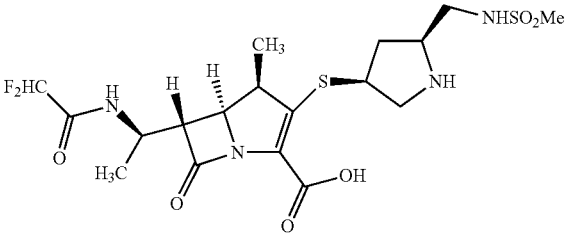<br>(4R,5S,6R)-6-((R)-1-(2,2-Difluoroacetamido)ethyl)-4-methyl-3-((3S,5S)-5-(methylsulfonamidomethyl)pyrrolidin-3-ylthio)-7-oxo-1-azabicyclo[3.2.0]hept-2-ene-2-carboxylic acid | $^1$H NMR ($D_2O$) δ ppm: 1.22 (d, 3H) 1.37 (d, 3H), 2.73 (m, 2H) 3.13 (s, 3H), 3.36 (m, 3H), 3.60 (m, 3H), 3.85 (d, 2H), 4.05 (d, 1H), 4.17 (t, 1H), 4.45 (d, 1H), 6.02-6.29 (t, 1H). MS m/z: 497.1 (M + 1). |
| 86 | 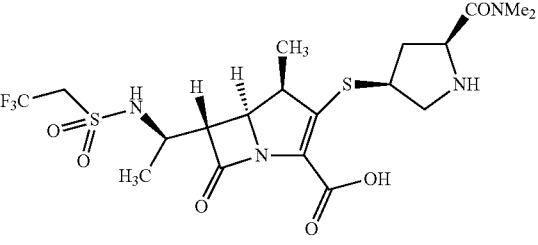<br>(4R,5S,6S)-3-((3S,5S)-5-(Dimethylcarbamoyl)pyrrolidin-3-ylthio)-4-methyl-7-oxo-6-((R)-1-(2,2,2-trifluoroethylsulfonamido)ethyl)-1-azabicyclo[3.2.0]hept-2-ene-2-carboxylic acid | $^1$H NMR ($D_2O$) δ ppm: 1.21-1.25 (d, 3H) 1.30-1.32 (d, 3H), 2.73 (s, 3H), 3.13 (s, 3H), 3.34 (m, 4H), 3.60-3.61 (m, 2H), 3.97 (m, 2H), 4.16-4.17 (d, 2H), 4.44-4.47 (t, 1H), 4.61-4.80 (d, 1H). |

-continued

| Example | Structure | Analytical Data |
|---|---|---|
| 87 | (4R,5S,6R)-3-((3S,5S)-5-(Dimethylcarbamoyl)pyrrolidin-3-ylthio)-4-methyl-7-oxo-6-((R)-1-(2,2,3,3,3-pentafluoropropanamido)ethyl)-1-azabicyclo[3.2.0]hept-2-ene-2-carboxylic acid | $^1$H NMR (D$_2$O) δ ppm: 1.20-1.21 (d, 3H) 1.38-1.40 (d, 3H), 3.00-3.07 (s, 3H), 3.35 (s, 3H), 3.35-3.42 (m, 2H), 3.60-3.62 (m, 2H), 4.06 (m, 2H), 4.16-4.18 (m, 2H), 4.48 (m, 1H), 4.71-4.80 (m, 1H). |
| 88 | (4R,5S,6R)-6-((R)-1-(2,2-Difluoroacetamido)ethyl)-4-methyl-7-oxo-3-(4-(pyridin-4-yl)thiazol-2-ylthio)-1-azabicyclo[3.2.0]hept-2-ene-2-carboxylic acid | $^1$H NMR (D$_2$O) δ ppm: 1.05-1.11 (d, 3H), 1.21 (d, 3H), 3.32-3.34 (d, 1H) 3.61-3.63 (d, 2H), 4.21-4.23 (m, 1H), 4.43-4.45 (m, 1H), 5.98-6.25 (t, 1H), 7.86 (d, 1H), 8.22 (s, 1H), 8.6 (d, 1H). MS m/z: 481.2 (M + 1). |
| 89 | (4R,5S,6R)-6-((R)-1-(2,2-Difluoroacetamido)ethyl)-3-((3S,5S)-5-((3,3-dimethylureido)methyl)pyrrolidin-3-ylthio)-4-methyl-7-oxo-1-azabicyclo[3.2.0]hept-2-ene-2-carboxylic acid | $^1$H NMR (D$_2$O) δ ppm: 1.20-1.21 (d, 3H), 1.30-1.37 (d, 3H) 2.64 (m, 1H), 2.92 (s, 6H), 3.32 (dd, 2H), 3.46 (m, 1H), 3.58-3.59 (dd, 2H), 3.73-3.74 (d, 2H), 3.97 (m, 2H), 4.13-4.16 (d, 2H), 4.43-4.47 (t, 1H), 6.02-6.29 (t, 1H). MS m/z: 490.2 (M + 1). |
| 90 | (4R,5S,6R)-6-((R)-1-(2,2-Difluoroacetamido)ethyl)-4-methyl-3-((3S,5S)-5-(morpholinomethyl)pyrrolidin-3-ylthio)-7-oxo-1-azabicyclo[3.2.0]hept-2-ene-2-carboxylic acid | $^1$H NMR (D$_2$O) δ ppm: 1.27 (d, 3H), 1.35-1.37 (d, 3H) 2.57-2.69 (dd, 1H) 2.70-2.77 (dd, 2H), 2.82-2.88 (m, 3H) 3.34-3.38 (dd, 3H), 3.58-3.60 (d, 2H), 3.63-3.64 (m 2H), 3.77 (m, 4H), 4.14 (d, 2H), 4.42 (t, 1H), 6.02-6.29 (t, 1H). MS m/z: 489.2 (M + 1). |

| Example | Structure | Analytical Data |
|---|---|---|
| 91 | (4R,5S,6R)-6-((R)-1-(2-(Dimethoxyphosphoryl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.22 (d, 3H), 1.32-1.41 (d, 3H), 2.66 (s, 2H) 3.00 (s, 3H), 3.07 (s, 3H), 3.47 (d, 1H), 3.53 (m, 2H), 3.55-3.60 (d, 2H), 3.72 (s, 6H), 3.81-3.84 (d, 2H), 4.16 (m, 2H), 4.36-4.38 (m, 1H). MS m/z: 533.1 (M + 1). |
| 92 | (4R,5S,6R)-3-(2-Aminoethylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.06-1.07 (d, 3H), 1.27-1.29 (d, 3H), 2.93-2.94 (m, 1H), 3.11-3.14 (dd, 2H) 3.17-3.19 (dd, 1H), 3.59-3.60 (d, 1H) 4.13-4.16 (m, 1H), 4.43-4.47 (t, 1H) 6.02-6.29 (t, 1H). MS m/z: 364.1 (M + 1). |
| 93 | (4R,5S,6R)-3-(2-(tert-Butoxycarbonylamino)ethylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.00-1.02 (d, 3H), 1.19-1.22 (d, 3H), 1.36 (d, 9H), 2.67 (d, 1H), 3.03-3.06 (m, 2H) 3.24 (m, 1H), 3.77-3.80 (d, 1H) 4.16-4.18 (t, 1H), 6.08-6.35 (t, 1H) 7.12-7.13 (d, 1H), 8.90-8.92 (d, 1H). MS m/z: 462 (M − 1). |
| 94 | 4-(2-((4R,5S,6R)-2-Carboxy-6-((R)-1-(2,2-difluoroacetamido)ethyl)-4-methyl-7-oxo-1-azabicyclo[3.2.0]hept-2-en-3-ylthio)thiazol-4-yl)-1-methylpyridinium iodide | $^1$H NMR (D$_2$O) δ ppm: 1.09-1.19 (d, 3H), 1.33-1.35 (d, 3H), 3.63-3.64 (m, 1H) 3.64-3.65 (d, 1H), 4.22-4.23 (m, 1H), 4.25 (s, 3H), 4.36 (d, 1H), 5.98-6.11 (t, 1H), 8.37-8.39 (dd, 2H), 8.6 (d, 1H), 8.75-8.77 (dd, 2H). MS m/z: 495.1. |

Example 95: (4R,5S,6R)-3-((3R,5S)-5-((R)-3-aminopyrrolidine-1-carbonyl)pyrrolidin-3-ylthio)-4-methyl-6-((S)-1-(2-(methylamino)acetamido)ethyl)-7-oxo-1-azabicyclo[3.2.0]hept-2-ene-2-carboxylic acid

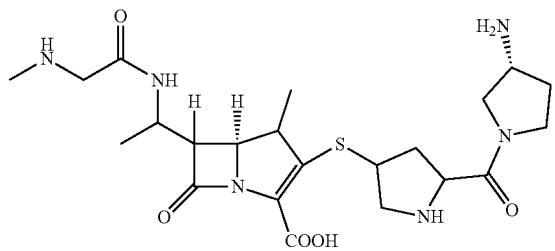 [SMILES: CNCC(=O)NC(C)C1C(=O)N2C(C(=O)O)=C(SC3CNC(C(=O)N4CC[C@@H](N)C4)C3)C(C)[C@H]12]

Step-1: (4R,5R,6R)-4-nitrobenzyl 3-(diphenoxyphosphoryloxy)-4-methyl-6-((R)-1-(2-(methyl((4-nitrobenzyloxy)carbonyl)amino)acetamido)ethyl)-7-oxo-1-azabicyclo[3.2.0]hept-2-ene-2-carboxylate

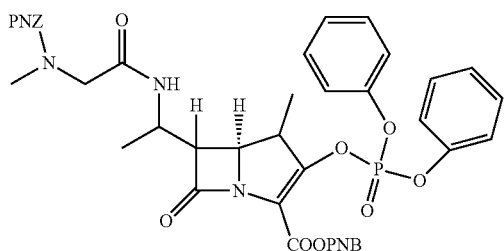

Rhodium octanoate (0.1 g, 0.128 mmoles) was added to a solution of (R)-4-nitrobenzyl 2-diazo-4-((2R,3R)-3-((R)-1-(2-(methyl((4-nitrobenzyloxy)carbonyl)amino) acetamido) ethyl)-4-oxoazetidin-2-yl)-3-oxopentanoate (3 g, 4.69 mmoles) in acetone (60 mL) and heated to reflux for 1.5 hours. The reaction mixture was cooled to −50 to −40° C. and diphenyl chlorophosphate (1.64 g, 6.1 mmoles), diisopropylethylamine (1.1 mL, 6.71 mmoles) and dimethylaminopyridine (0.05 g, 0.41 mmoles) were added successively and continued stirring for a period of 1 hour at -10° C. The reaction mixture was treated with 0.5 M phosphate buffer (pH 7.4) and extracted with ethyl acetate (150 mL). The organic layer was separated and washed with water and brine. After drying over sodium sulphate the organic layer was evaporated to obtain the oily product. The crude product on purification by column chromatography yields the title compound as a pale yellow solid. (2 g, 49.6%).

Step-2: (4R,5S,6R)-4-nitrobenzyl4-methyl-6-((R)-1-(2-(methyl((4-nitrobenzyloxy) carbonyl)amino)acetamido)ethyl)-3-((3S,5S)-1-((4-nitrobenzyloxy)carbonyl)-5-((R)-3-((4-nitrobenzyloxy)carbonylamino)pyrrolidine-1-carbonyl)pyrrolidin-3-ylthio)-7-oxo-1-azabicycio[3.2.0]hept-2-ene-2-carboxylate

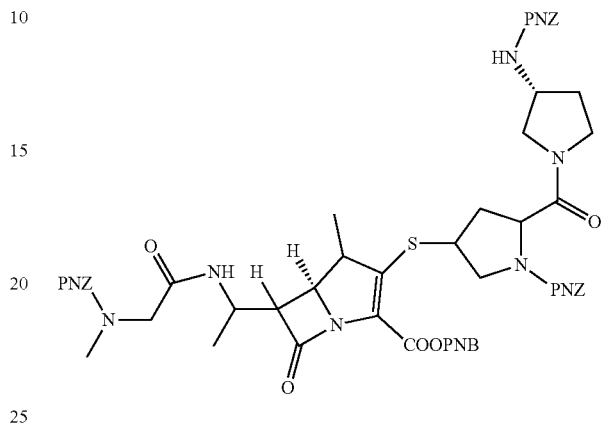

A cooled solution (0° C.) of (4R,5R,6R)-4-nitrobenzyl3-(diphenoxyphosphoryloxy) -4-methyl-6-((R)-1-(2-(methyl ((4-nitrobenzyloxy)carbonyl)amino)acetamido)ethyl)-7-oxo -1-azabicyclo[3.2.0]hept-2-ene-2-carboxylate (5 g, 8.72 mmoles) and (2S,4R)-4-nitrobenzyl4-mercapto-2-((R)-3-((4-nitrobenzyloxy)carbonylamino)pyrrolidine-1-carbonyl) pyrrolidine-1-carboxylate (7.5 g, 8.72 mmoles) in acetonitrile was degassed using nitrogen for 10 minutes and N,N-diisopropylethylamine (2.2 mL, 13.3 mM) was added and degassed using nitrogen for a further period of 10 minutes. The reaction mixture was stirred for 3 hours at 0° C. under nitrogen. The reaction mixture was treated with 0.5 M phosphate buffer (pH 7.4) and extracted with EtOAc (150 mL). The organic layer was separated and washed with water and brine. After drying over sodium sulphate the organic layer was evaporated to obtain the oily product. The crude product on purification by column chromatography (15-17% methanol in dichloromethane) yields the title compound as an off-white solid. (6.2 g, 60%)

Step-3: (4R,5S,6R)-3-((3R,5S)-5-((R)-3-aminopyrrolidine-1-carbonyl)pyrrolidin-3-ylthio)-4-methyl-6-((R)-1-(2-(methylamino)acetamido)ethyl)-7-oxo-1-azabicyclo[3.2.0] hept-2-ene-2-carboxylic acid

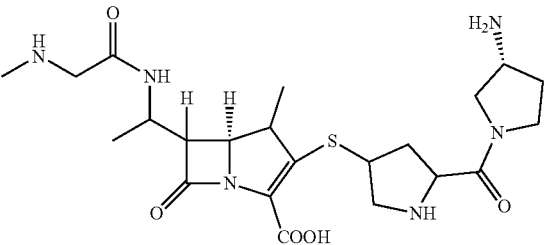 [SMILES: CNCC(=O)NC(C)C1C(=O)N2C(C(=O)O)=C(SC3CNC(C(=O)N4CC[C@@H](N)C4)C3)C(C)[C@H]12]

(4R,5S,6R)-4-nitrobenzyl4-methyl-6-((R)-1-(2-(methyl ((4-nitrobenzyloxy) carbonyl)amino)acetamido)ethyl)-3-((3S,5S)-1-(4-nitrobenzyloxy)carbonyl)-5-((R)-3-((4-nitrobenzyloxy)carbonylamino)pyrrolidine-1-carbonyl)

pyrrolidin-3-ylthio)-7-oxo-1-azabicyclo[3.2.0]hept-2-ene-2-carboxylate (0.5 g) in 20 mL of tetrahydrofuran:water (2:1) mixture and suspension of Pd/C (2 g) was hydrogenated for a period of 1.5 hours. The reaction mixture was filtered over celite and washed with 30 mL of tetrahydrofuran: water (2:1) mixture. The filtrate was washed with EtOAc (30 mL×6). The aqueous layer was treated with charcoal (1 g) and filtered. The filtrate was lyophilized to yield the title compound (0.1 g, 50%). $^1$H NMR (D$_2$O)—1.07-1.08 (d, 3H), 1.20-1.29 (d, 3H), 1.92 (m, 1H), 2.12 (m, 2H), 2.46 (m, 2H), 2.76 (s, 3H), 2.92 (m, 1H), 3.34-3.38 (m, 2H), 3.40 (d, 3H), 3.60-3.64 (d, 2H), 3.76-3.78 (d, 3H), 3.93-3.96 (m, 1H), 4.02 (m, 1H), 4.48 (m, 1H). MS m/z: 493.6 (M−1).

Examples 96, 97, 100-135, 137-145, 147-166, 168-176, 178-186, 188-200, 202, 205-206, 209-231, 235-238, 241-273, 275-292, 294-297, 299-312, 314-318, 320-325, 329-361 and 363-368 were prepared by treating the compound of formula (10) with appropriate R$^4$COOH according to the procedure given in the preparations 12, 16 and 17, followed by the procedure given in Example 1.

Examples 136, 201, 203, 204, 239, 240 and 362 were prepared by following the procedure provided in preparation 13.

Example 187 was prepared by following the procedure provided in preparation 19.

Example 98 and 99 were prepared by following the procedure given in preparation 23.

Examples 146, 167, 177, 207, 208, 232-234 were prepared by following the procedure described in the preparation 20 using appropriate alkynes (cf. Scheme 2a).

Example 274 and 293 were prepared by following the procedure provided in preparation 24.

| Examples | Structure | Analytical Data |
|---|---|---|
| 96 | 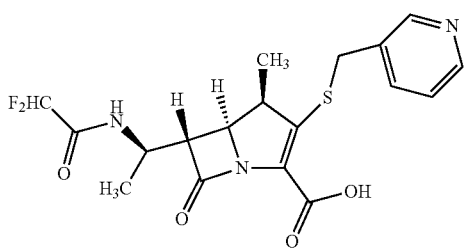<br>(4R,5S,6R)-6-((R)-1-(2,2-Difluoroacetamido)ethyl)-4-methyl-7-oxo-3-(pyridin-3-ylmethylthio)-1-azabicyclo[3.2.0]hept-2-ene-2-carboxylic acid | $^1$H NMR (D$_2$O) δ ppm: 1.15 (d, 3H), 1.34 (d, 3H), 3.30 (t, 1H), 3.54 (d, 1H), 4.02 (m, 2H), 4.19 (m, 2H), 6.14 (t, 1H), 7.46 (t, 1H), 7.92 (d, 1H), 8.52 (d, 2H). MS m/z: 412.4 (M + 1) |
| 97 | 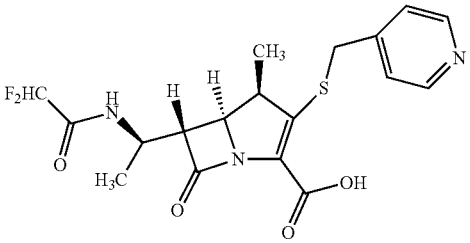<br>(4R,5S,6R)-6-((R)-1-(2,2-Difluoroacetamido)ethyl)-4-methyl-7-oxo-3-(pyridin-4-ylmethylthio)-1-azabicyclo[3.2.0]hept-2-ene-2-carboxylic acid | $^1$H NMR (D$_2$O) δ ppm: 1.15 (d, 3H), 1.34 (d, 3H), 3.26 (t, 1H), 3.54 (d, 1H), 3.95 (d, 1H), 4.02 (d, 1H), 4.18 (d, 1H), 4.40 (t, 1H), 6.14 (t, 1H), 7.47 (d, 2H), 8.47 (d, 2H). MS m/z: 412.4 (M + 1) |
| 98 | 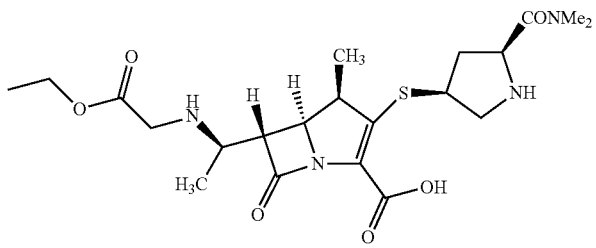<br>(4R,5S,6R)-3-((3S,5S)-5-(Dimethylcarbamoyl)pyrrolidin-3-ylthio)-6-((R)-1-(2-methoxy-2-oxoethylamino)ethyl)-4-methyl-7-oxo-1-azabicyclo[3.2.0]hept-2-ene-2-carboxylic acid | $^1$H NMR (D$_2$O) δ ppm: 1.24 (d, 3H), 1.29 (d, 3H), 1.96 (m, 2H), 2.99 (d, 3H), 3.07 (s, 3H), 3.37 (m, 3H), 3.48 (d, 2H), 3.54 (d, 1H), 4.06 (m, 2H), 4.24 (m, 2H), 4.26 (m, 3H). MS m/z: 469.5 (M + 1) |

| Examples | Structure | Analytical Data |
|---|---|---|
| 99 | 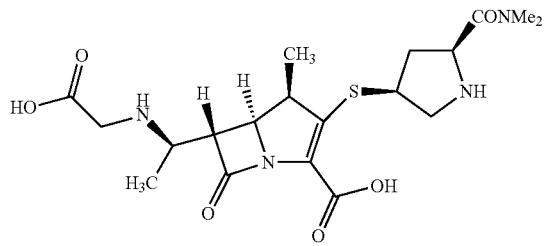<br>(4R,5S,6R)-6-((R)-1-(Carboxymethylamino)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.52 (t, 3H), 1.53 (t, 3H), 1.98 (m, 2H), 3.07 (d, 3H), 3.08 (d, 3H), 3.4-3.5 (m, 2H), 3.5 (m, 1H), 3.55 (d, 2H), 3.72 (d, 1H), 3.79 (m, 1H), 4.65 (m, 1H), 4.29 (d, 2H). MS m/z: 439 (M − 1) |
| 100 | 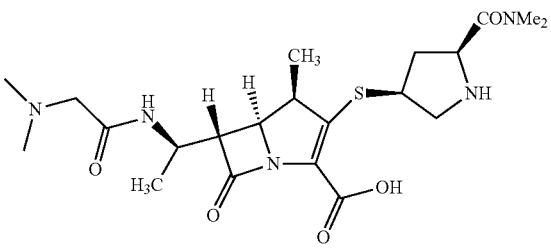<br>(4R,5S,6R)-6-((R)-1-(2-(Dimethylamino)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.71 (t, 3H), 1.75 (t, 3H), 1.92 (t, 1H), 2.29 (s, 1H), 2.80-2.89 (m, 6H), 2.98 (d, 2H), 3.07 (s, 3H), 3.09 (d, 3H), 3.20 (d, 1H), 3.58 (d, 1H), 3.72 (d, 1H), 4.16 (d, 2H), 4.36-4.39 (d, 1H), 4.45 (t, 1H), 4.82 (t, 1H). MS m/z: 466.6 (M − 1) |
| 101 | 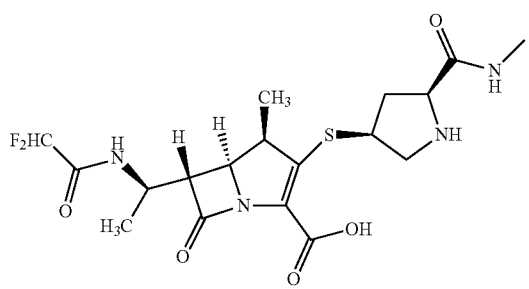<br>(4R,5S,6R)-6-((R)-1-(2,2-Difluoroacetamido)ethyl)-4-methyl-3-((3S,5S)-5-(methylcarbamoyl)pyrrolidin-3-ylthio)-7-oxo-1-azabicyclo[3.2.0]hept-2-ene-2-carboxylic acid | $^1$H NMR (D$_2$O) δ ppm: 1.21 (d, 3H), 1.37 (d, 3H), 2.08 (d, 1H), 2.81 (s, 3H), 2.90 (t, 1H), 3.36 (m, 2H), 3.60 (d, 1H), 3.71 (m, 1H), 3.99 (s, 1H), 4.17 (d, 1H), 4.39-4.47 (dd, 2H), 6.16 (t, 1H): MS m/z: 447.5 (M + 1) |
| 102 | 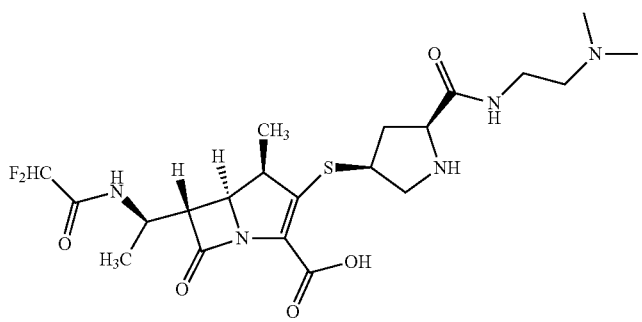<br>(4R,5S,6R)-6-((R)-1-(2,2-Difluoroacetamido)ethyl)-3-((3S,5S)-5-(2-(dimethylamino)ethylcarbamoyl)-pyrrolidin-3-ylthio)-4-methyl-7-oxo-1-azabicyclo[3.2.0]hept-2-ene-2-carboxylic acid | $^1$H NMR (D$_2$O) δ ppm: 1.28 (d, 3H), 1.37 (d, 3H), 1.47 (s, 1H), 2.03 (t, 1H), 2.97 (d, 6H), 2.96 (t, 1H), 2.97 (t, 3H), 3.22 (d, 2H), 3.67 (d, 2H), 3.91 (m, 1H), 4.16 (d, 2H), 4.45 (s, 1H), 6.16 (t, 1H). MS m/z: 504.6 (M + 1) |

| Examples | Structure | Analytical Data |
|---|---|---|
| 103 | (4R,5S,6R)-3-((3S,5S)-5-((S)-3-Aminopyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.20 (d, 3H), 1.38 (d, 3H), 1.35 (d, 1H), 2.09-2.21 (dd, 1H), 2.19-2.49 (dd, 1H), 2.81-2.87 (m, 1H), 3.18 (m, 1H), 3.36 (dd, 2H), 3.59 (d, 2H), 3.77 (m, 2H), 3.78-3.88 (m, 2H), 3.98 (m, 1H), 4.14-4.23 (m, 2H), 4.45 (t, 1H), 6.16 (t, 1H). MS m/z: 502.5 (M + 1) |
| 104 | (4R,5S,6R)-6-((R)-1-(2,2-Difluoroacetamido)ethyl)-3-((3S,5S)-5-(2-hydroxyethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.2 (d, 3H), 1.37 (d, 3H), 2.08 (d, 1H), 2.91 (m, 1H), 3.36 (d, 2H), 3.41 (s, 3H), 3.6 (d, 1H), 3.69 (s, 3H), 3.98 (s, 1H), 4.17 (d, 1H), 4.44-4.47 (dd, 1H), 4.81 (t, 1H), 6.16 (t, 1H). MS m/z: 477.5 (M + 1) |
| 105 | (4R,5S,6R)-6-((R)-1-(2,2-Difluoroacetamido)ethyl)-3-((3S,5S)-5-(methoxycarbamnyl)pyrrolidin-3-ylthio)-4-methyl-7-oxo-1-azabicyclo[3.2.0]hept-2-ene-2-carboxylic acid | $^1$H NMR (D$_2$O) δ ppm: 1.24 (d, 3H), 1.35 (m, 1H), 1.49 (d, 3H), 2.37 (m, 1H), 2.85 (m, 1H), 3.36 (m, 1H), 3.58 (d, 1H), 3.60 (q, 1H), 3.76 (s, 3H), 3.96 (t, 1H), 3.98 (d, 1H), 4.28 (t, 1H), 4.45 (t, 1H), 6.16 (t, 1H). MS m/z: 516.6 (M + 1) |
| 106 | (4R,5S,6R)-6-((R)-1-(2,2-Difluoroacetamido)ethyl)-4-methyl-3-((3S,5S)-5-((S)-3-(methylamino)pyrrolidine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.36 (d, 3H), 1.82 (d, 3H), 1.92 (s, 1H), 2.11 (s, 1H), 2.18 (d, 1H), 2.45-2.55 (m, 2H), 2.77 (s, 2H), 2.89 (d, 1H), 3.39 (m, 1H), 3.65 (d, 3H), 3.74-3.79 (m, 4H), 4.45 (d, 2H), 4.75 (d, 1H), 4.81 (d, 1H), 6.16 (t, 1H). MS m/z: 515.58 (M + 1) |

-continued

| Examples | Structure | Analytical Data |
|---|---|---|
| 107 | 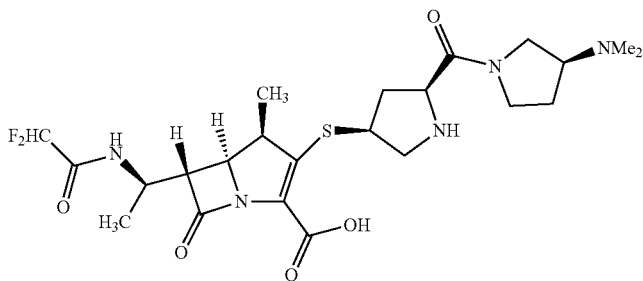<br>(4R,5S,6R)-6-((R)-1-(2,2-Difluoroacetamido)ethyl)-3-((3S,5S)-5-((S)-3-(dimethylamino)pyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.21 (d, 3H), 1.38 (3, 3H), 1.92 (m, 1H), 2.09 (m, 1H), 2.54 (m, 1H), 2.78 (s, 2H), 2.83 (s, 3H), 3.26 (dd, 1H), 3.59 (d, 2H), 3.75-3.82 (m, 4H), 3.94-4.14 (m, 4H), 4.41 (d, 2H), 4.45-4.74 (m, 2H) 6.16 (t, 1H). MS m/z: 530.6 (M + 1) |
| 108 | 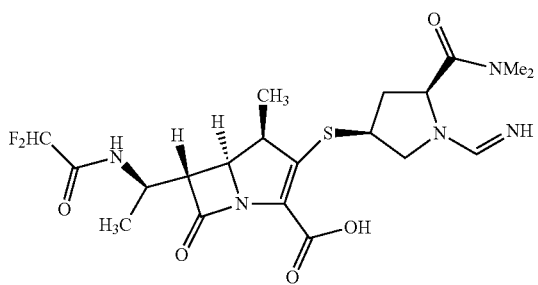<br>(4R,5S,6R)-6-((R)-1-(2,2-Difluoroacetamido)ethyl)-3-((3S,5S)-5-(dimethylcarbamoyl)-1-(iminomethyl)pyrrolidin-3-ylthio)-4-methyl-7-oxo-1-azabicyclo[3.2.0]hept-2-ene-2-carboxylic acid | $^1$H NMR (D$_2$O) δ ppm: 1.23 (d, 3H), 1.47 (d, 3H), 2.99 (s, 3H), 3.02 (m, 1H), 3.10 (s, 3H), 3.36 (m, 1H), 3.37-3.53 (m, 2H), 3.59 (m, 1H), 4.00 (m, 1H), 4.09-4.18 (m, 2H), 4.46 (m, 2H), 5.20 (m, 1H), 6.02 (t, 1H). MS m/z: 488.5 (M + 1) |
| 109 | 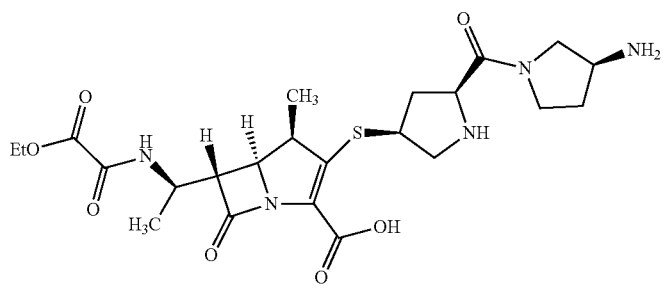<br>(4R,5S,6R)-3-((3S,5S)-5-((S)-3-Aminopyrrolidine-1-carbonyl)pyrrolidin-3-ylthio)-6-((R)-1-(2-ethoxy-2-oxoacetamido)ethyl)-4-methyl-7-oxo-1-azabicyclo[3.2.0]hept-2-ene-2-carboxylic acid | $^1$H NMR (D$_2$O) δ ppm: 1.07 (d, 3H), 1.24-1.34 (m, 6H), 1.85-1.92 (m, 2H), 2.15-2.30 (m, 2H), 2.92 (m, 2H), 3.25 (m, 1H), 3.35 (m, 1H), 3.57 (m, 1H), 3.65 (m, 2H), 3.83 (d, 1H), 3.92 (d, 1H), 4.16 (m, 2H), 4.39 (m, 2H), 4.42-4.92 (m, 2H). MS m/z: 524.60 (M + 1) |

| Examples | Structure | Analytical Data |
|---|---|---|
| 110 | 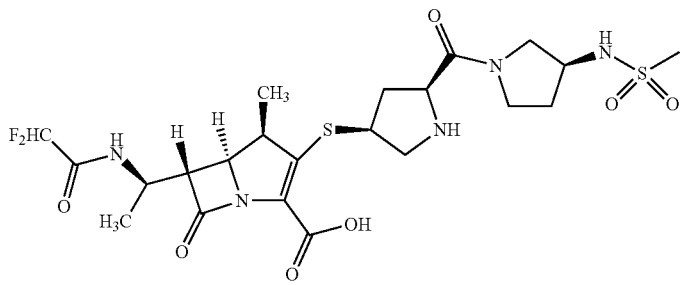

(4R,5S,6R)-6-((R)-1-(2,2-Difluoroacetamido)ethyl)-4-methyl-3-((3S,5S)-5-((S)-3-(methylsulfonamido)pyrrolidine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.32 (d, 3H), 1.38 (d, 3H), 1.92 (d, 1H), 2.00 (dd, 1H), 2.34 (m, 1H), 2.97 (m, 1H), 3.15 (s, 3H), 3.36 (s, 2H), 3.54 (m, 1H), 3.59 (d, 3H), 3.86 (d, 1H), 3.97 (t, 1H), 4.17 (d, 1H), 4.43-4.80 (m, 2H), 4.80 (t, 2H), 6.16 (t, 1H). MS m/z: 580.64 (M + 1) |
| 111 | 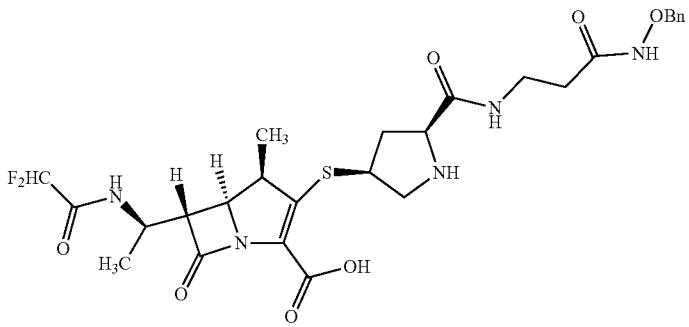

(4R,5S,6R)-3-((3S,5S)-5-(3-(Benzyloxyamino)-3-oxopropylcarbamoyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.27 (d, 3H), 1.33 (d, 3H), 2.36-2.43 (m, 2H), 2.82 (m, 1H), 3.33 (m, 1H), 3.39 (m, 2H), 3.56-3.58 (m, 2H), 3.71 (m, 1H), 3.99 (m, 1H), 4.13-4.16 (m, 2H), 4.39-4.46 (m, 2H), 4.91 (s, 2H), 6.02 (t, 1H) 7.47 (d, 2H), 7.38-7.45 (m, 3H). MS m/z: 610.64 (M + 1) |
| 112 | 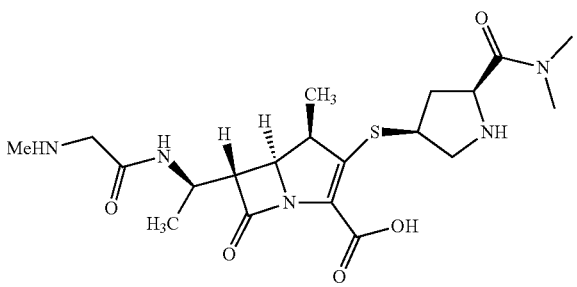

(4R,5S,6R)-3-((3S,5S)-5-(Dimethylcarbamoyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.22 (d, 3H), 1.26 (d, 3H), 1.87 (m, 1H), 2.76 (s, 3H), 2.99 (s, 3H), 3.09 (s, 3H), 3.59 (s, 2H), 3.78 (d, 3H), 3.85 (m, 2H), 3.99 (t, 1H), 4.16 (d, 1H), 4.47 (t, 1H), 4.61 (t, 1H). MS m/z: 452.5 (M − 1) |

| Examples | Structure | Analytical Data |
|---|---|---|
| 113 | 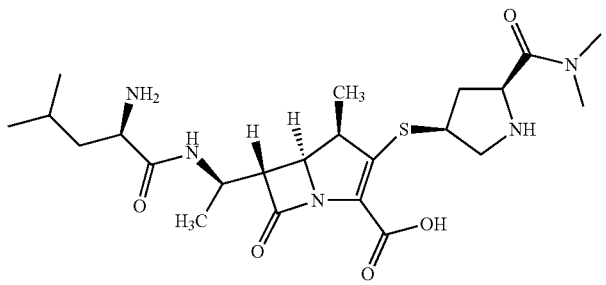<br>(4R,5S,6R)-6-((R)-1-((R)-2-Amino-4-methylpentanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 0.92-0.99 (m, 6H), 1.17 (d, 3H), 1.22 (d, 1H), 1.28 (d, 2H), 1.69-1.80 (m, 3H), 2.99 (s, 3H), 3.07 (s, 3H), 3.33 (dd, 1H), 3.43 (d, 2H), 3.52 (m, 2H), 3.54 (m, 2H), 4.14 (m, 2H), 4.57 (m, 2H). MS m/z: 496.64 (M + 1) |
| 114 | 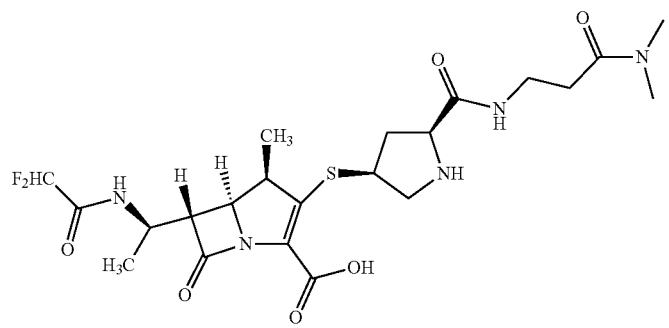<br>(4R,5S,6R)-6-((R)-1-(2,2-Difluoroacetamido)ethyl)-3-((3S,5S)-5-(3-(dimethylamino)-3-oxopropylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.69 (d, 3H), 1.27 (d, 3H), 1.90-1.98 (m, 1H), 2.59 (d, 2H), 2.82 (s, 4H), 2.96 (s, 3H), 3.36-3.48 (m, 3H), 3.62 (m, 1H), 3.65 (m, 1H), 4.04 (m, 1H), 4.33 (m, 2H), 4.70 (m, 2H), 6.16 (t, 1H). MS m/z: 515.6 (M + 1) |
| 115 | 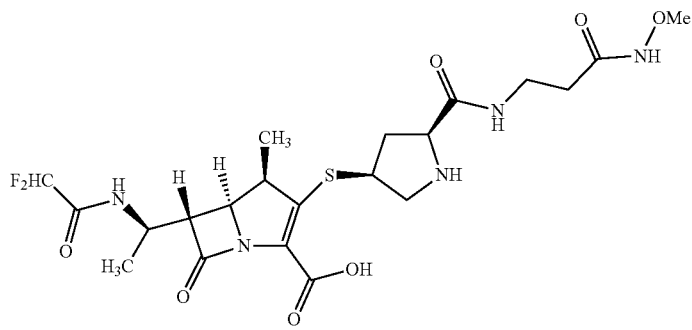<br>(4R,5S,6R)-6-((R)-1-(2,2-Difluoroacetamido)ethyl)-3-((3S,5S)-5-(3-(methoxyamino)-3-oxopropylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.12 (d, 3H), 1.92 (d, 3H), 2.22 (m, 1H), 2.23-2.69 (m, 2H), 2.73 (m, 1H), 3.13-3.20 (s, 3H), 3.13-3.19 (m, 2H), 3.39-3.52 (s, 3H), 3.79 (m, 1H), 3.82-3.96 (m, 2H), 4.21-4.61 (m, 2H), 6.14 (t, 1H). MS m/z: 534.6 (M + 1) |

| Examples | Structure | Analytical Data |
|---|---|---|
| 116 | 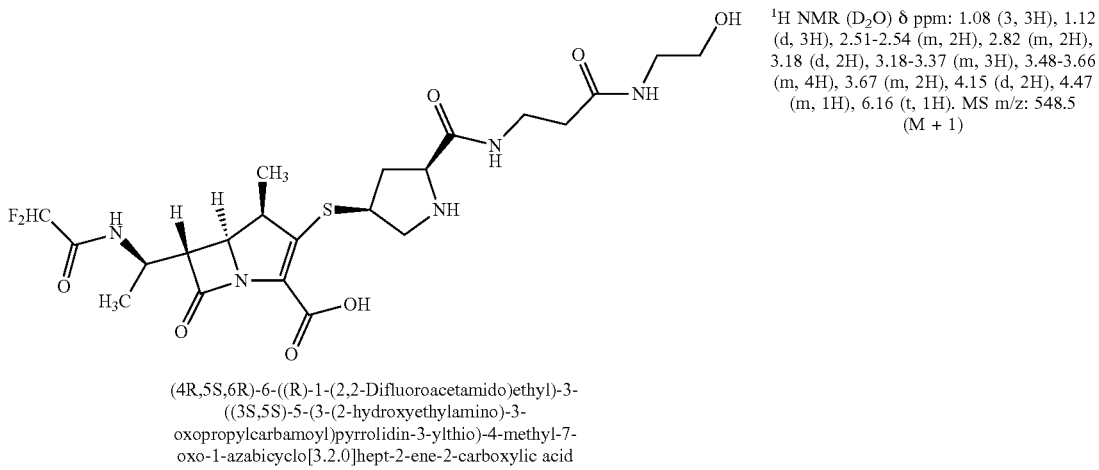<br>(4R,5S,6R)-6-((R)-1-(2,2-Difluoroacetamido)ethyl)-3-((3S,5S)-5-(3-(2-hydroxyethylamino)-3-oxopropylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.08 (3, 3H), 1.12 (d, 3H), 2.51-2.54 (m, 2H), 2.82 (m, 2H), 3.18 (d, 2H), 3.18-3.37 (m, 3H), 3.48-3.66 (m, 4H), 3.67 (m, 2H), 4.15 (d, 2H), 4.47 (m, 1H), 6.16 (t, 1H). MS m/z: 548.5 (M + 1) |
| 117 | 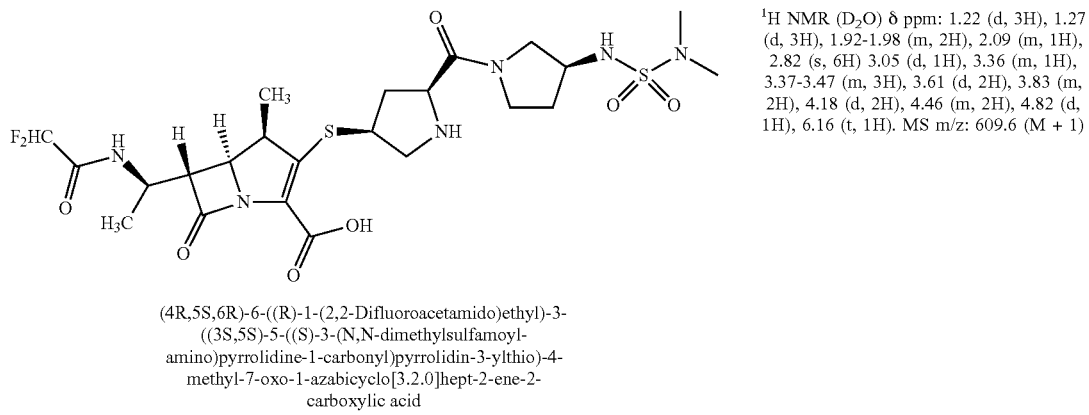<br>(4R,5S,6R)-6-((R)-1-(2,2-Difluoroacetamido)ethyl)-3-((3S,5S)-5-((S)-3-(N,N-dimethylsulfamoyl-amino)pyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.22 (d, 3H), 1.27 (d, 3H), 1.92-1.98 (m, 2H), 2.09 (m, 1H), 2.82 (s, 6H) 3.05 (d, 1H), 3.36 (m, 1H), 3.37-3.47 (m, 3H), 3.61 (d, 2H), 3.83 (m, 2H), 4.18 (d, 2H), 4.46 (m, 2H), 4.82 (d, 1H), 6.16 (t, 1H). MS m/z: 609.6 (M + 1) |
| 118 | 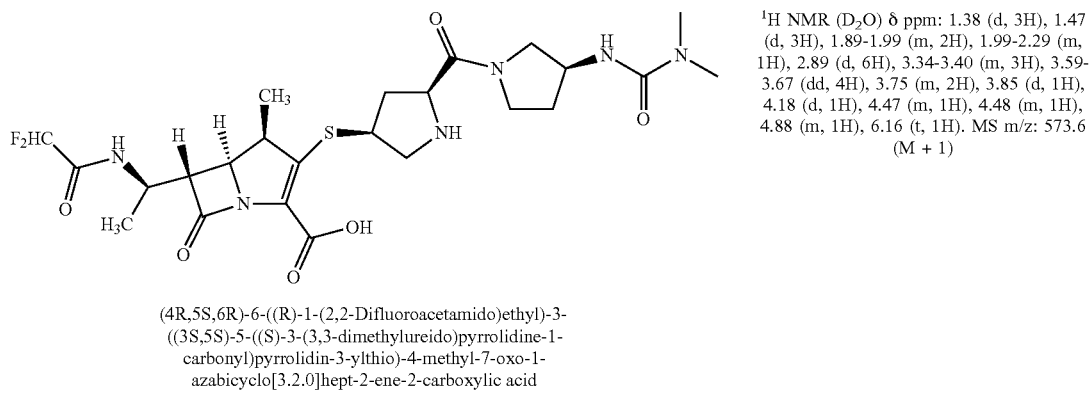<br>(4R,5S,6R)-6-((R)-1-(2,2-Difluoroacetamido)ethyl)-3-((3S,5S)-5-((S)-3-(3,3-dimethylureido)pyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.38 (d, 3H), 1.47 (d, 3H), 1.89-1.99 (m, 2H), 1.99-2.29 (m, 1H), 2.89 (d, 6H), 3.34-3.40 (m, 3H), 3.59-3.67 (dd, 4H), 3.75 (m, 2H), 3.85 (d, 1H), 4.18 (d, 1H), 4.47 (m, 1H), 4.48 (m, 1H), 4.88 (m, 1H), 6.16 (t, 1H). MS m/z: 573.6 (M + 1) |

| Examples | Structure | Analytical Data |
|---|---|---|
| 119 | 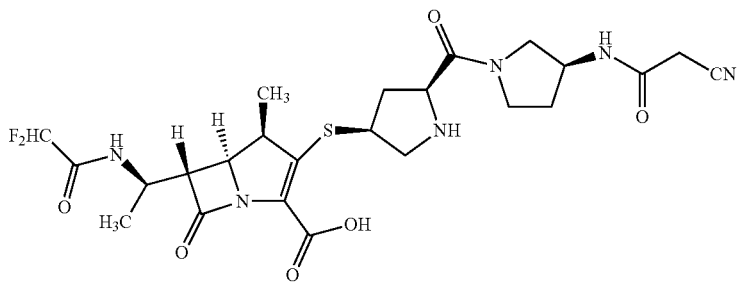

(4R,5S,6R)-3-((3S,5S)-5-((S)-3-(2-Cyanoacetamido)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.21 (d, 3H), 1.42 (d, 3H), 1.98 (m, 1H), 2.72-2.34 (dd, 1H), 2.97 (m, 1H), 3.36-3.49 (m, 3H), 3.51 (d, 1H), 3.62-3.74 (m, 2H), 3.80 (m, 2H), 3.85 (m, 1H), 3.90 (m, 1H), 4.17 (d, 2H), 4.81 (m, 4H), 6.16 (t, 1H). MS m/z: 569.6 (M + 1) |
| 120 | 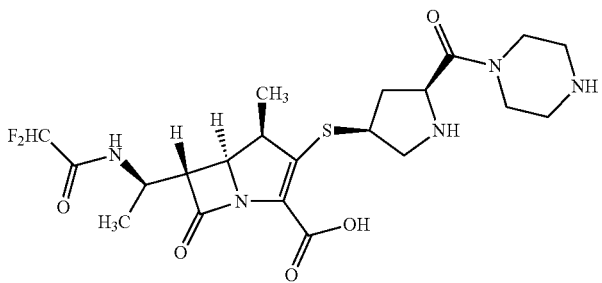

(4R,5S,6R)-6-((R)-1-(2,2-Difluoroacetamido)ethyl)-4-methyl-7-oxo-3-((3S,5S)-5-(piperazine-1-carbonyl)pyrrolidin-3-ylthio)-1-azabicyclo[3.2.0]hept-2-ene-2-carboxylic acid | $^1$H NMR (D$_2$O) δ ppm: 1.06 (d, 3H), 1.22 (d, 3H), 1.80 (m, 1H), 2.71 (m, 1H), 2.89 (m, 1H), 3.25-3.36 (m, 5H), 3.44 (m, 1H), 3.58 (d, 1H), 3.64 (m, 1H), 3.84-3.91 (m, 5H), 4.15 (d, 1H), 4.45 (d, 1H), 6.02 (t, 1H). MS m/z: 502.6 (M + 1) |
| 121 | 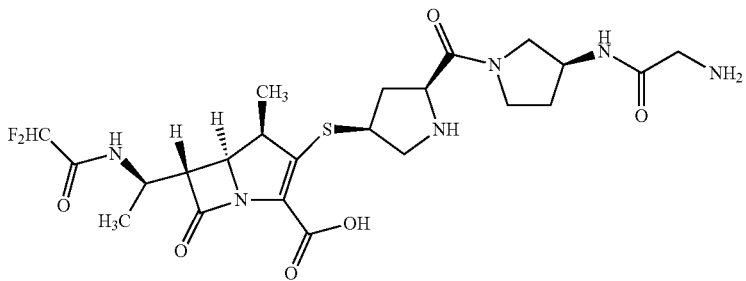

(4R,5S,6R)-3-((3S,5S)-5-((S)-3-(2-Aminoacetamido)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 0.99 (d, 3H), 1.09 (d, 3H), 1.36 (d, 3H), 1.96 (dd, 1H), 2.21 (dd, 1H), 2.78 (d, 1H), 3.18 (m, 3H), 3.18-3.31 (m, 3H), 3.52 (t, 3H), 3.66 (t, 1H), 4.21 (d, 1H), 4.52 (m, 2H), 6.05 (t, 1H). MS m/z: 559.60 (M + 1) |

| Examples | Structure | Analytical Data |
|---|---|---|
| 122 | 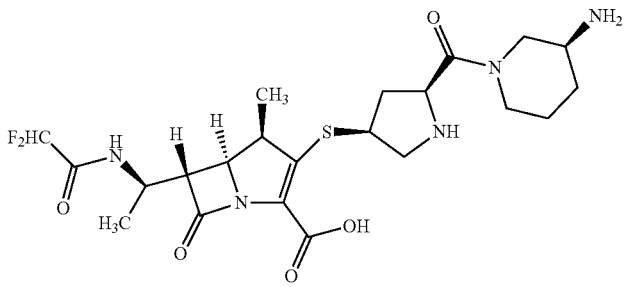<br>(4R,5S,6R)-3-((3S,5S)-5-((S)-3-Aminopiperidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.21 (d, 3H), 1.31 (d, 3H), 1.36 (d, 2H), 1.73 (m, 1H), 1.93 (d, 1H), 2.2 (d, 1H), 3.17-3.22 (q, 2H), 3.31-3.36 (q, 2H), 3.39-3.47 (m, 2H), 3.59 (m, 1H), 3.72-4.15 (m, 2H), 4.16 (m, 1H), 4.18 (m, 1H), 4.44 (m, 1H), 4.47 (m 2H), 6.16 (t, 1H). MS m/z: 516.6 (M + 1) |
| 123 | 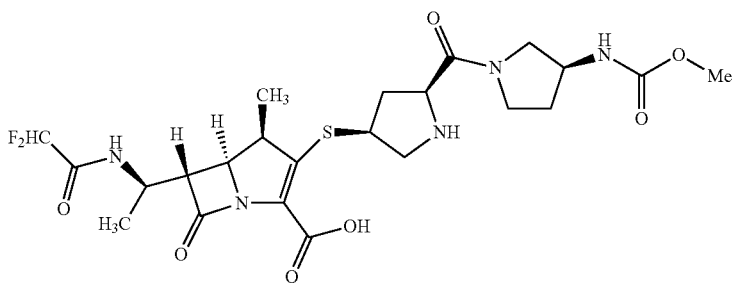<br>(4R,5S,6R)-6-((R)-1-(2,2-Difluoroacetamido)ethyl)-3-((3S,5S)-5-((S)-3-(methoxycarbonylamino)pyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.21 (d, 3H), 1.38 (3, 3H), 2.54 (m, 1H), 2.78 (s, 3H), 2.83 (s, 3H), 3.26 (dd, 1H), 3.59 (d, 2H), 3.75-3.82 (m, 3H), 3.94-4.14 (m, 4H), 4.41 (d, 1H), 4.41-4.74 (m, 2H), 6.16 (t, 1H). MS m/z: 560.6 (M + 1) |
| 124 | 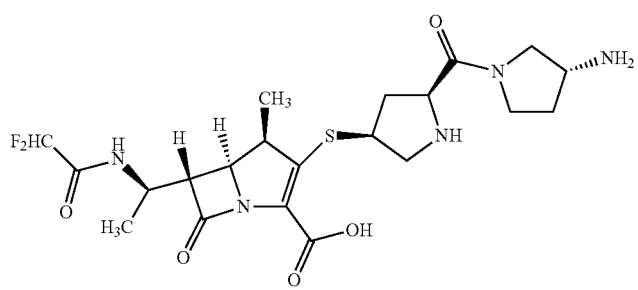<br>(4R,5S,6R)-3-((3S,5S)-5-((R)-3-Aminopyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.32 (d, 3H), 1.38 (d, 3H), 1.99 (d, 2H), 2.09 (d, 1H), 2.19 (m, 1H), 3.05 (m, 1H), 3.36 (m, 1H), 3.44 (m, 1H), 3.48 (d, 1H), 3.66 (m, 1H), 3.89-3.73 (m, 3H), 4.06 (m, 1H), 4.40 (d, 1H), 4.47 (m, 1H), 4.68 (m, 1h), 4.82 (m, 1H), 6.16 (t, 1H). MS m/z: 502.6 (M + 1) |

| Examples | Structure | Analytical Data |
|---|---|---|
| 125 | 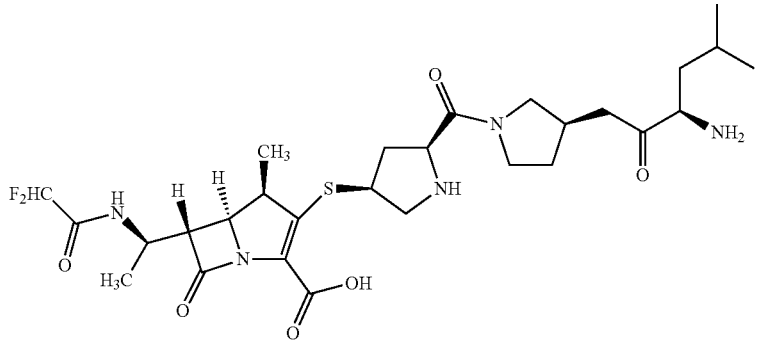<br>(4R,5S,6R)-3-((3S,5S)-5-((S)-3-((R)-2-Amino-4-methylpentanamido)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 0.92-0.99 (m, 6H) 1.15 (d, 3H), 1.17 (d, 3H), 1.75 (m, 1H), 1.77 (d, 2H), 1.91 (d, 3H), 2.04 (m, 1H), 2.23 (m, 2H), 2.85 (d, 2H), 3.19 (m, 2H), 3.36 (m, 2H), 3.57 (m, 1H), 3.75 (m, 1H), 4.14 (d, 2H), 4.44 (m, 2H), 6.29 (t, 1H). MS m/z: 615.70 (M + 1) |
| 126 | 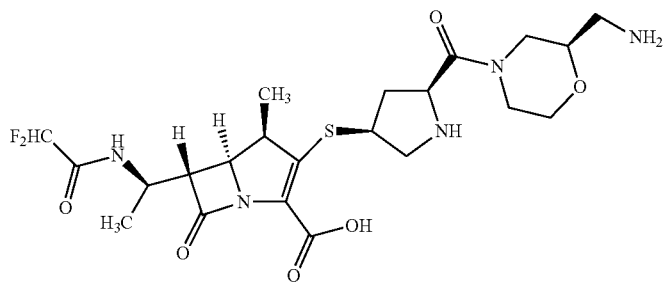<br>(4R,5S,6R)-3-((3S,5S)-5-((S)-2-(Aminomethyl)morpholine-4-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.19-1.21 (m, 3H), 1.35-1.37 (m, 3H), 1.82-1.84 (m, 1H), 2.85-2.88 (m, 2H), 3.07-3.13 (m, 2H), 3.24-3.27 (m, 1H), 3.32-3.33 (m, 3H), 3.45 (m, 3H), 3.57-3.68 (m, 2H), 3.81-3.93 (m, 2H), 4.14-4.16 (m, 1H), 4.32-4.35 (m, 1H), 4.43-4.47 (m, 1H) 6.29 (t, 1H). MS m/z: 532.6 (M + 1) |
| 127 | 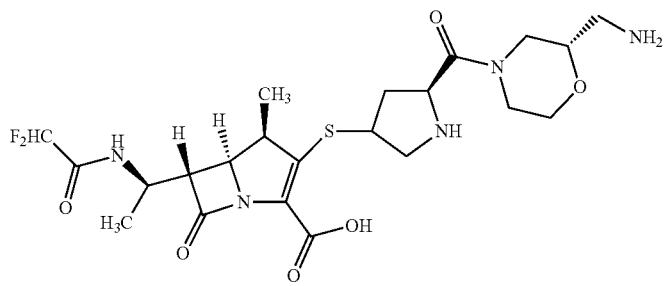<br>(4R,5S,6R)-3-((3S,5S)-5-((S)-2-(Aminomethyl)morpholine-4-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.17-1.19 (m, 3H), 1.28-1.32 (m, 3H), 1.92 (m, 1H), 2.82 (m, 2H), 3.07-3.12 (m, 2H), 3.21-3.27 (m, 2H), 3.34-3.44 (m, 3H), 3.57-3.86 (m, 3H), 3.91 (m, 2H), 4.06-4.09 (m, 1H), 4.14-4.16 (m, 1H), 4.32-4.47 (m, 2H) 6.29 (t, 1H). MS m/z: 532.6 (M + 1) |

| Examples | Structure | Analytical Data |
|---|---|---|
| 128 | 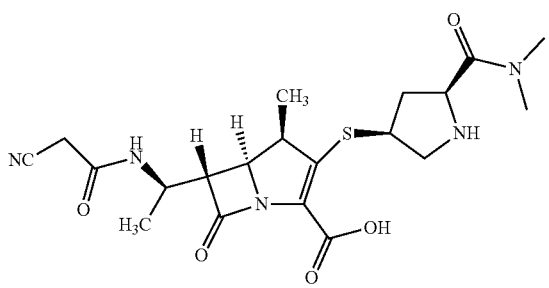<br>(4R,5S,6R)-6-((R)-1-(2-Cyanoacetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.20-1.21 (m, 3H), 1.30-1.31 (m, 3H), 1.95-2.01 (m, 1H), 3.00-3.33 (d, 6H), 3.35-3.37 (m, 2H), 3.45-3.48 (m, 1H), 3.56-3.58 (m, 2H), 3.70-3.77 (m, 3H), 4.04 (m, 1H), 4.15-4.17 (m, 1H), 4.36-4.39 (m, 1H). MS m/z: 450.5 (M + 1) |
| 129 | 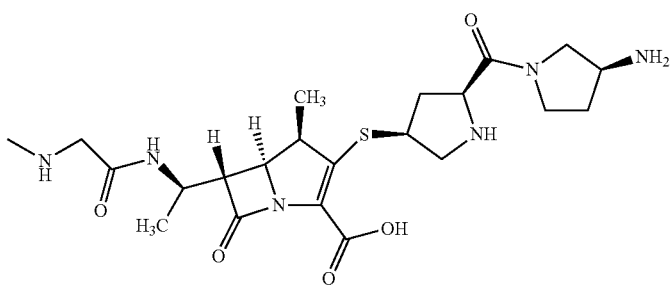<br>(4R,5S,6R)-3-((3S,5S)-5-((S)-3-Aminopyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.20-1.22 (m, 3H), 1.25-1.29 (m, 3H), 1.91 (m, 1H), 2.09 (m, 1H), 2.23 (m, 1H), 2.47 (m, 2H), 2.75 (s, 3H), 3.19 (m, 1H), 3.39 (m, 2H), 3.58 (m, 3H), 3.6-3.87 (m, 4H), 4.03 (m, 1H), 4.13 (m, 1H), 4.25 (m, 1H), 4.46 (m, 1H). MS m/z: 493.6 (M − 1) |
| 130 | 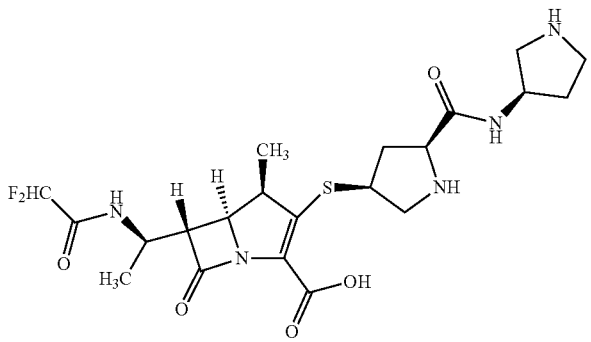<br>(4R,5S,6R)-6-((R)-1-(2,2-Difluoroacetamido)ethyl)-4-methyl-7-oxo-3-((3S,5S)-5-((S)-pyrrolidin-3-ylcarbamoyl)pyrrolidin-3-ylthio)-1-azabicyclo[3.2.0]hept-2-eoe-2-carboxylic acid | $^1$H NMR (D$_2$O) δ ppm: 1.20-1.24 (m, 3H), 1.29-1.37 (m, 3H), 1.93 (m, 1H), 2.12-2.19 (m, 2H), 2.39-2.40 (m, 1H), 2.87-2.89 (m, 1H), 3.33-3.49 (m, 3H), 3.62-3.68 (m, 2H), 3.70-3.73 (m, 2H), 3.80 (m, 2H), 4.17-4.29 (m, 1H), 4.43-4.51 (m, 2H) 6.02 (t, 1H). MS m/z: 502.6 (M + 1) |

| Examples | Structure | Analytical Data |
|---|---|---|
| 131 | 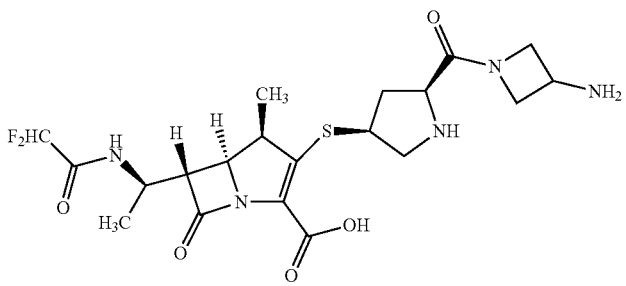<br>(4R,5S,6R)-3-((3S,5S)-5-(3-Aminoazetidine-1-carbooyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.19-1.21 (m, 3H), 1.25-1.29 (m, 3H), 1.92 (m, 1H), 2.83 (m, 2H), 3.27-3.34 (m, 2H), 3.53-3.59 (m, 2H) 3.93 (m, 2H), 4.07-4.47 (m, 5H), 4.60-4.64 (m, 1H) 6.09 (t, 1H). MS m/z: 488.52 (M + 1) |
| 132 | 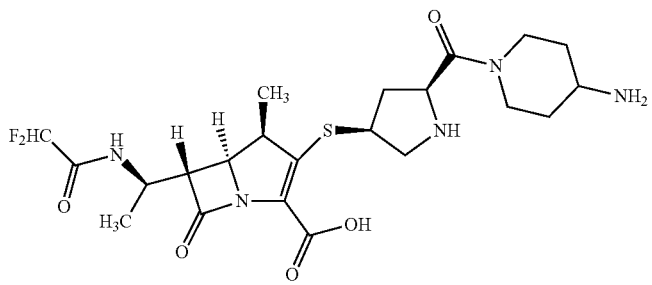<br>(4R,5S,6R)-3-((3S,5S)-5-(4-Aminopiperidine-1-carbooyl)pyrrolidin-3-ylthio)-6-((R)-1-(2,2-difluoroacetamido)ethyl)-4-methyl-7-oxo-1-azabicyclo[3.2.0]bept-2-ene-2-carboxylic acid | $^1$H NMR (D$_2$O) δ ppm: 1.21-1.22 (m, 3H), 1.30-1.37 (m, 3H), 1.57-1.63 (m, 3H), 1.92 (m, 1H), 2.13-2.16 (m, 2H), 2.81-2.92 (m, 2H), 3.26-3.36 (m, 3H), 3.51-3.59 (m, 3H), 3.94 (m, 2H), 4.14-4.16 (m, 1H), 4.43-4.48 (m, 2H), 6.02-6.29 (m, 1H). MS m/z: 516.6 (M + 1) |
| 133 | 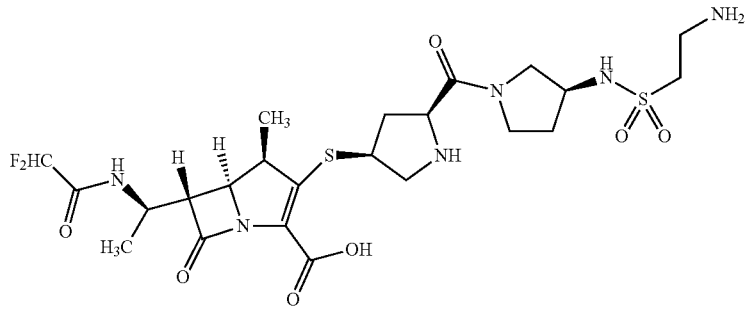<br>(4R,5S,6R)-3-((3S,5S)-5-((S)-3-(2-Aminoethylsulooamido)pyrrolidine-1-carbooyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.05-1.21 (m, 3H), 1.30-1.37 (m, 3H), 2.01 (m, 2H), 2.30-2.34 (m, 2H), 2.98 (m, 2H), 3.35 (m, 2H), 3.47-3.49 (m, 2H), 3.60-3.62 (m, 2H), 3.74-3.76 (m, 2H), 3.78 (m, 2H), 3.94 (m, 2H), 4.14-4.17 (m, 2H), 4.43-4.46 (m, 1H), 6.01 (t, 1H). MS m/z: 609.7 (M + 1) |

| Examples | Structure | Analytical Data |
|---|---|---|
| 134 | 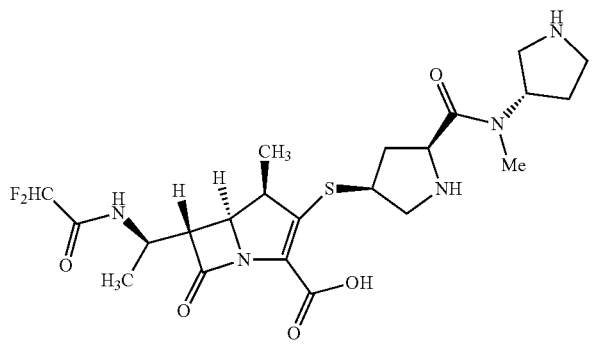<br>(4R,5S,6R)-6-((R)-1-(2,2-Difluoroacetamido)ethyl)-4-methyl-3-((3S,5S)-5-(methyl((S)-pyrrolidin-3-yl)carbamoyl)pyrrolidin-3-ylthio)-7-oxo-1-azabicyclo[3.2.0]hept-2-ene-2-carboxylic acid | $^1$H NMR (D$_2$O) δ ppm: 1.19-1.21 (m, 3H), 1.32-1.37 (m, 3H), 1.92 (m, 1H), 2.19-2.23 (m, 1H), 2.43-2.46 (m, 1H), 2.92 (m, 1H), 3.08-3.10 (s, 3H), 3.28-3.37 (m, 3H), 3.50 3.68 (m, 6H), 3.96 (m, 1H), 4.14-4.17 (m, 1H), 4.43-4.47 (m, 1H), 4.59-4.63 (m, 1H), 6.02-6.29 (t, 1H). MS m/z: 516.6 (M + 1) |
| 135 | 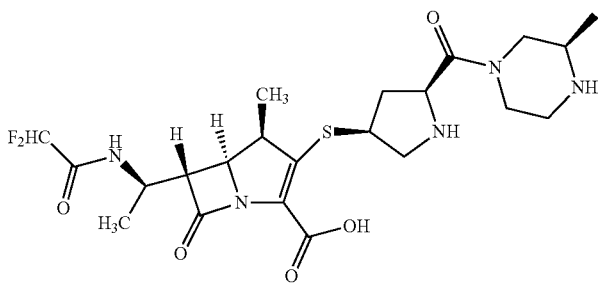<br>(4R,5S,6R)-6-((R)-1-(2,2-Difluoroacetamido)ethyl)-4-methyl-3-((3S,5S)-5-((S)-3-methylpiperazine-1-carbonyl)pyrrolidin-3-ylthio)-7-oxo-1-azabicyclo[3.2.0]hept-2-ene-2-carboxylic | $^1$H NMR (D$_2$O) δ ppm: 1.20-1.21 (d, 3H), 1.35-1.37 (d, 6H), 1.82-1.84 (m, 1H), 2.96 (m, 1H), 3.15-3.57 (m, 6H), 3.59 (m, 1H), 3.84-3.91 (m, 5H) 4.14-4.17 (m, 1H), 4.20 (m, 1H), 4.42-4.47 (m, 1H), 6.02 (t, 1H). MS m/z: 516.6 (M + 1) |
| 136 | 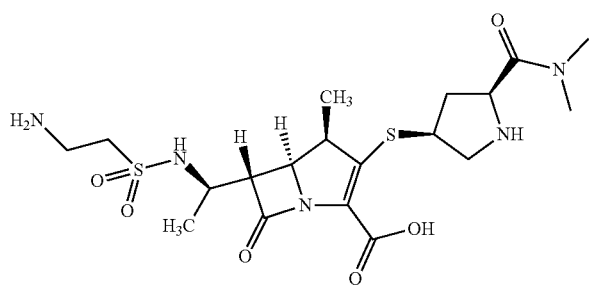<br>(4R,5S,6S)-6-((R)-1-(2-Aminoethylsulfonamido)ethyl)-3-((3S,5S)-5-(dimethylcarbmaoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.32-1.37 (m, 3H), 1.37 (m, 3H), 2.56-2.62 (m, 1H), 2.99-3.08 (m, 4H), 3.32 (m, 3H), 3.39-3.48 (m, 3H), 3.52-3.59 (m, 4H), 3.82-3.98 (m, 1H), 4.05-4.25 (m, 3H), 4.55 (m, 1H). MS m/z: 490.61 (M + 1) |

| Examples | Structure | Analytical Data |
|---|---|---|
| 137 | 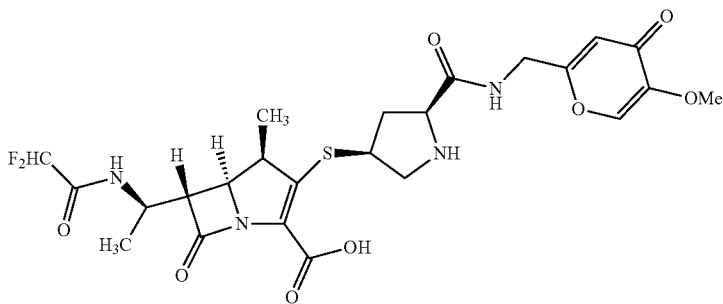<br>(4R,5S,6R)-6-((R)-1-(2,2-Difluoroacetamido)ethyl)-3-((3S,5S)-5-((5-methoxy-4-oxo-4H-pyran-2-yl)methylcarbamoyl)pyrrolidin-3-ylthio)-4-methyl-7-oxo-1-azahicyclo[3.2.0]hept-2-ene-2-carboxylic acid | $^1$H NMR (D$_2$O) δ ppm: 1.23-1.32 (m, 6H), 2.96-2.99 (m, 1H), 3.29-3.45 (m, 2H), 3.57-3.59 (m, 1H), 3.69-3.74 (m, 1H), 3.78 (s, 3H), 4.00-4.03 (m, 2H), 4.13-4.16 (m, 1H), 4.38-4.49 (m, 4H), 6.20-6.29 (m, 1H), 6.51 (s, 1H), 8.08 (s, 1H). MS m/z: 571.6 (M + 1) |
| 138 | 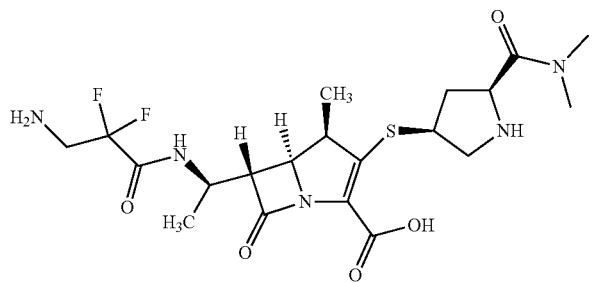<br>(4R,5S,6R)-6-((R)-1-(3-Amino-2,2-difluoropropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.20-1.22 (m, 3H), 1.29-1.32 (m, 3H), 2.96-3.00 (m, 4H), 3.07-3.11 (m, 3H), 3.31-3.39 (m, 4H), 3.60-3.66 (m, 2H), 3.81 (m, 1H), 4.01 (m, 1H), 4.16-4.18 (m, 1H), 4.46-4.49 (m, 1H), 4.71-4.81 (m, 1H). MS m/z: 490.5 (M + 1) |
| 139 | 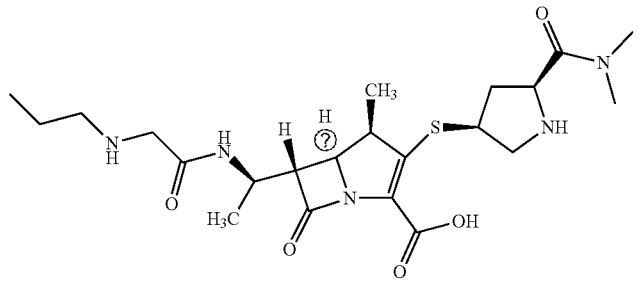<br>(4R,5S,6R)-3-((3S,5S)-5-(Dimethylcarbamoyl)pyrrolidin-3-ylthio)-4-methyl-7-oxo-6-((R)-1-(2-(propylamino)acetamido)ethyl)-1-azahicyclo[3.2.0]hept-2-ene-2-carboxylic acid | $^1$H NMR (D$_2$O) δ ppm: 0.98-1.08 (m, 6H), 1.20-1.29 (m, 5H), 1.70-1.82 (m, 3H), 2.96-3.07 (m, 7H), 3.27-3.59 (m, 4H), 3.83-3.86 (m, 2H), 3.91-3.94 (m, 2H), 4.13-4.15 (m, 1H), 4.46-4.47 (m, 1H). MS m/z: 480.6 (M − 1) |

| Examples | Structure | Analytical Data |
|---|---|---|
| 140 | 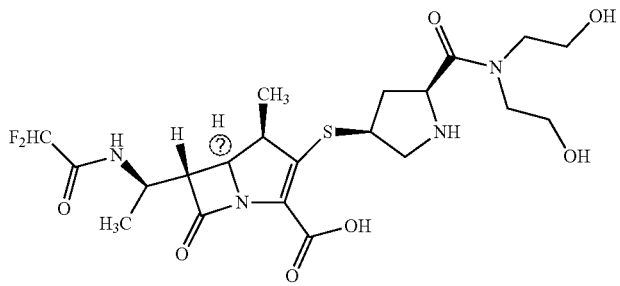<br>(4R,5S,6R)-3-((3S,5S)-5-(bis(2-Hydroxyethyl)carbamoyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.27-1.30 (m, 3H), 1.35-1.37 (m, 3H), 3.08 (m, 2H), 3.35-3.37 (m, 2H), 3.44-3.48 (m, 4H), 3.54 (m, 3H), 3.73-3.76 (m, 4H), 4.03 (m, 1H), 4.15-4.18 (m, 1H), 4.44-4.47 (m, 1H) 6.02 (t, 1H). MS m/z: 521.6 (M + 1) |
| 141 | 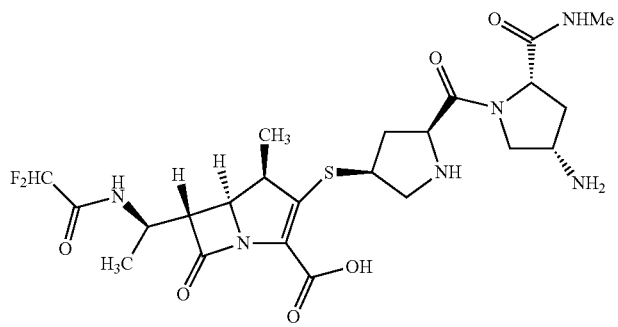<br>(4R,5S,6R)-3-((3S,5S)-5-((2S,4S)-4-Amino-2-(methylcarbamoyl)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.32-1.37 (m, 6H), 2.77-2.89 (m, 2H), 3.00 (s, 3H), 3.19-3.23 (m, 4H), 3.33-3.37 (m, 2H), 3.57-3.59 (m, 2H), 3.77-3.90 (m, 2H), 4.10-4.16 (m, 2H), 4.43-4.47 (m, 2H), 6.20-6.29 (t, 1H). MS m/z: 559.60 (M + 1) |
| 142 | 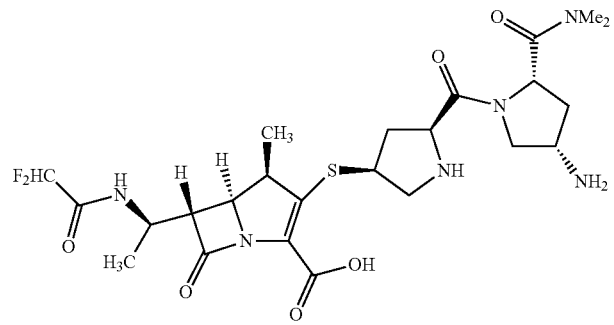<br>(4R,5S,6R)-3-((3S,5S)-5-((2S,4S)-4-Amino-2-(dimethylcarbamoyl)pyrrolidine-1-carbooyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.20-1.37 (m, 6H), 2.69-2.82 (m, 6H), 3.20-3.21 (m, 1H), 3.33-3.39 (m, 3H), 3.57-3.59 (m, 2H), 3.77-3.80 (m, 2H), 3.91-4.00 (m, 2H), 4.07-4.16 (m, 3H), 4.30 (m, 1H), 4.43-4.47 (m, 1H), 4.74-4.89 (m, 1H), 6.02-6.29 (t, 1H). MS m/z: 573.6 (M + 1) |

| Examples | Structure | Analytical Data |
|---|---|---|
| 143 | 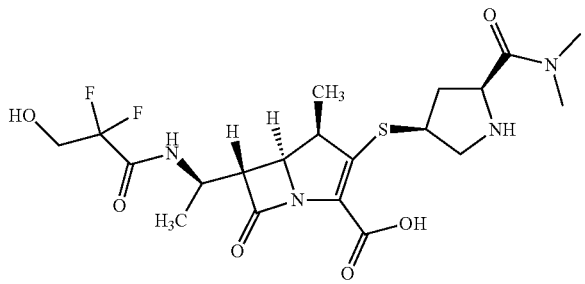<br>(4R,5S,6R)-6-((R)-1-(2,2-Difluoro-3-hydroxypropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.13-1.33 (m, 6H), 3.00-3.07 (d, 6H), 3.31-3.35 (m, 2H), 3.39-3.42 (m, 1H), 3.56-3.59 (m, 1H), 3.95-4.01 (m, 3H), 4.13-4.15 (m, 3H), 4.46-4.50 (m, 1H), 4.71 (m, 1H). MS m/z: 491.5 (M + 1) |
| 144 | 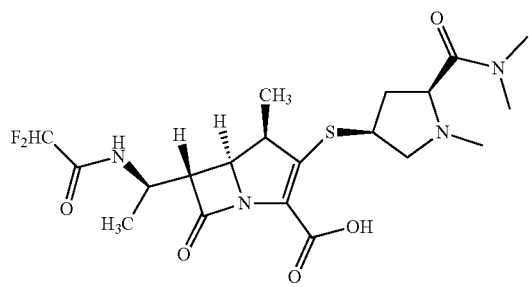<br>(4R,5S,6R)-6-((R)-1-(2,2-Difluoroacetamido)ethyl)-3-((3S,5S)-5-(dimethylcarhamoyl)-1-methylpyrrolidin-3-ylthio)-4-methyl-7-oxo-1-azabicyclo[3.2.0]hept-2-ene-2-carboxylic acid | $^1$H NMR (D$_2$O) δ ppm: 1.19-1.46 (m, 6H), 2.08 (m, 1H), 2.84-2.87 (m, 3H), 2.95-2.97 (m, 6H), 3.25-3.35 (m, 3H), 3.58-3.59 (m, 3H), 3.98 (m, 1H), 4.43-4.47 (m, 2H), 6.02-6.29 (m, 1H). MS m/z: 475.6 (M + 1) |
| 145 | 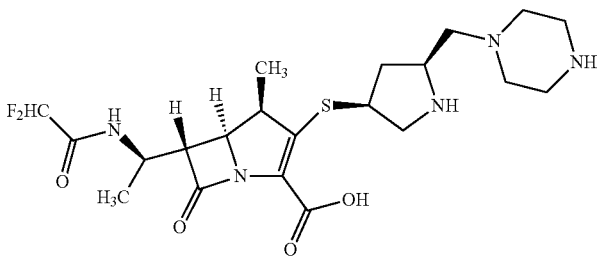<br>(4R,5S,6R)-6-((R)-1-(2,2-Difluoroacetamido)ethyl)-4-methyl-7-oxo-3-((3S,5S)-5-(piperazin-1-ylmethyl)pyrrolidin-3-ylthio)-1-azabicyclo[3.2.0]hept-2-eoe-2-carboxylic acid | $^1$H NMR (D$_2$O) δ ppm: 1.32-1.37 (m, 6H), 1.58-1.61 (m, 1H), 2.65-2.89 (m, 6H), 3.27 (m, 4H), 3.30-3.37 (m, 2H), 3.49-3.60 (m, 2H), 3.77-3.96 (m, 2H), 4.13-4.16 (m, 2H), 4.43-4.7 (m, 1H), 6.02-6.29 (m 1H). MS m/z: 488.6 (M + 1) |
| 146 | 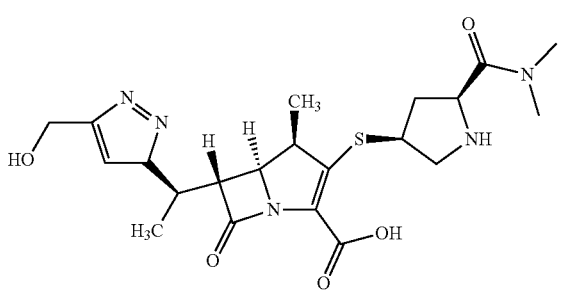<br>(4R,5S,6S)-3-((3S,5S)-5-(Dimethylcarbamoyl)pyrrolidin-3-ylthio)-6-((R)-1-(4-(hydroxymethyl)-1H-1,2,3-triazol-1-yl)ethyl)-4-methyl-7-oxo-1-azabicyclo[3.2.0]hept-2-ene-2-carboxylic acid | $^1$H NMR (D$_2$O) δ ppm: 1.12-1.14 (d, 3H), 1.67-1.87 (d, 3H), 2.90-3.05 (m, 3H), 3.11 (d, 3H), 3.22-3.26 (d, 1H), 338-3.39 (d, 1H), 3.96-3.98 (dd, 2H), 4.12-4.14 (m, 2H), 4.15 (d, 1H), 4.74 (m, 4H), 5.25-5.29 (m, 1H), 7.21-7.23 (d, 1H). MS m/z: 465.5 (M + 1) |

| Examples | Structure | Analytical Data |
|---|---|---|
| 147 | 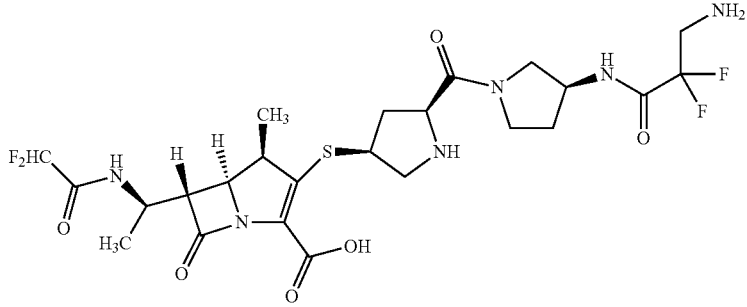<br>(4R,5S,6R)-3-((3S,5S)-5-((S)-3-(3-Amino-2,2-difluoropropanamido)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.21 (d, 3H), 1.33 (d, 3H), 2.09-2.11 (m, 2H), 2.33-2.37 (m, 2H), 2.98 (m, 2H), 3.32-3.39 (d, 3H), 3.51-3.53 (d, 2H), 3.60-3.63 (d, 2H), 3.9-3.98 (m, 2H), 4.15-4.17 (d, 2H), 4.42-4.45 (d, 1H), 4.52-4.55 (m, 1H), 6.02-6.29 (t, 1H). MS m/z: 609.6 (M + 1) |
| 148 | 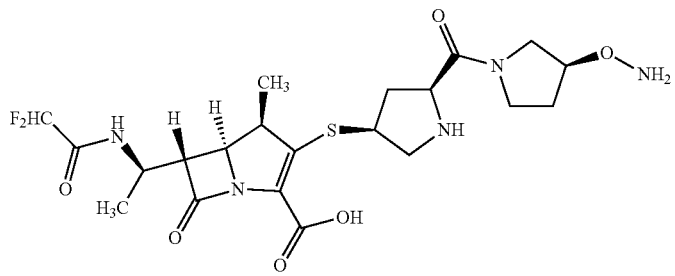<br>(4R,5S,6R)-3-((3S,5S)-5-((S)-3-(Aminooxy)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.05-1.07 (d, 3H), 1.25-1.37 (d, 3H), 1.92 (m, 2H), 3.1 (m, 2H), 3.12-3.33 (m, 3H), 3.55-3.59 (m, 3H), 3.71-75 (d, 3H), 4.15-4.17 (m, 2H), 4.81 (s, 2H), 6.02-6.29 (t, 1H). MS m/z: 518.6 (M + 1) |
| 149 | 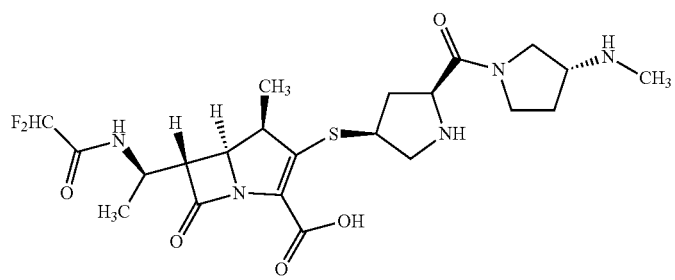<br>(4R,5S,6R)-6-((R)-1-(2,2-Difluoroacetamido)ethyl)-4-methyl-3-((3S,5S)-5-((R)-3-(methylamino)pyrrolidine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.03-1.07 (d, 3H), 1.20-1.21 (d, 3H), 1.92 (m, 1H), 2.01 (d, 1H), 2.21 (m, 1H), 2.41-2.48 (m, 2H), 2.70-2.75 (m, 3H), 3.18-3.21 (d, 3H), 3.5-3.8 (m, 6H), 4.02-4.15 (d, 2H), 4.41 (d, 1H), 6.02-6.29 (t, 1H). MS m/z: 516.6 (M + 1) |

| Examples | Structure | Analytical Data |
|---|---|---|
| 150 | 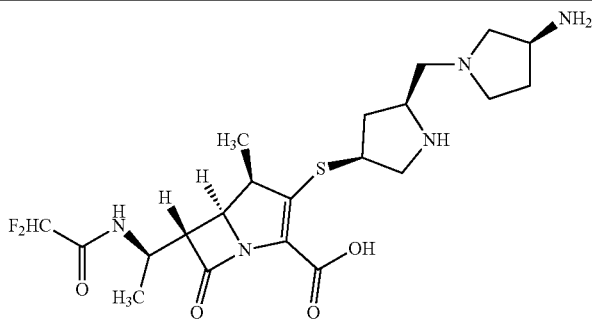<br>(4R,5S,6R)-3-(((3S,5S)-5-(((S)-3-Aminopyrrolidin-1-yl)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.06-1.07 (d, 3H), 1.22-1.28 (d, 3H), 2.32 (m, 1H), 2.46-2.48 (d, 1H), 2.72-2.78 (m, 2H), 2.80-2.82 (d, 2H), 2.88-2.89 (d, 2H), 3.32-3.33 (d, 2H), 3.35-3.37 (d, 2H), 3.58-3.60 (m, 2H), 3.87-3.88 (m, 2H), 4.14-4.17 (m, 1H), 4.45 (d, 2H), 6.02-6.29 (t, 1H). MS m/z: 488.5 (M + 1) |
| 151 | 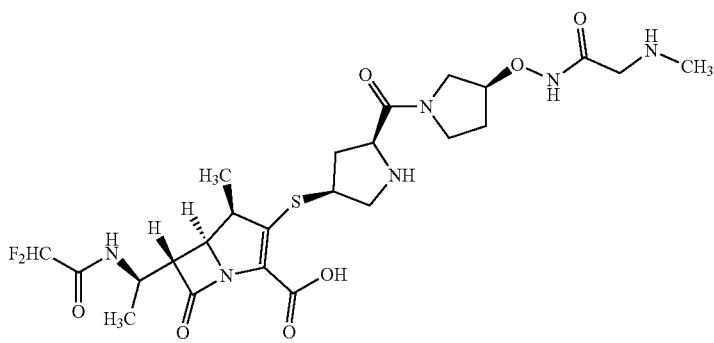<br>(4R,5S,6R)-6-((R)-1-(2,2-Difluoroacetamido)ethyl)-4-methyl-3-((3S,5S)-5-((S)-3-(2-(methylamino)acetamidooxy)pyrrolidine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.05-1.07 (d, 3H), 1.20-1.22 (d, 3H), 2.23-2.25 (m, 2H), 2.47-2.50 (m, 2H), 2.73-2.77 (d, 2H), 2.98 (m, 2H), 3.35-3.53 (2, 3H), 3.4-3.7 (m, 4H), 3.82 (m, 3H), 4.15-4.17 (m, 2H), 4.25 (d, 1H), 4.53 (m, 1H), 6.02-6.29 (t, 1H). MS m/z: 589.6 (M + 1) |
| 152 | 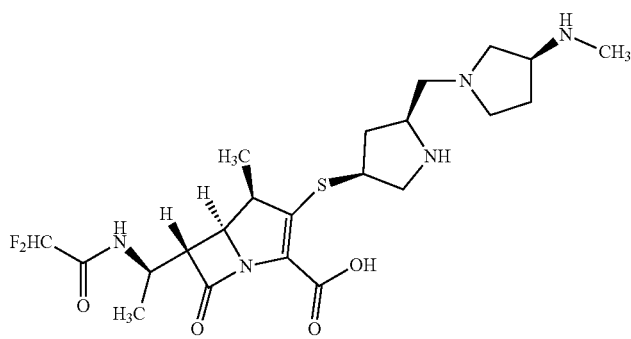<br>(4R,5S,6R)-6-((R)-1-(2,2-Difluoroacetamido)ethyl)-4-methyl-3-((3S,5S)-5-(((S)-3-(methylamino)pyrrolidin-1-yl)methyl)pyrimidin-3-ylthio)-7-oxn-1-azabicyclo[3.2.0]hept-2-ene-2-carboxylic acid | $^1$H NMR (D$_2$O) δ ppm: 1.06-1.07 (d, 3H), 1.22-1.28 (d, 3H), 2.32 (m, 1H), 2.46-2.48 (m, 2H), 2.72-2.78 (m, 2H), 2.81-2.83 (d, 2H), 2.88-2.89 (m, 2H), 3.31-3.32 (d, 2H), 3.33 (s, 3H), 3.35-3.37 (d, 2H), 3.57-3.59 (m, 1H), 3.87-3.88 (m, 2H), 4.15-4.16 (m, 1H), 4.46 (d, 2H), 6.20-6.29 (t, 1H). MS m/z: 502.5 (M + 1) |

| Examples | Structure | Analytical Data |
|---|---|---|
| 153 | 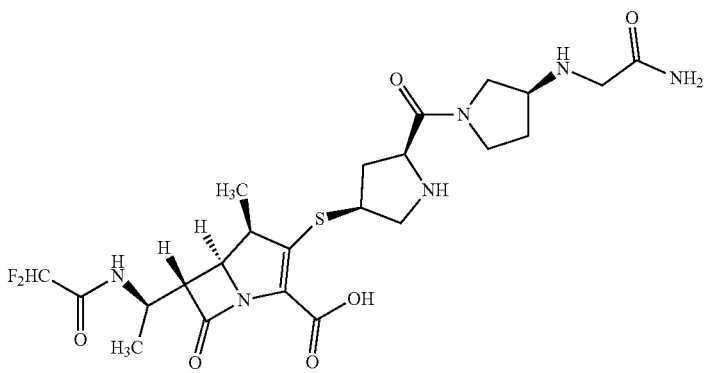<br>(4R,5S,6R)-3-((3S,5S)-5-((S)-3-(2-Amino-2-oxoethylamino)pyrrolidine-1-carbonyl)pyrrolidin-3-ylthio)-6-((R)-1-(2,2-difluoroacetamido)ethyl)-4-methyl-7-nxo-1-azabicyclo[3.2.0]hept-2-ene-2-carboxylic acid | $^1$H NMR (D$_2$O) δ ppm: 1.21-1.23 (d, 3H), 1.31-1.33 (d, 3H), 2.98 (m, 2H), 3.12 (d, 2H), 3.33-3.34 (m, 4H), 3.51-3.53 (m, 4H), 3.82-3.84 (m, 3H), 4.35-4.45 (d, 2H), 4.47 (m, 2H), 6.02-6.29 (t, 1H). MS m/z: 559.60 (M + 1) |
| 154 | 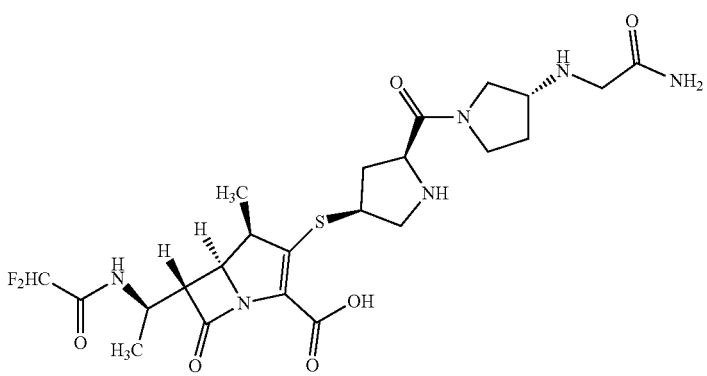<br>(4R,5S,6R)-3-((3S,5S)-5-((R)-3-(2-Amino-2-oxoethylamino)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.27-1.29 (d, 3H), 1.32-1.37 (d, 3H), 3.02 (d, 2H), 3.35-3.43 (m, 6H), 3.51-3.52 (m, 3H), 3.81-3.82 (m, 4H), 4.01-4.15 (m, 2H), 4.43-4.45 (m, 2H), 4.57 (d, 1H), 6.02-6.29 (t, 1H). MS m/z: 559.6 (M + 1) |
| 155 | 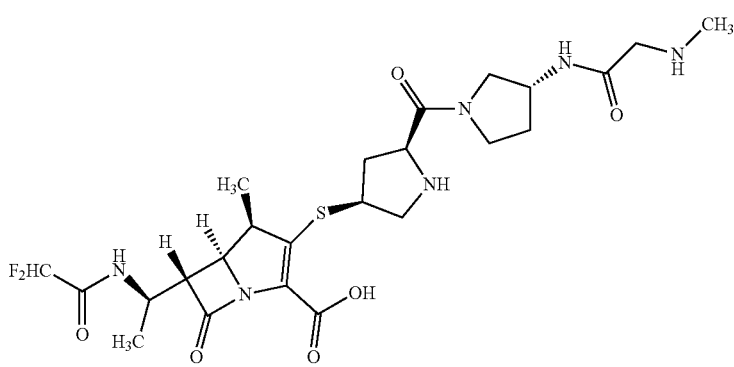<br>(4R,5S,6R)-6-((R)-1-(2,2-Difluoroacetamido)ethyl)-4-methyl-3-((3S,5S)-5-((R)-3-(2-(methylamino)acetamido)pyrrolidine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.02-1.07 (d, 3H), 1.20-1.28 (d, 3H), 2.23-2.27 (m, 2H), 2.82-3.14 (m, 4H), 3.15-3.17 (m, 5H), 3.61-3.62 (s, 3H), 3.81-3.83 (d, 4H), 4.02 (d, 2H), 4.41 (d, 2H), 6.02-6.29 (t, 1H). MS m/z: 573.6 (M + 1) |

| Examples | Structure | Analytical Data |
|---|---|---|
| 156 | 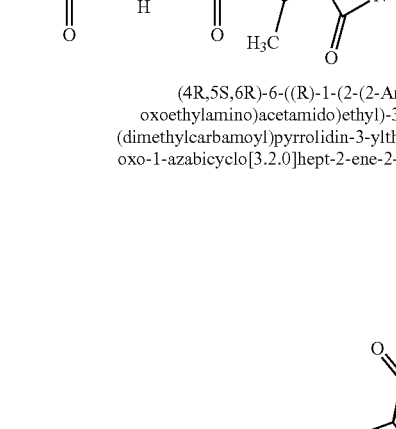<br>(4R,5S,6R)-6-((R)-1-(2-(2-Amino-2-oxoethylamino)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.17-1.19 (d, 3H), 1.21-1.29 (d, 3H), 2.99-3.00 (m, 3H), 3.07-3.09 (d, 3H), 3.37-3.46 (m, 3H), 3.51-3.52 (m, 3H), 3.81-3.82 (m, 2H), 4.01-4.15 (m, 2H), 4.43-4.45 (m, 2H), 4.57 (d, 1H), 6.02-6.29 (t, 1H). MS m/z: 495.6 (M − 1) |
| 157 | 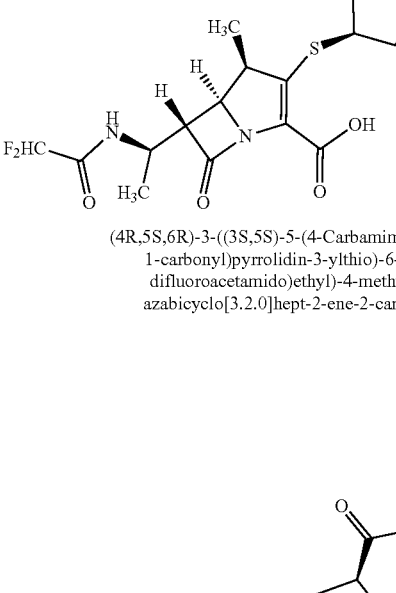<br>(4R,5S,6R)-3-((3S,5S)-5-(4-Carbamimidoylpiperazine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.19-1.21 (d, 3H), 1.32-1.37 (d, 3H), 2.86 (m, 1H), 3.19-3.22 (m, 2H), 3.32-3.37 (d, 3H), 3.46-3.57 (m, 5H), 3.61-3.62 (m, 4H), 3.90 (m, 1H), 4.14-4.16 (m, 1H), 4.36-4.38 (m, 1H) 6.02 (t, 1H). MS m/z: 544.6 (M + 1) |
| 158 | 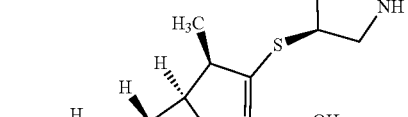<br>(4R,5S,6R)-6-((R)-1-(2,2-difluoroacetamido)ethyl)-4-methyl-3-((3S,5S)-5-(4-(2-(methylamino)-acetyl)piperazine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.19-1.27 (d, 3H), 1.30-1.37 (d, 3H), 2.91 (s, 3H), 3.31-3.33 (m, 2H), 3.54-3.56 (m, 3H), 3.5-3.57 (m, 4H), 3.63-3.68 (d, 4H), 3.94 (d, 4H), 4.14-4.19 (m, 2H), 4.55 (m, 1H), 6.02-6.29 (t, 1H). MS m/z: 573.6 (M + 1) |

| Examples | Structure | Analytical Data |
|---|---|---|
| 159 | 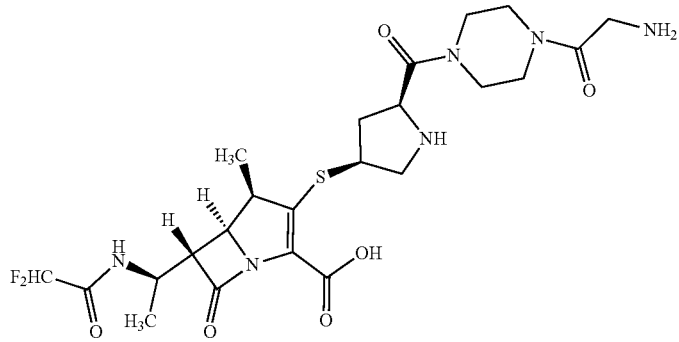<br>(4R,5S,6R)-3-((3S,5S)-5-(4-(2-Aminoacetyl)piperazine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.21-1.27 (d, 3H), 1.29-1.35 (d, 3H), 2.89-2.91 (m, 3H), 3.27-3.33 (d, 2H), 3.35-3.37 (d, 3H), 3.57-3.59 (d, 3H), 3.62-3.64 (d, 2H), 3.70-3.71 (d, 2H), 3.92-3.98 (d, 2H), 4.05-4.06 (d, 1H), 4.14-4.16 (d, 1H), 4.75-4.81 (d, 2H), 6.02-6.29 (t, 1H). MS m/z: 559.60 (M + 1) |
| 160 | 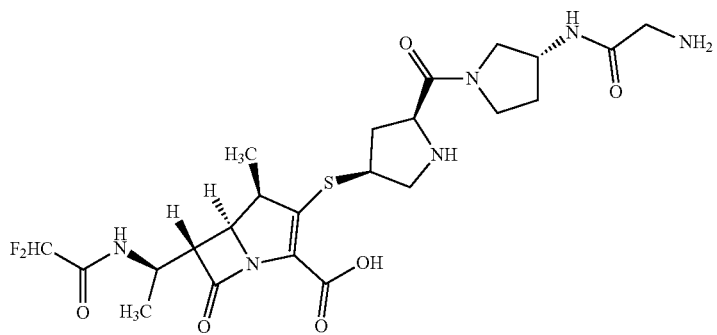<br>(4R,5S,6R)-3-((3S,5S)-5-((R)-3-(2-Aminoacetamido)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.27-1.29 (d, 3H), 1.32-1.36 (d, 3H), 3.02 (m, 3H), 3.35-3.43 (m, 5H), 3.48-3.56 (d, 3H), 3.82 (m, 3H), 4.01-4.15 (m, 2H), 4.18 (m, 1H), 4.43-4.53 (m, 1H), 4.57-4.79 (m, 1H), 6.02-6.29 (t, 1H). MS m/z: 559.6 (M + 1) |
| 161 | 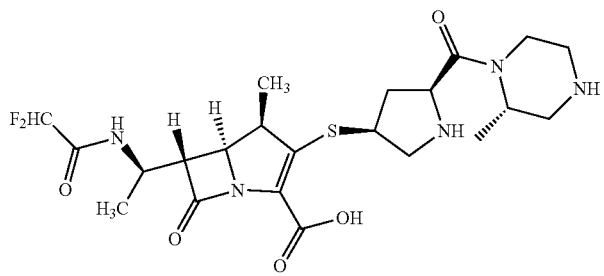<br>(4R,5S,6R)-6-((R)-1-(2,2-Difluoroacetamido)ethyl)-4-methyl-3-((3S,5S)-5-((S)-2-methylpiperazine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.06-1.07 (d, 3H), 1.21-1.25 (d, 3H), 3.13 (m, 2H), 3.33 (m, 4H), 3.46 (m, 3H), 3.58-3.59 (m, 3H), 3.82 (m, 3H), 3.98 (m, 2H), 4.15-4.17 (m, 1H), 4.43-4.47 (t, 2H), 6.02-6.29 (t, 1H). MS m/z: 516.6 (M − 1) |

| Examples | Structure | Analytical Data |
|---|---|---|
| 162 | 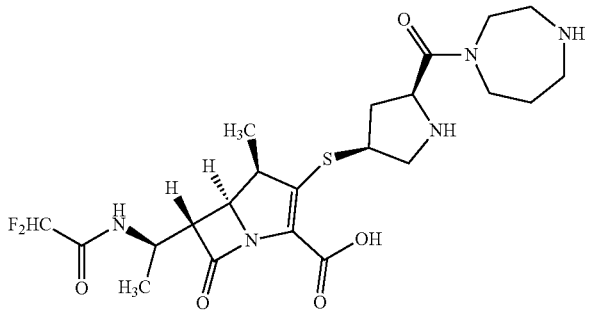<br>(4R,5S,6R)-3-((3S,5S-5-(1,4-Diazepane-1-carbonyl)pyrrolidin-3-ylthio)-6-((R)-1-(2,2-difluoroacetamido)ethyl)-4-methyl-7-oxo-1-azahicyclo[3.2.0]hept-2-ene-2-carboxylic acid | $^1$H NMR (D$_2$O) δ ppm: 1.06-1.10 (d, 3H), 1.30-1.37 (d, 3H), 2.75 (d, 4H), 2.95 (m, 1H), 3.01-3.11 (d 3H), 3.30 (m, 4H), 3.60-3.62 (d, 3H), 3.72 (d, 1H), 3.80-4.01 (m, 2H), 4.15-4.17 (d, 1H), 4.58 (m, 1H), 6.02-6.29 (t, 1H). MS m/z: 516.6 (M + 1) |
| 163 | 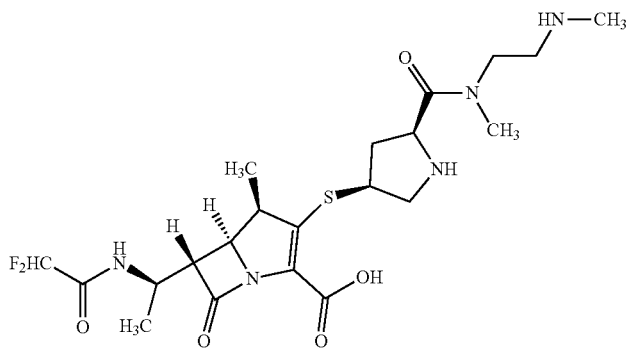<br>(4R,5S,6R)-6-((R)-1-(2,2-Difluoroacetamido)ethyl)-4-methyl-3-((3S,5S)-5-(methyl(2-(methylamino)ethyl)carbamoyl)pyrrolidin-3-ylthio)-7-oxo-1-azabicyclo[3.2.0]hept-2-ene-2-carboxylic acid | $^1$H NMR (D$_2$O) δ ppm: 1.06-1.07 (d, 3H), 1.30-1.37 (d, 3H), 2.20-2.21 (m, 2H), 3.01 (m, 1H), 3.33-3.39 (m, 6H), 3.55-3.58 (d, 2H), 3.60 (d, 1H), 3.78 (d, 2H), 3.78-3.82 (d, 2H), 4.15-4.17 (d, 2H), 4.15-4.17 (d, 1H), 4.43-4.47 (t, 1H), 6.02-6.29 (t, 1H). MS m/z: 504.6 (M + 1) |
| 164 | 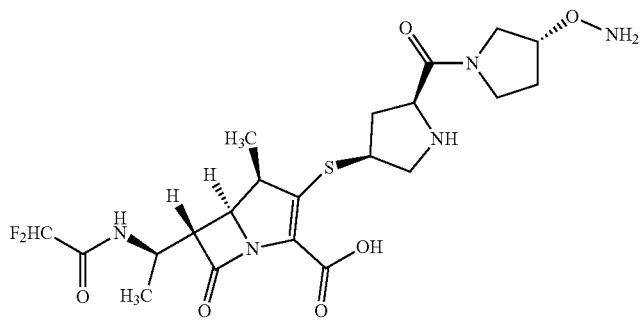<br>(4R,5S,6R)-3-((3S,5S)-5-((R)-3-(Aminooxy)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.05-1.07 (d, 3H), 1.30-1.37 (d, 3H), 2.02-2.14 (m, 2H), 3.04 (m, 1H), 3.33-3.35 (d, 1H), 3.37 (dd, 1H), 3.41-3.42 (d, 1H), 3.52-3.58 (d, 4H), 3.72-3.74 (d, 2H), 4.02-4.04 (d, 1H), 4.15-4.18 (d, 1H), 4.43-4.47 (m, 1H), 4.56-4.60 (m, 1H), 4.63-4.65 (m, 1H), 6.02-6.29 (t, 1H). MS m/z: 518.6 (M + 1) |

| Examples | Structure | Analytical Data |
|---|---|---|
| 165 | 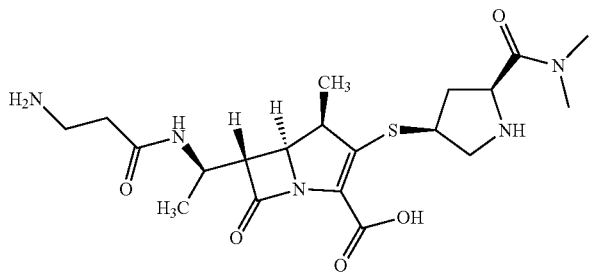<br>(4R,5S,6R)-6-((R)-1-(3-Aminopropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.02-1.05 (d, 3H), 1.08-1.11 (d, 3H), 2.81 (m, 3H), 3.01-3.21 (s, 3H), 3.22-3.25 (d, 3H), 3.26-3.29 (d, 3H), 3.51-3.52 (m, 3H) 3.80 (d, 2H), 4.02-4.06 (m, 1H), 4.09-4.13 (m, 1H), 4.61 (d, 1H). MS m/z: 452.6 (M − 1) |
| 166 | 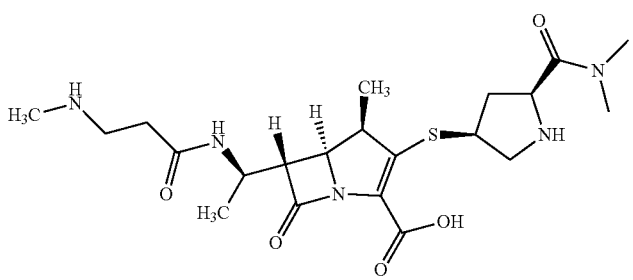<br>(4R,5S,6R)-3-((3S,5S)-5-(Dimethylcarbamoyl)pyrrolidin-3-ylthio)-4-methyl-6-((R)-1-(3-(methylamino)propanamido)ethyl)-7-oxo-1-azabicyclo[3.2.0]hept-2-ene-2-carboxylic acid | $^1$H NMR (D$_2$O) δ ppm: 0.86-0.88 (m, 3H), 1.21-1.34 (d, 3H), 2.50-2.85 (s, 3H), 2.86-3.01 (s, 3H), 3.26-3.29 (m, 6H), 3.51-3.52 (m, 3H) 3.80 (m, 3H), 4.02-4.07 (d, 2H), 4.09-4.13 (m, 1H), 4.49 (d, 1H) 4.61 (d, 1H). MS m/z: 466.6 (M − 1) |
| 167 | 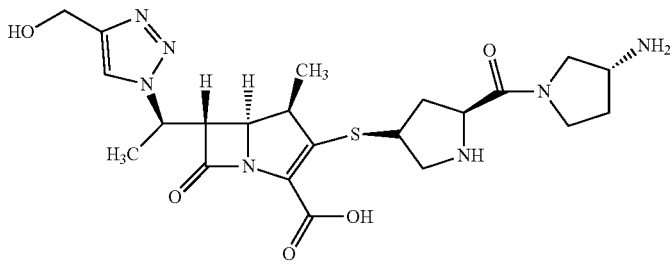<br>(4R,5S,6R)-3-((3R,5S)-5-((R)-3-Aminopyrrolidine-1-carbonyl)pyrrolidin-3-ylthio)-6-((R)-1-(4-(hydroxymethyl)-1H-1,2,3-triazol-1-yl)ethyl)-4-methyl-7-oxo-1-azabicyclo[3.2.0]hept-2-ene-2-carboxylic acid | $^1$H NMR (D$_2$O) δ ppm: 0.9-0.95 (d, 3H), 1.01-1.19 (d, 6H), 1.92-2.60 (m, 5H), 3.24 (m, 1H), 3.34-3.36 (d, 2H), 3.63-3.68 (d, 3H), 3.70 (d, 1H), 3.96 (d, 2H), 4.96 (m, 2H), 7.21-7.23 (s, 1H). MS m/z: 506.6 (M + 1) |
| 168 | 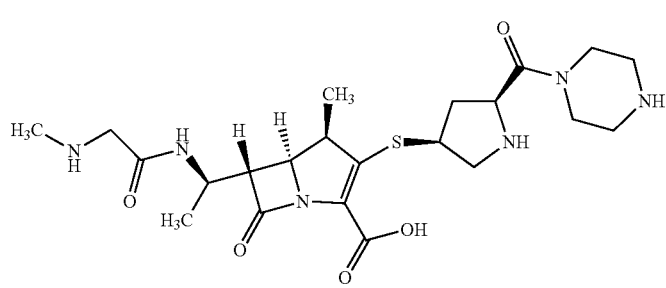<br>(4R,5S,6R)-4-Methyl-6-((R)-1-(2-(methylamino)acetamido)ethyl)-7-oxo-3-((3S,5S)-5-(piperazine-1-carbonyl)pyrrolidin-3-ylthio)-1-azabicycln[3.2.0]hept-2-ene-2-carboxylic acid | $^1$H NMR (D$_2$O) δ ppm: 1.07-1.08 (d, 3H), 1.20-1.22 (d, 3H), 2.60-2.62 (m, 2H), 2.75-2.76 (d, 3H), 2.96 (m, 2H), 3.28-3.33 (m, 4H), 3.58-3.59 (d, 3H), 3.81-3.88 (dd, 1H), 3.92 (m, 4H), 4.13 (m, 2H), 4.13-4.15 (d, 1H) 4.46 (d, 1H). MS m/z: 493.6 (M − 1) |

| Examples | Structure | Analytical Data |
|---|---|---|
| 169 | 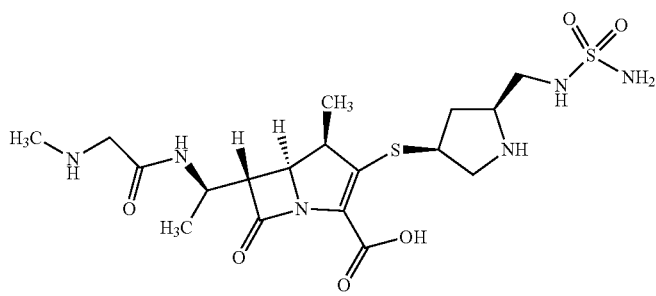<br>(4R,5S,6R)-4-Methyl-6-((R)-1-(2-(methylamino)acetamido)ethyl)-7-oxo-3-((3S,5S)-5-((sulfamoylamino)methyl)pyrrolidin-3-ylthio)-1-azabicyclo[3.2.0]hept-2-ene-2-carboxylic acid | $^1$H NMR (D$_2$O) δ ppm: 1.21-1.22 (d, 3H), 1.25-1.29 (d, 3H), 2.75 (s, 3H), 3.36-3.38 (d, 3H), 3.38 (m, 2H), 3.50 (m, 2H), 3.61 (m, 2H), 3.87 (m, 2H), 4.52 (m, 2H) 4.63 (m, 1H). MS m/z: 489.6 (M + 1) |
| 170 | 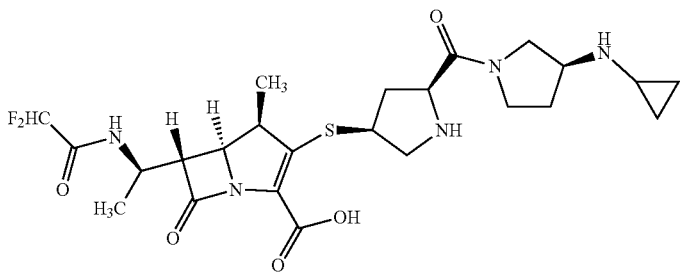<br>(4R,5S,6R)-3-((3S,5S)-5-((S)-3-(Cyclopropylamino)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 0.88 (m, 4H), 1.02 (m, 1H), 1.21-1.27 (d, 3H), 1.46 (d, 3H), 2.44-2.66 (3H, m), 3.00-3.03 (m, 1H), 3.35-3.4 (d, 2H), 3.60-3.64 (d, 2H), 3.72-3.77 (d, 2H), 3.79 (d, 2H), 4.01-4.08 (d, 2H), 4.11-4.15 (d, 2H), 4.43-4.47 (d, 1H), 6.02-6.29 (t, 1H). MS m/z: 542.6 (M + 1) |
| 171 | 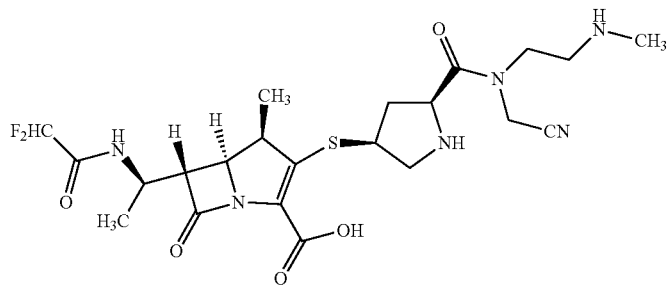<br>(4R,5S,6R)-3-((3S,5S)-5-((Cyanomethyl)(2-(methylamino)ethyl)carbamoyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.06-1.07 (d, 3H), 1.21 (d, 3H), 2.76 (m, 4H), 3.03-3.09 (t, 3H), 3.33-3.35 (d, 3H), 3.73 (m, 3H), 4.16-4.18 (d, 2H), 4.26 (d, 1H), 4.30 (d, 2H), 6.02-6.29 (t, 1H). MS m/z: 529.6 (M + 1) |

-continued

| Examples | Structure | Analytical Data |
|---|---|---|
| 172 | 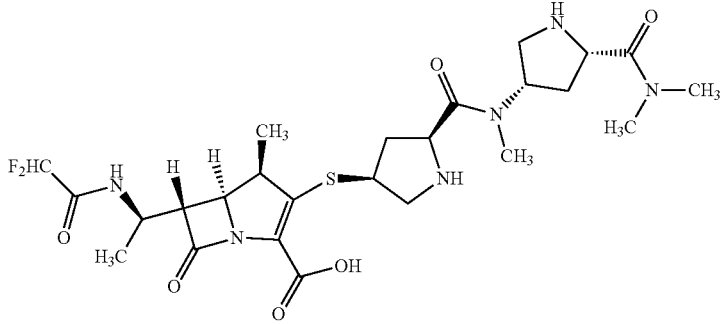<br>(4R,5S,6R)-6-((R)-1-(2,2-Difluoroacetamido)ethyl)-3-((3S,5S)-4-(((3S,5S)-5-(dimethylcarbamoyl)pyrrolidin-3-yl)(methyl)carbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.07-1.20 (d, 3H), 1.26-1.28 (d, 3H), 1.80-1.82 (m, 1H), 2.82 (s, 3H), 2.89 (s, 3H), 3.07 (s, 3H), 3.17 (d, 2H), 3.26 (d, 3H), 3.34-3.35 (d, 3H), 3.57-3.59 (m, 3H), 4.14-4.16 (m, 2 H), 4.45-4.63 (d, 2H), 6.02-6.29 (t, 1H). MS m/z: 587.7 (M + 1) |
| 173 | 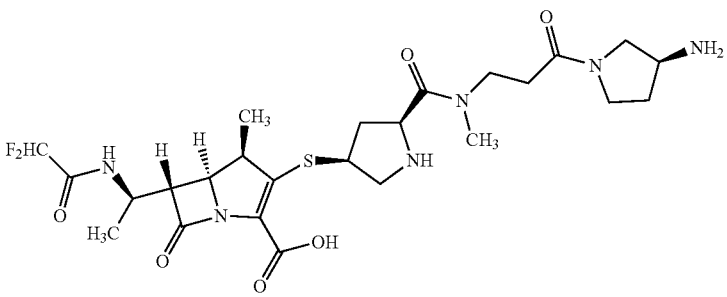<br>(4R,5S,6R)-3-((3S,5S)-5-((3-((S)-3-Aminopyrrolidin-1-yl)-3-oxopropyl)(methyl)carbamoyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.21-1.23 (d, 3H), 1.28-1.35 (d, 3H), 2.30 (m, 2H), 2.48 (d, 2H), 2.64-2.66 (m, 2H), 2.77 (d, 2H), 2.96 (d, 2H), 3.09-3.27 (s, 3H), 3.27 (m, 2H), 3.61 (m, 2H), 3.71 (m, 3H), 4.01 (d, 2H), 4.21 (d, 1H), 4.44 (d, 1H), 6.02-6.29 (t, 1H). MS m/z: 587.7 (M + 1) |
| 174 | 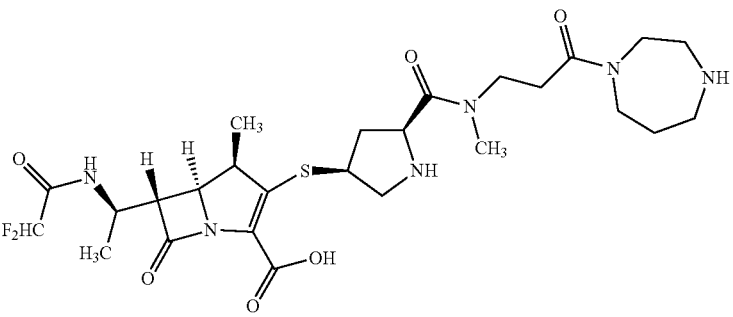<br>(4R,5S,6R)-3-((3S,5S)-5-((3-(1,4-Diazepan-1-yl)-3-oxopropyl)(methyl)carbamoyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.05-1.07 (d, 3H), 1.20-1.37 (d, 6H), 2.75 (m, 3H), 2.95 (m, 3H), 3.08 (m, 3H), 3.32-3.46 (m, 6H), 3.58-3.59 (d, 2H), 3.74-3.81 (d, 2H), 4.14 (d, 2H), 4.45 (m, 3H), 6.02-6.29 (t, 1H). MS m/z: 601.6 (M + 1) |

| Examples | Structure | Analytical Data |
|---|---|---|
| 175 | 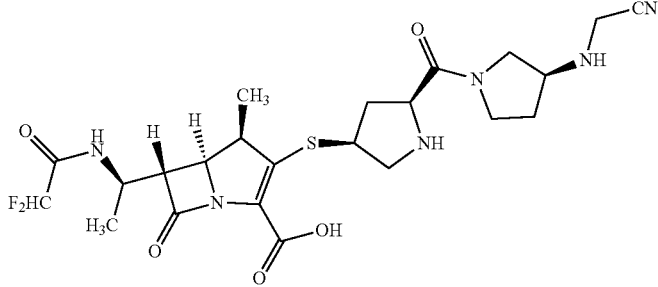<br>(4R,5S,6R)-3-((3S,5S)-5-((S)-3-(Cyanomethylamino)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.19-1.21 (d, 3H), 1.35-1.36 (d, 3H), 1.97-1.99 (m, 1H), 2.22-2.35 (m, 2H), 3.02-3.15 (m, 1H), 3.32-3.36 (m, 1H), 3.44-3.48 (m, 2H), 3.58-3.70 (m, 3H), 3.73-3.78 (m, 2H), 3.81-3.88 (m, 2H), 4.04-4.06 (m, 1H), 4.14-4.15 (m, 2H), 4.43-4.44 (m, 1H), 4.67-4.81 (m, 1H), 6.01-6.28 (t, 1H). MS m/z: 541.6 (M + 1) |
| 176 | 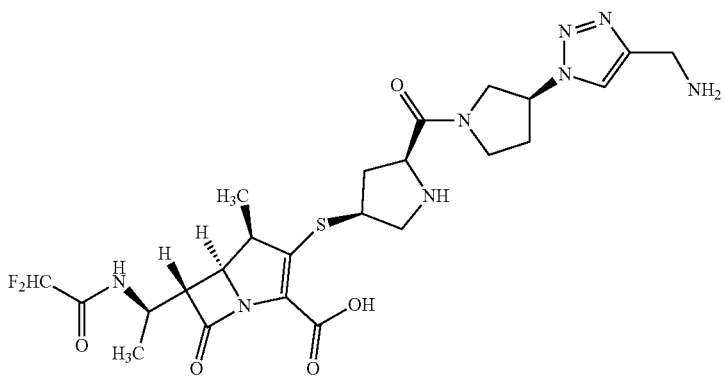<br>(4R,5S,6R)-3-((3S,5S)-5-((S)-3-(4-(Aminomethyl)-1H-1,2,3-triazol-1-yl)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.17-1.20 (d, 3H), 1.36-1.37 (d, 3H), 1.92 (m, 1H), 2.57-2.74 (m, 3H), 3.11 (m, 2H), 3.31-3.46 (m, 2H), 3.58-3.59 (m, 1H), 3.72-3.77 (m, 3H), 3.87 (m, 1H), 4.04-4.07 (m, 2H), 4.16 (m, 1H), 4.34 (m, 2H), 4.41-4.45 (m, 1H), 5.44 (m, 1H), 6.02-6.29 (t, 1H). MS m/z: 583.6 (M + 1) |
| 177 | 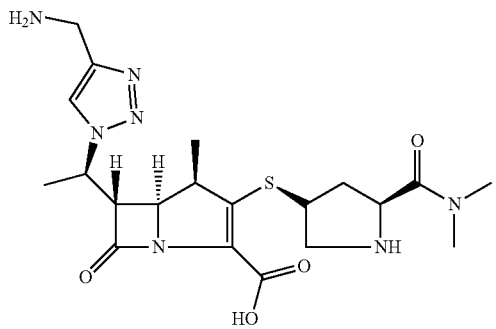<br>(4R,5S,6S)-6-((R)-1-(4-(Aminomethyl)-1H-1,2,3-triazol-1-yl)ethyl)-3-((3R,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.01-1.03 (d, 3H), 1.67-1.69 (d, 3H), 1.75-1.77 (d, 1H), 1.92 (m, 2H), 2.99 (s, 3H), 3.09 (s, 3H), 3.35 (m, 3H), 3.75-3.78 (m, 2H), 3.84-3.97 (m, 2H), 4.35 (s, 2H), 8.24 (s, 1H). MS m/z: 464.6 (M + 1) |

| Examples | Structure | Analytical Data |
|---|---|---|
| 178 | 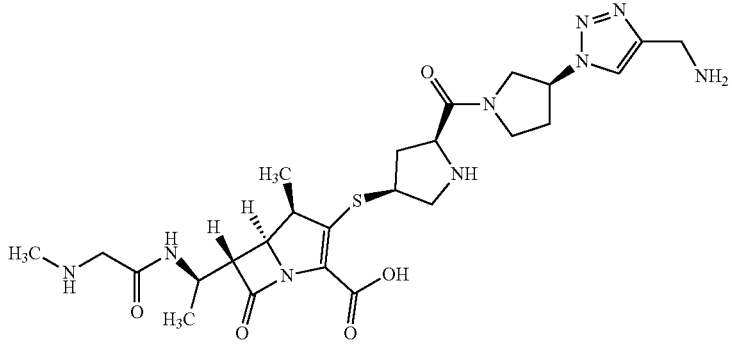<br>(4R,5S,6R)-3-((3S,5S)-5-((S)-3-(4-(Aminomethyl)-1H-1,2,3-triazol-1-yl)pyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-1-carboxylic acid | $^1$H NMR (D$_2$O) δ ppm: 1.06-1.07 (d, 3H), 1.14-1.16 (d, 3H), 1.92 (m, 1H), 2.76 (s, 3H), 2.96 (m, 2H), 3.11 (m, 2H), 3.38-3.40 (d, 3H), 3.40-3.41 (m, 2H), 3.58-3.60 (m, 2H), 3.76-3.78 (d, 3H), 3.93-3.96 (m, 2H), 4.01-4.03 (m, 3H), 4.25 (s, 2H). MS m/z: 574.6 (M − 1) |
| 179 | 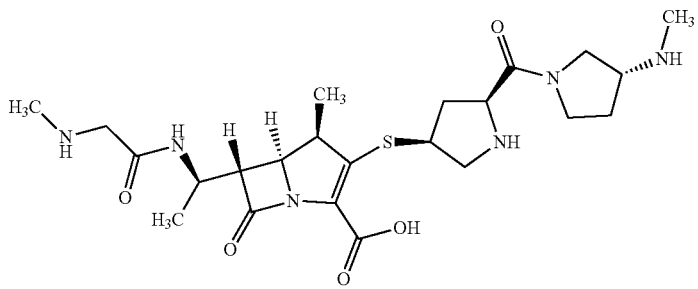<br>(4R,5S,6R)-4-Methyl-6-((R)-1-(2-(methylamino)acetamido)ethyl)-3-((3S,5S)-5-((R)-3-(methylamino)pyrrolidine-1-carbonyl)pyrrolidin-3-ylthio)-7-oxo-1-azabicyclo[3.2.0]hept-2-ene-2-carboxylic acid | $^1$H NMR (D$_2$O) δ ppm: 1.06-1.07 (d, 3H), 1.15-1.17 (d, 3H), 1.91 (m, 1H), 2.12 (m, 1H), 2.43-2.47 (m, 2H), 2.48 (m, 2H), 2.99 (m, 1H), 3.02 (m, 1H), 3.13 (m, 3H), 3.45-3.47 (m, 4H), 3.58-3.60 (m, 2H), 3.76-3.78 (d, 3H), 3.93-3.96 (m, 2H), 4.02 (m, 2H), 4.34 (m, 1H). MS m/z: 507.6 (M − 1) |
| 180 | 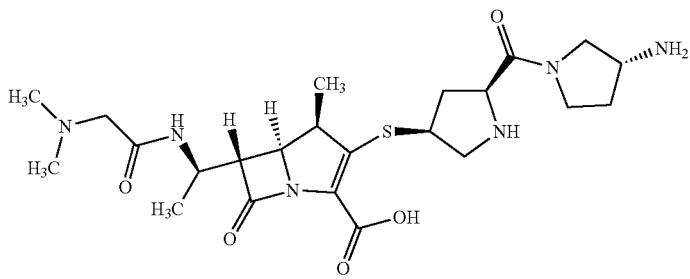<br>(4R,5S,6R)-3-((3S,5S)-5-((R)-3-Aminopyrrolidine-1-carbonyl)pyrrolidin-3-ylthio)-6-((R)-1-(2-(dimethylamino)acetamido)ethyl)-4-methyl-7-oxo-1-azabicyclo[3.2.0]hept-2-ene-2-carboxylic acid | $^1$H NMR (D$_2$O) δ ppm: 1.08-1.10 (d, 3H), 1.20-1.22 (d, 3H), 1.91 (m, 1H), 2.46 (m, 2H), 2.81 (s, 6H), 2.92 (m, 1H), 3.59 (d, 2H), 3.34-3.38 (m, 2H), 3.40 (d, 3H), 3.60-3.64 (m, 2H), 3.71 (d, 1H), 3.82 (m, 3H), 4.01 (m, 1H), 4.46 (m, 1H). MS m/z: 507.6 (M − 1) |

| Examples | Structure | Analytical Data |
|---|---|---|
| 181 | 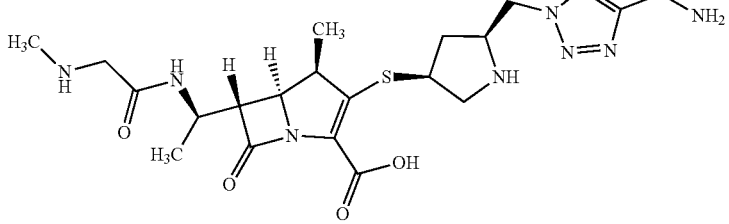<br>(4R,5S,6R)-3-((3S,5S)-5-((4-(Aminomethyl)-1H-1,2,3-triazol-1-yl)methyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.18-1.19 (d, 3H), 1.20-1.21 (d, 3H), 1.27-1.29 (d, 2H), 1.91 (m, 1H), 2.23 (d, 1H), 2.73 (s, 3H), 3.05 (m, 2H), 3.22-3.26 (d, 2H), 3.35 (d, 1H), 3.48-3.50 (dd, 1H), 3.76-3.78 (dd, 2H), 4.01 (m, 1H), 4.12 (s, 2H), 4.35-4.37 (d, 1H) 4.63 (m, 1H). MS m/z: 491.6 (M − 1) |
| 182 | 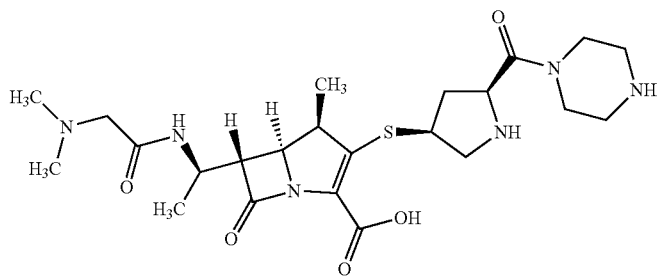<br>(4R,5S,6R)-6-((R)-1-(2-(Dimethylamino)acetamido)ethyl)-4-methyl-7-oxo-3-((3S,5S)-5-(piperazine-1-carbonyl)pyrrolidin-3-ylthio)-1-azabicyclo[3.2.0]hept-2-ene-2-carboxylic acid | $^1$H NMR (D$_2$O) δ ppm: 1.07-1.08 (d, 3H), 1.22-1.29 (d, 3H), 1.82-1.85 (m, 1H), 2.60-2.62 (m, 2H) 2.55 (m, 1H), 2.76 (s, 3H), 2.91-2.93 (m, 1H), 3.30 (s, 6H), 3.47 (m, 1H), 3.76-3.78 (m, 8H), 4.21 (m, 1H), 4.44-4.52 (m, 2H). MS m/z: 507.6 (M − 1) |
| 183 | 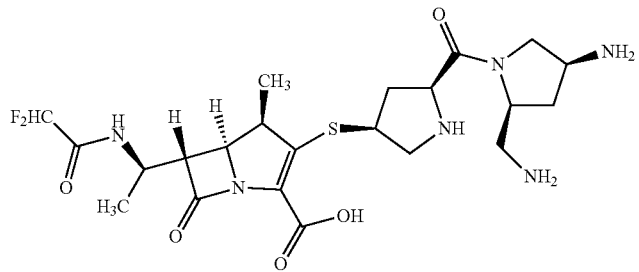<br>(4R,5S,6R)-3-((3S,5S)-5-((2S,4S)-4-Amino-2-(aminomethyl)pyrroldine-1-cahonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.07 (d, 3H), 1.32-1.35 (d, 3H), 1.91-1.95 (m, 2H), 2.46 (m, 1H), 2.56 (m, 4H), 2.48 (m, 1H), 3.31 (m, 2H), 3.55 (d, 1H), 3.74-3.76 (m, 1H), 3.92 (m, 1H), 4.00-4.02 (m, 1H), 4.14-4.17 (d, 1H), 4.34-4.47 (m, 3H), 6.02-6.29 (t, 1H). MS m/z: 531.6 (M + 1) |
| 184 | 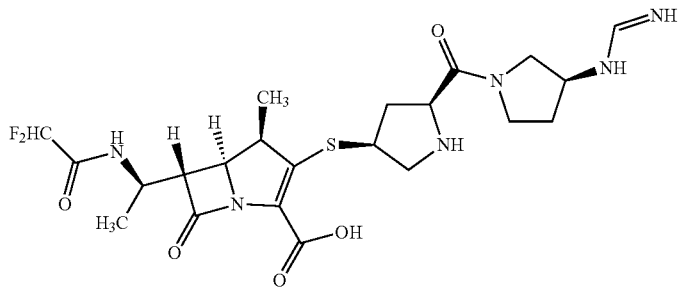<br>(4R,5S,6R)-6-((R)-1-(2,2-Difluoroacetamido)ethyl)-3-((3S,5S)-5-((S)-3-formimidamidopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.06-1.07 (d, 3H), 1.32-1.35 (d, 3H), 2.16-2.27 (m, 1H), 2.95 (m, 1H), 2.81-2.87 (m, 2H), 3.18 (m, 2H), 3.35 (m, 2H), 3.58-3.60 (d, 3H), 3.71-3.72 (m, 3H), 4.15-4.17 (m, 2H), 4.42 (d, 2H), 6.02-6.29 (t, 1H). MS m/z: 529.6 (M + 1) |

| Examples | Structure | Analytical Data |
|---|---|---|
| 185 | 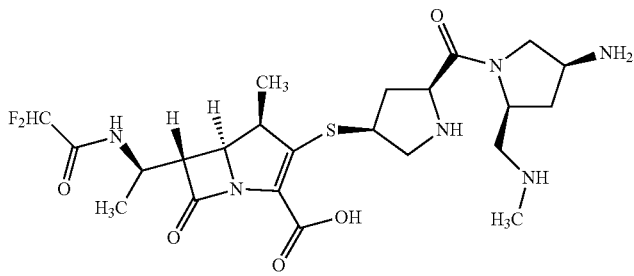<br>(4R,5S,6R)-3-((3S,5S)-5-((2S,4S)-4-Amino-2-((methylamino)methyl)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.11-1.16 (d, 3H), 1.32-1.35 (d, 3H), 1.79-1.80 (m, 2H), 2.46 (m, 2H), 2.75-2.76 (s, 3H), 2.86 (m, 2H), 3.23-3.26 (d, 3H), 3.34 (m, 1H), 3.56 (d, 1H), 3.73 (m, 1H), 3.92 (m, 1H), 4.06-4.07 (d, 1H), 4.15-4.17 (d, 1H), 4.39-4.45 (m, 3H), 6.19 (t, 1H). MS m/z: 545.6 (M + 1) |
| 186 | 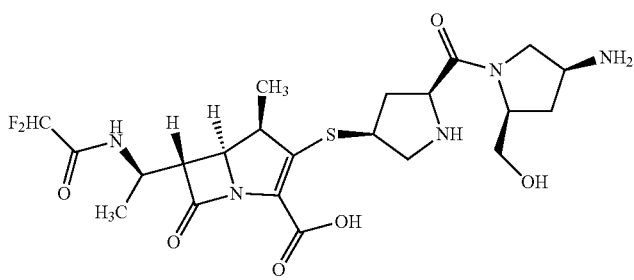<br>(4R,5S,6R)-3-((3S,5S)-5-((2S,4S)-4-Amino-2-(hydroxymethyl)pyrroldine-1-carhonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.21-1.26 (d, 3H), 1.30-1.32 (d, 3H), 1.79-1.80 (m, 2H), 2.65-2.69 (m, 1H), 2.81-2.82 (m, 1H), 3.22-3.32 (d, 2H), 3.34 (m, 1H), 3.57-3.59 (m, 3H), 3.90-3.92 (m, 1H), 4.06-4.08 (m, 3H), 4.15-4.17 (d, 1H) 4.39-4.47 (dd, 3H), 6.19 (t, 1H). MS m/z: 532.6 (M + 1) |
| 187 | 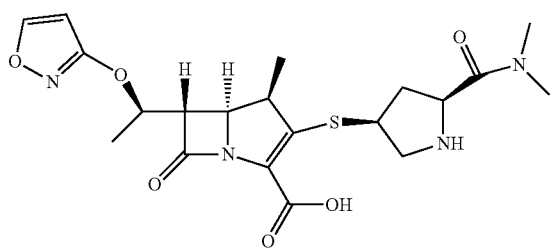<br>(4R,5S,6S)-3-((3S,5S)-5-(Dimethylcarbamoyl)pyrrolidin-3-ylthio)-6-((R)-1-(isoxazol-3-yloxy)ethyl)-4-methyl-7-oxo-1-azabicyclo[3.2.0]hept-2-ene-2-carboxylic acid | $^1$H NMR (D$_2$O) δ ppm: 0.93-0.96 (d, 3H), 1.25-1.36 (d, 3H), 1.87-1.91 (m, 1H), 3.00 (s, 3H), 3.07 (s, 3H), 3.22-3.26 (d, 2H), 3.39-3.40 (m, 2H) 3.54-3.60 (d, 1H), 3.81 (d, 1H), 4.07-4.08 (m, 1H), 4.35 (d, 1H), 5.12 (m, 1H), 6.22 (s, 1H), 8.39-8.45 (s, 1H). MS m/z: 451.5 (M + 1) |
| 188 | 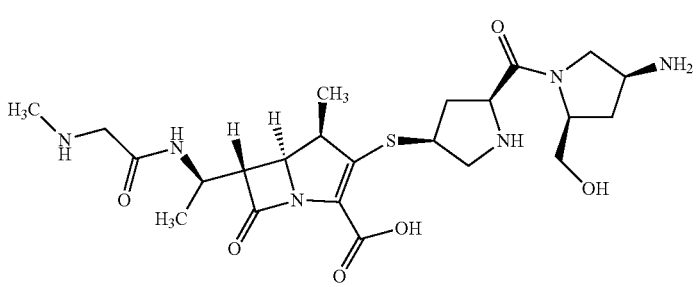<br>(4R,5S,6R)-3-((3S,5S)-5-((2S,4S)-4-Amino-2-(hydroxymethyl)pyrroldiine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.04-1.06 (d, 3H), 1.13-1.21 (d, 3H), 1.79-1.80 (m, 2H), 2.46-2.51 (d, 1H), 2.65-2.69 (m, 1H), 2.73 (s, 3H), 2.81-2.82 (m, 1H), 3.06 (m, 1H), 3.22-3.32 (d, 2H), 3.35 (d, 1H), 3.58-3.61 (m, 2H), 3.80-3.83 (d, 2H), 4.04-4.08 (d, 3H), 4.15-4.17 (d, 1H) 4.34-4.35 (m, 3H). MS m/z: 523.6 (M + 1) |

| Examples | Structure | Analytical Data |
|---|---|---|
| 189 | 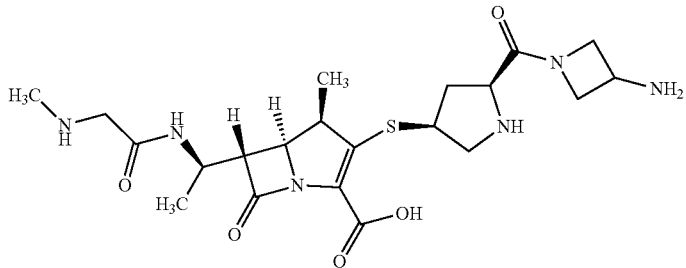<br>(4R,5S,6R)-3-((3S,5S)-5-(3-Aminoazetidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.13-1.15 (d, 3H), 1.19-1.20 (d, 3H), 2.12-2.13 (m 3H), 2.55-2.56 (m, 1H), 2.75-2.76 (s, 3H), 2.92-2.95 (m, 2H), 3.29-3.38 (d, 3H), 3.54-3.58 (d, 2H), 3.83-3.85 (d, 2H), 3.87-3.89 (m, 1H), 4.01-4.05 (d, 1H), 4.41-4.45 (m, 1H), 4.51-4.52 (m, 1H). MS m/z: 479.6 (M − 1) |
| 190 | 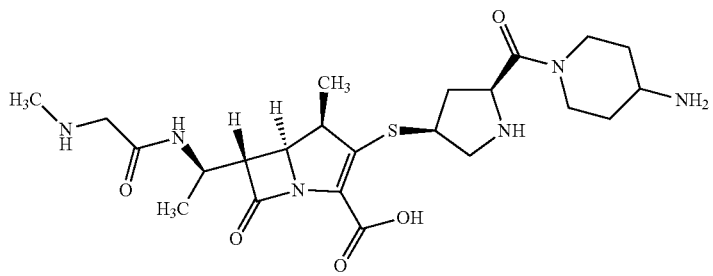<br>(4R,5S,6R)-3-((3S,5S)-5-(4-Aminopiperidine-1-carbooyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.13-1.15 (d, 3H), 1.19-1.21 (d, 3H), 1.60-1.63 (m, 2H), 2.13-2.17 (m, 3H), 2.55-2.57 (m, 2H), 2.76-2.77 (s, 3H), 2.93-2.95 (m, 3H), 3.29-3.38 (m, 3H), 3.54-3.59 (d, 2H), 3.83-3.85 (d, 2H), 3.86-3.87 (m, 1H), 4.14-4.16 (d, 1H), 4.45-4.46 (m, 1H), 4.52-4.53 (d, 1H). MS m/z: 507.6 (M − 1) |
| 191 | 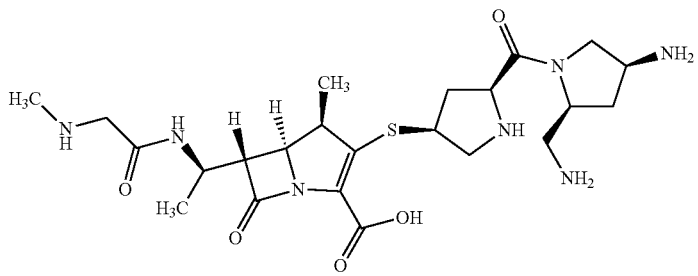<br>(4R,5S,6R)-3-((3S,5S)-5-((2S,4S)-4-Amino-2-(aminomethyl)pyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.03-1.06 (m, 3H), 1.17-1.25 (m, 3H), 1.89 (m, 1H), 2.46 (m, 2H), 2.67-2.71 (m, 2H), 2.86 (d, 3H), 3.21-3.28 (m, 3H), 3.40-3.42 (m, 2H), 3.56 (d, 1H), 3.72-3.91 (m, 4H), 3.92 (m, 1H) 4.06-4.07 (d, 1H), 4.13-4.28 (m, 2H), 4.41 (m, 1H). MS m/z: 522.6 (M − 1) |
| 192 | 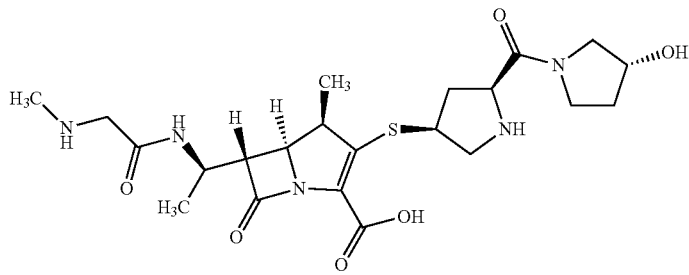<br>(4R,5S,6R)-3-((3S,5S)-5-((R)-3-Hydroxypyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.20-1.22 (d, 3H), 1.28-1.29 (d, 3H), 1.81 (m, 1H), 2.09-2.10 (m, 2H), 2.76 (s, 3H), 2.94 (m, 1H), 3.30 (m, 1H), 3.43-3.46 (m, 2H), 3.50-3.55 (m, 3H), 3.65-3.69 (m, 3H), 3.72-3.76 (m, 2H), 3.94 (m, 1H), 4.13-4.15 (m, 1H), 4.45-4.48 (m, 1H), 4.55-4.59 (m, 1H). MS m/z: 494.6 (M − 1) |

| Examples | Structure | Analytical Data |
|---|---|---|
| 193 | 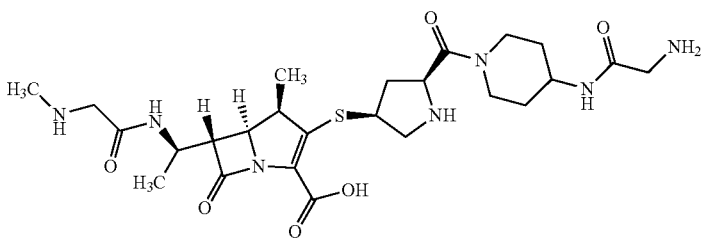<br>(4R,5S,6R)-3-((3S,5S)-5-(4-(2-Aminoacetamido)piperidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.15-1.21 (m, 3H), 1.23-1.29 (m, 3H), 1.42-1.53 (m, 3H), 1.92 (m, 1H), 2.05-2.08 (m, 3H), 2.7 (s, 3H), 3.00-3.02 (m, 3H), 3.33-3.37 (m, 3H), 3.61-3.65 (m, 2H), 3.77 (s, 2H), 3.81-3.82 (m, 2H), 4.01-4.14 (m, 2H), 4.16-4.29 (m, 1H), 4.46-4.48 (m, 1H). MS m/z: 564.6 (M − 1) |
| 194 | 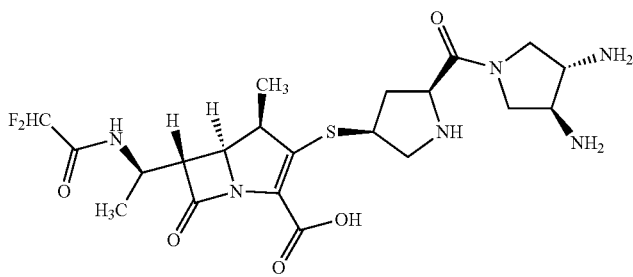<br>(4R,5S,6R)-3-((3S,5S)-5-((3S,4S)-3,4-Diaminopyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.13-1.22 (m, 3H), 1.26-1.28 (m, 3H), 1.92 (m, 1H), 3.00-3.02 (m, 1H), 3.21-3.22 (m, 1H), 3.32-3.37 (m, 4H), 3.40-3.48 (m, 2H), 3.88-3.90 (m, 3H), 4.03-4.16 (m, 2H), 4.29-4.45 (m, 2H) 6.19 (t, 1H). MS m/z: 517.6 (M + 1) |
| 195 | 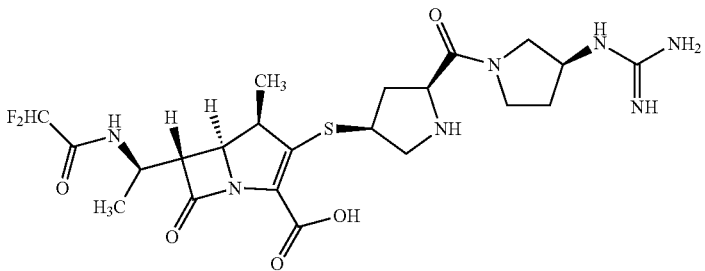<br>(4R,5S,6R)-6-((R)-1-(2,2-Difluoroacetamido)ethyl)-3-((3S,5S)-5-((S)-3-guanidinopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.29-1.31 (d, 3H), 1.35-1.37 (m, 3H), 1.92-1.95 (m, 1H), 3.02 (m, 1H), 3.35-3.43 (m, 3H), 3.58-3.60 (m, 3H), 3.68-3.70 (m, 2H), 3.78-3.82 (m, 1H), 4.01 (m, 1H), 4.15-4.18 (m, 1H), 4.25-4.27 (m, 2H), 4.44-4.59 (m, 2H) 6.19 (t, 1H). MS m/z: 544.6 (M + 1) |
| 196 | 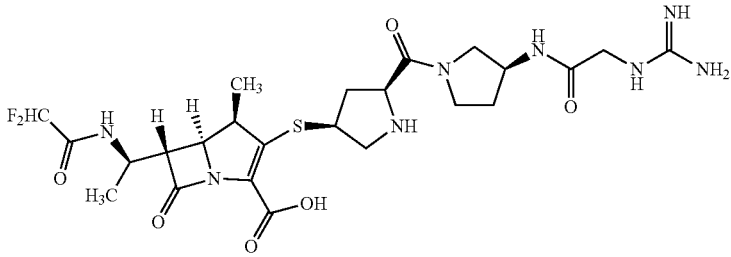<br>(4R,5S,6R)-6-((R)-1-(2,2-Difluoroacetamido)ethyl)-3-((3S,5S)-5-((S)-3-(2-guanidinoacetamido)pyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.27-1.29 (d, 3H), 1.35-1.37 (m, 3H), 1.81 (m, 1H), 2.24-2.25 (m, 2H), 3.01-3.03 (m, 2H), 3.35 (m, 2H), 3.46 (m, 2H), 3.69 (m, 2H), 3.77 (m, 2H), 3.84 (m, 2H), 4.08-4.17 (m, 1H), 4.44-4.47 (m, 2H), 4.60-4.63 (m, 1H) 6.19 (t, 1H). MS m/z: 601.6 (M + 1) |

| Examples | Structure | Analytical Data |
|---|---|---|
| 197 | 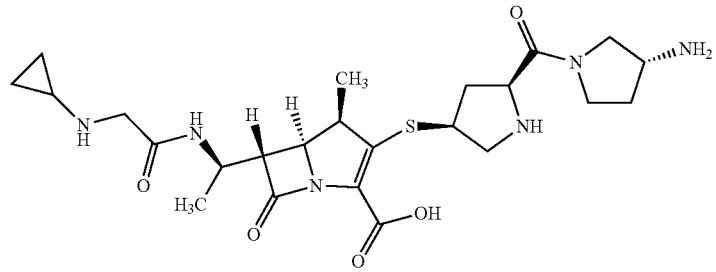<br>(4R,5S,6R)-3-((3S,5S)-5-((R)-3-Aminopyrrolidine-1-carbonyl)pyrrolidin-3-ylthio)-6-((R)-1-(2-(cyclopropylamino)acetamido)ethyl)-4-methyl-7-oxo-1-azabicyclo[3.2.0]hept-2-ene-2-carboxylic acid | $^1$H NMR (D$_2$O) δ ppm: 0.75 (d, 3H), 1.02-1.04 (m, 2H), 1.24-1.35 (d, 6H), 1.92 (m, 2H), 2.00-2.11 (m, 2H), 2.24 (m, 2H), 2.46 (m, 2H), 2.54 (m, 1H), 3.38-3.58 (d, 2H), 3.66 (d, 3H), 3.87-3.88 (m, 2H), 4.11-4.13 (m, 2H), 4.42 (d, 1H). MS m/z: 519.6 (M − 1) |
| 198 | 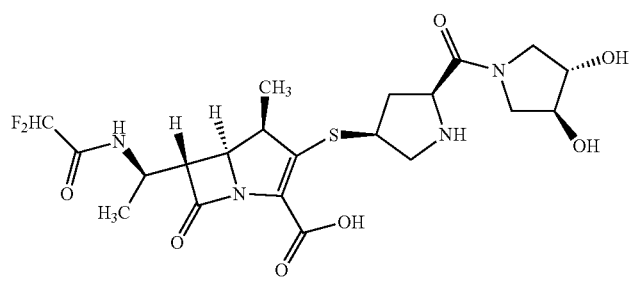<br>(4R,5S,6R)-6-((R)-1-(2,2-Difluoroacetamido)ethyl)-3-((3S,5S)-5-((3S,4S)-3,4-dihydroxypyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.19-1.21 (d, 3H), 1.35-1.37 (d, 3H), 3.02-3.06 (m, 1H), 3.02-3.06 (m, 1H), 3.33-3.35 (m, 2H), 3.44-3.45 (dd, 2H), 3.60-3.62 (d, 2H), 3.71-3.78 (m, 3H), 4.03-4.05 (m, 1H), 4.16-4.18 (d, 1H), 4.30-4.34 (m, 1H), 4.47 (m, 1H), 4.65 (m, 1H), 6.29 (t, 1H). MS m/z: 519.5 (M + 1) |
| 199 | 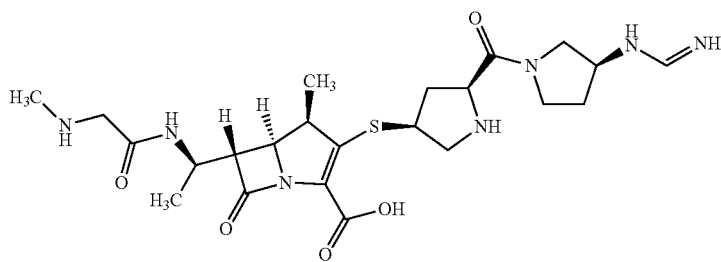<br>(4R,5S,6R)-3-((3S,5S)-5-((S)-3-Formimidamidnpyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.07-1.09 (d, 3H), 1.17-1.27 (d, 3H), 1.83 (m, 1H), 2.31 (m, 1H), 2.57 (m, 2H), 2.76 (m, 3H), 2.96-2.98 (m, 2H), 3.32-3.25 (m, 2H), 3.40-3.51 (m, 4H), 3.88-3.92 (m, 4H), 4.04 (m, 1H), 4.13-4.15 (m, 1H), 4.39-4.48 (m, 2H). MS m/z: 520.6 (M − 1) |
| 200 | 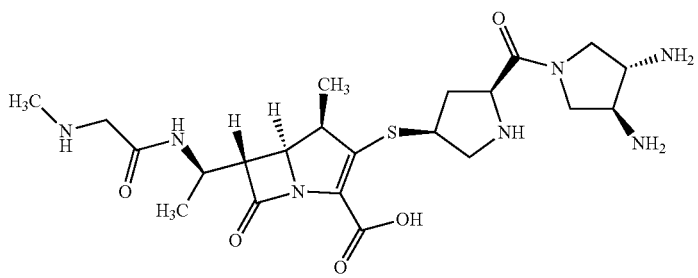<br>(4R,5S,6R)-3-((3S,5S)-5-((3S,4S)-3,4-Diaminopyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.07-1.08 (d, 3H), 1.20-1.22 (d, 3H), 1.81-1.82 (m, 1H), 2.76 (m, 1H), 2.81 (m, 2H), 2.95 (m, 2H), 3.12-3.13 (d, 1H), 3.35-3.53 (m, 3H), 3.61 (d, 1H), 3.62-3.71 (m, 3H), 3.81-3.99 (m, 3H), 4.05 (d, 1H), 4.11 (d, 1H), 4.3-4.41 (m, 1H), 4.51 (m, 1H). MS m/z: 508.6 (M − 1) |

| Examples | Structure | Analytical Data |
|---|---|---|
| 201 | 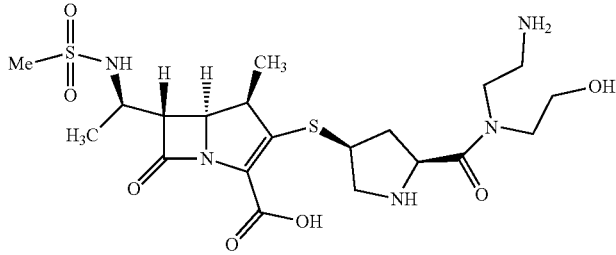<br>(4R,5S,6R)-3-((3S,5S)-5-((2-Aminoethyl)(2-hydroxyethyl)carbamoyl)pyrrolidin-3-ylthio)-4-methyl-6-((R)-1-(methylsulfonamido)ethyl)-7-oxo-1-azabicyclo[3.2.0]hept-2-ene-2-carboxylic acid | $^1$H NMR (D$_2$O) δ ppm: 1.19-1.21 (d, 3H), 1.35-1.37 (d, 3H), 1.98 (m, 1H), 2.55-2.57 (m, 1H), 2.88-2.89 (d, 1H), 3.14 (s, 3H), 3.20-3.26 (m, 2H), 3.31 (d, 3H), 3.49-3.50 (d, 4H), 3.59-3.78 (d, 3H), 3.88-3.90 (m, 1H), 3.96-3.99 (m, 1H), 4.20-4.22 (m, 1H). MS m/z: 520.6 (M + 1) |
| 202 | 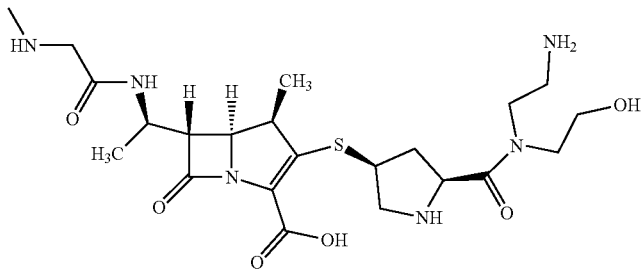<br>(4R,5S,6R)-3-((3S,5S)-5-((2-Aminoethyl)(2-hydroxyethyl)carbamoyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.07-1.09 (d, 3H), 1.13-1.28 (d, 3H), 1.98 (m, 1H), 2.43-2.44 (m, 2H), 2.81 (s, 3H), 2.95 (d, 2H), 3.08-3.1 (d, 3H), 3.21-3.26 (m, 2H), 3.76-3.79 (m, 3H), 3.82-3.87 (m, 3H), 3.97 (d, 3H), 4.13-4.15 (m, 1H), 4.45 (m, 1H). MS m/z: 511.6 (M − 1) |
| 203 | 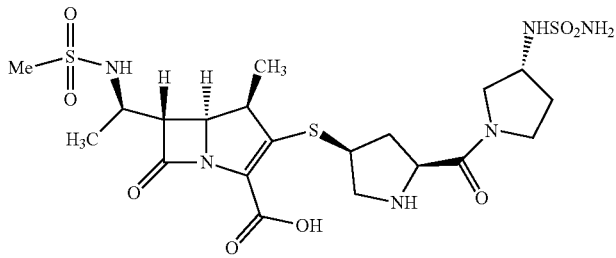<br>(4R,5S,6R)-4-Methyl-6-((R)-1-(methylsulfonamido)ethyl)-7-oxo-3-((3S,5S)-5-((R)-3-(sulfamoylamino)pyrrolidine-1-carbonyl)pyrrolidin-3-ylthio)-1-azabicyclo[3.2.0]hept-2-ene-2-carboxylic acid | $^1$H NMR (D$_2$O) δ ppm: 1.23-1.25 (d, 3H), 1.34-1.39 (d, 3H), 2.08-2.12 (m, 2H), 2.31 (m, 2H), 2.55-2.57 (m, 1H), 2.98 (m, 1H), 3.11 (s, 3H), 3.14-3.18 (d, 2H), 3.20-3.26 (m, 2H), 3.38-3.34 (d, 2H), 3.78-3.80 (m, 2H), 4.15 (m, 1H), 4.22 (m, 1H), 4.70-4.77 (m, 1H). MS m/z: 581.7 (M + 1) |
| 204 | 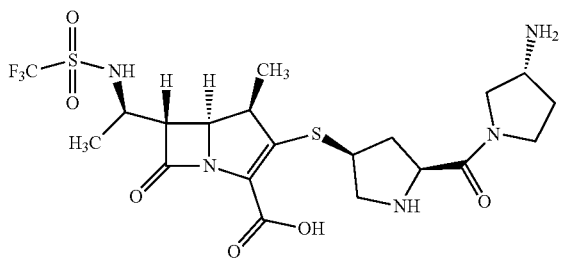<br>(4R,5S,6R)-3-((3S,5S)-5-((R)-3-Aminopyrrolidine-1-carbonyl)pyrrolidin-3-ylthio)-4-methyl-7-oxo-6-((R)-1-(trifluoromethylsulfonamido)ethyl)-1-azabicyclo[3.2.0]hept-2-ene-2-carboxylic acid | $^1$H NMR (D$_2$O) δ ppm: 1.03-1.05 (d, 3H), 1.20-1.21 (d, 3H), 1.98 (m, 1H), 2.02-2.03 (m, 1H), 2.43-2.45 (d, 1H), 2.92 (m, 1H), 3.17-3.18 (m, 1H), 3.35-3.36 (m, 2H), 3.43-3.45 (m, 2H), 3.59-3.60 (m, 3H), 3.78-3.80 (m, 2H), 4.04-4.15 (m, 1H), 4.17 (d, 1H), 4.49 (t, 1H). MS m/z: 556.6 (M + 1) |

-continued

| Examples | Structure | Analytical Data |
|---|---|---|
| 205 | 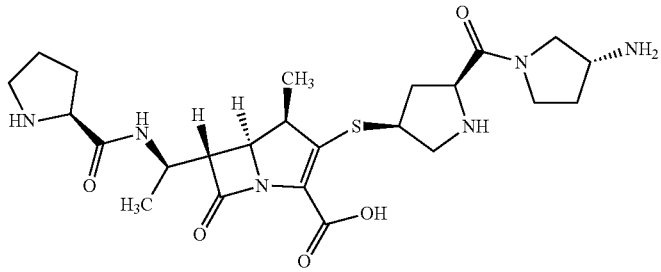<br>(4R,5S,6R)-3-((3S,5S)-5-((R)-3-Aminopyrrolidine-1-carbonyl)pyrrolidin-3-ylthio)-4-methyl-7-oxo-6-((R)-1-((S)-pyrrolidine-2-carboxamido)ethyl)-1-azabicyclo[3.2.0]hept-2-ene-2-carboxylic acid | $^1$H NMR (D$_2$O) δ ppm: 1.15-1.20 (d, 3H), 1.29-1.30 (d, 3H), 1.75-1.78 (m, 1H), 2.21-2.22 (m, 3H), 2.46-2.48 (m, 2H), 2.85 (m, 1H), 3.20-3.22 (d, 1H), 3.37-3.38 (m, 2H), 3.60 (m, 3H), 3.72-3.78 (m, 3H), 3.87-3.90 (m, 3H), 4.04-4.08 (m, 2H), 4.13-4.16 (d, 1H), 4.35 (m, 1H), 4.44-4.46 (m, 1H). MS m/z: 519.6 (M − 1) |
| 206 | 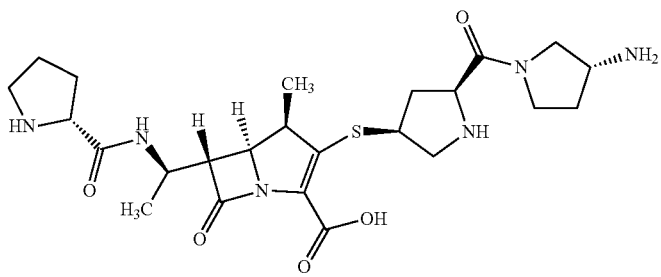<br>(4R,5S,6R)-3-((3S,5S)-5-((R)-3-Aminopyrrolidine-1-carbonyl)pyrrolidin-3-ylthio)-4-methyl-7-oxo-6-((R)-1-((R)-pyrrolidine-2-carboxamido)ethyl)-1-azabicyclo[3.2.0]hept-2-ene-2-carboxylic acid | $^1$H NMR (D$_2$O) δ ppm: 1.15-1.20 (d, 3H), 1.29-1.30 (d, 3H), 1.75-1.78 (m, 1H), 2.21-2.22 (m, 3H), 2.46-2.48 (m, 2H), 2.85 (m, 1H), 3.20-3.22 (d, 1H), 3.37-3.38 (m, 2H), 3.60 (m, 3H), 3.72-3.78 (m, 3H), 3.87-3.90 (m, 3H), 4.04-4.08 (m, 2H), 4.13-4.16 (d, 1H), 4.35 (m, 1H), 4.44-4.46 (m, 1H). MS m/z: 519.6 (M − 1) |
| 207 | 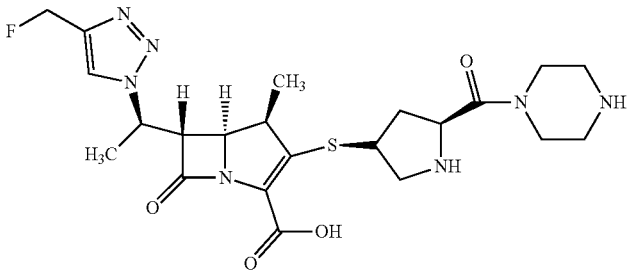<br>(4R,5S,6S)-6-((R)-1-(4-(Fluoromethyl)-1H-1,2,3-triazol-1-yl)ethyl)-4-methyl-7-oxo-3-((3R,5S)-5-(piperazine-1-carbonyl)pyrrolidin-3-ylthio)-1-azabicyclo[3.2.0]hept-2-ene-2-carboxylic acid | $^1$H NMR (D$_2$O) δ ppm: 0.95-0.97 (d, 3H), 1.63-1.92 (m, 3H), 2.72 (m, 1H), 3.22-3.24 (m, 6H), 3.60-3.64 (m, 2H), 3.82-3.85 (m, 8H), 4.02 (m, 1H), 8.31 (s, 1H), 5.31 (s, 1H), 5.6 (s, 1H). MS m/z: 508.6 (M + 1) |
| 208 | 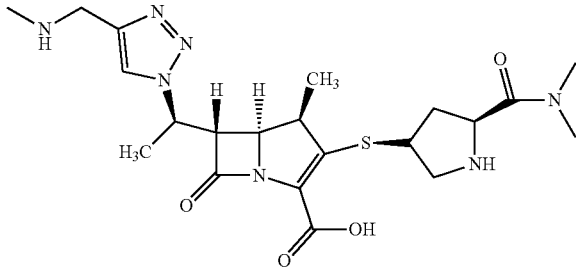<br>(4R,5S,6S)-3-((3R,5S)-5-(Dimethylcarbamoyl)pyrrolidin-3-ylthio)-4-methyl-6-((R)-1-(4-((methylamino)methyl)-1H-1,2,3-triazol-1-yl)ethyl)-7-oxo-1-azabicyclo[3.2.0]hept-2-ene-2-carboxylic acid | $^1$H NMR (D$_2$O) δ ppm: 0.95 (d, 3H), 1.72-1.76 (d, 3H), 1.98 (m, 1H), 2.72-2.76 (d, 2H), 2.87 (s, 3H), 3.06-3.09 (s, 3H), 3.10 (s, 3H), 3.22-3.26 (d, 2H), 3.36-3.37 (d, 2H), 3.48-3.50 (dd, 1H), 3.61 (m, 1H) 3.81 (m, 2H), 4.07-4.08 (m, 1H) 4.39 (m, 1H). MS m/z: 478.6 (M + 1) |

| Examples | Structure | Analytical Data |
|---|---|---|
| 209 | 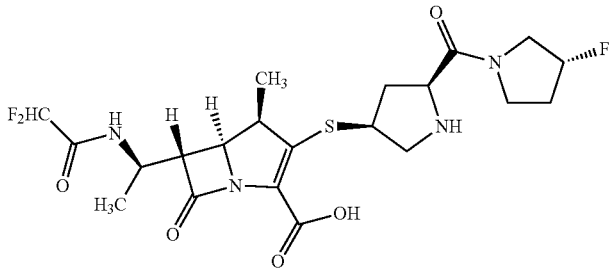<br>(4R,5S,6R)-6-((R)-1-(2,2-Difluoroacetamido)ethyl)-3-((3S,5S)-5-((R)-3-fluoropyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.19-1.21 (d, 3H), 1.35-1.37 (d, 3H), 1.47 (s, 1H), 1.92-2.10 (m, 3H), 2.34-2.4 (m, 1H), 3.00-3.07 (d, 2H), 3.33-3.41 (m, 2H), 3.58-3.60 (m, 3H), 3.72-3.77 (m, 2H), 3.82-3.98 (m, 1H), 4.15-4.17 (m, 1H), 4.44-4.47 (m, 1H), 4.63 (m, 1H) 5.36-5.52 (m, 1H), 6.02-6.2 (t, 1H). MS m/z: 505 (M + 1) |
| 210 | 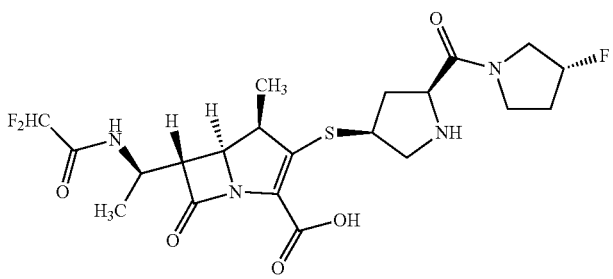<br>(4R,5S,6R)-6-((R)-1-(2,2-Difluoroacetamido)ethyl)-3-((3S,5S)-5-((S)-3-fluoropyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.20-1.21 (d, 3H), 1.36-1.37 (d, 3H), 1.48 (s, 1H), 1.92-2.3 (m, 4H), 3.00-3.07 (d, 2H), 3.33-3.4 (m, 2H), 3.58-3.60 (m, 3H), 3.72-3.77 (m, 2H), 3.82-3.98 (m, 1H), 4.15-4.17 (m, 1H), 4.44-4.47 (m, 1H), 4.63 (m, 1H), 5.36-5.52 (m, 1H), 6.02-6.29 (t, 1H). MS m/z: 505 (M + 1) |
| 211 | 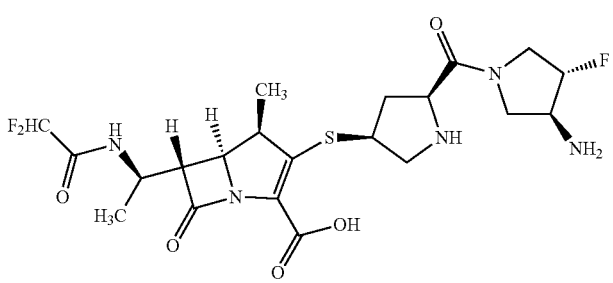<br>(4R,5S,6R)-3-((3S,5S)-5-((3S,4S)-3-Amino-4-fluoropyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.20-1.21 (d, 3H), 1.29-1.30 (d, 3H), 1.98-2.00 (m, 2H), 2.56-2.89 (m, 4H), 3.31-3.59 (m, 6H), 3.94 (m, 2H), 4.16-4.31 (m, 2H), 4.45-4.47 (m 2H), 6.02-6.29 (t, 1H). MS m/z: 518 (M − 1) |
| 212 | 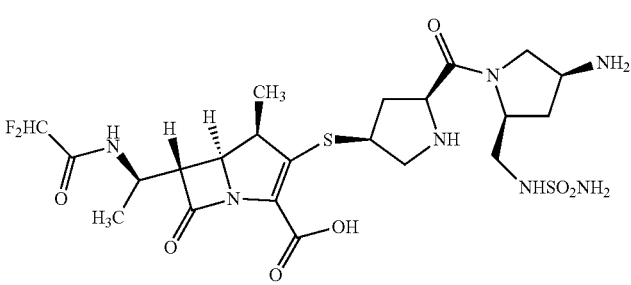<br>(4R,5S,6R)-3-((3S,5S)-5-((2S,4S)-4-amino-2-((sulfamoylamino)methyl)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.20-1.21 (d, 3H), 1.29-1.30 (d, 3H), 1.34-1.37 (m, 2H), 1.92 (m, 1H), 1.98-2.00 (m, 2H), 2.47-2.51 (m, 1H), 2.87-2.94 (m, 1H), 3.27-3.35 (m, 3H), 3.49-3.59 (m, 3H), 3.87-3.94 (m, 1H), 4.14-4.16 (m, 1H), 4.31-4.45 (m, 1H), 4.45-4.47 (m, 2H), 6.02-6.29 (t, 1H). MS m/z: 610 (M + 1) |

| Examples | Structure | Analytical Data |
|---|---|---|
| 213 | 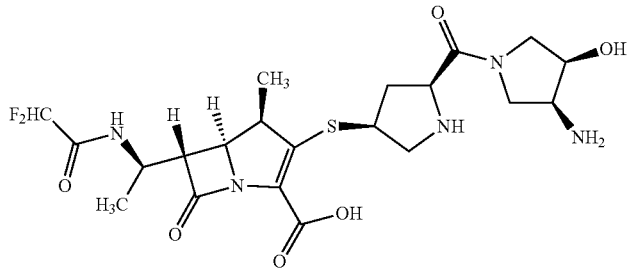

(4R,5S,6R)-3-((3S,5S)-5-((3S,4R)-3-Amino-4-hydroxypyrroldine-1-carbonyl)pyrrolidin-3-ylthio)-6-((R)-1-(2,2-difluoroacetamido)ethyl)-4-methyl-7-oxo-1-azabicyclo[3.2.0]hent-2-ene-2-carboxylic acid | $^1$H NMR (D$_2$O) δ ppm: 1.20 (d, 3H), 1.36-1.37 (d, 3H), 1.79 (m, 1H), 2.90 (m, 1H), 3.30-3.35 (m, 2H), 3.53-3.63 (m, 3H), 3.71 (m, 2H), 3.78-3.80 (m, 3H), 3.92 (m, 1H), 4.02-4.12 (m, 1H), 4.15-4.17 (m, 1H), 4.45 (m, 1H), 4.61 (m, 1H). MS m/z: 516 (M − 1) |
| 214 | 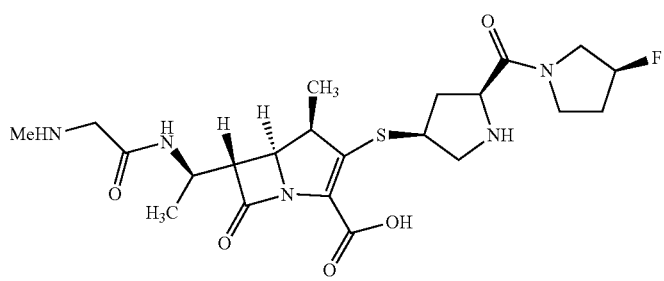

(4R,5S,6R)-3-((3S,5S)-5-((S)-3-Fluoropyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.09-1.12 (m, 3H), 1.28-1.34 (d, 3H), 2.47-2.49 (m, 2H), 2.76 (s, 3H), 2.99-3.09 (m, 1H), 3.30 (m, 1H), 3.35-3.39 (m, 1H), 3.34-3.46 (m, 2H), 3.50-3.55 (m, 3H), 3.65-3.69 (m, 3H), 3.72-3.76 (m, 2H), 3.94 (m, 1H), 4.12-4.14 (m, 1H), 4.16-4.18 (d, 1H) 4.45-4.48 (m, 1H), 4.55-4.59 (m, 1H). MS m/z: 498 (M + 1) |
| 215 | 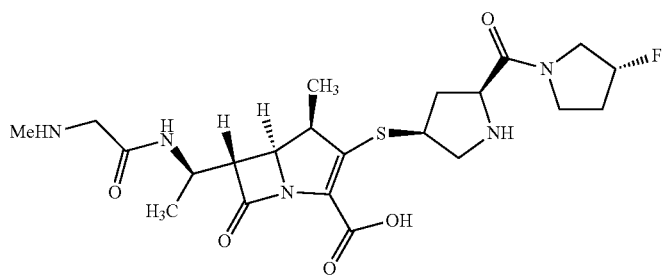

(4R,5S,6R)-3-((3S,5S)-5-((R)-3-Fluoropyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.05-1.07 (d, 3H), 1.30-1.31 (d, 3H), 2.43-2.45 (d, 2H), 2.76 (s, 3H), 2.99-3.09 (dd, 1H), 2.76 (s, 3H), 3.30 (m, 1H), 3.43-3.46 (m, 2H), 3.50-3.55 (m, 3H), 3.58-3.63 (m, 2H), 3.72-3.76 (m, 2H), 4.14-4.16 (m, 1H), 4.18-4.19 (m, 1H), 4.46-4.48 (m, 1H) 4.55-4.59 (m, 1H). MS m/z: 498 (M + 1) |
| 216 | 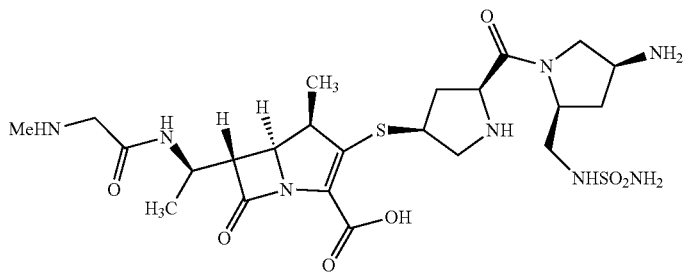

(4R,5S,6R)-3-((3S,5S)-5-((2S,4S)-4-Amino-2-((sulfamoylamino)methyl)pyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.20-1.22 (d, 3H), 1.32-1.34 (d, 3H), 1.98-2.00 (m, 2H), 2.07-2.09 (m, 1H), 2.47-2.51 (m, 1H), 2.63-2.74 (m, 1H), 3.05-3.12 (m, 1H), 3.32-3.35 (m, 3H), 3.39-3.49 (m, 2H), 3.53-3.55 (m, 1H), 3.57-3.59 (m, 1H), 3.74-3.78 (d, 1H), 3.81-3.90 (m, 4H), 4.07-4.15 (m, 1H), 4.23-4.29 (m, 1H), 4.29-4.31 (m, 2H), 4.45-4.46 (d, 1H). MS m/z: 603 (M + 1) |

| Examples | Structure | Analytical Data |
|---|---|---|
| 217 | 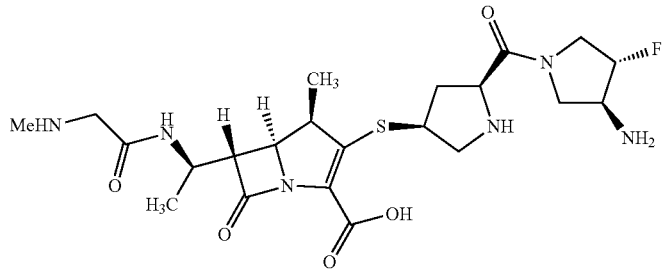<br>(4R,5S,6R)-3-((3S,5S)-5-((3S,4S)-3-Amino-4-fluoropyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carbnxylic acid | $^1$H NMR (D$_2$O) δ ppm: 1.07-1.08 (d, 3H), 1.22-1.29 (d, 3H), 2.02-2.05 (m, 1H), 2.03-2.04 (m, 1H), 2.75-.276 (d, 3H), 2.98-2.99 (m, 1H), 3.24-3.25 (m, 1H), 3.32-3.41 (m, 3H), 3.52-3.56 (m, 1H), 3.73-3.82 (m, 2H), 3.87-3.93 (m, 4H), 4.13-4.15 (m, 1H), 4.41-4.45 (m, 1H), 4.46-4.48 (m, 1H), 4.49-4.58 (m, 1H). MS m/z: 512 (M+) |
| 218 | 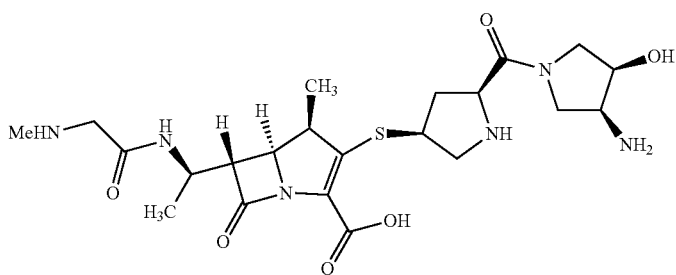<br>(4R,5S,6R)-3-((3S,5S)-5-((3S,4R)-3-Amino-4-hydroxypyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.07-1.8 (d, 3H), 1.25-1.27 (d, 3H), 1.79 (m, 1H), 2.7 (s, 3H), 2.84 (m, 1H), 3.23 (d, 1H), 3.40-3.42 (m, 2H), 3.43-3.44 (m, 1H), 3.52-3.58 (m, 1H), 3.7 (m, 2H), 3.79-3.81 (m, 5H), 4.02-4.12 (m, 1H), 4.13-4.15 (m, 1H), 4.4 (m, 1H), 4.58 (m, 1H). MS m/z: 510 (M+) |
| 219 | 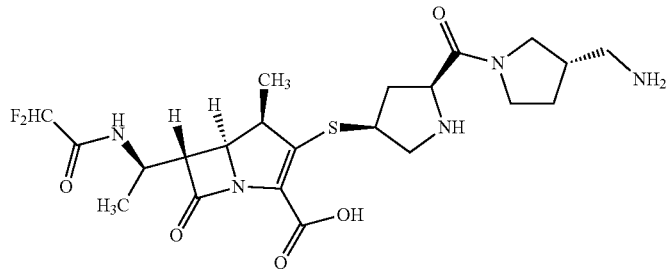<br>(4R,5S,6R)-3-((3S,5S)-5-((S)-3-(Aminomethyl)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.20 (d, 3H), 1.26 (d, 3H), 1.35 (m, 2H), 1.86 (m, 1H), 1.92 (m, 1H), 2.27 (m, 1H), 2.93 (m, 1H), 3.11 (m, 2H), 3.22 (m, 1H), 3.35 (m, 2H), 3.45 (m, 1H), 3.58 (m, 2H), 3.67 (m, 1H), 3.78 (m, 2H), 3.9 (m, 1H), 4.15 (m, 1H), 4.45 (m, 2H), 6.15 (t, 1H). MS m/z: 515 (M+) |
| 220 | 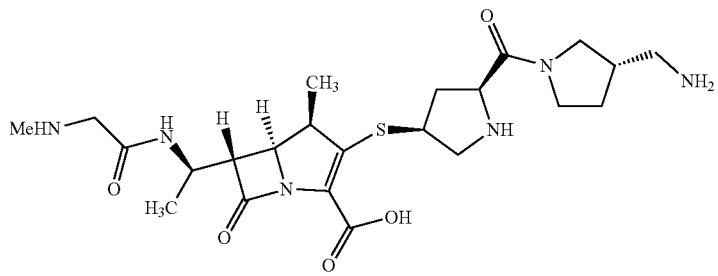<br>(4R,5S,6R)-3-((3S,5S)-5-((S)-3-(Aminomethyl)pyrrolidine-1-carbonyl)pyrrolidin-3-ylthio)-4-methyl-6-((R)-1-(2-(methylamino)acetamidn)ethyl)-7-oxo-1-azabicyclo[3.2.0]hept-2-ene-2-carboxylic acid | $^1$H NMR (D$_2$O) δ ppm: 1.22 (d, 3H), 1.28 (d, 3H), 1.29 (m, 1H), 1.35 (m, 2H), 1.86 (m, 1H), 1.92 (m, 1H), 2.0 (m, 1H), 2.27 (m, 1H), 1.69 (m, 2H), 2.93 (m, 1H), 3.11 (m, 2H), 3.22 (m, 1H), 3.35 (m, 2H), 3.45 (m, 1H), 3.58 (m, 2H), 3.67 (m, 1H), 3.78 (m, 2H), 3.9 (m, 1H), 4.15 (m, 1H), 4.45 (t, 2H), 6.15 (t, 1H). MS m/z: 508 (M+) |

| Examples | Structure | Analytical Data |
|---|---|---|
| 221 | 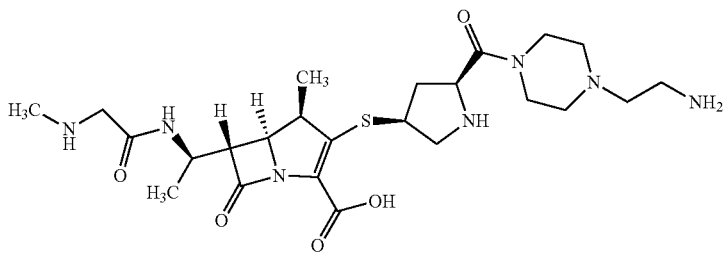<br>(4R,5S,6R)-3-((3S,5S)-5-(4-(2-Aminoethyl)piperazine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$H NMR (D$_2$O) δ ppm: 1.0 (d, 3H), 1.29 (d, 3H), 2.43-2.48 (m, 2H), 2.58-2.62 (m, 4H), 2.68-2.72 (m, 4H), 2.81-2.83 (m, 2H), 2.9 (m, 2H), 3.02 (m, 2H), 3.17 (m, 2H), 3.39 (m, 2H), 3.64-3.69 (m, 2H), 3.8 (m, 2H) 3.93 (m, 3H). MS m/z: 538 (M + 1) |
| 222 | 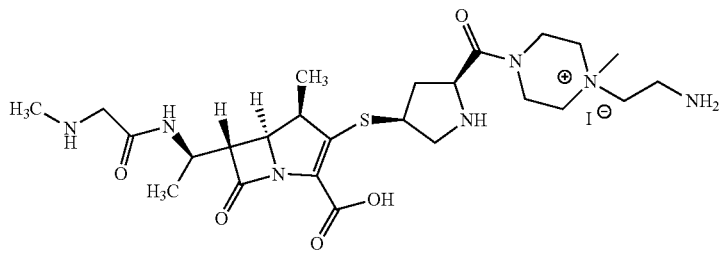<br>1-(2-Aminoethyl)-4-((2S,4S)-4-((4R,5S,6R)-2-carbonyl-4-methyl-6-((R)-1-(2-(methylamino)acetamido)ethyl)-7-oxo-1-azabicyclo[3.2.0]hept-2-en-3-ylthio)pyrrolidine-2-carbonyl)-1-methylpiperazin-1-ium iodide | $^1$H NMR (D$_2$O) δ ppm: 1.04-1.08 (d, 3H), 1.18-1.20 (m, 3H), 2.47-2.53 (m, 2H), 2.73 (m, 2H), 2.81-2.83 (m, 1H), 3.02 (m, 1H), 3.19-3.22 (m, 6H), 3.64-3.69 (m, 6H), 3.81 (m, 2H), 3.98 (m, 6H), 4.02-4.24 (m, 4H). MS m/z: 680 (M + 1) |
| 223 | 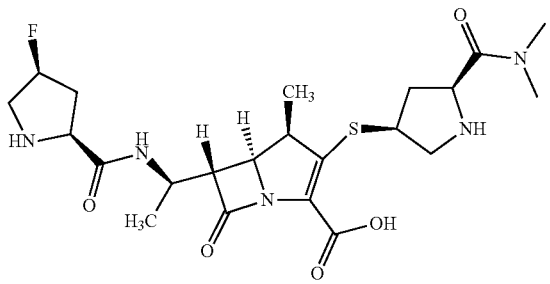<br>(4R,5S,6R)-3-((3S,5S)-5-(Dimethylcarbamoyl)pyrrolidin-3-ylthio)-6-((R)-1-((2S,4S)-4-fluoropyrrolidine-2-carboxamido)ethyl)-4-methyl-7-oxo-1-azabicyclo[3.2.0]hept-2-ene-2-carboxylic acid | $^1$H NMR (D$_2$O) δ ppm: 1.03-1.09 (d, 3H), 1.18-1.30 (d, 3H), 1.90 (m, 2H), 2.06-2.08 (m, 1H), 2.46-2.51 (m, 2H), 2.99-3.00 (m, 4H), 3.07-3.11 (m, 3H), 3.36-3.44 (m, 4H), 3.61-3.67 (m, 1H), 3.76 (m, 1H), 4.15 (m, 2H), 4.54 (m, 2H). MS m/z: 497 (M+) |

| Examples | Structure | Analytical Data |
|---|---|---|
| 224 | 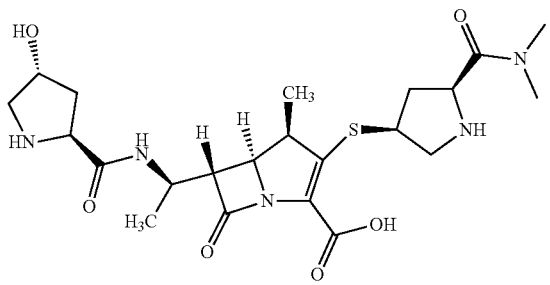<br>(4R,5S,6R)-3-((3S,5S)-5-(Dimethylcarbamoyl)pyrrolidin-3-ylthio)-6-((R)-1-((2S,4R)-4-hydroxypyrrolidine-2-carboxamido)ethyl)-4-methyl-7-oxo-1-azabicyclo[3.2.0]hept-2-ene-2-carboxylic acid | $^1$H NMR (D$_2$O) δ ppm: 1.07-1.09 (d, 3H), 1.19-1.26 (d, 3H), 1.34 (m, 1H), 1.92 (m, 4H), 2.15 (m, 2H), 2.47 (m, 2H), 2.99 (m, 4H), 3.07-3.09 (m, 3H), 3.35-3.39 (m, 4H), 3.60 (m, 2H), 3.73-3.77 (m, 2H), 4.69 (m, 2H). MS m/z: 496 (M + 1) |
| 225 | 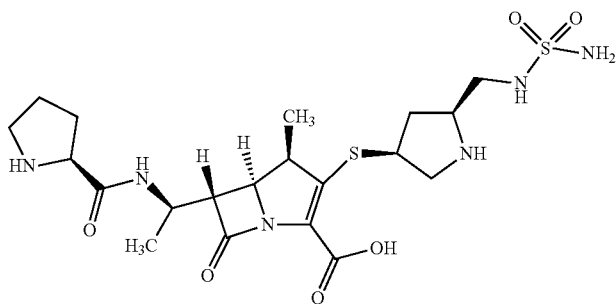<br>(4R,5S,6R)-4-Methyl-7-oxo-6-((R)-1-((S)-pyrrolidine-2-carboxamido)ethyl)-3-((3S,5S)-5-((sulfamoylamino)methyl)pyrrolidin-3-ylthio)-1-azabicyclo[3.2.0]hept-2-ene-2-carboxylic acid | $^1$H NMR (D$_2$O) δ ppm: 1.22 (d, 3H), 1.29-1.30 (d, 3H), 1.72-1.75 (m, 2H), 1.92 (m, 2H), 2.44-2.47 (m, 2H), 2.69-2.77 (m, 1H), 3.32-3.48 (m, 7H), 3.62-3.67 (m, 2H), 3.4-3.76 (d, 1H), 3.85-3.86 (d, 1H), 4.02 (m, 1H), 4.14-4.16 (m, 1H), 4.42-4.43 (m, 1H), 4.45 (m, 1H). MS m/z: 516 (M + 1) |
| 226 | 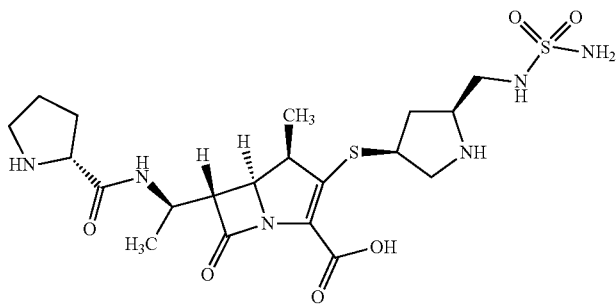<br>(4R,5S,6R)-4-Methyl-7-oxo-6-((R)-1-((R)-pyrrolidine-2-carboxamido)ethyl)-3-((3S,5S)-5-((sulfamoylamino)methyl)pyrrolidin-3-ylthio)-1-azabicyclo[3.2.0]hept-2-ene-2-carboxylic acid | $^1$H NMR (D$_2$O) δ ppm: 1.29-1.31 (d, 3H), 1.34 (d, 3H), 1.72-1.74 (m, 1H), 1.92 (m, 2H), 2.07-2.08 (m, 2H), 2.46-2.47 (m, 1H), 2.73-2.76 (m, 1H), 3.32-3.38 (m, 4H), 3.67-3.74 (m, 2H), 3.77 (m, 1H), 3.89-4.01 (m, 1H), 4.14 (m, 1H), 4.15-4.17 (m, 1H), 4.33-4.35 (m, 1H), 4.44 (m, 1H), 4.46-4.47 (m, 1H), 4.69-4.74 (m, 1H). MS m/z: 516 (M+) |

| Examples | Structure | Analytical Data |
|---|---|---|
| 227 | 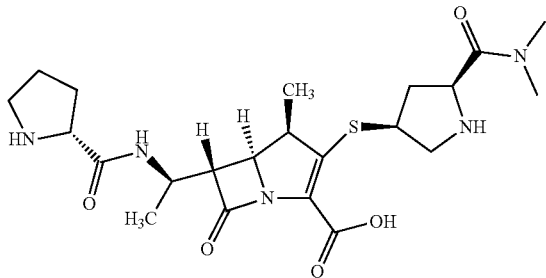<br>(4R,5S,6R)-3-((3S,5S)-5-(Dimethylcarbamoyl)pyrrolidin-3-ylthio)-4-methyl-7-oxo-6-((R)-1-((R)-pyrrolidine-2-carboxamido)ethyl)-1-azabicyclo[3.2.0]hept-2-ene-2-carboxylic acid | $^1$H NMR (D$_2$O) δ ppm: 1.06-1.08 (d, 3H), 1.22-1.26 (d, 3H), 1.86 (m, 1H), 1.91 (m, 1H), 2.46 (m, 2H), 2.99 (m, 3H), 3.36 (m, 3H), 3.45 (m, 3H), 3.59 (m, 3H), 3.74-3.77 (m, 1H), 3.97 (m, 1H), 4.15-4.17 (m, 1H), 4.36 (m, 2H), 4.46 (m, 1H), 4.61 (m, 1H). MS m/z: 480 (M + 1) |
| 228 | 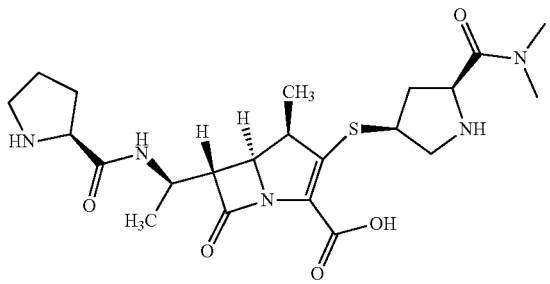<br>(4R,5S,6R)-3-((3S,5S)-5-(Dimethylcarbamoyl)pyrrolidin-3-ylthio)-4-methyl-7-oxo-6-((R)-1-pyrrolidine-2-carboxamido)ethyl)-1-azabicyclo[3.2.0]hept-2-ene-2-carboxylic acid | $^1$H NMR (D$_2$O) δ ppm: 1.22-1.25 (d, 3H), 1.31-1.34 (d, 3H), 1.89-1.92 (m, 1H), 2.06-2.08 (m, 2H), 2.45-2.46 (m, 2H), 2.99 (s, 3H), 3.07 (s, 3h), 3.36-3.40 (m, 3H), 3.44-3.46 (m, 2H), 3.55-3.58 (m, 1H), 3.78-3.82 (m, 1H), 3.92-3.98 (m, 1H), 4.14-4.16 (m, 1H), 4.33-4.35 (m, 1H), 4.42-4.44 (m, 1H), 4.45-4.48 (m, 1H). Mass 478 (M − 1). MS m/z: 478 (M − 1) |
| 229 | 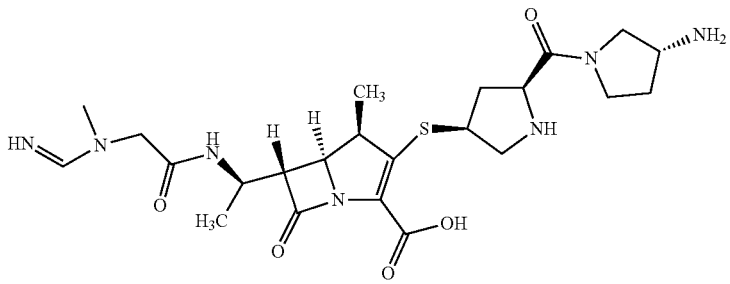<br>(4R,5S,6R)-3-((3S,5S)-5-((R)-3-Aminopyrrolidine-1-carbonyl)pyrrolidin-3-ylthio)-4-methyl-6-((R)-1-(2-(N-methylformimidamido)acetamido)ethyl)-7-oxo-1-azabicyclo[3.2.0]hept-2-ene-2-carboxylic acid | $^1$H NMR (D$_2$O) δ ppm: 1.20-1.22 (d, 3H), 1.31-1.34 (d, 3H), 1.89-1.92 (m, 1H), 2.04-2.08 (m, 1H), 2.10-2.12 (m, 1H), 2.46-2.48 (m, 2H), 2.88-2.92 (m, 1H), 3.07 (s, 3H), 3.22-3.28 (m, 2H), 3.32-3.40- (m, 2H), 3.60-3.63 (m, 2H), 3.66-3.67 (m, 2H), 3.89-3.91 (m, 2H), 4.07-4.12 (m, 2H), 4.22-4.24 (m, 1H), 4.45-4.48 (m, 1H). MS m/z: 522 (M + 1) |
| 230 | 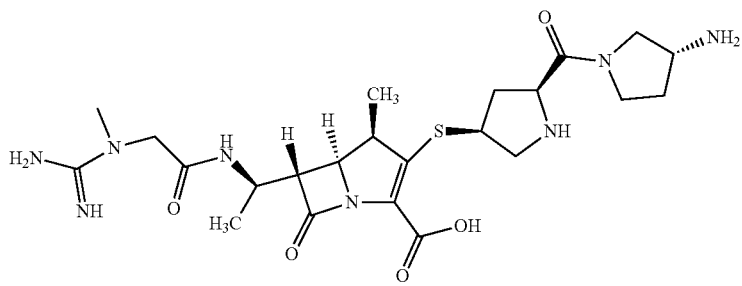<br>(4R,5S,6R)-3-((3S,5S)-5-((R)-3-Aminopyrrolidine-1-carbonyl)pyrrolidin-3-ylthio)-4-methyl-6-((R)-1-(2-(1-methylguanidino)acetamido)ethyl)-7-oxo-1-azabicyclo[3.2.0]hept-2-ene-2-carboxylic acid | $^1$H NMR (D$_2$O) δ ppm: 1.20-1.22 (d, 3H), 1.27-1.29 (d, 3H), 1.89-1.92 (m, 1H), 2.01-2.03 (m, 1H), 2.08-2.12 (m, 1H), 2.48-2.52 (m, 2H), 2.82-2.89 (m, 1H), 3.04 (s, 3H), 3.45-3.45 (m, 1H), 3.48-3.49 (m, 1H), 3.57-3.60 (m, 1H), 3.75-3.79 (m, 3H), 3.87-3.91 (m, 2H), 3.94-3.96 (m, 1H), 4.12-4.17 (m, 2H), 4.38-4.44 (m, 1H), 3.43-3.46 (m, 1H). |

| Examples | Structure | Analytical Data |
|---|---|---|
| 231 | 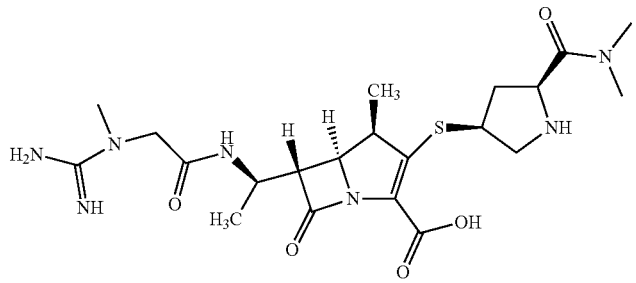<br>(4R,5S,6R)-3-((3S,5S)-5-(Dimethylcarbamoyl)pyrrolidin-3-ylthio)-4-methyl-6-((R)-1-(2-(1-methylguanidino)acetamido)ethyl)-7-oxo-1-azabicyclo[3.2.0]hept-2-ene-2-carboxylic acid | $^1$H NMR (D$_2$O) δ ppm: 1.20-1.22 (d, 3H), 1.27-1.29 (d, 3H), 1.80-1.83 (m, 1H), 2.02-2.03 (m, 1H), 2.44-2.46 (m, 1H), 2.95-2.96 (m, 1H), 2.99 (s, 3H), 3.07 (s, 3H), 3.08-3.11 (m, 2H), 3.33-3.35 (m, 2H), 3.49-3.52 (m, 1H), 3.93-3.97 (m, 1H), 4.14-4.18 (m, 3H), 4.45-4.47 (m, 2H). MS m/z: 496 (M + 1) |
| 232 | 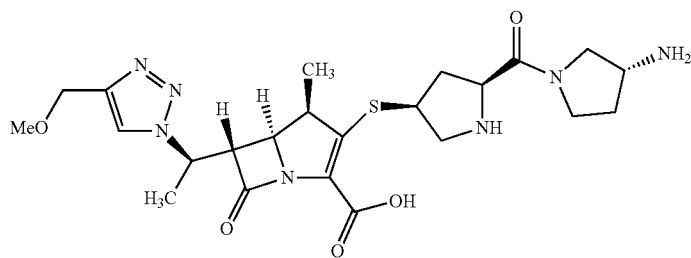<br>(4R,5S,6S)-3-((3S,5S)-5-((R)-3-Aminopyrrolidine-1-carbonyl)pyrrolidin-3-ylthio)-6-((R)-1-(4-(methoxymethyl)-1H-1,2,3-triazol-1-yl)ethyl)-4-methyl-7-oxo-1-azabicyclo[3.2.0]hept-2-ene-2-carboxylic acid | $^1$H NMR (D$_2$O) δ ppm: 1.24-1.26 (d, 3H), 1.66-1.68 (m, 1H) 1.76-1.78 (m, 3H), 2.06-2.08 (m, 1H), 2.18-2.22 (m, 1H) 2.32-2.34 (m, 1H), 2.40-2.43 (m, 1H), 2.46-2.5 (m, 1H), 2.88-2.92 (m, 1H), 3.40 (s, 3H), 3.66-3.71 (m, 2H), 3.73-3.77 (m, 1H), 3.87-3.91 (m, 4H), 3.92-3.94 (m, 2H) 3.96-3.98 (m, 1H), 4.06-4.12 (m, 1H), 4.13-4.15 (m, 1H) 8.19 (s, 1H). MS m/z: 520 (M + 1) |
| 233 | 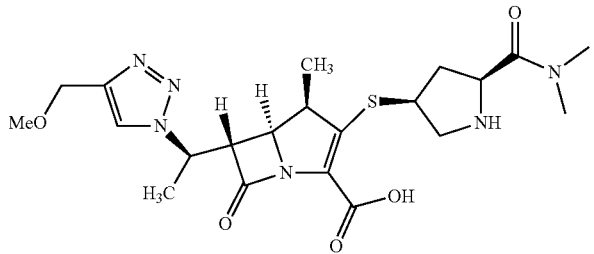<br>(4R,5S,6S)-3-((3S,5S)-5-(Dimethylcarbamoyl)pyrrolidin-3-ylthio)-6-((R)-1-(4-(methoxymethyl)-1H-1,2,3-triazol-1-yl)ethyl)-4-methyl-7-oxo-1-azabicyclo[3.2.0]hept-2-ene-2-carboxylic acid | $^1$H NMR (D$_2$O) δ ppm: 1.12-1.14 (d, 3H), 1.67-1.68 (m, 1H), 1.76-1.78 (d, 3H), 1.95-1.98 (m, 1H), 2.99 (s, 3H), 3.06 (s, 3H), 3.09-3.12 (m, 2H), 3.24-3.26 (m, 1H), 3.40 (s, 3H), 3.41 (m, 1H), 3.67-3.72 (m, 3H), 3.97-3.99 (m, 2H), 4.13-4.15 (m, 1H), 8.19 (s, 1H). MS m/z: 477 (M − 1) |
| 234 | 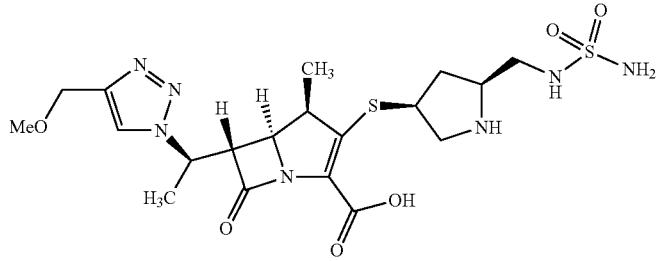<br>(4R,5S,6S)-6-((R)-1-(4-(Methoxymethyl)-1H-1,2,3-triazol-1-yl)ethyl)-4-methyl-7-oxo-3-((3S,5S)-5-((sulfamoylamino)methyl)pyrrolidin-3-ylthio)-1-azabicyclo[3.2.0]hept-2-ene-2-carboxylic acid | $^1$H NMR (D$_2$O) δ ppm: 1.13-1.14 (d, 3H), 1.69-1.72 (m, 1H), 1.76-1.78 (d, 3H), 2.69-2.73 (m, 2H), 3.22-3.24 (m, 1H), 3.36 (s, 3H), 3.39-3.44 (m, 2H) 3.54-3.55 (m, 2H), 3.62-3.67 (m, 2H), 3.92-3.99 (m, 3H), 4.13-4.15 (m, 1H), 8.19 (s, 1H). MS m/z: 514 (M − 1) |

| Examples | Structure | Analytical Data |
|---|---|---|
| 235 | 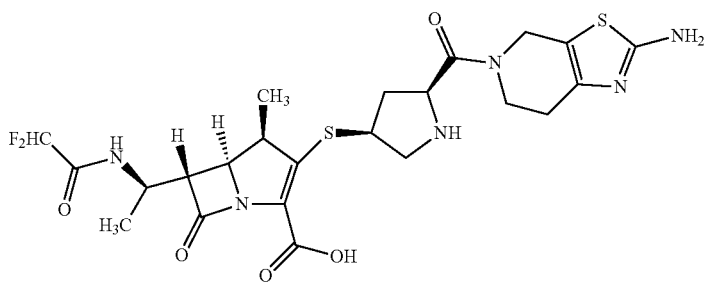<br>(4R,5S,6R)-3-((3S,5S)-5-(2-Amino-4,5,6,7-tetrahydrothiazolo[5,4-c]pyridine-5-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.14-1.18 (d, 3H), 1.35-1.36 (d, 3H), 1.95 (m, 1H), 2.66 (d, 1H), 2.99-3.01 (m, 1H), 3.23-3.33 (d, 1H), 3.44-3.47 (m, 2H), 3.54-3.59 (d, 2H), 3.81-3.89 (m, 3H), 4.03-4.08 (m, 2H), 4.40 (M, 2H), 4.64 (m, 1H), 6.15-6.29 (t, 1H). MS m/z: 571 (M + 1). |
| 236 | 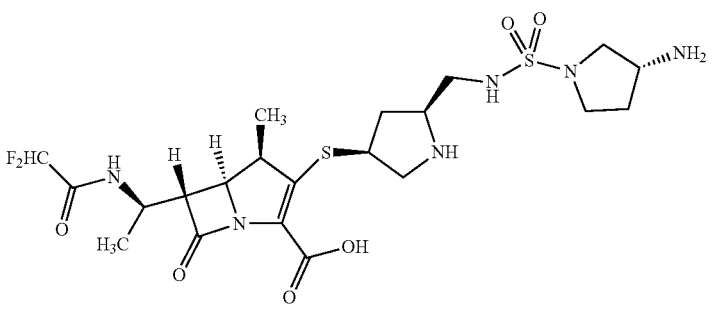<br>(4R,5S,6R)-3-((3S,5S)-5-(((R)-3-Aminopyrrolidine-1-sulfonamido)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.02-1.2 (d, 3H), 1.21-1.27 (d, 3H), 1.7-1.72 (m, 1H), 2.13 (m, 1H), 2.46 (m, 1H), 2.68 (m, 1H), 3.34-3.45 (m, 6H), 3.60-3.65 (m, 5H), 3.83 (m, 1H), 4.05 (m, 1H), 4.43 (m, 1H), 4.80 (m, 1H), 6.02-6.09 (t, 1H). MS m/z: 566 (M+) |
| 237 | 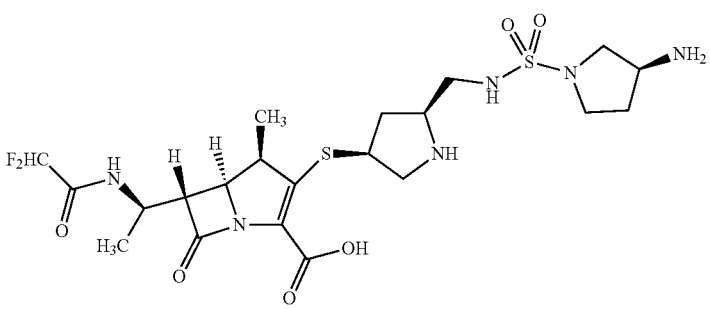<br>(4R,5S,6R)-3-((3S,5S)-5-(((R)-3-Aminopyrrolidine-1-sulfonamido)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.07-1.20 (d, 3H), 1.28-1.30 (m, 3H), 1.9 (m, 1H), 2.16 (m, 1H), 2.47-2.48 (m, 1H), 2.71-2.73 (m, 1H), 3.32-3.46 (m, 6H), 3.65 (m, 5H), 3.85 (m, 1H), 4.12 (m, 1H), 4.43 (m, 1H), 4.47 (m, 1H), 6.02-6.29 (t, 1H). MS m/z: 566 (M+) |

-continued

| Examples | Structure | Analytical Data |
|---|---|---|
| 238 | 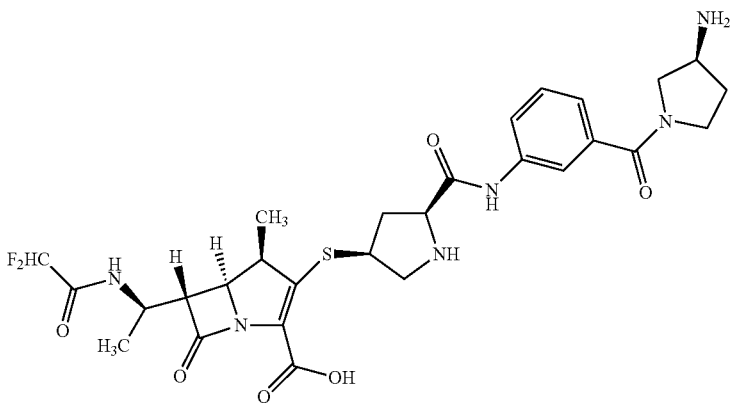<br>(4R,5S,6R)-3-((3S,5S)-5-(3-((R)-3-Aminopyrrolidine-1-carbonyl)phenylcarbamoyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$H NMR (D$_2$O) δ ppm: 1.02-1.2 (d, 3H), 1.26-1.28 (d, 3H), 1.42 (m, 1H), 2.13-2.49 (m, 3H), 3.59 (m, 2H), 3.63-3.66 (m, 2H), 3.34-3.89 (m, 2H), 3.94-3.97 (m, 3H), 4.09-4.14 (m, 2H), 4.44 (m, 1H), 6.02-6.29 (m, 1H) 7.65-7.92 (m, 3H), 8.2 (s, 1H). MS m/z: 620 (M+) |
| 239 | 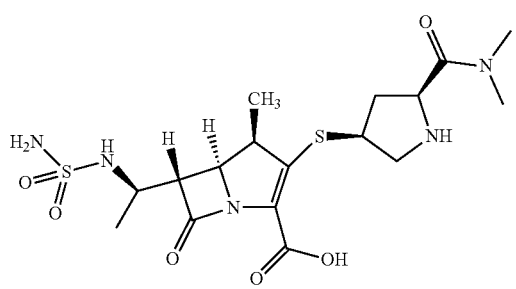<br>(4R,5S,6S)-3-((3S,5S)-5-(Dimethylcarbamoyl)pyrrolidin-3-ylthio)-4-methyl-7-oxo-6-((R)-1-(sulfamoylamino)ethyl)-1-azabicyclo[3.2.0]hept-2-ene-2-carboxylic acid | $^1$H NMR (D$_2$O) δ ppm: 1.01-1.2 (d, 3H), 1.21-1.28 (d, 3H), 1.95 (m, 1H), 2.51-2.53 (m, 1H), 2.91 (s, 3H), 3.01 (s, 3H), 3.35-3.43 (m, 2H), 3.65-3.67 (m, 2H), 3.80-3.84 (m, 2H), 4.08-4.09 (m, 2H). MS m/z: 462 (M + 1) |
| 240 | 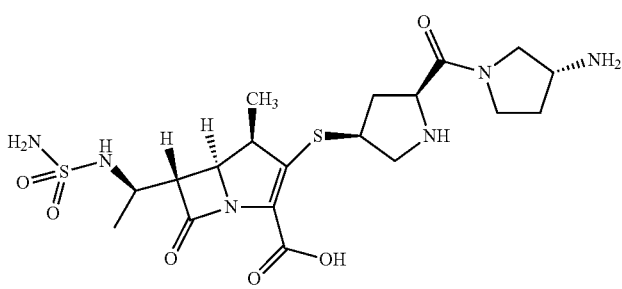<br>(4R,5S,6S)-3-((3S,5S)-5-((R)-3-Aminopyrrolidine-1-carbonyl)pyrrolidin-3-ylthio)-4-methyl-7-oxo-6-((R)-1-(sulfamoylamino)ethyl)-1-azabicyclo[3.2.0]hept-2-ene-2-carboxylic acid | $^1$H NMR (D$_2$O) δ ppm: 0.97-1.09 (d, 3H), 1.23-1.29 (d, 3H), 2.13-2.25 (m, 4H), 2.63 (m, 2H), 2.79-2.82 (m, 2H), 3.35-3.50 (m, 2H), 3.61-3.64 (m, 1H), 3.90 (m, 3H), 4.01 (m, 1H), 4.24 (m, 1H), 4.64 (m, 1H). MS m/z: 502 (M+) |

| Examples | Structure | Analytical Data |
|---|---|---|
| 241 | 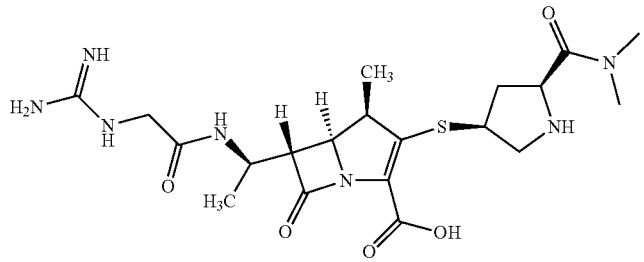<br>(4R,5S,6R)-3-((3S,5S)-5-(Dimethylcarbamoyl)pyrrolidin-3-ylthio)-6-((R)-1-(2-guanidinoacetamido)ethyl)-4-methyl-7-oxo-1-azabicyclo[3.2.0]hept-2-ene-2-carboxylic acid | $^1$H NMR (D$_2$O) δ ppm: 1.06-1.30 (d, 6H), 1.92 (m, 1H), 2.95 (s, 3H), 3.14 (s, 3H), 3.32 (m, 2H), 3.4 (m, 2H), 3.73-3.76 (m, 2H), 3.88-3.99 (m, 2H), 4.02 (m, 1H), 4.30-4.32 (m, 1H), 4.45 (m, 1H). MS m/z: 481 (M+) |
| 242 | 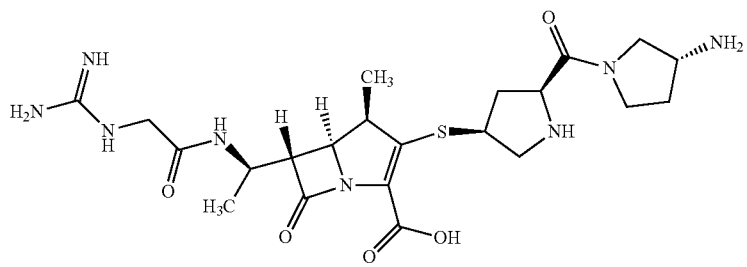<br>(4R,5S,6R)-3-((3S,5S)-5-((R)-3-Aminopyrrolidine-1-carbonyl)pyrrolidin-3-ylthio)-6-((R)-1-(2-guanidinnacetamido)ethyl)-4-methyl-7-oxo-1-azabicyclo[3.2.0]hept-2-ene-2-carboxylic acid | $^1$H NMR (D$_2$O) δ ppm: 1.19-1.22 (d, 3H), 1.26-1.30 (d, 3H), 1.72-1.83 (m, 1H), 2.15-2.18 (m, 1H), 2.33-2.35 (m, 1H), 2.43-2.46 (m, 1H), 2.74-2.78 (m, 1H), 3.09-3.12 (m, 1H), 3.23-3.26 (m, 1H), 3.36-3.39 (m, 2H), 3.54-3.57 (m, 1H), 3.68-3.73 (m, 2H), 3.74-3.78 (m, 2H), 3.98-4.02 (m, 2H), 4.13-4.15 (m, 1H), 4.34-4.43 (m, 1H), 4.45-4.47 (m, 1H). |
| 243 | 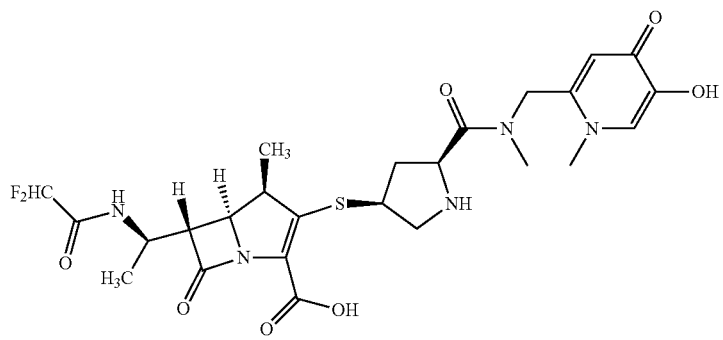<br>(4R,5S,6R)-6-((R)-1-(2,2-Difluoroacetamido)ethyl)-3-((3S,5S)-5-(((5-hydroxy-1-methyl-4-oxo-1,4-dihydropyridin-2-yl)methyl)(methyl)carbamoyl)pyrrolidin-3-ylthio)-4-methyl-7-oxo-1-azabicyclo[3.2.0]hept-2-ene-2-carboxylic acid | $^1$H NMR (D$_2$O) δ ppm: 1.07-1.17 (d, 3H), 1.37-1.38 (d, 3H), 3.04 (m, 2H), 1.86-1.92 (1H), 3.15 (s, 3H), 3.31-3.37 (m, 3H), 3.47 (m, 1H), 3.74 (s, 3H), 3.75 (m, 1H), 3.97 (m, 1H), 4.17 (m, 1H), 4.46 (m, 1h), 4.6-4.68 (m, 1H), 6.08-6.29 (t, 1H), 6.38 (s, 1H), 7.65 (s, 1H). |
| 244 | 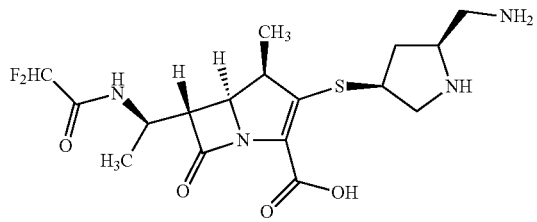<br>(4R,5S,6R)-3-((3S,5S)-5-(Aminomethyl)pyrrolidin-3-ylthio)-6-((R)-1-(2,2-dilfuoroacetamido)ethyl)-4-methyl-7-oxo-1-azabicyclo[3.2.0]hept-2-ene-2-carboxylic acid | $^1$H NMR (D$_2$O) δ ppm: 1.20-1.21 (d, 3H), 1.35-1.37 (d, 3H), 1.89-1.93 (m, 1H), 2.06-2.08 (m, 1H), 2.44-2.68 (m, 1H), 3.08-3.12 (m, 1H), 3.34-3.35 (m, 1H), 3.43-3.46 (m, m2H), 3.57-3.59 (m, 1H), 3.67-3.71 (m, 1H), 3.84-3.86 (m, 1H), 4.13-4.16 (m, 1H), 4.25-4.26 (m, 1H), 6.02-6.29 (t, 1H). MS m/z: 419 (M + 1) |

| Examples | Structure | Analytical Data |
|---|---|---|
| 245 | 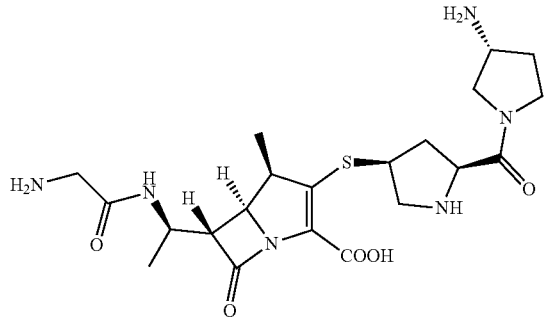<br>(4R,5S,6R)-6-((R)-1-(2-Aminoacetamido)ethyl)-3-((3S,5S)-5-((R)-3-aminopyrrolidine-1-carbooyl)pyrrolidin-3-ylthio)-4-methyl-7-oxo-1-azabicyclo[3.2.0]hept-2-ene-2-carboxylic acid | $^1$H NMR (D$_2$O) δ ppm: 1.20-1.22 (d, 3H), 1.31-1.33 (d, 3H), 1.88-1.92 (m, 1H), 2.10-2.13 (m, 1H), 2.22-2.24 (m, 1H), 2.47-2.49 (m, 1H), 2.89-2.93 (m, 1H), 3.23-3.27 (m, 1H), 3.38-3.40 (m, 1H), 3.48-3.49 (m, 1H), 3.57-3.58 (m, 2H), 3.63-3.67 (m, 1H), 3.70-3.72 (m, 1H), 3.78-3.80 (m, 2H), 3.84-3.86 (m, 2H), 3.91-4.05 (m, 1H), 4.13-4.16 (m, 1H), 4.34-4.36 (m, 1H), 4.44-4.45 (m, 1H). |
| 246 | 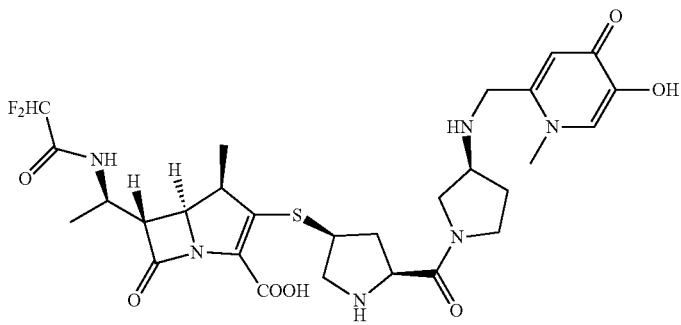<br>(4R,5S,6R)-6-((R)-1-(2,2-Difluoroacetamido)ethyl)-3-((3S,5S)-5-((R)-3-((5-hydroxy-1-methyl-4-oxo-1,4-dihydropyridin-2-yl)methylamino)pyrrolidine-1-carbonyl)pyrrolidin-3-ylthio)-4-methyl-7-oxn-1-azabicyclo[3.2.0]hept-2-ene-2-carboxylic acid | $^1$H NMR (D$_2$O) δ ppm: 1.20-1.22 (d, 3H), 1.35-1.37 (d, 3H), 1.84-1.88 (m, 1H), 1.98-2.00 (m, 1H), 2.22-2.27 (m, 1H), 2.88-2.92 (m, 1H), 3.36-3.43 (m, 2H), 3.46-3.48 (m, 2H), 3.57-3.59 (m, 3H), 3.65-3.71 (m, 3H), 3.74-3.80 (m, 2H), 3.82-3.85 (m, 2H), 4.01-4.03 (m, 1H), 4.14-4.16 (m, 1H), 4.32-4.34 (m, 1H), 4.44-4.45 (m, 1H), 6.02-6.29 (t, 1H), 6.61 (s, 1H), 7.43 (s, 1H). MS m/z: 639 (M + 1) |
| 247 | 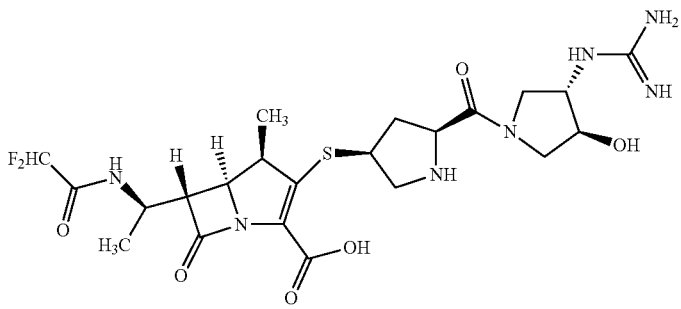<br>(4R,5S,6R)-6-((R)-1-(2,2-Difluoroacetamido)ethyl)-3-((3S,5S)-5-((3S,4S)-3-guanidino-4-hydroxypyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) δ ppm: 1.25-1.27 (d, 3H), 1.35-1.37 (d, 3H), 1.96-1.98 (m, 1H), 2.06-2.10 (m, 1H), 3.02-3.04 (m, 1H), 3.20-3.22 (m, 1H), 3.34-3.38 (m, 1H), 3.41-3.48 (m, 1H), 3.60-3.64 (m, 1H), 3.69-3.78 (m, 2H), 3.90-3.93 (m, 1H), 4.00-4.02 (m, 1H), 4.25-4.26 (m, 1H), 4.27-4.27 (m, 1H), 4.28-4.30 (m, 1H), 4.43-4.51 (m, 2H) 6.02-6.29 (t, 1H). MS m/z: 559 (M+) |

| Examples | Structure | Analytical Data |
|---|---|---|
| 248 | 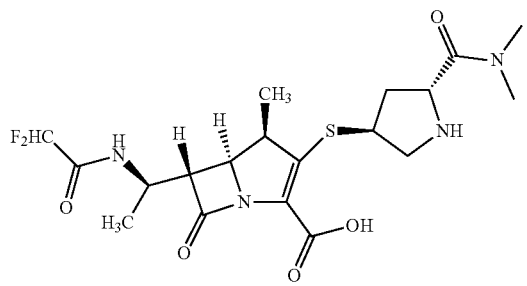<br>(4R,5S,6R)-6-((R)-1-(2,2-difluoroacetamido)ethyl)-3-((3S,5R)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 1.28 (d, 3H), 1.36 (d, 3H), 2.38-2.50 (m, 1H), 2.96 (s, 3H), 2.99 (m, 2H), 3.01 (m, 1H), 3.29 (m, 1H), 3.36 (s, 3H), 3.42-3.5 (m, 1H), 3.61-3.68 (m, 1H), 4.01 (d, 1H), 4.18 (d, 1H), 4.44-4.47 (m, 1H), 6.03-6.29 (t, 1H). Mass-(460.50) 461.1 |
| 249 | 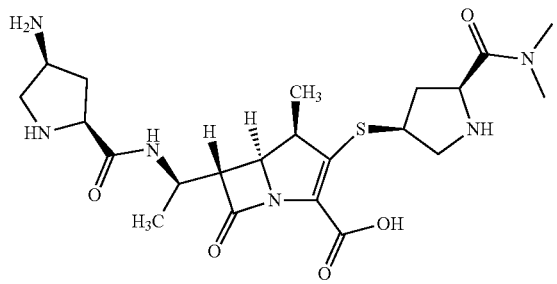<br>(4R,5S,6R)-6-((R)-1-((2R,4S)-4-aminopyrrolidine-2-carboxamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 1.22 (d, 3H), 1.28 (d, 3H), 1.34 (m, 1H), 1.57 (m, 1H), 1.82 (m, 1H), 2.08 (d, 1H), 2.30 (m, 1H), 2.30 (m, 1H), 2.99 (s, 3H), 3.12 (d, 3H), 3.32-3.46 (m, 3H), 3.60-3.81 (m, 2H), 4.00 (m, 2H), 4.42 (m, 1H), 4.59 (m, 1H), 4.72 (m, 1H), 5.25 (m, 1H). Mass (494.61) 495.1. |
| 250 | 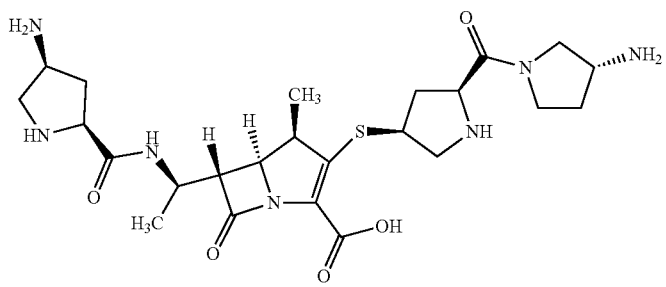<br>(4R,5S,6R)-3-((3S,5S)-5-((R)-3-aminopyrrolidine-1-carbonyl)pyrrolidin-3-ylthio)-6-((R)-1-((2R,4S)-4-aminopyrrolidine-2-carboxamido)ethyl)-4-methyl-7-oxo-1-azabicyclo[3.2.0]hept-2-ene-2-carboxylic acid | $^1$HNMR (D$_2$O)- 1.10 (d, 3H), 1.21 (d, 3H), 1.98 (m, 1H), 2.15 (m, 1H), 2.55 (m, 2H), 2.89 (m, 1H), 3.27-3.45 (m, 2H), 3.41 (d, 1H), 3.59 (m, 5H), 3.84 (d, 2H), 3.96 (m, 1H), 4.56 (m, 1H), 4.74 (m, 1H), 5.28 (m, 1H). Mass (535.66) 536.2. |

| Examples | Structure | Analytical Data |
|---|---|---|
| 251 | 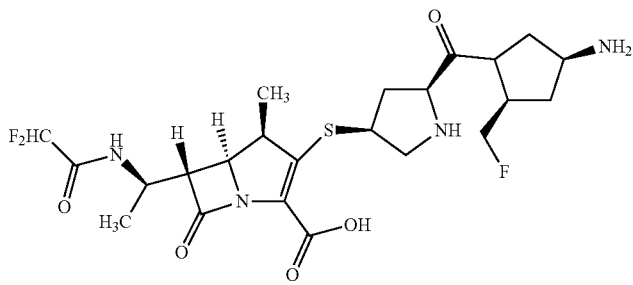<br>(4R,5S,6R)-3-((3S,5S)-5-((2S,4S)-4-amino-2-(fluoromethyl)pyrrolidine-1-carbonyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$HNMR (D$_2$O)- 1.22 (d, 3H), 1.37 (d, 3H), 1.47 (m, 1H), 1.92-2.03 (m, 2H), 2.40 (m, 1H), 3.07 (d, 2H), 3.37-3.44 (m, 2H), 3.54-3.75 (m, 6H), 4.18 (d, 1H), 4.47 (d, 1H), 4.67-4.86 (m, 1H), 5.42-5.62 (dd, 1H), 6.08-6.29 (t, 1H). Mass (533.56) 533.1. |
| 252 | 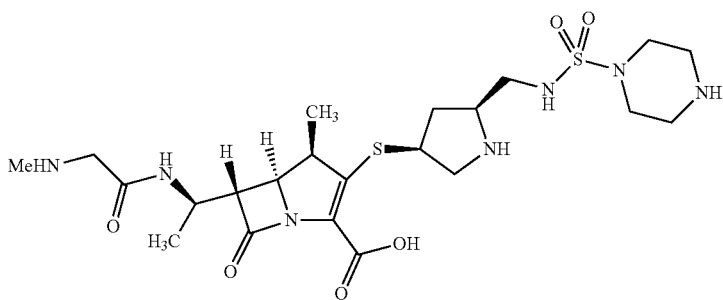<br>(4R,5S,6R)-4-methyl-6-((R)-1-(2-(methylamino)acetamido)ethyl)-7-oxo-3-((3S,5S)-5-((piperazine-1-sulfonamido)methyl)pyrrolidin-3-ylthio)-1-azabicyclo[3.2.0]hept-2-ene-2-carboxylic acid | $^1$HNMR (D$_2$O)- 1.22 (d, 3H), 1.32 (d, 3H), 1.62-1.68 (m, 1H), 1.76-1.83 (m, 1H), 2.45-2.51 (m, 2H), 2.60-2.66 (m, 2H), 2.73 (s, 3H), 2.78 (m, 1H), 3.32-3.37 (m, 3H), 3.44-3.48 (m, 3H), 3.55-3.61 (m, 2H), 3.72-3.78 (m, 2H), 3.81-3.90 (m, 3H), 4.12-4.16 (dd, 1H), 4.44-4.48 (m, 1H). Mass (559.70) 560.1. |
| 253 | 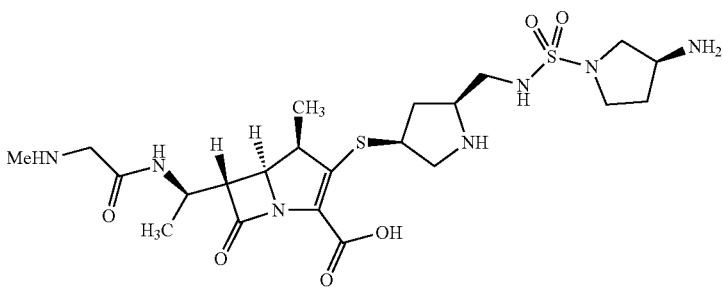<br>(4R,5S,6R)-3-((3S,5S)-5-(((S)-3-aminopyrrolidine-1-sulfonamido)methyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.22 (d, 3H), 1.29 (d, 3H), 1.79-1.83 (m, 1H), 2.08-2.12 (m, 1H), 2.44-2.50 (m, 2H), 2.73 (m, 2H), 2.75 (d, 2H), 3.30-3.33 (m, 2H), 3.46 (m, 2H), 3.48 (m, 2H), 3.52 (m, 1H), 3.59 (m, 1H), 3.59-3.62 (m, 1H), 3.72-3.79 (m, 1H), 3.84 (m, 1H), 3.86 (m, 1H), 4.04-4.05 (m, 1H), 4.14-4.16 (m, 1H), 4.36-4.39 (m, 1H), 4.44-4.48 (m, 1H). Mass (559.70) 560.2. |

-continued

| Examples | Structure | Analytical Data |
|---|---|---|
| 254 | (4R,5S,6R)-3-((3S,5S)-5-((5-hydroxy-1-methyl-4-oxo-1,4-dihydropyridine-2-carboxamido)methyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.29 (d, 3H), 1.69 (m, 1H), 2.74 (m, 1H), 2.75 (d, 6H), 3.28-3.38 (m, 2H), 3.55 (m, 2H), 3.73 (m, 1H), 3.76-3.84 (m, 1H), 3.90 (s, 3H), 4.47 (s, 3H), 6.74 (s, 1H), 7.06 (s, 1H). Mass (562.64) 561.1 |
| 255 | (4R,5S,6R)-3-((3S,5S)-5-(((1S,3R)-3-aminocyclopentanecarboxamido)methyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.29 (d, 3H), 1.84-1.89 (m, 2H), 1.91 (m, 3H), 1.96-1.98 (m, 1H), 2.32-2.39 (m, 1H), 2.63-2.70 (m, 1H), 3.75 (s, 3H), 2.97-3.01 (m, 1H), 3.28-3.38 (m, 2H), 3.54 (d, 1H), 3.58-3.59 (dd, 3H), 3.78-3.85 (m, 2H), 3.86 (d, 2H), 3.97 (br, 1H), 4.14 (d, 1H), 4.44-4.47 (m, 1H). Mass (522.66) 522. |
| 256 | (4R,5S,6R)-3-(1-(4,5-dihydrothiazol-2-yl)azetidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.16-1.18 (d, 3H), 1.25-1.27 (d, 3H), 1.92 (s, 1H), 2.77 (s, 3H), 3.17-3.21 (m, 3.56-3.58 (m, 1H), 3.60-3.64 (m, 2H), 3.87 (d, 2H), 3.97-4.01 (m, 2H), 4.10-4.13 (dd, 1H), 4.15 (br, s, 1H), 4.18-4.25 (m, 2H), 4.34-4.35 (m, 1H), 4.44-4.47 (m, 1H), 4.69-4.71 (m, 2H). Mass (453.58) 454.1 |
| 257 | (4R,5S,6R)-3-(2-(2-(aminomethyl)-5-bydroxy-4-oxopyridin-1(4H)-yl)ethylthio)-4-methyl-6-((R)-1-(2-(methylamino)acetamido)ethyl)-7-oxo-1-azabicyclo[3.2.0]bept-2-ene-2-carboxylic acid | $^1$HNMR (D$_2$O)- 1.05 (d, 3H), 1.24 (d, 3H), 1.39-1.42 (m, 1H), 1.92 (s, 1H), 2.77 (d, 2H), 2.80 (m, 2H), 2.98 (m, 1H), 3.05-3.21 (m, 1H), 3.44-3.49 (m, 2H), 3.51-3.55 (m, 1H), 3.72-3.74 (m, 1H), 3.92-4.03 (m, 3H), 4.1-4.25 (m, 2H), 4.40 (d, 3H), 6.62 (d, 1H), 7.70 (s, 1H). Mass (479.55) 480.1 |

| Examples | Structure | Analytical Data |
|---|---|---|
| 258 | 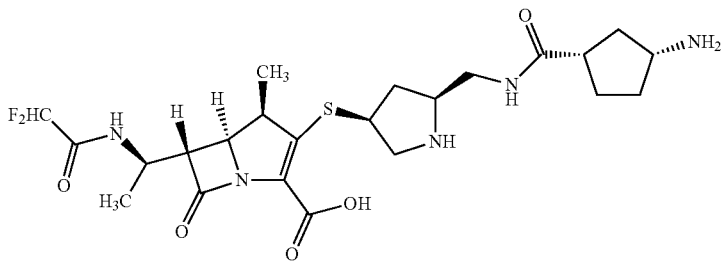<br>(4R,5S,6R)-3-((3S,5S)-5-(((1S,3R)-3-aminocyclopentanecarboxamido)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$HNMR ($D_2O$)- 1.21 (d, 3H), 1.31 (d, 3H), 1.84-1.86 (m, 1H), 2.07-2.08 (m, 2H), 2.32-2.33 (m, 2H), 2.46-4.48 (m, 3H), 2.97-2.98 (m, 2H), 3.32-3.33 (m, 2H), 3.50-3.52 (m, 2H), 3.72-3.74 (m, 2H), 3.98-4.01 (m, 1H), 3.4.014-4.17 (m, 1H), 4.27-4.29 (m, 1H) 4.45-54.48 (m, 1H) 6.16 (t, 1H). Mass- (529.60) 530. |
| 259 | 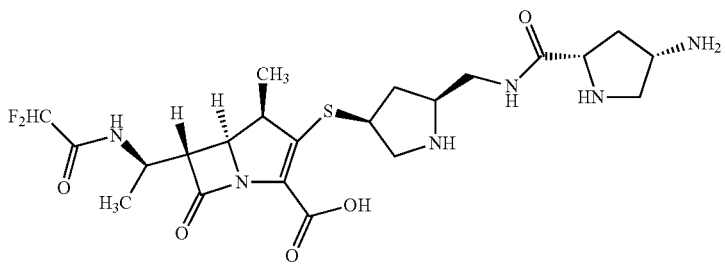<br>(4R,5S,6R)-3-((3S,5S)-5-(((2S,4S)-4-aminopyrrolidine-2-carboxamido)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$HNMR (D2O)- 1.21 (d, 3H), 1.35 (d, 3H), 2.46-2.48 (m, 1H), 2.61-2.68 (m, 2H), 3.05 (d, 1H), 3.34 (m, 2H), 3.58-3.65 (m, 4H), 3.89-4.16 (m, 3H), 4.10 (d, 1H), 4.44 (d, 1H), 6.15 (t, 1H). Mass (530.59) 531.2. |
| 260 | 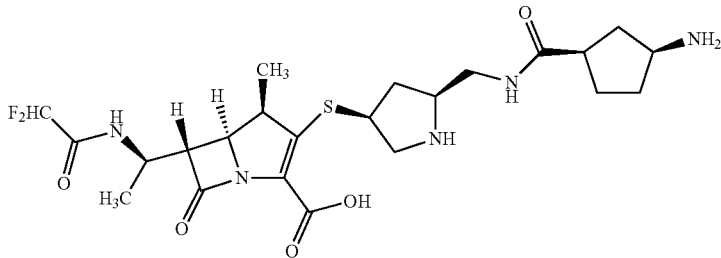<br>(4R,5S,6R)-3-((3S,5S)-5-(((1R,3S)-3-aminocyclopentanecarboxamido)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$HNMR ($D_2O$)- 1.21 (d, 3H), 1.33 (d, 3H), 1.84-1.87 (m, 1H), 2.08-2.11 (m, 2H), 2.31-2.33 (m, 2H), 2.64-2.68 (m, 2H), 2.86-2.99 (m, 2H), 3.33-3.35 (m, 2H), 3.49 (m, 1H), 3.52-3.56 (m, 2 H), 3.60-3.64 (m, 1H), 3.68-3.69 (m, 1H), 3.71 (m, 1H), 3.77-3.79 (m, 1H), 4.14-4.16 (m, 1H), 4.30-4.47 (m, 1H), 6.16 (t, 1H). Mass (529.60) 530.2. |
| 261 | 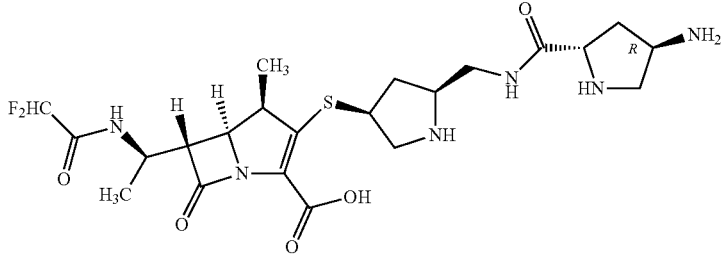<br>(4R,5S,6R)-3-((3S,5S)-5-(((2S,4R)-4-aminopyrrolidine-2-carboxamido)methyl)pyrrolidin-3-ylthio)-6-((R)-1-(2,2-difluoroacetamido)ethyl)-4-methyl-7-oxo-1-azabicyclo[3.2.0]hept-2-ene-2-carboxylic acid | $^1$HNMR ($D_2O$)- 1.21 (d, 3H), 1.36 (d, 3H), 2.32-2.33 (m, 1H), 2.45-2.48 (m 2H), 3.07-3.10 (m, 1 H), 3.30-3.33 (m, 4H), 3.52-3.57 (m, 4H), 3.74-3.79 (m, 3H), 3.91-3.94 (m, 3H), 4.07-4.11 (m, 2H), 6.15 (t, 1H). Mass (530.59) 531.2. |

| Examples | Structure | Analytical Data |
|---|---|---|
| 262 | (4R,5S,6R)-3-((3S,5S)-5-((((1R,3S)-3-aminocyclopentanecarboxamido)methyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.28 (d, 3H), 1.84-1.89 (m, 2H), 1.96-1.98 (m, 1H), 2.32-2.39 (m, 2H), 2.63-2.70 (m, 2H), 3.75 (s, 3H), 2.97-3.01 (m, 2H), 3.28-3.38 (m, 2H), 3.54 (d, 1H), 3.58-3.59 (dd, 3H), 3.78-3.85 (m, 2H), 3.86 (d, 2H), 3.97 (br, 1H), 4.14 (d, 1H), 4.44-4.47 (m, 1H). Mass (522.66) 523. |
| 263 | (4R,5S,6R)-6-((R)-1-(2,2-difluoroacetamido)ethyl)-3-(1-(4,5-dihydrothiazol-2-yl)azetidin-3-ylthio)-4-methyl-7-oxo-1-azabicyclo[3.2.0]hept-2-ene-2-carboxylic acid | $^1$HNMR (D$_2$O)- 1.17 (d, 3H), 1.36 (d, 3H), 3.18-3.19 (m, 1H), 3.56-3.62 (m, 2H), 3.63-3.65 (m, 2H), 3.98-4.01 (m, 2H), 4.12-4.14 (m, 1H), 4.23-4.26 (m, 1H), 4.42-4.46 (m, 2H), 4.56 (m, 2H), 6.16 (t, 1H). Mass (460.52) 461.0. |
| 264 | (4R,5S,6R)-3-((3S,5S)-5-((2S,4S)-4-amino-2-methylpiperidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.22 (d, 3H), 1.32 (d, 3H), 1.78-1.81 (m, 1H), 2.2 (m, 1H), 2.76 (s, 3H), 2.86 (m, 2H), 3.20-3.22 (m, 2H), 3.32-3.36 (m, 3H), 3.57-3.58 (m, 2H), 3.76-3.78 (m, 3H), 3.84-3.85 (m, 3H), 3.89 (m, 2H), 4.12-4.15 (m, 1H), 4.29-4.37 (m, 2H), 4.4-4.48 (m, 1H). Mass (522.66) 523.2. |
| 265 | (4R,5S,6R)-3-(((2S,4S)-1-acetyl-4-aminopyrrolidin-2-yl)methylthio)-6-((R)-1-(2,2-difluoroacetamido)ethyl)-4-methyl-7-oxo-1-azabicyclo[3.2.0]hept-2-ene-2-carboxylic acid | $^1$HNMR (D$_2$O)- 1.18 (d, 3H), 1.36 (d, 3H), 1.99-2.01 (m, 1H), 2.16 (s, 3H), 2.7-2.75 (m, 1H), 2.87-2.92 (m, 1H), 3.41-3.44 (m, 1H), 3.48 (m, 1H), 3.57-3.59 (m, 2H), 3.86-3.90 (m, 1H), 4.10-4.13 (m, 2H), 4.22-4.24 (m, 1H), 4.42-4.47 (m, 1H), 6.16 (t, 1H). Mass (460.50) 461.1. |

| Examples | Structure | Analytical Data |
|---|---|---|
| 266 | 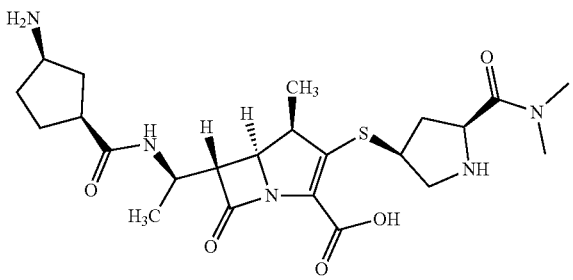<br>(4R,5S,6R)-6-((R)-1-((2S,3R)-3-aminocyclopentanecarboxamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 1.27 (d, 3H), 1.37 (d, 3H), 1.8-1.86 (m, 2H), 1.91-1.96 (m, 2H), 2.14-2.20 (m, 2H), 2.31-2.33 (m, 1H), 2.59-2.60 (m, 1H), 2.95-296 (m, 1H), 2.99 (s, 3H), 3.07 (s, 3H), 3.21-3.22 (m, 1H), 3.40-3.45 (m, 2H), 3.73-3.77 (m, 2H), 3.91 (m, 1H), 4.13-4.15 (m, 1H), 4.43-4.47 (m, 2H). MS (493.62) 494. |
| 267 | 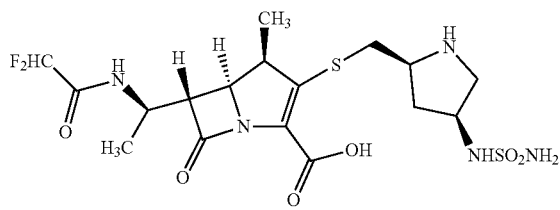<br>(4R,5S,6R)-6-((R)-1-(2,2-difluoroacetamido)ethyl)-4-methyl-7-oxo-3-(((2S,4S)-4-(sulfamoylamino)pyrrolidin-2-yl)methylthio)-1-azabicyclo[3.2.0]hept-2-ene-2-carboxylic acid | $^1$HNMR (D$_2$O)- 1.19 (d, 3H), 1.36 (d, 3H), 1.71-1.73 (m, 1H), 2.60-2.68 (m, 1H), 3.05-3.07 (m, 1H), 3.16-3.18 (m, 2H), 3.33-3.35 (m, 2H), 3.57-3.58 (m, 2H), 3.60-3.63 (m, 1H), 4.06-4.08 (m, 2H), 4.43-4.47 (m, 1H), 6.16 (t, 1H). Mass (497.54) 498.0. |
| 268 | 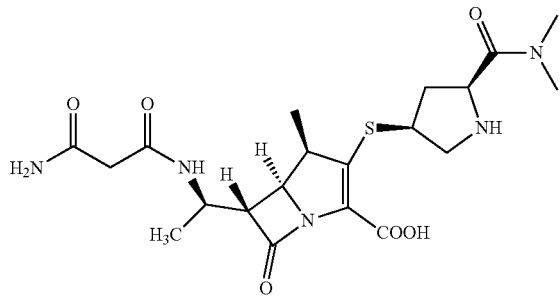<br>(4R,5S,6R)-6-((R)-1-(3-amino-3-oxopropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 1.17 (d, 3H), 1.42 (d, 3H), 1.92 (s, 3H), 3.04 (s, 5H), 3.28-3.31 (m, 2H), 3.34-3.38 (m, 2H), 3.41-3.48 (t, 1H), 3.53-3.65 (m, 2H), 3.91-3.99 (m, 3H), 4.16 (d, 1H), 4.35-4.39 (q, 1H), 4.55-4.58 (dd, 1H), 4.61-4.65 (m, 2H). Mass (467.65)-468.1. |
| 269 | 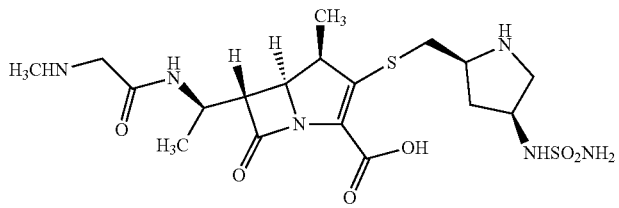<br>(4R,5S,6R)-4-methyl-6-((R)-1-(2-(methylamino)acetamido)ethyl)-7-oxo-3-(((2S,4S)-4-(sulfamoylamino)pyrrolidin-2-yl)methylthio)-1-azabicyclo[3.2.0]hept-2-ene-2-carboxylic acid | $^1$HNMR (D$_2$O)- 1.24 (d, 3H), 1.30 (d, 3H), 1.47-1.48 (m, 4H), 2.43-2.50 (m, 1H), 2.63-2.72 (m, 4H), 2.75 (s, 3H), 3.18-3.23 (q, 2H), 3.32-3.35 (m, 1H), 3.59-3.65 (m, 1H), 3.72-3.79 (m, 1H), 3.84 (m, 2H), 4.13-4.23 (m, 1H), 4.36-4.47 (m, 1H). Mass (490.60) 491.2. |

| Examples | Structure | Analytical Data |
|---|---|---|
| 270 | 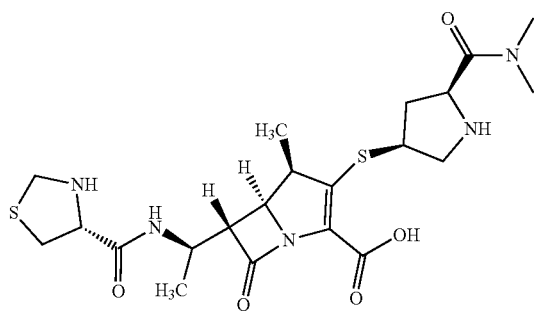<br>(4R,5S,6R)-3-((3S,5S)-5-(dimethylcarbamoyl)pyrrolidin-3-ylthio)-4-methyl-7-oxo-6-((R)-1-((R)-thiazolidine-4-carboxamido)ethyl)-1-azabicyclo[3.2.0]hept-2-ene-2-carboxylic acid | $^1$HNMR ($D_2O$)- 1.20 (d, 3H), 1.31 (d, 3H), 1.52 (s, 1H), 1.91 (m, 2H), 2.68 (s, 1H), 2.99 (s, 4H), 3.07 (s, 3H), 3.14-3.35 (m, 1H), 3.35 (m, 3H), 3.59 (m, 2H), 4.00 (m, 2H), 4.12-4.17 (m, 2H), 4.27-4.39 (m, 2H), 4.57-4.73 (m, 2H). Mass (497.63) 498.1. |
| 271 | 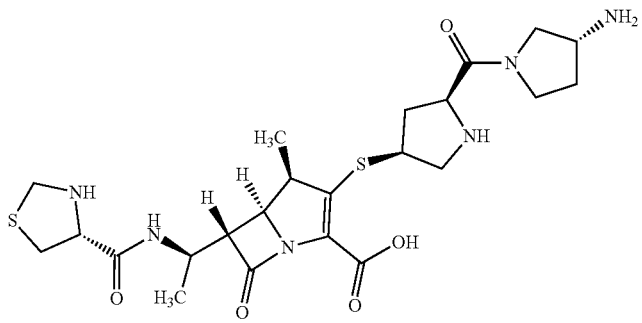<br>(4R,5S,6R)-3-((3S,5S)-5-((R)-3-aminopyrrolidine-1-carbonyl)pyrrolidin-3-ylthio)-4-methyl-7-oxo-6-((R)-1-((R)-thiazolidine-4-carboxamido)ethyl)-1-azabicyclo[3.2.0]hept-2-ene-2-carboxylic acid | $^1$HNMR ($D_2O$)- 1.21 (d, 3H), 1.32 (d, 3H), 1.52 (m, 1H), 1.84 (m, 1H), 1.91 (m, 1H), 2.12 (m, 1H), 2.24 (m, 1H), 2.48 (m, 2H), 2.68 (m, 2H), 2.84 (m, 2H), 3.12-3.15 (m, 4H), 3.37 (m, 2H), 3.58-3.61 (m, 2H), 3.70-3.76 (m, 2H), 3.87 (s, 2H), 3.99-4.25 (m, 4H), 4.39-4.71 (m, 1H). Mass (538.68) 537. |
| 272 | 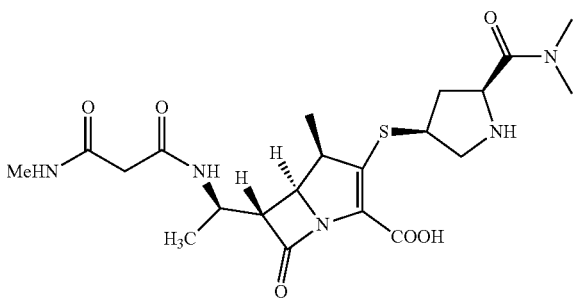<br>(4R,5S,6R)-3-((3S,5S)-5-(dimethylcarbamoyl)pyrrolidin-3-ylthio)-4-methyl-6-((R)-1-(3-(methylamino)-3-oxopropanamido)ethyl)-7-oxo-1-azabicyclo[3.2.0]hept-2-ene-2-carboxylic acid | $^1$HNMR ($D_2O$)- 1.33 (d, 3H), 1.46 (d, 3H), 1.92-1.97 (m, 2H), 2.56 (m, 1H), 2.73 (s, 3H), 2.76 (s, 3H), 2.95-2.99 (m, 2H), 3.07 (m, 2H), 3.09 (m, 2H), 3.11 (m, 1H), 3.25-3.29 (m, 2H), 3.36-3.4 (m, 2H), 3.71-3.77 (m, 1H), 3.92-3.98 (m, 2H), 4.12-4.75 (m, 2H). Mass (481.57) 482.2 |

-continued

| Examples | Structure | Analytical Data |
|---|---|---|
| 273 | 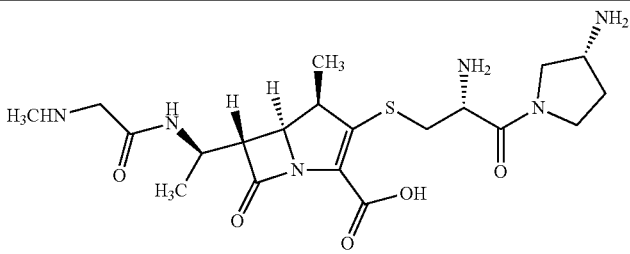<br>(4R,5S,6R)-3-((R)-2-amino-3-((R)-3-aminopyrrolidin-1-yl)-3-oxopropylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.24 (d, 3H), 1.33 (d, 3H), 1.82-1.83 (m, 2H), 2.53-2.56 (m, 2H), 2.76 (s, 3H), 3.05 (m, 2H), 3.17-3.20 (m, 2H), 3.32-3.37 (m, 2H), 3.72-3.73 (m, 2H), 3.78 (d, 2H), 4.02-4.07 (m, 2H). Mass (468.57) 469.5 |
| 274 | 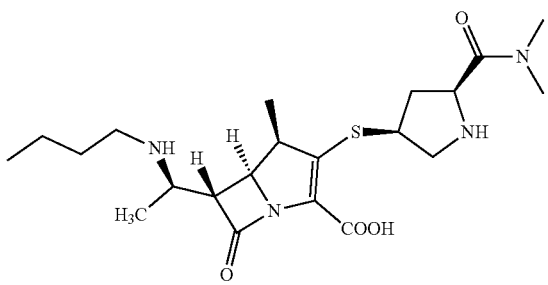<br>(4S,5S,6R)-6-((R)-1-(butylamino)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 0.96 (s, 3H), 1.22 (d, 3H), 1.25 (d, 3H), 1.31 (d, 3H), 1.49-1.56 (m, 2H), 2.99 (m, 1H), 3.04 (s, 3H), 3.07 (s, 3H), 3.09 (m, 1H), 3.35-3.45 (m, 2H), 3.58-3.59 (m, 1H), 3.72-3.73 (m, 1H), 3.82 (m, 1H), 3.86 (m, 1H), 4.00 (m, 1H), 4.26 (d, 1H), 4.62 (m, 1H). Mass (438.58) 439.2 |
| 275 | 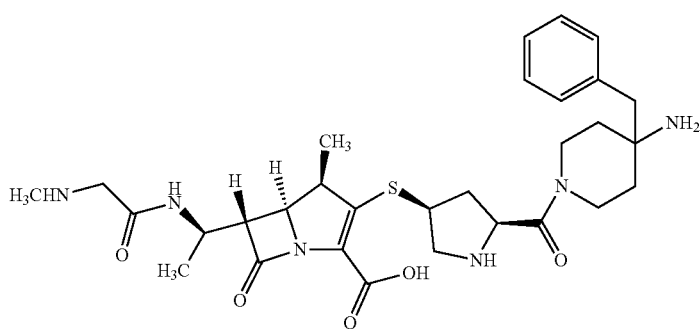<br>(4R,5S,6R)-3-((3S,5S)-5-(4-amino-4-benzylpiperidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.24 (d, 3H), 1.33 (d, 3H), 1.82-1.83 (m, 2H), 2.53-2.56 (m, 2H), 2.76 (s, 3H), 3.05 (m 3H), 3.17-3.20 (m, 4H), 3.32-3.37 (m, 4H), 3.72-3.73 (m, 2H), 3.72-3.73 (m, 2H), 3.78 (d, 2H), 4.02-4.07 (m, 2H), 7.31 (d, 2H), 7.45 (d, 2H). Mass (598.76) 599.5 |
| 276 | 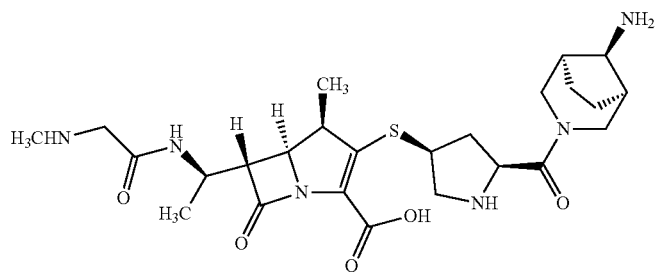<br>(4R,5S,6R)-3-((3S,5S)-5-((1R,5S,8S)-8-amino-3-azabicyclo[3.2.1]octane-3-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.29 (d, 3H), 1.55-1.64 (m, 3H), 1.78 (m, 1H), 2.43-2.47 (m, 3H), 2.76 (s, 3H), 2.97 (m, 1H), 3.12 (m, 1H), 3.33 (m, 1H), 3.44-3.47 (m, 2H), 3.58-3.78 (m, 3H), 3.86 (d, 2H), 3.99 (m, 1H), 4.08-4.13 (m, 2H), 4.40 (m, 1H), 4.49 (m, 1H), 4.55-4.59 (m, 1H). Mass (522.66) 523.2 |

| Examples | Structure | Analytical Data |
|---|---|---|
| 277 | 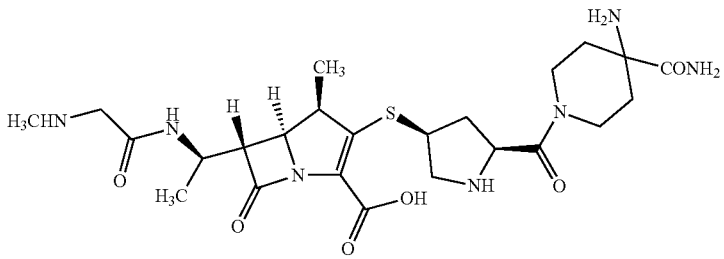<br>(4R,5S,6R)-3-((3S,5S)-5-(4-amino-4-carbamoylpiperidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.35 (d, 3H), 1.74-1.81 (m, 2H), 2.00-2.12 (m 4H), 2.47-2.58 (m, 1H), 2.76 (s, 3H), 3.00-3.05 (m, 1H), 3.34-3.46 (m, 2H), 3.59-3.68 (m, 2H), 3.72-3.78 (m, 2H), 3.81 (m, 1H), 3.85 (m, 1H), 3.89 (d, 2H), 4.05 (d, 1H), 4.37 (m, 1H), 4.45-4.48 (m, 1H), 4.71-4.76 (m, 1H). Mass (551.66) 552.2 |
| 278 | 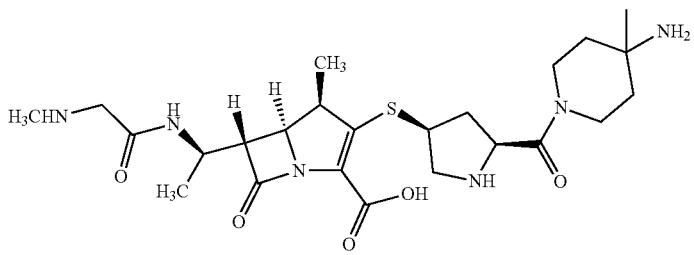<br>(4R,5S,6R)-3-((3S,5S)-5-(4-amino-4-carbamoylpiperidine-1-carbonyl)pyrroldin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.33 (d, 3H), 1.50 (s, 3H), 1.81-1.84 (m, 3H), 2.43-2.50 (m, 2H), 2.76 (s, 3H) 2.90-.299 (m, 1H), 3.20-3.33 (m, 2H), 3.38-3.50 (m, 2H), 3.59-3.60 (m, 1H), 3.72-3.78 (m, 2H), 3.88 (d, 2H), 3.96 (m, 1H), 4.05-4.08 (m, 2H), 4.46-4.49 (m, 1H), 4.54-4.56 (m, 1H). Mass (522.66) 523.4 |
| 279 | 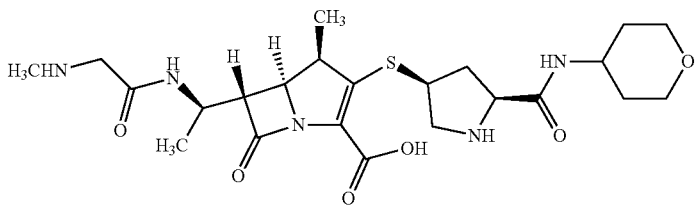<br>(4R,5S,6R)-4-methyl-6-((R)-1-(2-(methylamino)acetamido)ethyl)-7-oxo-3-((3S,5S)-5-(tetrahydro-2H-pyran-4-ylcarbamoyl)pyrrolidin-3-ylthio)-1-azabicyclo[3.2.0]hept-2-ene-2-carboxylic acid | $^1$HNMR (D$_2$O)- 1.22 (d, 3H), 1.36 (d, 3H), 1.57-1.60 (m, 2H), 1.87 (m, 2H), 2.06 (m, 2H), 2.56-2.60 (m, 2H), 2.76 (s, 3H), 3.07 (m, 1H), 3.20-3.22 (m, 1H), 3.35-3.42 (m, 2H), 3.54-3.59 (m, 2H), 3.72 (m, 2H), 3.97 (m, 1H), 4.00-4.09 (m, 2H), 4.12-4.14 (m, 1H), 4.46 (m, 1H). Mass (509.62) 509.61. |
| 280 | 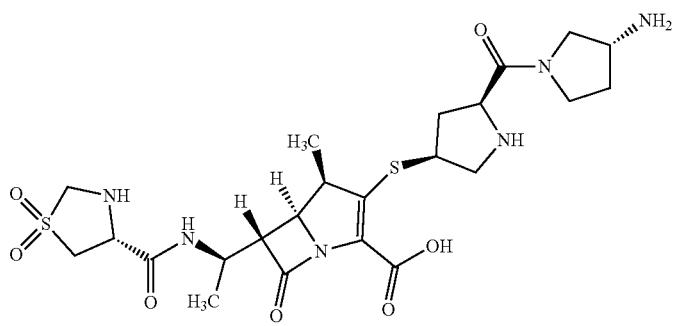<br>(4R,5S,6R)-3-((3S,5S)-5-((R)-3-aminopyrrolidine-1-carbonyl)pyrrolidin-3-ylthio)-4-methyl-7-oxo-6-((R)-1-((R)-1,1-dioxothiazolidine-4-carboxamido)ethyl)-1-azabicyclo[3.2.0]hept-2-ene-2-carboxylic acid | $^1$HNMR (D$_2$O)- 1.21 (d, 3H), 1.33 (d, 3H), 1.92-1.95 (m, 1H), 2.26 (m, 2H), 2.47-2.52 (m, 2H), 2.75-2.78 (m, 2H), 2.95-3.00 (m, 2H), 3.30-3.39 (m, 2H), 3.61-3.67 (m, 3H), 3.70-3.79 (m, 2H), 3.91 (m, 2H), 4.07-4.26 (m, 1H), 4.26-4.28 (m, 2H), 4.14-4.47 (m, 1H). Mass (570.68) 570.1 |

| Examples | Structure | Analytical Data |
|---|---|---|
| 281 | 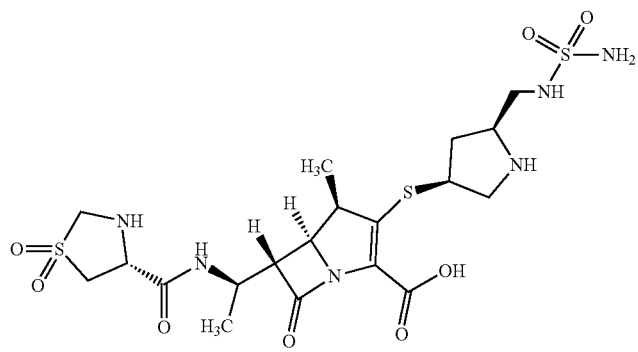<br>(4R,5S,6R)-4-methyl-7-oxo-3-((3S,5S)-5-((sulfamoylamino)methyl)pyrrolidin-3-ylthio)-6-((R)-1-((R)-1,1-dioxothiazolidine-4-carboxamido)ethyl)-1-azabicyclo[3.2.0]hept-2-ene-2-carboxylic acid | $^1$HNMR (D$_2$O)- 1.24 (d, 3H), 1.33 (d, 3H), 1.74-1.78 (m, 2H), 2.79-2.81 (m, 2H), 3.32-3.49 (m, 4H), 3.52-3.55 (m, 2H), 3.63-3.68 (m, 1H), 3.93-3.96 (m, 1H), 4.03-4.06 (m, 1H), 4.10-4.13 (m, 2H), 4.40-4.49 (m, 2H). Mass (566.67) 566.5 |
| 282 | 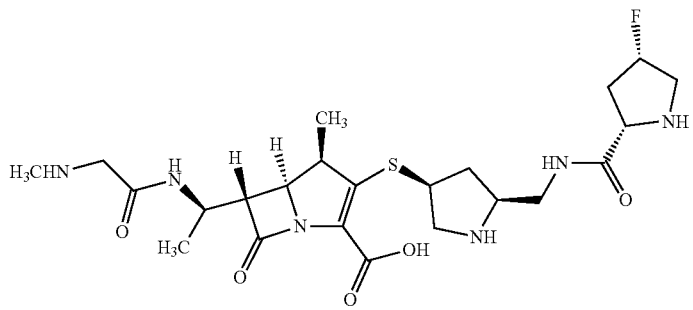<br>(4R,5S,6R)-3-((3S,5S)-5-(((2S,4S)-4-fluoropyrrolidine-2-carboxamido)methyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.21 (d, 3H), 1.28 (d, 3H), 1.86 (m, 2H), 2.08 (m, 2H), 2.23 (m, 1H), 2.47-2.48 (m, 1H), 2.60-2.68 (m, 1H), 2.70 (m, 1H), 2.75 (s, 3H), 3.33-3.42 (m, 3H), 3.56-3.63 (m, 2H), 3.72-3.76 (m, 2H), 3.86 (d, 2H), 4.05 (m, 1H), 4.13-4.16 (m, 1H), 4.40-4.43 (m, 1H), 5.30-5.49 (d, 1H). Mass (526.62) 527.1. |
| 283 | 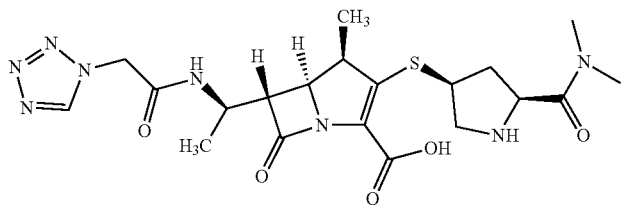<br>(4R,5S,6R)-6-((R)-1-(2-(1H-tetrazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 1.28 (d, 3H), 1.34 (d, 3H), 1.97-1.99 (m, 1H), 2.99 (s, 3H), 3.00 (s, 3H), 3.04 (m, 1H), 3.31-3.36 (m, 1H), 3.44-3.48 (m, 1H), 3.57-3.60 (m, 1H), 3.73-3.77 (m, 1H), 4.05 (m, 1H), 4.13-4.16 (m, 1H), 4.40-4.43 (m, 1H), 5.42 (d, 2H), 9.27 (s, 1H). Mass (492.55) 493.8 |

| Examples | Structure | Analytical Data |
|---|---|---|
| 284 | 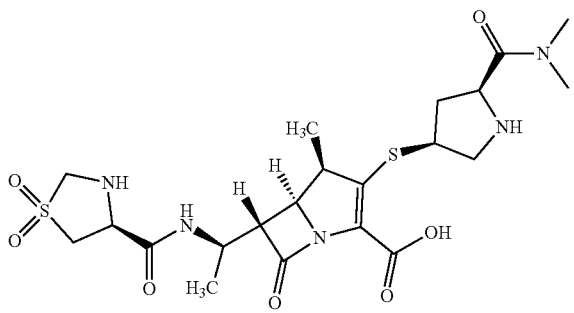<br>(4R,5S,6R)-3-((3S,5S)-5-(dimethylcarbamoyl)pyrrolidin-3-ylthio)-4-methyl-7-oxo-6-((R)-1-((R)-1,1-dioxothiazolidine-4-carboxamido)ethyl)-1-azabicyclo[3.2.0]hept-2-ene-2-carboxylic acid | $^1$HNMR (D$_2$O)- 1.29 (d, 3H), 1.36 (d, 3H), 1.84 (m, 1H), 2.60-2.79 (m, 2H), 3.00 (s, 3H), 3.05 (m, 1H), 3.07 (s, 3H), 3.38 (m, 2H), 3.48 (d, 2H), 3.63 (m, 2H), 3.76 (m, 1H), 4.06-4.17 (m, 2H), 4.42 (m, 2H). Mass (529.63) 529.1. |
| 285 | 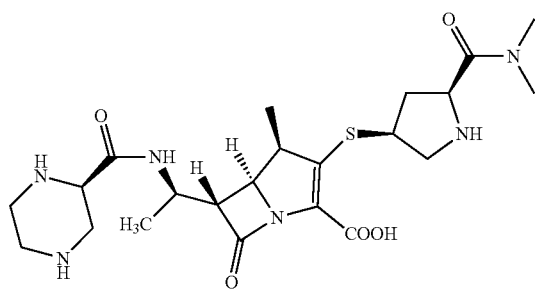<br>(4R,5S,6R)-3-((3S,5S)-5-(dimethylcarbamoyl)pyrrolidin-3-ylthio)-4-methyl-7-oxo-6-((R)-1-((R)-piperazine-2-carboxamido)ethyl)-1-azabicyclo[3.2.0]hept-2-ene-2-carboxylic acid | $^1$HNMR (D$_2$O)- 1.21 (d, 3H), 1.31 (d, 3H), 1.92 (m, 1H), 2.94 (d, 3H), 3.00 (d, 3H), 3.04 (m, 2H), 3.07 (m, 2H), 3.20-3.25 (m, 2H), 3.48 (m, 2H), 3.59-3.60 (m, 4H), 3.96 (m, 2H), 3.99-4.00 (m, 1H), 4.52-4.55 (m, 1H). Mass (494.61) 495.1 |
| 286 | 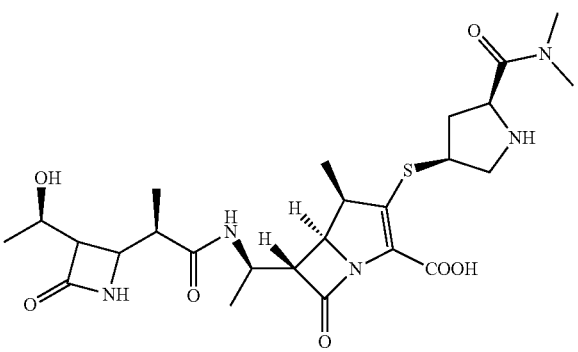<br>(4R,5S,6R)-3-((3S,5S)-5-(dimethylcarbamoyl)pyrrolidin-3-ylthio)-6-((R)-1-((2R)-2-(3-((R)-1-hydroxyethyl)-4-oxoazetidin-2-yl)propanamido)ethyl)-4-methyl-7-oxo-1-azabicyclo[3.2.0]hept-2-ene-2-carboxylic acid | $^1$HNMR (D$_2$O)- 1.27 (m, 6H), 1.33 (d, 3H), 1.39 (d, 3H), 2.98 (d, 1H), 2.99 (s, 3H), 3.07 (s, 3H), 3.08 (m, 1H), 3.18-3.20 (m, 1H), 3.40-3.44 (m, 2H), 3.55-3.58 (m, 1H), 3.71-3.76 (m, 1H), 3.86-3.88 (m, 1H), 3.95-3.96 (m, 2H), 3.99-4.02 (m, 2H), 4.10 (m, 1H), 4.52-4.55 (m, 1H). Mass (551.66) 522. |

| Examples | Structure | Analytical Data |
|---|---|---|
| 287 | 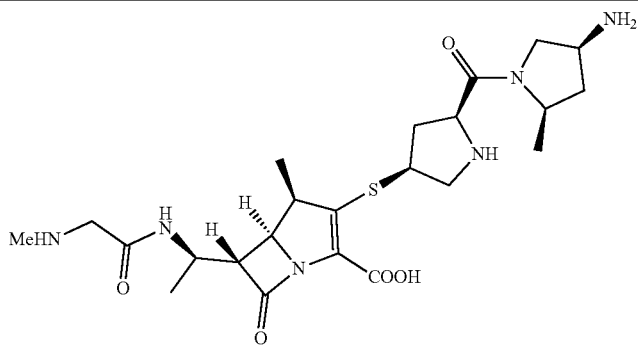<br>(4R,5S,6R)-3-((3S,5S)-5-((2R,4S)-4-amino-2-methylpyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.24 (d, 3H), 1.31 (d, 3H), 1.35 (d, 3H), 1.72-1.75 (m, 1H), 2.08 (m, 1H), 2.45 (m, 2H), 2.70 (m, 2H), 2.76 (s, 3H), 2.89 (m, 1H), 3.29-3.40 (m, 2H), 3.58 (m, 2H), 3.74-3.76 (m, 1H), 3.96 (d, 2H), 4.15 (d, 2H), 4.21-4.23 (m, 1H), 4.45-4.46 (m, 1H). Mass (508.63) 509. |
| 288 | 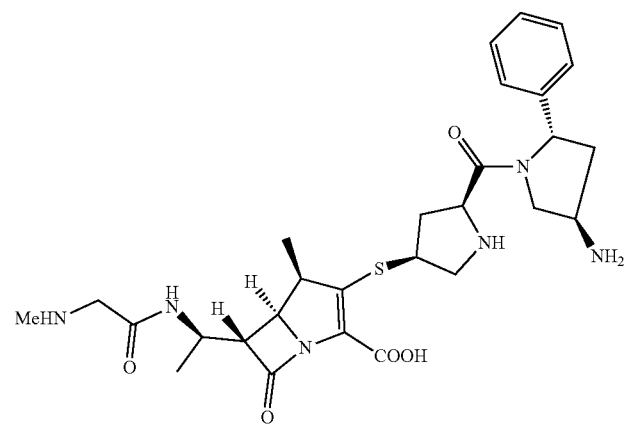<br>(4R,5S,6R)-3-((3S,5S)-5-((2S,4S)-4-amino-2-phenylpyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.23 (d, 3H), 1.32 (d, 3H), 1.92 (m, 1H), 2.46 (m, 1H), 2.76 (s, 3H), 2.98 (m, 1H), 3.34 (m, 1H), 3.52-3.89 (m, 4H), 3.94-3.95 (m, 2H), 4.02-4.08 (m, 2H), 4.11-4.14 (m, 2H), 4.47 (m, 1H), 7.37-7.50 (m, 5H). Mass (570.70) 571.3. |
| 289 | 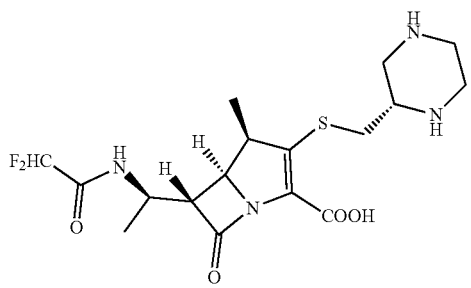<br>(4R,5S,6R)-6-((R)-1-(2,2-difluoroacetamido)ethyl)-4-methyl-7-oxo-3-((S)-piperazin-2-ylmethylthio)-1-azabicyclo[3.2.0]hept-2-ene-2-carboxylic acid | $^1$HNMR (D$_2$O)- 1.26 (d, 3H), 1.36 (d, 3H), 2.75-2.81 (m, 2H), 2.94-3.00 (m, 1H), 3.21-3.28 (m, 3H), 3.34-3.42 (m, 2H), 3.55-3.58 (m, 2H), 4.15 (d, 2H), 4.46 (m, 1H), 6.16 (t, 1H). Mass (418.46) 419.2. |

| Examples | Structure | Analytical Data |
|---|---|---|
| 290 | 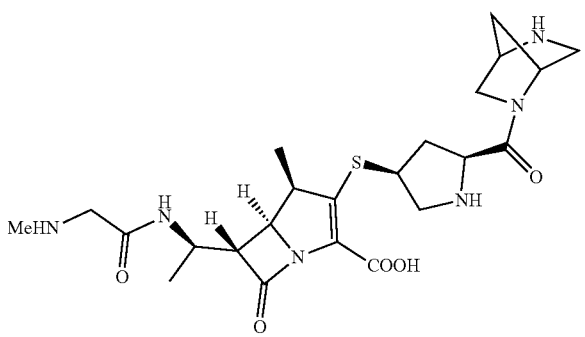<br>(4R,5S,6R)-3-((3S,5S)-5-((1R,4R)-2,5-diazabicyclo[3.2.0]heptane-2-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.26 (d, 3H), 1.36 (d, 3H), 1.39-1.46 (m, 1H), 1.89 (m, 1H), 2.28 (m, 1H), 2.76 (m, 3H), 2.98 (m, 1H), 3.36-3.42 (m, 1H), 3.49 (m, 3H), 3.58 (m, 1H), 3.65 (m, 1H), 3.74-3.76 (m, 2H), 3.87 (d, 2H), 3.98 (m, 1H), 4.13 (d, 1H), 4.26 (m, 1H), 4.47 (m, 1H), 4.60 (m, 2H). Mass (506.62) 507.3 |
| 291 | 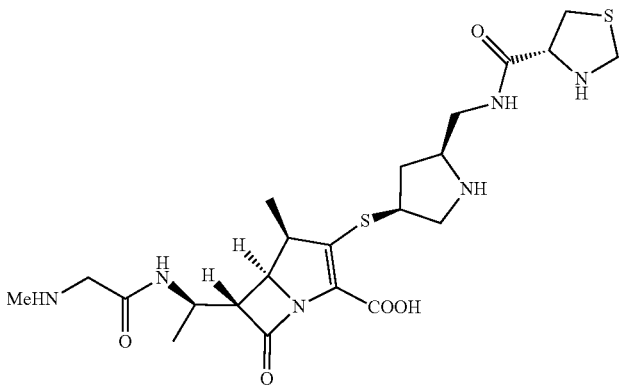<br>(4R,5S,6R)-4-methyl-6-((R)-1-(2-(methylamino)acetamido)ethyl)-7-oxo-3-((3S,5S)-5-(((R)-thiazolidine-4-carboxamido)methyl)pyrrolidin-3-ylthio)-1-azabicyclo[3.2.0]hept-2-ene-2-carboxylic acid | $^1$HNMR (D$_2$O)- 1.11 (d, 3H), 1.26 (d, 3H), 1.55 (m, 1H), 1.69 (m, 1H), 1.92 (s, 2H), 2.67 (m, 1H), 2.70-2.76 (m, 3H), 3.18-3.22 (m, 1H), 3.56-3.60 (m, 2H), 3.91-3.92 (m, 1H), 3.98 (d, 3H), 4.12-4.15 (m, 3H), 4.44 (m, 1H), 4.46-4.47 (m, 1H), 4.69 (m, 1H), 4.82 (m, 1H). Mass (526.67) 527.1. |
| 292 | 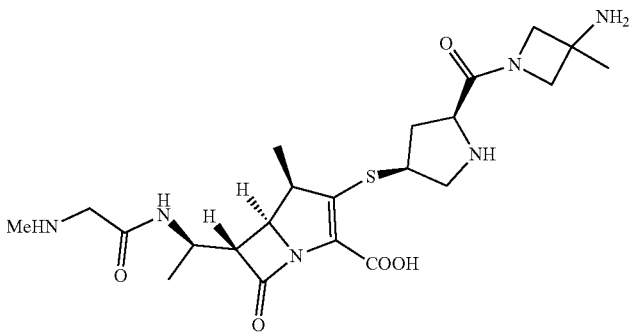<br>(4R,5S,6R)-3-((3S,5S)-5-(3-amino-3-methylazetidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O)- 1.22 (d, 6H), 1.67 (d, 3H), 1.92 (d, 3H), 2.46-2.47 (m, 1H), 2.60-2.61 (m, 2H), 2.76-2.78 (m, 2H), 3.32 (m, 1H), 3.85 (m, 2H), 3.88-3.89 (m, 2H), 4.17 (m, 2H), 4.42-4.46 (m, 2H), 4.81-4.84 (m, 2H). Mass (494.61) 495.2 |

| Examples | Structure | Analytical Data |
|---|---|---|
| 293 | 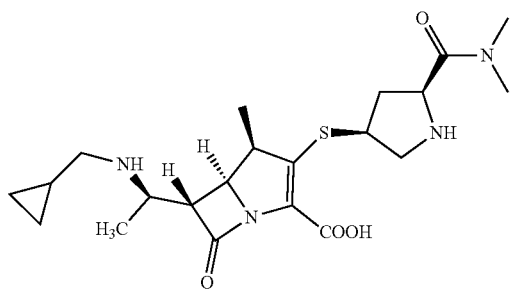<br>(4R,5S,6R)-6-((R)-1-(cyclopropylmethylamino)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 0.71 (d, 3H), 1.23 (d, 3H), 1.28-1.29 (m, 2H), 1.46-1.49 (m, 2H), 1.57-1.58 (m, 1H), 2.32 (m, 1H), 2.94-2.99 (m, 1H), 3.02-3.06 (m, 1H), 3.10-3.11 (m, 2H), 3.12-3.13 (m, 2H), 3.16-3.19 (m, 1H), 3.42-3.46 (m, 2H), 3.73 (m, 2H), 3.75-3.88 (m, 2H), 3.89-3.91 (m, 1H), 4.25-4.27 (m, 1H), 4.73-4.74 (m, 1H), 4.80 (m, 1H). Mass (436.57) 437.4. |
| 294 | 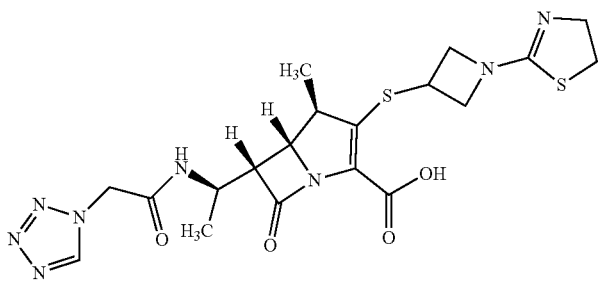<br>(4R,5S,6R)-6-((R)-1-(2-(1H-tetrazol-1-yl)acetamido)ethyl)-3-(1-(4,5-dihydrothiazol-2-yl)azetidin-3-ylthio)-4-methyl-7-oxo-1-azabicyclo[3.2.0]hept-2-ene-2-carboxylic acid | $^1$HNMR (D$_2$O)- 1.16 (d, 3H), 1.33 (d, 3H), 3.55-3.62 (m, 2H), 3.98-4.01 (m, 2H), 4.11 (d, 2H), 4.19-4.24 (m, 2H), 4.35-4.42 (m, 1H), 4.73 (d, 2H), 4.85 (d, 2H), 5.41 (d, 2H), 9.27 (s, 1H). Mass (492.58) 493.4 |
| 295 | 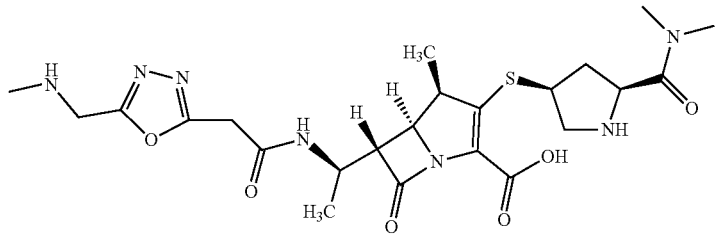<br>(4R,5S,6R)-3-((3S,5S)-5-(dimethylcarbamoyl)pyrrolidin-3-ylthio)-4-methyl-6-((R)-1-(2-(5-((methylamino)methyl)-1,3,4-oxadiazol-2-yl)acetamido)ethyl)-7-oxo-1-azabicyclo[3.2.0]hept-2-ene-2-carboxylic acid | $^1$HNMR (D$_2$O)- 1.22 (d, 3H), 1.31 (d, 3H), 1.92-1.96 (m, 3H), 2.72-2.76 (s, 3H), 2.99-3.00 (s, 3H), 3.15 (m, 3H), 3.38-3.39 (m, 3H), 4.07 (d, 4H), 4.39-4.45 (m, 4H). Mass (535.62) 536 |
| 296 | 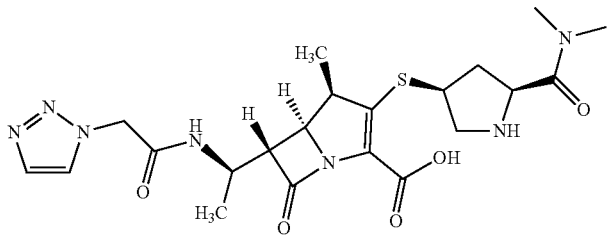<br>(4R,5S,6R)-6-((R)-1-(2-(1H-1,2,3-triazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)- 1.24 (d, 3H), 1.34 (d, 3H), 3.00-3.11 (s, 3H), 3.31-3.35 (s, 3H), 3.40 (d, 2H), 3.43 (d, 2H), 3.56 (d, 2H), 3.67-3.71 (m, 2H), 4.13 (d, 1H), 4.37-4.43 (m, 1H), 4.71-4.74 (m, 1H), 5.28-5.30 (m, 2H), 7.85 (s, 1H). Mass (491.56) 492.6 |

| Examples | Structure | Analytical Data |
|---|---|---|
| 297 | 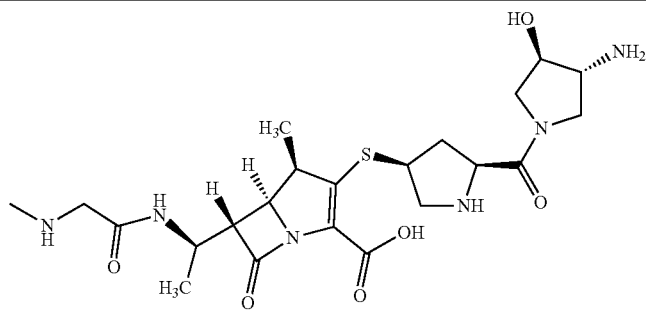<br>(4R,5S,6R)-3-((3S,5S)-5-((3R,4R)-3-amino-4-hydroxypyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR ($D_2O$)- 1.22 (d, 3H), 1.29 (d, 3H), 1.92 (m, 1H), 2.75-2.78 (m, 2H), 2.90-2.91 (d, 1H), 3.25-3.27 (m, 1H), 3.55-3.58 (m, 1H), 3.69 (m, 1H), 3.72 (m, 1H), 3.74 (d, 1H), 3.80 (m, 1H), 3.83 (s, 3H), 3.85 (m, 1H), 3.88 (d, 1H), 3.92 (m, 1H), 4.14 (d, 1H), 4.36 (d, 1H), 4.47 (d, 1H), 4.51 (d, 1H), 4.61 (d, 1H). Mass (510.61) 511.2 |

Preparation of Example 298: (4R,5S,6R)-6-((R)-1-(2-(1H-tetrazol-1-yl) acetamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid Step 1: (R)-4-Nitrobenzyl 4-((2R,3R)-3-((R)-1-(2-(1H-tetrazol-1-yl)acetamido)ethyl)-4-oxoazetidin-2-yl)-2-diazo-3-oxopentanoate

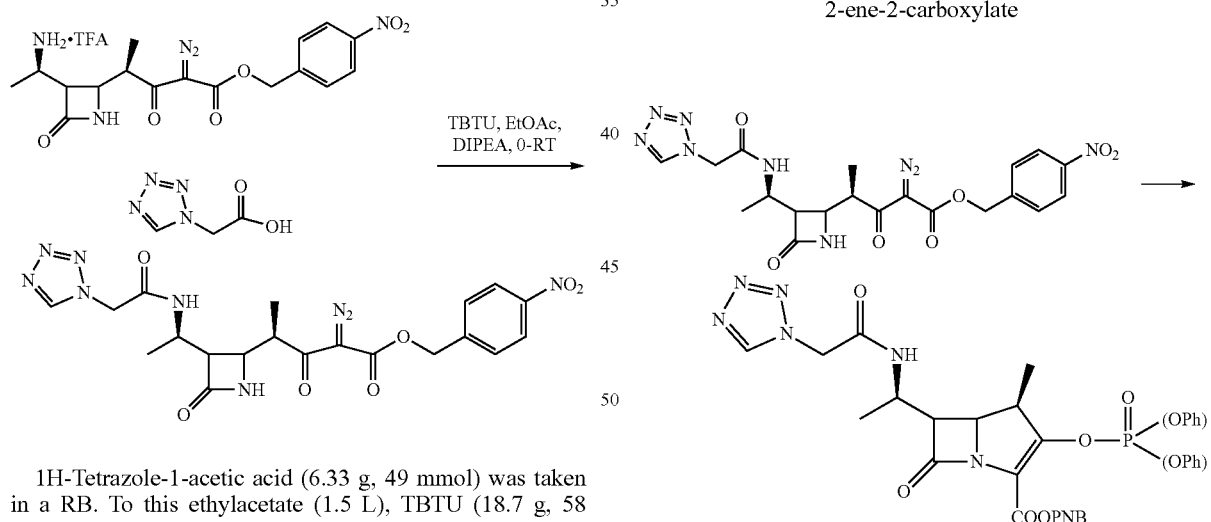

1H-Tetrazole-1-acetic acid (6.33 g, 49 mmol) was taken in a RB. To this ethylacetate (1.5 L), TBTU (18.7 g, 58 mmol), diisopropylethylamine (14 mL, 80.38 mmol) was added under $N_2$ atmosphere and reaction mixture was stirred for 1 hour. Trifluoroacetate salt of (R)-4-nitrobenzyl 4-((2R,3R)-3-((R)-1-aminoethyl)-4-oxoazetidin-2-yl)-2-diazo-3-oxopentanoate (17.5 g, 44 mmol) was diluted with ethyl acetate (75 mL) and was neutralized using diisopropylethylamine (5 mL) at 0° C. This solution was then added to the aforementioned reaction mixture at 0° C. under $N_2$ atmosphere. After the addition was complete the reaction mixture was brought to room temperature and stirred for 14 hours under $N_2$ atmosphere. After the completion of the reaction, the reaction mixture was diluted with water and extracted by ethyl acetate. The organic layer was dried using sodium sulphate and evaporated under vacuum. The crude was then purified by column chromatography to give the product (14 g, 63%). $^1$H NMR (DMSO-$d_6$, 400 MHz): 9.35 (1H, s), 8.44-8.42 (1H, d), 8.31 (1H, s), 8.27-8.25 (2H, d), 7.72-7.70 (2H, d), 5.45-5.44 (2H, d), 5.23-5.09 (2H, m), 4.08-4.02 (1H, m), 3.64-3.63 (1H, t), 3.45-3.43 (1H, q), 2.94-2.78 (1H, q), 1.2-1.19 (3H, d), 1.17-1.16 (3H, d).

Step 2: (4R,5R,6R)-4-Nitrobenzyl 6-((R)-1-(2-(1H-tetrazol-1-yl)acetamido)ethyl)-3-(diphenoxyphosphoryloxy)-4-methyl-7-oxo-1-azabicyclo[3.2.0]hept-2-ene-2-carboxylate (R)-4-Nitrobenzyl 4-((2R,3R)-3-((R)-1-(2-(1H-tetrazol-1-yl)acetamido)ethyl)-4-oxoazetidin-2-yl)-2-diazo-3-oxopentanoate (4 g, 8 mmol) was dissolved in 100 mL of acetone under $N_2$ atmosphere. To this solution was added rhodium octanoate (100 mg, 0.128 mmoles) and heated to 60° C. for 2.5 hours. After the completion of the reaction, the reaction mixture was then cooled to −30° C. and diphenylchlorophosphate (2.72 mL, 12.8 mmoles), diisopropylethylamine (2.6 mL, 13.6 mmol) and catalytic amount of dimethylaminopyridine (292 mg, 2.4 mmol) was added successively. The reaction mixture was then stirred for 1 hour at −10° C. Diisopropylethylamine (1.7 mL) and buffer solution pH=7 was added and the reaction mixture was quenched with water. The aqueous layer was extracted with dichloromethane and the organic layer evaporated under vacuum at room temperature. The crude thus obtained was purified by column chromatography to give the product as a solid (2.7 g, 47%). $^1$H NMR: 9.35 (1H, s), 8.62-8.60 (1H, d), 8.14-8.12 (2H, m), 7.62-7.60 (2H, d), 7.46-7.37 (4H, m), 7.32-7.20 (6H, m), 5.33-5.31 (2H, d), 5.28-5.24 (2H, q), 4.23-4.21 (1H, d), 4.17-4.14 (1H, m), 3.59-3.56 (1H, q), 3.5-3.4 (1H, d), 1.23-1.21 (3H, d), 1.18-1.17 (3H, d).

Step 3: (4R,5S,6R)-4-nitrobenzyl 6-((R)-1-(2-(1H-tetrazol-1-yl)acetamido)ethyl)-4-methyl-3-((3S,5S)-1-((4-nitrobenzyloxy)carbonyl)-5-((R)-3-((4-nitrobenzyloxy)carbonylamino)pyrrolidine-1-carbonyl)pyrrolidin-3-ylthio)-7-oxo-1-azabicyclo[3.2.0]hept-2-ene-2-carboxylate give the product (1.45 g, 66%) as a solid. M/S: 1027 (M+1); HPLC: 85.35%; $^1$H NMR (DMSO-d6, 400 MHz): 9.345 (1H, d), 8.64-8.61 (1H, t), 8.24-8.22 (5H, m), 7.77-7.70 (2H, t), 7.65-7.60 (2H, t), 7.54-7.52 (1H, d), 7.49-7.47 (1H, d), 5.76-5.45 (2H, d), 5.33-5.29 (2H, d), 5.24-5.20 (1H, d), 5.17-5.12 (2H, d), 5.07-5.04 (2H, d), 4.64-4.62 (1H, d), 4.21-4.12 (4H, m), 3.91-3.83 (2H, d), 3.59-3.53 (2H, d), 3.46-3.45 (2H, d), 3.23-3.14 (2H, m), 2.85-2.80 (2H, d), 1.70-1.68 (3H, t), 1.24-1.23 (3H, d), 1.19-1.17 (3H, d)

Step 4: (4R,5S,6R)-6-((R)-1-(2-(1H-tetrazol-1-yl)acetamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid

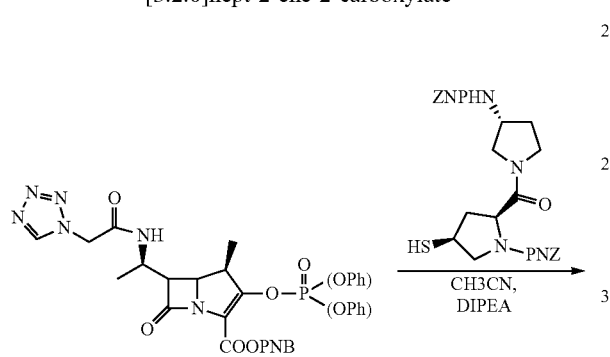

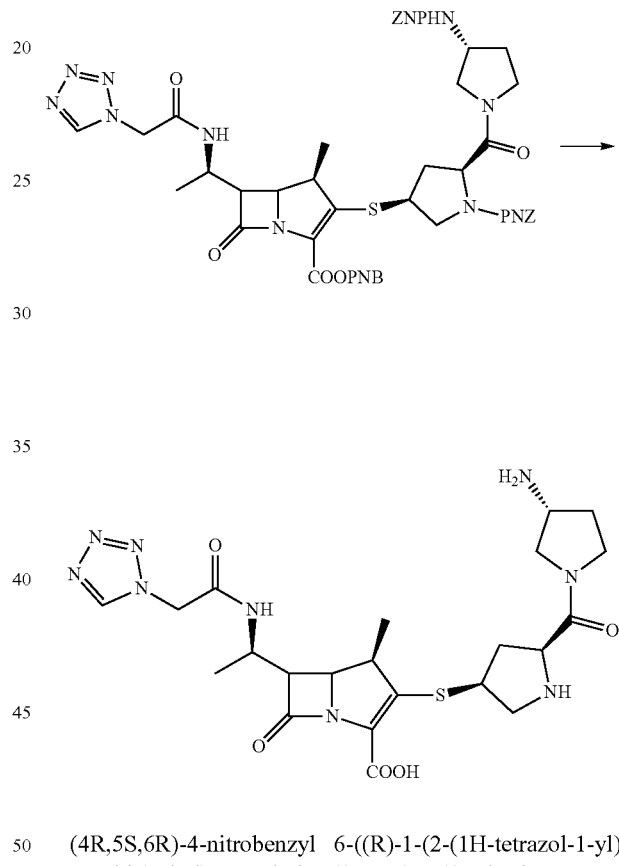

(4R,5R,6R)-4-nitrobenzyl 6-((R)-1-(2-(1H-tetrazol-1-yl)acetamido)ethyl)-3-(diphenoxyphosphoryloxy)-4-methyl-7-oxo-1-azabicyclo[3.2.0]hept-2-ene-2-carboxylate (1.5 g, 21 mmoles) was taken in acetonitrile (150 mL) at 0° C. The solution was then degassed for 10 minutes using N$_2$ atmosphere. To this solution was added the thiol (1.22 g, 21 mmoles) at 0° C. under N$_2$ followed by addition of diisopropylethylamine (0.58 mL, 1.5 eq.). The resultant solution was degassed again for 15 minutes. The reaction mixture was stirred under N$_2$ at 0° C. for 2 hours. After the completion of reaction, the reaction mixture was quenched using water and extracted by ethyl acetate. The organic layer was then washed with water, brine, dried over sodium sulphate and evaporated under vacuum to give the crude. The crude reaction mixture was purified by column chromatography to (4R,5S,6R)-4-nitrobenzyl 6-((R)-1-(2-(1H-tetrazol-1-yl)acetamido)ethyl)-4-methyl-3-((3S,5S)-1-((4-nitrobenzyloxy)carbonyl)-5-((R)-3-((4-nitrobenzyloxy)carbonylamino)pyrrolidine-1-carbonyl)pyrrolidin-3-ylthio)-7-oxo-1-azabicyclo[3.2.0]hept-2-ene-2-carboxylate (1.45 g, 1 mmol) was taken in a Parr shaker vessel and to this was added 80 mL of THF, 40 mL of water and 4.35 g of Pd/C. The reaction was kept for 1.5 hours at 5 Kg hydrogen pressure. The reaction mixture was then filtered through filter paper and was washed with ethyl acetate (5×50 mL). The reaction mixture was treated with charcoal and filtered. The aqeuous layer was again given ethyl acetate washing and was kept under lyophilization for 2 days to give the final product as a white solid (400 mg, 51.34%).

The compounds of Examples 299-312 were prepared according to the procedure for Example 298.

| Example | Structure | Analytical Data |
|---|---|---|
| 298 | (4R,5S,6R)-6-((R) - 1-(2-(1H-tetrazol-1-ylacetamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 3.33-3.40 (m, 1H), 3.67-3.71 (m, 1H), 3.73 (m, 1H), 3.78 (d, 2H), 3.90 (m, 1H), 4.12-4.14 (m, 4H), 4.14-4.15 (m, 2H), 4.16 (d, 1H), 4.41 (d, 1H), 4.60 (d, 1H), 4.84 (d, 1H), 5.42 (d, 2H), 9.27 (s, 1H). Mass (533.60) 534.5 |
| 299 | (4R,5S,6R)-6-((R) - 1-(3-amino-3-oxopropanamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.29 (d, 3H), 1.40 (d, 3H), 1.92-1.98 (m, 1H)), 2.04-2.08 (m, 1H), 2.26 (s, 1H), 2.46-2.60 (m, 2H), 2.82 (d, 2H), 3.01 (d, 1H), 3.31-3.37 (m, 2H), 3.71-3.79 (m, 2H), 4.02-4.07 (m, 2H), 4.35-4.41 (m, 1H), 4.54-4.58 (m, 1H), 4.60-4.62 (m, 2H), 4.75-4.82 (m, 1H). Mass (508.59) 509.2 |
| 300 | (4R,5S,6R)-6-((R) - 1-(2-(1H-1,2,4-triazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.23 (d, 3H), 133 (d, 3H), 1.92-1.97 (m, 2H), 3.00 (s, 3H), 3.41-3.42 (s, 3H), 3.50-3.56 (m, 1H), 3.71-3.77 (m, 2H), 4.31-4.39 (m, 2H), 4.72-4.75 (m, 2H), 4.74-4.82 (m, 1H), 5.10-5.15 (m, 2H), 8.11 (s, 1H), 8.51 (s, 1H). Mass (491.56) 492.6. |
| 301 | (4R,5S,6R)-3-((3S,5S)-5-(dimethylcarbamoyl)pyrrolidin-3-ylthio)-4-methyl-6-((R) - 1-(2-(2-methyl-2H-tetrazol-5-yl)acetamido)ethyl)-7-oxo-1-azabicyclo[3.2.0]hept-2-ene-2-carboxylic acid | $^1$HNMR (D$_2$O) - 1.33 (d, 3H), 1.42 (d, 3H), 1.96-1.99 (m, 1H), 2.99 (s, 3H), 3.06-3.11 (s, 4H) 3.38-46 (m, 3H), 3.67-3.72 (m, 2H), 3.90-3.99 (m, 2H), 4.38-4.44 (m, 5H), 4.58 4.61 (m, 1H). Mass (506.58) 507.2 |

-continued

| Example | Structure | Analytical Data |
|---|---|---|
| 302 | (4R,5S,6R)-3-((3S,5S)-5-((R)-5-aminopyrrolidine-1-carbonyl)pyrrolidin-3-ylthio)-4-methyl-6-((R) - 1-(2-(2-methyl-2H-tetrazol-5-yl)acetamido)ethyl)-7-oxo-1-azabicyclo[3.2.0]hept-2-ene-2-carboxylic acid | $^1$HNMR (D$_2$O) - 1.33 (d, 3H), 1.42 (d, 3H), 1.92 (m, 1H), 2.11-2.25 (m, 1H), 2.48-2.49 (m, 2H), 3.28-3.49 (m, 2H), 3.51-3.63 (m, 3H), 3.71-3.77 (m, 2H), 3.87-3.90 (m, 3H), 3.92-3.97 (m, 4H), 4.06-4.15 (m, 2H), 4.73 (m, 2H). Mass (547.63) 548.4 |
| 303 | (4R,5S,6R)-3-((3S,5S)-5-(dimethylcarbamoyl)pyrrolidin-3-ylthio)-4-methyl-7-oxo-6-((R) - 1-(pyrazine-2-carboxamido)ethyl) - 1-azabicyclo[3.2.0]hept-2-ene-2-carboxylic acid | $^1$HNMR (D$_2$O) - 1.21 (d, 3 H), 1.45 (d, 3H), 2.99-3.02 (s, 3H), 3.04-3.09 (m, 2H), 3.33-3.36 (s, 3H), 3.40-3.42 (m, 2H) 3.65-3.71 (m, 2H), 4.25 (d, 2H), 4.65-4.72 (m, 2H), 8.74-8 85 (m, 2H), 9.17 (s, 1H). Mass (488.56) 489.6 |
| 304 | (4R,5S,6R)-3-((3S,5S)-5-(dimethylcarbamoyl)pyrrolidin-3-ylthio)-4-methyl-6-((R) - 1-(2-(1-methyl-1H-tetrazol-5-yl)acetamido)ethyl)-7-oxo-1-azabicyclo[3.2.0]hept-2-ene-2-carboxylic acid | $^1$HNMR (D$_2$O) - 1.22 (d, 3H), 1.33 (d, 3H), 2.99-3.02 (s, 3H), 3.09-3.11 (m, 4H), 3.34-3.38 (s, 3H), 3.46-3.56 (m, 3H), 3.58-3.65 (m, 2H), 3.74-3.78 (m, 3H), 4.02 (d, 2H), 4.31-4.38 (m, 1H). Mass (506.58) 507.2 |
| 305 | (4R,5S,6R)-6-((R) - 1-(2-(1H-tetrazol-1-yl)acetamido)ethyl)-4-methyl-7-oxo-3-((3S,5S)-5-((sulfamoylamino)methyl)pyrrolidin-3-ylthio)-1-azabicyclo[3.2.0]hept-2-ene-2-carboxylic acid | $^1$HNMR (D$_2$O) - 1.16 (d, 3H), 1.35 (d, 3H), 3.32-3.45 (m, 2H), 3.56-3.58 (m, 3H), 3.68-3.73 (m, 3H), 3.95-4.04 (m, 2H), 4.14 (d, 1H), 4.38-4.72 (m, 1H), 5.41 (d, 2H), 9.26 (s, 1H). Mass (529.59) 530.6 |

| Example | Structure | Analytical Data |
|---|---|---|
| 306 | (4R,5S,6R)-6-((R) - 1-(2-(1H-tetrazol-1-yl)acetamido)ethyl)-3-(6,7-dihydro-5H-pyrazolo[1,2-a][1,2,4]triazol-4-ium-6-ylthio)-4-methyl-7-oxo-1-azabicyclo[3.2.0]hept-2-ene-2-carboxylate | $^1$HNMR ($D_2O$) - 1.24 (d, 3H), 1.35 (d, 3H), 3.35-3.39 (m, 1H), 3.64-3.65 (m, 2H), 4.22 (d, 2H), 4.43-4.45 (m, 2H), 5.05-5.14 (m, 2H), 5.43 (d, 2H), 9.03 (d, 1H), 9.26 (d, 1H). Mass (459.48) 460 |
| 307 | (4R,5S,6R)-6-((R) - 1-(2-(2H-tetrazol-2-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR ($D_2O$) - 1.21 (d, 3H), 1.35 (d, 3H), 2.97-2.99 (s, 3H), 3.08 (d, 3H), 3.32-3.38 (m, 2H), 3.55-3.59 (m, 2H), 3.98 (m, 2H), 4.13 (d, 1H), 4.15-4.17 (m, 1H), 4.42 (d, 2H), 5.61-5.63 (m, 2H), 8.85 (s, 1H). Mass (492.55) 493.1 |
| 308 | (4R,5S,6R)-3-((3S,5S)-5-(dimethylcarbamoyl)pyrrolidin-3-ylthio)-4-methyl-6-((R) - 1-(1-methyl-3-(trifluoromethyl)-1H-pyrazole-4-carboxamido)ethyl)-7-oxo-1-azabicyclo[3.2.0]hept-2-ene-2-carboxylic acid | $^1$HNMR ($D_2O$) - 1.33 (d, 3H), 1.46 (d, 3H), 2.97 (s, 3H), 3.02 (s, 3H), 3.03-3.04 (m, 2H), 3.09-3.11 (m, 1H), 3.23 (m, 2H), 3.48-3.51 (m, 2H), 3.98-4.01 (m, 5H), 4.53 (m, 1H), 7.95 (s, 1H). Mass (558.57) 559.2 |

| Example | Structure | Analytical Data |
|---|---|---|
| 309 | 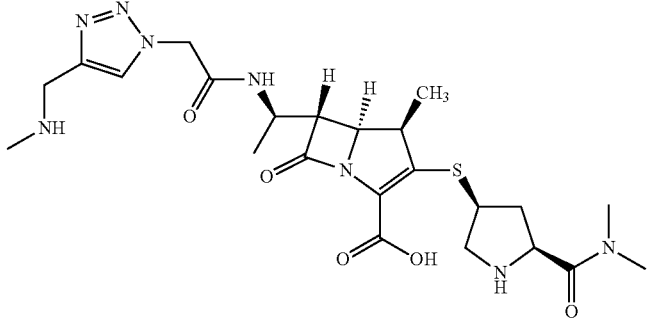<br>(4R,5S,6R)-3-((3S,5S)-5-(dimethylcarbamoyl)pyrrolidin-3-ylthio)-4-methyl-6-((R) - 1-(2-(4-((methylamino)methyl)-1H-1,2,3-triazol-1-yl)acetamido)ethyl)-7-oxo-1-azabicyclo[3.2.0]hept-2-ene-2-carboxylic acid | $^1$HNMR (D$_2$O) - 1.21 (d, 3H), 1.32 (d, 3H), 1.78 (m, 1H), 2.92-2.94 (m, 2H), 2.99 (s, 3H), 3.11 (s, 3H), 3.40-3.44 (m, 3H), 3.45-3.48 (m, 2H), 3.57 (m, 2H), 3 94 (m, 1H), 4.15-4.18 (m, 1H), 4.40 (s, 2H), 4.44-4.46 (m, 1H), 5.32 (m, 2H), 8.19-8.22 (s, 1H). Mass (534.63) 535.6 |
| 310 | 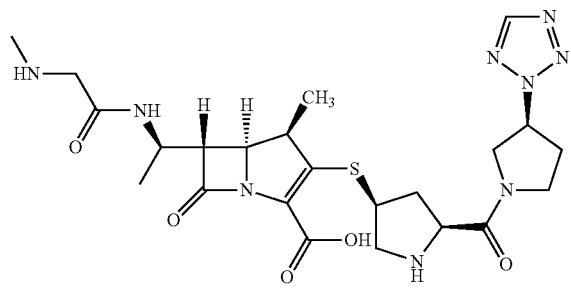 [SMILES: CNCC(=O)N[C@H](C)[C@H]1C(=O)N2C(C(=O)O)=C(S[C@@H]3CN[C@H](C(=O)N4CC[C@H](n5ncnn5)C4)C3)[C@H](C)[C@H]12]<br>(4R,5S,6R)-3-((3S,5S)-5-((S)-3-(2H-tetrazol-2-yl)pyrrolidine-1-carbonyl)pyrrolidin-3-ylthio)-4-methyl-6-((R) - 1-(2-(methylamino)acetamido)ethyl)-7-oxo-1-azabicyclo[3.2.0]hept-2-ene-2-carboxylic acid | $^1$HNMR (D$_2$O) - 1.21 (d, 3H), 1,28 (d, 3H), 2.47 (m, 1H), 2.66 (m, 3H), 2.94-3.11 (m, 2H), 3.22-3.23 (m, 1H), 3.44-3.49 (m, 3H), 3.72 (m, 1H), 3.87 (m, 3H), 4.03-4.26 (m, 5H), 4.44 (d, 2H), 5.77 (m, 1H), 8.81 (s, 1H). Mass (547.63) 548.1 |
| 311 | 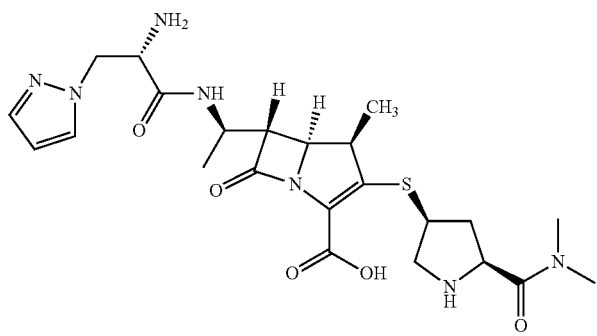 [SMILES: C[C@@H](NC(=O)[C@@H](N)Cn1cccn1)[C@H]1C(=O)N2C(C(=O)O)=C(S[C@@H]3CN[C@H](C(=O)N(C)C)C3)[C@H](C)[C@H]12]<br>(4R,5S,6R)-6-((R) - 1-((S)-2-amino-3-(1H-pyrazol-1-yl)propanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.11 (d, 3H), 1.13 (d, 3H), 2.99 (s, 3H), 3.08 (s, 3H), 3.50-3.51 (m, 3H), 3.64-3.75 (m, 3H), 3.97-4.08 (m, 4H), 4.25-4.28 (m, 1H), 4.43-4.48 (m, 2H), 6.39 (m, 1H), 7.62-7.63 (d, 2H). Mass (519.62) 520.4 |

| Example | Structure | Analytical Data |
|---|---|---|
| 312 | 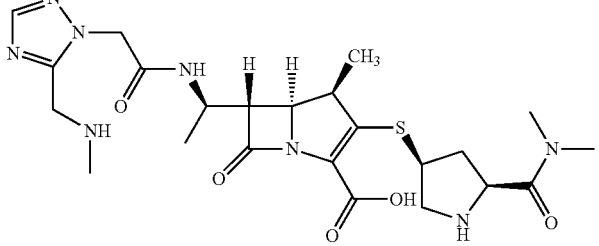<br>(4R,5S,6R)-3-((3S,5S)-5-(dimethylcarbamoyl)pyrrolidin-3-ylthio)-4-methyl-6-((R) - 1-(2-(5-((methylamino)methyl)-1H-tetrazol-1-yl)acetamido)ethyl)-7-oxo-1-azabicyclo[3.2.0]hept-2-ene-2-carboxylic acid | ¹HNMR (D₂O) - 1.21 (d, 3H), 1.33 (d, 3H), 2.62 (s, 3H). 3.00 (s, 3H), 3.09 (s, 3H), 3.35-3.40 (m, 3H), 3.59-3.64 (m, 3H), 3.98-4.01 (m, 1H), 4.15-4.17 (d, 1H), 4.35 (m, 2H), 4.42-4.45 (m, 1H), 4.71-4.73 (m, 1H), 5.44 (s, 2H). Mass (535.62) 536.2 |

Preparation of Example 313: (4R,5S,6S)-6-((R)-1-(1H-tetrazol-1-yl)ethyl)-3-((3S,5S)-5-(dimethylcarbamoyl)pyrrobdin-3-ylthio)-4-methyl-7-oxo-1-azabicyclo[3.2.0]hept-2-ene-2-carboxylic acid Steps 2B & 3B:

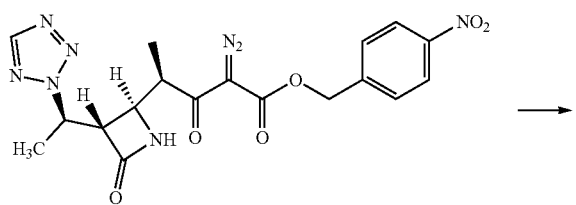

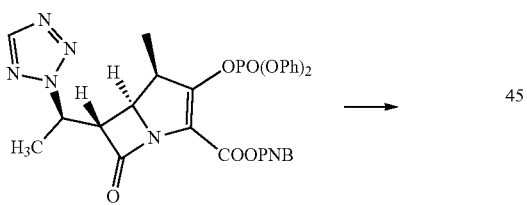

Similar to the procedure described in Step 2A and Step 3A, (R)-4-nitrobenzyl 4-((2R,3S)-3-((R)-1-(2H-tetrazol-2-yl)ethyl)-4-oxoazetidin-2-yl)-2-diazo-3-oxopentanoate (600 mg) to (4R,5S,6S)-4-nitrobenzyl 6-((R)-1-(2H-tetrazol-2-yl)ethyl)-3-((3S,5S)-5-(dimethylcarbamoyl)-1-((4-nitrobenzyloxy)carbonyl)pyrrolidin-3-ylthio)-4-methyl-7-oxo-1-azabicyclo[3.2.0]hept-2-ene-2-carboxylate was converted to its enol phosphate (0.28 g, 39.9%) and then finally to the titled product (270 mg, 27%). ¹H NMR: 9.53 (1H, s), 8.21-8.26 (4H, m), 7.71 (2H, m), 7.64-7.62 (1H, m), 7.53-7.51 (1H, d), 5.47-5.43 (1H, m), 5.29-5.20 (2H, m), 5.06-5.02 (2H, m), 4.83-4.72 (1H, m), 4.26-4.21 (1H, m), 4.12-4.08 (1H, m), 4.01-4.00 (1H, m), 3.85-3.81 (1H, m), 3.59-3.53 (1H, m), 3.18-3.12 (1H, m), 3.01-2.95 (3H, d), 2.86 (3H, d), 2.80 (1H, m), 1.70 (3H, d), 1.62-1.60 (1H, m), 1.14 (3H, d).

Step 4B: (4R,5S,6S)-6-((R)-1-(2H-tetrazol-2-yl)ethyl)-3-((3S,5S)-5-(dimethylcarbamoyl)-pyrrolidin-3-ylthio)-4-methyl-7-oxo-1-azabicyclo[3.2.0]hept-2-ene-2-carboxylic acid (4R,5S,6S)-4-nitrobenzyl 6-((R)-1-(2H-tetrazol-2-yl)ethyl)-3-((3S,5S)-5-(dimethylcarbamoyl)-1-((4-nitrobenzyloxy)carbonyl)pyrrolidin-3-ylthio)-4-methyl-7-oxo-1-azabicyclo[3.2.0]hept-2-ene-2-carboxylate (270 mg) was converted to the above title product by following the similar procedure described in Step 4A (100 mg, 67%).

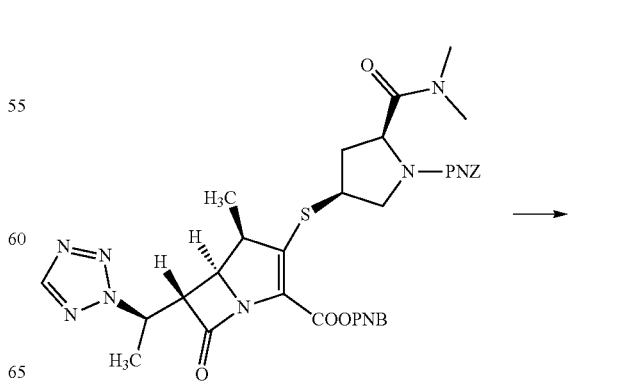

-continued

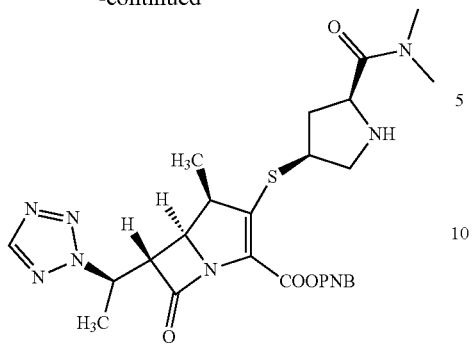

5

10

| Example | Structure | Analytical Data |
|---|---|---|
| 313 | 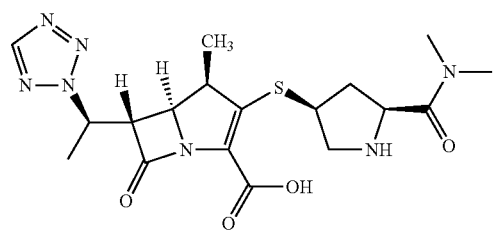 [SMILES: C[C@H]([C@H]1C(=O)N2C(C(=O)O)=C(S[C@@H]3CN[C@H](C(=O)N(C)C)C3)[C@H](C)[C@H]12)n1ncnn1]<br><br>(4R,5S,6S)-6-((R) - 1-(2H-tetrazol-2-yl)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) - 1.19 (d, 3H), 1.84 (d, 3H), 2.99 (s, 3H), 3.06 (s, 3H), 3.27-3.31 (m, 2H), 3.37-3.40 (m, 1H), 3.63-3.67 (m, 1H), 3.8 (m, 1H), 4.10 (d, 1H), 4.20 (d, 1H), 4.68 (m, 2H), 5.59-5.63 (m, 1H), 8.82 (s, 1H). Mass (435.50) 436.1 |
| 314 | 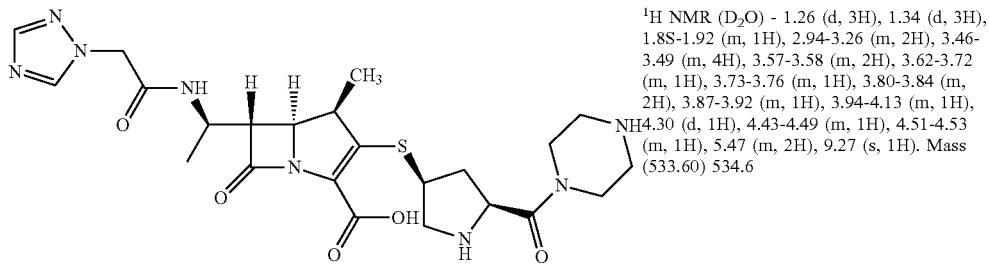<br><br>(4R,5S,6R)-6-((R) - 1-(2-(1H-tetrazol-1-yl)acetamido)ethyl)-4-methyl-7-oxo-3-((3S,5S)-5-(piperazine-1-carbonyl)pyrrolidin-3-ylthio) - 1-azabicyclo[3.2.0]hept-2-ene-2- | $^1$H NMR (D$_2$O) - 1.26 (d, 3H), 1.34 (d, 3H), 1.8S-1.92 (m, 1H), 2.94-3.26 (m, 2H), 3.46-3.49 (m, 4H), 3.57-3.58 (m, 2H), 3.62-3.72 (m, 1H), 3.73-3.76 (m, 1H), 3.80-3.84 (m, 2H), 3.87-3.92 (m, 1H), 3.94-4.13 (m, 1H), 4.30 (d, 1H), 4.43-4.49 (m, 1H), 4.51-4.53 (m, 1H), 5.47 (m, 2H), 9.27 (s, 1H). Mass (533.60) 534.6 |
| 315 | 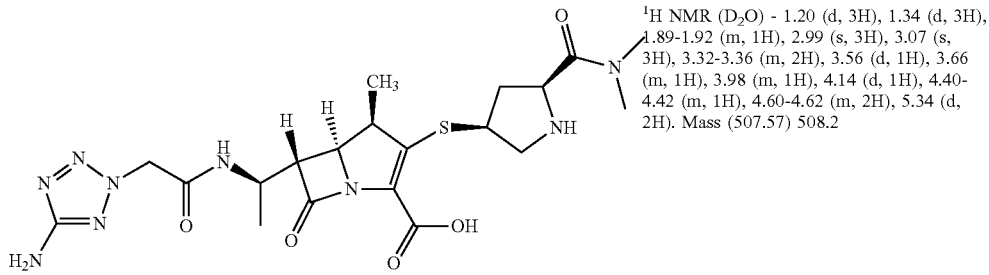<br><br>(4R,5S,6R)-6-((R) - 1-(2-(5-amino-2H-tetrazol-2-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) - 1.20 (d, 3H), 1.34 (d, 3H), 1.89-1.92 (m, 1H), 2.99 (s, 3H), 3.07 (s, 3H), 3.32-3.36 (m, 2H), 3.56 (d, 1H), 3.66 (m, 1H), 3.98 (m, 1H), 4.14 (d, 1H), 4.40-4.42 (m, 1H), 4.60-4.62 (m, 2H), 5.34 (d, 2H). Mass (507.57) 508.2 |

| Example | Structure | Analytical Data |
|---|---|---|
| 316 | (4R,5S,6R)-6-((R) - 1-(2-(5-amino-2H-tetrazol-2-yl)acetamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.20 (d, 3H), 1.34 (d, 3H), 1.80-1.85 (m, 1H), 2.08-2.30 (m, 2H), 2.44-2.48 (m, 2H), 2.70-3.00 (m, 3H), 3.19 (d, 3H), 3.29-3.57 (m, 3H), 3.54-3.78 (m, 2H), 4.14 (d, 1H), 4.38-4.42 (m, 1H), 5.29-5.32 (m, 1H). Mass (548.62) 549.1 |
| 317 | (4R,5S,6R)-6-((R) - 1-(2-(5-amino-3-(trifluoromethyl) - 1H-1,2,4-triazol-1-yl)acetamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.12 (d, 3H), 1.33 (d, 3H), 2.25-2.26 (m, 2H), 2.48-2.50 (m, 1H), 2.60-2.67 (m, 1H), 2.8-3.00 (m, 1H), 3.34 (d, 2H), 3.55 (d, 2H), 3.65 (d, 2H), 3.76 (d, 2H), 3.88 (d, 2H), 3.94 (d, 1H), 4.13-4.15 (m, 1H), 4.41-4.57 (m, 2H). Mass (615.63) 616.1 |
| 318 | (4R,5S,6R)-3-((3S,5S)-5-(dimethylcarbamoyl)pyrrolidin-3-ylthio)-4-methyl-6-((R) - 1-(2-methyl-2-(1H-tetrazol-1-yl)propanaraido)ethyl)-7-oxo-1-azabicyclop[3.2.0]hept-2-ene-2-carboxylic acid | $^1$H NMR (D$_2$O) - 1.15 (d, 3H), 1.35 (d, 3H), 1.88-1.93 (s, 6H), 3.01 (s, 3H), 3.07 (s, 3H), 3.34-3.40 (m, 2H), 3.49 (d, 2H), 3.63-3.64 (m, 2H), 4.00-4.17 (m, 2H), 4.37-4.41 (m, 1H), 4.674.71 (m, 1H), 9.36 (s, 1H). Mass-(520.61) 521 |

Preparation of Example 319: (4R,5S,6S)-6-((R)-1-(1H-tetrazol-1-yl)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid

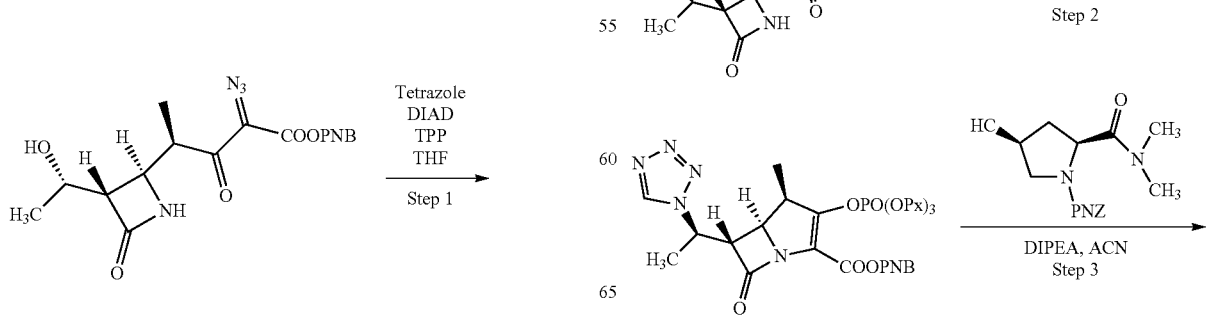

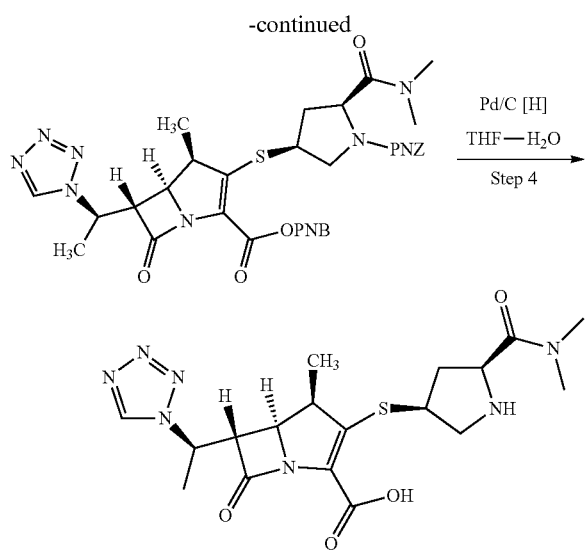

Step 1: (R)-4-nitrobenzyl 4-((2R,3S)-3-((R)-1-(1H-tetrazol-1-yl)ethyl)-4-oxoazetidin-2-yl)-2-diazo-3-oxopentanoate (A) and (R)-4-nitrobenzyl 4-((2R,3S)-3-((R)-1-(2H-tetrazol-2-yl)ethyl)-4-oxoazetidin-2-yl)-2-diazo-3-oxopentanoate (B)

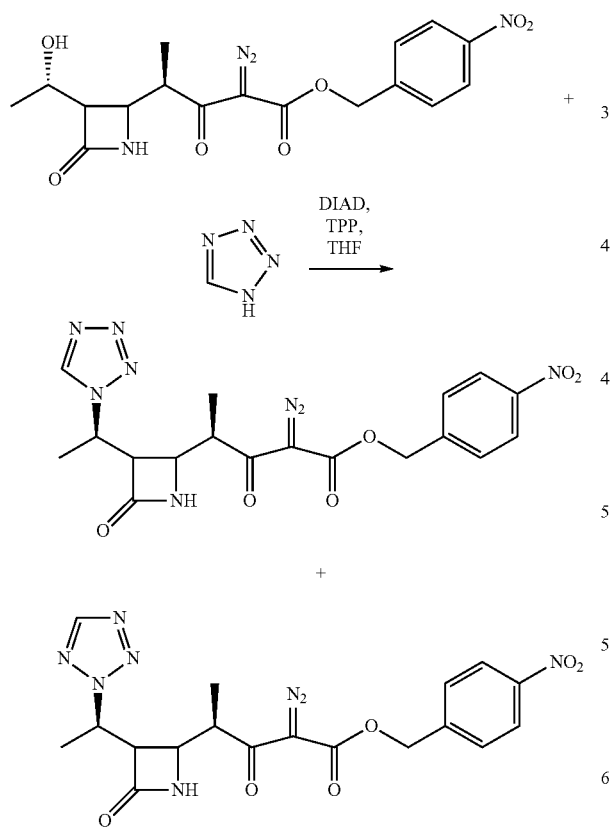

To a solution of (R)-4-nitrobenzyl 2-diazo-4-((2R,3S)-3-((S)-1-hydroxyethyl)-4-oxoazetidin-2-yl)-3-oxopentanoate (900 mg, 2.307 mmol), triphenylphosphine (967 mg, 3.691 mmol) and tetrazole (193 mg, 2.768 mmol) in tetrahydrofuran (9 mL) was added. Then diisopropylazodicarboxylate (746 mg, 3.691 mmol) at 0° C. was added to the reaction mixture and was brought to room temperature and stirred for 10 hours. After the completion of the reaction, the reaction mixture was quenched with water and the crude product extracted with ethyl acetate. The organic layer was evaporated to get the crude product which was purified by column chromatography to obtain products A (300 mg, 29.3%) and B (480 mg, 47%). $^1$H NMR: Product A: (DMSO-$d_6$, 400 MHz): 9.36 (s, 1H), 8.50 (s, 1H), 8.27-8.25 (d, 2H), 8.28-7.70 (d, 2H), 5.43 (s, 2H), 5.16-5.12 (t, 1H) 3.54 (s, 2H), 3.45-3.42 (d, 1H), 1.59-1.57 (d, 3H), 0.98-0.96 (d, 3H). Product B: (DMSO-$d_6$, 400 MHz): 8.95 (s, 1H), 8.48 (s, 1H), 8.27-8.25 (d, 2H), 5.43 (s, 2H), 3.56-3.47 (m, 2H), 1.61-1.59 (d, 3H), 0.96-0.95 (d, 3H).

Step 2A: (4R,5R,6S)-4-nitrobenzyl 6-((R)-1-(1H-tetrazol-1-yl)ethyl)-3-(diphenoxyphosphoryloxy)-4-methyl-7-oxo-1-azabicyclo[3.2.0]hept-2-ene-2-carboxylate

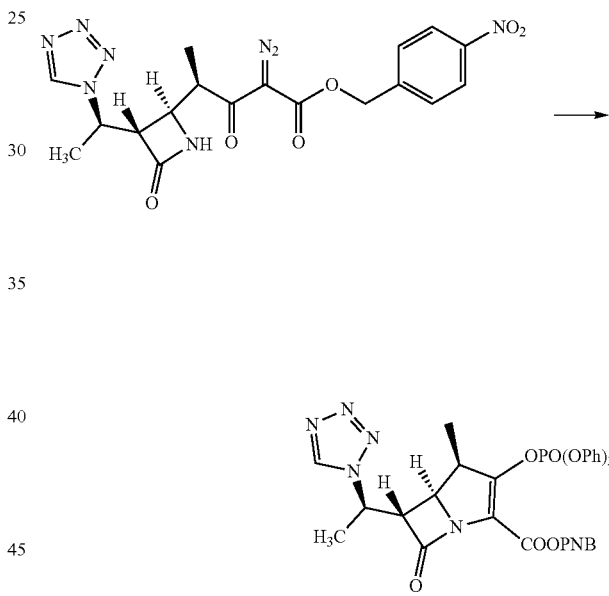

(R)-4-nitrobenzyl 4-((2R,3S)-3-((R)-1-(2H-tetrazol-2-yl)ethyl)-4-oxoazetidin-2-yl)-2-diazo-3-oxopentanoate (530 mg, 1.19 mmol) was taken in 30 mL of acetone under $N_2$ atmosphere. To this solution was added rhodium octanoate (0.025 g, 0.0324 mmol) and the resultant reaction mixture was heated to 65-70° C. for 1.5 hours. After the completion of reaction, the reaction mixture was cooled to −40° C. followed by addition of diphenylchlorophosphate (0.4 mL, 1.93 mmol), diisopropylethylamine (0.35 mL, 2 mmol) and catalytic amount of dimethylaminopyridine. The reaction mixture was brought to −20° C. and stirred for 1 hour. At −20° C. Disopropylethylamine (0.35 mL) was added to the reaction mixture and was quenched with water and extracted with dichloromethane. The organic layer was then dried over sodium sulphate and concentrated under vacuum at room temperature to give the crude product. This crude product was purified by column chromatography to give the product as a solid (250 mg, 32.2%).

245

Step 3A: (4R,5S,6S)-4-nitrobenzyl 6-((R)-1-(1H-tetrazol-1-yl)ethyl)-3-((3S,5S)-5-(dimethylcarbamoyl)-1-((4-nitrobenzyloxy)carbonyl)pyrrolidin-3-ylthio)-4-methyl-7-oxo-1-azabicyclo[3.2.0]hept-2-ene-2-carboxylate

246

Step 4A: (4R,5S,6S)-6-((R)-1-(1H-tetrazol-1-yl)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid

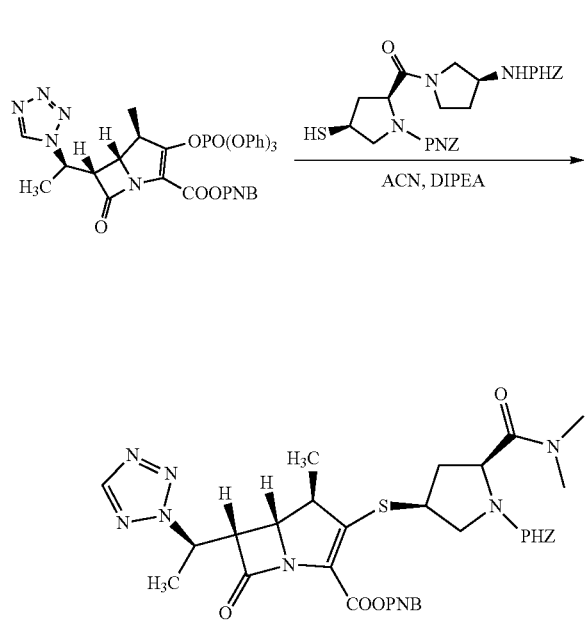

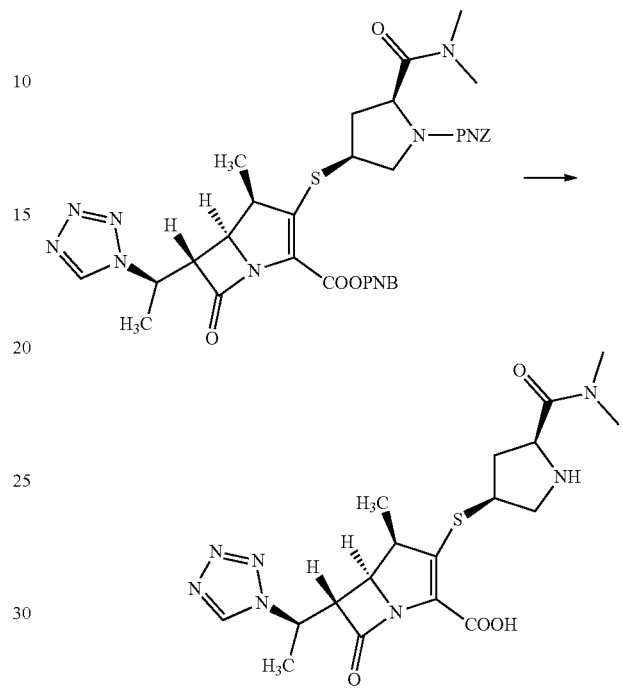

The product obtained (0.25 g, 0.39 mmol) from step 2A was taken in 10 mL of acetonitrile and cooled to 0° C. and degassed for 10 minutes. To this reaction mixture was added the thiol (0.22 g, 0.39 mmol) followed by diisopropylethylamine (0.1 mL, 0.57 mmol) under $N_2$ atmosphere. The reaction mixture was again degassed for 10-15 minutes. Further the reaction mixture was stirred at 0° C. for 2 hours. After the completion of reaction, the reaction mixture was added with water and extracted using ethyl acetate. The organic layer was concentrated and the resultant crude mixture was purified by column chromatography to give the product (260 mg, 33.6%). $^1$H NMR: (DMSO-$d_6$, 400 MHz): 9.05 (1H, s), 8.26-8.21 (4H, m), 7.72-7.51 (4H, m), 5.65-5.61 (1H, q), 5.47-5.06 (4H, m), 4.81-4.72 (1H, m), 4.06-4.05 (1H, m), 3.83-3.81 (2H, m), 3.58-3.56 (2H, m), 3.10 (1H, m), 3.02-2.95 (3H, d), 2.81 (3H, d), 2.80 (1H, m), 1.73-1.71 (3H, d), 1.60 (1H, m), 1.18-1.16 (3H, d).

(4R,5S,6S)-4-nitrobenzyl 6-((R)-1-(1H-tetrazol-1-yl)ethyl)-3-((3S,5S)-5-(dimethylcarbamoyl)-1-((4-nitrobenzyloxy)carbonyl)pyrrobdin-3-ylthio)-4-methyl-7-oxo-1-azabicyclo[3.2.0]hept-2-ene-2-carboxylate (250 mg, 0.33 mmol) was hydrogenated using Pd/C (500 mg) in a mixture of THF-$H_2O$ (20 mL:10 mL) for 1.5 hours at 5 Kg hydrogen pressure. After the regular work up, the titled compound was obtained (70 mg, 49%).

Examples 326-328 were prepared by following the procedure described in preparations 313 & 319 using appropriately substituted tetrazoles.

Example 328 was prepared by reacting compound obtained by Step 2A with appropriate $R_1$—SH group followed by the procedure of steps 3A and 4A or Example 319.

Examples 334 and 335 were prepared by reacting compound obtained by Step 2 with appropriate R1-SH group followed by the procedure in step 3 of Example 347.

| Example | Structure | Analytical Data |
|---|---|---|
| 319 | (4R,5S,6S)-6-((R) - 1-(1H-tetrazol-1-yl)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR ($D_2O$) - 1.17 (d, 3H), 1.81 (d, 3H), 2.99 (s, 3H), 3.06 (d, 3H), 3.31 (d, 1H), 3.35-3.40 (m, 1H), 3.61-3.66 (m, 2H), 3.99 (d, 1H), 4.03-4.06 (m, 1H), 4.20-.4.23 (m, 1H), 4.67-4.71 (m, 2H), 5.39-5.42 (m, 1H), 9.34 (s, 1H). Mass (435.50) 436 |

| Example | Structure | Analytical Data |
|---|---|---|
| 320 | 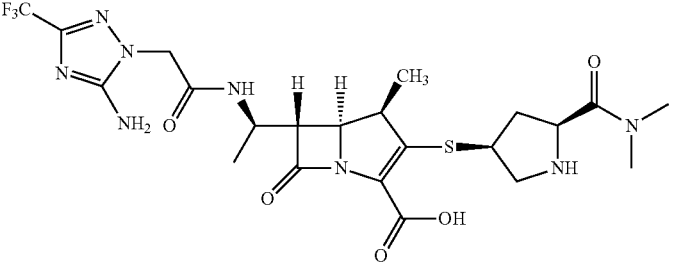 [SMILES: C[C@@H](NC(=O)Cn1nc(C(F)(F)F)nc1N)[C@H]1C(=O)N2C(C(=O)O)=C(S[C@@H]3CN[C@H](C(=O)N(C)C)C3)[C@H](C)[C@H]12]<br>(4R,5S,6R)-6-((R) - 1-(2-(5-amino-3-(trifluoromethyl) - 1H-1,2,4-triazol-1-yl)acetamido)ethyl)-3-((3S,5S)-5-(dimethylcarbamoyl)pyrrolidin-3-ylthio)-4-methyl-7-oxo-1-azabiayclo[3.2.0]hept-2-ene-2-carboxylic acid | $^1$HNMR (D$_2$O) - 1.33 (d, 3H), 1.19 (d, 3H), 2.99-3.00 (s, 3H), 3.04 (d, 1H), 3.09 (d, 3H), 3.30-3.34 (m, 1H), 3.42-3.47 (m, 1H), 3.55-3.58 (m, 1H), 3.69-3.74 (m, 1H), 4.01-4.04 (m, 1H), 4.13-4.16 (m, 1H), 4.39-4.43 (m, 1H), 4.75-.477 (m, 3H), 4.8-4.87 (m, 1H). Mass (574.58) 575.1 |
| 321 | 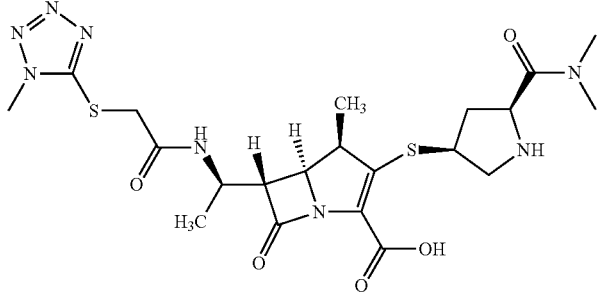<br>(4R,5S,6R)-3-((3S,5S)-5-(dimethylcirbamoyl)pyrrolidin-3-ylthio)-4-methyl-6-((R) - 1-(2-(1-methyl-1H-tetrazol-5-ylthio)acetamido)ethyl)-7-oxo-1-azabicyclo[3.2.0]hept-2-ene-2-carboxylic acid | $^1$HNMR (D$_2$O) - 1.12 (d, 3H), 1.29 (d, 3H), 3.00 (s, 3H), 3.08 (s, 3H), 3.10-3.14 (m, 1H), 3.20-3.24 (m, 1H), 3.43-3.48 (m, 1H), 3.49-3.51 (m, 2H), 3.80-3.85 (m, 2H), 3.92-3.94 (m, 2H), 4.03-4.12 (m, 4H), 4.32-4.36 (m, 1H), 4.81-4.84 (m, 1H). Mass (538.64) 539.5 |
| 322 | 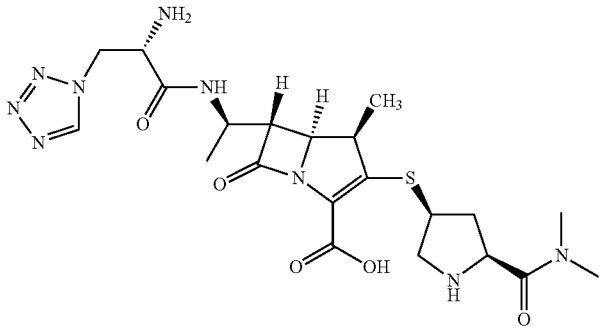 [SMILES: C[C@@H](NC(=O)[C@@H](N)Cn1cnnn1)[C@H]1C(=O)N2C(C(=O)O)=C(S[C@@H]3CN[C@H](C(=O)N(C)C)C3)[C@H](C)[C@H]12]<br>(4R,5S,6R)-6-((R) - 1-((S)-2-amino-3-(1H-tetrazol-1-yl)propanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) - 1.65 (d, 3H), 1.20 (d, 3H), 2.4-2.6 (m 1H), 3.00 (s, 3H), 3.07-3.08 (s, 3H), 3.22-3.36 (m, 2H), 3.45 (d, 2H), 3.74-3.77 (m, 1H), 3.99-4.04 (m, 3H), 4.28-4.32 (m, 1H), 4.70-4.82 (m, 3H) 9.24 (s, 1H). Mass (521.59) 522.3 |

| Example | Structure | Analytical Data |
|---|---|---|
| 323 | (4R,5S,6R)-6-((R) - 1-((S)-2-amino-3-(2H-tetrazol-2-yl)propanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) - 1.15 (d, 3H), 1.20 (d, 3H), 2.40-2.46 (m, 1H), 2.99 (s, 3H), 3.07-3.09 (s, 3H) 3.33-3.42 (m, 3H), 3.50 (d, 1H), 3.63-3.67 (m, 2H), 4.04-4.09 (m, 3H), 4.27-4.30 (m, 1H), 4.65-4.74 (m, 1H), 4.94-5.04 (m, 1H), 8.81 (s, 1H). Mass (521.59) 522.5 |
| 324 | (4R,5S,6R)-6-((R) - 1-(2-((1H-tetrazol-1-yl)acetamido)ethyl)-3-((3S,5S)-5-((S)-3-aminopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.20 (d, 3H), 1.34 (d, 3H) 3.23-3.26 (m, 1H), 3.31-3.36 (m, 1H), 3.45-3.48 (m, 1H), 3.58 (d, 1H), 3.67-3.79 (m, 2H), 3.83 (d, 2H), 3.93-4.04 (m, 4H), 4.14 (d, 2H), 4.32-4.38 (m, 3H), 5.40-5.47 (m, 2H), 9.25 (s, 1H). Mass (533.60) 534 |
| 325 | (4R,5S,6R)-6-((R) - 1-((Z)-2-(2-aminothiazol-4-yl)-2-(methoxyimino)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) - 1.22 (d, 3H), 1.37 (d, 3H), 1.82 (d, 1H), 2.98 (d, 3H), 3.08 (d, 3H), 3.29-3.33 (m, 2H), 3.49 (d, 2H), 3.60 (d, 1H), 3.98 (s, 3H), 4.20-4.23 (m, 1H), 4.52-4.54 (m, 2H), 4.55 (d, 1H), 8.9 (s, 1H). Mass (565.67) 566.2 |
| 326 | (4R,5S,6S)-6-((R) - 1-(5-amino-2H-tetrazol-2-yl)ethyl)-3-((3S,5S)-5-(dimethylcarbamoyl)pyrrolidin-3-ylthio)-4- | $^1$H NMR (D$_2$O) - 1.19 (d, 3H), 1.75 (d, 3H), 2.99 (s, 3H), 3.06-3.09 (s, 3H), 3.27-331 (m, 2H), 3.36 (d, 1H), 3.61-3.64 (m, 1H), 3.94 (d, 2H), 4.16 (d, 1H), 4.17-4.20 (m, 2H), 5.33 (d, 1H). Mass (450.52) 451 |

| Example | Structure | Analytical Data |
|---|---|---|
| | methyl-7-oxo-1-azabicyclo[3.2.0]hept-2-ene-2-carboxylic acid | |
| 327 | (4R,5S,6S)-6-((R) - 1-(5-amino-2H-tetrazol-2-yl)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.19 (d, 3H), 1.75 (d, 3H), 2.14 (d, 1H), 2.39-2.51 (m, 2H), 2.89-2.92 (m, 1H), 3.25-3.31 (m, 2H), 3.44-3.48 (m, 1H), 3.50-3.59 (m, 1H), 3.71-3.77 (m, 4H), 3.86-3.88 (m, 1H), 3 90-3.98 (m, 1H), 4.04 (d, 1H), 4.14 (d, 1H), 5.31-5.35 (m, 1H). Mass (491.57) 492.5 |
| 328 | (4R,5S,6S)-6-((R) - 1-(1H-tetrazol-1-yl)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.18 (d, 3H), 1.77 (d, 3H), 2.00-2.25 (m, 2H), 2.45-2.49 (m, 2H), 2.88-3.00 (m, 1H), 3.23-3.33 (m, 1H), 3.44-3.47 (m, 1H), 3.60 (d, 1H), 3 69-3.77 (m, 3H), 3.86-3.91 (m, 2H), 4.03-4.10 (m, 2H), 4.20-4.22 (m, 1H), 4.38 (m, 1H), 5.39-5.42 (m, 1H). Mass (476.55) 477.2 |
| 329 | (4R,5S,6R)-6-((R) - 1-(2-(1H-tetrazol-1-yl)acetamido)ethyl)-3-((3S,5S)-5-((3R,4R)-3-amino-4-hydroxypyrrolidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.20 (d, 3H), 1.34 (d, 3H), 1.88-1.92 (m, 1H), 2.92-2.97 (m, 1H), 3.27-3.37 (m, 2H), 3.51-3.57 (m, 3H), 3.59-3.70 (m, 3H), 3.78-3.95 (m, 3H), 4.15 (d, 1H), 4.35-4.46 (m, 3H), 5.38-5.47 (m, 2H). Mass (549.60) 550.5 |
| 330 | (4R,5S,6R)-3-((3S,5S)-5-(dimethylcarbamoyl)pyrrolidin-3-ylthio)-4-methyl-6-((R) - 1-(2-(5-methyl-1H-tetrazol-1-yl)acetamido)ethyl)-7-oxo-1-azabicyclo[3.2.0]hept-2-ene-2-carboxylic acid | $^1$H NMR (D$_2$O) - 1.21 (d, 3H), 1.35 (d, 3H), 1.86-1.93 (m, 1H), 2.60 (s, 3H), 2.99 (s, 3H), 3.09 (s, 3H), 3.3-3.40 (m, 2H), 3.58-3.65 (m, 2H), 3.98-4.01 (m, 2H), 4.16 (d, 1H), 4.40-4.44 (m, 1H), 4.64-4.68 (m, 1H), 5.31 (s, 2H). Mass (506.58) 507.2 |

| Example | Structure | Analytical Data |
|---|---|---|
| 331 | (4R,5S,6R)-3-((3S,5S)-5-((R)-3-aminopyrrolidine-1-carbonyl)pyrrolidin-3-ylthio)-4-methyl-6-((R) - 1-(2-(5-methyl-1H-tetrazal-1-yl)acetamido)ethyl)-7-oxo-1-azabicyclo[3.2.0]hept-2-ene-2-carboxylic acid | $^1$H NMR (D$_2$O) - 1.22 (d, 3H), 1.34 (d, 3H), 1.87 (m, 1H), 2.24 (dd, 1H), 2.23 (m, 1H), 2.57 (s, 3H), 2.87 (m, 1H), 3.22 (m, 1H), 3.24 (m, 2H), 3.36 (m, 2H), 3.58 (m, 2H), 3.85 (dd, 2H), 3.91 (dd, 1H), 4.04 (d, 1H), 4.30 (m, 1H), 4.42 (t, 1H), 5.03 (s, 3H). Mass (547.63) 548.1 |
| 332 | (4R,5S,6R)-6-((R) - 1-(2-(1H-tetrazol-1-yl)acetamido)ethyl)-3-((3S,5S)-5-(4-amino-4-methylpiperidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.03 (d, 3H), 1.27 (d, 3H), 1.50 (s, 3H), 1.85-1.99 (m, 2H), 3.26 (m, 1H), 3.33 (d, 1H), 3.57 (d, 1H), 3.59 (m, 3H), 3.79 (m, 4H), 3.98 (m, 1H), 4.40 (m, 4H), 4.43 (d, 1H), 4.63 (t, 1H), 5.44 (d, 2H), 9.27 (s, 1H). Mass (561.66) 562.5 |
| 333 | (4R,5S,6R)-6-((R) - 1-(2-(1H-tetrazol-1-yl)acetamido)ethyl)-3-((3S,5S)-5-(6-amino-3-azabicyclo[3.1.0]hexane-3-carbonyl)pyrrolidin-3-ylthin)-4-methyl-7-oxo-1-azabicyclo[3.2.0]hept-2-ene-2-carboxylic acid | $^1$H NMR (D$_2$O) - 1.21 (d, 3H), 1.35 (d, 3H), 1.80 (m, 1H), 1.92 (m, 2H), 2.12 (dd, 2H), 2.47 (m, 1H), 2.84 (m, 1H), 3.30-3.32 (m, 2H), 3.56 (d, 2H), 3.56-3.63 (d, 2H), 3.62-3.89 (m, 3H), 4.19 (d, 1H), 4.42 (dd, 1H), 5.43 (m, 2H), 9.27 (d, 1H). Mass (545.61) 546.1 |
| 334 | (4R,5S,6R)-3-((3S,5S)-5-((R)-3-aminopyrrolidine-1-carbonyl)pyrrolidin-3-ylthio)-4-methyl-7-oxo-6-((R) - 1-(2-(5-(trifluoromethyl)-2H-tetrazol-2-yl)acetamido)ethyl) - 1-azabicyclo[3.2.0]hept-2-ene-2-carboxylic acid | $^1$H NMR (D$_2$O) - 1.22 (d, 3H), 1.37 (d, 3H), 2.23 (m, 1H), 2.49 (m, 2H), 2.90 (m, 1H), 324 (t, 1H), 3.44-3.35 (m, 2H). 3.59 (m, 2H), 3.76-3.68 (m, 2H), 3.86-3.91 (m, 2H), 4.04 (m, 1H), 4.15 (d, 1H), 4.26-4.33 (dd, 1H), 4.44 (m, 1H), 5.76 (t, 2H). Mass (601.60) 602.3 |

| Example | Structure | Analytical Data |
|---|---|---|
| 335 | 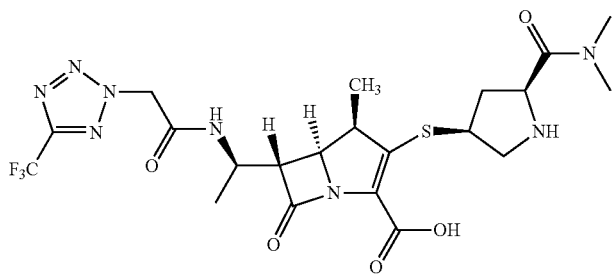 [SMILES: C[C@@H](NC(=O)Cn1nnc(C(F)(F)F)n1)[C@H]1C(=O)N2C(C(=O)O)=C(S[C@@H]3CN[C@H](C(=O)N(C)C)C3)[C@H](C)[C@H]12]<br>(4R,5S,4R)-3-((3S,5S)-5-(dimethylcarbamoyl)pyrrolidin-3-ylthio)-4-methyl-7-oxo-6-((R) - 1-(2-(5-(trifluoromethyl)-2H-tetrazol-2-yl)acetamido)ethyl) - 1-azabicyclo[3.2.0]hept-2-ene-2-carboxylic acid | $^1$H NMR (D$_2$O) - 1.22 (d, 3H), 1.37 (d, 3H), 1.98 (m, 1H), 1.98-(m, 1H), 2.98-3.00 (m, 1H), 3.04 (s, 3H), 3.08 (s, 3H), 3.34-3.41 (m, 2H), 3.68 (dd, 2H), 4.01 (t, 1H), 4.18 (d, 1H), 4.42 (t, 1H), 4.68 (t, 1H), 5.73 (s, 2H). Mass (560.55) 561.1 |
| 336 | 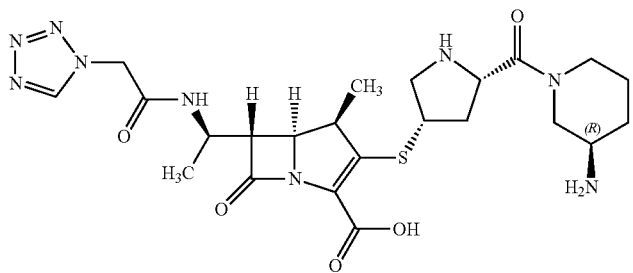<br>(4R,5S,6R)-6-((R) - 1-(2-(1H-tetrazol-1-yl)acetamido)ethyl)-3-((3S,5S)-5-((R)-3-aminopiperidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.21 (d, 3H) 1.35 (d, 3H), 1.57 (m, 1H), 1.79 (m, 2H), 1.92 (m, 1H), 2.17 (m, 1H), 3.27 (m, 1H), 3.42 (m, 2H), 3.44 (m, 3H), 3.58 (d, 2H), 3.65 (m, 2H), 3.94 (m, 1H), 4.16 (d, 2H), 4.42 (dd, 2H), 5.43 (d, 2H), 9.28 (s, 1H). Mass (547.63) 548.2 |
| 337 | 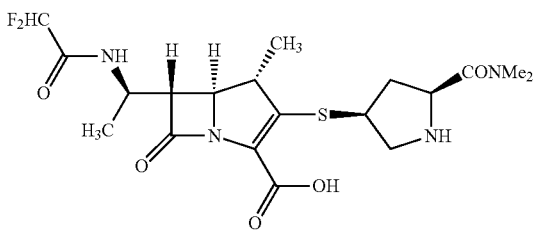<br>(4S,5S,6R)-6-((R) - 1-(2,2-difluoroacetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$H NMR (D$_2$O) - 1.22 (d, 3H), 1.38 (d, 3H), 1.90 (m, 2H), 2.99 (s, 3H), 3.04 (m, 1H), 3.09 (s, 3H), 3.36 (m, 2H), 3.62 (m, 2H), 4.01 (m, 1H), 4.18 (d, 1H), 4.46 (t, 1H), 4.65 (m, 1H), 6.16 (t, 1H). Mass (460.50) 461.1 |
| 338 | 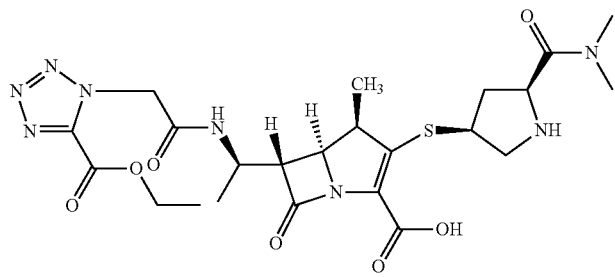 [SMILES: CCOC(=O)c1nnnn1CC(=O)N[C@H](C)[C@H]1C(=O)N2C(C(=O)O)=C(S[C@@H]3CN[C@H](C(=O)N(C)C)C3)[C@H](C)[C@H]12]<br>(4R,5S,6R)-3-((3S,5S)-5-(dimethylcarbamoyl)pyrrolidin-3-ylthio)-6-((R) - 1-(2-(5-(ethoxycarbonyl) - 1H-tetrazol-1-yl)acetamido)ethyl)-4-methyl-7-oxo-1-azabicyclo[3.2.0]hept-2-ene-2-carboxylic acid | $^1$H NMR (D$_2$O) - 1.22 (d, 3H), 1.37 (d, 3H), 1.40-1.44 (m, 3H), 1.82-1.84 (m, 1H), 1.87 (m, 1H), 2.99 (s, 3H), 3.09 (s, 3H), 3.37 (m, 2H), 3.55 (m, 2H), 3.98 (m, 1H), 4.17 (m, 1H), 4.41 (m, 1H), 4.57 (m, 3H), 5.65 (d, 2H). Mass (564.61) 565.5 |

-continued

| Example | Structure | Analytical Data |
|---|---|---|
| 339 | (4R,5S,6R)-3-((3S,5S)-5-((R)-3-aminopyrrolidine-1-carbonyl)pyrrolidin-3-ylthio)-6-((R) - 1-(2-(5-(ethoxycarbonyl) - 1H-tetrazol-1-yl)acetamido)ethyl)-4-methyl-7-oxo-1-azabicyclo[3.2.0]hept-2-ene-2-carboxylic acid | $^1$H NMR (D$_2$O) - 1.23 (d, 3H), 1.32 (d, 3H), 1.42 (m, 3H), 2.12 (m, 1H), 2.24 (m, 1H), 2.49 (m, 1H), 2.90 (m, 1H), 3.34 (m, 1H), 3.37-3.39 (m, 2H), 3.57-3.60 (m, 2H), 3.70-3.75 (m, 2H), 3.88 (m, 2H), 4.07 (m, 1H), 4.29 (m, 1H), 4.35 (m, 2H), 4.52 (m, 2H), 5.65 (d, 2H). Mass (605.67) 606.1 |
| 340 | (4R,5S,6R)-6-((R) - 1-(2-(1H-tetrazol-1-yl)acetamido)ethyl)-3-((3S,5S)-5-(4-aminopiperidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.21 (d, 3H), 1.33 (d, 3H), 1.57-1.60 (m, 2H), 1.84 (m, 1H), 2.17 (m, 2H), 2.93 (m, 2H), 3.29-3.37 (m, 3H), 3.50-3.58 (m, 3H), 3.96 (m, 2H), 4.16 (d, 1H), 4.42 (m, 1H), 4.48-4.57 (m, 2H), 5.44 (d, 2H), 9.28 (s, 1H). Mass (547.63) 548.2 |
| 341 | (4R,5S,6R)-6-((R) - 1-(2-(1H-tetrazol-1-yl)acetamido)ethyl)-3-((3S,5S)-5-((S)-3-aminopiperidin-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.18 (d, 3H), 1.32 (d, 3H), 1.66-1.8 (m, 2H), 1.92 (s, 3H), 2.90-2.93 (m, 1H), 3.13-3.19 (m, 1H), 3.27-3.43 (m, 3H), 3.45-3.50 (m, 2H), 3.56 (d, 1H), 3.70-3.73 (m, 1H), 3.93 (d, 1H), 4.15 (d, 1H), 4.36-4.47 (m, 2H), 4.50-4.80 (m, 1H), 5.38-5.48 (m, 2H), 9.27 (s, 1H). Mass (547.63) 548.2 |
| 342 | (4R,5S,6R)-6-((R) - 1-(2-(1H-tetrazol-1-yl)acetamido)ethyl)-3-((3S,5S)-5-(4-(3-aminoazetidin-1-yl)piperidine-1-carbonyl)pyrrolidin-3-ylthino)-4-methyl-7-oxo-1-azabicyclo[3.2.0]hept-2-ene-2-carboxylic acid | $^1$H NMR (D$_2$O) - 1.20 (d, 3H), 1.34 (d, 3H), 1.76-1.81 (m, 1H), 1.91 (m, 1H), 2.83-2.89 (m, 2H), 2.99-3.02 (m, 2H), 3.19-3.35 (m, 3H), 3.45-3.49 (m, 3H), 3.58 (m, 3H), 3.87-3.97 (m, 3H), 4.04 (d, 2H), 4.14 (d, 1H), 4.40-4.43 (m, 2H), 4.47-4.54 (m, 1H), 5.43 (d, 2H), 9.27 (s, 1H). Mass (602.71) 603.2. |

| Example | Structure | Analytical Data |
|---|---|---|
| 343 | 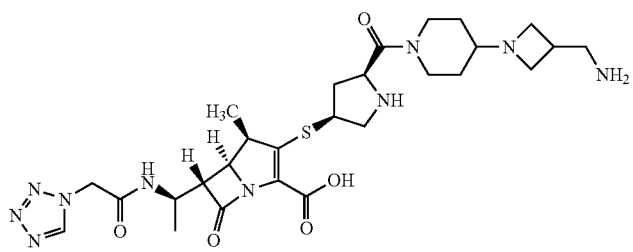 [SMILES: C[C@@H](NC(=O)Cn1cnnn1)[C@H]1C(=O)N2C(C(=O)O)=C(S[C@@H]3CN[C@H](C(=O)N4CCC(N5CC(CN)C5)CC4)C3)[C@H](C)[C@H]12]<br>(4R,5S,6R)-6-((R) - 1-(2-(1H-tetrazol-1-yl)acetamido)ethyl)-3-((3S,5S)-5-(4-(3-(aminomethyl)azetidin-1-yl)piperidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.26 (d, 3H), 1.32 (d, 3H), 1.81 (m, 1H), 1.91 (m, 1H), 2.00 (m, 3H), 2.81-2.90 (m, 3H), 3.02 (d, 2H), 3.18-3,35 (m, 5H), 3.48-3.57 (m, 4H), 3.87-3.95 (3H), 4.14 (d, 1H), 4.42-4.53 (m, 3H), 5.43 (d, 2H), 9.27 (s, 1H) C$_{27}$H$_{40}$N$_{10}$O$_5$S; HPLC-96.6%; Mass (616.74) 617.2 |
| 344 | 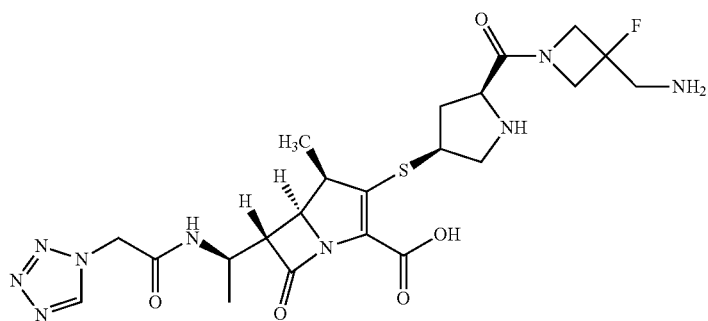 [SMILES: C[C@@H](NC(=O)Cn1cnnn1)[C@H]1C(=O)N2C(C(=O)O)=C(S[C@@H]3CN[C@H](C(=O)N4CC(F)(CN)C4)C3)[C@H](C)[C@H]12]<br>(4R,5S,6R)-6-((R) - 1-(2-(1H-tetrazol-1-yl)acetamido)ethyl)-3-((3S,5S)-5-(3-(aminomethyl)-3-fluoroazetidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.20 (d, 3H), 1.32 (d, 3H), 1.80-1.82 (m, 1H), 1.92 (m, 1H), 2.74 (m, 1H), 3.12 (m, 1H), 3.35 (d, 2H), 3.54 (d, 2H), 3.74-3.85 (m, 2H), 4.04-4.15 (m, 1H), 4.32 (d,- 2H), 4.42 (m, 1H), 4.56 (d, 2H), 5.44 (d, 2H), 9.27 (s, 1H). Mass (551.59) 552.1 |
| 345 | 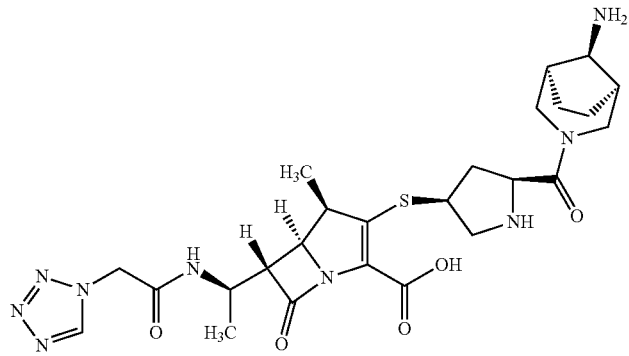 [SMILES: C[C@@H](NC(=O)Cn1cnnn1)[C@H]1C(=O)N2C(C(=O)O)=C(S[C@@H]3CN[C@H](C(=O)N4C[C@H]5CC[C@@H](C4)[C@H]5N)C3)[C@H](C)[C@H]12]<br>(4R,5S,6R)-6-((R) - 1-(2-(1H-tetrazol-1-yl)acetamido)ethyl)-3-((3S,5S)-5-((1R,5S,8S)-8-amino-3-azabicyclo[3.2.0]octane-3-carbonyl)pyrrolidin-3-ylthio)-4-methyl-7-oxo-1-azabicyclo[3.2.0]hept-2-ene-2-carboxylic acid | $^1$H NMR (D$_2$O) - 1.21 (d, 3H), 1.37 (d, 3H), 1.60-(m, 1H), 1.73-1.79 (m, 1H), 1.91 (m, 2H), 2.23 (m, 2H), 2.52 (d, 3H), 320-3.22 (m, 3H), 3.52-3.64 (m, 6H), 3.75 (m, 1H), 3.77-4.13 (m, 3H), 4.22-4.51 (m, 1H), 5.44 (d, 2H), 9.27 (s, 1H). Mass (573.67) 574.2 |

| Example | Structure | Analytical Data |
|---|---|---|
| 346 | 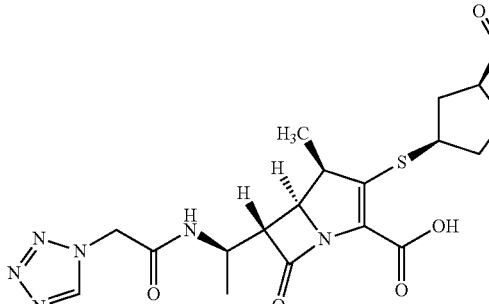<br>(4R,5S,6R)-6-((R) - 1-(2-(1H-tetrazol-1-yl)acetamido)ethyl)-3-((3S,5S)-5-(4-(aminomethyl)-4-fluoropiperidine-1-carbonyl)pyrrolidin-3-ylthio)-4-methyl-7-oxo-1-azabicyclo[3.2.0]hept-2-ene-2-carboxylic acid | $^1$H NMR (D$_2$O) - 1.29 (d, 3H), 1.64 (d, 3H), 1.80 (m, 2H), 2 23 (m, 3H), 2.56 (m, 2H), 2.92 (m, 2H), 3.25-3.30 (m, 2H), 3.59 (m, 3H), 3.75 (m, 2H), 3.96 (m, 1H), 4.42 (m, 2H), 5.43 (m, 3H), 9.28 (s, 1H). Mass (579.65) 580. |

Preparation of Example 347 ((4R,5S,6R)-3-((3S,5S)-5-((R)-3-aminopyrrolidine-1-carbonyl)pyrrolidin-3-ylthio)-4-methyl-7-oxo-6-((R)-1-(2-(5-(trifluoromethyl)-1H-tetrazol-1-yl)acetamido)ethyl)-1-azabicyclo[3.2.0]hept-2-ene-2-carboxylic acid)

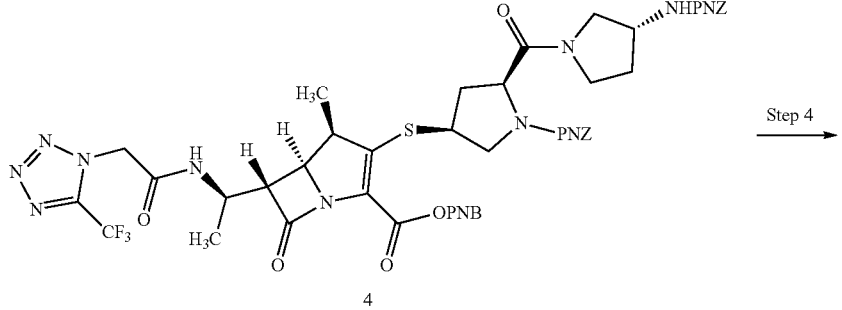

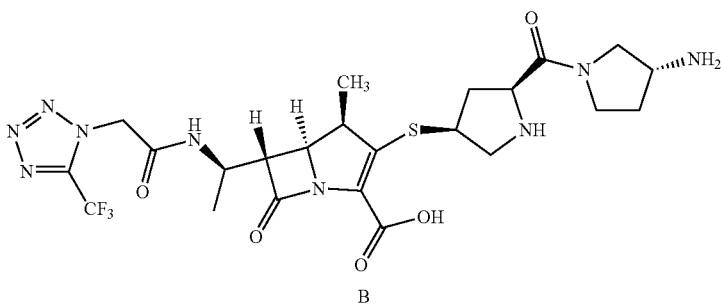

Preparation of C

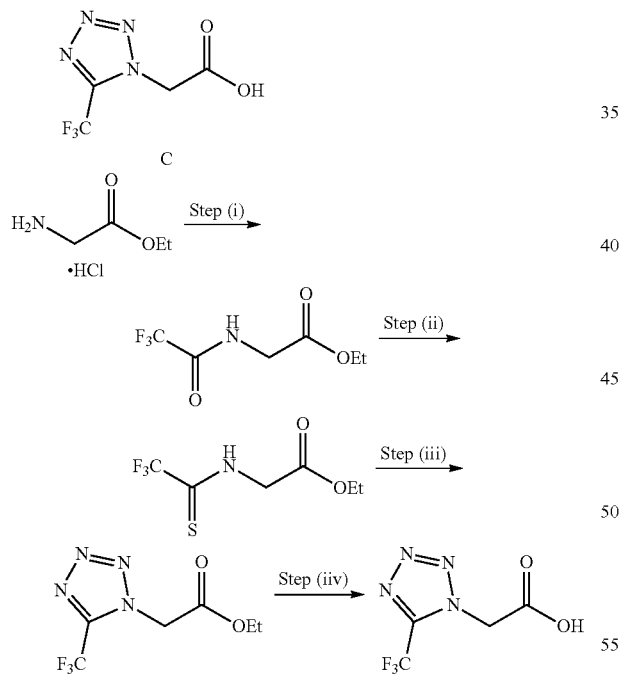

Step (i): Ethyl 2-(2,2,2-trifluoroacetamido)acetate

Ethyl trifluoroacetate (10.7 g, 0.075 moles) was dissolved in methanol (mL) and cooled to 0° C. Glycine ester hydrochloride (10.5 g, 0.075 mol) was added to this solution and the reaction mixture was stirred for 5 minutes. Triethylamine (15.7 mL, 0.112 moles) was added dropwise at 0° C. and stirred for 15 minutes. The reaction mixture was then brought to room temperature and stirred overnight. The solvent of the reaction mixture was evaporated under vacuum and water was added to the crude followed by extraction with ethyl acetate. The organic layer was then washed with water, brine, dried over sodium sulphate and concentrated to give the crude product (15 g). NMR: (CDCl$_3$, 400 MHz): 6.85 (s, 1H), 4.25-4.30 (m, 2H), 4.12-4.15 (m, 2H), 1.30-1.33 (m, 3H).

Step (ii): Ethyl 2-(2,2,2-trifluoroethanethioamido)acetate

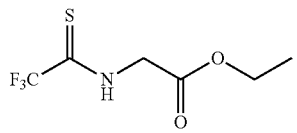

Ethyl 2-(2,2,2-trifluoroacetamido)acetate (15 g, 0.0753 mol) was dissolved in toluene (20 mL) and cooled to 0° C. Solid NaHCO$_3$ was added to the reaction mixture and stirred for 5 minutes. P$_2$S$_5$ (10 g, 0.045 mmol, 0.6 eq.) was added portion wise very slowly and stirred for 10 minutes at 0° C. The reaction mixture was then heated to 70° C. for 6 hours. After the completion of reaction, the reaction mixture was brought to room temperature and quenched with water slowly at 0° C. and extracted with ethyl acetate. The organic layer was washed with 5% NaHCO$_3$ solution, water and brine respectively and dried over sodium sulphate. The crude reaction mixture was then concentrated under vacuum and the product was isolated by column chromatography (11 g, 67.8%). $^1$H NMR: (CDCl3, 400 MHz): 8.46 (s, 1H), 4.29-4.38 (m, 2H), 4.12-4.15 (m, 2H), 1.30-1.35 (m, 3H).

Step (iii): Ethyl 2-(5-(trifluoromethyl)-1H-tetrazol-1-yl)acetate

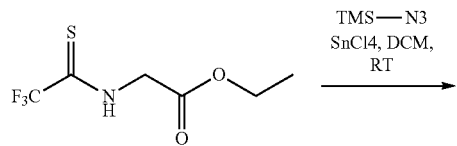

Ethyl 2-(2,2,2-trifluoroethanethioamido)acetate (11 g, 0.051 mol) was dissolved in dichloromethane (110 mL) at ambient temperature. Azidotrimethylsilane (13.5 ml, 0.102 mol) was added dropwise to this solution and stirred for 10 minutes. A solution of SnCl$_4$ (13.3 mL, 0.127 mmol) in dichloromethane (mL) was added dropwise and stirred for 15 minutes. The reaction mixture was then stirred overnight at room temperature. The reaction mixture was then quenched with saturated NaHCO$_3$ solution slowly at 0° C., filtered through celite bed, washed with dichloromethane. The organic layer was then separated, washed with water, brine, dried over sodium sulphate and concentrated under vacuum to give the crude product. The crude product was then purified by column chromatography to give the product (6 g, 52.6%). $^1$H NMR (DMSO-d$_6$, 400 MHz): 5.83 (s, 2H), 4.20-4.26 (m, 2H), 1.18-1.23 (m, 3H).

Step (iv): 2-(5-(Trifluoromethyl)-1H-tetrazol-1-yl)acetic acid

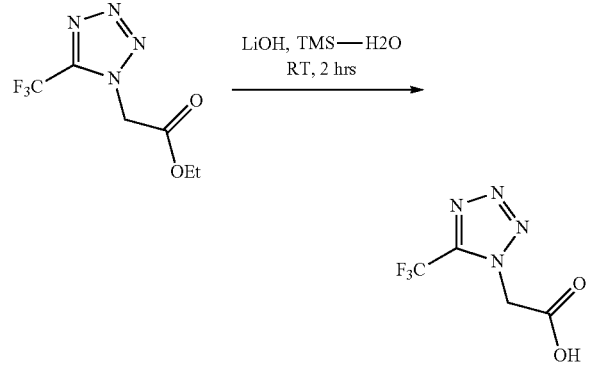

2-(5-(Trifluoromethyl)-1H-tetrazol-1-yl)acetic acid (7.3 g, 0.033 moles) was dissolved in THF (70 mL). A solution of LiOH.H$_2$O (1.5 g, 0.036 mol) in water (80 mL) was added dropwise at room temperature and the resultant reaction mixture was stirred for 2 hours. After the completion of reaction, the solvent was evaporated under vacuum and the resultant crude was dissolved in water. The aqueous layer was washed with ethyl acetate and was then acidified with 2N HCl and extracted with ethyl acetate. The organic layer was washed with water, brine, dried over sodium sulfate and concentrated under vacuum to give the desired product (5.6 g, 87.6%). $^1$H NMR (DMSO-d$_6$ 400 MHz): 14.00 (br s, 1H), 5.69 (s, 2H).

Preparation of Example 347 (4R,5S,6R)-3-((3S,5S)-5-((R)-3-aminopyrrolidine-1-carbonyl)pyrrolidin-3-ylthio)-4-methyl-7-oxo-6-((R)-1-(2-(5-(trifluoromethyl)-1H-tetrazol-1-yl)acetamido)ethyl)-1-azabicyclo[3.2.0]hept-2-ene-2-carboxylic acid Step 1: (R)-4-Nitrobenzyl2-diazo-3-oxo-4-((2R,3R)-4-oxo-3-((R)-1-(2-(5-(trifluoromethyl)-1H-tetrazol-1-yl)acetamido)ethyl)azetidin-2-yl)pentanoate

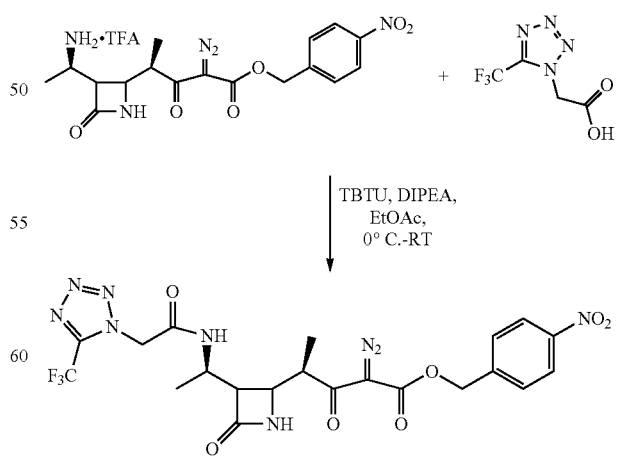

5-Trifluoro-Tetrazole acetic acid (2.1 g, 0.011 mol) was dissolved in ethyl acetate (mL) cooled to 0° C. and to this solution was added TBTU (4.47 g, 0.014 mol) and stirred for 5 minutes at the same temperature. Diisopropylethylamine (3.8 ml, 0.022 mol) was added dropwise and stirred for 10 minutes at 0° C. The reaction mixture was then brought to room temperature and further stirred for 1 hour. The reaction mixture was again cooled to 0° C. and to it was added a solution of the trifluoroacetate salt of (R)-4-nitrobenzyl 4-((2R,3R)-3-((R)-1-aminoethyl)-4-oxoazetidin-2-yl)-2-diazo-3-oxopentanoate, (3.7 g, 0.007 mol) in ethyl acetate (25 mL) followed by diisopropylethylamine (3.8 mL) drop wise and stirred for 10 minutes at 0° C. The reaction mixture was then brought to room temperature and stirred overnight. After the completion of the reaction, the reaction mixture was quenched with water and extracted with ethyl acetate. The organic layer was washed with water, followed by brine, dried over sodium sulphate and concentrated under vacuum to give the crude which was then purified by column chromatography to give the product (1 g, 23.9%). $^1$H NMR (CDCl$_3$, 400 MHz): 1.19-1.21 (3H, d), 1.35-1.37 (3H, d), 2.86-2.88 (1H, m), 3.58-3.69 (2H, m), 4.24-4.33 (1H, m), 5.22-5.29 (2H, m), 5.35 (2H, s), 6.04 (1H, s), 6.71-6.73 (1H, d), 7.53-7.55 (2H, d), 8.25-8.28 (2H, d).

Step 2: (4R,5R,6R)-4-nitrobenzyl 3-(diphenoxyphosphoryloxy)-4-methyl-7-oxo-6-((R)-1-(2-(5-(trifluoromethyl)-1H-tetrazol-1-yl)acetamido)ethyl)-1-azabicyclo[3.2.0]hept-2-ene-2-carboxylate

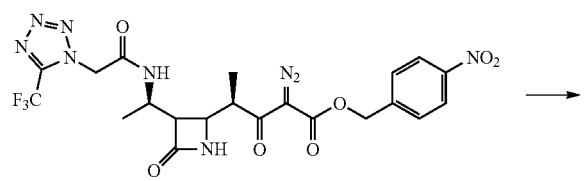

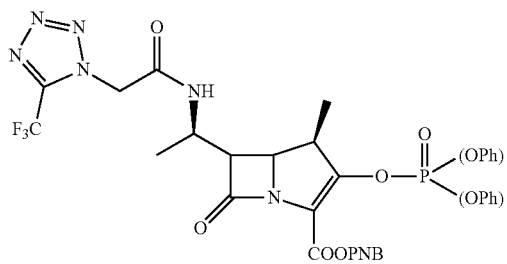

(R)-4-nitrobenzyl 2-diazo-3-oxo-4-((2R,3R)-4-oxo-3-((R)-1-(2-(5-(trifluoromethyl)-1H-tetrazol-1-yl)acetamido) ethyl)azetidin-2-yl)pentanoate (1.1 g, 1.94 mmol) was dissolved in 50 mL of acetone under N$_2$ atmosphere. To this solution was added rhodium octanoate (40 mg, 0.051 mmol) and heated to 70° C. for 1 hour. The reaction mixture was then cooled to −40° C. and diphenylchlorophosphate (0.64 mL, 3.1 mmol), diisopropylethylamine (0.6 mL, 3.44 mmol) and catalytic amount of dimethylaminopyridine was added successively. The reaction mixture was then stirred for 1 hour at −20° C. Diisopropylethylamine (0.6 mL) was again added to the reaction mixture and was quenched with water. The aqueous layer was extracted with dichloromethane and the organic layer evaporated under vacuum at room temperature. The crude thus obtained was purified by column chromatography to give the product as a solid (850 mg).

Step 3: (4R,5S,6R)-4-Nitrobenzyl 4-methyl-3-((3S,5S)-1-((4-nitrobenzyloxy) carbonyl)-5-((R)-3-((4-nitrobenzyloxy)carbonylamino)pyrrolidine-1-carbonyl) pyrrolidin-3-ylthio)-7-oxo-6-((R)-1-(2-(5-(trifluoromethyl)-1H-tetrazol-1-yl) acetamido)ethyl)-1-azabicyclo[3.2.0]hept-2-ene-2-carboxylate

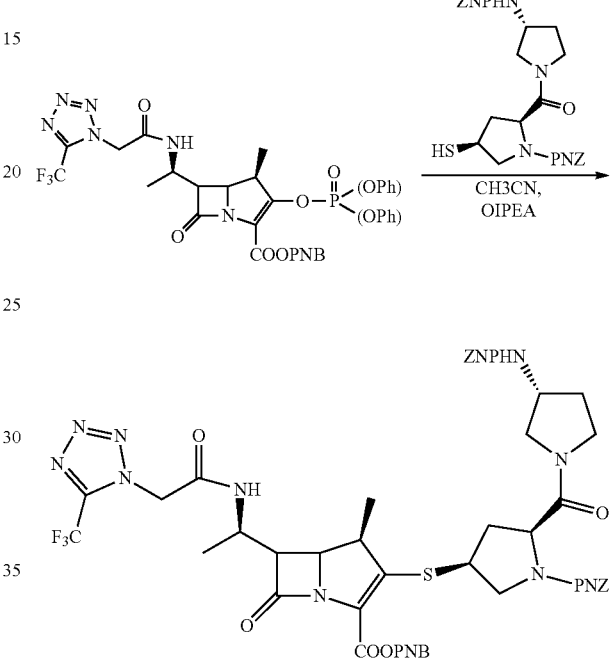

(4R,5R,6R)-4-Nitrobenzyl 3-(diphenoxyphosphoryloxy)-4-methyl-7-oxo-6-((R)-1-(2-(5-(trifluoromethyl)-1H-tetrazol-1-yl)acetamido)ethyl)-1-azabicyclo[3.2.0]hept-2-ene-2-carboxylate (500 mg, 0.65 mmol) was taken in acetonitrile (10 mL) at 0° C. The solution was then degassed for 10 minutes using N$_2$ atmosphere. To this solution was added the thiol (0.372 g, 0.65 mmol) at 0° C. under N$_2$ atmosphere followed by addition of diisopropylethylamine (0.2 mL, 1.15 mmol). The resultant solution was degassed again for 15 minutes. The reaction mixture was stirred under N$_2$ at 0° C. for 2 hours. After the completion of reaction, the reaction mixture was quenched using water and extracted by ethyl acetate. The organic layer was then washed with water, brine, dried over sodium sulphate and evaporated under vacuum to give the crude. The crude reaction mixture was purified by column chromatography to give the product (450 mg, 64%) as a solid. $^1$H NMR (DMSO-d$_6$, 400 MHz): 1.18-1.19 (3H, d), 1.22-1.24 (3H, d), 1.73 (2H, m), 2.83 (1H, m), 3.14-3.17 (2H, m), 3.47-3.69 (4H, m), 3.88-3.90 (2H, m), 4.12-4.22 (4H, m), 4.54 (1H, m), 5.07-5.09 (1H, m), 5.17-5.2 (3H, m), 5.41-5.44 (1H, d), 5.48-5.52 (3H, m), 7.47-7.49 (2H, m), 7.52-7.54 (2H, m), 7.60-7.62 (3H, m), 7.70-7.72 (1H, m), 8.20-8.24 (6H, m), 8.75-8.77 (1H, d).

Example 348 was prepared by reacting compound obtained by Step 2 with appropriate R$^1$—SH group followed by the procedure of step 3 of Example 347.

| Example | Structure | Analytical Data |
|---|---|---|
| 347 | (4R,5S,6R)-3-((3S,5S)-5-((R)-3-aminopyrrolidine-1-carbonyl)pyrrolidin-3-ylthio)-4-methyl-7-oxo-6-((R)-1-(2-(5-(trifluoromethyl)-1H-tetrazol-1-yl)acetamido)ethyl)-1-azabicyclo[3.2.0]hept-2-ene-2-carboxylic acid | $^1$HNMR (D$_2$O) - 1.27 (d, 3H), 1.36 (d, 3H), 1.86 (m, 1H), 2.49 (d, 1H), 2.89 (m, 2H), 3.43 (m, 2H), 3.58 (m, 2H), 3.62 (d, 2H), 3.73 (d, 2H), 4.06 (d, 2H), 4.16 (d, 1H), 4.28-4.42 (m, 2H), 5.62 (m, 2H). Mass (601.60) 602.5 |
| 348 | (4R,5S,6R)-3-((3S,5S)-5-(dimethylcarbamoyl)pyrrolidin-3-ylthio)-4-methyl-7-oxo-6-((R)-1-(2-(5-(trifluoromethyl)-1H-tetrazol-1-yl)acetamido)ethyl)-1-azabicyclo[3.2.0]hept-2-ene-2-carboxylic acid | $^1$HNMR (D$_2$O) - 1.22-(d, 3H), 1.36 (d, 3H), 1.86 (m, 1H), 3.07 (s, 3H), 3.12 (s, 3H), 3.37 (d, 3H), 3.59 (m, 2H), 3.98 (m, 1H), 4.86 (d, 1H), 4.41 (m, 1H), 4.61 (m, 1H), 5.61 (s, 2H). Mass (560.55) 561.1 |
| 349 | (4R,5S,6R)-3-((3S,5S)-5-((R)-3-aminopyrrolidine-1-carbonyl)pyrrolidin-3-ylthio)-6-((R)-1-(2-(5-(difluoromethyl)-1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.21 (d, 3H), 1.35 (d, 3H), 1.92 (m, 1H), 1.92-2.38 (m, 1H) 2.40-2.49 (m, 2H), 2.89-2.96 (m, 2H), 3.23-3.34 (m, 2H), 3.47 (m, 1H), 3.57 (m, 2H), 4.06 (m, 2H), 4.13-4.15 (m, 2H), 4.40-4.80 (m, 2H), 5.55 (s, 2H), 7.46 (t, 1H). Mass (583.61) 584.2 |
| 350 | (4R,5S,6R)-6-((R)-1-(2-(5-(difluoromethyl)-1H-tetrazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.21 (d, 3H), 1.36 (d, 3H), 1.84-1.89 (m, 1H), 3.03 (s, 3H), 3.07 (s, 3H), 3.33-3.38 (m, 2H), 3.56-3.62 (m, 2H), 3.99 (m, 2H), 4.16 (d, 1H), 4.42 (m, 1H), 4.63 (m, 1H), 5.35 (s, 2H), 7.46 (t, 1H). Mass (542.56) 543.5 |

| Example | Structure | Analytical Data |
|---|---|---|
| 351 | (4R,5S,6R)-6-((R)-1-(2-(1H-tetrazol-1-yl)acetamido)ethyl)-3-((3S,5S)-5-(3,3-difluoro-1,8-diazaspiro[4.5]decane-8-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.34 (d, 3H), 1.82 (m, 4H), 1.92 (m, 2H), 2.39 (m, 2H), 3.04 (d, 1H), 3.44 (m, 3H), 3.59 (m, 3H), 3.66-3.70 (m, 3H), 3.89-4.00 (m, 1H), 4.02 (m, 1H), 4.16 (d, 1H), 4.44 (m, 1H), 5.42 (m, 2H), 9.27 (s, 1H). Mass (623.68) 624.1 |
| 352 | (4R,5S,6R)-3-((3S,5S)-5-(1,8-diazaspiro[4.5]decane-8-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.21 (d, 3H), 1.35 (d, 3H), 1.89 (m, 1H), 1.98 (d, 5H), 2.15 (m, 4H), 2.92 (m, 1H), 3.29 (m, 2H), 3.33-3.47 (m, 4H), 3.58 (d, 1H), 3.79 (d, 1H), 4.16 (d, 1H), 4.42 (m, 2H), 4.52 (m, 1H), 4.53 (m, 1H), 5.43 (s, 2H), 9.28 (s, 1H). Mass (587.69) 588.5 |
| 353 | (4R,5S,6R)-6-((R)-1-(2-(1H-tetrazol-1-yl)acetamido)ethyl)-4-methyl-3-((3S,5S)-5-((4aS,7aR)-octahydropyrrolo[3,4-b][1,4]oxazine-6-carbonyl)pyrrolidin-3-ylthio)-7-oxo-1-azabicyclo[3.2.0]hept-2-ene-2-carboxylic acid | $^1$HNMR (D$_2$O) - 1.28 (d, 3H), 1.35 (d, 3H), 1.92 (s, 4H), 2.88-3.11 (m, 1H), 3.32-3.35 (m, 1H), 3.39 (m, 2H), 3.57 (d, 1H), 3.59-3.76 (m, 5H), 3.91-4.00 (m, 2H), 4.16 (d, 1H), 4.40 (m, 1H), 4.57 (m, 1H), 4.87 (m, 1H), 5.43 (s, 2H), 9.28 (s, 1H). Mass (575.64) 576.1 |
| 354 | (4R,5S,6R)-6-((R)-1-(2-(1H-tetrazol-1-yl)acetamido)ethyl)-4-methyl-7-oxo-3-((3S,5S)-5-((R)-thiazolidine-4-carboxamido)methyl)pyrrolidin-3-ylthio)-1-azabicyclo[3.2.0]hept-2-ene-2-carboxylic acid | $^1$HNMR (D$_2$O) - 1.21 (d, 3H), 1.35 (d, 3H), 2.23 (m, 1H), 3.12 (m, 2H), 3.30 (d, 2H), 3.32-3.33 (m, 2H), 3.35 (m, 2H), 3.59 (m, 2H), 3.89 (m, 1H), 4.09 (m, 1H), 4.13-4.19 (m, 2H), 4.22 (m, 1H), 4.41 (m, 1H), 5.43 (d, 2H), 9.27 (s, 1H). Mass (565.67) 566.0 |

| Example | Structure | Analytical Data |
|---|---|---|
| 355 | (4R,5S,6R)-3-((3S,5S)-5-((R)-3-aminopyrrolidine-1-carbonyl)pyrrolidin-3-ylthio)-6-((R)-1-(2-(5-tert-butyl-1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.22 (d, 3H), 1.36 (d, 3H), 1.46 (s, 9H), 1.92 (m, 1H), 2.08-2.24 (m, 1H), 2.23-2.50 (m, 2H), 2.89-2.95 (m, 1H), 3.30-3.54 (m, 2H), 3.56-3.58 (m, 2H), 3.71-3.81 (m, 2H), 3.87-3.94 (m, 2H), 4.06-4.16 (m, 2H), 4.41-4.43 (m, 2H), 5.47 (d, 2H). Mass (589.71) - 590 |
| 356 | (4R,5S,6R)-6-((R)-1-(2-(5-tert-butyl-1H-tetrazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.22 (d, 3H), 1.36 (d, 3H), 1.46 (s, 9H) 1.96 (m, 1H), 3.07 (s, 3H), 3.30 (s, 3H), 3.39 (m, 1H), 3.43 (m, 1H), 3.59 (d, 1H), 3.66-3.69 (m, 1H), 4.02 (m, 1H), 4.42 (m, 1H), 4.69 (m, 1H), 4.71 (d, 2H), 5.48-5.51 (m, 2H). Mass (548.66) 549. |
| 357 | (4R,5S,6R)-3-((3S,5S)-5-(dimethylcarbamoyl)pyrrolidin-3-ylthio)-4-methyl-7-oxo-6-((R)-1-(2-(5-(thiophen-2-yl)-1H-tetrazol-1-yl)acetamido)ethyl)-1-azabicyclo[3.2.0]hept-2-ene-2-carboxylic acid | $^1$HNMR (D$_2$O) - 1.14 (d, 3H), 1.33 (d, 3H), 2.99 (s, 3H), 3.07 (s, 3H), 3.18 (m, 1H), 3.20 (m, 2H), 3.33 (d, 2H), 3.48-3.52 (m, 1H), 3.94 (m, 1H), 4.08 (d, 1H), 4.34-4.38 (m, 1H), 4.58 (m, 1H), 5.58 (s, 2H) 7.35 (s, 1H), 7.74 (s, 1H), 7.91 (d, 1H). Mass (574.68) 574.8 |
| 358 | (4R,5S,6R)-3-((3S,5S)-5-((R)-3-aminopyrrolidine-1-carbonyl)pyrrolidin-3-ylthio)-4-methyl-7-oxo-6-((R)-1-(2-(5-(thiophen-2-yl)-1H-tetrazol-1-yl)acetamido)ethyl)-1-azabicyclo[3.2.0]hept-2-ene-2-carboxylic acid | $^1$HNMR (D$_2$O) - 1.21 (d, 3H), 1.36 (d, 3H), 1.73-1.80 (m, 3H), 2.23 (m, 1H), 2.45-2.49 (m, 1H), 2.83-2.91 (m, 1H), 3.19 (d, 2H), 3.31-3.37 (m, 1H), 3.48 (d, 1H), 3.62 (d, 1H), 3.70 (m, 1H), 3.79 (m, 2H), 4.07 (d, 1H), 4.20-4.27 (m, 1H), 4.34-4.38 (m, 1H), 5.57 (s, 2H), 7.36 (m, 1H), 7.74 (m, 1H), 7.91 (d, 1H). Mass 615.73 615.8 |

| Example | Structure | Analytical Data |
|---|---|---|
| 359 | 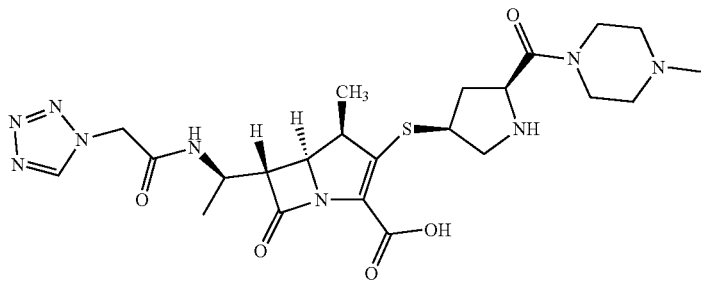 [SMILES: C[C@@H](NC(=O)Cn1cnnn1)[C@H]1C(=O)N2C(C(=O)O)=C(S[C@@H]3CN[C@H](C(=O)N4CCN(C)CC4)C3)[C@H](C)[C@H]12]<br>(4R,5S,6R)-6-((R)-1-(2-(1H-tetrazol-1-yl)acetamido)ethyl)-4-methyl-3-((3S,5S)-5-(4-methylpiperazine-1-carbonyl)pyrrolidin-3-ylthio)-7-oxo-1-azabicyclo[3.2.0]hept-2-ene-2-carboxylic acid | $^1$HNMR (D$_2$O) - 1.21 (d, 3H), 1.35 (d, 3H), 2.64 (s, 3H), 2.98 (m, 4H), 3.36 (m, 2H), 3.58 (m, 3H), 3.99 (m, 4H), 4.15 (m, 2H), 4.43 (m, 1H), 4.63 (d, 1H), 4.81 (d, 1H), 5.43 (m, 2H), 9.37 (s, 1H). Mass (547.63) 547.9 |
| 360 | 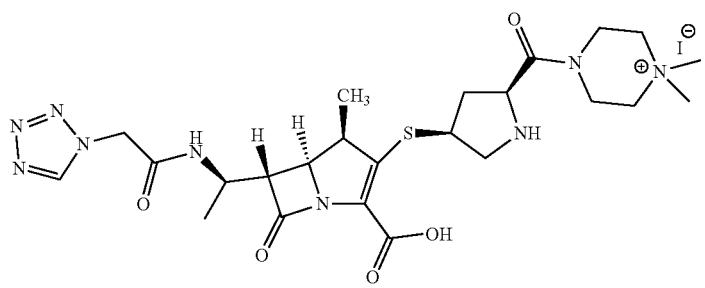 [SMILES: C[C@@H](NC(=O)Cn1cnnn1)[C@H]1C(=O)N2C(C(=O)O)=C(S[C@@H]3CN[C@H](C(=O)N4CC[N+](C)(C)CC4)C3)[C@H](C)[C@H]12 ; [I-]]<br>4-((2S,4S)-((4R,5S,6R)-6-((R)-1-(2-(1H-tetrazol-1-yl)acetamido)ethyl)-2-carboxy-4-methyl-7-oxo-1-azabicyclo[3.2.0]hept-2-en-3-ylthio)pyrrolidine-2-carbonyl)-1,1-dimethylpiperazin-1-ium iodide | $^1$HNMR (D$_2$O) - 1.26 (d, 3H), 1.34 (d, 3H), 1.84-1.88 (m, 1H), 2.89-2.96 (m, 1H), 3.20-3.36 (m, 7H), 3.50 (m, 2H), 3.52 (m, 2H), 3.75 (m, 5H), 3.96 (m, 1H), 4.15 (m, 1H), 4.43-4.56 (m, 2H), 4.81 (m, 1H), 4.81 (m, 1H), 5.47-5.48 (m, 2H), 9.28 (s, 1H). Mass (iodide 689.57, free base, 562.66) 561.9 |
| 361 | 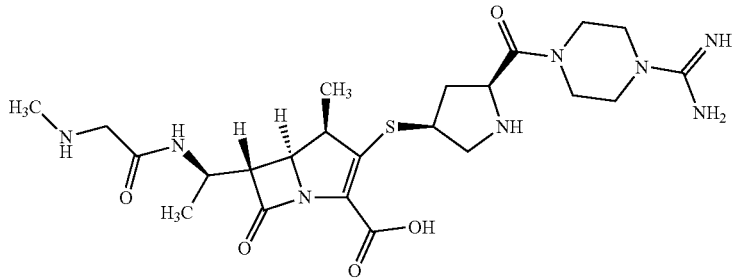 [SMILES: CNCC(=O)N[C@H](C)[C@H]1C(=O)N2C(C(=O)O)=C(S[C@@H]3CN[C@H](C(=O)N4CCN(C(=N)N)CC4)C3)[C@H](C)[C@H]12]<br>(4R,5S,6R)-3-((3S,5S)-5-(4-carbamimidoylpiperazine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | $^1$HNMR (D$_2$O) - 1.15-1.17 (d, 3H), 1.28-1.30 (d, 3H), 2.43 (m, 1H) 2.69 (s, 3H), 2.70-2.74 (m, 2H), 3.10-3.12 (m, 2H), 3.15-3.16 (m, 1H), 3.37-3.38 (m, 2H), 3.61-3.74 (m, 4H), 3.78-3.82 (m, 5H), 4.12-4.17 (m, 2H), 4.45-4.47 (m, 1H), Mass 537.2 (M + 1) HPLC 92.1%, C$_{23}$H$_{36}$N$_8$O$_5$S |
| 362 | 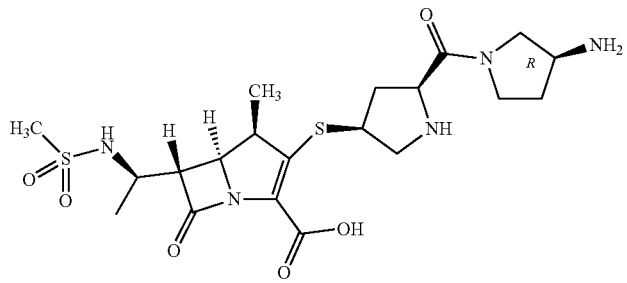<br>(4R,5S,6S)-3-((3S,5S)-5-((R)-3-aminopyrrolidine-1-carbonyl)pyrrolidin-3-ylthio)-4-methyl-6-((R)-1-(methylsulfonamido)ethyl)-7-oxo-1-azabicyclo[3.2.0]hept-2-ene-2-carboxylic acid | $^1$HNMR (D$_2$O) - 1.21-1.23 (d, 3H), 1.37-1.39 (d, 3H), 2.26 (m, 1H), 2.48 (m, 1H), 2.94-2.97, (s, 3H), 3.14 (m, 1H), 3.39-3.40 (m, 2H), 3.50-3.51 (m, 2H), 3.55-3.61 (m, 1H), 3.75-3.89 (m, 2H), 3.90-4.07 (m, 3H), 4.07 (m, 1H), 4.22-4.24 (d, 1H), 4.45-4.46 (m, 1H), HPLC 93.1%; C$_{20}$H$_{31}$N$_5$O$_6$S$_2$ Mass 502.4 (M + H). |

| Example | Structure | Analytical Data |
|---|---|---|
| 363 | 4-((2S,4S)-4-((4R,5S,6R)-6-((R)-1-(2-(1H-tetrazol-1-yl)acetamido)ethyl)-2-carboxy-4-methyl-7-oxo-1-azabicyclo[3.2.0]hept-2-en-3-ylthio)pyrrolidine-2-carbonyl)-1-(2-amino-2-oxoethyl)-1-methylpiperazin-1-ium iodide | $^1$HNMR (D$_2$O) 1.19-1.20 (d, 3H), 1.33-1.34 (d, 3H), 2.83 (m, 1H), 3.18-3.22 (m, 1H), 3.27 (m, 1H), 3.36 (m, 1H), 3.45 (s, 3H), 3.56 (d, 1H), 3.80 (m, 3H), 3.89 (m, 3H), 3.99 (m, 3H), 4.12-4.15 (d, 2H), 4.30 (m, 2H), 4.41 (m, 2H), 5.42 (m, 2H), 9.27 (s, 1H); C$_{25}$H$_{37}$IN$_{10}$O$_6$S; HPLC 90.1%; Mass 606.2 (M + 1) |
| 364 | (4R,5S,6R)-6-((R)-1-(2-(1H-tetrazol-1-yl)acetamido)ethyl)-3-((3S,5S)-5-(4-(2-aminoethyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) 1.24-1.25 (d, 3H), 1.31-1.32 (d, 3H), 2.55-2.69 (m, 4H), 2.71-2.73 (m, 3H), 2.84-2.86 (m, 1H), 3.14-3.17 (m, 2H), 3.20-3.24 (m, 1H), 3.39-3.42 (m, 2H), 3.67-3.68 (m, 1H), 3.70-3.71 (m, 4H), 3.89-3.92 (m, 1H), 4.17-4.20 (m, 1H), 4.40-4.80 (m, 2H), 5.42 (d, 2H), 9.26 (s, 1H); C$_{24}$H$_{36}$N$_{10}$O$_5$S; HPLC 91.1%; Mass 577.2 |
| 365 | (4R,5S,6R)-3-((3S,5S)-5-(1,7-diazaspiro[3.5]nonane-7-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.06-1.08 (d, 3H), 1.20-1.22 (d, 3H), 1.62 (m, 1H), 1.99-2.08 (m, 4H), 2.38-2.43 (m, 2H), 2.78-2.82 (m, 1H), 3.09-3.19 (m, 1H), 3.22-3.30 (m, 3H), 3.43-3.45 (d, 1H), 3.50-3.60 (m, 2H), 3.79 (m, 2H), 3.90-3.94 (m, 2H), 4.00-4.02 (m, 1H), 4.29-4.30 (d, 2H), 5.29-5.30 (d, 2H), 9.14 (s, 1H), Mass 574.2 (M + 1); C$_{25}$H$_{35}$N$_9$O$_5$S HPLC 90.4% |
| 366 | (4R,5S,6R)-6-((R-1-(2-(1H-tetrazol-1-yl)acetamido)ethyl)-3-((3S,5S)-5-(2,7-diazaspiro[3.5]nonane-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.13-1.15 (d, 3H), 1.20-1.22 (d, 3H), 1.69 (m, 1H), 1.95 (m, 4H), 2.60-2.43 (m, 2H), 2.72-2.80 (m, 1H), 3.09 (m, 4H), 3.22-3.24 (m, 1H), 3.44-3.45 (d, 1H), 3.72-3.80 (m, 3H), 3.92-4.03 (m, 3H), 4.17-4.19 (m, 1H), 4.28 (m, 1H), 5.30 (d, 2H), 9.14 (s, 1H), Mass 574.2 (M + 1); C$_{25}$H$_{35}$N$_9$O$_5$S HPLC 90% |

| Example | Structure | Analytical Data |
|---|---|---|
| 367 | (4R,5S,6R)-6-((R)-1-(2-(1H-tetrazol-1-yl)acetamido)ethyl)-3-((3S,5S)-5-(4-carbamimidoylpiperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.07-1.09 (d, 3H), 1.21-1.23 (d, 3H), 2.76 (m, 1H), 3.21-3.30 (m, 3H), 3.49-3.50 (m, 5H), 3.63-3.64 (m, 5H), 3.80 (m, 1H), 4.01-4.03 (m, 1H), 4.28-4.31 (m, 2H), 5.31 (m, 2H), 9.14 (s, 1H), Mass 576.4 (M + 1); C$_{23}$H$_{33}$N$_{11}$O$_5$S; HPLC 91% |
| 368 | (4R,5S,6R)-6-((R)-1-(2-(1H-tetrazol-1-yl)acetamido)ethyl)-3-((3S,5S)-5-(2,7-diazaspiro[3.5]nonane-7-carbonyl)pyrrolidin-3-ylthio)-4-methyl-7-oxo-1-azabicyclo[3.2.0]hept-2-ene-2-carboxylic acid | $^1$HNMR (D$_2$O) - 1.17-1.19 (d, 3H), 1.32-1.33 (d, 3H), 1.79 (m, 1H), 1.90 (m, 4H), 2.92 (m, 1H), 3.30-3.34 (m, 2H), 3.48-3.52 (m, 3H), 3.55-3.57 (m, 3H), 3.97 (m, 5H), 4.11-4.13 (m, 1H), 4.38-4.42 (m, 1H), 4.53 (m, 1H), 5.40-5.41 (m, 2H) 9.26 (s, 1H), Mass 574.2 (M + 1); C$_{25}$H$_{35}$N$_9$O$_5$S; HPLC 91.5% |

Examples 369-378 and 383-451 were prepared by treating the compound of formula (10) with appropriate R$^4$COOH according to the procedure given in the preparations 12, 16 and 17, followed by the procedure given in Example 1.

The cyclisation to obtain carbapenem and reaction of its enolic phosphate with various R$^1$—SH is similar to that described for preparation of Example 1 (Step 1 & Step 2) or Example 95 (Step 1 to 3) or Example 298 (Step 2 to 4).

| Example | Structure | Analytical Data |
|---|---|---|
| 369 | (4R,5S,6R)-6-((R)-1-(3-(1H-tetrazol-1-yl)propanamido)ethyl)-3-((3S,5S)-5-((R)-3-aminopyrrolidine-1-carbonyl)pyrrolidin-3-ylthio)-4-methy-7-oxo-1-azabicyclo[3.2.0]hept-2-ene-2-carboxylic acid | $^1$HNMR (D$_2$O) - 1.11 (d, 3H) 1.23 (d, 3H), 2.04-2.08 (m, 1H), 2.51-2.72 (m, 2H), 2.95 (m, 1H), 3.07-3.19 (m, 2H), 3.34-3.46 (m, 3H); 3.63-3.70 (m, 6H), 3.73 (m, 1H), 3.78 (m, 2H, 3.8-4.28 (m, 3H), 9.24 (s, 1H); C23H33N9O5S; HPLC 98.9%; Mass 548.3 (M + 1) |

| Example | Structure | Analytical Data |
|---|---|---|
| 370 | 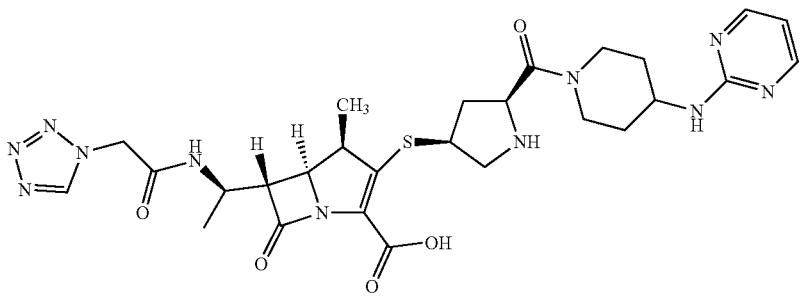 [SMILES: C[C@@H](NC(=O)Cn1cnnn1)[C@H]1C(=O)N2C(C(=O)O)=C(S[C@@H]3CN[C@H](C(=O)N4CCC(Nc5ncccn5)CC4)C3)[C@H](C)[C@H]12]<br>(4R,5S,6R)-6-((R)-1-(2-(1H-tetrazol-1-yl)acetamido)ethyl)-4-methyl-7-oxo-3-((3S,5S)-5-(4-(pyrimidin-2-ylamino)piperidine-1-carbonyl)pyrrolidin-3-ylthio)-1-azabicyclo[3.2.0]hept-2-ene-2-carboxylic acid | $^1$HNMR (D$_2$O) - 1.26 (d, 3H), 1.31 (d, 3H), 3.01-3.10 (m, 4H), 3.33-3.35 (m, 3H), 3.78-3.82 (m, 3H), 3.80-3.82 (m, 5H), 4.0-4.1 (m, 4H), 5.4 (m, 2H), 8.3-8.31 (m, 3H), 9.26 (s, 1H); C27H35N11O5S; HPLC 90.1%; Mass 626.20 (M + 1) |
| 371 | 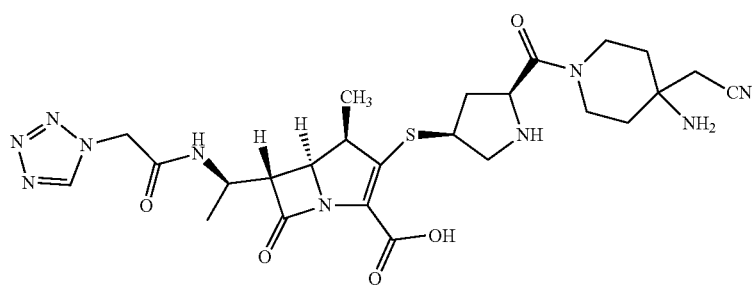 [SMILES: C[C@@H](NC(=O)Cn1cnnn1)[C@H]1C(=O)N2C(C(=O)O)=C(S[C@@H]3CN[C@H](C(=O)N4CCC(N)(CC#N)CC4)C3)[C@H](C)[C@H]12]<br>(4R,5S,6R)-6-((R)-1-(2-(1H-tetrazol-1-yl)acetamido)ethyl)-3-((3S,5S)-5-(4-amino-4-(cyanomethyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.29 (d, 3H), 1.76 (m, 2H), 2.80 (m, 2H), 3.01 (m, 1H), 3.34-3.40 (m, 2H), 3.5 (m, 2H), 3.34-3.40 (m, 2H), 3.5 (m, 4H), 3.86-3.89 (m, 2H), 4.0 (m, 1H), 4.14-4.16 (m, 1H), 4.42 (m, 1H), 5.42 (m, 2H), 9.27 (s, 1H); C25H34N10O5S; HPLC 91%; Mass 587.2 (M + 1) |
| 372 | 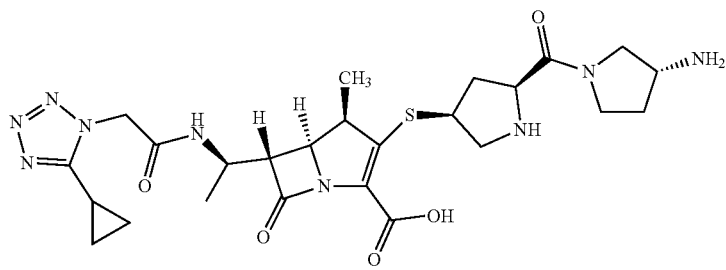 [SMILES: C[C@@H](NC(=O)Cn1nnnc1C1CC1)[C@H]1C(=O)N2C(C(=O)O)=C(S[C@@H]3CN[C@H](C(=O)N4CC[C@@H](N)C4)C3)[C@H](C)[C@H]12]<br>(4R,5S,6R)-3-((3S,5S)-5-((R)-3-aminopyrrolidine-1-carbonyl)pyrrolidin-3-ylthio)-6-((R)-1-(2-(5-cyclopropyl-1H-tetrazol-1-yl)acetamido)ethyl)-4-methyl-7-oxo-1-azabicyclo[3.2.0]hept-2-ene-2-carboxylic acid | 1HNMR (D$_2$O)-0.98-1.10 (m, 2H) 1.19-1.21 (d, 3H), 1.25-1.27 (m, 2H) 1.32 (m, 3H), 1.60-2.00 (m, 3H), 2.03-2.04 (m, 2H), 2.09-2.31 (m, 1H), 2.32-2.60 (m, 1H), 2.70-3.06 (m, 1H), 3.18-3.42 (m, 2H), 3.60-3.63 (m, 1H), 3.70-3.72 (m, 1H), 3.75-3.78 (m, 2H), 3.88-3.93 (m, 2H), 4.03-4.15 (m, 1H), 4.41-4.44 (m, 1H), 5.40 (s, 2H); C25H35N9O5S; HPLC 90.1%; Mass 574.2 (M + 1) |
| 373 | 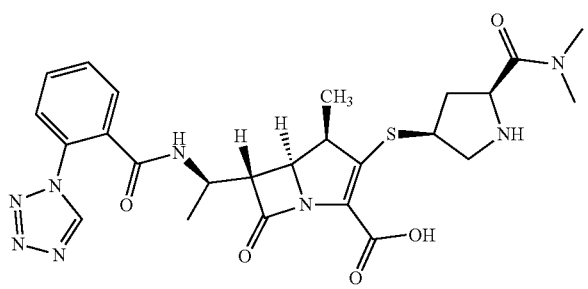 [SMILES: C[C@@H](NC(=O)c1ccccc1-n1cnnn1)[C@H]1C(=O)N2C(C(=O)O)=C(S[C@@H]3CN[C@H](C(=O)N(C)C)C3)[C@H](C)[C@H]12] | $^1$HNMR (D$_2$O) - 1.18 (d, 3H), 1.34 (d, 3H), 3.00 (s, 3H), 3.02 (m, 1H), 3.06 (s, 3H), 3.07-3.08 (m, 1H), 3.40-3.45 (m, 3H), 3.63-3.75 (m, 1H), 4.02-4.04 (m, 2H), 4.25-4.47 (m, 1H), 4.52-4.68 (m, 1H), 7.69-7.78 (m, 4H), 9.57 (s, 1H); C25H30N8O5S; HPLC 92.2% Mass 555.1 (M + 1) |

-continued

| Example | Structure | Analytical Data |
|---|---|---|
| 374 | (4R,5S,6R)-6-((R)-1-(2-(1H-tetrazol-1-yl)benzamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.33 (d, 3H), 1.91 (m, 1H), 2.89-2.30 (m, 1H), 3.25 (m, 1H), 3.31 (m, 1H), 3.42-3.44 (m, 2H), 3.44-3.50 (m, 2H), 3.60-3.69 (m, 1H), 3.73-3.79 (m, 2H), 3.85-3.90 (m, 2H), 4.02-4.04 (m, 2H), 4.36-4.38 (m, 1H), 4.40 (m, 1H), 7.69 (m, 1H), 7.70-7.81 (m, 3H), 9.57 (s, 1H); C27H33N9O5S; HPLC 96.6%; Mass 596.2 (M + 1) |
| 375 | 4-((2S,4S)-4-((4R,5S,6R)-6-((R)-1-(2-(1H-tetrazol-1-yl)acetamido)ethyl)-2-carboxy-4-methyl-7-oxo-1-azabicyclo[3.2.0]hept-2-en-3-ylthio)pyrrolidine-2-carbonyl)-1-(2-aminoethyl)-1-methylpiperazin-1-ium iodide | $^1$HNMR (D$_2$O) - 1.20 (d, 3H), 1.34 (d, 3H), 2.89 (m, 2H), 3.29 (m, 2H), 3.31 (s, 3H), 3.36 (m, 2H), 3.56-3.64 (m, 8H), 3.90-3.98 (m, 5H), 4.09 (m, 1H), 4.40-4.43 (m, 2H), 5.42-5.43 (m, 2H), 9.27 (s, 1H); C25H39IN10O5S; HPLC 91.1%; Mass 592.2 free base (M + 1) |
| 376 | (4R,5S,6R)-6-((R)-1-(2-(1H-tetrazol-1-yl)acetamido)ethyl)-4-methyl-7-oxo-3-(1-sulfamoylazetidin-3-ylthio)-1-azabicyclo[3.2.0]hept-2-ene-2-carboxylic acid | $^1$HNMR (D$_2$O) - 1.22 (d, 3H), 1.31 (d, 3H), 3.18-3.21 (m, 1H), 3.52-3.54 (m, 1H), 3.76-3.82 (m, 2H), 4.08-4.15 (m, 2H), 4.24-4.29 (m, 2H), 4.38-4.41(m, 1H), 5.41-5.45 (m, 2H), 9.25 (s, 1H); C16H22N8O6S2; HPLC 90.2%; Mass 487.1 (M + 1) |
| 377 | (4R,5S,6R)-6-((R)-1-(2-(1H-tetrazol-1-yl)acetamido)ethyl)-3-((3S,5S)-5-(8-azaspiro[bicyclo[3.2.1]octane-3,3'-pyrrolidine]-8-ylcarbonyl)pyrrolidin-3-ylthio)-4-methyl-7-oxo-1-azabicyclo[3.2.0]hept-2-ene-2-carboxylic acid | $^1$HNMR (D$_2$O) - 1.11 (d, 3H), 1.24 (d, 3H), 1.72 (m, 6H), 1.82 (m, 4H), 2.90-2.94 (m, 1H), 2.9 (m, 2H), 3.12-3.26 (m, 1H), 3.41-3.45 (m, 3H), 3.45-3.46 (m, 4H), 3.47-3.48 (m, 1H), 4.02-4.05 (m, 1H), 4.26-4.32 (m, 2H), 4.71 (m, 1H), 5.30-5.32 (m, 2H), 9.17 (s, 1H); C28H39N9O5S; HPLC 91.2%; Mass 614.4 (M + 1) |

-continued

| Example | Structure | Analytical Data |
|---|---|---|
| 378 | (4R,5S,6R)-6-((R)-1-2-(5-cyclopropyl-1H-tetrazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.02-1.05 (m, 2H) 1.20 (d, 3H), 1.25-1.27 (m, 2H), 1.32 (d, 3H), 1.95-2.02 (m, 3H), 2.99-3.01 (s, 3H), 3.30 (s, 4H), 3.32-3.34 (m, 1H), 3.43-3.48 (m, 1H), 3.58-3.60 (m, 1H), 3.73-3.77 (m, 1H), 4.02-4.05 (m, 1H), 4.14-4.17 (m, 1H), 4.39-4.43 (m, 1H), 5.38 (s, 2H); C23H32N8O5S; HPLC 96.1%; Mass 533.3 (M + 1) |
| 379 | (4R,5S,6S)-6-((R)-1-((1H-tetrazol-1-yl)methylsulfonamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxcylic acid | $^1$HNMR (D$_2$O) - 1.16 (d, 3H), 1.27 (d, 3H), 1.77-1.80 (m, 2H)T, 2.86-2.88 (m, 3H), 2.90-2.97 (m, 2H), 3.26-3.31 (m, 2H), 3.35-3.37 (m, 3H), 3.51-3.56 (m, 1H), 3.88-3.92 (m, 1H), 4.11-4.13 (m, 1H), 4.56-4.58 (m, 1H), 6.00-6.01 (m, 2H), 9.4 (s, 1H); C19H28N8O6S2; HPLC 96.9%; Mass 529.5 (M + 1) |
| 380 | (4R,5S,6S)-6-((R)-1-((1H-tetrazol-1-yl)methylsulfonamido)ethyl)-3-((3S,5S)-5-((R)-3-aminopyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.08 (d, 3H), 1.25 (d, 3H), 2.35-2.37 (m, 1H), 2.80-2.90 (m, 1H), 3.16-3.20 (m, 2H), 3.28-3.43 (m, 3H), 3.48-3.55 (m, 1H), 3.56-3.68(m, 3H), 3.74-3.84 (m, 2H), 3.86-4.10 (m, 2H), 4.10-4.13 (m, 1H), 4.13-4.29 (m, 1H), 6.00 (m, 2H), 9.36 (s, 1H); C21H31N9O6S2; HPLC 92.5%; Mass 570.6 (M + 1) |
| 381 | (4R,5S,6S)-6-((R)-1-(2H-tetrazol-2-yl)methylsulfonamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O)-0.96 (d, 3H), 1.16 (d, 3H), 1.80-1.83 (m, 1H), 2.67 (s, 3H), 2.85 (s, 3H), 3.05-3.09 (m, 1H), 3.12-3.18 (m, 2H), 3.21-3.33 (m, 2H), 3.71-3.73 (m, 2H), 3.99-4.02 (m, 1H), 4.27-4.32 (m, 1H), 4.46-4.48 (m, 1H), 6.0 (s, 1H), 8.6 (s, 1H) C19H28N8O6S2; Mass 528.61 (M + 1) |

| Example | Structure | Analytical Data |
|---|---|---|
| 382 | 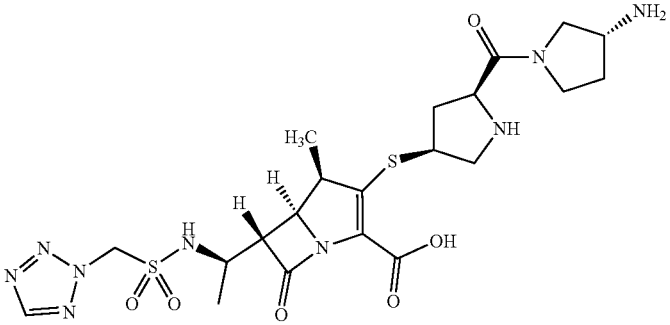 [SMILES: C[C@@H](NS(=O)(=O)Cn1ncnn1)[C@H]1C(=O)N2C(C(=O)O)=C(S[C@@H]3CN[C@H](C(=O)N4CC[C@@H](N)C4)C3)[C@H](C)[C@H]12]<br>(4R,5S,6S)-6-((R)-1-((2H-tetrazol-2-yl)methylsulfonamido)ethyl)-3-((3S,5S)-5-((R)-3-aminopyrroldine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.12 (d, 3H), 1.28 (d, 3H), 2.38-2.42 (m, 2H), 2.82 (m, 1H), 3.18-322 (m, 1H), 3.21-3.41 (m, 3H), 3.51-3.72 (m, 4H), 3.77-3.91 (m, 2H), 3.03-3.97 (m, 2H), 4.16-4.18 (m, 1H), 4.31 (m, 1H), 6.19-6.24 (m, 2H), 8.85 (s, 1H) C21H31N9O6S2; HPLC 93% Mass 570.3 (M + 1) |
| 383 | 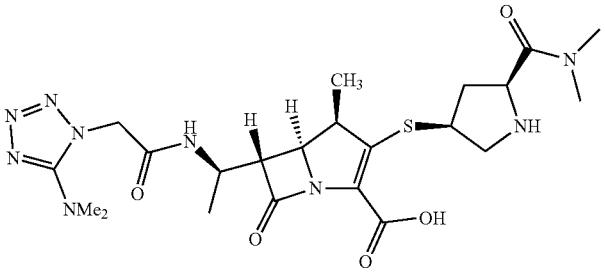 [SMILES: C[C@@H](NC(=O)Cn1nnnc1N(C)C)[C@H]1C(=O)N2C(C(=O)O)=C(S[C@@H]3CN[C@H](C(=O)N(C)C)C3)[C@H](C)[C@H]12]<br>(4R,5S,6R)-6-((R)-1-(2-(5-(dimethylamino)-1H-tetrazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.16 (d, 3H), 1.22 (d, 3H), 1.72-1.75 (m, 1H), 2.83 (s, 3H), 2.95 (s, 9H), 3.19-3.26 (m, 3H), 3.46-3.47 (m, 2H), 3.86 (m, 1H), 4.03-4.05 (m, 1H), 4.30-4.33 (m, 1H), 4.50-4.70 (m, 1H), 5.1 (s, 2H) C22H33N9O5S; HPLC 94.4%; Mass 536.4 (M + 1) |
| 384 | 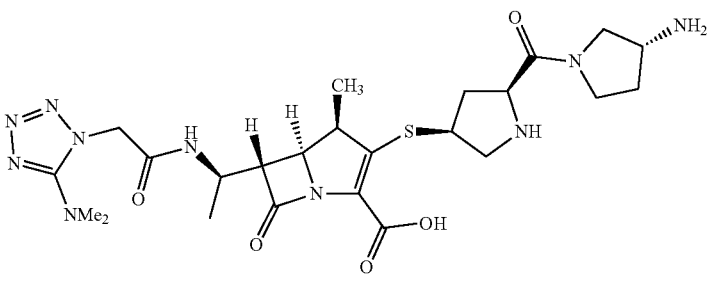 [SMILES: C[C@@H](NC(=O)Cn1nnnc1N(C)C)[C@H]1C(=O)N2C(C(=O)O)=C(S[C@@H]3CN[C@H](C(=O)N4CC[C@@H](N)C4)C3)[C@H](C)[C@H]12]<br>(4R,5S,6R)-3-((3S,5S)-5-((R)-3-aminopyrrolidine-1-carbonyl)pyrrolidin-3-ylthio)-6-((R)-1-(2-(5-(dimethylamino)-1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.16 (d, 3H), 1.22 (d, 3H), 1.8 (m, 1H), 2.03-2.23 (m, 1H), 2.34-2.36 (m, 1H), 2.84 (m, 2H), 2.94 (m, 6H), 3.17 (m, 1H), 3.38-3.39 (m, 2H), 3.46-3.47 (m, 2H), 3.58-3.60 (m, 2H), 3.75-3.78 (m, 2H), 3.94-3.99 (m, 2H), 4.31-4.33 (m, 1H), 5.1 (s, 2H); C24H36N10O5S; HPLC 90%; Mass 575.7 (M − 1) |
| 385 | 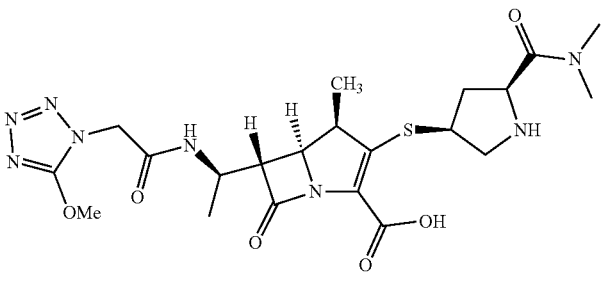 [SMILES: COc1nnnn1CC(=O)N[C@H](C)[C@H]1C(=O)N2C(C(=O)O)=C(S[C@@H]3CN[C@H](C(=O)N(C)C)C3)[C@H](C)[C@H]12]<br>(4R,5S,6R)-3-((3S,5S)-5-(dimethylcarbamoyl)pyrrolidin-3-ylthio)-6-((R)-1-(2-(5-methoxy-1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.12 (d, 3H), 1.22 (d, 3H), 1.80-1.85 (m, 1H), 2.91 (s, 3H), 2.95 (s, 3H), 3.19 (m, 2H), 3.20-3.24 (m, 2H), 3.45-3.46 (m, 1H), 3.55-3.59 (m, 1H), 3.90 (m, 1H), 4.02 (m, 1H), 4.12 (s, 3H), 4.27-4.30 (m, 1H), 4.99 (s, 2H); C21H30N8O6S; HPLC 96.1%; Mass 523.4 (M + 1) |

| Example | Structure | Analytical Data |
|---|---|---|
| 386 | 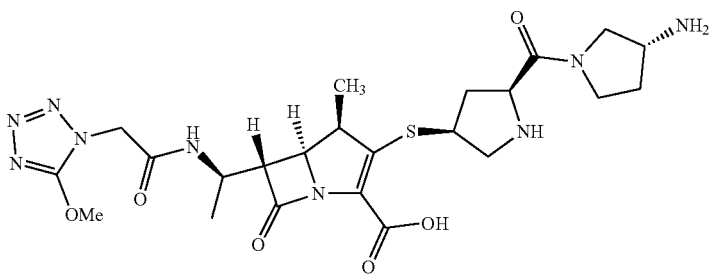 [SMILES: COc1nnnn1CC(=O)N[C@H](C)[C@H]1C(=O)N2C(C(=O)O)=C(S[C@@H]3CN[C@H](C(=O)N4CC[C@@H](N)C4)C3)[C@H](C)[C@H]12]<br>(4R,5S,6R)-3-((3S,5S)-5-((R)-3-aminopyrrolidine-1-carbooyl)pyrrolidin-3-ylthio)-6-((R)-1-(2-(5-methoxy-1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.11 (d, 3H), 1.22 (d, 3H), 2.14-2.15 (m, 1H), 2.35-2.39 (m, 1H), 2.85-3.00 (m, 1H), 3.20-3.26 (m, 2H), 3.45-3.46 (m, 2H), 3.50-3.56 (m, 2H), 3.81-3.86 (m, 2H), 3.96-3.97 (m, 2H), 4.02-4.04 (m, 2H), 4.12 (s, 3H), 4.26-4.28 (m, 1H), 4.36 (m, 1H), 4.94-4.95 (m, 2H); C23H33N9O6S; HPLC 90.9%; Mass 564.4 (M + 1) |
| 387 | 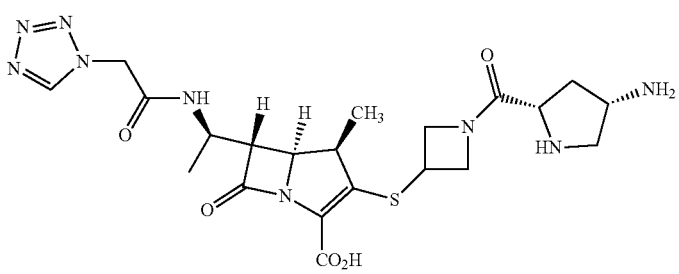 [SMILES: C[C@@H](NC(=O)Cn1cnnn1)[C@H]1C(=O)N2C(C(=O)O)=C(SC3CN(C(=O)[C@@H]4C[C@H](N)CN4)C3)[C@H](C)[C@H]12]<br>(4R,5S,6R)-6-((R)-1-(2-(1H-tetrazol-1-yl)acetamido)ethyl)-3-(1-((2S,4S)-4-aminopyrrolidine-2-carbonyl)azetidin-3-ylthio)-4-methyl-7-oxo-1-azabicyclo[3.2.0]hept-2-ene-2-carboxylic acid | $^1$HNMR (D$_2$O) - 1.18 (d, 3H), 1.32 (m, 3H), 2.49-2.56 (m, 1H), 3.11-3.18 (m, 1H), 3.33 (m, 1H), 3.55-3.57 (m, 2H), 3.73-3.78 (m, 1H), 3.96 (m, 2H), 4.02-4.04 (m, 2H), 4.23 (m, 2H), 4.34-4.49 (m, 2H), 4.75-4.82 (m, 1H), 5.38 (s, 2H), 9.26 (s, 1H); C21H29N9O5S; HPLC 91.1%; Mass 520.4 (M + 1) |
| 388 | 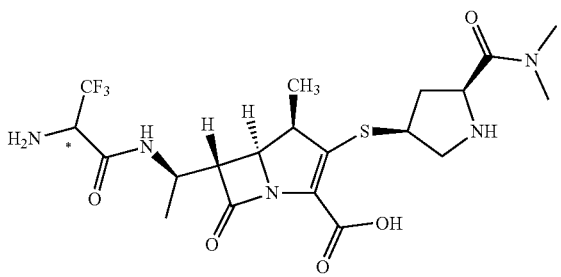 [SMILES: C[C@@H](NC(=O)C(N)C(F)(F)F)[C@H]1C(=O)N2C(C(=O)O)=C(S[C@@H]3CN[C@H](C(=O)N(C)C)C3)[C@H](C)[C@H]12]<br>(4R,5S,6R)-6-((1R-1-(2-amino-3,3,3-trifluoropropanamido)ethyl-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.34 (d, 3H), 1.94-1.99 (m, 1H), 3.00 (s, 3H), 3.06 (s, 3H), 3.27 (m, 2H), 3.44-3.48 (m, 2H), 3.71-3.73 (m, 2H), 4.02-4.09 (m, 3H), 4.45 (m, 1H); C20H28F3N5O5S; HPLC 94.9%; Mass 508.3 (M + 1) |
| 389 | 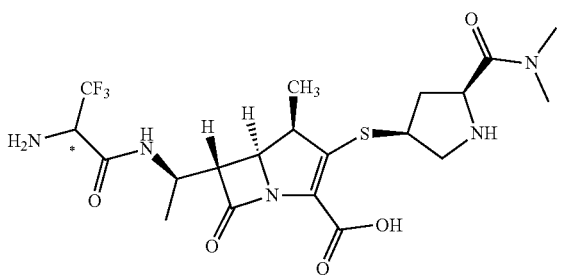 [SMILES: C[C@@H](NC(=O)C(N)C(F)(F)F)[C@H]1C(=O)N2C(C(=O)O)=C(S[C@@H]3CN[C@H](C(=O)N(C)C)C3)[C@H](C)[C@H]12]<br>(4R,5S,6R)-6-((1R)-(2-amino-3,3,3-trifluoropropanamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.21 (d, 3H), 1.33 (d, 3H), 1.92 (m, 1H), 3.02 (s, 3H), 3.07 (s, 3H), 3.35-3.42 (m, 3H), 3.59-3.61 (m, 3H), 4.02-4.17 (m, 3H), 4.41 (m, 1H); C20H28F3N5O5S; HPLC 91.7%; Mass 508.3 (M + 1) |

-continued

| Example | Structure | Analytical Data |
|---|---|---|
| 390 | (4R,5S,6R)-3-((3S,5S)-5-((R)-3-aminopyrrolidine-1-carbonyl)pyrrolidin-3-ylthio)-6-((R)-1-(2-(5,6-dihydrotetrazolo[1,5-a]pyrazin-7(8H)-yl)acetamido)ethyl)-4-methyl-7-oxo-1-azabicyclo[3.2.0]hept-2-ene-2-carboxylic acid | $^1$HNMR (D$_2$O) - 1.12 (d, 3H), 1.18 (d, 3H), 3.0-3.1 (m, 4H), 3.15-3.20 (m, 5H), 3.30-3.34 (m, 4H), 3.44-3.55 (m, 3H), 3.58-3.61 (m, 4H), 4.29-4.30 (m, 1H), 4.32-4.41 (m, 3H), 4.42-4.75 (m, 1H); C25H36N10O5S; HPLC 91.5%; Mass 589.2 (M + 1) |
| 391 | (4R,5S,6R)-6-((R-1-(2-(1H-tetrazol-1-yl)acetamido)ethyl)-3-((3S,5S)-5-(((R)-3-aminopyrrolidin-1-yl)methyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.27 (d, 3H), 1.92 (m, 3H), 2.66-2.67 (m, 2H), 2.73-2.79 (m, 2H), 2.84-2.95 (m, 4H), 3.31-3.32 (m, 2H), 3.58-3.59 (m, 2H), 3.89 (s, 2H), 4.12 (s, 1H), 4.39-4.41 (m, 1H), 5.41 (m, 2H), 9.26 (s, 1H); C22H33N9O4S; HPLC 97.8%; Mass 520.4 (M + 1) |
| 392 | (4R,5S,6R)-6-((R)-1-(2-(5-amino-1H-tetrazol-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.32 (d, 3H), 2.08 (m, 1H), 2.97-2.98 (m, 1H), 2.99 (s, 3H), 3.07-3.08 (m, 1H), 3.11 (s, 3H), 3.30-3.32 (m, 2H), 3.55 (m, 2H), 3.96 (m, 1H), 4.13-4.15 (m, 1H), 4.40-4.55 (m, 1H), 5.05-5.07 (d, 2H); C20H29N9O5S; HPLC 90.1%; Mass 508.3 (M + 1) |
| 393 | (4R,5S,6R)-6-((R)-1-(2-(1H-tetrazol-1-yl)acetamido)ethyl)-3-((3S,5S)-5-((R)-3-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 2.91-3.10 (m, 1H), 3.32-3.40 (m, 2H), 3.47-3.52 (m, 1H), 3.59-3.63 (d, 5H), 3.70-3.75 (m, 2H), 4.00 (m, 1H), 4.14-4.16 (m, 2H), 4.40-4.43 (m, 1H), 4.56-4.59 (m, 2H), 5.42-5.43 (d, 2H), 9.27 (s, 1H); C22H30N8O6S; HPLC 95%; Mass 535.3 (M + 1) |

| Example | Structure | Analytical Data |
|---|---|---|
| 394 | (4R,5S,6R)-3-((3S,5S)-5-((R)-3-aminopyrrolidine-1-carbonyl)pyrrolidin-3-ylthio)-4-methyl-7-oxo-6-((R)-1-(2-(5-(trifluoromethyl)-1,3,4-oxadiazol-2-yl)acetamido)ethyl)-1-azabicyclo[3.2.0]hept-2-ene-2-carboxylic acid | $^1$HNMR (D$_2$O) - 1.21 (d, 3H), 1.34 (d, 3H), 1.71-1.90 (m, 1H), 2.32-2.56 (m, 1H), 2.75-2.94 (m, 1H), 3.20-3.23 (d, 2H), 3.36-3.42 (m, 2H), 3.55-3.61 (m, 2H), 3.64-3.76 (m, 3H), 3.85-3.90 (m, 2H), 4.04-4.08 (m, 2H), 4.13-4.15 (m, 1H), 4.17-4.29 (m, 1H), 4.39-4.42 (m, 1H); C24H30F3N7O6S; HPLC 90.1%; Mass 602.3 (M + 1) |
| 395 | (4R,5S,6R)-6-((R)-1-(2-(1H-tetrazol-1-yl)acetamido)ethyl)-3-((3S,5S)-5-(4-(2-aminoacetyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 2.94-2.98 (m, 1H), 3.35 (m, 3H), 3.56-3.71 (m, 10H), 3.97 (m, 1H), 4.07 (m, 2H), 4.13-4.15 (m, 1H), 4.41-4.43 (m, 1H), 4.61-4.79 (m, 1H), 5.42 (m, 2H), 9.27 (s, 1H); C24H34N10O6S; HPLC 91%; Mass 591.4 (M + 1) |
| 396 | (4R,5S,6R)-6-((R)-1-(2-(1H-tetrazol-1-yl)acetamido)ethyl)-3-((3S,5S)-5-((3R,4R)-3,4-dihydroxypyrrolidine-1-carbonyl)pyrrolidin-3-ylthio)-methyl-7-oxo-1-azabicyclo[3.2.0]hept-2-ene-2-carboxylic acid | $^1$HNMR (D$_2$O) - 1.20 (d, 3H), 1.34 (d, 3H), 2.08-2.14 (m, 1H), 2.99-3.03 (m, 1H), 3.32-3.38 (m, 2H), 3.51-3.69 (m, 4H), 3.75-3.81 (m, 2H), 4.01-4.03 (m, 1H), 4.14-4.16 (m, 1H), 4.29-4.34 (m, 2H), 4.40-4.43 (m, 1H), 4.58-4.62 (m, 1H), 5.42-5.43 (m, 2H), 9.27 (s, 1H) C22H30N8O7S; HPLC 90.1%; Mass 551.5 (M + 1) |
| 397 | (4R,5S,6R)-6-((R)-1-(2-(1H-tetrazol-1-yl)acetamido)ethyl)-3-((3S,5S)-5-(8-azaspiro[bicyclo[3.2.1]octane-3,3'-pyrrolidine]-1'-ylcarbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 2.04-2.08 (m, 5H), 2.22-2.23 (m, 6H), 2.91-2.92 (m, 1H), 3.28-3.40 (m, 4H), 3.49-3.58 (m, 2H), 3.63-3.77 (m, 2H), 3.94-3.95 (m, 1H), 4.14 (m, 3H), 4.34-4.41 (m, 2H), 5.42 (m, 2H), 9.27 (s, 1H); C28H39N9O5S; HPLC 94.3%; Mass 614.4 (M + 1) |

-continued

| Example | Structure | Analytical Data |
|---|---|---|
| 398 | (4R,5S,6R)-6-((R)-1-(2-(1H-tetrazol-1-yl)acetamido)ethyl)-3-((3S,5S)-5-((R)-3-(2-aminoacetamido)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 1.99-2.13 (m, 1H), 2.19-2.30 (m, 1H), 2.79-3.10 (m, 1H), 3.32-3.34 (d, 2H), 3.46-3.59 (m, 1H), 3.77 (m, 4H), 3.95 (m, 4H), 4.14 (m, 1H), 4.15-4.24 (m, 1H), 4.46-4.51 (m, 3H), 5.42 (m, 2H), 9.27 (s, 1H); C24H34N10O6S; HPLC 90.15; Mass 591.4 (M + 1) |
| 399 | (4R,5S,6R)-6-((R)-1-(2-(1H-tetrazol-1-yl)acetamido)ethyl)-3-((3S,5S)-5-((R)-3-guanidinopyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.28-1.30 (d, 3H), 1.73-1.80 (m, 2H), 1.92 (m, 2H), 3.02-3.08 (m, 2H), 3.34-3.36 (m, 2H), 3.58-3.78 (m, 4H), 4.00 (m, 1H), 4.13-4.16 (m, 1H), 4.41 (m, 2H), 4.58 (m, 1H), 5.41 (m, 2H), 9.27 (s, 1H); C23H33N11O5S; HPLC 90.1%; Mass 576.3 (M + 1) |
| 400 | (4R,5S,6R)-6-((R)-1-(2-(1H-tetrazol-1-yl)acetamido)ethyl)-3-((3S,5S)-5-((3R,4S)-3-amino-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.34 (d, 3H), 2.97 (m, 1H), 3.36-3.37 (m, 2H), 3.63-3.65 (m, 2H), 3.95-3.99 (m, 2H), 4.13-4.16 (m, 4H), 4.52-4.54 (m, 2H), 4.55-4.63 (m, 3H), 5.46 (m, 2H), 9.27 (s, 1H); C22H31N9O6S; HPLC 94.4% Mass 550.2 (M + 1) |
| 401 | (4R,5S,6R)-6-((R)-1-(2-(1H-tetrazol-1-yl)acetamido)ethyl)-3-((3S,5S)-5-((R)-3-(2-aminoethylamino)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 2.95 (m, 4H), 3.13-3.23 (m, 1H), 3.30-3.34 (m, 2H), 3.35-3.50 (m, 2H), 3.59-3.63 (m, 2H), 3.72-3.76 (m, 2H), 3.98 (m, 2H), 4.13-4.16 (m, 4H), 4.40-4.50 (m, 2H), 5.43 (m, 2H), 9.27 (s, 1H); C24H36N10O5S; HPLC 90%; Mass 577.4 (M + 1) |

| Example | Structure | Analytical Data |
|---|---|---|
| 402 | (4R,5S,6R)-6-((R)-1-(2-(1H-tetrazol-1-yl)acetamido)ethyl)-4-methyl-7-oxo-3-((3S,5S)-5-(pyridin-4-ylcarbamoyl)pyrrolidin-3-ylthio)-1-azabicyclo[3.2.0]hept-2-ene-2-carboxylic acid | $^1$HNMR (D$_2$O) - 1.19 (d, 3H), 1.34 (d, 3H), 3.27-3.34 (m, 3H), 3.56-3.65 (m, 3H), 4.11-4.14 (m, 2H), 4.39-4.42 (m, 2H), 5.42 (m, 2H), 7.71-7.72 (m, 2H), 8.49-8.51 (m, 2H) 9.27 (s, 1H); C23H27N9O5S; HPLC 91.56%; Mass 542.8 (M + 1) |
| 403 | (4R,5S,6R)-3-((3S,5S)-5-((R)-3-aminopyrrolidine-1-carbonyl)pyrrolidin-3-ylthio)-6-((R)-1-(2-(5-carboxy-1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.17 (d, 3H), 1.36 (d, 3H), 2.28 (m, 1H), 2.49 (m, 1H), 3.05 (m, 1H), 3.38-3.58 (m, 2H), 3.49-3.51 (m, 2H), 3.64-3.67 (m, 2H), 3.74-3.80 (m, 3H), 3.90 (m, 2H), 3.93-4.10 (m, 2H), 4.69 (m, 1H), 5.52 (m, 2H); C23H31N9O7S; HPLC 94.3%; Mass 578.3 (M + 1) |
| 404 | (4R,5S,6R)-6-((R)-1-(2-(1H-tetrazol-1-yl)acetamido)ethyl)-3-((3S,5S)-5-(4-(aminomethyl)piperidine-1-carbanoyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.29 (m, 3H), 1.87 (m, 4H), 1.92 (m, 1H), 2.94-2.95 (m, 1H), 3.23 (m, 3H), 3.30-3.33 (m, 1H), 3.56-3.58 (m, 2H), 3.80 (m, 2H), 4.10-4.15 (m, 2H), 4.39-4.40 (m, 1H), 4.82 (m, 2H), 4.89 (m, 1H), 5.40-5.42 (m, 3H), 9.27 (s, 1H); C24H35N9O5S; HPLC 90.1%; Mass 562.2 (M + 1) |
| 405 | (4R,5S,6R)-6-((R)-1-(2-(1H-tetrazol-1-yl)acetamido)ethyl)-3-((3S,5S)-5-(3-amino-3-methylazetidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 1.63 (s, 3H), 2.84 (m, 1H), 3.35 (m, 2H), 3.58 (m, 3H), 3.73 (m, 1H), 3.94 (m, 1H), 4.13-4.16 (m, 2H), 4.32-4.38 (m, 4H), 5.41-5.42 (d, 2H), 9.27 (s, 1H); C22H31N9O5S; HPLC 90%; Mass 533.60 (M + 1) |

| Example | Structure | Analytical Data |
|---|---|---|
| 406 | (4R,5S,6R)-6-((R)-1-(2-(1H-tetrazol-1-yl)acetamido)ethyl)-4-methyl-7-oxo-3-((3S,5S)-5-(4-((S)-pyrrolidin-3-yl]piperazine-1-carbonyl]pyrrolidin-3-ylthio)-1-azabicyclo[3.2.0]hept-2-ene-2-carboxylic acid | ¹HNMR (D₂O) - 1.27 (d, 3H), 1.33-1.35 (d, 3H), 2.0-2.05 (m, 1H), 3.21(m, 1H), 3.31-3.35 (m, 1H), 3.47 (m, 1H), 3.58-3.61 (m, 9H), 3.70-3.78 (m, 2H), 3.79 (m, 2H), 3.90 (m, 4H), 4.11-4.13 (m, 1H), 4.38-4.42 (m, 1H), 5.41-5.46 (m, 3H), 8.0 (m, 1H),9.27 (s, 1H); C26H38N10O5S; HPLC 96.4%; Mass 603.4 (M + 1) |
| 407 | (4R,5S,6R)-6-((R)-1-(2-(1H-tetrazol-1-yl)acetamido)ethyl)-3-(azetidin-3-ylthio)-4-methyl-7-oxo-1-azabicyclo[3.2.0]hept-2-ene-2-carboxylic acid | ¹HNMR (D₂O) - 1.14 (d, 3H), 1.33 (d, 3H), 3.15 (m, 1H), 3.55-3.57 (m, 1H), 4.0-4.1 (m, 4H), 4.12 (m, 1H), 4.31-4.35 (m, 2H), 4.52-4.59 (m, 2H), 9.27 (s; 1H); C16H21N7O4S; HPLC 99.9%; Mass 408.2 (M + 1) |
| 408 | (4R,5S,6R)-6-((R)-1-(2-(1H-tetrazol-1-yl)acetamido)ethyl)-3-((3S,5S)-5-(4-(azetidin-3-yl)piperazine-1-carbonyl)pyrrolidin-3-ylthio)-4-methyl-7-oxo-1-azabicyclo[3.2.0]hept-2-ene-2-carboxylic acid | ¹HNMR (D₂O) - 1.19 (d, 3H), 1.34 (d, 3H), 2.50 (d, 2H), 2.99 (m, 2H), 3.30-3.32 (m, 1H), 3.43-3.58 (m, 1H), 3.63-3.67 (m, 1H), 3.69-3.72 (m, 6H), 3.90 (m, 4H), 4.10-4.13 (m, 1H), 4.15-4.22 (m, 4H), 4.39-4.43 (m, 1H), 5.41-5.42 (m, 2H), 9.27-9-31 (d, 1H); C25H36N10O5S; HPLC 97.3%; Mass 590.4 (M + 1) |
| 409 | (4R,5S,6R)-6-((R)-1-(2-(1H-tetrazol-1-yl)acetamido)ethyl)-3-((3S,5S)-5-(4-((R)-3-aminopyrrolidin-1-yl)piperidine-1-carbonyl)pyrrolidin-3-ylthio)-4-methyl-7-oxo-1-azabicyclo[3.2.0]hept-2-ene-2-carboxylic acid | ¹HNMR (D₂O) - 1.19 (d, 3H), 1.34 (d, 3H), 2.86-2.89 (m, 1H), 3.18-3.20 (m, 1H), 3.22-3.27 (m, 2H), 3.55-3.59 (m, 9H), 3.64-3.69 (m, 1H), 3.71-3.85 (m, 4H), 4.13-4.35 (m, 1H), 4.35-4.39 (m, 2H). 4.40-4.43 (m, 1H), 4.82 (m, 1H), 5.4-5.42 (m, 3H), 7.21-7.33 (m, 1H), 7.41-7.43 (m, 1H), 9.27 (s, 1H); C27H40N10O5S; HPLC 90%; Mass 617.4 (M + 1) |

| Example | Structure | Analytical Data |
|---|---|---|
| 410 | 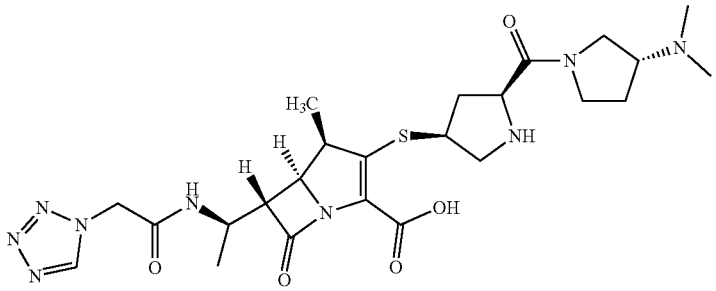 [SMILES: C[C@@H](NC(=O)Cn1cnnn1)[C@H]1C(=O)N2C(C(=O)O)=C(S[C@@H]3CN[C@H](C(=O)N4CC[C@@H](N(C)C)C4)C3)[C@H](C)[C@H]12]<br>(4R,5S,6R)-6-((R)-1-(2-(1H-tetrazol-1-yl)acetamido)ethyl)-3-((3S,5S)-5-((R)-3-(dimethylamino)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.24 (d, 3H), 1.33 (m, 3H), 2.31 (m, 1H), 2.56 (m, 1H), 2.90 (s, 6H), 3.10-3.2 (m, 1H), 3.54-3.6 (m, 1H), 3.59 (m, 2H), 3.71-3.76 (m, 2H), 3.95 (m, 1H), 4.0 (m, 4H), 4.13-4.16 (m, 2H), 4.40-4.43 (m, 1H), 4.50-4.80 (m, 1H), 5.30-5.42 (m, 2H), 9.25 (s, 1H); C24H35N9O5S; HPLC 94.55%; Mass 562.6 (M + 1) |
| 411 | 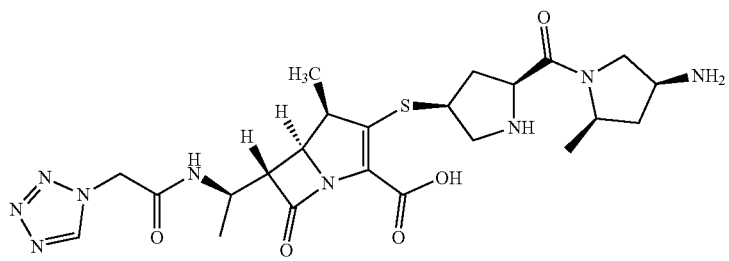 [SMILES: C[C@@H]1C[C@H](N)CN1C(=O)[C@@H]1C[C@H](SC2=C(C(=O)O)N3C(=O)[C@H]([C@@H](C)NC(=O)Cn4cnnn4)[C@H]3[C@H]2C)CN1]<br>(4R,5S,6R)-6-((R)-1-(2-(1H-tetrazol-1-yl)acetamido)ethyl)-3-((3S,5S)-5-((2R,4S)-4-amino-2-methylpyrrolidine-1-carbonyl)pyrrolidin-3-ylthio)-4-methyl-7-oxo-1-azabicyclo[3.2.0]hept-2-ene-2-carboxylic acid | 1HNMR (D$_2$O) - 1.77 (d, 3H), 1.79 (d, 6H), 2.46 (m, 1H), 2.70-2.74 (m, 1H), 3.70-3.73 (m, 2H), 3.77 (m, 2H), 3.88 (m, 1H), 4.03-4.05 (m, 2H), 4.08 (m, 1H), 4.13-4.15 (m, 1H), 4.21-4.23 (m, 1H), 4.33 (m, 1H), 4.39-4.41 (m, 1H), 4.42-4.65 (m, 1H), 4.82-4.90 (m, 2H), 5.41-5.42 (m, 1H), 9.27 (s, 1H); C23H33N9O5S; HPLC 93.8%; Mass 548.2 (M + 1) |
| 412 | 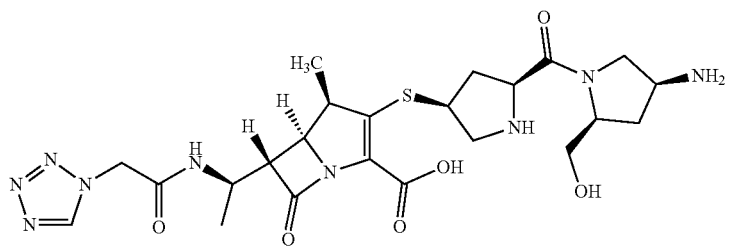 [SMILES: C[C@@H](NC(=O)Cn1cnnn1)[C@H]1C(=O)N2C(C(=O)O)=C(S[C@@H]3CN[C@H](C(=O)N4C[C@@H](N)C[C@H]4CO)C3)[C@H](C)[C@H]12]<br>(4R,5S,6R)-6-((R)-1-(2-(1H-tetrazol-1-yl)acetamido)ethyl)-3-((3S,5S)-5-((2S,4S)-4-amino-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.29 (d, 3H), 2.94 (m, 2H), 3.32 (m, 2H), 3.57-3.59 (m, 2H), 3.62-3.65 (m, 2H), 3.96 (m, 1H), 4.07-4.10 (m, 3H), 4.13-4.15 (m, 4H), 4.41 (m, 2H), 5.40-5.42 (m, 2H), 9.25-9.27 (s, 1H); C23H33N9O6S HPLC 92.7%; Mass 564.0 (M + 1) |
| 413 | 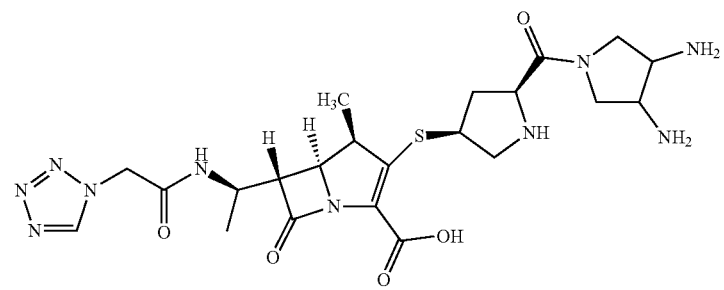 [SMILES: C[C@@H](NC(=O)Cn1cnnn1)[C@H]1C(=O)N2C(C(=O)O)=C(S[C@@H]3CN[C@H](C(=O)N4CC(N)C(N)C4)C3)[C@H](C)[C@H]12]<br>(4R,5S,6R)-6-((R)-1-(2-(1H-tetrazol-1-yl)acetamido)ethyl)-3-((3S,5S)-5-(3,4-diaminopyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (3, 3H), 2.96-3.00 (m, 1H), 3.33-3.36 (m, 2H), 3.49 (m, 1H), 3.55-3.58 (m, 1H), 3.61-3.63 (m, 2H), 3.71 (m, 2H), 3.92-3.97 (m, 2H), 4.08 (m, 1H), 4.13-4.16 (m, 1H), 4.39-4.43 (m, 1H), 4.50 (m, 1H), 4.82 (m, 1H), 5.42-5.47 (m, 2H), 9.27 (s, 1H); C22H32N10O5S HPLC 90.6%; Mass 549.2 (M + 1) |

| Example | Structure | Analytical Data |
|---|---|---|
| 414 | (4R,5S,6R)-6-((R)-1-(2-(1H-tetrazol-1-yl)acetamido)ethyl)-3-((3S,5S)-5-((3S,4S)-3-amino-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.29 (d, 3H), 1.34 (d, 3H), 1.92 (m, 2H), 3.21-3.31 (m, 1H), 3.59-3.63 (m, 2H), 3.89-3.92 (m, 4H), 4.00-4.03 (m, 1H), 4.14-4.16 (m, 3H), 4.40-4.43 (m, 1H), 4.61-4.63 (m, 2H); 5.41-5.46 (m, 2H), 9.27 (s, 1H); C22H31N9O6S; HPLC 95%; Mass 550.4 (M + 1) |
| 415 | (4R,5S,6R)-6-((R)-1-(2-(1H-tetrazol-1-yl)acetamido)ethyl)-3-(2-aminoethylthio)-4-methyl-7-oxo-1-azabicyclo[3.2.0]hept-2-ene-2-carboxylic acid | $^1$HNMR (D$_2$O) - 1.14 (d, 3H), 1.28 (d, 3H), 3.01-3.05 (m, 1H), 3.23-3.27 (m, 1H), 3.38-3.40 (m, 2H), 3.57-3.59 (m, 1H), 3.72 (m, 1H), 4.12-4.15 (m, 1H), 4.40-4.43 (m, 1H), 4.82 (m, 1H), 5.40-5.47 (m, 1H), 9.27 (s, 1H); C15H21N7O4S; HPLC 90.95; Mass 396.3 (M + 1) |
| 416 | (4R,5S,6R)-6-((R)-1-(2-(1H-tetrazol-1-yl)acetamido)ethyl)-3-((3S,5S)-5-(4-(2-hydroxyethyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 1.92 (m, 1H), 2.55-2.69 (m, 3H) 2.84-3.01 (m, 4H), 3.32-3.39 (m, 4H), 3.57-3.61 (m, 2H), 3.80-3.83 (m, 2H), 4.00 (m, 2H), 4.13-4.15 (m, 1H), 4.40-4.43 (m, 1H), 4.69-4.71 (m, 1H), 4.82 (m, 1H), 5.41-5.42 (m, 2H) 9.27 (s, 1H); C24H35N9O6S; HPLC 96.1%; Mass 578.2 (M + 1) |
| 417 | 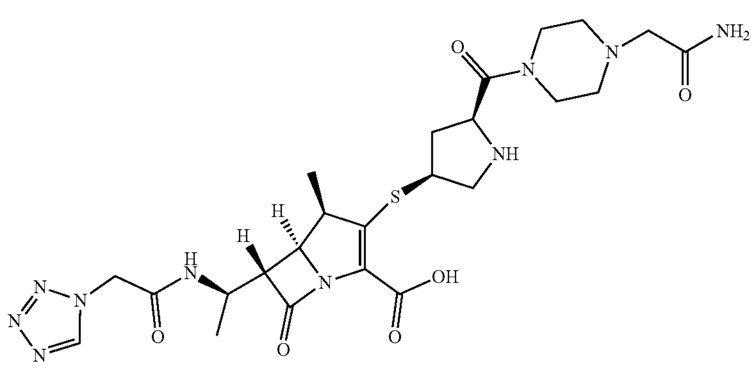 [SMILES: C[C@@H](NC(=O)Cn1cnnn1)[C@H]1C(=O)N2C(C(=O)O)=C(S[C@@H]3CN[C@H](C(=O)N4CCN(CC(N)=O)CC4)C3)[C@H](C)[C@H]12] | $^1$HNMR (D$_2$O) - 1.20 (d, 3H), 1.34 (d, 3H), 1.86-1.92 (m, 1H), 2.60-2.63 (m, 3H), 3.01-3.18 (m, 1H), 3.32-3.36 (m, 3H), 3.57-3.62 (m, 2H), 3.71-3.99 (m, 4H), 4.14-4.16 (m, 1H), 4.40-4.43 (m, 1H), 4.63-4.67 (m, 1H), 4.82 (m, 1H), 5.37-5.42 (m, 2H), 7.21-7.23 (m, 1H), 7.39-7.43 (m, 1H), 9.27 (s, 1H); C24H34N10O6S; HPLC 96.7%; Mass 591.4 (M + 1) |

| Example | Structure | Analytical Data |
|---|---|---|

418

(4R,5S,6R)-6-((R)-1-(2-(1H-tetrazol-1-yl)acetamido)ethyl)-3-((3S,5S)-5-(4-(2-amino-2-oxoethyl)piperazine-1-carbonyl)pyrrolidin-3-ylthio)-4-methyl-7-oxo-1-azabicyclo[3.2.0]hept-2-ene-2-carboxylic acid $^1$HNMR (D$_2$O) - 1.34 (d, 3H), 1.79 (d, 3H), 1.95 (m, 3H), 2.45 (m, 5H), 3.22 (m, 3H), 3.34 (m, 2H), 3.57 (m, 3H), 3.72 (m, 3H), 3.97 (m, 3H), 4.13 (m, 2H), 4.41 (m, 2H), 5.40-5.42 (m, 2H), 9.27 (s, 1H); C27H39N9O5S; HPLC 93.7%; Mass 602.4 (M + 1)

419

(4R,5S,6R)-3-((3S,5S)-5-(1,9-diazaspiro[5.5]undecane-9-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid $^1$HNMR (D$_2$O) - 1.29 (d, 3H), 1.34 (d, 3H), 1.86-1.92 (m, 2H) 2.93 (m, 3H), 3.28-3.31 (m, 4H), 3.55-3.61 (m, 9H), 4.13-4.15 (m, 1H), 4.59-4.61 (m, 1H), 4.75 (m, 1H), 4.89 (m, 1H), 5.37-5.47 (m, 2H), 9.27 (m, 1H); C25H36N10O6S; HPLC 92.3%; Mass 605.3 (M + 1)

420

(4R,5S,6R)-6-((R)-1-(2-(1H-tetrazol-1-yl)acetamido)ethyl)-3-((3S,5S)-5-(4-(3-aminopropanoyl)piperazine-1-carbonyl)pyrrolidin-3-ylthio)-4-methyl-7-oxo-1-azabicyclo[3.2.0]hept-2-ene-2-carboxylic acid $^1$HNMR (D$_2$O) - 1.20 (d, 3H), 1.34 (d, 3H), 3.07-3.21 (m, 1H), 3.36-3.55 (m, 3H), 3.71-3.73 (m, 9H), 3.85-3.98 (m, 4H), 4.24-4.28 (m, 1H), 4.49-4.51 (m, 2H), 4.79-4.87 (m, 1H), 5.42 (m, 2H), 9.27 (s, 1H); C25H36N10O7S; HPLC 96.3%; Mass 621.2 (M + 1)

(4R,5S,6R)-6-((R)-1-(2-(1H-tetrazol-1-yl)acetamido)ethyl)-3-((3S,5S)-5-(4-((S)-2-amino-3-hydroxypropanoyl)piperazine-1-carbonyl)pyrrolidin-3-ylthio)-4-methyl-7-oxo-1-azabicyclo[3.2.0]hept-2-ene-2-carboxylic acid

| Example | Structure | Analytical Data |
|---|---|---|
| 421 | 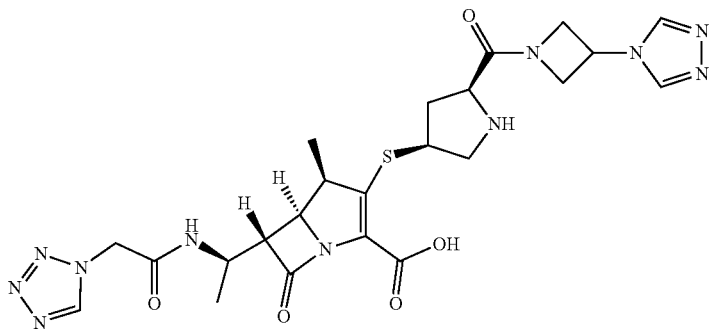 [SMILES: C[C@@H](NC(=O)Cn1cnnn1)[C@H]1C(=O)N2C(C(=O)O)=C(S[C@@H]3CN[C@H](C(=O)N4CC(n5cnnc5)C4)C3)[C@H](C)[C@H]12]<br>(4R,5S,6R)-6-((R)-1-(2-(1H-tetrazol-1-yl)acetamido)ethyl)-3-((3S,5S)-5-(3-(2H-1,2,3-triazol-2-yl)azetidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.21 (d, 3H), 1.34 (d, 3H), 2.89 (m, 1H), 3.32-3.36 (m, 2H), 3.57-3.62 (m, 2H), 3.96 (m, 1H), 4.13-4.16 (d, 1H), 4.42-4.45 (m, 4H), 4.75-4.82 (m, 3H), 5.3-5.37 (m, 2H), 5.5 (m, 1H), 8.1 (s, 1H), 8.54 (s, 1H), 9.27 (s, 1H); C23H29N11O5S; HPLC 93.5% Mass 572.2 (M + 1) |
| 422 | 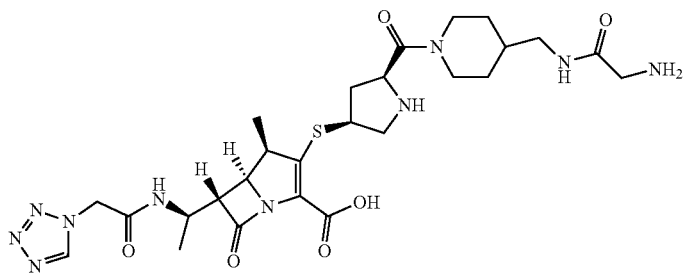 [SMILES: C[C@@H](NC(=O)Cn1cnnn1)[C@H]1C(=O)N2C(C(=O)O)=C(S[C@@H]3CN[C@H](C(=O)N4CCC(CNC(=O)CN)CC4)C3)[C@H](C)[C@H]12]<br>(4R,5S,6R)-6-((R)-1-(2-(1H-tetrazol-1-yl)acetamido)ethyl)-3-((3S,5S)-5-(4-((2-aminoacetamido)methyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) 1.29 (d, 3H), 1.34 (d, 3H), 1.82 (m, 4H), 2.47 (m, 1H), 2.79 (m, 1H), 2.94 (m, 1H), 3.2 (m, 2H), 3.34 (m, 1H), 3.57 (m, 4H), 3.76 (m, 4H), 3.98 (m, 1H), 4.13 (m, 1H), 4.40 (m, 1H), 4.54 (m, 2H), 5.42-5.43 (m, 2H), 9.27 (s, 1H); C26H38N10O6S; HPLC 90%; Mass 619.2 (M + 1) |
| 423 | 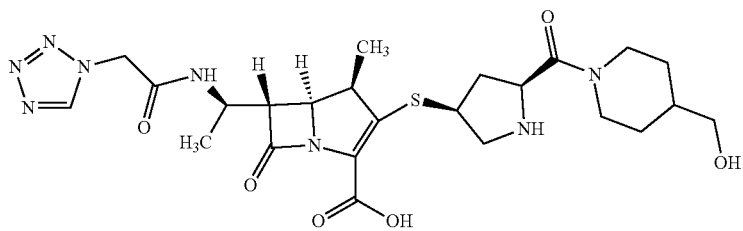 [SMILES: C[C@@H](NC(=O)Cn1cnnn1)[C@H]1C(=O)N2C(C(=O)O)=C(S[C@@H]3CN[C@H](C(=O)N4CCC(CO)CC4)C3)[C@H](C)[C@H]12]<br>(4R,5S,6R)-6-((R)-1-(2-(1H-tetrazol-1-yl)acetamido)ethyl)-3-((3S,5S)-5-(4-(hydroxymethyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.34 (d, 3H), 1.83 (m, 6H), 2.84 (m, 1H), 3.0 (m, 1H), 3.32 (m, 1H), 3.48 (m, 1H), 3.57 (m, 2H), 3.70 (m, 1H), 3.78 (m, 3H), 4.0 (m, 1H), 4.13 (m, 1H), 4.40 (m, 2H), 5.42 (m, 3H), 9.27 (s, 1H); C24H34N8O6S; HPLC 90.2%; Mass 563.2 (M + 1) |
| 424 | 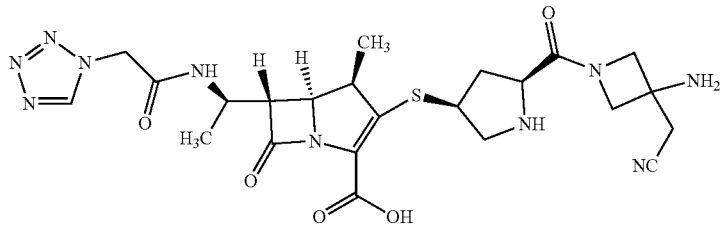 [SMILES: C[C@@H](NC(=O)Cn1cnnn1)[C@H]1C(=O)N2C(C(=O)O)=C(S[C@@H]3CN[C@H](C(=O)N4CC(N)(CC#N)C4)C3)[C@H](C)[C@H]12]<br>(4R,5S,6R)-6-((R)-1-(2-(1H-tetrazol-1-yl)acetamido)ethyl)-3-((3S,5S)-5-(3-amino-3-(cyanomethyl)azetidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (3, 3H), 1.85-1.92 (m, 1H), 2.82 (m, 2H), 3.0 (m, 3H), 3.26 (m, 1H), 3.34 (m, 1H), 3.56 (m, 2H), 3.97 (m, 2H), 4.12-4.15 (m, 2H), 4.40-4.50 (m, 2H), 5.4 (m, 2H), 9.27 (s, 1H); C23H30N10O5S; HPLC 91.9%; Mass 559.2 (M + 1) |

| Example | Structure | Analytical Data |
|---|---|---|
| 425 | (4R,5S,6R)-6-((R)-1-(2-(1H-tetrazol-1-yl)acetamido)ethyl)-3-((3S,5S)-5-(4-amino-3-fluoropiperidine-1-carbonyl)pyrrolidin-3-ylthio)-4-methyl-7-oxo-1-azabicyclo[3.2.0]hept-2-ene-2-carboxylic acid<br>* cis Peak I | ¹HNMR (D₂O) - 1.04 (d, 3H), 1.34 (d, 3H) 1.75 (m, 2H), 2.90 (m, 3H), 3.25-3.34 (m, 5H), 3.56-3.72 (m, 4H), 3.98-3.99 (m, 1H), 4.12-4.14 (m, 1H), 4.40-4.48 (m, 2H), 5.43 (d, 2H), 9.27 (s, 1H); C23H32FN9O5S; HPLC 92.7%; Mass 566.2 (M + 1) |
| 426 | (4R,5S,6R)-6-((R)-1-(2-(1H-tetrazol-1-yl)acetamido)ethyl)-3-((3S,5S)-5-(4-(3-hydroxyazetidin-1-yl)piperidine-1-carbonyl)pyrrolidin-3-ylthio)-4-methyl-7-oxo-1-azabicyclo[3.2.0]hept-2-ene-2-carboxylic acid | ¹HNMR (D₂O) - 1.20 (d, 3H), 1.3 (d, 3H), 1.83-1.85 (m, 2H), 2.82-2.97 (m, 3H), 3.21-3.35 (m, 4H), 3.52-3.58 (m, 4H), 3.89-3.95 (m, 4H), 4.15-4.29 (m, 1H), 4.41-4.43 (m, 2H), 4.48-4.51 (m, 1H), 4.58-4.65 (m, 1H), 4.67-4.68 (m, 1H), 4.76-4.83 (m, 1H), 5.43(m, 2H), 9.27 (s, 1H); C26H37N9O6S; HPLC 96.6%; Mass 604.2 (M + 1) |
| 427 | (4R,5S,6R)-6-((R)-1-(2-(1H-tetrazol-1-yl)acetamido)ethyl)-3-((3S,5S)-5-((3S,4S)-3-guanidino-4-hydroxypyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.20 (d, 3H), 1.34 (d, 3H), 1.82 (m, 2H), 2.85 (m, 1H), 3.35 (m, 1H), 3.63 (m, 3H), 3.74 (m, 3H), 3.89-4.07 (m, 3H), 4.13 (m, 1H), 4.41-4.45 (m, 2H), 5.42-5.43 (m, 2H), 9.27 (s, 1H); C23H33N11O6S; HPLC 94.1%; Mass 592.4 (M + 1) |
| 428 | (4R,5S,6R)-6-((R)-1-(2-(1H-tetrazol-1-yl)acetamido)ethyl)-3-((3S,5S)-5-(4-((R)-3-aminopyrrolidine-1-carbonyl)piperidine-1-carbonyl)pyrrolidin-3-ylthio)-4-methyl-7-oxo-1-azabicyclo[3.2.0]hept-2-ene-2-carboxylic acid | ¹HNMR (D₂O) - 1.20 (d, 3H), 1.30 (d, 3H), 1.45 (m, 2H), 1.92 (m, 4H), 2.38-2.48 (m, 1H), 2.89-2.93 (m, 3H), 3.28-3.33 (m, 3H), 3.57-3.59 (m, 3H), 3.76-3.78 (m, 4H), 4.0 (m, 3H), 4.13 (m, 1H), 4.40-4.43 (m, 2H), 5.47-5.54 (m, 2H), 9.27 (s, 1H); C28H40N10O6S; HPLC 91%; Mass 645.6 (M + 1) |
| 429 | 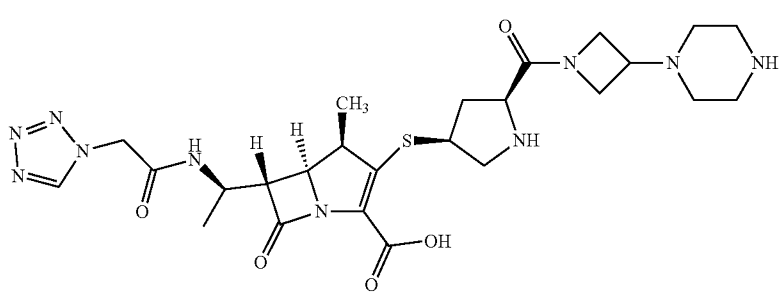 [SMILES: C[C@@H](NC(=O)Cn1cnnn1)[C@H]1C(=O)N2C(C(=O)O)=C(S[C@@H]3CN[C@H](C(=O)N4CC(N5CCNCC5)C4)C3)[C@H](C)[C@H]12] | ¹HNMR (D₂O) - 1.20-(d, 3H), 1.34 (d, 3H), 2.7 (m, 3H), 3.24-3.32 (m, 6H), 3.50-3.58 (m, 4H), 3.95 (m, 1H), 4.13-4.15 (m, 2H), 4.18-4.23 (m, 4H), 4.39-4.43 (m, 2H), 5.42-5.47 (m, 3H), 9.27 (s, 1H); C25H36N10O5S; HPLC 90% Mass 589.3 (M + 1) |

| Example | Structure | Analytical Data |
|---|---|---|
| | (4R,5S,6R)-6-((R)-1-(2-(1H-tetrazol-1-yl)acetamido)ethyl)-4-methyl-7-oxo-3-((3S,5S)-5-(3-(piperazin-1-yl)azetidine-1-carbonyl)pyrrolidin-3-ylthio)-1-azabicyclo[3.2.0]hept-2-ene-carboxylic acid | |
| 430 | 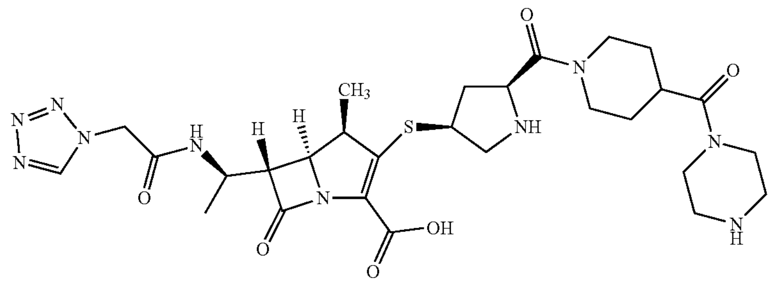 [SMILES: C[C@@H](NC(=O)Cn1cnnn1)[C@H]1C(=O)N2C(C(=O)O)=C(S[C@@H]3CN[C@H](C(=O)N4CCC(C(=O)N5CCNCC5)CC4)C3)[C@H](C)[C@H]12] | ¹HNMR (D₂O) - 1.19 (d, 3H), 1.30 (d, 3H), 1.57-1.67 (m, 2H), 1.87-1.90 (m, 3H), 2.9 (m, 2H), 3.1 (m, 1H), 3.26 (m, 5H), 3.5 (m, 4H), 3.83 (m, 2H), 3.87 (m, 2H), 3.98 (m, 3H), 4.4 (m, 3H), 5.4-5.45 (d, 2H), 9.26 (s, 1H); C28H40N10O6S; Mass 644.75 (M + 1) |
| | (4R,5S,6R)-6-((R)-1-(2-(1H-tetrazol-1-yl)acetamido)ethyl)-4-methyl-7-oxo-3-((3S,5S)-5-(4-(piperazine-1-carbonyl)piperidine-1-carbonyl)pyrrolidin-3-ylthio)-1-azabicyclo[3.2.0]hept-2-ene-2-carboxylic acid | |
| 431 | 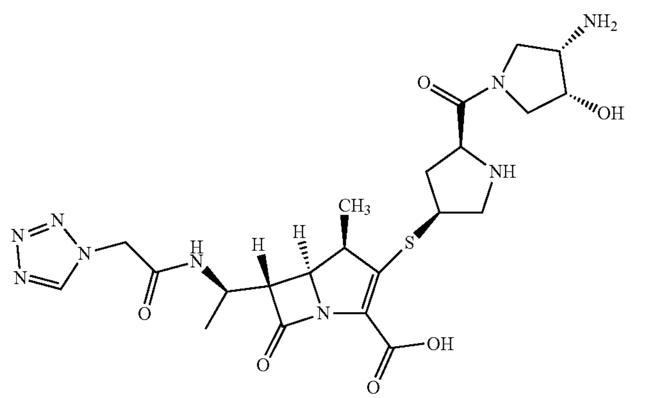 [SMILES: C[C@@H](NC(=O)Cn1cnnn1)[C@H]1C(=O)N2C(C(=O)O)=C(S[C@@H]3CN[C@H](C(=O)N4C[C@@H](O)[C@@H](N)C4)C3)[C@H](C)[C@H]12] | ¹HNMR (D₂O) - 1.17 (d,3 H), 1.30 (d, 3H), 2.81 (m, 1H), 3.17 (m, 1H), 3.30-3.34 (m, 2H), 3.53-3.57 (m, 3H), 3.92-3.93 (m, 2H), 4.12-4.21 (m, 2H), 4.36-4.40 (m, 2H), 4.44-4.55 (m, 1H), 4.88 (m, 2H), 5.44 (m, 2H), 9.24 (s, 1H); C22H31N9O6S; HPLC 90.6%; Mass 550.1 (M + 1) |
| | (4R,5S,6R)-6-((R)-1-(2-(1H-tetrazol-1-yl)acetamido)ethyl)-3-((3S,5S)-5-((3S,4R)-3-amino-4-hydroxypyrrolidine-1-carbonyl)pyrrolidin-3-ylthio)-4-methyl-7-oxo-1-azabicyclo[3.2.0]hept-2-ene-2-carboxylic acid | |
| 432 | 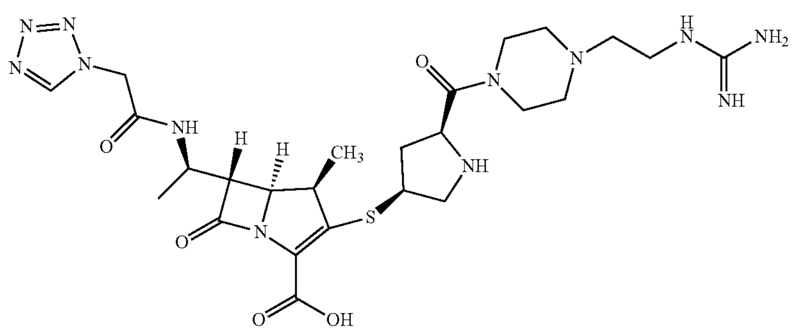 [SMILES: C[C@@H](NC(=O)Cn1cnnn1)[C@H]1C(=O)N2C(C(=O)O)=C(S[C@@H]3CN[C@H](C(=O)N4CCN(CCNC(=N)N)CC4)C3)[C@H](C)[C@H]12] | ¹HNMR (D₂O) - 1.16 (d. 3H), 1.31 (d, 3H), 1.80-1.82 (m, 1H). 2.55-2.68 (m, 4H), 2.87-2.91 (m, 1H), 3.26-3.37 (m, 4H), 3.51-3.54 (m, 4H), 3.66 (m, 2H), 3.93 (m, 1H), 4.09-4.12 (m, 1H), 4.37-4.40 (m, 1H), 4.49-4.53 (m, 1H), 4.89 (m, 2H), 5.40 (s, 2H), 9.24 (s, 1H); C25H38N12O5S; HPLC 96.5%; Mass 619.2 (M + 1) |
| | (4R,5S,6R)-6-((R)-1-(2-(1H-tetrazol-1-yl)acetamido)ethyl)-3-((3S,5S)-5-(4-(2-guanidinoethyl)piperazine-1-carbonyl)pyrrolidin-3-ylthio)-4-methyl-7-oxo-1-azabicyclo[3.2.0]hept-2-ene-2-carboxylic acid | |

| Example | Structure | Analytical Data |
|---|---|---|
| 433 | 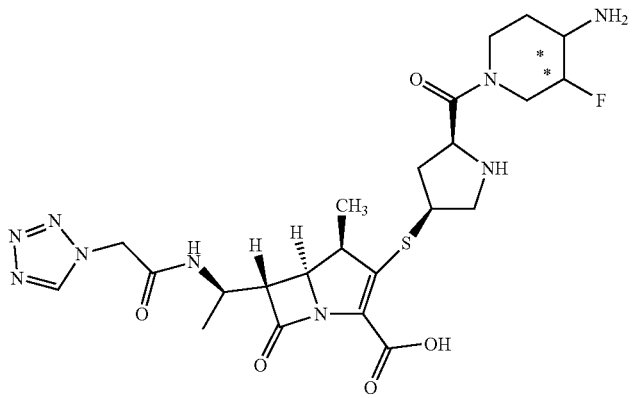 [SMILES: C[C@@H](NC(=O)Cn1cnnn1)[C@H]1C(=O)N2C(C(=O)O)=C(S[C@@H]3CN[C@H](C(=O)N4CCC(N)C(F)C4)C3)[C@H](C)[C@H]12]<br>(4R,5S,6R)-6-((R)-1-(2-(1H-tetrazol-1-yl)acetamido)ethyl)-3-((3S,5S)-5-(4-amino-3-fluoropiperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.16 (d, 3H), 1.31 (d, 3H), 1.81-1.84 (m, 1H), 2.88-2.90 (m, 2H), 3.27-3.33 (m, 4H). 3.42-3.44 (m, 1H), 3.48 (m, 1H), 3.53-3.54 (m, 1H), 3.69 (m, 2H) 3.92 (m, 1H), 4.09-4.11 (m, 1H), 4.27-4.34 (m, 1H), 4.36-4.40 (m, 1H), 4.55-4.57 (m, 1H), 4.90 (m, 1H), 5.40 (s, 2H), 9.24 (s, 1H); C23H32FN9O5S; HPLC 93.7% Mass 566.3 (M + 1) |
| 434 | 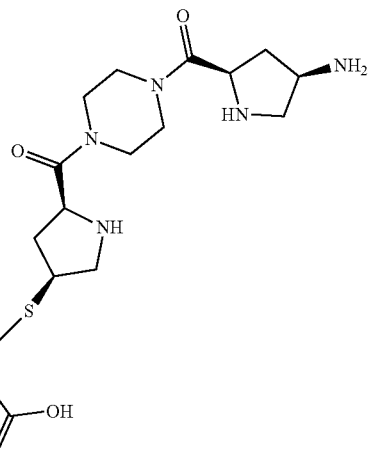<br>(4R,5S,6R)-6-((R)-1-(2-(1H-tetrazol-1-yl)acetamido)ethyl)-3-((3S,5S)-5-(4-((2R,4R)-4-aminopyrrolidine-2-carbonyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.16 (d, 3H), 1.30 (d, 3H), 1.90 (m, 2H), 2.66-2.67 (m, 1H), 2.97-2.98 (m, 1H), 3.11-3.12 (m, 1H), 3.27-3.34 (m, 3H), 3.57-3.58 (m, 2H), 3.65-3.67 (m, 5H), 3.92-3.95 (m, 2H), 4.09-4.11 (m, 1H), 4.36-4.39 (m, 2H), 4.64-4.65 (m, 2H), 4.98 (m, 2H), 5.39 (s, 2H), 9.23 (s, 1H); C27H39N11O6S HPLC 93%; Mass 646.2 (M + 1) |
| 435 | 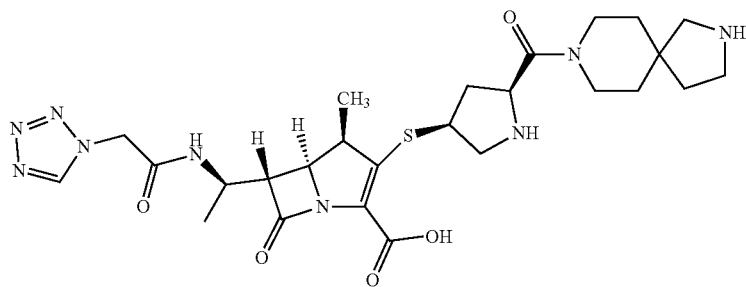 [SMILES: C[C@@H](NC(=O)Cn1cnnn1)[C@H]1C(=O)N2C(C(=O)O)=C(S[C@@H]3CN[C@H](C(=O)N4CCC5(CCNC5)CC4)C3)[C@H](C)[C@H]12]<br>(4R,5S,6R)-6-((R)-1-(2-(1H-tetrazol-1-yl)acetamido)ethyl)-3-((3S,5S)-5-(2,8-diazaspiro[4.5]decane-8-carbonyl)pyrrolidin-3-ylthio)-4-methyl-7-oxo-1-azabicyclo[3.2.0]hept-2-ene-2-carboxylic acid | 1HNMR (D$_2$O) - 1.17 (d, 3H), 1.31 (d, 3H), 1.67-1.68 (m, 2H), 1.70-1.71 (m, 2H), 1.82-1.85 (m, 1H), 2.94-.297 (m, 1H), 3.19-3.20 (m, 2H), 3.32-3.35 (2H), 3.37-3.42 (m, 4H), 3.43-3.45 (m, 4H), 3.50-3.53 (m, 1H), 3.54-3.56 (m, 1H), 3.96-3.98 (m, 1H), 4.10-4.11 (m, 1H), 4.37-4.39 (m, 1H), 4.58-4.60 (m, 1H), 5.38-5.40 (m, 2H), 9.24 (s, 1H); C26H37N9O5S; HPLC 90.1%; Mass 588.49 (M + 1) |

| Example | Structure | Analytical Data |
|---|---|---|
| 436 | (4R,5S,6R)-6-((R)-1-(2-(1H-tetrazol-1-yl)acetamido)ethyl)-3-((3S,5S)-5-(bis(2-hydroxyethyl)carbarnoyl)pyrrolidin-3-ylthio)-4-methyl-7-oxo-1-azabicyclo[3.2.0]hept-2-ene-2-carboxylic acid | $^1$HNMR (D$_2$O) - 1.12 (d, 3H), 1.31 (d, 3H), 2.5 (m, 1H), 3.32-3.35 (m, 1H), 3.42-3.44 (m, 1H), 3.46-3.49 (m, 2H), 3.53-3.56 (m, 2H), 3.57 (m, 2H), 3.59-3.60 (m, 2H), 3.74-3.95 (m, 1H), 4.11-4.13 (m, 1H), 4.37-4.39 (m, 1H), 4.41-4.63 (m, 1H), 4.80-4.85 (m, 1H), 4.85 (m, 2H), 5.37-5.40 (m, 2H), 9.23 (s, 1H) C22H32N8O7S; HPLC 90.1%; Mass 553.2 (M + 1) |
| 437 | (4R,5S,6R)-6-((R)-1-(2-(1H-tetrazol-1-yl)acetamido)ethyl)-3-((3S,5S)-5-(4-((2-amino-2-oxoethylamino)methyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H) 1.31 (d, 3H), 1.86-1.89 (m, 2H), 2.04-2.06 (m, 1H), 2.82-2.84 (m, 1H), 2.91-2.93 (m, 3H), 3.2-3.24 (m, 1H), 3.29-3.32 (m, 3H), 3.52-3.58 (m, 4H), 3.79-3.80 (m, 3H), 3.95-3.96 (m, 1H), 4.10-4.13 (m, 1H), 4.31-4.38 (m, 2H), 4.57-4.59 (m, 1H), 5.37-5.40 (m, 2H), 9.23 (s, 1H); C26H38N10O6S; HPLC 92.4%; Mass 619.4 (M + 1) |
| 438 | (4R,5S,6R)-6-((R)-1-(2-(1H-tetrazol-1-yl)acetamido)ethyl)-3-methyl-3-((3S,5S)-5-(octahydro-1H-pyrrolo[3,2-c]pyridine-1-carbonyl)pyrrolidin-3-ylthio)-7-oxo-1-azabicyclo[3.2.0]hept-2-ene-2-carboxylic acid  cis peak-I | $^1$HNMR (D$_2$O) - 1.17 (d, 3H), 1.32 (d, 3H), 1.97 (m, 1H), 2.12-2.17 (m, 3H), 2.64 (m, 3H), 3.00-3.07 (m, 3H), 3.27-3.31 (m, 2H), 3.42-3.43 (m, 2H), 3.65-3.70 (m, 3H), 4.01 (m, 1H), 4.11-4.13 (m, 1H), 4.28-4.30 (m, 1H), 4.37-4.40 (m, 1H), 4.53-4.57 (m, 1H), 5.40 (d, 2H), 9.25 (s, 1H); C25H35N9O5S; HPLC 92.6%; Mass 574.4 (M + 1) |
| 439 | cis peak-II | $^1$HNMR (D$_2$O) - 1.17 (d, 3H), 1.30-1.32 (d, 3H), 1.75-1.77 (m, 2H), 2.11-2.16 (m, 3H), 3.22-3.23 (m, 3H), 3.30-3.36 (m, 2H), 3.40-3.44 (m, 3H), 3.53-3.55 (m, 2H), 3.79-3.89 (m, 3H), 4.09-4.10 (m, 1H), 4.22-4.27 (m, 1H), 4.37-4.40 (m, 2H), 5.40 (m, 2H), 9.24 (s, 1H); C25H35N9O5S; HPLC 97.4%; Mass 574.2 (M + 1) |

| Example | Structure | Analytical Data |
|---|---|---|
| | (4R,5S,6R)-6-((R)-1-(2-(1H-tetrazol-1-yl)acetamido)ethyl)-4-methyl-3-((3S,5S)-5-(octahydro-1H-pyrrolo[3,2-c]pyridine-1-carbonyl)pyrrolidin-3-ylthio)-7-oxo-1-azabicyclo[3.2.0]hept-2-ene-2-carboxylic acid | |
| 440 | 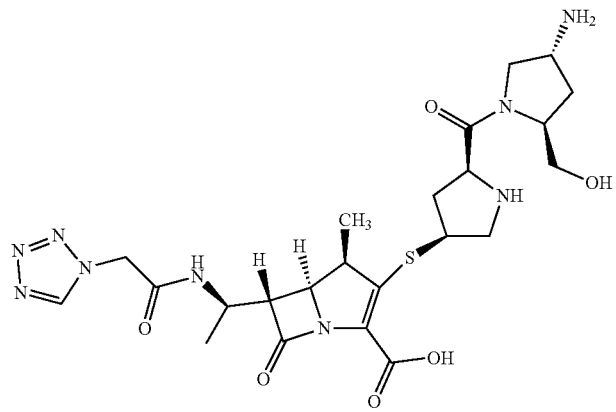 [SMILES: C[C@@H](NC(=O)Cn1cnnn1)[C@H]1C(=O)N2C(C(=O)O)=C(S[C@@H]3CN[C@H](C(=O)N4C[C@H](N)C[C@H]4CO)C3)[C@H](C)[C@H]12] | $^1$HNMR (D$_2$O) - 1.16-1.18 (d, 3H), 1.31-1.32 (d, 3H), 2.24-2.28 (m, 1H), 2.42-2.49 (m, 1H), 2.98 (m, 1H), 3.38 (m, 2H), 3.62-3.65 (m, 4H), 3.76-3.77 (m, 2H), 3.87-3.89 (m, 2H), 3.92 (m, 1H), 4.11-4.17 (m, 2H), 4.37-4.40 (m, 2H), 5.39 (s, 2H), 9.24 (s, 1H); C23H33N9O6S; HPLC 94.6%; Mass 564.3 (M + 1) |
| | (4R,5S,6R)-6-((R)-1-(2-(1H-tetrazol-1-yl)acetamido)ethyl)-3-((3S,5S)-5-((2S,4R)-4-amino-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | |
| 441 | 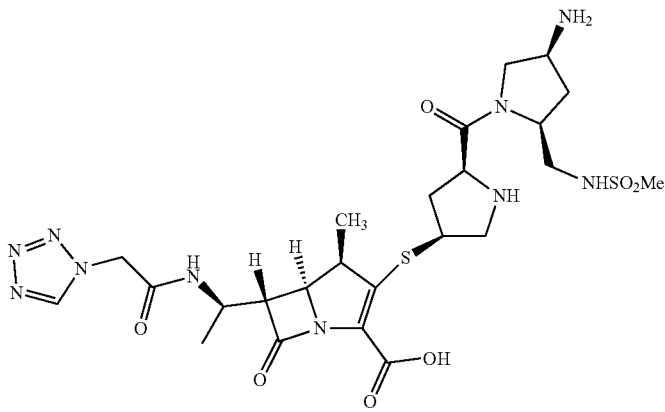 | $^1$HNMR (D$_2$O) - 1.17-1.19 (d, 3H), 1.31-1.33 (d, 3H), 1.99-2.02 (m, 2H), 2.62-2.68 (m, 1H), 2.92-2.97 (m, 2H), 3.09-3.33 (m, 4H), 3.52-3.62 (m, 3H), 3.92 (m, 2H), 4.11-4.13 (m, 2H), 4.28 (m, 1H), 4.37-4.41 (m, 3H), 4.98 (m, 1H), 5.40 (s, 2H), 9.25 (s, 1H); C24H36N10O7S2; HPLC 91.2%; Mass 641.2 (M + 1) |
| | (4R,5S,6R)-6-((R)-1-(2-(1H-tetrazol-1-yl)acetamido)ethyl)-3-((3S,5S)-5-((2S,4S)-4-amino-2-(methylsulfonamido-methyl)pyrrolidine-1-carbonyl)pyrrolidin-3-ylthio)-4-methyl-7-oxo-1-azabicyclo[3.2.0]hept-2-ene-2-carboxylic acid | |
| 442 | 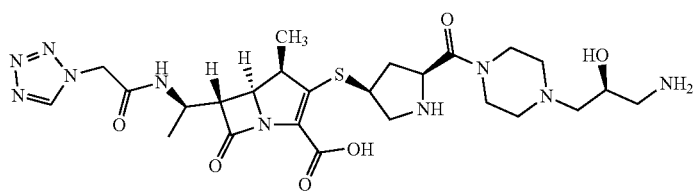 [SMILES: C[C@@H](NC(=O)Cn1cnnn1)[C@H]1C(=O)N2C(C(=O)O)=C(S[C@@H]3CN[C@H](C(=O)N4CCN(C[C@@H](O)CN)CC4)C3)[C@H](C)[C@H]12] | $^1$HNMR (D$_2$O) - 1.28 (d, 3H), 1.33 (d, 3H), 2.55-2.58 (m, 6H), 2.60-2.63 (m, 2H), 2.93-2.96 (m, 3H), 3.14-3.15 (m, 1H), 3.15-3.18 (m, 3H), 3.51-3.55 (m, 2H), 3.56-3.58 (m, 2H), 3.95 (m, 1H), 4.12-4.15 (m, 1H), 4.39-4.42 (m, 1H), 4.7 (m, 1H), 5.40-5.42 (m, 2H), 9.26 (s, 1H); C25H38N10O6S; HPLC 96.9% Mass 607.20 (M + 1) |
| | (4R,5S,6R)-6-((R)-1-(2-(1H-tetrazol-1-yl)acetamido)ethyl)-3-((3S,5S)-5-(4-((S)-3-amino-2-hydroxypropyl)piperazine-1-carbonyl)pyrrolidin-3-ylthio)-4-methyl-7-oxo-1-azabicyclo[3.2.0]hept-2-ene-2-carboxylic acid | |

| Example | Structure | Analytical Data |
|---|---|---|
| 443 | (4R,5S,6R)-6-((R)-1-(2-(1H-tetrazol-1-yl)acetamido)ethyl)-3-((3S,5S)-5-(4-((2-aminoethylamino)methyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (m, 3H), 1.33 (d, 3H), 1.93 (m, 1H), 2.3 (m, 2H), 2.79 (m, 2H), 2.8)1 (m, 2H), 2.96 (m, 3H), 3.10 (m, 1H), 3.21-3.22 (m, 2H), 3.58-3.61 (m, 3H), 3.81-3.84 (m, 3H), 4.0 (m, 1H), 4.2 (m, 1H), 4.26-4.28 (m, 2H), 4.40-4.42 (m, 2H), 5.39-5.43 (m, 2H), 9.27 (s, 1H); C26H40N10O5S; HPLC 90.2% Mass 605.2 (M + 1) |
| 444 | (4R,5S,6R)-6-((R)-1-(2-(1H-tetrazol-1-yl)acetamido)ethyl)-3-((3S,5S)-5-((2S,4R)-4-amino-2-(aminoethyl)pyrrolidine-1-carbooyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.31 (d, 3H), 2.23 (m, 1H), 2.40-2.43 (m, 2H), 2.86 (m, 1H), 3.19-3.27 (m, 4H), 3.50-3.56 (m, 2H), 3.76 (m, 1H), 3.95 (m, 2H), 4.07-4.13 (m, 2H), 4.35-4.42 (m, 2H), 4.55 (m, 1H), 5.40-5.44 (m, 2H), 9.2 (s, 1H); C23H34N10O5S; HPLC 90.0%; Mass 563.4 (M + 1) |
| 445 | (4R,5S,6R)-6-((R)-1-(2-(1H-tetrazol-1-yl)acetamido)ethyl)-3-((3S,5S)-5-(4-(3-aminopropyl)piperazine-1-carbooyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.32 (d, 3H), 1.90 (m, 1H), 2.59 (m, 4H), 2.60 (m, 2H), 3.01-3.05 (m, 4H), 3.36-3.38 (m, 2H), 3.56-3.57 (m, 5H), 3.71 (m, 3H), 4.01-4.05 (m, 1H), 4.11-4.13 (m, 1H), 4.39 (m, 1H), 5.39-5.40 (m, 2H), 9.25 (s, 1H); C25H38N10O5S; HPLC 96.4%; Mass 591.4 (M + 1) |
| 446 | (4R,5S,6R)-6-((R)-1-(2-(1H-tetrazol-1-yl)acetamido)ethyl)-3-((3S,5S)-5-(4-(2-guanidinoacetyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.16 (d, 3H), 1.31 (d, 3H), 1.78-1.84 (m, 1H), 2.94-2.95 (m, 1H), 3.28-3.34 (m, 2H), 3.53-3.58 (m, 5H), 3.62-3.68 (m, 4H), 3.95 (m, 1H), 4.09-4.11 (m, 2H), 4.23 (m, 2H), 4.30-4.38 (m, 1H), 4.58 (m, 1H), 5.39-5.43 (m, 2H), 9.24 (s, 1H); C25H36N12O6S HPLC 93.6%; Mass 633.6 (M + 1) |

| Example | Structure | Analytical Data |
|---|---|---|
| 447 | 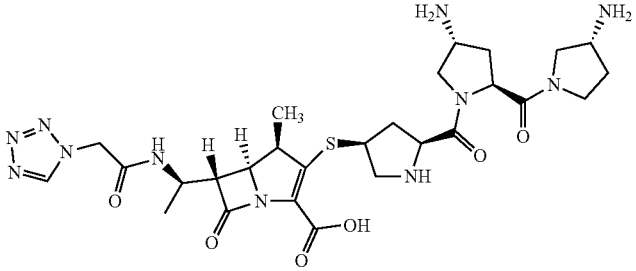 [SMILES: C[C@@H](NC(=O)Cn1cnnn1)[C@H]1C(=O)N2C(C(=O)O)=C(S[C@@H]3CN[C@H](C(=O)N4C[C@H](N)C[C@H]4C(=O)N4CC[C@@H](N)C4)C3)[C@H](C)[C@H]12]<br>(4R,5S,6R)-6-((R)-1-(2-(1H-tetrazol-1-yl)acetamido)ethyl)-3-((3S,5S)-5-((2S,4R)-4-amino-2-((R)-3-aminopyrrolidine-1-carbonyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.08 (d, 3H), 1.21 (d, 3H), 2.25 (m, 2H), 2.35-2.44 (m, 2H), 2.87 (m, 1H), 3.14 (m, 1H), 3.22-3.26 (m, 2H), 3.29-3.30 (m, 2H), 3.43-3.46 (m, 1H), 3.50-3.59 (m, 2H), 3.78 (m, 1H), 3.80-3.86 (m, 3H), 3.93-3.95 (m, 1H), 4.00-4.02 (m, 2H), 4.27-4.29 (m, 2H), 4.82-4.86 (m, 1H), 5.32-5.34 (m, 2H), 9.14 (s, 1H); C27H39N11O6S HPLC 93.0%; Mass 646.4 (M + 1) |
| 448 | 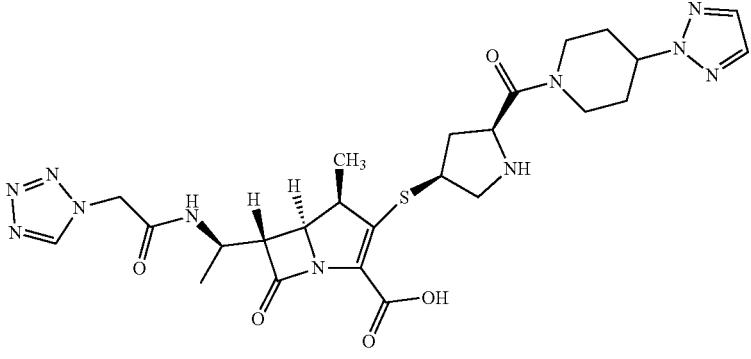 [SMILES: C[C@@H](NC(=O)Cn1cnnn1)[C@H]1C(=O)N2C(C(=O)O)=C(S[C@@H]3CN[C@H](C(=O)N4CCC(n5nccn5)CC4)C3)[C@H](C)[C@H]12]<br>(4R,5S,6R)-6-((R)-1-(2-(1H-tetrazol-1-yl)acetamido)ethyl)-3-((3S,5S)-5-(4-(2H-1,2,3-triazol-2-yl)piperidine-1-carbooyl)pyrrolidin-3-ylthio)-4-methyl-7-oxo-1-azabicyclo[3.2.0]hept-2-ene-2-carboxylic acid | $^1$HNMR (D$_2$O) - 1.17-1.19 (d, 3H), 1.31-1.33 (d, 3H), 2.00-2.07 (m, 2H), 2.28-2.31 (m, 2H), 3.11-3.14 (m, 2H), 3.31 (m, 1H), 3.45-3.48 (m, 2H), 3.55-3.58 (m, 1H), 3.70-3.80 (m, 1H), 3.85-3.95 (m, 1H), 4.05 (m, 1H), 4.12-4.14 (m, 1H), 4.38-4.42 (m, 2H), 4.79-4.91 (m, 3H), 5.39-5.40 (s, 2H); 7.78 (s, 2H), 9.24 (s, 1H); C25H33N11O5S; HPLC 97.4%; Mass 600.4 (M + 1) |
| 449 | 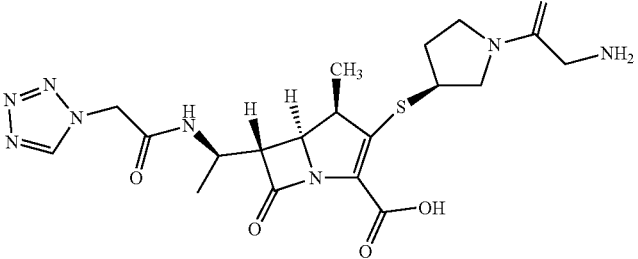<br>(4R,5S,6R)-6-((R)-1-(2-(1H-tetrazol-1-yl)acetamido)ethyl)-3-((S)-1-(2-aminoacetyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.27 (d, 3H), 2.3-2.5 (m, 1H), 3.32-3.41 (m, 3H), 3.56-3.60 (m, 2H), 3.63-3.88 (m, 2H), 3.90-3.96 (m, 3H), 4.11-4.15 (m, 1H), 4.38-4.42 (m, 1H), 5.40-5.41 (d, 2H), 9.25 (s, 1H); C19H26N8O5S; HPLC 95.3%; Mass 479.3 (M + 1) |
| 450 | 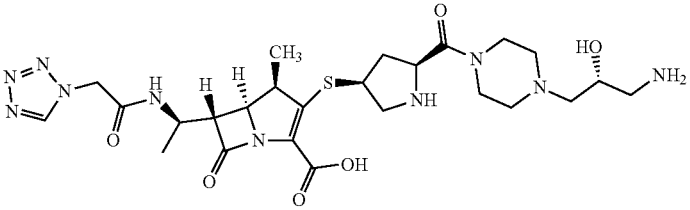 [SMILES: C[C@@H](NC(=O)Cn1cnnn1)[C@H]1C(=O)N2C(C(=O)O)=C(S[C@@H]3CN[C@H](C(=O)N4CCN(C[C@H](O)CN)CC4)C3)[C@H](C)[C@H]12]<br>(4R,5S,6R)-6-((R)-1-(2-(1H-tetrazol-1-yl)acetamido)ethyl)-3-((3S,5S)-5-(4-((R)-3-amino-2-hydroxypropyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.32 (m, 3H), 1.89 (m, 2H), 2.54-2.59 (m, 4H), 2.60-2.62 (m, 2H), 2.90-2.92 (d, 2H), 3.13-3.14 (m, 1H), 3.3 (m, 2H), 3.54-3.57 (m, 4H), 3.59 (m, 1H), 4.1-4.13 (m, 1H), 4.14 (m, 2H), 4.39 (m, 1H), 4.7 (m, 1H), 5.39-5.40 (m, 2H), 9.25 (s, 1H); C25H38N10O6S; HPLC 90.1%; Mass 607.2 (M + 1) |

| Example | Structure | Analytical Data |
|---|---|---|
| 451 | 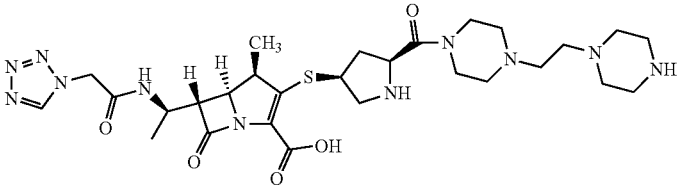 [SMILES: C[C@@H](NC(=O)Cn1cnnn1)[C@H]1C(=O)N2C(C(=O)O)=C(S[C@@H]3CN[C@H](C(=O)N4CCN(CCN5CCNCC5)CC4)C3)[C@H](C)[C@H]12]<br>(4R,5S,6R)-6-((R)-1-(2-(1H-tetrazol-1-yl)acetamido)ethyl)-3-methyl-7-oxo-3-((3S,5S)-5-(4-(2-(piperazin-1-yl)ethyl)piperazine-1-carbonyl)pyrrolidin-3-ylthio)-1-azabicyclo[3.2.0]hept-2-ene-2-carboxylic acid | $^1$HNMR (D$_2$O) - 1.20 (d, 3H), 1.34 (d, 3H), 1.92 (m, 1H), 2.68-2.76 (m, 6H), 2.82 (m, 4H), 3.01 (m, 3H), 3.28-3.33 (m, 6H), 3.57-3.59 (m, 6H), 4.00-4.16 (m, 2H), 4.39-4.43 (m, 2H), 5.41-5.42 (m, 2H), 9.27 (s, 1H); C28H43N11O5S; HPLC 92.9%; Mass 646.6 (M + 1) |

The following examples 452-601 were prepared adopting the procedure for synthesizing example 298.

| Example | Structure | Analytical Data |
|---|---|---|
| 452 | 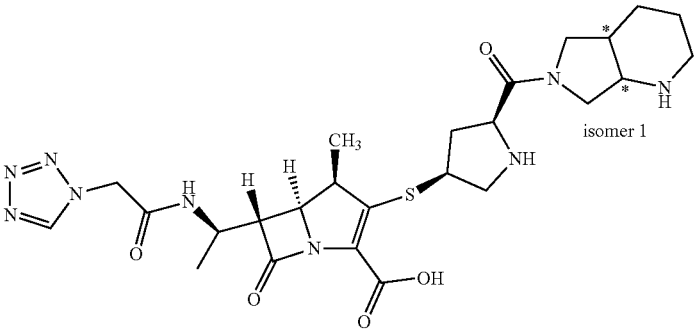 [SMILES: C[C@@H](NC(=O)Cn1cnnn1)[C@H]1C(=O)N2C(C(=O)O)=C(S[C@@H]3CN[C@H](C(=O)N4CC5CCCNC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[3,4-b]pyridine-6-carbonyl)pyrrolidin-3-ylthio)-7-oxo-1-azabicyclo[3.2.0]hept-2-ene-2-carboxylic acid | $^1$HNMR (D$_2$O) - 1.17 (d, 3H), 1.31 (d, 3H), 1.77-1.89 (m, 4H), 2.80-2.84 (m, 2H), 2.97-2.99 (m, 1H), 3.11-3.14 (m, 2H), 3.30-3.34 (m, 3H), 3.43 (m, 1H), 3.49-3.54 (m, 1H), 3.68-3.71 (m, 1H), 3.77-3.89 (m, 4H), 4.11-4.15 (m, 1H), 4.24- 4.26 (m, 1H), 4.37-4.39 (m, 1H), 5.42-5.44 (d, 2H), 9.24 (s, 1H) C25H35N9O5S HPLC 95.3% Mass (M + 1) 574.1 |
| 453 | 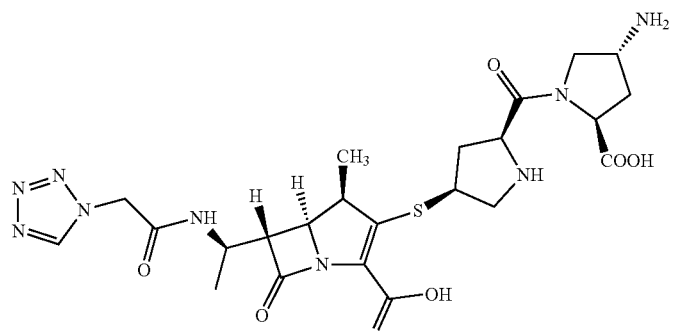<br>(4R,5S,6R)-6-((R)-1-(2-(1H-tetrazol-1-yl)acetamido)ethyl)-3-((3S,5S)-5-((2S,4R)-4-amino-2-carboxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.31 (d, 3H), 2.06-2.08 (m, H), 2.30-2.34 (m, 1H), 2.59-2.61 (m, 2H), 3.03-3.05 (m, 1H), 3.31-3.33 (m, 1H), 3.43-3.48 (m, 1H), 3.55-3.57 (m, 1H), 3.72-3.77 (m, 2H), 3.94-4.02 (m, 2H), 4.12-4.14 (m, 1H), 4.37-4.43 (m, 2H), 4.47-4.49 (m, 1H), 5.40-5.44 (d, 2H), 9.24 (s, 1H) C23H31N9O7S 25 HPLC 94.8%, Mass (M + 1) 578.4 |

| Example | Structure | Analytical Data |
|---|---|---|
| 454 | (4R,5S,6R)-6-((R)-1-(2-(1H-tetrazol-1-yl)acetamido)ethyl)-3-((3S,5S)-5-((2S,4S)-4-amino-2-((sulfamoylamino)-methyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.31 (d, 3H), 1.89-1.96 (m, 1H), 2.59-2.76 (m, 2H), 2.78 (m, 1H), 3.11-3.14 (m, 1H), 3.22-3.29 (m, 2H), 3.41-3.46 (m, 2H), 3.48-3.49 (m, 1H), 3.54-3.55 (m, 2H), 3.75 (m, 2H), 3.94-4.12 (m, 2H) 4.29-4.37 (m, 2H), 5.40-5.44 (d, 2H), 9.23 (s, 1H) C23H35N11O7S2 HPLC 90.1%, Mass (M+ 1) 642.6 |
| 455 | (4R,5S,6R)-6-((R)-1-(2-(1H-tetrazol-1-yl)acetamido)ethyl)-3-((3S,5S)-5-((2S,4R)-4-amino-2-((sulfamoylamino)methyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) 1.17 (d, 3H), 1.30 (d, 3H), 1.88 (m, 1H), 2.22 (m, 1H), 2.33 (m, 1H), 2.42 (m, 1H), 2.89 (m, 1H), 3.18 (m, 1H), 3.20-3.25 (m, 1H), 3.30-3.34 (m, 1H), 3.53-3.54 (d, 2H), 3.70-3.77 (m, 2H), 3.86-3.89 (m, 2H) 4.10-4.11 (m, 2H), 4.28-4.38 (m, 2H), 5.41-5.43 (d, 2H), 9.20 (s, 1H) C23H35N11O7S2 HPLC 90.2%, Mass (M + 1) 642.2 |
| 456 | (4R,5S,6R)-6-((R)-1-(2-(1H-tetrazol-1-yl)acetamido)ethyl)-3-((3S,5S)-5-(4-((S)-2,3-diaminopropanoyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.32 (d, 3H), 1.91 (m, 1H), 2.88-2.91 (m, 2H), 3.32-3.33 (m, 2H), 3.55-3.57 (m, 2H), 3.61-3.65 (m, 4H), 3.71-3.74 (m, 4H), 3.80-3.82 (m, 1H), 3,96 (m, 1H), 4.11-4.13 (m, 2H), 4.37-4.41 (m, 2H), 5.42-5.45 (d, 2H), 9.27 (s, 1H) C25H37N11O6S HPLC 90.2%, Mass (M + 1) 621.4 |

| Example | Structure | Analytical Data |
|---|---|---|
| 457 | 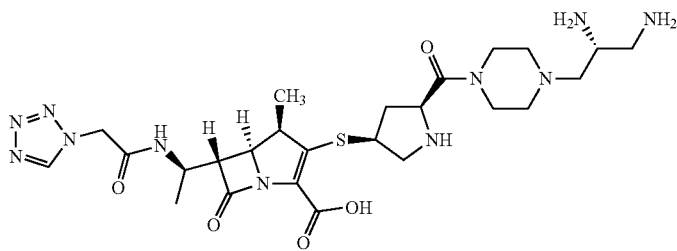 [SMILES: C[C@@H](NC(=O)Cn1cnnn1)[C@H]1C(=O)N2C(C(=O)O)=C(S[C@@H]3CN[C@H](C(=O)N4CCN(C[C@H](N)CN)CC4)C3)[C@H](C)[C@H]12]<br>(4R,5S,6R)-6-((R)-1-(2-(1H-tetrazol-1-yl)acetamido)ethyl)-3-((3S,5S)-5-(4-((R)-2,3-diaminopropyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.32 (d, 3H), 1.82-1.86 (m, 1H), 1.89 (m, 2H), 2.72-2.77 (m, 3H), 2.94-2.97 (m, 1H), 3.07-3.10 (m, 1H), 3.23-3.33 (m, 3H), 3.54-3.56 (m, 3H), 3.70-3.75 (m, 2H), 3.95 (m, 1H), 4.11-4.13 (m, 1H), 4.37-4.41 (m, 2H), 4.60-4.80 (m, 2H), 5.35-5.45 (m, 2H), 8.43 (m, 1H), 9.23 (s, 1H), C25H39N11O5S HPLC 90.9%, Mass 606.6 (M + 1) |
| 458 | 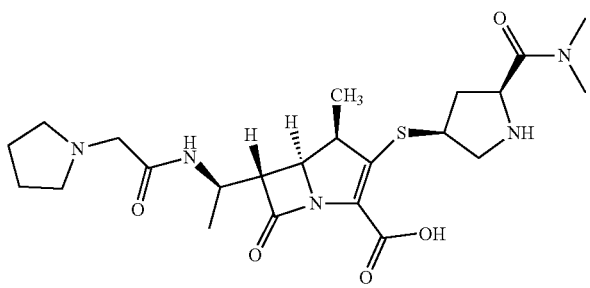 [SMILES: C[C@@H](NC(=O)CN1CCCC1)[C@H]1C(=O)N2C(C(=O)O)=C(S[C@@H]3CN[C@H](C(=O)N(C)C)C3)[C@H](C)[C@H]12]<br>(4R,5S,6R)-3-((3S,5S)-5-(dimethylcarbamoyl)pyrrolidin-3-ylthio)-4-methyl-7-oxo-6-((R)-1-(2-(pyrrolidin-1-yl)acetamido)ethyl)-1-azabicyclo[3.2.0]hept-2-eoe-2-carboxylic acid | $^1$HNMR (D$_2$O) - 1.22 (d, 3H), 1.28 (d, 3H), 1.34 (m, 1H), 1.57 (m, 1H), 1.82 (m, 1H), 2.08 (d, 1H), 2.30 (m, 1H), 2.32 (m, 1H), 2.99 (s, 3H), 3.12 (d, 3H), 3.23-3.24 (d, 2H), 3.32-3.46 (m, 3H), 3.60-3.81 (m, 2H), 4.00 (d, 2H), 4.42 (m, 2H), 4.59 (m, 1H), 4.72 (m, 1H), 5.25 (m, 1H) C23H35N5O5S HPLC 90.9%, Mass (M + 1) 494.6 |
| 459 | 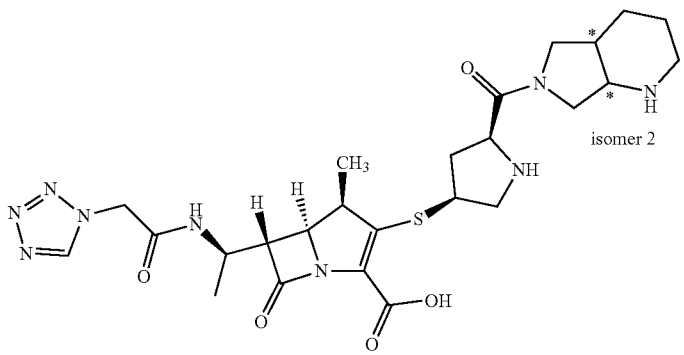 [SMILES: C[C@@H](NC(=O)Cn1cnnn1)[C@H]1C(=O)N2C(C(=O)O)=C(S[C@@H]3CN[C@H](C(=O)N4CC5CCCNC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[3,4-b]pyridine-6-carbonyl)pyrrolidin-3-ylthio)-7-oxo-1-azabicyclo[3.2.0]hept-2-eoe-2-carboxylic acid | $^1$HNMR (D$_2$O) - 1.19 (d, 3H), 1.33 (d, 3H), 1.81-1.91 (m, 4H), 2.88 (m, 2H), 3.16 (m, 1H), 3.20-3.28 (m, 2H), 3.36-3.39 (m, 3H), 3.57-3.59 (m, 2H), 3.72-3.77 (m, 2H), 3.83-3.87 (m, 1H), 3.90-3.92 (m, 2H), 4.12-4.14 (m, 1H), 4.25-4.29 (m, 1H), 4.39-4.42 (m, 1H), 5.41-5.42 (m, 2H), 9.27 (s, 1H) C25H35N9O5S HPLC 96.7%, Mass 574.4 (M + 1) |

| Example | Structure | Analytical Data |
|---|---|---|
| 460 | 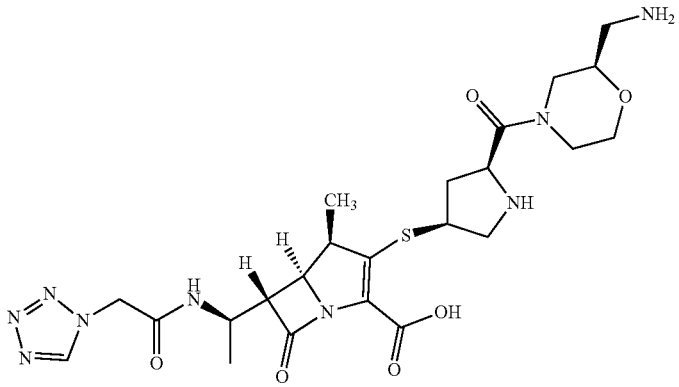 [SMILES: C[C@@H](NC(=O)Cn1cnnn1)[C@H]1C(=O)N2C(C(=O)O)=C(S[C@@H]3CN[C@H](C(=O)N4CCO[C@H](CN)C4)C3)[C@H](C)[C@H]12]<br>(4R,5S,5R)-6-((R)-1-(2-(1H-tetrazol-1-yl)acetamido)ethyl)-3-((3S,5S)-5-((R)-2-(aminomethyl)morpholine-4-carbonyl)pyrrolidin-3-ylthio)-4-methyl-7-oxo-1-azabicyclo[3.2.0]hept-2-ene-2-carboxylic acid | ¹HNMR (D₂O) - 1.17 (d, 3H), 1.32 (d, 3H), 1.89 (m, 1H), 2.72-2.77 (m, 3H), 2.94-2.97 (m, 1H), 3.07-3.10 (m, 1H), 3.23-3.33 (m, 2H), 3.54-3.56 (m, 2H), 3.70-3.75 (m, 2H), 3.95 (m, 1H), 4.11-4.13 (m, 1H), 4.37-4.41 (m, 2H), 4.60-4.80 (m, 2H), 5.35-5.45 (m, 2H), 8.43 (m, 1H), 9.23 (s, 1H) C23H33N9O6S HPLC 90%, Mass (M + 1) 564.1 |
| 461 | 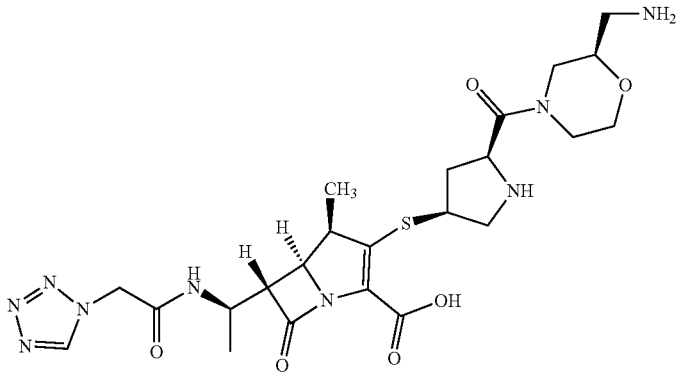 [SMILES: C[C@@H](NC(=O)Cn1cnnn1)[C@H]1C(=O)N2C(C(=O)O)=C(S[C@@H]3CN[C@H](C(=O)N4CCO[C@H](CN)C4)C3)[C@H](C)[C@H]12]<br>(4R,5S,6R)-6-((R)-1-(2-(1H-tetrazol-1-yl)acetamido)ethyl)-3-((3S,5S)-5-((S)-2-(aminomethyl)morpholine-4-carbonyl)pyrrolidin-3-ylthio)-4-methyl-7-oxo-1-azabicyclo[3.2.0]hept-2-ene-2-carboxylic acid | ¹HNMR (D₂O) - 1.17 (d, 3H), 1.32 (d, 3H), 1.87 (m, 1 H), 2.68-2.73 (m, 3H), 2.90-2.94 (m, 1H), 3.02-3.08 (m, 1H), 3.28-3.42 (m, 2H), 3.58-3.62 (m, 2H), 3.72-3.78 (m, 2H), 4.01 (m, 1H), 4.14-4.18 (m, 1H), 4.40-4.44 (m, 2H), 4.72-4.94 (m, 2H), 5.44-5.48 (m, 2H), 8.52 (m, 1H), 9.26 (s, 1H) C23H33N9O6S HPLC 95.1%, Mass (M + 1) 564.1 |
| 462 | 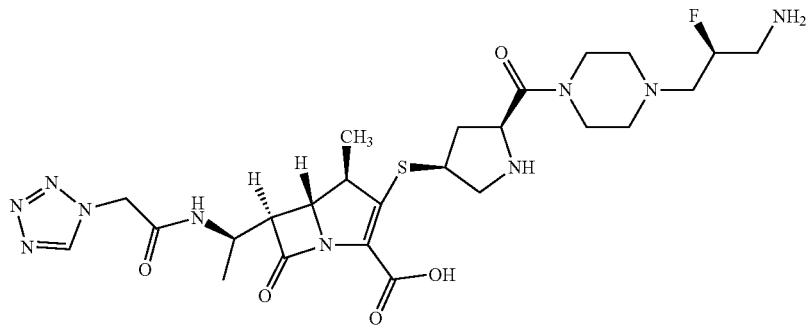 [SMILES: C[C@@H](NC(=O)Cn1cnnn1)[C@@H]1C(=O)N2C(C(=O)O)=C(S[C@@H]3CN[C@H](C(=O)N4CCN(C[C@@H](F)CN)CC4)C3)[C@H](C)[C@@H]12]<br>(4R,5S,6R)-6-((R)-1-(2-(1H-tetrazol-1-yl)acetamido)ethyl)-3-((3S,5S)-5-(4-((S)-3-amino-2-fluoropropyl)piperazine-1-carbonyl)pyrrolidin-3-ylthio)-4-methyl-7-oxo-1-azabicyclo[3.2.0]hept-2-ene-2-carboxylic acid | ¹HNMR (D₂O) - 1.17 (d, 3H), 1.32 (d, 3H), 2.58-2.62 (m, 3H), 2.66-2.70 (m, 4H), 2.82-2.87 (m, 2H), 2.93-2.99 (m, 1H), 3.25-3.29 (m, 3H), 3.35-3.39 (m, 3H), 3.55-3.60 (m, 1H), 3.72-3.99 (m, 1H), 4.0-4.13 (m, 1H), 4.33-4.65 (m, 1H), 4.67-4.80 (m, 1H), 5.1 (m, 1H), 5.3 (m, 1H), 5.4 (m, 2H), 9.25 (s, 1H) C25H37FN10O5S HPLC 95.6%, Mass 609.5 (M + 1) |

| Example | Structure | Analytical Data |
|---|---|---|
| 463 | (4R,5S,6R)-6-((R)-1-(2-(1H-tetrazol-1-yl)acetamido)ethyl)-3-((3S,5S)-5-(4-(aminomethyl)-4-(hydroxymethyl)piperidine-1-carbonyl)pyrrolidin-3-ylthio)-4-methyl-7-oxo-1-azabicyclo[3.2.0]hept-2-ene-2-carboxylic acid | ¹HNMR (D₂O) - 1.27 (d, 3H), 1.33 (d, 3H), 1.65-1.80 (m, 1H), 2.44-2.48 (m, 1H), 3.13-3.14 (m, 1H), 3.30-3.36 (m, 1H), 3.52-3.58 (m, 3H), 3.62-3.65 (m, 3H), 3.71-3.77 (m, 3H), 3.99 (m, 2H), 4.13-4.15 (m, 3H), 4.31-4.39 (m, 2H), 4.40-4.69 (m, 1H), 4.79 (m, 1H), 5.30-5.46 (m, 2H), 9.25 (s, 1H) C25H37N9O6S HPLC 90%, Mass 591.7 (M + 1) |
| 464 | (4R,5S,6R)-6-((R)-1-(2-(1-tetrazol-1-yl)acetamido)ethyl)-3-((3S,5S)-5-((S)-2-(aminomethyl)pyrrolidine-1-carbooyl)pyrrolidin-3-ylthio)-4-methyl-7-oxo-1-azabicyclo[3.2.0]hept-2-ene-2-carboxylic acid | ¹HNMR (D₂O) - 1.17 (d, 3H), 1.31 (d, 3H), 1.89-1.96 (m, 1H), 2.42-2.44 (m, 2H) 2.59-2.76 (m, 1H), 2.78 (m, 1H), 3.11-3.14 (m, 1H), 3.22-3.29 (m, 2H), 3.41-3.46 (m, 2H), 3.48-3.49 (m, 1H), 3.54-3.55 (m, 2H), 3.75 (m, 2H), 3.94-4.12 (m, 2H) 4.29-4.37 (m, 2H), 5.40-5.44 (d, 2H), 9.23 (s, 1H) C23H33N9O5S HPLC 90%, Mass (M + 1) 548.2 |
| 465 | (4R,5S,6R)-6-((R)-1-(2-(1H-tetrazol-1-yl)acetamido)ethyl)-3-((3S,5S)-5-((R)-2-(aminomethyl)pyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.17 (d, 3H), 1.30 (d, 3H), 1.92 (m, 1H), 2.43-2.46 (m, 2H) 2.60-2.74 (m, 1H), 2.80-2,82 (m, 1H), 3.14-3.16 (m, 1H), 3.28-3.32 (m, 2H), 3.42-3.45 (m, 2H), 3.49-3.51 (m, LH), 3.56-3.58 (m, 2H), 3.72-3.78 (m, 2H), 3.90-4.10 (m, 2H) 4.31-4.38 (m, 2H), 5.41-5.43 (d, 2H), 9.23 (s, 1H) C23H33N9O5S HPLC 95.1%, Mass (M + 1) 548.2 |
| 466 | (4R,5S,6R)-6-((R)-1-(2-(1H-tetrazol-1-yl)acetamido)ethyl)-4-methyl-3-((3S,5S)-5-(octahydropyrrolo[3,4-b]pyrrole-1-carbonyl)pyrrolidin-3-ylthio)-7-oxo-1-azabicyclo[3.2.0]hept-2-ene-2-carboxylic acid<br>isomer 1 | ¹HNMR (D₂O) - 1.18 (d, 3H), 1.3 (d, 3H), 1.92 (m, 1H), 2.01-2.02 (m, 1H), 2.24-2.27 (m, 1H), 3.18-3.20 (m, 2H), 3.23-3.30 (m, 2H), 3.34-3.36 (m, 2H), 3.46-3.48 (m, 3H), 3.65-3.70 (m, 2H), 3.78-3.81 (m, 1H), 3.94-3.96 (m, 1H) 4.12-4.15 (m, 1H), 4.38-4.40 (m, 1H), 4.45-4.49 (m, 1H), 4.68-4.71 (m, 1H), 5.44-5.46 (d, 2H), 9.25 (s, 1H) C24H33N9O5S HPLC 97.9%, Mass (M + 1) 560.2 |

| Example | Structure | Analytical Data |
|---|---|---|
| 467 | 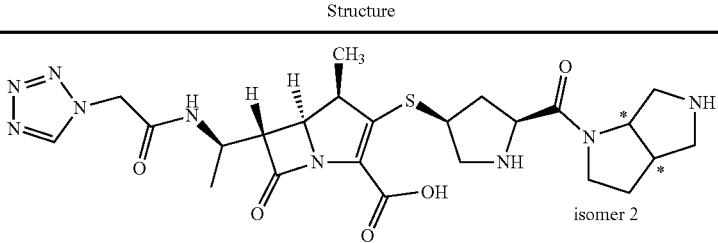<br>(4R,5S,6R)-6-((R)-1-(2-(1H-tetrazol-1-yl)acetamido)ethyl)-4-methyl-3-((3S,5S)-5-(octahydropyrrolo[3,4-b]pyrrole-1-carbonyl)pyrrolidin-3-ylthio)-7-oxo-1-azabicyclo[3.2.0]hept-2-ene-2-carboxylic acid | $^1$HNMR (D$_2$O) - 1.18 (d, 3H), 1.32 (d, 3H), 1.94-1.95 (m, 1H), 1.97-1.99 (m, 1H), 2.22-2.26 (m, 1H), 3.17-3.19 (m, 2H), 3.21-3.29 (m, 2H), 3.30-3.31 (m, 2H), 3.43-3.47 (m, 3H), 3.64-3.69 (m, 2H), 3.77 (m, 1H), 3.95 (m, 1H) 4.11-4.14 (m, 1H), 4.37-4.39 (m, 1H), 4.41-4.49 (m, 1H), 4.65-4.66 (m, 1H), 5.42-5.44 (d, 2H), 9.25 (s, 1H) C24H33N9O5S HPLC 92.7%, Mass (M +1) 560.2 |
| 468 | 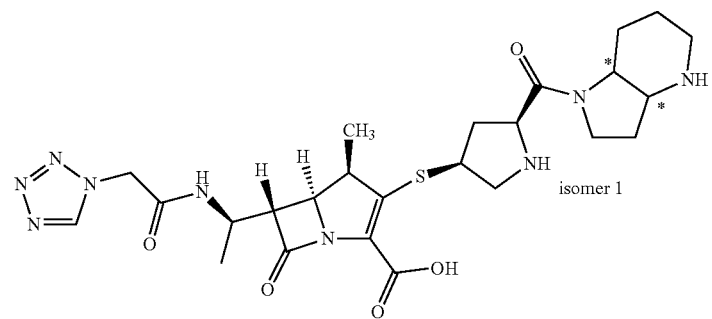 [SMILES: C[C@@H](NC(=O)Cn1cnnn1)[C@H]1C(=O)N2C(C(=O)O)=C(S[C@@H]3CN[C@H](C(=O)N4CCC5NCCCC54)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[3,2-b]pyridine-1-carbonyl)pyrrolidin-3-ylthio)-7-oxo-1-azabicyclo[3.2.0]hept-2-ene-2-carboxylic acid | $^1$HNMR (D$_2$O) - 1.20 (d, 3H), 1.34 (d, 3H), 1.64-1.68 (m, 2H), 1.81-1.91 (m, 2H), 2.23-2.27 (m, 2H), 2.46-2.49 (m, 1H), 2.91-3.01 (m, 1H), 3.15-3.18 (m, 1H), 3.23-3.28 (m, 1H), 3.31-3.48 (m, 2H), 3.58-3.65 (m, 3H), 3.89-3.96 (m, 3H), 4.12-4.15 (m, 1H), 4.29-4.43 (m, 3H), 5.42-5.44 (d, 2H), 9.27 (s, 1H) C25H35N9O5S HPLC 94.6%, Mass (M + 1) 574.2 |
| 469 | 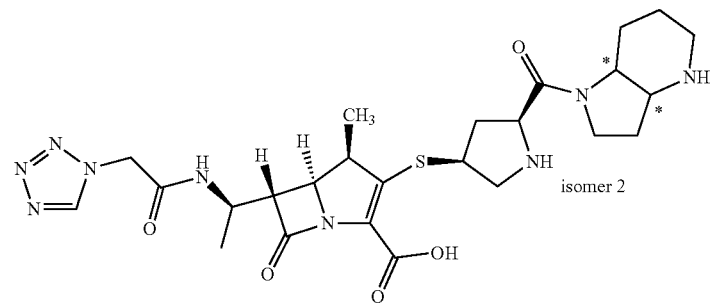 [SMILES: C[C@@H](NC(=O)Cn1cnnn1)[C@H]1C(=O)N2C(C(=O)O)=C(S[C@@H]3CN[C@H](C(=O)N4CCC5NCCCC54)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[3,2-b]pyridine-1-carbonyl)pyrrolidin-3-ylthio)-7-oxo-1-azabicyclo[3.2.0]hept-2-ene-2-carboxylic acid | $^1$HNMR (D$_2$O) - 1.20 (d, 3H), 1.34 (d, 3H), 1.70-1.93 (m, 4H), 2.14-2.17 (m, 1H), 2.37-2.47 (m, 2H), 2.98 (m, 1H), 3.21 (m, 1H), 3.32-3.35 (m, 2H), 3.57-3.58 (m, 2H), 3.72-3.79 (m, 2H), 3.94-3.98 (m, 2H), 4.13-4.15 (m, 2H), 4.32-4.44 (m, 3H), 5.42-5.44 (d, 2H), 9.27 (s, 1H) C25H35N9O5S HPLC 90%, Mass (M + 1) 574.2 |
| 470 | 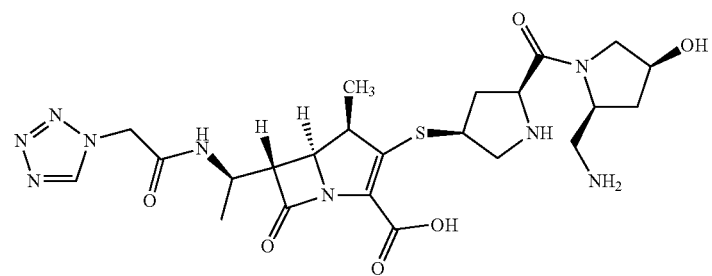 [SMILES: C[C@@H](NC(=O)Cn1cnnn1)[C@H]1C(=O)N2C(C(=O)O)=C(S[C@@H]3CN[C@H](C(=O)N4C[C@@H](O)C[C@H]4CN)C3)[C@H](C)[C@H]12]<br>(4R,5S,6R)-6-((R)-1-(2-(1H-tetrazol-1-yl)acetamido)ethyl)-3-((3S,5S)-5-((2S,4S)-2-(aminomethyl)-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.34 (d, 3H), 2.03-2.07 (m, 1H), 2.42-2.46 (m, 1H), 2.95-3.00 (m, 1H), 3.33-3.39 (m, 4H), 3.54-3.58 (m, 3H), 3.74-3.77 (m, 2H), 3.81-3.99 (m, 1H), 4.14-4.16 (m, 1H), 4.33-4.48 (m, 3H), 4.58 (m, 1H), 5.44-5.46 (m, 2H), 9.27 (s, 1H) C23H33N9O6S HPLC 92.4%, Mass (M + 1) 564.2 |

| Example | Structure | Analytical Data |
|---|---|---|
| 471 | (4R,5S,6R)-6-((R)-1-(2-(1H-tetrazol-1-yl)acetamido)ethyl)-4-methyl-3-((3S,5S)-5-((4aR,7aS)-octahydropyrrolo[3,4-b][1,4]oxazine-4-carbonyl)pyrrolidin-3-ylthio)-7-oxo-1-azabicyclo[3.2.0]hept-2-ene-2-carboxylic acid | $^1$HNMR (D$_2$O) - 1.20 (d, 3H), 1.33 (d, 3H), 1.81-1.84 (m, 1H), 2.86-2.92 (m, 1H), 3.31-3.34 (m, 2H), 3.37-3.40 (m, 1H), 3.47-3.53 (m, 4H), 3.55-3.62 (m, 3H), 3.94 (m, 1H), 4.02-4.04 (m, 1H), 4.12-4.14 (m, 1H), 4.31-4.38 (m, 2H), 4.40-4.42 (m, 1H), 4.56-4.57 (m, 1H), 5.02-5.04 (m, 1H), 5.44-5.46 (m, 2H), 9.26 (s, 1H) C23H33N9O6S HPLC 90.3%, Mass (M + 1) 564.1 |
| 472 | (4R,5S,6R)-6-((R)-1-(2-(1H-tetrazol-1-yl)acetamido)ethyl)-3-((3S,5S)-5-((S)-3-(aminomethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.33 (d, 3H), 1.82-1.85 (m, 2H), 2.16-2.30 (m, 1H), 2.4-2.6 (m, 1H), 2.93 (m, 1H), 3.10-3.13 (m, 2H), 3.32-3.33 (m, 2H), 3.56-3.57 (m, 2H), 3.63-3.65 (m, 1H), 3.71-3.79 (m, 2H), 3.96 (m, 1H), 4.12-4.14 (d, 2H), 4.40- 4.42 (m, 2H), 5.43-5.44 (d, 2H), 9.26 (s, 1H) C23H33N9O5S HPLC 90.9%, Mass 548.3 (M + 1) |
| 473 | (4R,5S,6R)-6-((R)-1-(2-(1H-tetrazol-1-yl)acetamido)ethyl)-3-((3S,5S)-5-((2R,4R)-4-amino-2-(aminomethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.33 (d, 3H), 1.78-1.80 (m, 1H), 2.42-2.44 (m, 1H), 2.80-2.84 (m, 1H), 3.15-3.18 (m, 2H), 3.30-3.36 (m, 3H), 3.54-3.56 (m, 2H), 3.70-3.77 (m, 1H), 3.84-3.94 (m, 3H), 4.11-4.12 (m, 1H), 4.23 (m, 1H), 4.30-4.39 (m, 2H), 5.43-5.45 (d, 2H), 9.25 (s, 1H) C23H34N10O5S HPLC 90.0%, Mass (M + 1) 563.2 |
| 474 | (4R,5S,6R)-6-((R)-1-(2-(1H-tetrazol-1-yl)acetamido)ethyl)-3-((3S,5S)-5-((2R,4R)-4-amino-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) 1.19 (d, 3H), 1.32 (d, 3H), 2.4 (m, 1H), 2.78 (m, 1H), 2.88 (m, 1H), 3.22-3.25 (m, 2H), 3.31-3.33 (m, 1H), 3.4 (m, 2H), 3.54-3.56 (m, 2H), 4.0 (m, 2H), 4.3-4.39 (m, 2H), 4.40-4.79 (m, 3H), 5.3-5.4 (m, 3H), 9.23 (s, 1H) C23H33N9O6S, HPLC 90.5%, Mass 564.3 (M + 1) |

| Example | Structure | Analytical Data |
|---|---|---|
| 475 | 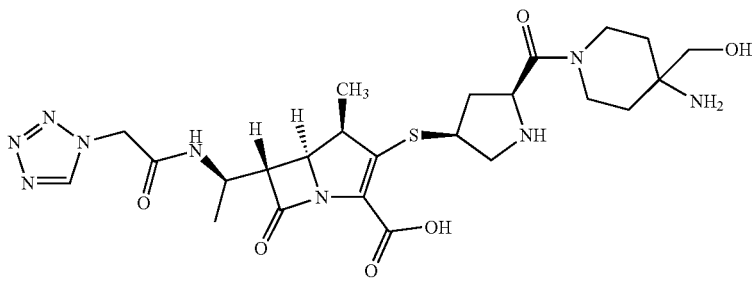 [SMILES: C[C@@H](NC(=O)Cn1cnnn1)[C@H]1C(=O)N2C(C(=O)O)=C(S[C@@H]3CN[C@H](C(=O)N4CCC(N)(CO)CC4)C3)[C@H](C)[C@H]12]<br>(4R,5S,6R)-6-((R)-1-(2-(1H-tetrazol-1-yl)acetamido)ethyl)-3-((3S,5S)-5-(4-amino-4-(hydroxymethyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.31 (d, 3H), 3.30-3.45 (m, 5H), 3.50-3.79 (m, 5H), 4.10-4.18 (m, 4H), 4.30-4.38 (m, 4H), 5.30-5.41 (m, 4H), 9.24 (s, 1H) C24H35N9O6S HPLC 94%, Mass 578.3 (M + 1) |
| 476 | 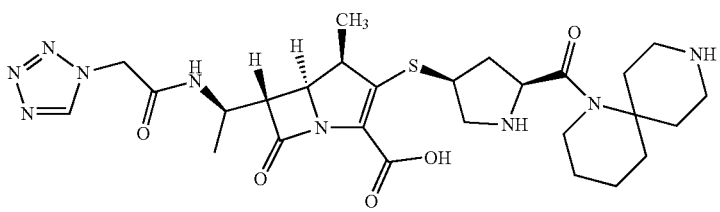 [SMILES: C[C@@H](NC(=O)Cn1cnnn1)[C@H]1C(=O)N2C(C(=O)O)=C(S[C@@H]3CN[C@H](C(=O)N4CCCCC45CCNCC5)C3)[C@H](C)[C@H]12]<br>(4R,5S,6R)-3-((3S,5S)-5-(1,9-diazaspiro[5.5]undecane1-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.18 (d, 3H), 1.33 (d, 3H), 1.68-1.81 (m, 8H), 1.96-2.0 (m, 1H), 2.98-3.05 (m, 3H), 3.21-3.26 (m, 3H), 3.28-3.30 (m, 2H), 3.41 (m, 2H), 3.48 (m, 2H), 3.55-3.57 (m, 2H), 4.12-4.15 (m, 2H), 4.40 (m, 1H), 5.40-5.41 (3, 2H), 9.26 (s, 1H) C27H39N9O5S HPLC 93.2%, Mass (M + 1) 602.2 |
| 477 | 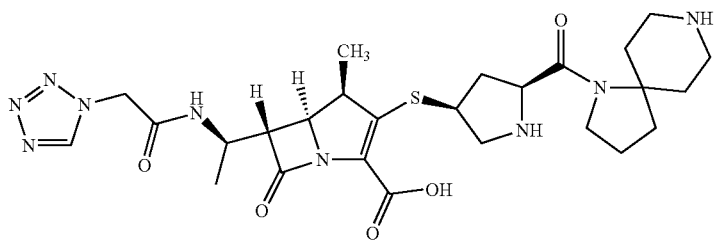 [SMILES: C[C@@H](NC(=O)Cn1cnnn1)[C@H]1C(=O)N2C(C(=O)O)=C(S[C@@H]3CN[C@H](C(=O)N4CCCC45CCNCC5)C3)[C@H](C)[C@H]12]<br>(4R,5S,6R)-3-((3S,5S)-5-(1,8-diazaspiro[4.5]decane-1-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.18 (d, 3H), 1.33 (d, 3H), 1.63-1.67 (m, 2H), 1.70-1.73 (m, 2H), 1.81-1.84 (m, 2H), 1.98-2.02 (m, 1H), 3.04-3.12 (m, 3H), 3.24-3.28 (m, 3H), 3.30-3.36 (m, 2H), 3.44-3.46 (m, 2H), 3.49-3.51 (m, 2H), 3.57-3.59 (m, 2H), 4.11-4.13 (m, 2H), 4.37-4.40 (m, 1H), 5.42-5.44 (3, 2H), 9.26 (s, 1H) C26H37N9O5S HPLC 95.1%, Mass (M + 1) 588.6 |
| 478 | 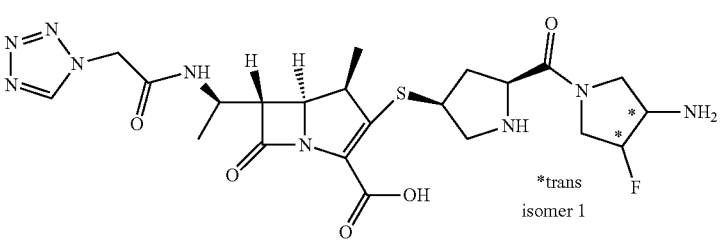 [SMILES: C[C@@H](NC(=O)Cn1cnnn1)[C@H]1C(=O)N2C(C(=O)O)=C(S[C@@H]3CN[C@H](C(=O)N4CC(N)C(F)C4)C3)[C@H](C)[C@H]12]<br>(4R,5S,6R)-6-((R)-1-(2-(1H-tetrazol-1-yl)acetamido)ethyl)-3-((3S,5S)-5-(3-amino-4-fluoropyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.33 (d, 3H), 2.42-2.46 (m, 1H), 2.93 (m, 1H), 3.10-3.13 (m, 2H), 3.32-3.33 (m, 2H), 3.56-3.57 (m, 2H), 3.63-3.65 (m, 1H), 3.71-379 (m, 2H), 3.96 (m, 1H), 4.12-4.14 (d, 2H), 4.40-4.42 (m, 2H), 5.43-5.44 (d, 2H), 9.26 (s, 1H) C22H30FN9O5S HPLC 97.9%, Mass (M + 1) 552.1 |

| Example | Structure | Analytical Data |
|---|---|---|
| 479 | (4R,5S,6R)-6-((R)-1-(2-(1H-tetrazol-1-yl)acetamido)ethyl)-3-((3S,5S)-5-(3-amino-4-fluoropyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.32 (d, 3H), 2.38-2.42 (m, 1H), 2.78-2.89 (m, 1H), 3.12-3.15 (m, 2H), 3.34-3.36 (m, 2H), 3.62-3.64 (m, 2H), 3.66-3.68 (m, 1H), 3.74-3.82 (m, 2H), 3.95-3.97 (m, 1H), 4.11-4.13 (d, 2H), 4.42-4.44 (m, 2H), 5.45-5.46 (d, 2H), 9.26 (s, 1H) C22H30FN9O5S HPLC 97.9%, Mass (M + 1) 552.1 |
| 480 | (4R,5R,6R)-6-((R)-1-(2-(1H-tetrazol-1-yl)acetamido)ethyl)-3-((3S,5S)-5-(4-(2-aminoethyl)piperidine-1-carbonyl)pyrrolidin-3-ylthio)-4,6-dimethyl-7-oxo-1-azabicycl | $^1$HNMR (D$_2$O) - 1.18 (d, 3H), 1.34 (d, 3H), 1.63-1.67 (m, 2H), 1.70-1.73 (m, 1H), 1.81-1.84 (m, 2H), 1.91 (m, 4H), 2.81-2.84 (m, 1H), 3.03-3.07 (m, 3H), 3.19-3.21 (m, 1H), 3.30-3.32 (m, 1H), 3.42-3.46 (m, 1H), 3.71-3.73 (m, 1H), 3.75-3.85 (m, 2H), 4.03-4.04 (m, 1H), 4.12-4.15 (m, 1H), 4.33-4.42 (m, 2H), 5.41-5.42 (m, 2H), 9.27 (s, 1H) C25H37N9O5S HPLC 95.1%, Mass 576.3 (M + 1) |
| 481 | (4R,5S,6R)-6-((R)-1-(2-(1H-tetrazol-1-yl)acetamido)ethyl)-3-((3S,5S)-5-(3-amino-5,6,7,8-tetrahydroimidazo[1,5-a]pyrazine-7-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.33 (d, 3H), 1.92 (m, 1H), 2.85-3.02 (m, 1H), 3.27-3.35 (m, 2H), 3.55-3.57 (m, 2H), 3.90-4.01 (m, 4H), 4.11-4.13 (m, 1H), 4.38-4.42 (m, 1H), 4.61 (m, 1H), 4.75 (m, 2H), 4.92-4.93 (m, 1H), 5.39-5.42 (m, 2H), 6.71 (s, 1H), 9.25 (s, 1H) C24H31N11O5S HPLC 90.1%, Mass 586.3 (M + 1) |
| 482 | (4R,5S,6R)-6-((R)-1-(2-(1H-tetrazol-1-yl)acetamido)ethyl)-3-((3S,5S)-5-(decahydro-1,6-naphthyridine-6-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.33 (d, 3H), 1.65-1.91 (m, 5H), 2.23 (m, 2H), 2.91-2.98 (m, 1H), 3.17 (m, 3H), 3.30 (m, 3H), 3.51-3.53 (m, 2H), 3.55-3.57 (m, 1H), 3.71-3.83 (m, 2H), 3.96 (m, 1H), 4.12-4.14 (m, 2H), 4.39-4.42 (m, 1H), 4.54-4.62 (m, 1H), 5.42-5.44 (d, 2H), 9.27 (s, 1H) C26H37N9O5S HPLC 92.3%, Mass 588.3 (M + 1) |

| Example | Structure | Analytical Data |
|---|---|---|
| 483 | (4R,5S,6R)-6-((R)-1-(2-(1H-tetrazol-1-yl)acetamido)ethyl)-4-methyl-7-oxo-3-((3S,5S)-5-(3-(piperazine-1-carbonyl)phenylcarbamoyl)pyrrolidin-3-ylthio)-1-azabicyclo[3.2.0] | $^1$HNMR (D$_2$O) - 1.18 (d, 3H), 1.33 (d, 3H), 2.45 (m, 1H), 2.98 (m, 1H), 3.28 (m, 2H), 3.30-3.34 (m, 2H), 3.41 (m, 1H), 3.54-3.57 (m, 2H), 3.77-3.79 (m, 2H), 3.98 (m, 1H), 4.00 (m, 2H), 4.12-4.13 (m, 2H), 4.29 (m, 1H), 4.38-4.42 (m, 1H), 5.41-5.42 (d, 2H), 7.32-7.33 (m, 1H), 7.55-7.56 (m, 2H), 7.67 (s, 1H), 9.26 (s, 1H) C29H36N10O6S HPLC 94.0%, Mass (M + 1) 653.2 |
| 484 | (4R,5S,6R)-6-((R)-1-(2-(1H-tetrazol-1-yl)acetamido)ethyl)-3-((3S,5S)-5-(4-(aminomethyl)phenyl-carbamoyl)-pyrrolidin-3-ylthio)-4-methyl-7-oxo-1-azabicyclo[3.2.0]hept-2-ene-2-carboxylic acid | $^1$HNMR (D$_2$O) - 1.19(d, 3H), 1.33 (d, 3H), 2.45 (m, 1H), 2.90-2.93 (m, 1H), 3.26-3.39 (m, 1H), 3.55-3.57 (m, 1H), 3.61-3.65 (m, 1H), 3.72-3.77 (m, 1H), 3.96 (m, 1H), 4.11-4.18 (m, 1H), 4.23 (s, 1H), 4.33-4.42 (m, 3H), 5.43-5.44 (d, 2H), 7.47-7.49 (d, 2H), 7.54-7.56 (d, 2H), 9.27 (s, 1H) C25H31N9O5S HPLC 91.2%, Mass (M + 1) 570.2 |
| 485 | (4R,5S,6R)-6-((R)-1-(2-(1H-tetrazol-1-yl)acetamido)ethyl)-3-((3S,5S)-5-((S)-3-(aminomethyl)piperazine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.34 (d, 3H), 2.45 (m, 1H), 2.95-2.98 (m, 2H), 3.00 (m, 2H), 3.10-3.18 (m, 1H), 3.31-3.35 (m, 3H), 3.56-3.58 (d, 2H), 3.71-3.78 (m, 2H), 3.96 (m, 1H), 4.12-4.15 (m, 2H), 4.24 (m, 1H), 4.41(m, 2H), 5.41-5.42 (d, 2H), 9.27 (s, 1H) C23H34N10O5S HPLC 92.4%, Mass (M + 1) 563.1 |
| 486 | (4R,5S,6R)-6-((R)-1-(2,2-difluoroacetamido)ethyl)-4-methyl-3-((3S,5S)-5-(octahydro-1H-pyrrolo[3,2-c]pyridine-1-carbonyl)pyrrolidin-3-ylthio)-7-oxo-1-azabicyclo[3.2.0]hept-2-ene-2-carboxylic acid<br>Isomer 1 | $^1$HNMR (D$_2$O) - 1.20 (d, 3H), 1.33 (d, 3H), 1.80-1.87 (m, 2H), 2.12-2.18 (m, 2H), 2.25 (m, 1H), 2.45 (m, 1H), 2.64-2.65 (m, 1H), 2.93-2.96 (m, 1H), 3.31-3.37 (m, 3H), 3.40-3.41 (m, 1H), 3.48 (m, 1H), 3.50-3.51 (m, 1H), 3.53-3.59 (m, 1H), 3.70-3.72 (m, 1H), 3.93-3.95 (m, 1H), 4.14-4.16 (m, 2H), 4.29 (m, 1H), 4.31-4.38 (m, 1H), 4.43-4.46 (m, 1H), 6.02-6.29 (t, 1H) C24H33F2N5O5S HPLC 92% Mass (M + 1) 542.4 |

| Example | Structure | Analytical Data |
|---|---|---|
| 487 | 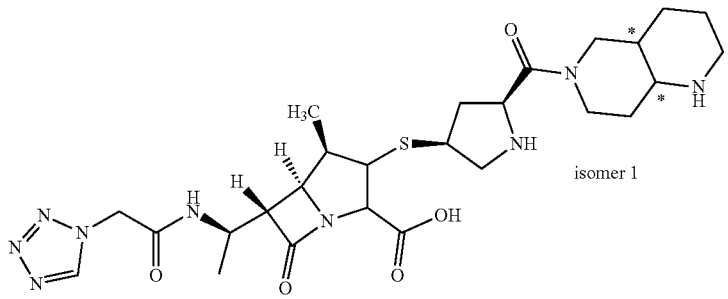 [SMILES: C[C@@H](NC(=O)Cn1cnnn1)[C@H]1C(=O)N2C(C(=O)O)C(S[C@@H]3CN[C@H](C(=O)N4CCC5NCCCC5C4)C3)[C@H](C)[C@H]12]<br>(4R,5S,6R)-6-((R)-1-(2-(1H-tetrazol-1-yl)acetamidin)ethyl)-3-((3S,5S)-5-(decahydro-1,6-naphthyridine-6-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.32 (d, 3H), 1.65-1.68 (m, 3H) 1.80-1.87 (m, 2H), 2.20-2.22 (m, 2H), 2.94-2.97 (m, 1H), 3.12-3.17 (m, 3H), 3.28-3.30 (m, 3H), 3.52-3.54 (m, 2H), 3.56-3.58 (m, 1H), 3.80-3.89 (m, 2H), 3.94-3.98 (m, 1H), 4.14-4.16 (m, 2H), 4.42-4.44 (m, 1H), 4.60-4.64 (m, 1H), 5.43-5.45 (d, 2H), 9.27 (s, 1H) C26H37N9O5S HPLC 97.9%, Mass (M + 1) 588.2 |
| 488 | 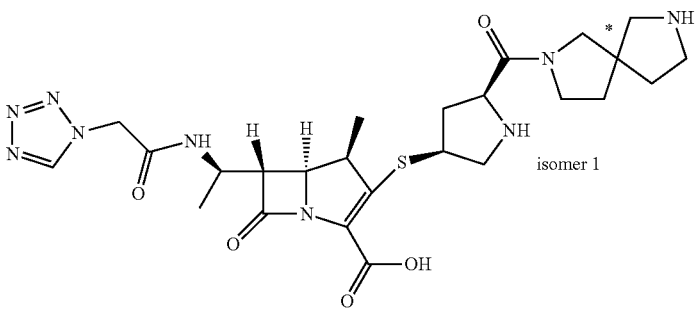 [SMILES: C[C@@H](NC(=O)Cn1cnnn1)[C@H]1C(=O)N2C(C(=O)O)=C(S[C@@H]3CN[C@H](C(=O)N4CCC5(CCNC5)C4)C3)[C@H](C)[C@H]12]<br>(4R,5S,6R)-6-((R)-1-(2-(1H-tetrazol-1-yl)acetamido)ethyl)-3-((3S,5S)-5-(2,7-diazaspiro[4.4]nonane-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.32 (d, 3H), 1.94-1.95 (m, 2H), 1.97-1.99 (m, 2H), 2.22-2.26 (m, 1H), 3.17-3.19 (m, 2H), 3.21-3.29 (m, 2H), 3.30-3.31 (in, 2H), 3.43-3.47 (m, 1H), 3.64-3.69 (m, 2H), 3.77 (m, 2H), 3.95 (m, 2H) 4.11-4.14 (m, 1H), 4.37-4.39 (m, 1H), 4.41-4.49 (m, 1H), 4.65-4.66 (m, 1H), 5.42-5.44 (d, 2H), 9.25 (s, 1H)<br>C25H35N9O5S HPLC 90% Mass (M + 1) 574.2 |
| 489 | 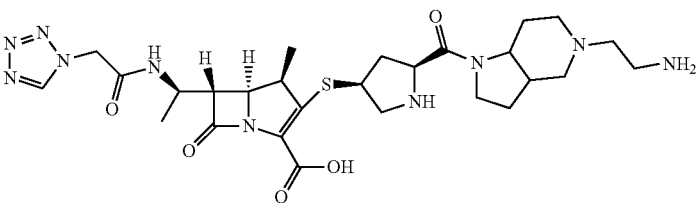 [SMILES: C[C@@H](NC(=O)Cn1cnnn1)[C@H]1C(=O)N2C(C(=O)O)=C(S[C@@H]3CN[C@H](C(=O)N4CCC5CN(CCN)CCC54)C3)[C@H](C)[C@H]12]<br>(4R,5S,6R)-6-((R)-1-(2-(1H-tetrazol-1-yl)acetamido)ethyl)-3-((3S,5S)-5-(5-(2-aminoethyl)octahydro-1H-pyrrolo[3,2-c]pyridine-1-carbonyl)pyrrolidin-3-ylthio)-4-methyl-7-oxo-1-azabicyclo[3.2.0]hept-2-ene-2-carboxylic acid | 1HNMR (D$_2$O) - 1.18 (d, 3H), 1.33 (d, 3H), 1.63-1.67 (m, 2H), 1.70-1.73 (m, 2H), 1.81-1.84 (m, 3H), 1.98-2.02 (m, 2H), 3.04-3.12 (m, 3H), 3.24-3.28 (m, 3H), 3.30-3.36 (m, 2H), 3.44-3.46 (m, 2H), 3.49-3.51 (m, 2H), 3.57-3.59 (m, 2H), 4.11-4.13 (m, 2H), 4.37-4.40 (m, 1H), 5.42-5.44 (d, 2H), 9.26 (s, 1H)<br>C27H40N10O5S HPLC 95.1% Mass (M + 1) 617.4 |
| 490 | 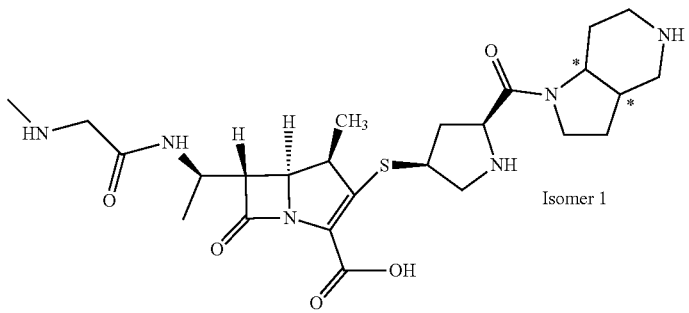 [SMILES: CNCC(=O)N[C@H](C)[C@H]1C(=O)N2C(C(=O)O)=C(S[C@@H]3CN[C@H](C(=O)N4CCC5CNCCC54)C3)[C@H](C)[C@H]12]<br>(4R,5S,6R)-4-methyl-6-((R)-1-(2-(methylamino)acetamido)ethyl)-3-((3S,5S)-5-(octahydro-1H-pyrrolo[3,2-c]pyridine-1-carbonyl)pyrrolidin-3-ylthin)-7-oxo-1-azabicyclo[3.2.0]hept-2-ene-2-carboxylic acid | $^1$HNMR (D$_2$O) - 1.20 (d, 3H), 1.33 (d, 3H), 1.80-1.87 (m, 2H), 2.12-2.18 (m, 2H), 2.25 (m, 1H), 2.45 (m, 1H), 2.64-2.65 (m, 1H), 2.93-2.96 (m, 1H), 3.31-3.37 (m, 3H), 3.40-3.41 (m, 1H), 3.48 (m, 1H), 3.50-3.51 (m, 1H), 3.53-3.59 (m, 1H), 3.70-3.72 (m, 1H), 3.90 (s, 3H), 3.98-4.03 (m, 3H), 4.14-4.16 (m, 2H), 4.29 (m, 1H), 4.31-4.38 (m, 1H), 4.43-4.46 (m, 1H)<br>C25H38N6O5S<br>HPLC 97.9% Mass (M + 1) 535.1 |

| Example | Structure | Analytical Data |
|---|---|---|
| 491 | 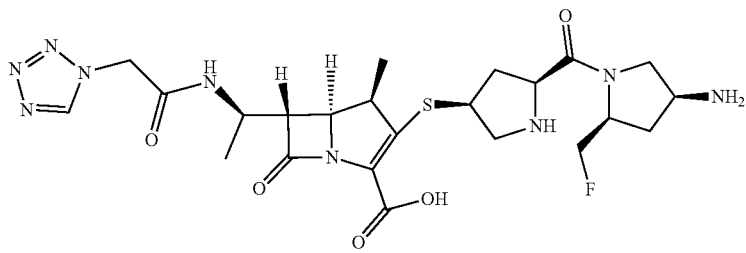 [SMILES: C[C@@H](NC(=O)Cn1cnnn1)[C@H]1C(=O)N2C(C(=O)O)=C(S[C@@H]3CN[C@H](C(=O)N4C[C@@H](N)C[C@H]4CF)C3)[C@H](C)[C@H]12]<br>(4R,5S,6R)-6-((R)-1-(2-(1H-tetrazol-1-yl)acetamido)ethyl)-3-((3S,5S)-5-((2S,4S)-4-amino-2-(fluoromethyl)pyrrolidine-1-carbonyl)pyrrolidin-3-ylthio)-4-methyl-7-oxo-1-azabicyclo[3.2.0]hept-2-eoe-2-carboxylic acid | $^1$HNMR (D$_2$O) - 1.19 (d, 3H), 1.33 (d, 3H), 1.82-1.85 (m, 1H), 2.16-2.23 (m, 1H), 2.4-2.6 (m, 1H), 2.93 (m, 1H), 3.10-3.13 (m, 2H), 3.32-3.33 (m, 2H), 3.56-3.57 (m, 2H), 3.63-3.65 (m, 1H), 3.71-379 (m, 2H), 3.96 (m, 1H), 4.12-4.14 (d, 2H), 4.40-4.42 (m, 2H), 5.43-5.44 (d, 2H), 9.26 (s, 1H) C23H32FN9O5S HPLC 97.9% Mass (M + 1) 566.2 |
| 492 | 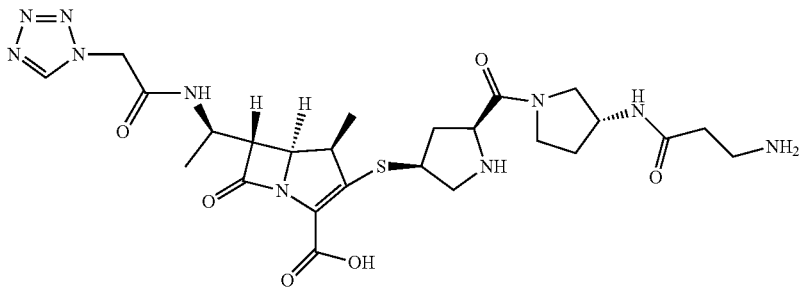 [SMILES: C[C@@H](NC(=O)Cn1cnnn1)[C@H]1C(=O)N2C(C(=O)O)=C(S[C@@H]3CN[C@H](C(=O)N4CC[C@@H](NC(=O)CCN)C4)C3)[C@H](C)[C@H]12]<br>(4R,5S,6R)-6-((R)-1-(2-(1H-tetrazol-1-yl)acetamido)ethyl)-3-((3S,5S)-5-((R)-3-(3-aminopropanamido)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 1.80-1.83 (m, 2H), 2.20-2.23 (m, 1H), 2.66-2.69 (m, 2H), 2.81-2.98 (m, 1H), 3.24-3.29 (m, 3H), 3.33-3.37 (m, 1H), 3.41-3.48 (m, 1H), 3.52-3.61 (m, 3H), 3.72-3.78 (m, 2H), 3.91-3.93 (m, 1H), 4.13-4.15 (m, 1H), 4.28 (m, 1H), 4.38-4.41 (m, 2H), 5.41-5.42 (m, 2H), 9.29 (s, 1H) C25H36N10O6S HPLC 97% Mass (M + 1) 605.1 |
| 493 | 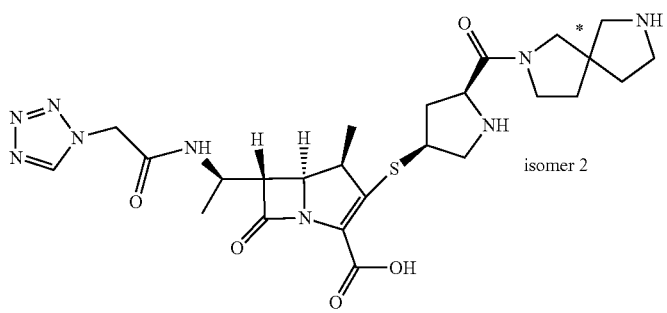 [SMILES: C[C@@H](NC(=O)Cn1cnnn1)[C@H]1C(=O)N2C(C(=O)O)=C(S[C@@H]3CN[C@H](C(=O)N4CCC5(CCNC5)C4)C3)[C@H](C)[C@H]12]<br>(4R,5S,6R)-6-((R)-1-(2-(1H-tetrazol-1-yl)acetamido)ethyl]-3-((3S,5S)-5-(2,7-diazaspiro[4.4]nonane-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.23 (d, 3H), 1.76-1.77 (m, 1H), 1.93-2.04 (m, 4H), 2.86 (m, 1H), 3.20-3.27 (m, 4H), 3.34-3.37 (m, 3H), 3.40-3.43 (m, 3H), 3.45-3.48 (m, 1H), 3.51-3.58 (m, 1H), 3.85-3.88 (m, 1H), 4.02-4.04 (m, 1H), 4.27-4.33 (m, 2H), 5.30-5.31 (m, 2H), 9.26 (s, 1H) C25H35N9O5S HPLC 97.9% Mass 574.3 (M + 1) |
| 494 | 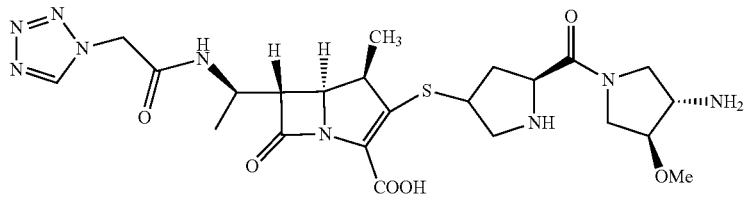 [SMILES: CO[C@H]1CN(C(=O)[C@@H]2CC(SC3=C(C(=O)O)N4C(=O)[C@H]([C@@H](C)NC(=O)Cn5cnnn5)[C@H]4[C@H]3C)CN2)C[C@@H]1N]<br>(4R,5S,6R)-6-((R)-1-(2-(1H-tetrazol-1-yl)acetamido)ethyl)-3-((3S,5S)-5-((3S,4S)-3-amino-4-methoxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.30 (d, 3H), 2.20-2.23 (m, 1H), 2.95 (m, 2H), 3.20-3.27 (m, 2H), 3.28-3.31 (m, 2H), 3.38-3.40 (m, 2H), 3.43 (s, 3H), 3.44-3.47 (m, 1H), 3.54-3.91 (m, 3H), 3.97 (m, 1H), 4.13-4.15 (m, 2H), 4.39-4.42 (m, 1H), 4.50-4.52 (m, 1H), 5.42-5.44 (d, 2H), 9.26 (s, 1H) C25H35N9O5S HPLC 96.2% Mass (M+l) 574.2 |

| Example | Structure | Analytical Data |
|---|---|---|
| 495 | 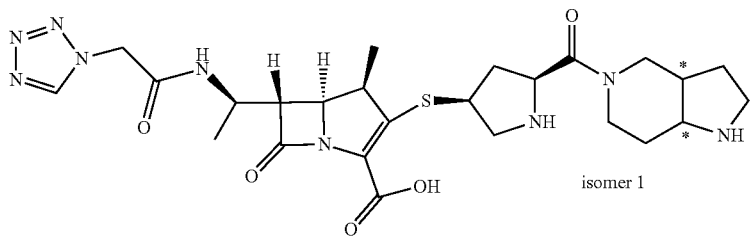 [SMILES: C[C@@H](NC(=O)Cn1cnnn1)[C@H]1C(=O)N2C(C(=O)O)=C(S[C@@H]3CN[C@H](C(=O)N4CCC5NCCC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[2,3-c]pyridine-6-carbonyl)pyrrolidin-3-ylthio)-7-oxo-1-azabicyclo[3.2.0]hept-2-ene-2-carboxylic acid | ¹HNMR (D₂O) - 1.19 (d, 3H), 1.33 (d, 3H), 1.77-1.80 (m, 2H), 2.14-2.20 (m, 2H), 2.65 (m, 1H), 2.98-3.08 (m, 1H), 3.29-3.33 (m, 2H), 3.36-3.37 (m, 1H), 3.39-3.49 (m, 2H), 3.52 (m, 1H), 3.58-3.69 (m, 2H), 3.71 (m, 2H), 3.88 (m, 1H), 3.99-4.05 (m, 3H), 4.12-4.15 (d, 1H), 4.38-4.40 (m, 1H), 5.40-5.41 (d, 2H), 9.26 (s, 1H) C25H35N9O5S HPLC 95.8% Mass (M + 1) 574.3 |
| 496 | 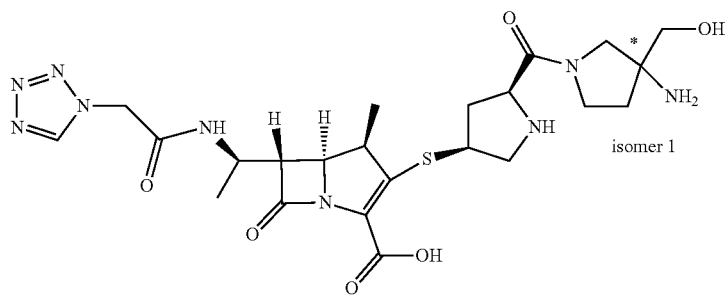 [SMILES: C[C@@H](NC(=O)Cn1cnnn1)[C@H]1C(=O)N2C(C(=O)O)=C(S[C@@H]3CN[C@H](C(=O)N4CCC(N)(CO)C4)C3)[C@H](C)[C@H]12]<br>(4R,5S,6R)-6-((R)-1-(2-(1H-tetrazol-1-yl)acetamido)ethyl)-3-((3S,5S)-5-(3-amino-3-(hydroxymethyl)pyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.09 (d, 3H), 1.18 (d, 3H), 2.01-2.24 (m, 2H), 2.98 (m, 1H), 3.20-3.23 (m, 2H), 3.46-3.47 (m, 2H), 3.50-3.51 (m, 2H), 3.58-3.65 (m, 3H), 3.68-3.73 (m, 2H), 3.86 (m, 1H), 4.02-4.04 (m, 1H), 4.28-4.32 (m, 2H), 5.30-5.31 (d, 2H), 9.26 (s, 1H) C23H33N9O6S HCPLC 99% Mass (M + 1) 564.6 |
| 497 | 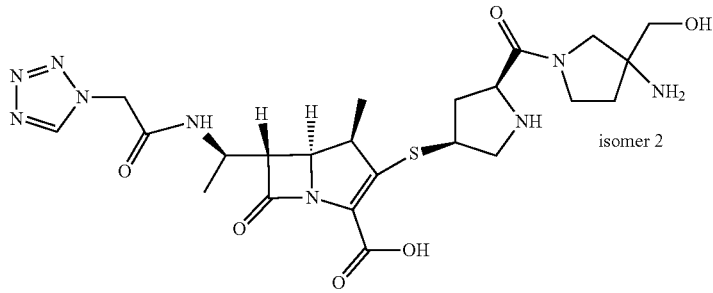 [SMILES: C[C@@H](NC(=O)Cn1cnnn1)[C@H]1C(=O)N2C(C(=O)O)=C(S[C@@H]3CN[C@H](C(=O)N4CCC(N)(CO)C4)C3)[C@H](C)[C@H]12]<br>(4R,5S,6R)-6-((R)-1-(2-(1H-tetrazol-1-yl)acetamido)ethyl)-3-((3S,5S)-5-(3-amino-3-(hydroxymethyl)pyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.19 (d, 3H), 1.33 (d, 3H), 2.21-2.25 (m, 2H), 2.96-2.98 (m, 1H), 3.22-3.25 (m, 2H), 3.47-3.49 (m, 2H), 3.51-3.54 (m, 2H), 3.59-3.65 (m, 3H), 3.71-3.76 (m, 2H), 3.92-3.96 (m, 1H), 4.04-4.06 (m, 1H) 4.30-4.34 (m, 2H), 5.32-5.33 (d, 2H), 9.25 (s, 1H) C23H33N9O6S HPLC 90.3% Mass (M + 1) 564.2 |
| 498 | 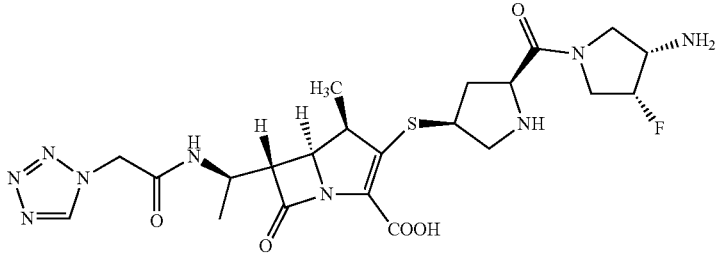 [SMILES: C[C@@H](NC(=O)Cn1cnnn1)[C@H]1C(=O)N2C(C(=O)O)=C(S[C@@H]3CN[C@H](C(=O)N4C[C@@H](F)[C@@H](N)C4)C3)[C@H](C)[C@H]12]<br>(4R,5S,6R)-6-((R)-1-(2-(1H-tetrazol-1-yl)acetamido)ethyl)-3-((3S,5S)-5-((3S,4R)-3-amino-4-fluoropyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.09 (d, 3H), 1.23 (d, 3H), 1.81 (m, 1H), 2.89-2.92 (m, 2H), 3.23-3.28 (m, 2H), 3.29 (m, 2H), 3.46-3.48 (m, 2H), 3.51-3.53 (m, 2H), 3.83-3.89 (m, 3H), 4.02-4.04 (m, 1H), 4.28-4.32 (m, 1H), 5.30-5.31 (d, 2H), 9.16 (s, 1H) C22H30FN9O5S HPLC 99% Mass (M + 1) 552.2 |

| Example | Structure | Analytical Data |
|---|---|---|
| 499 | 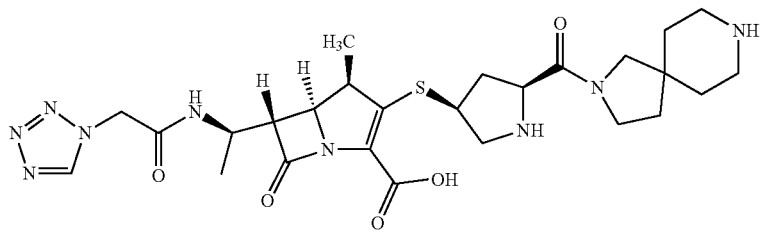 [SMILES: C[C@@H](NC(=O)Cn1cnnn1)[C@H]1C(=O)N2C(C(=O)O)=C(S[C@@H]3CN[C@H](C(=O)N4CCC5(CCNCC5)C4)C3)[C@H](C)[C@H]12]<br>(4R,5S,6R)-6-((R)-1-(2-(1H-tetrazol-1-yl)acetamido)ethyl)-3-((3S,5S)-5-(2,8-diazaspiro[4.5]decane-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.34 (d, 3H), 1.85-1.97 (m, 5H), 2.03-2.04 (m, 3H), 2.91-2.97 (m, 1H), 3.27-3.37 (m, 6H), 3.42-3.46 (m, 1H), 3.51-3.58 (m, 4H), 3.72 (m, 1H), 4.13-4.15 (m, 1H), 4.40-4.41 (m, 2H), 5.42-5.47 (d, 2H), 9.27 (s, 1H) C26H37N9O5S HPLC 98.8% Mass (M + 1) 588.1 |
| 500 | 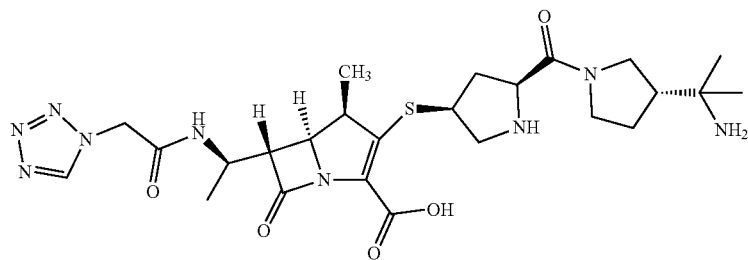 [SMILES: C[C@@H](NC(=O)Cn1cnnn1)[C@H]1C(=O)N2C(C(=O)O)=C(S[C@@H]3CN[C@H](C(=O)N4CC[C@@H](C(C)(C)N)C4)C3)[C@H](C)[C@H]12]<br>(4R,5S,6R)-6-((R)-1-(2-(1H-tetrazol-1-yl)acetamido)ethyl)-3-((3S,5S)-5-((R)-3-(2-aminopropan-2-yl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.33 (m, 9H), 2.21-2.25 (m, 2H), 2.96-2.98 (m, 1H), 3.22-3.25 (m, 2H), 3.47-3.49 (m, 2H), 3.51-3.54 (m, 2H), 3.59-3.65 (m, 3H), 3.71-3.76 (m, 1H), 3.92-3.96 (m, 1H), 4.04-4.06 (m, 1H) 4.30-4.34 (m, 2H), 5.32-5.33 (d, 2H), 9.25 (s, 1H) C25H37N9O5S HPLC 97.9% Mass (M + 1) 576.3 |
| 501 | 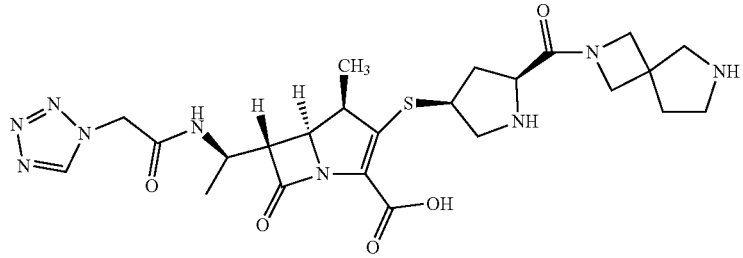 [SMILES: C[C@@H](NC(=O)Cn1cnnn1)[C@H]1C(=O)N2C(C(=O)O)=C(S[C@@H]3CN[C@H](C(=O)N4CC5(CCNC5)C4)C3)[C@H](C)[C@H]12]<br>(4R,5S,6R)-6-((R)-1-(2-(1H-tetrazol-1-yl)acetamido)ethyl)-3-((3S,5S)-5-(2,6-diazaspiro[3,4]octane-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.23 (d, 3H), 1.76-1.77 (m, 1H), 1.93-2.04 (m, 2H), 2.86 (m, 1H), 3.20-3.27 (m, 4H), 3.34-3.37 (m, 3H), 3.40-3.43 (m, 3H), 3.45-3.48 (m, 1H), 3.51-3.58 (m, 1H), 3.85-3.88 (m, 1H), 4.02-4.04 (m, 1H), 4.27-4.33 (m, 2H), 5.30-5.31 (d, 2H), 9.26 (s, 1H) C24H33N9O5S HPLC 97.9% Mass (M+l) 560.4 |
| 502 | 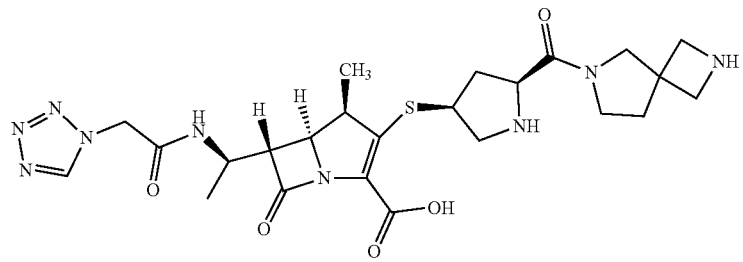 [SMILES: C[C@@H](NC(=O)Cn1cnnn1)[C@H]1C(=O)N2C(C(=O)O)=C(S[C@@H]3CN[C@H](C(=O)N4CCC5(CNC5)C4)C3)[C@H](C)[C@H]12]<br>(4R,5S,6R)-6-((R)-1-(2-(1H-tetrazol-1-yl)acetamido)ethyl)-3-((3S,5S)-5-(2,6-diazaspiro[3.4]octane-6-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.33 (d, 3H), 1.88 (m, 1H), 2.02-2.04 (m, 2H), 2.84-2.86 (m, 1H), 3.22-3.29 (m, 4H), 3.35-3.38 (m, 3H), 3.41-3.44 (m, 3H), 3.46-3.49 (m, 1H), 3.52-3.59 (m, 1H), 3.86-3.89 (m, 1H), 4.03-4.05 (m, 1H), 4.28-4.34 (m, 2H), 5.31-5.32 (d, 2H)} 9.26 (s, 1H) C24H33N9O5S HPLC 90% Mass (M + l) 560.4 |

| Example | Structure | Analytical Data |
|---|---|---|
| 503 | 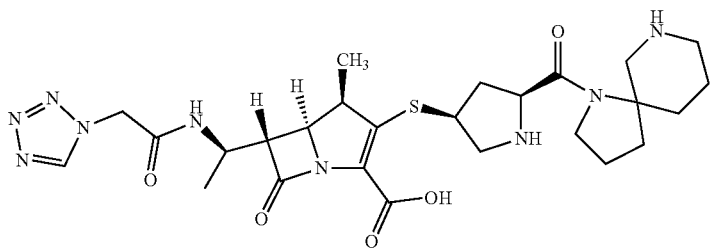 [SMILES: C[C@@H](NC(=O)Cn1cnnn1)[C@H]1C(=O)N2C(C(=O)O)=C(S[C@@H]3CN[C@H](C(=O)N4CCCC45CCCNC5)C3)[C@H](C)[C@H]12]<br>(4R,5S,6R)-3-((3S,5S)-5-(1,7-diazaspiro[4.5]decane-1-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.19 (d, 3H), 1.33 (d, 3H), 1.90-1.95 (m, 5H), 2.01-2.03 (m, 3H), 2.89-2.92 (m, 1H), 3.29-3.34 (m, 6H), 3.41-3.47 (m, 1H), 3.52-3.55 (m, 4H), 3.69-3.72 (m, 1H), 4.11-4.14 (m, 1H), 4.39-4.40 (m, 2H), 5.41-5.45 (d, 2H), 9.27 (s, 1H)<br>C26H37N9O5S HPLC 95.1% Mass (M + 1) 588.2 |
| 504 | 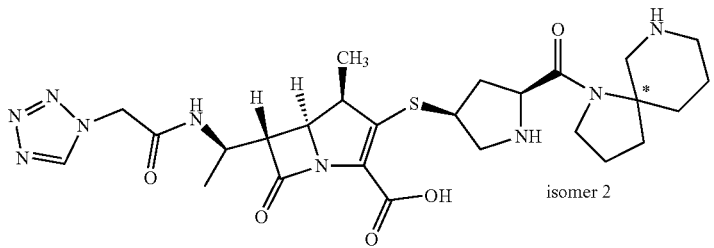 [SMILES: C[C@@H](NC(=O)Cn1cnnn1)[C@H]1C(=O)N2C(C(=O)O)=C(S[C@@H]3CN[C@H](C(=O)N4CCCC45CCCNC5)C3)[C@H](C)[C@H]12]<br>(4R,5S,6R)-3-((3S,5S)-5-(1,7-diazaspiro[4.5]decane-1-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | $^1$HNMR (D$_2$O) - 1.19 (d, 3H), 1.33 (d, 3H), 1.92-1.97 (m, 5H), 2.02-2.04 (m, 3H), 2.91-2.94 (m, 1H), 3.30-3.35 (m, 6H), 3.42-3.48 (m, 1H), 3.53-3.56 (m, 4H), 3.72-3.75 (m, 1H), 4.12-4.15 (m, 1H), 4.40-4.41 (m, 2H), 5.42-5.46 (d, 2H), 9.27 (s, 1H)<br>C26H37N9O5S<br>HPLC 97.9% Mass (M + 1) 588.2 |
| 505 | 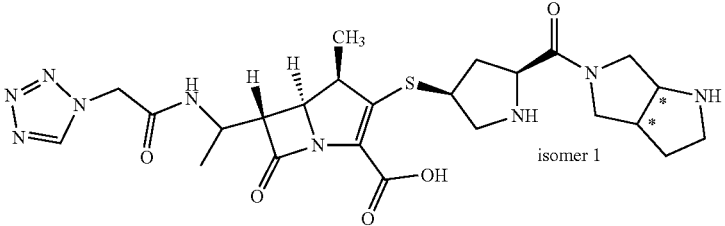 [SMILES: CC(NC(=O)Cn1cnnn1)[C@H]1C(=O)N2C(C(=O)O)=C(S[C@@H]3CN[C@H](C(=O)N4CC5CCNC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydropyrrolo[3,4-b]pyrrole-5-carbonyl)pyrrolidin-3-ylthio)-7-oxo-1-azabicyclo[3.2.0]hept-2-ene-2-carboxylic acid | $^1$HNMR (D$_2$O) - 1.19 (d, 3H), 1.33 (d, 3H), 1.82-1.87 (m, 2H), 1.92-2.01 (m, 2H), 2.33-2.39 (m, 2H), 2.94-2.98 (m, 2H), 3.28-3.34 (m, 2H), 3.44-3.47 (m, 3H), 3.50-3.52 (m, 1H), 3.72-3.77 (m, 1H), 3.89-3.93 (m, 2H), 4.13-4.15 (m, 1H), 4.40-4.43 (m, 2H), 5.43-5.47 (d, 2H), 9.27 (s, 1H)<br>C24H33N9O5S<br>HPLC 93.1% Mass (M + 1) 560.4 |
| 506 | 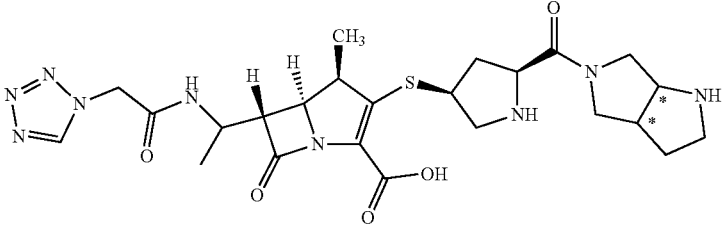 [SMILES: CC(NC(=O)Cn1cnnn1)[C@H]1C(=O)N2C(C(=O)O)=C(S[C@@H]3CN[C@H](C(=O)N4CC5CCNC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydropyrrolo[3,4-b]pyrrole-5-carbonyl)pyrrolidin-3-ylthio)-7-oxo-1-azabicyclo[3.2.0]hept-2-ene-2-carboxylic acid | $^1$HNMR (D$_2$O) - 1.18 (d, 3H), 1.32 (d, 3H), 1.85-1.91 (m, 2H), 2.01-2.03 (m, 2H), 2.35-2.41 (m, 2H), 2.98-3.01 (m, 2H), 3.30-3.36 (m, 2H), 3.46-3.49 (m, 3H), 3.52-3.54 (m, 1H), 3.74-3.79 (m, 1H), 3.91-3.95 (m, 2H), 4.14-4.16 (m, 1H), 4.42-4.45 (m, 2H), 5.44-5.48 (d, 2H), 9.27 (s, 1H)<br>C24H33N9O5S HPLC 90% Mass (M + 1) 560.4 |

| Example | Structure | Analytical Data |
|---|---|---|
| 507 | 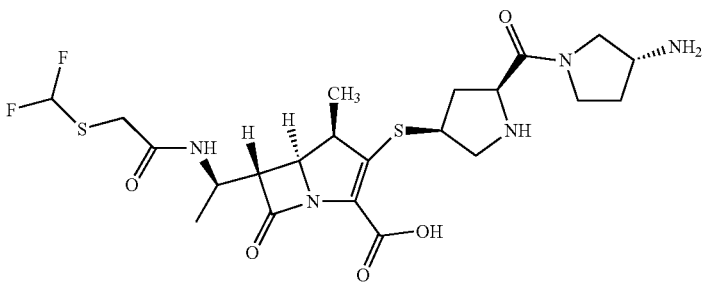 [SMILES: C[C@@H](NC(=O)CSC(F)F)[C@H]1C(=O)N2C(C(=O)O)=C(S[C@@H]3CN[C@H](C(=O)N4CC[C@@H](N)C4)C3)[C@H](C)[C@H]12]<br>(4R,5S,6R)-3-(((3S,5S)-5-((R)-3-aminopyrrolidine-1-carbonyl)pyrrolidin-3-ylthio)-6-((R)-1-(2-(difluoromethylthio)acetamido)ethyl)-4-methyl-7-oxo-1-azabicyclo[3.2.0]hept-2-ene-2-carboxylic acid | $^1$HNMR (D$_2$O) - 1.20 (d, 3H), 1.32 (d, 3H), 1.92-1.95 (m, 1H), 1.97-2.00 (m, 1H), 2.19-2.32 (m, 1H), 2.46-2.50 (m, 1H), 2.94-2.96 (m, 1H), 3.30-3.37 (m, 2H), 3.51-3.56 (m, 1H), 3.58-3.59 (m, 2H), 3.61-3.64 (m, 2H), 3.72-3.77 (m, 1H), 3.88-3.96 (m, 2H), 4.07-4.12 (m, 2H), 4.35-4.39 (m, 2H), 6.96-7.23 (t, 1H) C22H31F2N5O5S2 HPLC 90.7% Mass (M + 1) 548.1 |
| 508 | 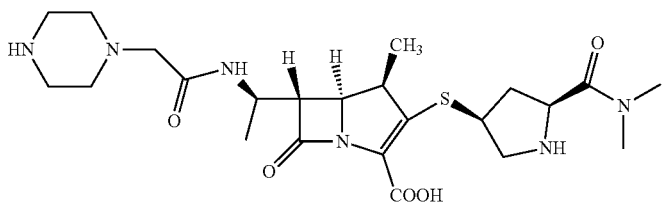 [SMILES: C[C@@H](NC(=O)CN1CCNCC1)[C@H]1C(=O)N2C(C(=O)O)=C(S[C@@H]3CN[C@H](C(=O)N(C)C)C3)[C@H](C)[C@H]12]<br>(4R,5S,6R)-3-(((3S,5S)-5-(dimethylcarbamoyl)pyrrolidin-3-ylthio)-4-methyl-7-oxo-6-((R)-1-(2-(piperazin-1-yl)acetamido)ethyl)-1-azabicyclo[3.2.0]hept-2-ene-2-carboxylic acid | $^1$HNMR (D$_2$O) - 1.27 (d, 3H), 1.37 (d, 3H), 1.91-1.96 (m, 2H), 2.31-2.33 (m, 1H), 2.59-2.60 (m, 1H), 2.94-3.26 (m, 1H), 2.99 (s, 3H), 3.07 (s, 3H), 3.21.3.22 (m, 1H), 3.40-3.45 (m, 2H), 3.47-3.49 (m, 4H), 3.57-3.58 (m, 2H), 3.73-3.77 (m, 2H), 3.91 (m, 1H), 4.13-4.15 (m, 1H), 4.43-4.47 (m, 2H) C23H36N6O5S HPLC 97.9% Mass (M + 1) 509.3 |
| 509 | 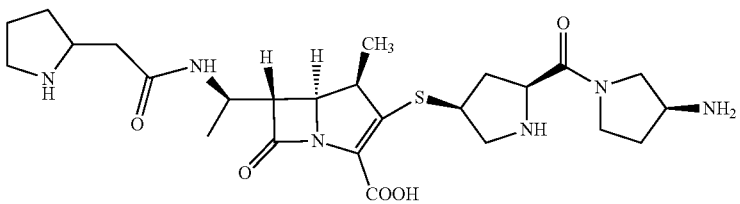 [SMILES: C[C@@H](NC(=O)CC1CCCN1)[C@H]1C(=O)N2C(C(=O)O)=C(S[C@@H]3CN[C@H](C(=O)N4CC[C@H](N)C4)C3)[C@H](C)[C@H]12]<br>(4R,5S,6R)-3-(((3S,5S)-5-((R)-3-aminopyrrolidine-1-carbonyl)pyrrolidin-3-ylthio)-4-methyl-7-oxo-6-((R)-1-(2-((S)-pyrrolidin-2-yl)acetamido)ethyl)-1-azabicyclo[3.2.0]hept-2-ene-2-carboxylic acid | $^1$HNMR (D$_2$O) - 1.20 (d, 3H), 1.34 (d, 3H), 1.80-1.85 (m, 1H), 2.08-2.13 (m, 1H), 2.19-2.32 (m, 1H), 2.44-2.48 (m, 3H), 2.70-3.00 (m, 3H), 2.94-2.96 (m, 1H), 3.19 (d, 3H), 3.29-3.37 (m, 3H), ), 3.40-3.45 (m, 2H), 3.47-3.49 (m, 4H), 3.54-3.78 (m, 2H), 4.14 (d, 1H), 4.38-4.42 (m, 1H), C25H38N6O5S HPLC 97.9% Mass (M + 1) 535.1 |
| 510 | 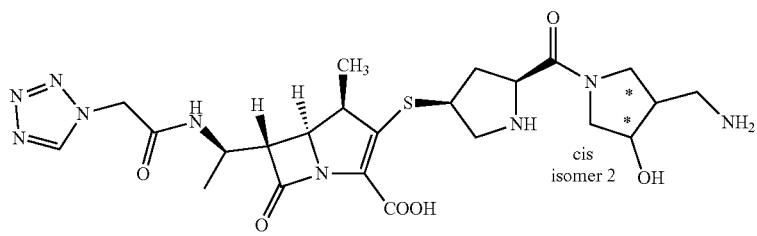 [SMILES: C[C@@H](NC(=O)Cn1cnnn1)[C@H]1C(=O)N2C(C(=O)O)=C(S[C@@H]3CN[C@H](C(=O)N4CC(O)C(CN)C4)C3)[C@H](C)[C@H]12]<br>(4R,5S,6R)-6-((R)-1-(2-(1H-tetrazol-1-yl)acetamido)ethyl)-3-(((3S,5S)-5-(3-(aminomethyl)-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.34 (d, 3H), 1.82-1.85 (m, 2H), 2.18-2.32 (m, 1H), 2.42-2.56 (m, 1H), 2.88-2.93 (m, 1H), 3.11-3.14 (m, 1H), 3.33-3.34 (m, 2H), 3.57-3.58 (m, 2H), 3.64-3.66 (m, 1H), 3.72-.38 (m,2H), 3.98-3.99 (m, 1H), 4.13-4.15 (d, 2H), 4.41-4.43 (m, 2H), 5.44-5.45 (d, 2H), 9.27 (s, 1H) C23H33N9O6S HPLC 90% Mass (M + 1) 564.2 |

| Example | Structure | Analytical Data |
|---|---|---|
| 511 | 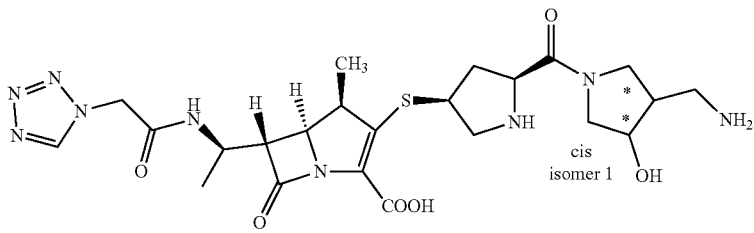 [SMILES: C[C@@H](NC(=O)Cn1cnnn1)[C@H]1C(=O)N2C(C(=O)O)=C(S[C@@H]3CN[C@H](C(=O)N4CC(O)C(CN)C4)C3)[C@H](C)[C@H]12]<br>(4R,5S,6R)-6-((R)-1-(2-(1H-tetrazol-1-yl)acetamido)ethyl)-3-((3S,5S)-5-(3-(aminomethyl)-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.16(d, 3H), 1.30 (d, 3H), 1.84-1.87 (m, 2H), 2.16-2.30 (m, 1H), 2.40-2.54 (m, 1H), 2.86-2.91 (m, 1H), 3.09-3.12 (m, 1H), 3.31-3.32 (m, 2H), 3.52-3.53 (m, 2H), 3.62-3.64 (m, 1H), 3.70-.36 (m, 2H), 3.95-3.96 (m, 1H), 4.11-4.13 (d, 2H), 4.38-4.40 (m, 2H), 5.41-5.42 (d, 2H), 9.27 (s, 1H) C23H33N9O6S HPLC 95.1% Mass (M + 1) 564.2 |
| 512 | 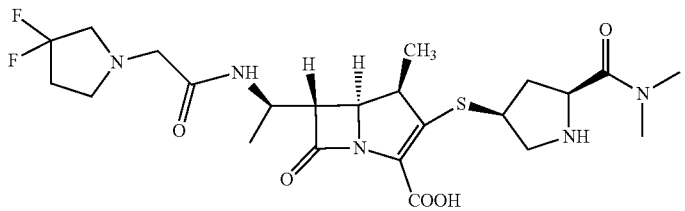 [SMILES: C[C@@H](NC(=O)CN1CCC(F)(F)C1)[C@H]1C(=O)N2C(C(=O)O)=C(S[C@@H]3CN[C@H](C(=O)N(C)C)C3)[C@H](C)[C@H]12]<br>(4R,5S,6R)-6-((R)-1-(2-(3,3-difluoropyrrolidin-1-yl)acetamido)ethyl)-3-((3S,5S)-5-(dimethylcarbamoyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.33 (d, 3H), 1.8-1.86 (m, 2H), 1.91-1.96 (m, 2H), 2.14-2.20 (m, 2H), 2.31-2.33 (m, 1H), 2.59-2.60 (m, 1H), 2.95-296 (m, 1H), 2.99 (s, 3H), 3.07 (s, 3H), 3.21.3.22 (m, 1H), 3.40-3.45 (m, 2H), 3.73-3.77 (m, 2H), 3.91 (m, 1H), 4.13-4.15 (m, 1H), 4.43-4.47 (m, 2H) C23H33F2N5O5S HPLC 97.9% Mass 530.1 (M + 1) |
| 513 | 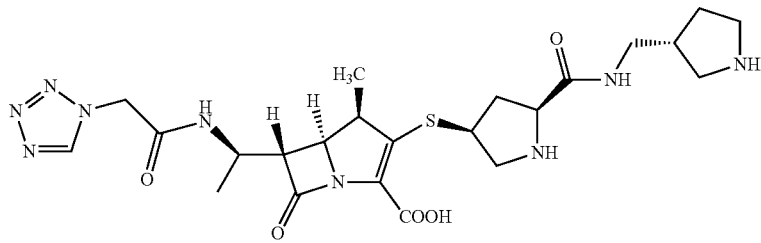 [SMILES: C[C@@H](NC(=O)Cn1cnnn1)[C@H]1C(=O)N2C(C(=O)O)=C(S[C@@H]3CN[C@H](C(=O)NC[C@@H]4CCNC4)C3)[C@H](C)[C@H]12]<br>(4R,5S,6R)-6-((R)-1-(2-(1H-tetrazol-1-yl)acetamido)ethyl)-4-methyl-7-oxo-3-((3S,5S)-5-((R)-pyrrolidin-3-ylmethylcarbamoyl)pyrrolidin-3-ylthio)-1-azabicyclo[3.2.0]hept-2-ene-2-carboxylic acid | $^1$HNMR (D$_2$O) - 1.18 (d, 3H), 1.32 (d, 3H), 1.85-1.88 (m, 2H), 2.18-2.32 (m, 1H), 2.42-2.46 (m, 1H), 2.89-2.93 (m, 1H), 3.12-3.15 (m, 2H), 3.33-3.34 (m, 2H), 3.57-3.58 (m, 2H), 3.63-3.65 (m, 1H), 3.71-.379 (m, 2H), 3.96 (m, 1H), 4.12-4.14 (d, 2H), 4.40-4.42 (m, 2H), 5.43-5.44 (d, 2H), 9.26 (s, 1H) C23H33N9O5S HPLC 97.9% Mass (M + 1) 548.3 |
| 514 | 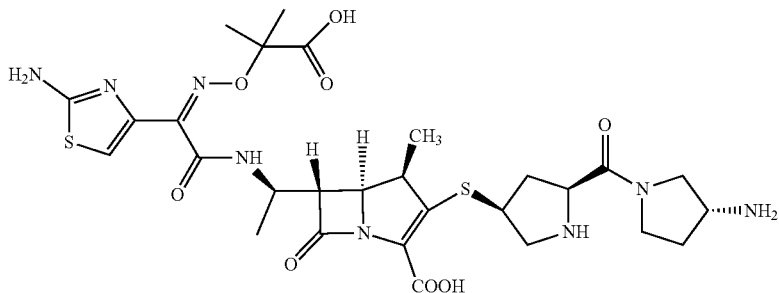 [SMILES: C[C@@H](NC(=O)/C(=N\OC(C)(C)C(=O)O)c1csc(N)n1)[C@H]1C(=O)N2C(C(=O)O)=C(S[C@@H]3CN[C@H](C(=O)N4CC[C@@H](N)C4)C3)[C@H](C)[C@H]12]<br>(4R,5S,6R)-3-((3S,5S)-5-((R)-3-aminopyrrolidine-1-carbonyl)pyrrolidin-3-ylthio)-6-((R)-1-((Z)-2-(2-aminothiazol-4-yl)-2-(2-carboxypropan-2-yloxyimino)acetamido)ethyl)-4-methyl-7-oxo-1-azabicyclo[3.2.0]hept-2-ene-2-carboxylic acid | $^1$HNMR (D$_2$O) - 1.20 (d, 3H), 1.34 (d, 9H), 1.79-1.82 (m, 1H), 2.08-2.11 (m, 1H), 2.35-2.38 (m, 1H), 3.33-3.40 (m, 1H), 3.67-3.71 (m, 1H), 3.73 (m, 1H), 3.78 (d, 2H), 3.90 (m, 1H), 4.12-4.14 (m, 2H), 4.14-4.15 (m, 2H), 4.16 (d, 1H), 4.41 (d, 1H), 4.60 (d, 1H), 4.84 (d, 1H), 8.54 (s, 1H), C28H38N8O8S2 HPLC 90% Mass (M + 1) 679.1 |

| Example | Structure | Analytical Data |
|---|---|---|
| 515 | 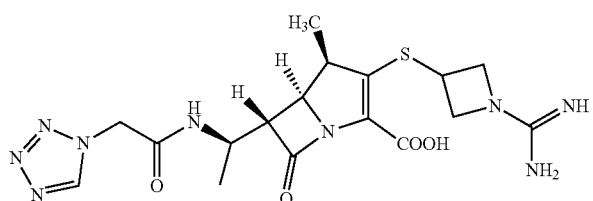<br>(4R,5S,6R)-6-((R)-1-(2-(1H-tetrazol-1-yl)acetamido)ethyl)-3-(1-carbamimidoylazetidin-3-ylthio)-4-methyl-7-oxo-1-azabicyclo[3.2.0]hept-2-ene-2-carboxylic acid | ¹HNMR (D₂O) - 1.28 (d, 3H), 1.34 (d, 3H), 2.86 (m, 1H), 3.02-3.06 (m, 1H), 3.44-3.48 (m, 1H), 3.57-3.60 (m, 1H), 3.73-3.77 (m, 1H), 4.05 (m, 2H), 4.27-4.33 (m, 2H), 5.42 (d, 2H), 9.27 (s, 1H) C17H23N9O4S HPLC 95.1% Mass (M + 1) 450.4 |
| 516 | 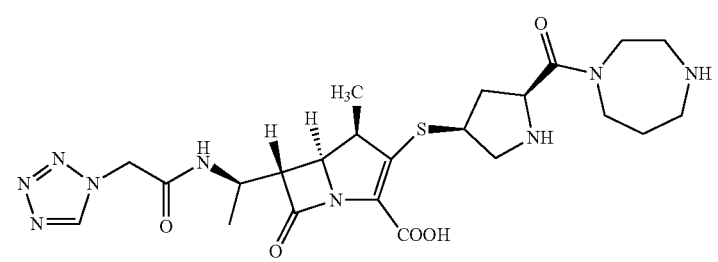 [SMILES: C[C@@H](NC(=O)Cn1cnnn1)[C@H]1C(=O)N2C(C(=O)O)=C(S[C@@H]3CN[C@H](C(=O)N4CCCNCC4)C3)[C@H](C)[C@H]12]<br>(4R,5S,6R)-3-((3S,5S)-5-(1,4-diazepane-1-carbonyl)pyrrolidin-3-ylthio)-6-((R)-1-(2-(1H-tetrazol-1-yl)acetamido)ethyl)-4-methyl-7-oxo-1-azabicyclo[3.2.0]hept-2-ene-2-carboxylic acid | ¹HNMR (D₂O) - 1.20 (d, 3H), 1.34 (d, 3H), 1.85-1.92 (m, 1H), 2.94-3.26 (m, 4H), 3.46-3.49 (m, 4H), 3.57-3.58 (m, 2H), 3.62-3.72 (m, 1H), 3.73-3.76 (m, 1H), 3.80-3.84 (m, 2H), 3.87-3.92 (m, 1H), 3.94-4.13 (m, 1H), 4.30 (d, 1H), 4.43-4.49 (m, 1H), 4.51-4.53 (m, 1H), 5.47 (m, 2H), 9.27 (s, 1H) C23H33N9O5S HPLC 97.9% Mass (M + 1) 548.1 |
| 517 | 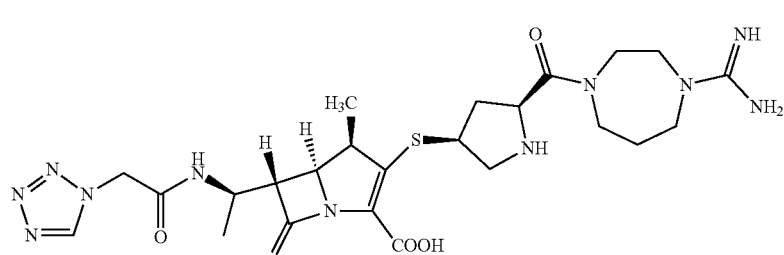<br>(4R,5S,6R)-6-((R)-1-(2-(1H-tetrazol-1-yl)acetamido)ethyl)-3-((3S,5S)-5-(4-carbamimidoyl-1,4-diazepane-1-carbonyl)pyrrolidin-3-ylthio)-4-methyl-7-oxo-1-azabocyclo[3.2.0]hept-2-ene-2-carboxylic acid | ¹HNMR (D₂O) 1.20 (d, 3H), 1.34 (d, 3H), 1.88-1.95 (m, 1H), 3.12-3.34 (m, 4H), 3.48-3.51 (m, 4H), 3.59-3.60 (m, 2H), 3.64-3.74 (m, 1H), 3.75-3.78 (m, 1H), 3.82-3.86 (m, 2H), 3.88-3.93 (m, 1H), 4.12-4.15 (m, 1H), 4.38 (d, 1H), 4.48-4.52 (m, 1H), 4.58-4.60 (m, 1H), 5.48 (m, 2H), 9.27 (s, 1H) 24H35N11O5S HPLC 97.9% Mass (M + 1) 590.2 |
| 518 | 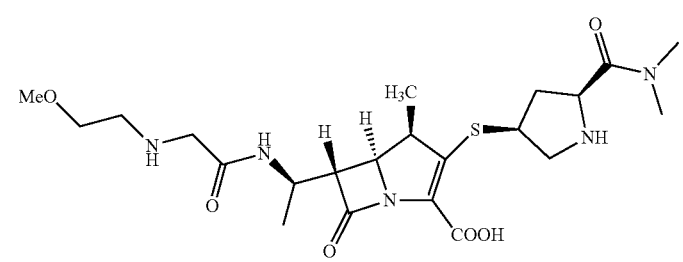 [SMILES: COCCNCC(=O)N[C@H](C)[C@H]1C(=O)N2C(C(=O)O)=C(S[C@@H]3CN[C@H](C(=O)N(C)C)C3)[C@H](C)[C@H]12]<br>(4R,5S,6R)-3-((3S,5S)-5-(dimethylcarbamoyl)pyrrolidin-3-ylthio)-6-((R)-1-(2-(2-methoxyethylamino)acetamido)ethyl)-4-methyl-7-oxo-1-azabicyclo[3.2.0]hept-2-ene-2-carboxylic acid | ¹HNMR (D₂O) - 1.21 (d, 3H), 1.29 (d, 3H), 1.94-2.0 (m, 1H), 3.00 (s, 3H), 3.03 (s, 3H), 3.28 (s, 3H), 3.35-3.37 (m, 1H), 3.41 (s, 3H), 3.57-3.58 (m, 1H), 3.60-3.62 (m, 2H), 3.72-3.73 (m, 3H), 3.90-3.91 (m, 2H), 4.03-4.04 (m, 1H), 4.14-4.16 (m, 1H), 4.44-4.47 (m, 1H) C22H35N5O6S HPLC 95.3% Mass (M + 1) 498.2 |

-continued

| Example | Structure | Analytical Data |
|---|---|---|
| 519 | 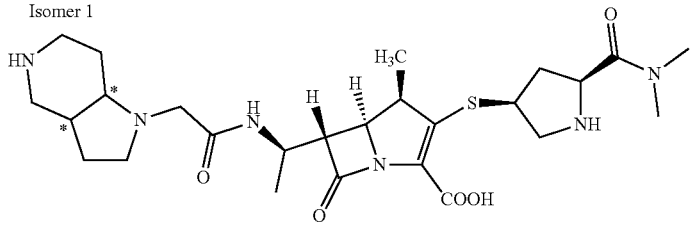 [SMILES: C[C@@H](NC(=O)CN1CCC2CNCCC21)[C@H]1C(=O)N2C(C(=O)O)=C(S[C@@H]3CN[C@H](C(=O)N(C)C)C3)[C@H](C)[C@H]12]
(4R,5S,6R)-3-((3S,5S)-5-(dimethylcarbamoyl)pyrrolidin-3-ylthio)-4-methyl-6-((1R)-1-(2-(octahydro-1H-pyrrolo[3,2-c]pyridin-1-yl)acetamido)ethyl)-7-oxo-1-azabicyclo[3.2.0]hept-2-ene-2-carboxylic acid | $^1$HNMR (D$_2$O) - 1.21 (d, 3H), 1.31 (d, 3H), 1.57-1.65 (m, 1H), 1.92-2.00 (m, 2H), 2.08-2.10 (m, 2H), 2.55-2.59 (m, 1H), 2.95 (m, 1H), 3.00 (s, 3H), 3.04 (m, 1H), 3.07 (s, 3H), 3.11-3.19 (m, 2H), 3.23-3.26 (m, 2H), 3.34-3.39 (m, 3H), 3.40-3.43 (m, 2H), 3.48 (m, 1H), 3.68-3.70 (m, 2H), 4.02-4.09 (m, 1H), 4.19-4.21 (m, 1H), 4.33 (m, 1H), 4.72-4.74 (m, 1H) C26H40N6O5S HPLC 97.5% Mass (M + 1) 549.1 |
| 520 | 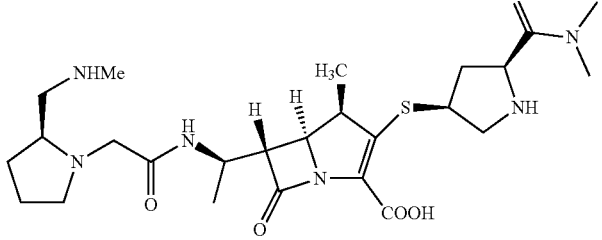
(4R,5S,6R)-3-((3S,5S)-5-(dimethylcarbamoyl)pyrrolidin-3-ylthio)-4-methyl-6-((R)-1-(2-((S)-2-((methylamino)methyl)pyrrolidin-1-yl)acetamido)ethyl)-7-oxo-1-azabicyclo[3.2.0]hept-2-ene-2-carboxylic acid | $^1$HNMR (D$_2$O) - 1.09 (d, 3H), 1.19 (d, 3H), 1.54-1.57 (m, 1H), 1.63-1.67 (m, 1H), 1.88 (m, 2H), 1.98-2.01 (m, 1H), 2.36-2.40 (m, 1H), 2.62 (s, 3H), 2.87 (m, 1H), 2.94 (s, 3H), 3.01 (m, 1H), 3.03 (s, 3H), 3.09 (m, 1H), 3.13 (m, 2H), 3.24 (m, 1H), 3.34 (m, 3H), 3.46 (m, 2H), 3.75-3.85 (m, 1H), 4.03-4.05 (m, 1H), 4.29-4.33 (m, 1H), 4.49 (m, 1H) C25H40N6O5S HPLC 93.1% Mass (M + 1) 537.2 |
| 521 | 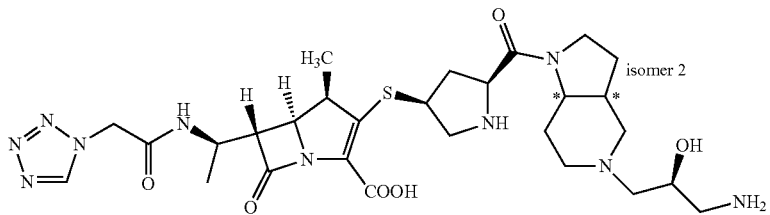 [SMILES: C[C@@H](NC(=O)Cn1cnnn1)[C@H]1C(=O)N2C(C(=O)O)=C(S[C@@H]3CN[C@H](C(=O)N4CCC5CN(C[C@@H](O)CN)CCC54)C3)[C@H](C)[C@H]12]
(4R,5S,6R)-6-((R)-1-(2-(1H-tetrazol-1-yl)acetamido)ethyl)-3-((3S,5S)-5-(5-((S)-3-amino-2-hydroxypropyl)octahydro-1H-pyrrolo[3,2-c]pyridine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.22 (d, 3H), 1.71-1.79 (m, 2H), 1.92-1.98 (m, 2H), 2.11 (m, 2H), 2.50 (m, 2H), 2.72 (m, 1H), 2.79-2.81 (m, 1H), 2.84-2.86 (m, 2H), 2.97 (m, 1H), 3.03-3.06 (m, 2H), 3.20-3.22 (m, 3H), 3.44-3.54 (m, 3H), 3.65 (m, 1H), 3.73-3.78 (m, 1H), 3.85 (m, 1H), 4.00-4.03 (m, 1H), 4.16 (m, 1H), 4.27-4.30 (m, 1H), 5.30-5.34 (d, 2H), 9.15 (s, 1H) C28H42N10O6S HPLC 99.8% Mass (M + 1) 647.3 |
| 522 | 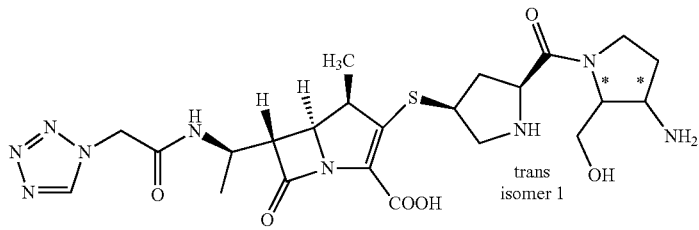 [SMILES: C[C@@H](NC(=O)Cn1cnnn1)[C@H]1C(=O)N2C(C(=O)O)=C(S[C@@H]3CN[C@H](C(=O)N4CCC(N)C4CO)C3)[C@H](C)[C@H]12]
(4R,5S,6R)-6-((R)-1-(2-(1H-tetrazol-1-yl)acetamido)ethyl)-3-((3S,5S)-5-((2S,3R)-3-amino-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.22 (d, 3H), 1.82-1.86 (m, 1H), 2.03-2.08 (m, 1H), 2.31-2.33 (m, 1H), 2.46-2.48 (m, 1H), 2.77-2.82 (m, 1H), 3.18-3.23 (m, 2H), 3.38-3.39 (m, 2H), 3.58-3.61 (m, 1H), 3.65-3.68 (m, 2H), 3.82-3.87 (m, 2H), 4.00-4.02 (m, 1H), 4.11 (m, 1H), 4.28-4.29 (m, 2H), 5.26-5.28 (d, 2H), 9.13 (s, 1H) C23H33N9O6S HPLC 91.7% Mass (M + 1) 564.2 |

| Example | Structure | Analytical Data |
|---|---|---|
| 523 | 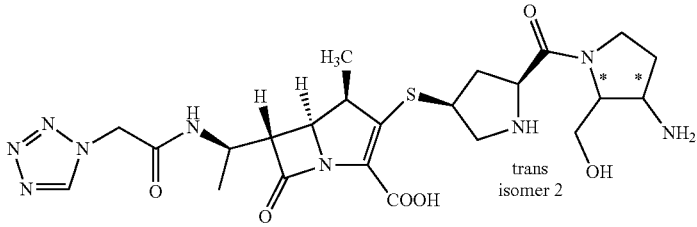 [SMILES: C[C@@H](NC(=O)Cn1cnnn1)[C@H]1C(=O)N2C(C(=O)O)=C(S[C@@H]3CN[C@H](C(=O)N4CCC(N)C4CO)C3)[C@H](C)[C@H]12]<br>(4R,5S,6R)-6-((R)-1-(2-(1H-tetrazol-1-yl)acetamido)ethyl)-3-((3S,5S)-5-((2S,3R)-3-amino-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | 1HNMR (D$_2$O) - 1.06 (d, 3H), 1.20 (d, 3H), 1.74-1.78 (m, 1H), 2.05-2.08 (m, 1H), 2.44-2.49 (m, 1H), 2.75-2.78 (m, 1H), 3.08-3.19 (m, 1H), 3.20-3.23 (m, 1H), 3.31-3.35 (m, 1H), 3.43-3.44 (m, 1H), 3.55-3.59 (m, 1H), 3.63-3.69 (m, 2H), 3.72-3.79 (m, 1H), 3.85 (m, 1H), 3.99 (m, 1H), 4.01 (m, 1H), 4.13 (m, 1H), 4.26-4.29 (m, 2H), 5.28-5.29 (d, 2H), 9.13 (s, 1H)<br>C23H33N9O6S HPLC 90.5% Mass (M + 1) 564.2 |
| 524 | 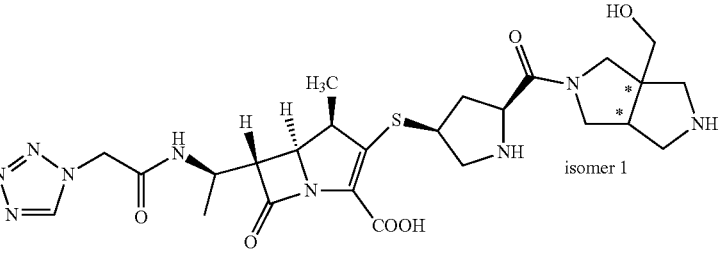<br>(4R,5S,6R)-6-((R)-1-(2-(1H-tetrazol-1-yl)acetamido)ethyl)-3-((3S,5S)-5-((3aR,6aR)-3a-(hydroxymethyl)octahydropyrrolo[3,4-c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.06 (d, 3H), 1.20 (d, 3H), 1.78 (m, 1H), 2.74 (m, 1H), 2.86 (m, 1H), 3.11-3.19 (m, 3H), 3.21-3.29 (m, 2H), 3.37-3.39 (m, 3H), 3.50 (m, 2H), 3.53-3.56 (m, 2H), 3.62 (m, 1H), 3.71-3.77 (m, 2H), 3.99-4.01 (m, 1H), 4.19-4.29 (m, 2H), 5.28-5.33 (d, 2H), 9.26 (s, 1H)<br>C25H35N9O6S HPLC 92.2% Mass (M + 1) 590.1 |
| 525 | 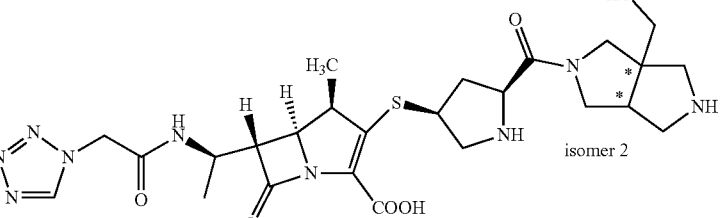<br>(4R,5S,6R)-6-((R)-1-(2-(1H-tetrazol-1-yl)acetamido)ethyl)-3-((3S,5S)-5-((3aS,6aS)-3a-(hydroxymethyl)octahydropyrrolo[3,4-c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.27 (d, 3H), 1.80 (m, 1H), 2.76 (m, 1H), 2.88 (m, 1H), 3.18-3.26 (m, 3H), 3.26-3.34 (m, 2H), 3.39-3.41 (m, 3H), 3.52 (m, 2H), 3.55-3.58 (m, 2H), 3.64 (m, 1H), 3.74-3.80 (m, 2H), 4.02-4.03 (m, 1H), 4.22-4.32 (m, 2H), 5.30-5.35 (d, 2H), 9.27 (s, 1H)<br>C25H35N9O6S HPLC 97.9% Mass (M + 1) 589.67 |
| 526 | 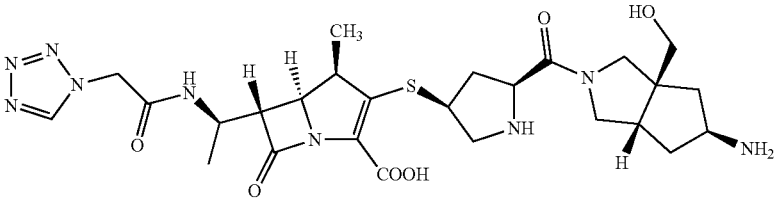 [SMILES: C[C@@H](NC(=O)Cn1cnnn1)[C@H]1C(=O)N2C(C(=O)O)=C(S[C@@H]3CN[C@H](C(=O)N4C[C@H]5C[C@H](N)C[C@@]5(CO)C4)C3)[C@H](C)[C@H]12]<br>(4R,5S,6R)-6-((R)-1-(2-(1H-tetrazol-1-yl)acetamido)ethyl)-3-((3S,5S)-5-((3aS,5S,6aS)-5-amino-3a-(hydroxymethyl)octahydrocyclopenta[c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.21 (d, 3H), 1.69-1.79 (m, 2H), 1.93-1.95 (m, 2H), 2.11-2.16 (m, 1H), 2.59-2.82 (m, 2H), 3.16-3.19 (m, 3H), 3.20-3.27 (m, 1H), 3.32-3.48 (m, 3H), 3.52-3.59 (m, 2H), 3.72 (m, 2H), 3.82 (m, 1H), 4.00-4.02 (m, 1H), 4.25-4.28 (m, 2H), 5.29-5.30 (m, 2H), 9.14 (s, 1H)<br>C26H37N9O6S HPLC 92.1% Mass (M + 1) 604.2 |

| Example | Structure | Analytical Data |
|---|---|---|
| 527 | 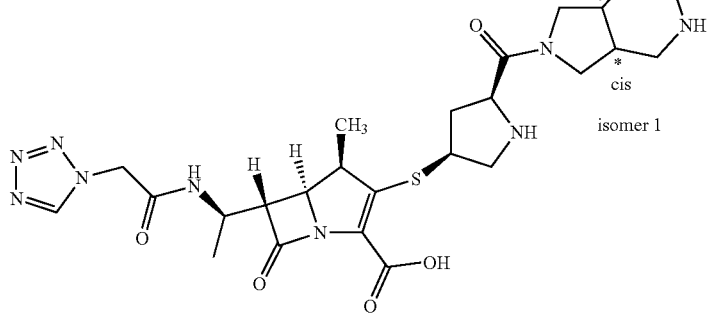<br>(4R,5S,6R)-6-((R)-1-(2-(1H-tetrazol-1-yl)acetamido)ethyl)-4-methyl-3-((3S,5S)-5-octahydro-1H-pyrrolo[3,4-c]pyridine-2-carbonyl)pyrrolidin-3-ylthio)-7-oxo-1-azabicyclo[3.2.0]hept-2-ene-2-carboxylic acid | $^1$HNMR (D$_2$O) - 1.06 (d, 3H), 1.22 (d, 3H), 1.41-1.48 (m, 1H), 1.63-1.72 (m, 1H), 1.89 (m, 1H), 2.50-2.56 (m, 2H), 2.91-2.97 (m, 2H), 3.02-3.07 (m, 2H), 3.21 (m, 2H), 3.32-3.35 (m, 2H), 3.41-3.42 (m, 1H), 3.45-3.46 (m, 2H), 3.67-3.71 (m, 1H), 3.87 (m, 1H), 3.98-4.00 (m, 1H), 4.26-4.29 (m, 1H), 5.29-5.33 (d, 2H), 9.13 (s, 1H) C24H33N9O6S HPLC 100% Mass 574.1 (M + 1) |
| 528 | 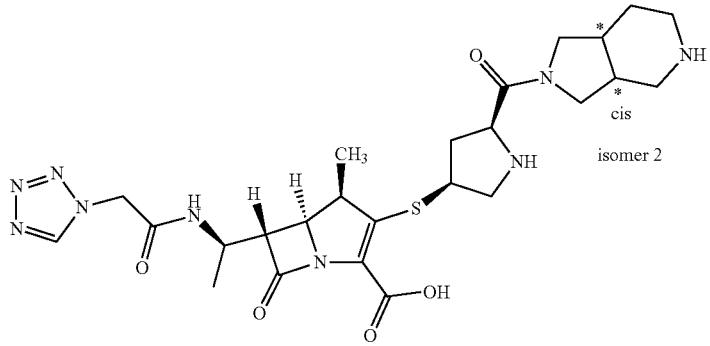 [SMILES: C[C@@H](NC(=O)Cn1cnnn1)[C@H]1C(=O)N2C(C(=O)O)=C(S[C@@H]3CN[C@H](C(=O)N4CC5CCNCC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[3,4-c]pyridine-2-carbonyl)pyrrolidin-3-ylthio)-7-oxo-1-azabicyclo[3.2.0]hept-2-ene-2-carboxylic acid | $^1$HNMR (D$_2$O) - 1.07 (d, 3H), 1.23 (d, 3H), 1.67 (m, 1H), 1.89 (m, 1H), 2.51-2.69 (m, 2H), 2.86 (m, 1H), 3.05-3.07 (m, 2H), 3.21-3.24 (m, 1H), 3.31-3.39 (m, 3H), 3.46 (m, 1H), 3.54-3.55 (m, 2H), 3.68-3.71 (m, 2H), 3.86 (m, 1H), 4.01-4.03 (m, 1H), 4.29-4.34 (m, 2H), 5.30-5.34 (d, 2H), 9.15 (s, 1H) C25H35N9O5S HPLC 99.8% Mass (M + 1) 574.1 |
| 529 | 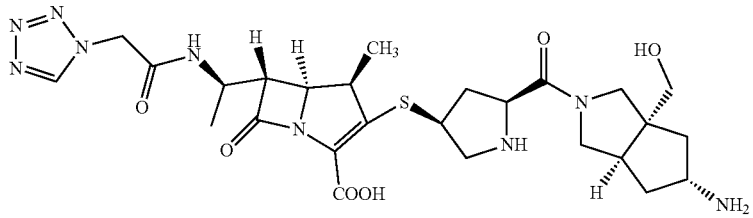 [SMILES: C[C@@H](NC(=O)Cn1cnnn1)[C@H]1C(=O)N2C(C(=O)O)=C(S[C@@H]3CN[C@H](C(=O)N4C[C@@H]5C[C@@H](N)C[C@]5(CO)C4)C3)[C@H](C)[C@H]12]<br>(4R,5S,6R)-6-((R)-1-(2-(1H-tetrazol-1-yl)acetamido)ethyl)-3-((3S,5S)-5-((3aR,5R,6aR)-5-amino-3a-(hydroxymethyl)octahydrocyclopenta[c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 11.06 (d, 3H), 1.20 (d, 3H), 1.72-1.78 (m, 2H), 1.94 (m, 2H), 2.11 (m, 1H), 2.56-2.83 (m, 3H), 3.19-3.27 (m, 3H), 3.30-3.47 (m, 3H), 3.57 (m, 3H), 3.73 (m, 1H), 3.83 (m, 2H), 4.01 (m, 1H), 4.29 (m, 1H), 5.28 (d, 2H), 9.13 (s, 1H) C26H37N9O6S HPLC 98.6% Mass (M + 1) 604.2 |
| 530 | 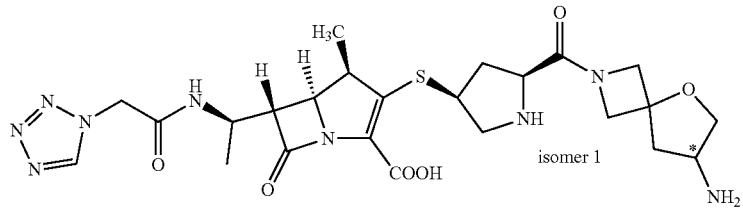 [SMILES: C[C@@H](NC(=O)Cn1cnnn1)[C@H]1C(=O)N2C(C(=O)O)=C(S[C@@H]3CN[C@H](C(=O)N4CC5(CC(N)CO5)C4)C3)[C@H](C)[C@H]12]<br>(4R,5S,6R)-6-((R)-1-(2-(1H-tetrazol-1-yl)acetamido)ethyl)-3-((3S,5S)-5-(7-amino-5-oxa-2-azaspiro[3,4]octane-2-carbonyl)pyrrolidin-3-ylthio)-4-methyl-7-oxo-1-azabicyclo[3.2.1]hept-2-ene-2-carboxylic acid | $^1$HNMR (D$_2$O) - 1.20 (d, 3H) 1.33 (d, 3H), 2.36-2.39 (m, 1H), 2.79-2.85 (m, 2H), 3.28-3.35 (m, 2H), 3.57-3.58 (m, 2H), 3.95 (m, 1H), 4.05-4.07 (m, 2H), 4.13-4.17 (m, 3H), 4.27 (m, 2H), 4.30-4.32 (m, 2H), 4.38-4.39 (m, 2H), 5.41-5.42 (3, 2H), 9.27 (s, 1H) C24H33N9O6S HPLC 97.3% Mass (M + 1) 576.4 |

| Example | Structure | Analytical Data |
|---|---|---|
| 531 | 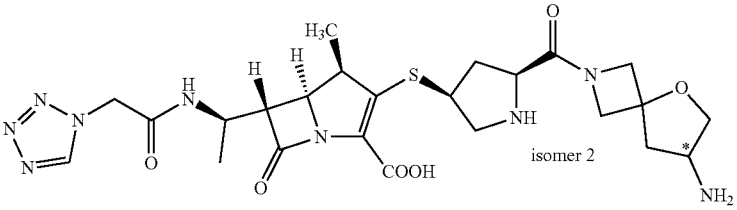 [SMILES: C[C@@H](NC(=O)Cn1cnnn1)[C@H]1C(=O)N2C(C(=O)O)=C(S[C@@H]3CN[C@H](C(=O)N4CC5(CC(N)CO5)C4)C3)[C@H](C)[C@H]12]<br>(4R,5S,6R)-6-((R)-1-(2-(1H-tetrazol-1-yl)acetamido)ethyl)-3-((3S,5S)-5-(7-amino-5-oxa-2-azaspiro[3.4]octane-2-carbonyl)pyrrolidin-3-ylthio)-4-methyl-7-oxo-1-azabicyclo[3.2.0]hept-2-ene-2-carboxylic acid | ¹HNMR (D₂O) - 1.21 (d, 3H), 1.34 (d, 3H), 2.38-2.41 (m, 1H), 2.81-2.87 (m, 2H), 3.30-3.37 (m, 2H), 3.59-3.60 (m, 2H), 3.97-3.99 (m, 1H), 4.07-4.09 (m, 2H), 4.15-4.19 (m, 3H), 4.29 (m, 2H), 4.32-4.34 (m, 2H), 4.40-4.41 (m, 2H), 5.43-5.44 (3, 2H), 9.27 (s, 1H) C24H33N9O6S HPLC 99.3% Mass (M + 1) 576.4 |
| 532 | 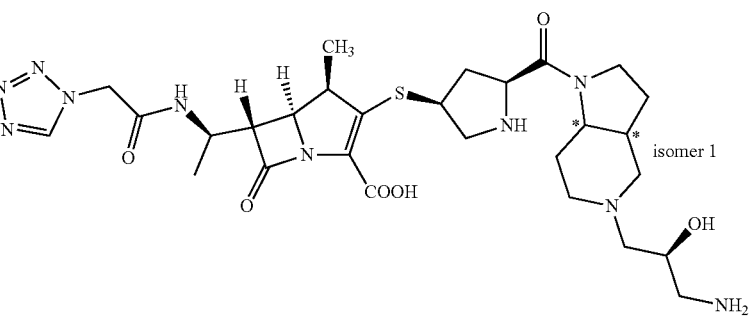 [SMILES: C[C@@H](NC(=O)Cn1cnnn1)[C@H]1C(=O)N2C(C(=O)O)=C(S[C@@H]3CN[C@H](C(=O)N4CCC5CN(C[C@@H](O)CN)CCC54)C3)[C@H](C)[C@H]12]<br>(4R,5S,6R)-6-((R)-1-(2-(1H-tetrazol-1-yl)acetamido)ethyl)-3-((3S,5S)-5-(5-((S)-3-amino-2-hydroxypropyl)octahydro-1H-pyrrolo[3,2-c]pyridine-1-carbonyl)pyrrolidin-3-ylthio)-4-methyl-7-oxo-1-azabicyclo[3.2.0]hept-2-ene-2-carboxylic acid | ¹HNMR (D₂O) - 1.20 (d, 3H), 1.34 (d, 3H), 1.80-1.82 (m, 3H), 2.11-2.23 (m, 3H), 2.62-2.92 (m, 3H), 2.97-3.17 (m, 3H), 3.20-3.33 (m, 3H), 3.35-3.42 (m, 2H), 3.52-3.58 (m, 3H), 3.72 (m, 2H), 3.99 (m, 1H), 4.13-4.15 (m, 2H), 4.32-4.43 (m, 2H), 5.42-5.43 (m, 2H), 9.27 (s, 1H) C28H42N10O6S HPLC 95.2% Mass (M + 1) 647.1 |
| 533 | 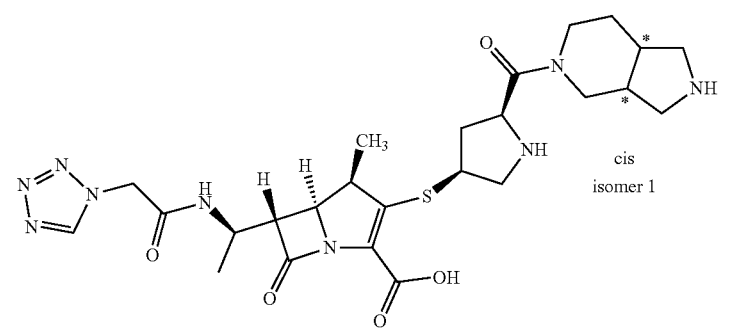 [SMILES: C[C@@H](NC(=O)Cn1cnnn1)[C@H]1C(=O)N2C(C(=O)O)=C(S[C@@H]3CN[C@H](C(=O)N4CCC5CNCC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydro-1H-pyrrolo[3,4-c]pyridine-5-carbonyl)pyrrolidin-3-ylthio)-7-oxo-1-azabicyclo[3.2.0]hept-2-ene-2-carboxylic acid | ¹HNMR (D₂O) - 1.20 (d, 3H), 1.34 (d, 3H), 1.92-1.94 (m, 3H), 2.69 (m, 3H), 3.09-3.16 (m, 3H), 3.24-3.32 (m, 3H), 3.42-3.45 (m, 3H), 3.50-3.58 (m, 2H), 3.70-3.75 (m, 2H), 4.00 (m, 1H), 4.14-4.16 (m, 1H), 4.39-4.43 (m, 1H), 5.42-5.43 (d, 2H), 9.27 (s, 1H) C25H35N9O5S HPLC 92.6% Mass (M + 1) 574.3 |
| 534 | 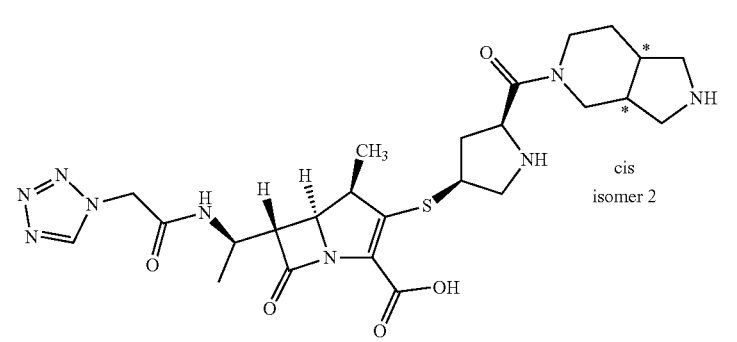 [SMILES: C[C@@H](NC(=O)Cn1cnnn1)[C@H]1C(=O)N2C(C(=O)O)=C(S[C@@H]3CN[C@H](C(=O)N4CCC5CNCC5C4)C3)[C@H](C)[C@H]12]<br>(4R,5S,6R)-6-((R)-1-(2-(1H-tetrazol-1-yl)acetamido)-ethyl)-3-((3S,5S)-5-(3a-(hydroxymethyl)octahydro-1H-pyrrolo[3,4-c]pyridine-5-carbonyl)pyrrolidin-3-ylthio)-4-methyl-7-oxo-1-azabicyclo[3.2.0]hept-2-ene-2-carboxylic acid | ¹HNMR (D₂O) - 1.20 (d, 3H), 1.34 (d, 3H), 1.92-1.95 (m, 2H), 2.67 (m, 3H), 2.98-3.07 (m, 2H), 3.23-3.26 (m, 2H), 3.32-3.29 (m, 3H), 3.51-3.59 (m, 3H), 3.62-3.66 (m, 2H), 3.71 (m, 2H), 3.90 (m, 1H), 4.13-4.15 (m, 1H), 4.41-4.43 (m, 1H), 5.41-5.42 (m, 2H), 9.27 (s, 1H) C25H35N9O5S HPLC 98.9% Mass (M + 1) 574.3 |

| Example | Structure | Analytical Data |
|---|---|---|
| 535 | (4R,5S,6R)-6-((R)-1-(2-(1H-tetrazol-1-yl)acetamido)-ethyl)-3-((3S,5S)-5-(3a-(hydroxymethyl)octahydro-1H-pyrrolo[3,4-c]pyridine-5-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 1.76-1.86 (m, 2H), 2.00 (m, 1H), 2.97-2.99 (m, 3H), 3.15-3.21 (m, 3H), 3.34-3.49 (m, 5H), 3.52-3.73 (m, 6H), 3.98 (m, 1H), 4.13-4.15 (m, 1H), 4.40-4.41 (m, 1H), 5.42-5.43 (m, 2H), 9.27 (s, 1H) C26H37N9O6S HPLC 97.8% Mass (M + 1) 604.2 |
| 536 | (4R,5S,6R)-6-((R)-1-(2-(1H-tetrazol-1-yl)acetamido)-ethyl)-3-((3S,5R)-5-(2-((R)-3-aminopyrrolidin-1-yl)-2-oxoethyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.34 (d, 3H), 1.81 (m, 1H), 2.09-2.12 (m, 1H), 2.47 (m, 2H), 2.81 (m, 2H), 3.05 (m, 2H), 3.37-3.40 (m, 2H), 3.60-3.77 (m, 3H), 3.95 (m, 2H), 4.04-4.09 (m, 2H), 4.13 (m, 1H), 4.41 (m, 1H), 5.42-5.43 (m, 2H), 9.27 (s, 1H) C23H33N9O5S HPLC 90.2% Mass (M + 1) 548.1 |
| 537 | (4R,5S,6R)-6-((R)-1-(2-(1H-tetrazol-1-yl)acetamido)ethyl)-4-methyl-3-((3S,5S)-5-(octahydro-1H-pyrrolo[3,4-c]pyridine-5-carbonyl)pyrrolidin-3-ylthio)-7-oxo-1-azabicyclo[3.2.0]hept-2-ene-2-carboxylic acid | $^1$HNMR (D$_2$O) - 1.19 (d, 3H), 1.33 (d, 3H), 1.74-1.84 (m, 2H), 1.98 (m, 1H), 2.95-2.97 (m, 3H), 3.13-3.19 (m, 3H), 3.33-3.47 (m, 5H), 3.50-3.71 (m, 6H), 3.96 (m, 1H), 4.11-4.13 (m, 1H), 4.38-4.39 (m, 1H), 5.40-5.41 (m, 2H), 9.25 (s, 1H) C26H37N9O6S HPLC 90.3% Mass (M + 1) 604.3 |
| 538 | (4R,5S,6R)-6-((R)-1-(2-(1H-tetrazol-1-yl)acetamido)ethyl)-3-((3S,5S)-5-((3aR,5S,6aS)-5-amino-3a-(aminomethyl)octahydro-cyclopenta[c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.21 (d, 3H), 1.74-1.80 (m, 2H), 1.96 (m, 2H), 2.13 (m, 1H), 2.58-2.85 (m, 3H), 3.21-3.29 (m, 3H), 3.32-3.49 (m, 3H), 3.59 (m, 3H), 3.75 (m, 1H), 3.85 (m, 2H), 4.03 (m, 1H), 4.31 (m, 1H), 5.30 (d, 2H), 9.15 (s, 1H) C26H38N10O5S HPLC 90% Mass (M + 1) 603.1 |

| Example | Structure | Analytical Data |
|---|---|---|
| 539 | 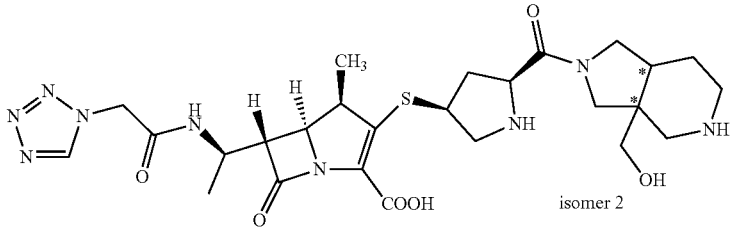 [SMILES: C[C@@H](NC(=O)Cn1cnnn1)[C@H]1C(=O)N2C(C(=O)O)=C(S[C@@H]3CN[C@H](C(=O)N4CC5CCNCC5(CO)C4)C3)[C@H](C)[C@H]12]<br>(4R,5S,6R)-6-((R)-1-(2-(1H-tetrazol-1-yl)acetamido)ethyl)-3-((3S,5S)-5-(3a-(hydroxymethyl)octahydro-1H-pyrrolo[3,4-c]pyridine-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.31 (d, 3H), 1.73-1.83 (m, 2H), 1.87 (m, 1H), 2.94-2.96 (m, 3H), 3.12-3.18 (m, 3H), 3.31-3.46 (m, 5H), 3.49-3.70 (m, 6H), 3.95 (m, 1H), 4.10-4.12 (m, 1H), 4.37-4.38 (m, 1H), 5.39-5.40 (m, 2H), 9.24 (s, 1H) C26H37N9O6S HPLC 95.1% Mass (M + 1) 604.3 |
| 540 | 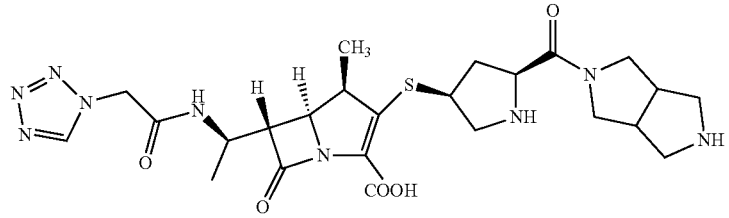 [SMILES: C[C@@H](NC(=O)Cn1cnnn1)[C@H]1C(=O)N2C(C(=O)O)=C(S[C@@H]3CN[C@H](C(=O)N4CC5CNCC5C4)C3)[C@H](C)[C@H]12]<br>(4R,5S,6R)-6-((R)-1-(2-(1H-tetrazol-1-yl)acetamido)ethyl)-4-methyl-3-((3S,5S)-5-(octahydropyrrolo-[3,4-c]pyrrole-2-carbonyl)pyrrolidin-3-ylthio)-7-oxo-1-azabicyclo[3.2.0]hept-2-ene-2-carboxylic acid | $^1$HNMR (D$_2$O) - 1.05 (d, 3H), 1.19 (d, 3H), 1.76 (m, 1H), 2.72 (m, 1H), 2.84 (m, 1H), 3.09-3.17 (m, 3H), 3.19-3.27 (m, 2H), 3.35-3.37 (m, 3H), 3.48 (m, 2H), 3.51-3.54 (m, 2H), 3.60 (m, 1H), 3.69-3.75 (m, 2H), 3.97-3.99 (m, 1H), 4.17-4.27 (m, 2H), 5.26-5.31 (d, 2H), 9.24 (s, 1H) C24H33N9O5S HPLC 97.9% Mass 574.3 (M + 1) 560.4 |
| 541 | 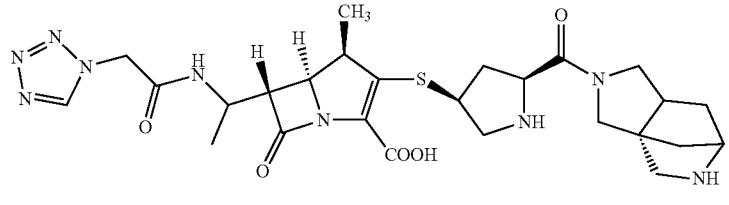 [SMILES: CC(NC(=O)Cn1cnnn1)[C@H]1C(=O)N2C(C(=O)O)=C(S[C@@H]3CN[C@H](C(=O)N4CC5CC6C[C@@]5(CN6)C4)C3)[C@H](C)[C@H]12]<br>(4R,5S,6R)-6-((R)-1-(2-(1H-tetrazol-1-yl)acetamido)ethyl)-3-((3S,5S)-5-((1R,7S)-3,8-Diaza-tricyclo[5.2.1.01,5]decane-3-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.23 (d, 3H), 1.74 (m, 1H), 1.81 (m, 4H), 2.46 (m, 1H), 2.86 (m, 1H), 3.15-3.18 (m, 1H), 3.25-3.32 (m, 4H), 3.48 (m, 3H), 3.75-3.78 (m, 1H), 3.87 (m, 2H), 4.02-4.04 (m, 1H), 4.13 (m, 1H), 4.30 (m, 1H), 4.41 (m, 1H), 5.31-5.34 (m, 2H), 9.16 (s, 1H) C26H35N9O5S HPLC 98.4% Mass (M + 1) 586.2 |
| 542 | 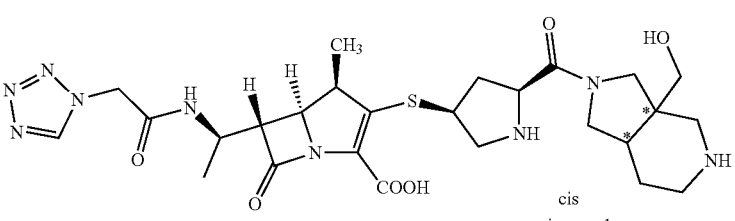<br>(4R,5S,6R)-6-((R)-1-(2-(1H-tetrazol-1-yl)acetamido)ethyl)-3-((3S,5S)-5-(3a-(hydroxymethyl)octahydro-1H-pyrrolo[3,4-c]pyridine-2-carbonyl)pyrrolidin-3-ylthio)-4-methyl-7-oxo-1-azabicyclo[3.2.0]hept-2-eoe-2-carboxylic acid | $^1$HNMR (D$_2$O) - 1.08 (d, 3H), 1.20 (d, 3H), 1.64-1.80 (m, 1H), 1.97-1.99 (m, 2H) 2.37-2.44 (m, 2H), 2.73 (m, 2H), 3.04-3.09 (m, 1H), 3.13-3.22 (m, 2H), 3.34 (m, 3H), 3.49 (m, 3H), 3.61 (m, 3H), 3.78-3.81 (m, 1H), 4.00-4.02 (m, 1H), 4.18 (m, 1H), 4.30-4.34 (m, 1H), 5.31-5.35 (m, 2H), 9.24 (s, 1H) C26H37N9O6S HPLC 97.4% Mass (M + 1) 604.1 |
| 543 | 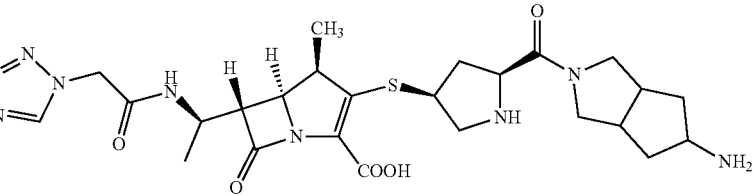<br>(4R,5S,6R)-6-((R)-1-(2-(1H-tetrazol-1-yl)acetamido)ethyl)-3-((3S,5S)-5-(5-aminooctahydrocyclopenta[c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.08 (d, 3H), 1.22 (d, 3H), 1.33-1.38 (m, 2H), 1.70-1.73 (m, 2H), 2.33-2.34 (m, 2H), 2.69-2.77 (m, 3H), 3.18-3.23 (m, 2H), 3.34-3.36 (m, 2H), 3.40-3.46 (m, 2H), 3.50-3.56 (m, 2H), 3.63-3.67 (m, 1H), 3.83 (m, 1H), 4.01-4.03 (m, 1H), 4.29-4.31 (m, 1H), 5.30-5.31 (m, 2H), 9.15 (s, 1H) C25H35N9O5S HPLC 90.3% Mass (M + 1) 574.3 |

| Example | Structure | Analytical Data |
|---|---|---|
| 544 | (4R,5S,6R)-6-((R)-1-(2-(1H-tetrazol-1-yl)acetamido)ethyl)-3-((3S,5S)-5-((3R,4R)-3-guanidino-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.23 (d, 3H), 1.92 (m, 1H), 2.93-2.97 (m, 2H), 3.21-3.22 (m, 2H),, 3.35-3.37 (m, 1H), 3.49-3.54 (m, 2H), 3.64-3.73 (m, 2H), 3.83-3.97 (m, 2H), 4.04-4.05 (m, 2H), 4.29-4.37 (m, 2H), 5.29-5.31 (m, 2H), 9.16 (s, 1H) C23H33N11O6S HPLC 98.2% Mass (M + 1) 592.2 |
| 545 | (4R,5S,6R)-6-((R)-1-(2-(1H-tetrazol-1-yl)acetamido)ethyl)-3-((3S,5S)-5-((3R,4S)-3-guanidino-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.10 (d, 3H), 1.24 (d, 3H), 1.93 (m, 1H), 2.95-2.99 (m, 2H), 3.24-3.26 (m, 2H), 3.37-3.39 (m, 1H), 3.51-3.56 (m, 2H), 3.66-3.75 (m, 2H), 3.85-3.99 (m, 2H), 4.06-4.07 (m, 2H), 4.31-4.39 (m, 2H), 5.31-5.33 (m, 2H), 9.18 (s, 1H) C23H33N11O6S HPLC 98.2% Mass (M + 1) 592.2 |
| 546 | (4R,5S,6R)-6-((R)-1-(2-(1H-tetrazol-1-yl)acetamido)ethyl)-3-((3S,5S)-5-((3S,4R)-3-guanidino-4-hydroxypyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.08 (d, 3H), 1.21 (d, 3H), 1.88-1.89 (m, 1H), 2.91-2.95 (m, 2H), 3.19-3.21 (m, 2H), 3.33-3.35 (m, 1H), 3.47-3.52 (m, 2H), 3.62-3.71 (m, 2H), 3.81-3.95 (m, 2H), 4.02-4.03 (m, 2H), 4.27-4.35 (m, 2H), 5.27-5.29 (m, 2H), 9.14 (s, 1H) C23H33N11O6S HPLC 92.6% Mass (M + 1) 592.2 |
| 547 | (4R,5S,6R)-6-((R)-1-(2-(1H-tetrazol-1-yl)acetamido)ethyl)-3-((3S,5S)-5-((3aS,5R,6S)-5-amino-6-hydroxy-3a-(hydroxymethyl)octahydro-cyclopenta[c]pyrrole-2-carbonyl)pyrrolidin-3-ylthio)-4-methyl-7-oxo-1-azabicyclo-[3.2.0]-hept-2-ene-2-carboxylic acid | $^1$HNMR (D$_2$O) - 1.20 (d, 3H), 1.21 (d, 3H), 1.80 (m, 1H), 1.86-1.96 (m, 2H), 2.08 (m, 2H), 2.48-2.54 (m, 2H), 2.87-2.93 (m, 2H), 3.21-3.28 (m, 3H), 3.38 (m, 2H), 3.47 (m, 1H), 3.52-3.57 (m, 1H), 3.82-3.88 (m, 1H), 4.01-4.03 (m, 1H), 4.08 (m, 1H), 4.28-4.29 (m, 1H), 4.31 (m, 1H), 5.30-5.31 (m, 2H), 9.15 (s, 1H) C26H37N9O7S HPLC 90.9% Mass (M + 1) 620.6 |
| 548 | (4R,5S,6R)-6-((R)-1-(2-(1H-tetrazol-1-yl)acetamido)ethyl)-3-((3S,5S)-5-((2S,3R,4R)-3-amino-4-hydroxy-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.18 (d, 3H), 1.23 (d, 3H), 1.89-1.93 (m, 1H), 2.93-2.96 (m, 1H), 3.21-3.25 (m, 1H), 3.31-3.34 (m, 2H), 3.47-3.48 (m, 2H), 3.51 (m, 2H), 3.57-3.59 (m, 1H), 3.61-3.69 (m, 1H), 3.73-3.88 (m, 2H), 4.03-4.08 (m, 2H), 4.29 (m, 1H), 4.32-4.39 (m, 1H), 5.31 (m, 2H), 9.16 (s, 1H) C23H33N9O7S HPLC 97.9% Mass (M + 1) 580.4 |

| Example | Structure | Analytical Data |
|---|---|---|
| 549 | 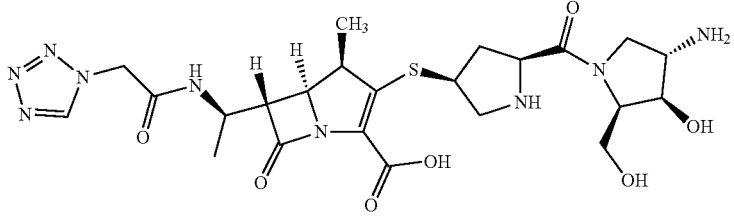 [SMILES: C[C@@H](NC(=O)Cn1cnnn1)[C@H]1C(=O)N2C(C(=O)O)=C(S[C@@H]3CN[C@H](C(=O)N4C[C@H](N)[C@@H](O)[C@H]4CO)C3)[C@H](C)[C@H]12]<br>(4R,5S,6R)-6-((R)-1-(2-(1H-tetrazol-1-yl)acetamido)ethyl)-3-((3S,5S)-5-((2R,3R,4S)-4-amino-3-hydroxy-2-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.16 (d, 3H), 1.21 (d, 3H), 1.88-1.92 (m, 1H), 2.95-2.98 (m, 1H), 3.23-3.27 (m, 1H), 3.33-3.36 (m, 2H), 3.49-3.50 (m, 2H), 3.53 (m, 2H), 3.59-3.61 (m, 1H), 3.63-3.71 (m, 1H), 3.75-3.90 (m, 2H), 4.05-4.10 (m, 2H), 4.31 (m, 1H), 4.34-4.41 (m, 1H), 5.33 (m, 2H), 9.17 (s, 1H) C23H33N9O7S<br>HPLC 99% Mass (M + 1) 580.4 |
| 550 | 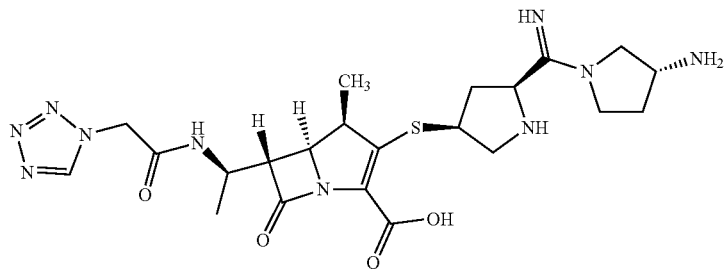 [SMILES: C[C@@H](NC(=O)Cn1cnnn1)[C@H]1C(=O)N2C(C(=O)O)=C(S[C@@H]3CN[C@H](C(=N)N4CC[C@@H](N)C4)C3)[C@H](C)[C@H]12]<br>(4R,5S,6R)-6-((R)-1-(2-(1H-tetrazol-1-yl)acetamido)ethyl)-3-((3S,5S)-5-((3aR,6aR)-3a-(hydroxymethyl)octahydropyrrolo[3,4-c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.09 (d, 3H), 1.24 (d, 3H), 1.81 (m, 1H), 2.19 (m, 1H), 2.43 (m, 1H), 2.76-2.80 (m, 2H), 3.24-3.28 (m, 1H), 3.44-3.46 (m, 3H), 3.55-3.64 (m, 3H), 3.84 (m, 2H), 4.01-4.03 (m, 1H), 4.28-4.32 (m, 2H), 5.31-5.32 (m, 2H), 9.16 (s,1H) C22H32N10O4S<br>HPLC 94.7% Mass (M + 1) 533.2 |
| 551 | 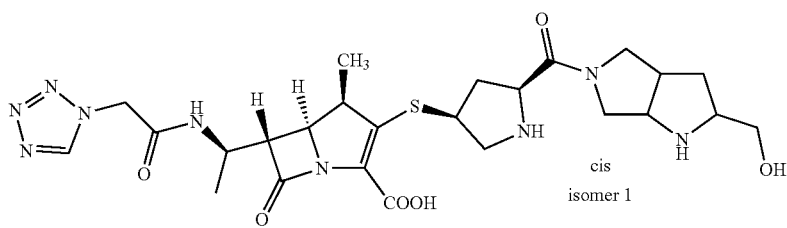 [SMILES: C[C@@H](NC(=O)Cn1cnnn1)[C@H]1C(=O)N2C(C(=O)O)=C(S[C@@H]3CN[C@H](C(=O)N4CC5CC(CO)NC5C4)C3)[C@H](C)[C@H]12]<br>(4R,5S,6R)-6-((R)-1-(2-(1H-tetrazol-1-yl)acetamido)ethyl)-3-((3S,5S)-5-(2-(hydroxymethyl)octahydropyrrolo[3,4-b]pyrrole-5-carbonyl)pyrrolidin-3-ylthio)-4-methyl-7-oxo-1-azabicyclo[3.2.0]hept-2-ene-2-carboxylic | $^1$HNMR (D$_2$O) - 1.09 (d, 3H), 1.24 (d, 3H), 1.99-2.03 (m, 3H), 2.86-2.87 (m, 3H), 3.25-3.35 (m, 4H), 3.46-3.48 (m, 3H), 3.61-3.64 (m, 2H), 3.74-3.87 (m, 3H), 4.03-4.05 (m, 1H), 4.29-4.32 (m, 1H), 4.40-4.42 (m, 1H), 5.31-5.32 (m, 2H), 9.16 (s, 1H) C25H35N9O6S<br>HPLC 97% Mass (M + 1) 590.1 |
| 552 | 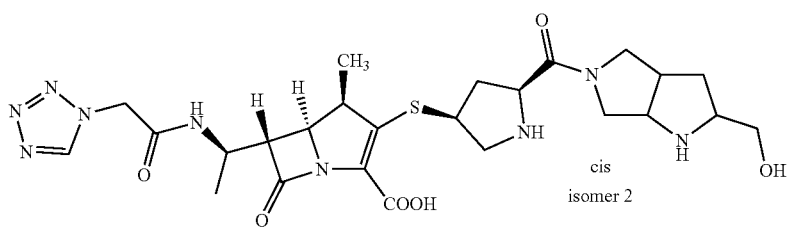 [SMILES: C[C@@H](NC(=O)Cn1cnnn1)[C@H]1C(=O)N2C(C(=O)O)=C(S[C@@H]3CN[C@H](C(=O)N4CC5CC(CO)NC5C4)C3)[C@H](C)[C@H]12]<br>(4R,5S,6R)-6-((R)-1-(2-(1H-tetrazol-1-yl)acetamido)ethyl)-3-(3S,5S)-5-((2S,3aS,6aS)-2-(hydroxymethyl)octahydropyrrolo[3,4-b]pyrrole-5-carbonyl)pyrrolidin-3-ylthio)-4-methyl-7-oxo-1-azabicyclo[3.2.0]hept-2-ene-2-carboxylic acid | $^1$HNMR (D$_2$O) - 1.10 (d, 3H), 1.25 (d, 3H), 2.01-2.05 (m, 3H), 2.88-2.89 (m, 3H), 3.27-3.37 (m, 4H), 3.48-3.50 (m, 3H), 3.63-3.66 (m, 2H), 3.76-3.89 (m, 3H), 4.05-4.07 (m, 1H), 4.31-4.34 (m, 1H), 4.42-4.44 (m, 1H), 5.33-5.34 (m, 2H), 9.17 (s, 1H) C25H35N9O6S HPLC 93.2% Mass (M + 1) 590.1 |

| Example | Structure | Analytical Data |
|---|---|---|
| 553 | (4R,5S,6R)-6-((R)-1-(2-(1H-tetrazol-1-yl)acetamido)ethyl)-3-((3S,5S)-5-((3R,4R)-4-amino-3-hydroxypiperidine-1-carbonyl)pyrrolidin-3-ylthio)-4-methyl-7-oxo-1-azabicyclo[3.2.0]hept-2-ene-2-carboxylic acid<br>trans isomer 1 | ¹HNMR (D₂O) - 1.16 (d, 3H), 1.24 (d, 3H), 1.50-1.56 (m, 1H), 1.75-1.78 (m, 2H), 2.03-2.06 (m, 1H), 2.81-2.87 (m, 2H), 2.96-2.99 (m, 1H), 3.15-3.23 (m, 3H), 3.41-3.48 (m, 2H), 3.74 (m, 2H), 3.87 (m, 1H), 4.02-4.05 (m, 1H), 4.29 (m, 1H), 4.31-4.32 (m, 1H), 5.31-5.32 (m, 2H), 9.16 (s, 1H) C23H33N9O6S HPLC 98.4% Mass (M + 1) 564.1 |
| 554 | (4R,5S,6R)-6-((R)-1-(2-(1H-tetrazol-1-yl)acetamido)ethyl)-3-((3S,5S)-5-((3S,4S)-4-amino-3-hydroxypiperidine-1-carbonyl)-pyrrolidin-3-ylthio)-4-methyl-7-oxo-1-azabicyclo[3.2.0]hept-2-ene-2-carboxylic acid<br>trans isomer 2 | ¹HNMR (D₂O) - 1.17 (d, 3H), 1.25 (d, 3H), 1.52-1.58 (m, 1H), 1.77-1.80 (m, 2H), 2.05-2.08 (m, 1H), 2.83-2.89 (m, 2H), 2.98-3.01 (m, 1H), 3.17-3.25 (m, 3H), 3.43-3.50 (m, 2H), 3.76 (m, 2H), 3.89 (m, 1H), 4.04-4.07 (m, 1H), 4.31 (m, 1H), 4.33-4.34 (m, 1H), 5.33-5.34 (m, 2H), 9.18 (s, 1H) C23H33N9O6S HPLC 98.4% Mass (M + 1) 564.1 |
| 555 | (4R,5S,6R)-6-((R)-1-(2-(1H-tetrazol-1-yl)acetamido)ethyl)-3-((3S,5S)-5-(6a-(hydroxymethyl)octahydropyrrolo[3,4-b]pyrrole-5-carbonyl)pyrrolidin-3-ylthio)-4-methyl-7-oxo-1-azabicyclo[3.2.0]hept-2-ene-2-carboxylic acid<br>cis isomer 1 | ¹HNMR (D₂O) - 1.09 (d, 3H), 1.24 (d, 3H), 1.82-1.90 (m, 5H), 2.30-2.33 (m, 1H), 2.88-2.91 (m, 2H), 3.22-3.38 (m, 2H), 3.41-3.49 (m, 3H), 3.58-3.65 (m, 2H), 3.78-3.79 (m, 3H), 3.92-3.98 (m, 2H), 4.04-4.06 (m, 1H), 5.32-5.3 (d, 2H), 9.17 (s, 1H) C25H35N9O6S HPLC 97.5% Mass (M + 1) 590.2 |
| 556 | (4R,5S,6R)-6-((R)-1-(2-(1H-tetrazol-1-yl)acetamido)ethyl)-3-((3S,5S)-5-(6a-(hydroxymethyl)octahydropyrrolo[3,4-b]pyrrole-5-carbonyl)pyrrolidin-3-ylthio)-4-methyl-7-oxo-1-azabicyclo[3.2.0]hept-2-ene-2-carboxylic acid<br>cis isomer 2 | ¹HNMR (D₂O) - 1.16 (d, 3H), 1.3 (d, 3H), 1.88-1.96 (m, 5H), 2.34-2.37 (m, 1H), 2.92-2.95 (m, 2H), 3.26-3.42 (m, 2H), 3.44-3.53 (m, 3H), 3.62-3.69 (m, 2H), 3.82-3.83 (m, 3H), 4.01-4.07 (m, 2H), 4.12-4.14 (m, 1H), 5.38-5.36 (d, 2H), 9.25 (s, 1H) C25H35N9O6S HPLC 97.9% Mass (M + 1) 590.6 |
| 557 | (4R,5S,6R)-6-((R)-1-(2-(1H-tetrazol-1-yl)acetamido)ethyl)-3-(5-oxa-2-azaspiro[3.4]octan-7-ylthio)-4-methyl-7-oxo-1-azabicyclo-[3.2.0]hept-2-ene-2-carboxylic acid<br>Isomer 1 | ¹HNMR (D₂O) - 1.09 (d, 3H), 1.23 (d, 3H), 1.89 (m, 1H), 2.22-2.26 (m, 1H), 2.56-2.62 (m, 1H), 3.15-3.18 (m, 1H), 3.45-3.47 (m, 1H), 3.77-3.84 (m, 2H), 4.01-4.03 (m, 1H), 4.08-4.09 (m, 1H), 4.17-4.32 (m, 2H), 4.17-4.32 (m, 2H), 5.26-5.36 (d, 2H), 9.16 (s, 1H) C19H25N7O5S HPLC 90.3% Mass (M + 1) 464.1 |

| Example | Structure | Analytical Data |
|---|---|---|
| 558 | (4R,5S,6R)-6-((R)-1-(2-(1H-tetrazol-1-yl)acetamido)ethyl)-3-(5-oxa-2-azaspiro[3.4]octan-7-ylthio)-4-methyl-7-oxo-1-azabicyclo[3.2.0]hept-2-ene-2-carboxylic acid | $^1$HNMR (D$_2$O) - 1.11 (d, 3H), 1.25 (d, 3H), 1.91 (m, 1H), 2.24-2.28 (m, 1H), 2.58-2.64 (m, 1H), 3.17-3.20 (m, 1H), 3.47-3.49 (m, 1H), 3.79-3.86 (m, 2H), 4.03-4.05 (m, 1H), 4.10-4.11 (m, 1H), 4.19-4.34 (m, 2H), 4.19-4.34 (m, 2H), 5.28-5.38 (d, 2H), 9.18 (s, 1H) C19H25N7O5S HPLC 90% Mass (M + 1) 464.1 |
| 559 | (4R,5S,6R)-6-((R)-1-(2-(1H-tetrazol-1-yl)acetamido)ethyl)-3-((3S,5S)-5-(5-carbamimidoyloctahydro-1H-pyrrolo[3,2-c]pyridine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.19 (d, 3H), 1.21 (d, 3H), 1.68-1.69 (m, 1H), 1.83-1.87 (m, 3H), 2.02-2.09 (m, 4H), 2.48-2.52 (m, 1H), 2.89-2.90 (m, 1H), 3.01-3.17 (m, 2H), 3.20-3.29 (m, 1H), 3.44-3.70 (m, 3H), 3.71-3.90 (m, 1H), 4.00-4.02 (m, 1H), 4.21-4.30 (m, 3H), 4.47-4.70 (m, 1H), 5.29-5.33 (m, 2H), 9.14 (s, 1H) C26H37N11O5S HPLC 98.7% Mass (M + 1) 616.2 |
| 560 | (4R,5S,6R)-6-((R)-1-(2-(1H-tetrazol-1-yl)acetamido)ethyl)-3-((3S,5S)-5-(5-carbamimidoyloctahydro-1H-pyrrolo[3,2-c]pyridine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.20 (d, 3H), 1.23 (d, 3H), 1.72-1.73 (m, 1H), 1.87-1.71 (m, 3H), 2.06-2.13 (m, 4H), 2.52-2.56 (m, 1H, 2.93-2.94 (m, 1H), 3.05-3.21 (m, 2H), 3.24-3.33 (m, 1H), 3.48-3.74 (m, 3H), 3.76-3.95 (m, 1H), 4.04-4.06 (m, 1H), 4.25-4.34 (m, 3H), 4.51-4.74 (m, 1H), 5.33-5.37 (m, 2H), 9.15 (s, 1H) C26H37N11O5S HPLC 98.7% Mass (M + 1) 616.2 |
| 561 | (4R,5S,6R)-6-((R)-1-(2-(1H-tetrazol-1-yl)acetamido)ethyl)-3-((3S,5S)-5-(6a-(hydroxymethyl)octahydropyrrolo[3,4-b]-pyrrole-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.21 (d, 3H), 1.69-1.81 (m, 3H), 2.19-2.20 (m, 1H), 2.81-2.82 (m, 1H), 2.99-3.01 (m, 1H), 3.09-3.22 (m, 3H), 3.37-3.52 (m, 4H), 3.62-3.66 (m, 4H), 3.81-3.82 (m, 1H), 3.93-3.96 (m, 2H), 4.28-4.29 (m, 1H), 5.30-5.31 (d, 2H), 9.14 (s, 1H) C25H35N9O6S HPLC 90.4% Mass (M + 1) 590.4 |

-continued

| Example | Structure | Analytical Data |
|---|---|---|
| 562 | 5-((2S,4S)-4-((4R,5S,6R)-6-((R)-1-(2-(1H-tetrazol-1-yl)acetamido)ethyl)-2-carboxy-4-methyl-7-oxo-1-azabicyclo[3.2.0]hept-2-en-3-yl-thio)pyrrolidine-2-carbonyl)octahydro-1H-pyrrolo[3,4-c]pyridine-3a-carboxylic acid (cis isomer 1) | ¹HNMR (D₂O) - 1.07 (d, 3H), 1.21 (d, 3H), 1.37-1.38 (m, 1H), 1.60-1.61 (m, 1H), 1.81-2.09 (m, 4H), 3.11-3.35 (m, 4H), 3.44-3.47 (m, 2H), 3.52-3.57 (m, 3H), 3.60-3.66 (m, 2H), 3.84-3.88 (m, 1H), 3.91-4.03 (m, 1H), 4.87-5.29 (m, 2H), 5.30-5.46 (m, 2H), 9.14 (s, 1H) C26H35N9O7S HPLC 94.7% Mass (M + 1) 618.3 |
| 563 | 5-((2S,4S)-4-((4R,5S,6R)-6-((R)-1-(2-(1H-tetrazol-1-yl)acetamido)ethyl)-2-carboxy-4-methyl-7-oxo-1-azabicyclo[3.2.0]hept-2-en-3-yl-thio)pyrrolidine-2-carbonyl)octahydro-1H-pyrrolo[3,4-c]pyridine-3a-carboxylic acid (cis isomer 2) | ¹HNMR (D₂O) - 1.09 (d, 3H), 1.23 (d, 3H), 1.41-1.42 (m, 1H), 1.64-1.65 (m, 1H), 1.85-2.13 (m, 4H), 3.15-3.39 (m, 4H), 3.48-3.51 (m, 2H), 3.56-3.61 (m, 3H), 3.64-3.70 (m, 2H), 3.88-3.92 (m, 1H), 3.95-4.07 (m, 1H), 4.91-5.33 (m, 2H), 5.34-5.50 (m, 2H), 9.15 (s, 1H) C26H35N9O7S HPLC 94.7% Mass (M + 1) 618.3 |
| 564 | (4R,5S,6R)-6-((R)-1-(2-(1H-tetrazol-1-yl)acetamido)ethyl)-3-((3S,5S)-5-((1S,7R)-3,8-Diaza-tricyclo[5.2.1.01,5]decane-3-carbonyl)-pyrrolidin-3-ylthio)-4-methyl-7-oxo-1-azabicyclo[3.2.0]hept-2-ene-2-carbnxylic acid | ¹HNMR (D₂O) - 1.07 (d, 3H), 1.21 (d, 3H), 1.71-1.79 (m, 3H), 1.85-2.05 (m, 2H), 2.33-2.45 (m, 1H), 2.82-2.84 (m, 1H), 2.98-3.01 (m, 1H), 3.12-3.27 (m, 3H), 3.38-3.44 (m, 2H), 3.61-3.66 (m, 1H), 3.73-3.75 (m, 2H), 3.81-3.89 (m, 1H), 4.00-4.02 (m, 1H), 4.10-4.20 (m, 2H), 4.30-4.47 (m, 2H), 5.25-5.34 (d, 2H), 9.13 (s, 1H) C26H35N9O5S HPLC 97.9% Mass (M + 1) 586.3 |
| 565 | (4R,5S,6R)-6-((R)-1-(2-(1H-tetrazol-1-yl)acetamido)ethyl)-3-((3S,5S)-5-((3S,4R)-3-amino-4-guanidinopyrrolidine-1-carbonyl)-pyrrolidin-3-ylthio)-4-methyl-7-oxo-1-azabicyclo[3.2.0]hept-2-ene-2-carboxylic acid | ¹HNMR (D₂O) - 1.09 (d, 3H), 1.24 (d, 3H), 1.81-1.89 (m, 2H), 2.86-2.88 (m, 1H), 3.24-3.30 (m, 2H), 3.36-3.48 (m, 3H), 3.55-3.68 (m, 3H), 3.70-3.75 (m, 1H), 3.80-3.89 (m, 1H), 4.03-4.05 (m, 1H), 4.15-4.70 (m, 2H), 5.27-5.36 (d, 2H), 9.16 (s, 1H) C23H34N12O5S HPLC 96.9% Mass (M + 1) 591.2 |

| Example | Structure | Analytical Data |
|---|---|---|
| 566 | (4R,5S,6R)-6-((R)-1-(2-(1H-tetrazol-1-yl)acetamido)ethyl)-3-((3S,5S)-5-(3-guanidinoazetidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.22 (d, 3H), 1.79-1.88 (m, 2H), 2.70-2.72 (m, 1H), 3.12-3.20 (m, 2H), 3.30-3.46 (m, 2H), 3.80-3.92 (m, 2H), 4.00-4.02 (m, 1H), 4.13-4.29 (m, 2H), 4.42-4.54 (m, 3H), 5.30-5.35 (d, 2H), 9.15 (s, 1H) C22H31N11O5S HPLC 97.2% Mass (M + 1) 562.3 |
| 567 | (4R,5S,6R)-6-((R)-1-(2-(1H-tetrazol-1-yl)acetamido)ethyl)-3-((3S,5S)-5-((R)-3-(2-guanidinoacetamido)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.21 (d, 3H), 1.78-1.87 (m, 3H), 1.96-1.98 (m, 1H), 2.09-2.16 (m, 2H), 2.81-2.83 (m, 1H), 3.19-3.25 (m, 2H), 3.46-3.48 (m, 3H), 3.60-3.63 (m, 1H), 3.83-3.87 (m, 3H), 4.01-4.02 (m, 1H), 4.21-4.32 (m, 2H), 5.24-5.33 (d, 2H), 9.14 (s, 1H) C25H36N12O6S HPLC 98.1% Mass (M + 1) 633.1 |
| 568 | (4R,5S,6R)-3-((3S,5S)-5-((R)-3-aminopyrrolidine-1-carbonyl)pyrroldin-3-ylthio)-6-((R)-1-(2-(azetidin-3-yl)acetamido)ethyl)-4-methyl-7-oxo-1-azabicyclo[3.2.0]hept-2-ene-2-carboxylic acid | $^1$HNMR (D$_2$O) - 1.18 (d, 3H), 1.22 (d, 3H), 1.73-1.78 (m, 1H), 1.88-2.20 (m, 2H), 2.41-2.44 (m, 2H), 2.54-2.66 (m, 3H), 2.79-2.82 (m, 2H), 3.11-3.14 (m, 1H), 3.26-3.37 (m, 3H), 3.53-3.68 (m, 2H), 3.70-3.74 (m, 3H), 3.81-3.84 (m, 3H), 3.90-3.95 (m, 1H), 3.97-4.04 (m, 1H), C24H36N6O5S HPLC 94.3% Mass (M + 1) 521.2 |
| 569 | (4R,5S,6R)-6-((R)-1-(2-(1H-tetrazol-1-yl)acetamido)ethyl)-3-((3S,5S)-5-(1-Carbamimidoyloctahydro-pyrrolo[3,4-b]-pyrrole-5-carbonyl)pyrrolidin-3-ylthio)-4-methyl-7-oxo-1-azabicyclo[3.2.0]hept-2-ene-2-carboxylic acid | $^1$HNMR (D$_2$O) - 1.06 (d, 3H), 1.20 (d, 3H), 1.78-1.79 (m, 1H), 1.86-1.87 (m, 2H), 2.87-2.89 (m, 1H), 3.19-3.27 (m, 4H), 3.43-3.49 (m, 4H), 3.59-3.65 (m, 1H), 3.72-3.77 (m, 2H), 3.87-3.88 (m, 1H), 3.99-4.01 (m, 1H), 4.37-4.43 (m, 2H), 5.28-5.32 (d, 2H), 9.13 (s, 1H) C25H35N11O5S HPLC 91.1% Mass (M + 1) 602.1 |
| 570 | (4R,5S,6R)-6-((R)-1-(2-(1H-tetrazol-1-yl)acetamido)ethyl)-3-((3S,5S)-5-(1-carbamimidoyl-octahydropyrrolo[3,4-b]-pyrrole-5-carbonyl)pyrrolidin-3-yl-thio)-4-methyl-7-oxo-1-azabicyclo[3.2.0]hept-2-ene-2-carboxylic acid | $^1$HNMR (D$_2$O) - 1.08 (d, 3H), 1.22 (d, 3H), 1.82-1.83 (m, 1H), 1.90-1.91 (m, 2H), 2.91-2.93 (m, 1H), 3.23-3.31 (m, 4H), 3.47-3.53 (m, 4H), 3.63-3.69 (m, 1H), 3.76-3.81 (m, 2H), 3.91-3.92 (m, 1H), 4.03-4.05 (m, 1H), 4.29-4.33 (m, 1H), 4.41-4.47 (m, 2H), 5.32-5.36 (d, 2H), 9.13 (s, 1H) C25H35N11O5S HPLC 96.9% Mass (M + 1) 602.1 |

| Example | Structure | Analytical Data |
|---|---|---|
| 571 | 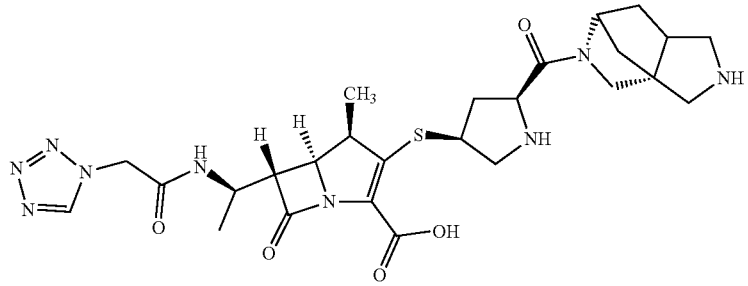<br>(4R,5S,6R)-6-((R)-1-(2-(1H-tetrazol-1-yl)acetamido)ethyl)-3-((3S,5S)-5-((1R,7R)-3,8-Diaza-tricyclo[5.2.1.01,5]decane-8-carbonyl)-pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.21 (d, 3H), 1.67-1.79 (m, 4H), 1.93-1.98 (m, 1H), 2.39-2.40 (m, 1H), 2.77-2.78 (m, 1H), 2.89-2.95 (m, 1H), 3.14-3.15 (m, 1H), 3.22-3.23 (m, 1H), 3.29-3.37 (m, 3H), 3.43-3.45 (m, 2H), 3.51-3.57 (m, 1H), 3.60-3.67 (m, 1H), 3.80-3.81 (m, 1H), 4.00-4.02 (m, 1H), 4.14-4.17 (m, 1H), 4.27-4.33 (m, 2H), 5.25-5.34 (m, 2H), 9.14 (s, 1H) C26H35N9O5S HPLC 97.9% Mass (M + 1) 586.2 |
| 572 | 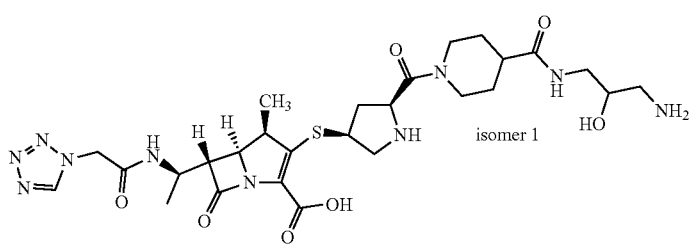 [SMILES: C[C@@H](NC(=O)Cn1cnnn1)[C@H]1C(=O)N2C(C(=O)O)=C(S[C@@H]3CN[C@H](C(=O)N4CCC(C(=O)NCC(O)CN)CC4)C3)[C@H](C)[C@H]12]<br>(4R,5S,6R)-6-((R)-1-(2-(1H-tetrazol-1-yl)acetamido)ethyl)-3-((3S,5S)-5-(4-(3-amino-2-hydroxypropylcarbamoyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.15 (d, 3H), 1.22 (d, 3H), 1.45-1.52 (m, 2H), 1.67-1.69 (m, 1H), 1.78-1.87 (m, 3H), 2.52-2.53 (m, 1H), 2.74-2.80 (m, 3H), 2.99-3.02 (m, 1H), 3.02-3.22 (m, 3H), 3.35-3.36 (m, 1H), 3.38-3.44 (m, 1H), 3.60-3.64 (m, 1H), 3.74-3.77 (m, 1H), 3.84-3.85 (m, 2H), 4.00-4.02 (m, 1H), 4.21-4.70 (m, 3H), 5.25-5.34 (m, 2H), 9.13 (s, 1H) C27H40N10O7S HPLC 96.5% Mass (M + 1) 649.2 |
| 573 | 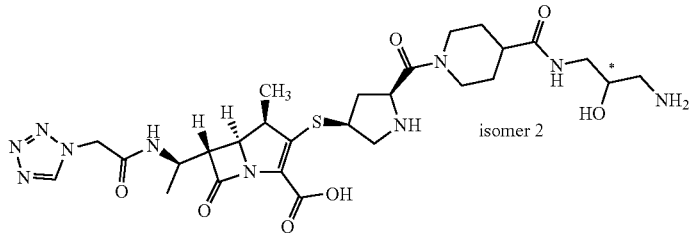 [SMILES: C[C@@H](NC(=O)Cn1cnnn1)[C@H]1C(=O)N2C(C(=O)O)=C(S[C@@H]3CN[C@H](C(=O)N4CCC(C(=O)NCC(O)CN)CC4)C3)[C@H](C)[C@H]12]<br>(4R,5S,6R)-6-((R)-1-(2-(1H-tetrazol-1-yl)acetamido)ethyl)-3-((3S,5S)-5-(4-(3-amino-2-hydroxypropylcarbamoyl)piperidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.24 (d, 3H), 1.48-1.55 (m, 2H), 1.70-1.72 (m, 1H), 1.81-1.90 (m, 3H), 2.55-2.56 (m, 1H), 2.77-2.83 (m, 3H), 3.02-3.05 (m, 1H), 3.05-3.25 (m, 3H), 3.38-3.39 (m, 1H), 3.41-3.47 (m, 1H), 3.63-3.67 (m, 1H), 3.77-3.81 (m, 1H), 3.87-3.88 (m, 2H), 4.03-4.05 (m, 1H), 4.24-4.73 (m, 3H), 5.28-5.37 (m, 2H), 9.15 (s, 1H) C27H40N10O7S HPLC 97.9% Mass (M + 1) 648.73 |
| 574 | 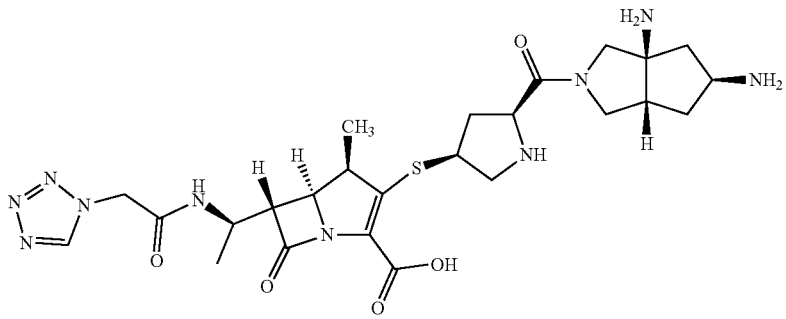 [SMILES: C[C@@H](NC(=O)Cn1cnnn1)[C@H]1C(=O)N2C(C(=O)O)=C(S[C@@H]3CN[C@H](C(=O)N4C[C@H]5C[C@H](N)C[C@@]5(N)C4)C3)[C@H](C)[C@H]12]<br>(4R,5S,6R)-6-((R)-1-(2-(1H-tetrazol-1-yl)acetamido)ethyl)-3-((3S,5S)-5-((3aS,5S,6aR)-3a,5-diaminooctahydrocyclo-penta[c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.07 (d, 3H), 1.21 (d, 3H), 1.64-1.69 (m, 2H), 1.70-1.78 (m, 2H), 1.84-1.95 (m, 1H), 2.09-2.10 (m, 1H), 2.33-2.35 (m, 1H), 2.42-2.46 (m, 1H), 2.76-2.77 (m, 1H), 3.08-3.09 (m, 1H), 3.18-3.19 (m, 1H), 3.20-3.22 (m, 2H), 3.27-3.30 (m, 1H), 3.43-3.46 (m, 1H), 3.44-3.50 (m, 2H), 3.60-3.66 (m, 1H), 3.91-3.99 (m, 2H), 5.27-5.29 (m, 2H), 9.14 (s, 1H) C25H36N10O5S HPLC 91.8% Mass (M + 1) 589.1 |

| Example | Structure | Analytical Data |
|---|---|---|
| 575 | (4R,5S,6R)-6-((R)-1-(2-(1H-tetrazol-1-yl)acetamido)ethyl)-3-((3S,5S)-5-(((R)-3-aminopyrrolidin-1-yl)(imino)-methylcarbamoyl)-pyrrolidin-3-yl-thio)-4-methyl-7-oxo-1-azabicyclo-[3.2.0]-hept-2-ene-2-carboxylic acid | ¹HNMR (D₂O) - 1.05 (d, 3H), 1.20 (d, 3H), 1.73 (m, 1H), 1.94 (m, 2H), 2.04 (m, 1H), 2.32 (m, 2H), 2.49 (m, 1H), 3.24 (m, 2H), 3.44-3.55 (m, 3H), 3.59 (m, 1H), 3.82 (m, 1H), 4.01-4.03 (m, 1H), 4.19-4.28 (m, 1H), 4.34 (m, 1H), 5.28-5.29 (d, 2H), 9.13 (s, 1H) C23H33N11O5S HPLC 97.1% Mass (M + 1) 576.4 |
| 576 | (4R,5S,6R)-6-((R)-1-(2-(1H-tetrazol-1-yl)acetamido)ethyl)-3-((3S,5S)-5-((2S,4S)-4-guanidino-2-(hydroxymethyl)-pyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.03 (d, 3H), 1.17 (d, 3H), 1.80-1.83 (m, 2H), 2.36-2.43 (m, 1H), 2.74-2.82 (m, 1H), 3.14-3.18 (m, 2H), 3.24-3.26 (m, 1H), 3.41-3.45 (m, 2H), 3.52-3.58 (m, 1H), 3.75-3.79 (m, 2H), 3.80-3.87 (m, 1H), 3.96-3.98 (m, 1H), 4.03-4.08 (m, 2H), 4.22-4.26 (m, 1H), 4.33-4.35 (m, 1H), 5.25-5.30 (d, 2H), 9.10 (s, 1H) C24H35N11O6S HPLC 99.1% Mass (M + 1) 606.1 |
| 577 | (4R,5S,6R)-6-((R)-1-(2-(1H-tetrazol-1-yl)acetamido)ethyl)-3-((3S,5S)-5-(1-(2-aminoethyl) octahydropyrrolo[3,4-b]pyrrole-5-carbonyl)pyrrolidin-3-ylthio)-4-methyl-7-oxo-1-azabicyclo[3.2.0]hept-2-ene-2-carboxylic acid | ¹HNMR (D₂O) - 1.07 (d, 3H), 1.21 (d, 3H), 1.51 (m, 1H), 1.86 (m, 1H), 2.27 (m, 1H), 2.74-2.90 (m, 3H), 3.01-3.14 (m, 3H), 3.22 (m, 4H), 3.34-3.55 (m, 4H), 3.68 (m, 2H), 3.72 (m, 1H), 3.84 (m, 1H), 3.99-4.02 (m, 1H), 4.28-4.30 (m, 2H), 5.29 (d, 2H), 9.14 (s, 1H) C26H38N10O5S HPLC 97.9% Mass (M + 1) 603.4 |
| 578 | (4R,5S,6R)-6-((R)-1-(2-(1H-tetrazol-1-yl)acetamido)ethyl)-3-((3S,5S)-5-(1-(2-aminoethyl) octahydropyrrolo[3,4-b]pyrrole-5-carbonyl)pyrrolidin-3-ylthio)-4-methyl-7-oxo-1-azabicyclo[3.2.0]hept-2-ene-2-carboxylic acid | ¹HNMR (D₂O) - 1.09 (d, 3H), 1.23 (d, 3H), 1.53 (m, 1H), 1.88 (m, 1H), 2.29 (m, 1H), 2.76-2.92 (m, 3H), 3.03-3.16 (m, 3H), 3.24 (m, 4H), 3.36-3.57 (m, 4H), 3.70 (m, 2H), 3.74 (m, 1H), 3.86 (m, 1H), 4.01-4.04 (m, 1H), 4.30-4.32 (m, 2H), 5.31 (d, 2H), 9.16 (s, 1H) C26H38N10O5S HPLC 91.6% Mass (M + 1) 603.4 |

| Example | Structure | Analytical Data |
|---|---|---|
| 579 | (4R,5S,6R)-6-((R)-1-(2-(1H-tetrazol-1-yl)acetamido)ethyl)-3-(2-guanidinoethylthio)-4-methyl-7-oxo-1-azabicyclo[3.2.0]hept-2-ene-carboxylic acid | ¹HNMR (D₂O)-0.93 (d, 3H), 1.21 (d, 3H), 1.86 (m, 1H), 2.70-2.77 (m, 1H), 2.97-3.03 (m, 1H), 3.23-3.28 (m, 1H), 3.30-3.36 (m, 1H), 3.40-3.42 (m, 1H), 3.95-3.98 (m, 1H), 4.26-4.31 (m, 1H), 5.31-5.33 (m, 2H), 9.14 (s, 1H) C16H23N9O4S HPLC 94.4% Mass (M + 1) 438.2 |
| 580 | (4R,5S,6R)-6-((R)-1-(2-(1H-tetrazol-1-yl)acetamido)ethyl)-3-((3S,5S)-5-((3aR,6aS)-2-iminooctahydropyrrolo[3,4-d]imidazole-5-carbonyl)pyrrolidin-3-ylthio)-methyl-7-oxo-1-azabicyclo[3.2.0]hept-2-ene-2-carboxylic acid | ¹HNMR (D₂O) - 1.05 (d, 3H), 1.31 (d, 3H), 1.71-1.79 (m, 1H), 1.88-1.97 (m, 1H), 2.14-2.43 (m, 1H), 2.89-3.01 (m, 1H), 3.20-3.36 (m, 2H), 3.42-3.49 (m, 1H), 3.53-3.55 (m, 2H), 3.61-3.68 (m, 1H), 3.76-3.79 (m, 1H), 3.82-3.85 (m, 2H), 3.85-3.86 (m, 1H), 3.99-4.03 (m, 1H), 4.09-4.11 (m, 1H), 5.34-5.43 (m, 2H), 9.26 (s, 11H) C23H31N11O5S HPLC 90.3% Mass (M + 1) 574.1 |
| 581 | (4R,5S,6R)-6-((R)-1-(2-(1H-tetrazol-yl)acetamido)ethyl)-3-((3S,5S)-5-(5-guanidinooctahydroyclopenta[c]pyrrole-2-carbonyl)pyrrolidin-3-ylthio))-4-methyl-7-oxo-1-azabicyclo[3.2.0]hept-2-ene-2-carboxylic acid | ¹HNMR (D₂O) - 1.08 (d, 3H), 1.22 (d, 3H), 1.51-1.52 (m, 1H), 1.61-1.62 (m, 1H), 1.69-1.70 (m, 1H), 1.81-1.82 (m, 1H), 2.20-2.30 (m, 1H), 2.62-2.69 (m, 2H), 2.89-2.90 (m, 1H), 2.91-2.96 (m, 1H), 3.06-3.08 (m, 1H), 3.10-3.11 (m, 1H), 3.23-3.24 (m, 1H) 3.33-3.36 (m, 1H), 3.43-3.47 (m, 2H), 3.52-3.58 (m, 2H), 3.62-3.69 (m, 1H), 3.80-3.82 (m, 1H), 3.90-4.03 (m, 1H), 4.29-4.47 (m, 1H), 5.30-5.33 (d, 2H), 9.15 (s, 1H) C26H37H11O5S HPLC 93.8% Mass (M + 1) 616.2 |
| 582 | (4R,5S,6R)-6-((R)-1-(2-(1H-tetrazol-1-yl)acetamido)-ethyl)-3-((3S,5S)-5-((S)-3-guanidino-pyrrolidine-1-carbonyl)pyrrolidin-3-ylthio))-4-methyl-7-oxo-1-azabicyclo[3.2.0]hept-ene-2-carboxylic acid | ¹HNMR (D₂O) - 1.09 (d, 3H), 1.22 (d, 3H), 2.23-2.27 (m, 2H), 2.86-2.92 (m, 1H), 3.21-3.22 (m, 1H), 3.26-3.29 (m, 1H), 3.30-3.39 (m, 1H), 3.45-3.46 (m, 2H), 3.50-3.58 (m, 3H), 3.60-3.67 (m, 1H), 3.74-3.78 (m, 1H), 3.78-3.88 (m, 1H), 3.90-4.03 (m, 1H), 4.13-4.18 (m, 1H), 4.27-4.30 (m, 1H), 5.30-5.34 (d, 2H), 9.15 (s, 1H) C23H33N11O5S HPLC 97.5% Mass (M + 1) 576.1 |

| Example | Structure | Analytical Data |
|---|---|---|
| 583 | 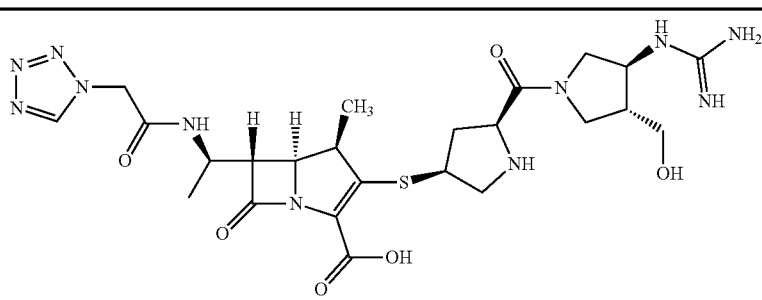<br>(4R,5S,6R)-6-((R)-1-(2-(1H-tetrazol-1-yl)acetamido)ethyl)-3-((3S,5S)-5-((3S,4R)-3-guanidino-4-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.31 (d, 3H), 1.82-1.83 (m, 1H), 1.97-1.98 (m, 1H), 2.50-2.57 (m, 1H), 2.88-2.89 (m, 1H), 3.23-3.32 (m, 2H), 3.32-3.38 (m, 2H), 3.41-3.44 (m, 1H), 3.54-3.55 (m, 1H), 3.67-3.78 (m, 2H), 3.90-3.92 (m, 2H), 4.03-4.07 (m, 2H), 4.32-4.38 (m, 2H), 5.35-5.44 (m, 2H), 9.24 (s, 1H)<br>C24H35N11O6S<br>HPLC 94.5% Mass (M + 1) 606.3 |
| 584 | 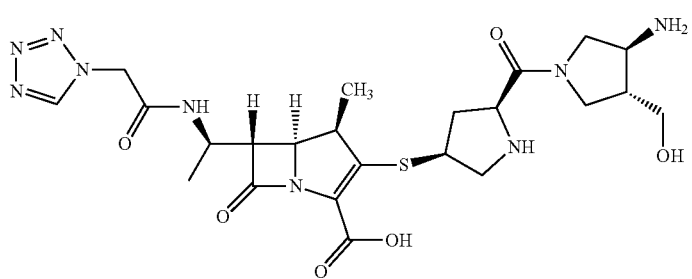 [SMILES: C[C@@H](NC(=O)Cn1cnnn1)[C@H]1C(=O)N2C(C(=O)O)=C(S[C@@H]3CN[C@H](C(=O)N4C[C@@H](CO)[C@H](N)C4)C3)[C@H](C)[C@H]12]<br>(4R,5S,6R)-6-((R)-1-(2-(1H-tetrazol-1-yl)acetamido)ethyl)-3-((3S,5S)-5-((3S,4R)-3-amino-4-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.31 (d, 3H), 1.89-1.97 (m, 2H), 2.61-2.71 (m, 2.99-3.00 (m, 2H), 3.28-3.43 (m, 2H), 3.44-3.46 (m, 1H), 3.54-3.67 (m, 4H), 3.70-3.78 (m, 3H), 3.81-3.88 (m, 1H), 3.91-3.96 (m, 1H), 3.99-4.06 (m, 1H), 5.34-5.43 (d, 2H), 9.25 (s, 1H) C23H33N9O6S<br>HPLC 94% Mass (M + 1) 564.4 |
| 585 | 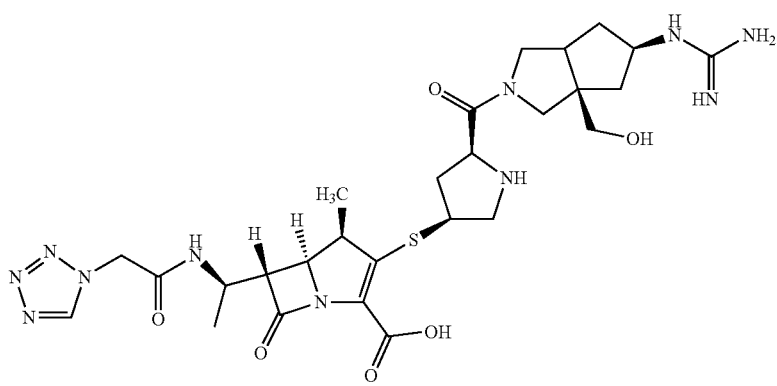 [SMILES: C[C@@H](NC(=O)Cn1cnnn1)[C@H]1C(=O)N2C(C(=O)O)=C(S[C@@H]3CN[C@H](C(=O)N4CC5C[C@@H](NC(=N)N)C[C@]5(CO)C4)C3)[C@H](C)[C@H]12]<br>(4R,5S,6R)-6-((R)-1-(2-(1H-tetrazol-1-yl)acetamido)ethyl)-3-((3S,5S)-5-((3aR,5R)-5-guanidino-3a-(hydroxymethyl)octahydrocyclopenta[c]pyrrole-2-carbonyl)pyrrolidin-3-ylthio)-4-methyl-7-oxo-1-azabicyclo[3.2.0]hept-2-ene-2-carboxylic acid | $^1$HNMR (D$_2$O) - 1.22 (d, 3H), 1.31 (d, 3H), 1.37-1.38 (m, 1H), 1.50-1.54 (m, 1H), 1.97-1.98 (m, 4H), 2.19-2.20 (m, 1H), 2.74-2.89 (m, 2H), 3.22-3.38 (m, 3H), 3.470-3.49 (m, 4H), 3.55-4.12 (m, 5H), 4.61 (m, 1H), 5.38-5.54 (d, 2H), 9.25 (s, 1H)<br>C27H39N11O6S<br>HPLC 95.8% Mass (M + 1) 646.1 |
| 586 | 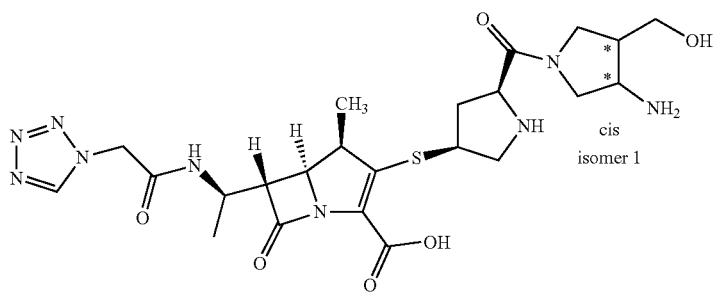 [SMILES: C[C@@H](NC(=O)Cn1cnnn1)[C@H]1C(=O)N2C(C(=O)O)=C(S[C@@H]3CN[C@H](C(=O)N4CC(N)C(CO)C4)C3)[C@H](C)[C@H]12]<br>(4R,5S,6R)-6-((R)-1-(2-(1H-tetrazol-1-yl)acetamido)ethyl)-3-((3S,5S)-5-(3-amino-4-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.31 (d, 3H), 1.82-1.96 (m, 1H), 2.74-2.95 (m, 2H), 3.27-3.33 (m, 2H), 3.41-3.44 (m, 3H), 3.51-3.53 (m, 2H), 3.66-3.77 (m, 4H), 3.83-3.86 (m, 2H), 4.38-4.80 (m, 2H), 5.34-5.43 (d, 2H), 9.23 (s, 1H)<br>C23H33N9O6S<br>HPLC 94.5% Mass (M + 1) 564.3 |

| Example | Structure | Analytical Data |
|---|---|---|
| 587 | 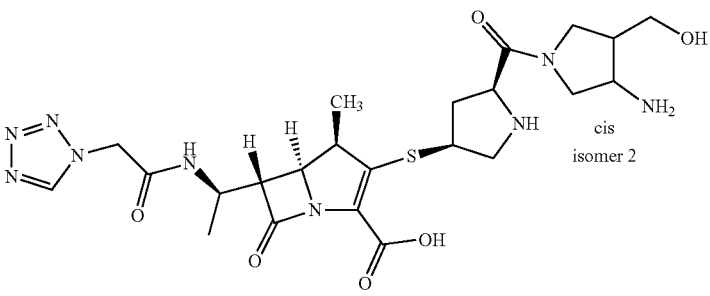 [SMILES: C[C@@H](NC(=O)Cn1cnnn1)[C@H]1C(=O)N2C(C(=O)O)=C(S[C@@H]3CN[C@H](C(=O)N4CC(N)C(CO)C4)C3)[C@H](C)[C@H]12]<br>(4R,5S,6R)-6-((R)-1-(2-(1H-tetrazol-1-yl)acetamido)ethyl)-3-((3S,5S)-5-(3-amino-4-(hydroxymethyl)pyrrolidine-1-carbonyl)pyrrolidin-3-ylthio)-4-methyl-7-oxo-1-azabicyclo[3.2.0]hept-2-ene-2-carboxylic acid | ¹HNMR (D₂O) - 1.18 (d, 3H), 1.33 (d, 3H), 1.84-1.98 (m, 1H), 2.76-2.97 (m, 2H), 3.29-3.35 (m, 2H), 3.43-3.46 (m, 3H), 3.53-3.55 (m, 2H), 3.68-3.79 (m, 4H), 3.85-3.88 (m, 2H), 4.40-4.82 (m, 2H), 5.36-5.45 (d, 2H), 9.25 (s, 1H) C23H33N9O6S<br>HPLC 98.2% Mass (M + 1) 564.3 |
| 588 | 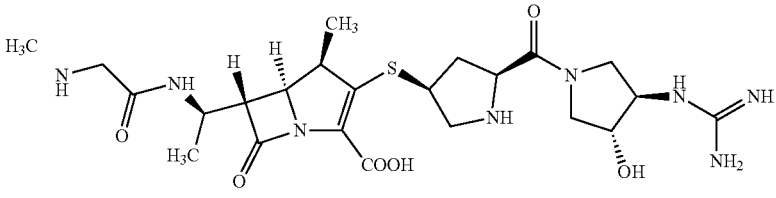<br>(4R,5S,6R)-3-((3S,5S)-5-((3R,4R)-3-guanidino-4-hydroxypyrrolidine-1-carbonyl)pyrrolidin-3-ylthio)-4-methyl-6-((R)-1-(2-(methylamino)acetamido)ethyl)-7-oxo-1-azabicyclo[3.2.0]hept-2-ene-2-carboxylic acid | ¹HNMR (D₂O) - 1.07 (d, 3H), 1.15 (d, 3H), 1.79-1.86 (m, 1H), 2.63 (s, 3H), 3.24-3.25 (m, 2H), 3.25-3.47 (m, 4H), 3.49-3.51 (m, 1H), 3.53-3.55 (m, 2H), 3.75-3.76 (m, 2H), 3.80-3.87 (m, 2H), 4.00-4.03 (m, 2H), 4.31-4.39 (m, 2H) C23H36N8O6S<br>HPLC 95.6% Mass (M + 1) 553.2 |
| 589 | 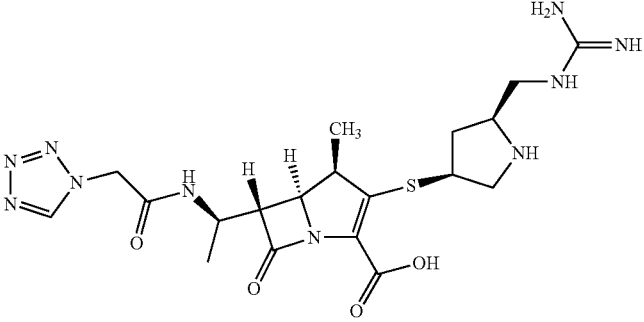 [SMILES: C[C@@H](NC(=O)Cn1cnnn1)[C@H]1C(=O)N2C(C(=O)O)=C(S[C@@H]3CN[C@H](CNC(=N)N)C3)[C@H](C)[C@H]12]<br>(4R,5S,6R)-6-((R)-1-(2-(1H-tetrazol-1-yl)acetamido)ethyl)-3-((3S,5S)-5-(guanidinomethyl)pyrrolidin-3-ylthio)-4-methyl-7-oxo-1-azabicyclo[3.2.0]hept-2-ene-2-carboxylic acid | ¹HNMR (D₂O) - 1.28 (d, 3H), 1.34 (d, 3H), 1.97-1.99 (m, 1H), 2.99 (m, 1H), 3.00 (m, 2H), 3.04 (m, 1H), 3.31-3.36 (m, 1H), 3.44-3.48 (m, 1H), 3.57-3.60 (m, 1H), 3.73-3.77 (m, 1H), 4.05 (m, 1H), 4.13-3.16 (m, 1H), 4.40-4.43 (m, 1H), 5.42 (d, 2H), 9.27 (s, 1H) C19H28N10O4S<br>HPLC 89.8% Mass (M + 1) 493.2 |
| 590 | 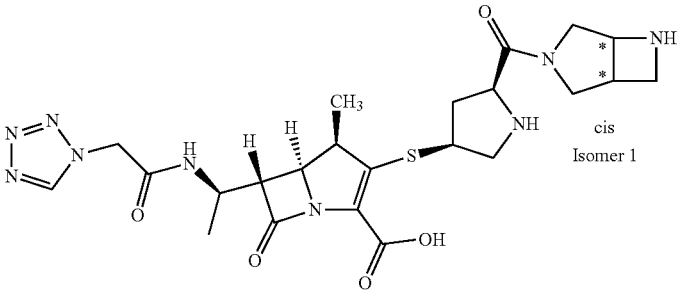 [SMILES: C[C@@H](NC(=O)Cn1cnnn1)[C@H]1C(=O)N2C(C(=O)O)=C(S[C@@H]3CN[C@H](C(=O)N4CC5CNC5C4)C3)[C@H](C)[C@H]12]<br>(4R,5S,6R)-6-((R)-1-(2-(1H-tetrazol-1-yl)acetamido)ethyl)-3-((3S,5S)-5-(3,6-diazabicyclo[3.2.0]heptane-3-carbonyl)pyrrolidin-3-ylthio)-4-methyl-7-axo-1-azabicyclo[3.2.0]hept-2-ene-2-carboxylic acid | ¹HNMR (D₂O) - 1.26 (d, 3H), 1.31 (d, 3H), 1.79-1.97 (m, 2H), 2.84-2.85 (m, 1H), 3.20-3.22 (m, 1H), 3.33-3.41 (m, 1H), 3.48-3.53 (m, 1H), 3.73-3.74 (m, 2H), 3.90-3.91 (m, 1H), 3.97-3.98 (m, 2H), 3.99-4.00 (m, 1H), 4.110-4.12 (m, 1H), 4.18-4.26 (m, 2H), 4.36-4.46 (m, 2H), 5.03-5.10 (m, 1H), 5.30-5.44 (s, 2H), 9.25 (s,1H) C23H31N9O5S<br>HPLC 96.1% Mass (M + 1) 546.2 |

US 11,180,504 B2

-continued

| Example | Structure | Analytical Data |
|---|---|---|
| 591 | 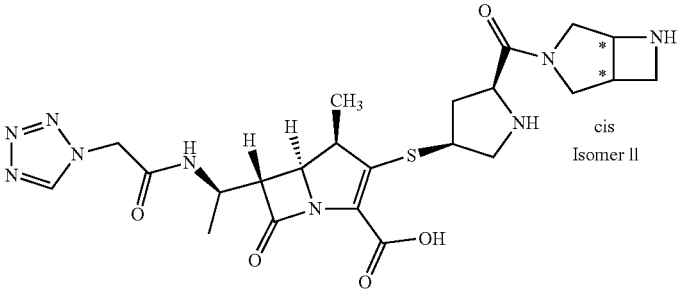 [SMILES: C[C@@H](NC(=O)Cn1cnnn1)[C@H]1C(=O)N2C(C(=O)O)=C(S[C@@H]3CN[C@H](C(=O)N4CC5CNC5C4)C3)[C@H](C)[C@H]12]<br>(4R,5S,6R)-6-((R)-1-(2-(1H-tetrazol-1-yl)acetamido)ethyl)-3-((3S,5S)-5-(3,6-diazabicyclo[3.2.0]heptane-3-carbonyl)pyrrolidin-3-ylthio)-4-methyl-7-oxo-1-azabicyclo[3.2.0]hept-2-ene-2-carboxylic acid | $^1$HNMR (D$_2$O) - 1.28(d, 3H), 1.33 (d, 3H), 1.81-1.99 (m, 2H), 2.86-2.87 (m, 1H), 3.22-3.24 (m, 1H), 3.35-3.43 (m, 1H), 3.50-3.55 (m, 1H), 3.75-3.76 (m, 2H), 3.92-3.93 (m, 1H), 3.99-4.00 (m, 2H), 4.01-4.02 (m, 1H), 4.12-4.14 (m, 1H), 4.20-4.28 (m, 2H), 4.38-4.48 (m, 2H), 5.05-5.12 (m, 1H), 5.32-5.46 (d, 2H), 9.25 (s, 1H) C23H31N9O5S HPLC 96.1% Mass (M + 1) 546.2 |
| 592 | 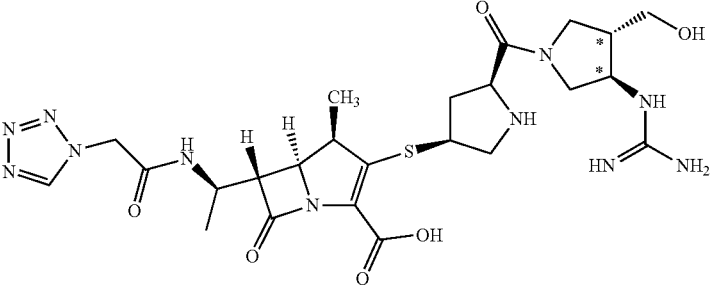 [SMILES: C[C@@H](NC(=O)Cn1cnnn1)[C@H]1C(=O)N2C(C(=O)O)=C(S[C@@H]3CN[C@H](C(=O)N4C[C@H](CO)[C@@H](NC(=N)N)C4)C3)[C@H](C)[C@H]12]<br>(4R,5S,6R)-6-((R)-1-(2-(1H-tetrazol-1-yl)acetamido)ethyl)-3-((3S,5S)-5-((3R,4S)-3-guanidino-4-diazabicyclo[3.2.0]heptane-3-(hydroxymethyl)pyrrolidine-1-carbonyl)pyrrolidin-3-ylthio)-4-methyl-7-oxo-1-azabicyclo[3.2.0]hept-2-ene-2-carboxylic acid | $^1$HNMR (D$_2$O) - 1.17 (d, 3H), 1.32 (d, 3H), 1.83-1.97 (m, 1H), 2.75-2.96 (m, 2H), 3.28-3.34 (m, 2H), 3.42-3.45 (m, 3H), 3.52-3.54 (m, 2H), 3.67-3.78 (m, 4H), 3.84-3.87 (m, 2H), 4.39-4.81 (m, 2H), 5.35-5.44 (d, 2H), 9.24 (s, 1H) C24H35N11O6S 27 HPLC 90% Mass (M + 1) 606.2 |
| 593 | 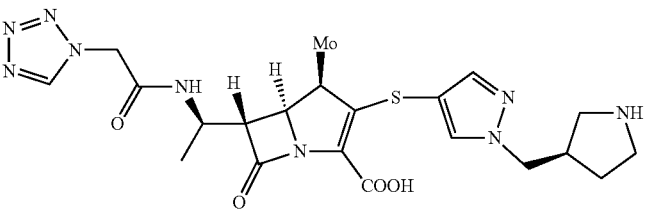<br>(4R,5S,6R)-6-((R)-1-(2-(1H-tetrazol-1-yl)acetamido)ethyl)-4-methyl-7-oxo-3-(1-((R)-pyrrolidin-3-ylmethyl)-1H-pyrazol-4-ylthio)-1-azabicyclo[3.2.0]hept-2-ene-2-carboxylic acid | $^1$HNMR (D$_2$O) - 1.97 (d, 3H), 1.29 (d, 3H), 1.78-1.80 1H), 1.94-1.98 (m, 2H), 2.14-2.22 (m, 1H), 2.86-2.96 (m, 2H), 3.05-3.10 (m, 1H), 3.34-3.44 (m, 2H), 3.96-3.99 (m, 1H), 4.31-4.33 (m, 3H), 5.36-5.40 (m, 2H), 7.70-7.73 (m, 1H), 7.93-7.97 (m, 1H), 9.23 (s, 1H) C21H27N9O4S HPLC 91.35% Mass (M + 1) 502.3 |
| 594 | 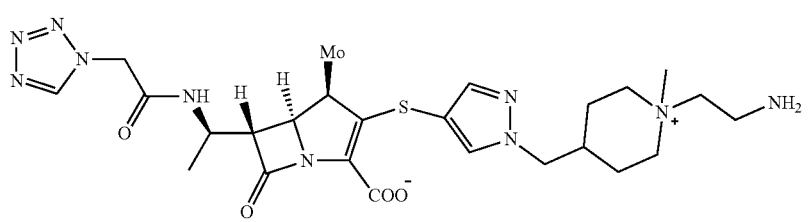<br>(4R,5S,6R)-6-((R)-1-(2-(1H-tetrazol-1-yl)acetamido)ethyl)-3-(1-((1-(2-aminoethyl)-1-methylpiperidinium-4-yl)methyl)-1H-pyrazol-4-ylthio)-4-methyl-7-oxo-1-azabicyclo[3.2.0]hept-2-ene-2-carboxylate | $^1$HNMR (D$_2$O) - 1.13 (d, 3H), 1.28 (d, 3H), 2.20-2.29 (m, 3H), 2.97 (m, 2H), 3.87-3.88 (m, 2H), 3.47-3.48 (m, 3H), 3.87-3.88 (m, 3H), 3.99-4.15 (m, 2H), 4.30 (m, 2H), 5.36 (d, 2H), 7.43-7.44 (m, 2H), 7.54-7.56 (m, 2H), 7.93 (s, 1H), 8.04 (s, 1H), 9.22 (s, 1H) C25H36N10O4S HPLC 91.4% Mass (M + 1) 573.1 |

| Example | Structure | Analytical Data |
|---|---|---|
| 595 | 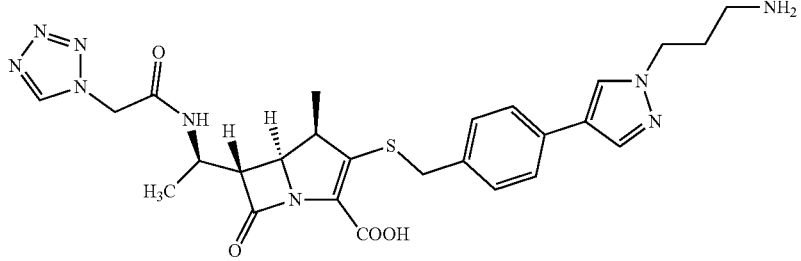 [SMILES: C[C@@H](NC(=O)Cn1cnnn1)[C@H]1C(=O)N2C(C(=O)O)=C(SCc3ccc(-c4cnn(CCCN)c4)cc3)[C@H](C)[C@H]12]<br>(4R,5S,6R)-6-((R)-1-(2-(1H-tetrazol-1-yl)acetamido)ethyl)-3-(4-(1-(3-aminopropyl)-1H-pyrazol-yl)benzylthio)-4-methyl-7-oxo-1-azabicyclo[3.2.0]hept-2-ene-2-carboxylic acid | $^1$HNMR (D$_2$O)-0.86-0.88 (d, 3H), 1.68 (d, 3H), 2.18-2.19 (m, 2H), 3.02-3.06 (m, 2H), 3.31-3.32 (m, 2H), 3.47-3.48 (m, 2H), 3.86-3.87 (m, 1H), 4.11-4.13 (m, 2H), 4.23-4.24 (m, 1H), 5.27-5.28 (m, 2H), 7.63 (m, 2H), 7.84 (m, 2H), 8.39 (s, 1H), 8.43 (s, 1H) 9.14 (s, 1H) C26H31N9O4S HPLC 94.4% Mass (M + 1) 566.2 |
| 596 | 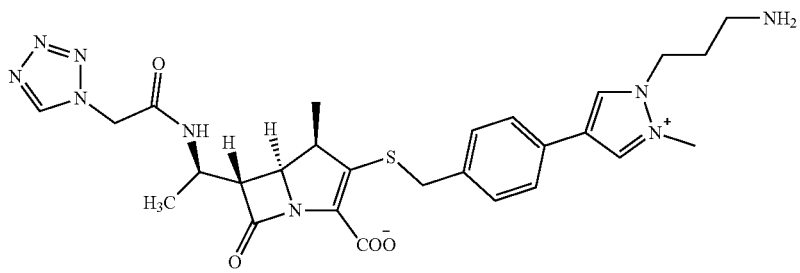<br>(4R,5S,6R)-6-((R)-1-(2-(1H-tetrazol-1-yl)acetamido)ethyl)-3-(4-(1-(3-aminopropyl)-2-methyl-1H-pyrazol-2-ium-4-yl)benzylthio)-4-methyl-7-oxo-1-azabicyclo[3.2.0]hept-2-ene-2-carboxylate | $^1$HNMR (D$_2$O) - 1.00 (d, 3H), 1.18 (d, 3H), 2.22-2.23 (d, 2H), 3.00-3.01 (m, 2H), 3.31-3.33 (m, 1H), 3.69-3.71 (m, 2H), 3.91-3.92 (m, 1H), 3.99-4.01 (m, 1H), 4.07 (s, 3H), 4.20-4.21 (m, 1H), 4.47-4.49 (m, 1H), 5.25-5.26 (m, 2H), 7.35-7.37 (m, 2H), 7.43-7.47 (m, 2H), 8.44 (s, 1H), 8.50 (s, 1H), 9.12 (s, 1H) C27H33N9O4S HPLC 96.7% (M + 1) 580.2 |
| 597 | 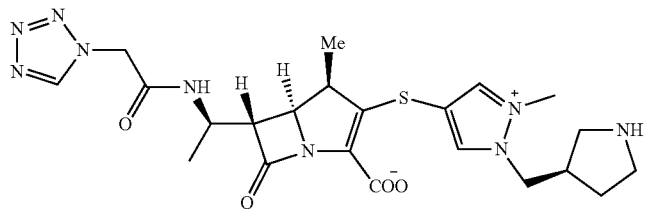<br>(4R,5S,6R)-6-((R)-1-(2-(1H-tetrazol-1-yl)acetamido)ethyl)-4-methyl-3-(2-methyl-1-((R)-pyrrolidin-3-ylmethyl)-1H-pyrazol-2-ium-4-ylthio)-7-oxo-1-azabicyclo[3.2.0]hept-2-ene-2-carboxylate | $^1$HNMR (D$_2$O)-0.89-0.91 (d, 3H), 1.20 (d, 3H), 1.79-1.80 (m, 1H), 2.15-2.16 (m, 1H), 2.76-2.77 (m, 1H), 2.99-3.06 (m, 2H), 3.41-3.42 (m, 2H), 3.50-3.51 (m, 1H), 3.92-3.94 (m, 1H), 3.99-4.00 (m, 1H), 4.05 (s, 3H), 4.10-4.11 (m, 1H), 4.44-4.45 (m, 1H), 5.24-5.25 (m, 2H), 8.45 (s, 1H), 8.55 (s, 1H), 9.13 (s, 1H) C22H29N9O4S HPLC 90% (M + 1) 516.2 |
| 598 | 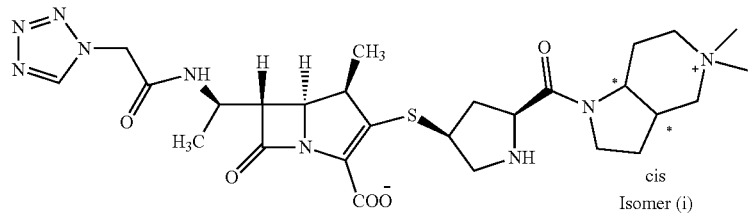<br>cis Isomer (i)<br>(4R,5S,6R)-6-((R)-1-(2-(1H-tetrazol-1-yl)acetamido)ethyl)-3-(4-(1-(3-aminopropyl)-2-methyl-1H-pyrazol-2-ium-4-yl)benzylthio)-4-methyl-7-oxo-1-azabicyclo[3.2.0]hept-2-ene-2-carboxylate | $^1$HNMR (D$_2$O) - 1.06 (d, 3H), 1.20 (d, 3H), 1.70-1.71 (m, 2H), 1.78-1.79 (m, 2H), 1.86-1.87 (m, 1H), 2.06-2.07 (m, 2H), 2.22-2.23 (m, 1H), 2.59-2.60 (m, 2H), 2.83-2.86 (m, 1H), 3.02 (s, 3H), 3.06 (s, 3H), 3.19 (m, 2H), 3.40-3.43 (m, 2H), 3.53-3.54 (m, 2H), 3.63-3.64 (m, 1H), 3.85-3.86 (m, 2H), 4.27-4.38 (m, 1H), 5.29-5.30 (d, 2H), 9.14 (s, 1H) C27H39N9O5S HPLC 94.7% (M + 1) 602.1 |

| Example | Structure | Analytical Data |
|---|---|---|
| 599 | (4R,5S,6R)-6-((R)-1-(2-(1H-tetrazol-1-yl)acetamido)ethyl)-3-(4-(1-(3-aminopropyl)-2-methyl-1H-pyrazol-2-ium-4-yl)benzylthio)-4-methyl-7-oxo-1-azabicyclo[3.2.0]hept-2-ene-2-carboxylate<br>cis Isomer (ii) | $^1$HNMR (D$_2$O) - 1.08 (d, 3H), 1.22 (d, 3H), 1.72-1.73 (m, 2H), 1.80-1.81 (m, 2H), 1.88-1.89 (m, 1H), 2.08-2.09 (m, 2H), 2.24-2.25 (m, 1H), 2.61-2.62 (m, 2H), 2.85-2.87 (m, 1H), 3.03 (s, 3H), 3.07 (s, 3H), 3.21(m, 2H), 3.42-3.45 (m, 2H), 3.55-3.56 (m, 2H), 3.64-3.65 (m, 1H), 3.87-3.88 (m, 2H), 4.29-4.40 (m, 1H), 5.31-5.32 (d, 2H), 9.15 (s, 1H) C27H39N9O5S HPLC 90% (M + 1) 602.1 |
| 600 | (4S,5R,6R)-6-((R)-1-(2-(1H-tetrazol-1-yl)acetamido)ethyl)-3-(((3S,4S)-3-guanidino-4-hydroxypyrrolidin-1-yl)methyl)-4-methyl-7-oxo-1-azabicyclo[3.2.0]hept-2-ene-2-carboxylic acid | $^1$HNMR (D$_2$O) - 1.16 (d, 3H), 1.26 (d, 3H), 3.19-3.21 (m, 2H), 3.23 (m, 1H), 3.47 (m, 1H), 3.51 (m, 1H), 3.84-3.86 (m, 1H), 3.98-4.05 (m, 1H), 4.12-4.16 (m, 2H), 4.22 (m, 2H), 4.49 (m, 1H), 5.30-5.46 (m, 2H), 9.25 (s, 1H) C19H28N10O5 HPLC 90% Mass (M + 1) 477.1 |

Example 600: Synthesis of (4S,5R,6R)-6-((R)-1-(2-(1H-tetrazol-1-yl)acetamido)ethyl)-3-(((3S,4S)-3-guanidino-4-hydroxypyrrolidin-1-yl)methyl)-4-methyl-7-oxo-1-azabicyclo[3.2.0]hept-2-ene-2-carboxylic acid Preparation 28: (4S,5R,6R)-4-nitrobenzyl 6-((R)-1-(2-(1H-tetrazol-1-yl)acetamido)ethyl)-3-((isobutoxy-carbonyloxy)methyl)-4-methyl-7-oxo-1-azabicyclo[3.2.0]hept-2-ene-2-carboxylate

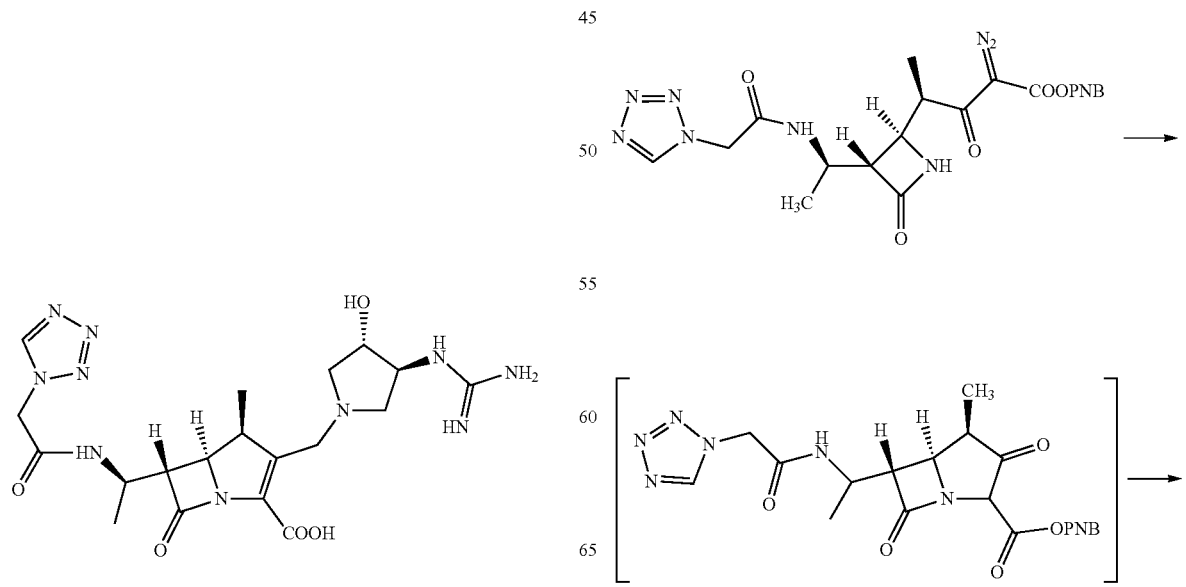

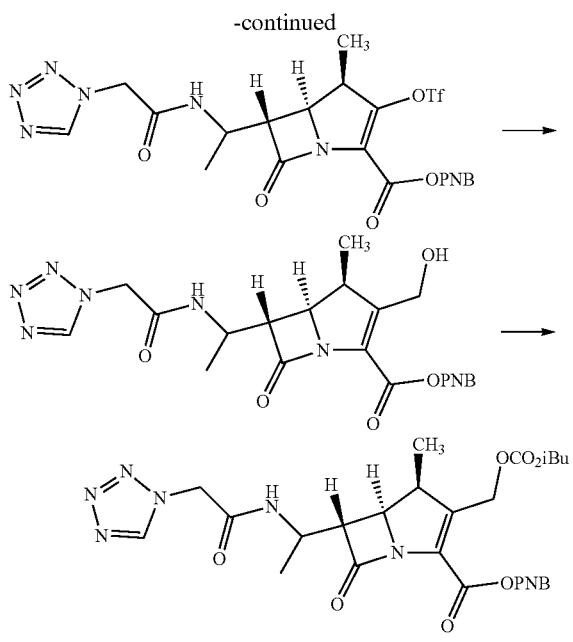

(R)-4-Nitrobenzyl 4-((2R,3R)-3-((R)-1-(2-(1H-tetrazol-1-yl)acetamido)ethyl)-4-oxoazetidin-2-yl)-2-diazo-3-oxopentanoate (10 g, 20 mmol) was dissolved in 200 mL of acetone under $N_2$ atmosphere. To this solution was added rhodium octanoate (750 mg, 0.96 mmoles) and heated to 60° C. for 2.5 hours. After the completion of the reaction, the reaction mixture was then cooled to −40° C. and triflic anhydride (4.6 mL, 28 mmoles), diisopropylethylamine (8.8 mL, 50.9 mmol) and catalytic amount of dimethylaminopyridine (750 mg, 6.14 mmol) was added successively. The reaction mixture was then stirred for 1 hour at −40° C. The reaction mixture was quenched with addition of 0.1M phosphate buffer (pH=7). The aqueous layer was extracted with dichloromethane and the organic layer evaporated under vacuum at room temperature to obtain crude. Partial purification of the crude was done by column chromatography to yield (4R,5R,6R)-4-nitrobenzyl 6-((R)-1-(2-(1H-tetrazol-1-yl)acetamido)ethyl)-4-methyl-7-oxo-3-(trifluoromethylsulfonyloxy)-1-azabicyclo[3.2.0]hept-2-ene-2-carboxylate (2.7 g, 47%).

A mixture containing (4R,5R,6R)-4-nitrobenzyl 6-((R)-1-(2-(1H-tetrazol-1-yl)acetamido)ethyl)-4-methyl-7-oxo-3-(trifluoromethylsulfonyloxy)-1-azabicyclo[3.2.0]hept-2-ene-2-carboxylate (2.6 g), tri-n-butylstannylmethanol (5.48 g, 17.1 mmol) and hexamethylphosphoramide (degassed) was stirred for 30 minutes. To the above a separately prepared solution containing tris(2-furyl)phosphine (0.32 g, 1.38 mmol), Pd(dba)$_3$ (0.513 g, 0.56 mmol) and zinc chloride (0.513 g, 3.77 mmol) in 10 mL of hexamethylphosphoramide (degassed) was added and heated to 70° C. for 1 hour in a sealed tube. Reaction mixture was diluted with diethyl ether and water.

The organic layer was separated and concentrated to obtain the crude. Column chromatographic purification of the crude was done to obtain 1 g of (4S,5R,6R)-4-nitrobenzyl 6-((R)-1-(2-(1H-tetrazol-1-yl)acetamido)ethyl)-3-(hydroxymethyl)-4-methyl-7-oxo-1-azabicyclo[3.2.0]hept-2-ene-2-carboxylate. $^1$HNMR CDCl$_3$ 1.17 (d, 3H), 1.39 (d, 3H), 3.22-3.24 (m, 1H), 3.41-3.43 (m, 1H), 4.09-4.12 (d, 1H), 4.34-4.37 (m, 1H), 4.38-4.39 (m, 1H), 4.58-4.62 (m, 1H), 5.12-5.13 (d, 2H), 5.26-5.29 (dd, 1H), 5.49-5.52 (dd, 1H), 6.13 (br s, 1H), 7.64-7.66 (m, 2H), 8.22-8.24 (d, 2H), 8.93 (s, 1H).

A mixture of N,N-diisopropylethylamine (1.36 mL, 7.85 mmol) and dimethylaminopyridine (0.015 g, 0.13 mmol) in tetrahydrofuran (30 mL) was cooled to 0° C. and isobutylchloroformate (0.5 mL, 3.84 mmol) was added and stirred for 5 minutes. To the above, a solution of (4S,5R,6R)-4-nitrobenzyl 6-((R)-1-(2-(1H-tetrazol-1-yl)acetamido)ethyl)-3-(hydroxymethyl)-4-methyl-7-oxo-1-azabicyclo[3.2.0] hept-2-ene-2-carboxylate (0.6 g, 1.24 mmol) dissolved in tetrahydrofuran (10 mL) was added at 0° C. and continued stirring at room temperature for 24 h.

Reaction mixture was concentrated under vacuo and purified the crude by column chromatography to obtain the titled compound, 0.4 g. $^1$HNMR CDCl$_3$—0.94-0.96 (d, 6H), 1.18 (d, 3H), 1.38 (d, 3H), 1.94-2.01 (m, 1H), 3.10-3.11 (m, 1H), 3.30-3.34 (m, 1H), 3.93-3.94 (d, 2H), 4.10-4.12 (d, 1H), 4.38-4.42 (m, 1H), 4.78-4.82 (m, 1H), 5.17 (d, 2H), 5.25-5.29 (m, 1H), 5.47-5.51 (m, 2H), 6.67-6.68 (br s, 1H), 7.63-7.65 (m, 2H), 8.23-8.25 (d, 2H), 8.87 (s, 1H).

Preparation 29: (4S,5R,6R)-4-nitrobenzyl 6-((R)-1-(2-(1H-tetrazol-1-yl)acetamido)ethyl)-3-(((3S,4S)-3-((E)-2,3-bis((4-nitrobenzyloxy)carbonyl)guanidino)-4-hydroxypyrrolidin-1-yl)methyl)-4-methyl-7-oxo-1-azabicyclo[3.2.0]hept-2-ene-2-carboxylate

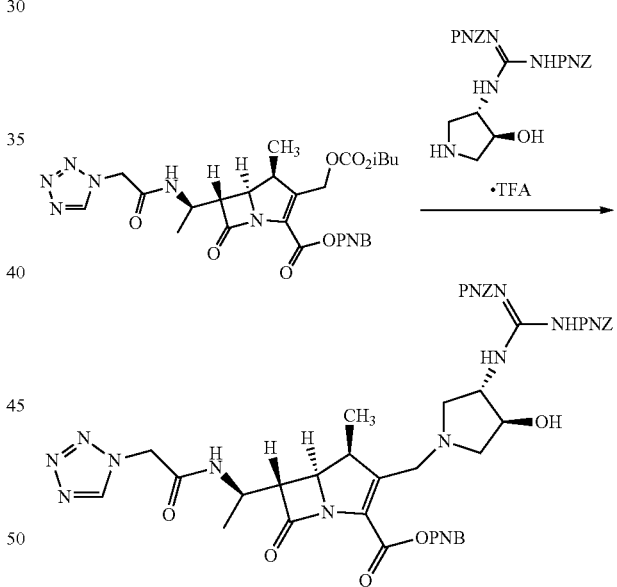

Pd(dba)$_3$ CHCl$_3$ (0.026 g, 0.025 mmol), triethylphosphite (0.18 ml, 0.104 mmol) and a mixture of 10 mL of tetrahydrofuran-toluene (degassed, 1:9) was stirred for 30 minutes. To the above, a solution containing mixture of 4-nitrobenzyl ((3S,4S)-4-hydroxypyrrolidin-3-ylamino)((4-nitrobenzyloxy)carbonylamino)methylenecarbamate, trifluoroacetate salt (0.085 g, 0.102 mmol, neutralized with diisopropylethylamine) and (4S,5R,6R)-4-nitrobenzyl 6-((R)-1-(2-(1H-tetrazol1-yl)acetamido)ethyl)-3-((isobutoxycarbonyloxy)methyl)-4-methyl-7-oxo-1-azabicyclo[3.2.0]hept-2-ene-2-carboxylate (0.1 g, 0.17 mmol) in 5 mL of tetrahydrofuran-toluene (degassed 1:9) was added and stirred at room temperature for 16 h. The reaction mixture was diluted with ethyl acetate and 0.1M phosphate buffer 7.0. Organic layer was separated and washed with water and brine. After drying over sodium sulphate, organic layer was concentrated to obtain crude. The crude was purified by column chromatography to obtain the titled compound (0.06 g). $^1$HNMR CDCl$_3$ 1.14 (d, 3H), 1.38 (d, 3H), 1.98-1.99 (m, 1H), 2.52-2.24 (m, 1H), 3.08 (m, 1H), 3.34 (m, 1H), 3.41 (m, 1H), 4.06 (m, 1H), 4.11-4.13 (m, 1H), 4.43 (m, 1H), 4.91-4.94 (m, 2H), 5.11-5.21 (m, 4H), 5.24-5.30 (m, 4H), 5.43-5.49 (m, 2H), 6.65 (br s, 1H), 7.51-7.56 (m, 6H), 8.19-8.24 (m, 6H), 8.87 (s, 1H)

The above compound was hydrogenated similar to Step 4 of example 298 to obtain the required compound (4S,5R,6R)-6-((R)-1-(2-(1H-tetrazol-1-yl)acetamido)ethyl)-3-(((3S,4S)-3-guanidino-4-hydroxypyrrolidin-1-yl)methyl)-4-methyl-7-oxo-1-azabicyclo[3.2.0]hept-2-ene-2-carboxylic acid. $^1$HNMR (D$_2$O)—1.16 (d, 3H), 1.26 (d, 3H), 3.19-3.21 (m, 2H), 3.23 (m, 1H), 3.47 (m, 1H), 3.51 (m, 1H), 3.84-3.86 (m, 1H), 3.98-4.05 (m, 1H), 4.12-4.16 (m, 2H), 4.22 (m, 2H), 4.49 (m, 1H), 5.30-5.46 (m, 2H), 9.25 (s, 1H) C19H28N10O5 HPLC 90% Mass (M+1) 477.1

Preparation 30: 2-((2R)-3-((R)-1-(tert-butyldimethylsilyloxy)ethyl)-4-oxoazetidin-2-yl)acetic acid

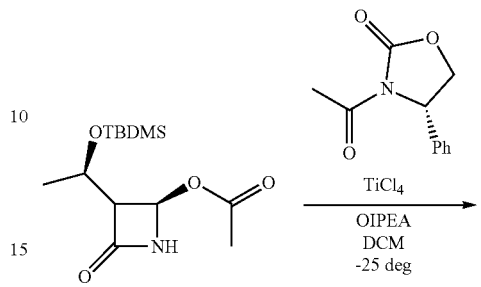

601

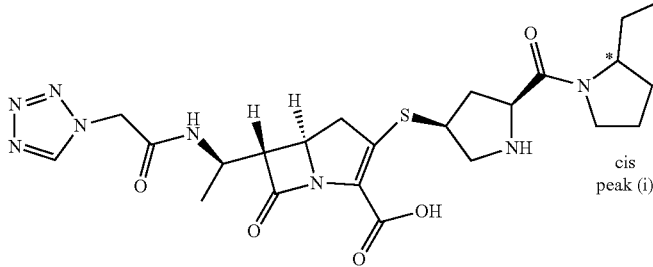

(5R,6R)-6-((R)-1-(2-(1H-tetrazol-1-yl)acetamido)ethyl)-3-((3S,5S)-5-(octahydro-1H-pyrrolo[3,2-c]pyridine-1-carbonyl)pyrrolidin-3-ylthio)-7-oxo-1-azabicyclo[3.2.0]hept-2-ene-2-carboxylic acid $^1$HNMR (D$_2$O) - 1.32 (d, 3H), 1.68-1.69 (m, 1H), 1.83-1.87 (m, 2H), 1.97 (m, 1H), 2.12-2.17 (m, 3H), 2.48-2.52 (m, 1H), 2.64 (m, 3H), 3.00-3.07 (m, 3H), 3.27-3.31 (m, 2H), 3.42-3.43 (d, 3H), 3.65-3.70 (m, 3H), 4.01 (m, 1H), 4.11-4.13 (d, 1H), 4.28-4.30 (m, 1H), 4.37-4.40 (m, 1H), 4.53-4.57 (m, 1H), 5.40 (d, 2H), 9.25 (s, 1H)
C25H37N9O6S
HPLC 90% Mass 592.2 (M + 1)

Example 601: Synthesis of (5R,6R)-6-((R)-1-(2-(1H-tetrazol-1-yl)acetamido)ethyl)-3-((3S,5S)-5-(octahydro-1H-pyrrolo[3,2-c]pyridine-1-carbonyl)pyrrolidin-3-ylthio)-7-oxo-1-azabicyclo[3.2.0]hept-2-ene-2-carboxylic acid

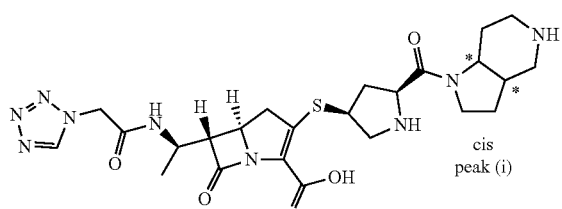

-continued

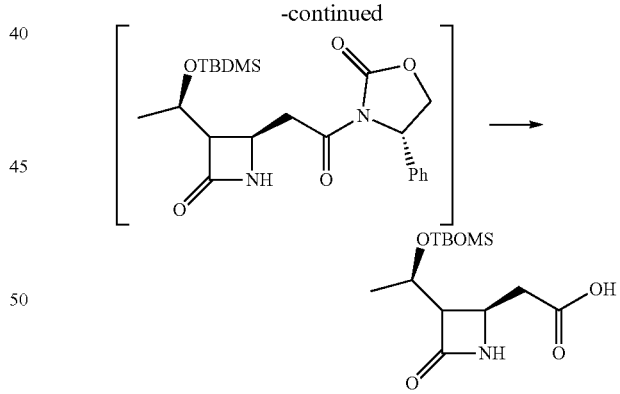

To a solution of (S)-4-phenyl-3-acetyl-2-oxazolidinone (42.8 g, 0.21 mol) in dichloromethane (250 mL), TiCl$_4$ (50 g, 0.26 mol) was added dropwise in 30 min at −20 to −25° C. After stirring the mixture for 30 min at −20 to −25° C., diisopropyl ethylamine (56 g, 0.24 mol) was added dropwise, and stirring continued for 1h at same temperature. To the above, (3R,4R)-4-acetoxy-3-[(R)-1-((tertbutyldimethylsilyl) oxy)ethyl]-2-azetidinone (50 g, 0.17 mol) dissolved in dichloromethane (100 mL) was added at −15 to −10° C. over a period of 20 minutes. Then the mixture was stirred at room temperature for 3 h. Reaction mixture was diluted with dichloromethane (300 mL) and washed with water and brine. After drying over sodium sulphate, the organic layer was concentrated under vacuum to obtain a residue. The residue was purified by column chromatography (Eluant—15% acetone in hexane) to obtain (4S)-3-(2-((2R)-3-((R)-1-(tert-butyldimethylsilyloxy)ethyl)-4-oxoazetidin-2-yl)acetyl)-4-phenyloxazolidin-2-one (28.5 g). This compound (28.5 g) was dissolved in 300 mL of mixture of acetone and water (2:1) and cooled to 0° C. Cooled hydrogen peroxide (30%, 22 mL) was added followed by dropwise addition of 1N sodium hydroxide solution (200 mL) at 0° C. in 30 minutes. After stirring for 15 minutes at the same temperature, the reaction was diluted with water (1 L). The aqueous layer was washed with ethyl acetate (500 mL×2). The aqueous layer was cooled to 0° C. and the pH was adjusted with 6 N HCl to 8. The aqueous layer was washed with ethyl acetate (500 mL×2). The aqueous layer was acidifed to pH 3 with dil HCl and extracted with ethyl acetate (400 mL×2). After drying over sodium sulphate the organic layer was evaporated to obtain 2-((2R)-3-((R)-1-(tert-butyldimethylsilyloxy)ethyl)-4-oxoazetidin-2-yl)acetic acid, 11.5 g
$^1$HNMR—CDCl$_3$—0.05 (d, 6H), 0.8 (s, 9H), 1.21 (d, 3H), 2.53-2.62 (m, 1H), 2.76-2.78 (m, 1H), 2.82-2.84 (d, 1H), 3.96-3.98 (d, 1H), 4.12-4.14 (m, 1H), 6.68 (br s, NH)

Scheme 1 was followed for preparing the below compound by using the starting material obtained above (2-((2R)-3-((R)-1-(tert-butyldimethylsilyloxy)ethyl)-4-oxoazetidin-2-yl)acetic acid)

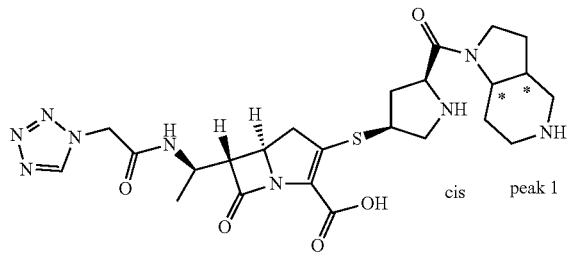 [SMILES: C[C@@H](NC(=O)Cn1cnnn1)[C@H]1C(=O)N2C(C(=O)O)=C(S[C@@H]3CN[C@H](C(=O)N4CCC5CNCCC54)C3)C[C@H]12]

cis    peak 1

$^1$HNMR (D$_2$O)—1.32 (d, 3H), 1.68-1.69 (m, 1H), 1.83-1.87 (m, 2H), 1.97 (m, 1H), 2.12-2.17 (m, 3H), 2.48-2.52 (m, 1H), 2.64 (m, 3H), 3.00-3.07 (m, 3H), 3.27-3.31 (m, 2H), 3.42-3.43 (d, 3H), 3.65-3.70 (m, 3H), 4.01 (m, 1H), 4.11-4.13 (d, 1H), 4.28-4.30 (m, 1H), 4.37-4.40 (m, 1H), 4.53-4.57 (m, 1H), 5.40 (d, 2H), 9.25 (s, 1H), C25H37N9O6S, HPLC 90%

Mass 592.2 (M+1)

Antibacterial Activity:

Compounds were evaluated for their antibacterial activity against Gram positive and Gram negative bacterial strains. These strains include methicillin-sensitive *Staphylococcus aureus*, carbapenem sensitive *Escherichia coli*, extended spectrum β lactamase (ESBL) SHV18 producing *Klebsiella pneumoniae*, carbapenemase producing *K. pneumoniae*, *Enterobacter* spp; *Morganello* spp; *citrobacter* spp; *serratia* spp; *acinetobacter* and carbapenem sensitive *Pseudomonas aeruginosa*.

EXPERIMENTAL

Antibacterial activity was evaluated by determining the minimum inhibitory concentration (MIC) of these compounds by broth micro-dilution method (CLSI guidelines, M7-A7/Jan 2006, M100-S18/Jan 2008). Two-fold serial dilutions of the test compounds in Mueller-Hinton broth were prepared in 96 well micro-titre plates. To these dilutions, equal amount of Mueller-Hinton broth containing bacterial suspensions were added to obtain a 5×10$^5$ colony forming units per mL. MIC of the test compounds was determined after incubating micro-titre plates at 35° C. for 22 hours. The minimum concentration of the compound that inhibited visible growth of bacteria is defined as MIC.

Results:

MIC of test compounds is presented in table 1.

TABLE 1

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 | ESBL -ve E. coli ATCC25922 | Meropenem suscept1ble P. aeruginosa ATCC27853 |
| | | | MIC DATA (µg/mL) | | |
| 1 | 8-16 | −0.5-1 | −2-4 | 0.25-1 | 32-64 |
| 5 | 8 | >128 | >128 | 8 | >128 |
| 7 | 2-8 | 2-4 | 2-4 | 0.5 | 32-64 |
| 9 | 8 | >128 | >128 | 128 | >128 |
| 10 | 16 | 2 | 4 | 1 | >128 |
| 11 | 8 | 64 | 32 | 4 | >128 |
| 12 | 8 | 128 | 32 | 4 | >128 |
| 13 | 4 | 8 | 4 | 1 | 64 |
| 14 | 4 | 4 | 4 | 0.5 | 128 |
| 15 | 2 | 16 | 16 | 1 | 128 |
| 16 | 4 | 64 | 16 | 4 | >128 |
| 17 | 4 | >128 | 32 | 16 | 128 |
| 18 | 8 | 64 | 8 | 4 | 32 |
| 19 | 1 | 8 | >128 | 1 | 128 |
| 20 | 2 | 8 | 16 | 1 | 128 |
| 21 | 2 | 4 | 4-16 | 2 | >128 |
| 22 | 2 | 64-128 | 32 | 8 | >128 |
| 23 | 16 | 1 | 8 | 0.5 | 32-128 |
| 24 | 16 | 1 | 4 | 0.5 | 32-64 |
| 25 | 4 | 8 | 8 | 1 | 128 |

TABLE 1-continued

| | MIC of test compounds | | | | |
|---|---|---|---|---|---|
| | Pheno type- Organism | | | | |
| Example | MSSA *S. aureus* ATCC29213 | ESBL +ve (SHV-18) *K. pneumoniae* ATCC700603 | KPC-2 *K. pneumoniae* ATCC BAA-1705 | ESBL −ve *E. coli* ATCC25922 | Meropenem susceptible *P. aeruginosa* ATCC27853 |
| | | | MIC DATA (µg/mL) | | |
| 26 | 4 | 4-8 | 8 | 1 | 128 |
| 27 | 16 | 1 | 4 | 0.5 | 64-128 |
| 28 | 8 | 2 | 4-8 | 2 | 4-8 |
| 29 | 4 | 8 | >128 | 1 | 128 |
| 30 | 2 | 8 | 8 | 1 | 128 |
| 31 | 16 | 16 | 4 | 4 | >128 |
| 32 | 1 | 1 | 1 | 0.5 | 32 |
| 33 | 4 | 32 | 16 | 4 | >128 |
| 34 | 4 | 8 | 8 | 1 | 128 |
| 35 | 1 | 4 | 2-4 | 1 | >128 |
| 36 | 1 | 16 | 16 | 2 | 128 |
| 37 | 16 | 1 | 16 | 1 | >128 |
| 38 | 0.25 | 1 | 2-4 | 1 | 32-64 |
| 39 | 16 | 16 | 16 | 4 | 16 |
| 40 | 4 | 8 | 4-8 | 1 | >128 |
| 41 | 2 | 16 | 16 | 1 | >128 |
| 42 | 2 | 1 | 8 | 1 | 128 |
| 43 | 2 | 4 | 8 | 1 | 64 |
| 44 | 32 | 4 | 8 | 4 | 16 |
| 45 | 1 | 4 | 16 | 1 | 4 |
| 46 | 1 | 4 | 8 | 1 | 16 |
| 47 | 2 | 128 | 64 | 2 | >128 |
| 48 | 16 | 1 | 64 | 0.5 | 8 |
| 49 | 2 | 2 | >128 | 1 | >128 |
| 50 | 1 | 8-16 | 2-4 | 1-2 | 16-32 |
| 51 | 8 | 32 | 32 | 4 | >128 |
| 52 | 1 | 128 | >128 | 8 | >128 |
| 54 | 1 | >128 | >128 | 8 | >128 |
| 56 | 64 | 16 | 16 | 8 | 64 |
| 57 | 32 | 16 | 128 | 4 | >128 |
| 58 | 32 | >128 | >128 | 16 | >128 |
| 59 | 32 | 16 | >128 | 2 | 32 |
| 60 | 32 | 32 | 64 | 16 | >128 |
| 61 | 1 | 16 | 16 | 1 | >128 |
| 63 | 8-16 | 16-32 | 8-16 | 1-2 | >128 |
| 64 | 2 | 8 | 8 | 1-2 | 64 |
| 66 | 8 | 8 | 4-8 | 2 | >128 |
| 67 | 4 | >128 | >128 | 8 | >128 |
| 68 | 32 | 8 | >128 | 4 | 32-64 |
| 70 | 16 | 8 | 16 | 4 | >128 |
| 71 | 8 | 128 | 64 | 16 | >128 |
| 72 | 32 | >128 | >128 | 32 | >128 |
| 73 | 4 | 4 | 8 | 1-2 | 4-16 |
| 74 | 8-16 | 1-2 | 4 | 1-2 | 8 |
| 75 | 4 | 8 | 16 | 1 | >128 |
| 76 | 2 | 8 | 8 | 1 | >128 |
| 77 | 4-8 | 1 | 4 | 0.5-1 | 32-64 |
| 78 | 8 | 2 | >128 | 1 | 128 |
| 79 | 4 | >128 | >128 | 32 | >128 |
| 80 | 4 | 32 | 64 | 4 | >128 |
| 81 | 1 | 8 | 8 | 1 | 64 |
| 82 | 8 | 2 | 8 | 1 | 128 |
| 83 | 2 | >128 | >128 | 64 | >128 |
| 84 | 4 | 4 | 16 | 1 | 128 |
| 85 | 1 | 2 | 2 | 0.5 | 64 |
| 86 | 2 | 8 | 8 | 1 | 128 |
| 87 | 2 | 8 | 8 | 1 | 64 |
| 88 | 0.25 | >128 | >128 | 128 | >128 |
| 89 | 0.5 | 8 | 4 | 0.5 | 128 |
| 90 | 1 | 32 | 4 | 1 | 128 |
| 91 | 16 | 32 | 32 | 4 | >128 |
| 92 | 1 | 4 | 4 | 0.5 | 32 |
| 93 | 16 | >128 | >128 | 128 | >128 |
| 94 | 0.25 | >128 | >128 | 64 | >128 |
| 95 | 32 | 2 | 2 | 1 | 2 |
| 96 | 1 | 64 | 32 | 4 | >128 |
| 97 | 1 | 128 | 64 | 8 | >128 |
| 98 | 32 | 32 | 32 | 8 | >128 |
| 99 | 128 | 16 | 64 | 64 | 16 |
| 100 | 16 | 8 | 4 | 1 | 32 |

TABLE 1-continued

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 | ESBL −ve E. coli ATCC25922 | Meropenem susceptible P. aeruginosa ATCC27853 |
| | | | MIC DATA (µg/mL) | | |
| 101 | 2 | 1 | 4 | 0.5 | 64 |
| 102 | 2 | 8 | 8 | 2 | 64 |
| 103 | 0.5 | 4 | 8 | 0.5 | 8 |
| 104 | 4 | 1 | 4 | 0.5 | 128 |
| 105 | 8 | 8 | 8 | 1 | 128 |
| 106 | 4 | 4 | 4 | 1 | 4 |
| 107 | 4 | 4 | 4 | 1 | 16 |
| 108 | 2 | 4 | 16 | 1 | 128 |
| 109 | 8 | 4 | 16 | 4 | 4 |
| 110 | 4 | 2 | 4 | 0.5 | 32 |
| 111 | 4 | 16 | 16 | 1 | >128 |
| 112 | 64 | 4 | 4 | 2 | 8 |
| 113 | 16 | 32 | 16 | 4 | >128 |
| 114 | 8 | 2 | 4 | 0.5 | >128 |
| 115 | 8 | 2 | 8 | 0.5 | >128 |
| 116 | 8 | 2 | 4 | 0.5 | >128 |
| 117 | 2 | 2 | 4 | 0.5 | >128 |
| 118 | 4 | 2 | 8 | 0.5 | 64 |
| 119 | 2 | 1 | 8 | 0.5 | 16 |
| 120 | 2 | 4 | 4 | 0.5 | 4 |
| 121 | 1 | 4 | 4 | 0.5 | 8 |
| 122 | 1 | 4 | 4 | 1 | 16 |
| 123 | 2 | 2 | 4 | 0.5 | 64 |
| 124 | 2 | 4 | 4 | 1 | 4 |
| 125 | 2 | 32 | 16 | 2 | 128 |
| 126 | 2 | 8 | 8 | 2 | 16 |
| 127 | 2 | 8 | 16 | 2 | 32 |
| 128 | 16 | 8 | 8 | 4 | 64 |
| 129 | 32 | 32 | 8 | 4 | 8 |
| 130 | 2 | 8 | 4 | 1 | 32 |
| 131 | 4 | 2 | 8 | 0.5 | 16 |
| 132 | 2 | 4 | 4 | 1 | 4 |
| 133 | 4 | 4 | 8 | 1 | 8 |
| 134 | 2 | 4 | 4 | 1 | 16 |
| 135 | 2 | 4 | 4 | 1 | 8 |
| 136 | >128 | 16 | 16 | 4 | 32 |
| 137 | 4 | 8 | 8 | 1 | >128 |
| 138 | 32 | 32 | 64 | 4 | >128 |
| 139 | 32 | 4 | 4 | 1 | 32 |
| 140 | 2 | 1 | 2 | 0.5 | 32 |
| 141 | 4-8 | 4-8 | 4-8 | 1 | 64 |
| 142 | 4-8 | 8 | 8 | 1 | 16-32 |
| 143 | 2 | 8 | 8 | 1 | 32-64 |
| 145 | 0.5 | 8-16 | 8 | 2 | 32 |
| 146 | 1-4 | 1-2 | 2 | 1 | 64 |
| 147 | 2 | 2 | 4-8 | 1 | 64-128 |
| 148 | 1-2 | 1 | 2-4 | 0.5 | 32-64 |
| 149 | 2 | 8 | 8 | 1 | 4 |
| 150 | 4 | 64 | 16 | 4 | 64 |
| 151 | 4 | 16 | 8 | 2 | 32 |
| 153 | 8 | 2 | 8 | 1 | 64 |
| 154 | 4 | 2 | 8 | 1 | 64 |
| 155 | 2 | 8 | 8 | 1 | 32 |
| 156 | 32 | 16 | 32 | 8 | >128 |
| 157 | 2 | 8 | 4 | 1 | 4 |
| 158 | 2 | 4 | 4 | 1 | 8 |
| 159 | 2 | 4 | 4 | 1 | 8 |
| 160 | 4 | 8 | 8 | 1 | 16 |
| 161 | 0.5 | 8 | 4 | 0.5 | 8 |
| 162 | 1 | 4 | 4 | 0.5 | 16 |
| 163 | 1 | 4 | 4 | 1 | 8 |
| 164 | 1 | 1 | 4 | 0.25 | 32 |
| 165 | 64 | 4 | 2 | 2 | 32 |
| 166 | 64 | 8 | 8 | 4 | 32 |
| 167 | 2 | 4 | 4 | 4 | 32 |
| 168 | 16 | 2 | 2 | 1 | 2 |
| 169 | 8 | 16 | 2 | 1 | 4 |
| 170 | 2 | 4 | 8 | 1 | 32 |
| 171 | 2 | 128 | 128 | 4 | >128 |
| 172 | 4 | 8 | 8 | 1 | 64 |

TABLE 1-continued

MIC of test compounds

| Example | MSSA S. aureus ATCC29213 | ESBL +ve (SHV-18) K. pneumoniae ATCC700603 | KPC-2 K. pneumoniae ATCC BAA-1705 | ESBL −ve E. coli ATCC25922 | Meropenem susceptible P. aeruginosa ATCC27853 |
|---|---|---|---|---|---|
| | | | MIC DATA (μg/mL) | | |
| 173 | 4 | 16 | 8 | 2 | 16 |
| 174 | 4 | 16 | 8 | 2 | 32 |
| 175 | 2 | 2 | 4 | 1 | 16 |
| 176 | 2 | 4 | 8 | 1 | 8 |
| 177 | 8 | 2 | 2 | 2 | 32 |
| 178 | 32 | 4 | 4 | 2 | 4 |
| 179 | 128 | 16 | 8 | 2 | 16 |
| 180 | 128 | 32 | 32 | 4 | 16 |
| 181 | >128 | >128 | 64 | 8 | 128 |
| 182 | 128 | 16 | 16 | 8 | 8 |
| 183 | 8 | 32 | 16 | 2 | 64 |
| 184 | 2 | 4 | 8 | 0.5 | 4 |
| 185 | 2 | 64 | 16 | 2 | 64 |
| 186 | 4 | 4 | 4 | 0.5 | 8 |
| 187 | 4 | 8 | 64 | 2 | 128 |
| 188 | 128 | 16 | 8 | 8 | 16 |
| 189 | >128 | 32 | 8 | 4 | 16 |
| 190 | 64 | 16 | 4 | 2 | 4 |
| 191 | 64 | 32 | 8 | 8 | 32 |
| 192 | 64 | 2 | 2 | 1 | 4 |
| 193 | 64 | 8 | 4 | 4 | 8 |
| 194 | 8 | 8 | 16 | 2 | 16 |
| 195 | 2 | 1 | 4 | 0.5 | 8 |
| 196 | 2 | 4 | 8 | 1 | 32 |
| 197 | 16 | 16 | 16 | 4 | 32 |
| 198 | 2 | 1 | 4 | 0.25 | 32 |
| 199 | 32 | 4 | 2 | 1 | 4 |
| 200 | 128 | 8 | 4 | 2 | 4 |
| 201 | 16 | 16 | 64 | 2 | 16 |
| 202 | 64 | 64 | 16 | 4 | 8 |
| 203 | 16 | 1 | 4 | 0.5 | 128 |
| 204 | 32 | >128 | >128 | 8 | >128 |
| 205 | 32 | 2 | 4 | 1 | 8 |
| 206 | 64 | 4 | 4 | 4 | 4 |
| 207 | 2 | 8 | 8 | 2 | >128 |
| 208 | 64 | 8 | 8 | 4 | >128 |
| 209 | 2 | 2 | 2 | 0.5 | 64 |
| 210 | 2 | 4 | 4 | 1 | 64 |
| 211 | 2 | 4 | 4 | 1 | 16 |
| 212 | 1 | 2 | 4 | 0.5 | 8 |
| 213 | 1 | 2 | 4 | 0.5 | 8 |
| 214 | 32 | 32 | 16 | 4 | >128 |
| 215 | 8 | 32 | 8 | 2 | >128 |
| 216 | 32 | 16 | 4 | 1 | 4 |
| 217 | 16 | 1 | 1 | 0.5 | 2 |
| 218 | 16 | 2 | 2 | 1 | 2 |
| 219 | 2 | 4 | 4 | 1 | 4 |
| 220 | 32 | 2 | 2 | 1 | 2 |
| 221 | 32 | 2 | 2 | 2 | 4 |
| 222 | 64 | 8 | 4 | 2 | 8 |
| 225 | 16 | 32 | 2 | 1 | 64 |
| 226 | 32 | 32 | 8 | 1 | 64 |
| 227 | 64 | 8 | 4 | 2 | 32 |
| 228 | 64 | 4 | 8 | 1 | 64 |
| 229 | 128 | 64 | 64 | 16 | 32 |
| 230 | 32 | 8 | 4 | 1 | 8 |
| 231 | 32 | 4 | 2 | 1 | 16 |
| 232 | 2 | 8 | 8 | 2 | >128 |
| 233 | 4 | 4 | 4 | 1 | >128 |
| 234 | 0.5 | 4 | 4 | 0.5 | >128 |
| 235 | 2 | — | 16 | 2 | >128 |
| 236 | 2 | — | 4 | 2 | 128 |
| 237 | 1 | — | 4 | 2 | 128 |
| 238 | 16 | — | NT | 16 | >128 |
| 241 | 16 | — | 2 | 2 | 32 |
| 242 | 16 | — | 2 | 2 | 8 |
| 243 | 32 | — | 32 | 16 | >128 |
| 244 | 1 | — | 4 | 1 | 64 |
| 245 | 8 | — | 4 | 2 | 4 |
| 246 | 32 | — | 128 | 8 | >128 |

TABLE 1-continued

MIC of test compounds

| Example | MSSA S. aureus ATCC29213 | ESBL +ve (SHV-18) K. pneumoniae ATCC700603 | KPC-2 K. pneumoniae ATCC BAA-1705 | ESBL −ve E. coli ATCC25922 | Meropenem susceptible P. aeruginosa ATCC27853 |
|---|---|---|---|---|---|
| | | | MIC DATA (µg/mL) | | |
| 247 | 32 | — | 32 | 4 | >128 |
| 248 | 1 | — | 4 | 1 | >128 |
| 251 | 0.5 | — | 0.5 | 0.25 | 32 |
| 252 | 16 | — | 4 | 2 | 16 |
| 253 | 32 | — | 16 | 16 | 16 |
| 254 | 64 | — | 16 | 8 | 128 |
| 255 | 8 | — | 8 | 4 | 32 |
| 256 | 4 | — | 2 | 1 | 32 |
| 257 | >128 | — | 16 | 4 | 128 |
| 258 | 1 | — | 16 | 4 | 128 |
| 259 | 2 | — | 16 | 4 | >128 |
| 260 | 1 | — | 8 | 4 | 32 |
| 261 | 2 | — | 16 | 2 | 64 |
| 262 | 32 | — | 16 | 4 | 64 |
| 263 | 0.25 | — | 2 | 0.25 | 128 |
| 264 | 16 | — | 4 | 2 | 8 |
| 265 | 2 | — | 8 | 2 | >128 |
| 266 | 64 | — | 8 | 2 | 128 |
| 267 | 0.5 | — | 2 | 1 | >128 |
| 268 | 8 | — | 4 | 2 | 32 |
| 269 | 16 | — | 4 | 4 | 128 |
| 270 | 4 | — | 4 | 1 | 64 |
| 271 | 2 | — | 4 | 1 | 8 |
| 272 | 128 | — | 64 | 64 | >128 |
| 273 | 128 | — | 32 | 16 | 128 |
| 274 | 32 | — | 16 | 16 | >128 |
| 275 | 64 | — | 64 | 16 | >128 |
| 276 | 32 | — | 4 | 2 | 8 |
| 277 | 64 | — | 4 | 2 | 16 |
| 278 | 16 | — | 2 | 2 | 4 |
| 279 | >128 | — | 16 | 4 | >128 |
| 280 | 64 | — | 8 | 8 | 16 |
| 281 | 32 | — | 16 | 8 | 64 |
| 282 | 32 | — | 2 | 1 | 32 |
| 283 | 16 | — | 0.5 | 0.25 | 8 |
| 284 | 1 | — | 4 | 1 | 64 |
| 285 | 64 | — | 8 | 4 | 128 |
| 287 | 128 | — | 8 | 4 | 16 |
| 288 | 128 | — | 16 | 4 | >128 |
| 289 | 8 | — | 16 | 8 | >128 |
| 290 | 32 | — | 4 | 2 | 8 |
| 291 | 32 | — | 2 | 2 | 8 |
| 292 | 128 | — | 8 | 4 | 16 |
| 293 | 128 | — | 128 | 32 | >128 |
| 294 | 1 | — | 1 | 0.06 | 16 |
| 295 | 16 | — | 16 | 2 | 64 |
| 296 | 4 | — | 2 | 0.5 | 64 |
| 297 | 16 | — | 2 | 1 | 4 |
| 298 | 1 | — | 1 | 0.125 | 1 |
| 299 | 16 | — | 8 | 4 | 16 |
| 300 | 16 | — | 4 | 1 | 128 |
| 301 | 16 | — | 64 | 4 | >128 |
| 302 | 2 | — | 16 | 1 | 128 |
| 303 | 2 | — | 64 | 4 | >128 |
| 304 | 8 | — | 4 | 1 | >128 |
| 305 | 2 | — | 1 | 0.25 | 8 |
| 306 | 2 | — | 1 | 0.25 | 4 |
| 307 | 1 | — | 4 | 0.25 | 128 |
| 309 | 16 | — | 4 | 1 | 32 |
| 310 | 32 | — | 4 | 1 | 64 |
| 311 | 32 | — | 32 | 8 | >128 |
| 312 | 16 | — | 4 | 1 | 64 |
| 313 | 4 | — | 16 | 1 | >128 |
| 314 | 4 | — | 2 | 0.25 | 4 |
| 315 | 4 | — | 2 | 0.125 | 64 |
| 316 | 4 | — | 16 | 0.25 | 16 |
| 317 | 2 | — | 8 | 0.5 | 128 |
| 318 | 16 | — | 128 | 2 | >128 |
| 319 | 2 | — | 1 | 0.25 | 32 |
| 320 | 2 | — | 4 | 1 | 128 |

TABLE 1-continued

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 MIC DATA (µg/mL) | ESBL −ve E. coli ATCC25922 | Meropenem susceptible P. aeruginosa ATCC27853 |
| 321 | 2 | — | 8 | 1 | >128 |
| 322 | 16 | — | 16 | 2 | >128 |
| 323 | 16 | — | 8 | 2 | >128 |
| 324 | 4 | — | 4 | 0.5 | 4 |
| 325 | 8 | — | 64 | 4 | >128 |
| 326 | 2 | — | 16 | 1 | 64 |
| 327 | 1 | — | 32 | 2 | 64 |
| 328 | 4 | — | 4 | 2 | 32 |
| 329 | 8 | — | 2 | 0.25 | 8 |
| 330 | 8 | — | 2 | 0.25 | 64 |
| 331 | 4 | — | 4 | 0.25 | 8 |
| 332 | 8 | — | 4 | 1 | 8 |
| 333 | 8 | — | 4 | 0.5 | 4 |
| 334 | 4 | — | 32 | 0.5 | 128 |
| 335 | 4 | — | 64 | 1 | >128 |
| 336 | 4 | — | 4 | 1 | 8 |
| 337 | 2 | — | 1 | 0.5 | 32 |
| 338 | 8 | — | 32 | 2 | 128 |
| 339 | 8 | — | 32 | 1 | 32 |
| 340 | 8 | — | 4 | 1 | 4 |
| 341 | 4 | — | 4 | 1 | 8 |
| 342 | 16 | — | 8 | 2 | 8 |
| 343 | 16 | — | 8 | 2 | 8 |
| 344 | 16 | — | 16 | 1 | 16 |
| 345 | 64 | — | 32 | 8 | 128 |
| 346 | 16 | — | 8 | 1 | 16 |
| 347 | 4 | — | 16 | 0.5 | >128 |
| 348 | 8 | — | 16 | 1 | >128 |
| 349 | 4 | — | 4 | 0.25 | 32 |
| 350 | 2 | — | 1 | 0.25 | 128 |
| 351 | 16 | — | 4 | 1 | >128 |
| 352 | 4 | — | 2 | 0.25 | 2 |
| 353 | 16 | — | 2 | 0.25 | 16 |
| 354 | 2 | — | 1 | 0.125 | 32 |
| 355 | 4 | — | 16 | 1 | 128 |
| 356 | 4 | — | 16 | 1 | >128 |
| 357 | 2 | — | 32 | 1 | >128 |
| 358 | 1 | — | 32 | 1 | >128 |
| 359 | 8 | — | 2 | 0.5 | 16 |
| 360 | 8 | — | 2 | 0.5 | 1 |
| 361 | 8 | 4 | 2 | 1 | 2 |
| 362 | 8 | 4 | 4 | 0.25 | 4 |
| 363 | 4 | | 2 | 0.25 | 1 |
| 364 | 4 | | 2 | 0.25 | 1 |
| 365 | 4 | | 2 | 0.25 | 2 |
| 366 | 4 | | 2 | 0.25 | 2 |
| 367 | 2 | | 2 | 0.25 | 1 |
| 368 | 2 | | 2 | 0.25 | 1 |
| 369 | 2 | — | 8 | 0.25 | 16 |
| 370 | 8 | — | 64 | 4 | >128 |
| 371 | 16 | — | 4 | 1 | 64 |
| 372 | 4 | — | 8 | 0.5 | 64 |
| 373 | 4 | — | >128 | 32 | >128 |
| 374 | 8 | — | >128 | 32 | >128 |
| 375 | 16 | — | 8 | 2 | 4 |
| 376 | 8 | — | 16 | 0.25 | >128 |
| 377 | 4 | — | 2 | 0.25 | 8 |
| 378 | 4 | — | 2 | 0.25 | 128 |
| 379 | 16 | — | 16 | 0.5 | >128 |
| 380 | 32 | — | 8 | 1 | 32 |
| 381 | 16 | — | 4 | 1 | >128 |
| 382 | 16 | — | 4 | 1 | 128 |
| 383 | 4 | — | 4 | 0.25 | >128 |
| 384 | 4 | — | 4 | 0.5 | 64 |
| 385 | 4 | — | 2 | 0.25 | 64 |
| 386 | 2 | — | 8 | 0.125 | 8 |
| 387 | 8 | — | 8 | 0.25 | 32 |
| 388 | 8 | — | 8 | 2 | >128 |
| 389 | 8 | — | 4 | 1 | >128 |
| 390 | 4 | — | 16 | 1 | 128 |

TABLE 1-continued

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 MIC DATA (µg/mL) | ESBL −ve E. coli ATCC25922 | Meropenem susceptible P. aeruginosa ATCC27853 |
| 391 | 1 | — | 0.5 | 0.5 | 4 |
| 392 | 4 | — | 4 | 1 | 64 |
| 393 | 4 | — | 1 | 0.125 | 8 |
| 394 | 8 | — | 32 | 2 | 128 |
| 395 | 2 | — | 1 | 0.125 | 1 |
| 396 | 4 | — | 1 | 0.125 | 4 |
| 397 | 2 | — | 1 | 0.25 | 2 |
| 398 | 4 | — | 1 | 0.25 | 2 |
| 399 | 2 | — | 2 | 0.125 | 8 |
| 400 | 4 | — | 1 | 0.125 | 1 |
| 401 | 8 | — | 2 | 0.5 | 2 |
| 402 | 1 | — | 1 | 0.06 | 32 |
| 403 | 4 | — | 8 | 0.5 | 16 |
| 404 | 1 | — | 0.5 | 0.25 | 1 |
| 405 | 4 | — | 2 | 0.125 | 4 |
| 406 | 4 | — | 2 | 0.25 | 16 |
| 407 | 2 | — | 1 | 0.5 | 8 |
| 408 | 4 | — | 2 | 1 | 2 |
| 409 | 4 | — | 2 | 1 | 4 |
| 410 | 2 | — | 4 | 0.5 | 4 |
| 411 | 2 | — | 1 | 0.25 | 1 |
| 412 | 2 | — | 2 | 0.25 | 1 |
| 413 | 2 | — | 2 | 0.25 | 2 |
| 414 | 4 | — | 2 | 0.5 | 4 |
| 415 | 4 | — | 1 | 2 | 16 |
| 416 | 4 | — | 2 | 0.5 | 8 |
| 417 | 8 | — | 2 | 0.5 | 16 |
| 418 | 8 | — | 4 | 1 | 8 |
| 419 | 4 | — | 1 | 0.25 | 1 |
| 420 | 4 | — | 1 | 0.25 | 2 |
| 421 | 4 | — | 2 | 0.125 | 32 |
| 422 | 4 | — | 2 | 0.25 | 4 |
| 423 | 8 | — | 2 | 0.5 | 32 |
| 424 | 16 | — | 2 | 0.25 | 16 |
| 425 | 4 | — | 2 | 0.25 | 2 |
| 426 | 4 | — | 1 | 0.25 | 2 |
| 427 | 2 | — | 1 | 0.25 | 2 |
| 428 | 4 | — | 4 | 0.5 | 2 |
| 429 | 4 | — | 2 | 0.25 | 2 |
| 430 | 4 | — | 2 | 0.5 | 4 |
| 431 | 2 | — | 0.5 | 0.25 | 1 |
| 432 | 2 | — | 1 | 0.25 | 1 |
| 433 | 2 | — | 1 | 0.25 | 1 |
| 434 | 2 | — | 2 | 0.5 | 2 |
| 435 | 2 | — | 1 | 0.25 | 1 |
| 436 | 8 | — | 1 | 0.25 | 8 |
| 437 | 2 | — | 1 | 0.25 | 2 |
| 438 | 2 | — | 1 | 0.25 | 2 |
| 439 | 2 | — | 1 | 0.25 | 1 |
| 440 | 2 | — | 1 | 0.25 | 1 |
| 441 | 4 | — | 2 | 0.25 | 8 |
| 442 | 2 | — | 1 | 0.125 | 0.5 |
| 443 | 4 | — | 2 | 0.5 | 1 |
| 444 | 2 | — | 2 | 0.5 | 2 |
| 445 | 2 | — | 1 | 0.25 | 1 |
| 446 | 2 | — | 1 | 0.25 | 4 |
| 447 | 16 | — | 4 | 0.5 | 16 |
| 448 | 4 | — | 8 | 0.5 | >128 |
| 449 | 4 | — | 4 | 0.5 | 64 |
| 450 | 8 | — | 1 | 0.25 | 1 |
| 451 | 8 | — | 1 | 0.25 | 2 |
| 452 | 2 | — | 1 | 0.25 | 2 |
| 453 | 16 | — | 2 | 0.125 | 8 |
| 454 | 8 | — | 4 | 0.5 | 4 |
| 455 | 4 | — | 2 | 0.5 | 4 |
| 456 | 2 | — | 2 | 0.5 | 2 |
| 457 | 2 | — | 1 | 0.25 | 1 |
| 458 | 16 | — | 1 | 0.5 | 16 |
| 459 | 1 | — | 1 | 0.125 | 2 |
| 460 | 4 | — | 2 | 0.5 | 4 |

TABLE 1-continued

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 | ESBL −ve E. coli ATCC25922 | Meropenem susceptible P. aeruginosa ATCC27853 |
| | | | MIC DATA (µg/mL) | | |
| 461 | 4 | — | 2 | 0.5 | 4 |
| 462 | 4 | — | 1 | 0.25 | 2 |
| 463 | 4 | — | 1 | 0.5 | 2 |
| 464 | 4 | — | 4 | 1 | 16 |
| 465 | 4 | — | 2 | 0.5 | 16 |
| 466 | 4 | — | 2 | 0.5 | 4 |
| 467 | 8 | — | 2 | 1 | 8 |
| 468 | 4 | — | 2 | 0.5 | 8 |
| 469 | 4 | — | 2 | 0.5 | 4 |
| 470 | 4 | — | 2 | 0.5 | 4 |
| 471 | 2 | — | 2 | 0.5 | 4 |
| 472 | 4 | — | 2 | 0.5 | 2 |
| 473 | 4 | — | 2 | 0.5 | 4 |
| 474 | 4 | — | 2 | 0.25 | 2 |
| 475 | 4 | — | 2 | 0.5 | 2 |
| 476 | 2 | — | 2 | 1 | 32 |
| 477 | 2 | — | 2 | 0.5 | 64 |
| 478 | 8 | — | 1 | 0.125 | 8 |
| 479 | 8 | — | 2 | 0.25 | 16 |
| 480 | 2 | — | 1 | 0.25 | 2 |
| 481 | 2 | — | 2 | 0.125 | 2 |
| 482 | 4 | — | 4 | 0.25 | 4 |
| 483 | 4 | — | 4 | 0.5 | 128 |
| 484 | 2 | — | 4 | 1 | 32 |
| 485 | 8 | — | 4 | 0.5 | 4 |
| 486 | 2 | — | 8 | 0.5 | 64 |
| 487 | 2 | — | 1 | 0.25 | 8 |
| 488 | 4 | — | 1 | 0.25 | 2 |
| 489 | 4 | — | 1 | 0.5 | 16 |
| 490 | 32 | — | 2 | 2 | 32 |
| 491 | 4 | — | 2 | 0.25 | 8 |
| 492 | 4 | — | 2 | 0.5 | 2 |
| 493 | 2 | — | 1 | 0.125 | 0.5 |
| 494 | 8 | — | 4 | 0.25 | 16 |
| 495 | 2 | — | 1 | 0.25 | 1 |
| 496 | 2 | — | 2 | 0.25 | 2 |
| 497 | 4 | — | 2 | 0.25 | 4 |
| 498 | 2 | — | 2 | 0.125 | 8 |
| 499 | 2 | — | 1 | 0.25 | 1 |
| 500 | 2 | — | 2 | 0.25 | 2 |
| 501 | 4 | — | 1 | 0.25 | 1 |
| 502 | 4 | — | 1 | 0.25 | 2 |
| 503 | 2 | — | 1 | 0.5 | 16 |
| 504 | 2 | — | 4 | 0.5 | 32 |
| 505 | 2 | — | 1 | 0.25 | 1 |
| 506 | 4 | — | 1 | 0.25 | 1 |
| 507 | 2 | — | 8 | 1 | 64 |
| 508 | 16 | — | 8 | 2 | 128 |
| 509 | 32 | — | 4 | 4 | 32 |
| 510 | 4 | — | 4 | 0.25 | 1 |
| 511 | 4 | — | 2 | 0.25 | 1 |
| 512 | 8 | — | 64 | 2 | >128 |
| 513 | 4 | — | 1 | 0.25 | 16 |
| 514 | 16 | — | 16 | 0.5 | 32 |
| 515 | 2 | — | 1 | 0.25 | 16 |
| 516 | 2 | — | 2 | 0.25 | 2 |
| 517 | 4 | — | 2 | 0.5 | 4 |
| 518 | 8 | — | 4 | 1 | 128 |
| 519 | 16 | — | 16 | 2 | >128 |
| 520 | 16 | — | 16 | 2 | >128 |
| 521 | 2 | — | 0.5 | 0.5 | 2 |
| 522 | 4 | — | 2 | 0.25 | 1 |
| 523 | 2 | — | 1 | 0.125 | 1 |
| 524 | 4 | — | 2 | 0.25 | 1 |
| 525 | 4 | — | 2 | 0.25 | 0.5 |
| 526 | 4 | — | 2 | 0.25 | 1 |
| 527 | 4 | — | 1 | 0.125 | 1 |
| 528 | 4 | — | 1 | 0.25 | 1 |
| 529 | 4 | — | 2 | 0.25 | 1 |
| 530 | 2 | — | 1 | 0.25 | 0.5 |

TABLE 1-continued

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 MIC DATA (µg/mL) | ESBL −ve E. coli ATCC25922 | Meropenem susceptible P. aeruginosa ATCC27853 |
| 531 | 4 | — | 2 | 0.125 | 1 |
| 532 | 4 | — | 2 | 0.25 | 2 |
| 533 | 4 | — | 2 | 0.25 | 2 |
| 534 | 2 | — | 1 | 0.125 | 1 |
| 535 | 2 | — | 2 | 0.25 | 1 |
| 536 | 2 | — | 2 | 0.25 | 4 |
| 537 | 4 | — | 2 | 0.25 | 2 |
| 538 | 4 | — | 2 | 0.25 | 1 |
| 539 | 4 | — | 1 | 0.25 | 2 |
| 540 | 4 | — | 2 | 0.25 | 1 |
| 541 | 2 | — | 1 | 0.25 | 1 |
| 542 | 4 | — | 2 | 0.25 | 2 |
| 543 | 2 | — | 1 | 0.5 | 2 |
| 544 | 1 | — | 0.5 | 0.25 | 1 |
| 545 | 1 | — | 0.5 | 0.125 | 1 |
| 546 | 1 | — | 1 | 0.25 | 2 |
| 547 | 4 | — | 2 | 0.5 | 2 |
| 548 | 8 | — | 1 | 0.25 | 4 |
| 549 | 4 | — | 1 | 0.125 | 1 |
| 550 | 1 | — | 2 | 0.25 | 8 |
| 551 | 4 | — | 2 | 0.25 | 2 |
| 552 | 4 | — | 2 | 0.25 | 2 |
| 553 | 2 | — | 1 | 0.25 | 2 |
| 554 | 4 | — | 2 | 0.5 | 2 |
| 555 | 4 | — | 1 | 0.25 | 2 |
| 556 | 2 | — | 1 | 0.125 | 4 |
| 557 | 4 | — | 4 | 0.125 | 16 |
| 558 | 16 | — | 2 | 0.5 | 128 |
| 559 | 1 | — | 1 | 0.25 | 4 |
| 560 | 1 | — | 0.5 | 0.125 | 1 |
| 561 | 4 | — | 2 | 0.5 | 8 |
| 562 | 16 | — | 2 | 0.5 | 2 |
| 563 | 16 | — | 2 | 0.25 | 2 |
| 564 | 2 | — | 1 | 0.125 | 1 |
| 565 | 2 | — | 2 | 0.25 | 1 |
| 566 | 0.5 | — | 0.5 | 0.06 | 0.25 |
| 567 | 1 | — | 0.5 | 0.125 | 1 |
| 568 | 16 | — | 2 | 1 | 4 |
| 569 | 2 | — | 1 | 0.25 | 2 |
| 570 | 1 | — | 1 | 0.125 | 2 |
| 571 | 1 | — | 0.5 | 0.06 | 1 |
| 572 | 4 | — | 2 | 0.25 | 4 |
| 573 | 4 | — | 2 | 0.125 | 1 |
| 574 | 8 | — | 4 | 0.5 | 2 |
| 575 | 16 | — | 0.5 | 0.125 | >128 |
| 576 | 1 | — | 0.5 | 0.125 | 0.25 |
| 577 | 4 | — | 2 | 0.25 | 4 |
| 578 | 2 | — | 1 | 0.25 | 4 |
| 579 | 4 | — | 1 | 0.25 | 16 |
| 580 | 2 | — | 1 | 0.25 | 0.5 |
| 581 | 8 | — | 8 | 0.5 | 64 |
| 582 | 2 | — | 2 | 0.25 | 0.5 |
| 583 | 1 | — | 1 | 0.03 | 0.5 |
| 584 | 2 | — | 1 | 0.25 | 1 |
| 585 | 2 | — | 1 | 0.125 | 4 |
| 586 | 4 | — | 1 | 0.25 | 2 |
| 587 | 4 | — | 2 | 0.25 | 2 |
| 588 | 32 | — | 4 | 4 | 4 |
| 589 | 4 | — | 2 | 0.5 | 16 |
| 590 | 4 | — | 1 | 0.25 | 1 |
| 591 | 2 | — | 1 | 0.25 | 1 |
| 592 | 2 | — | 0.5 | 0.125 | 0.5 |
| 593 | 16 | — | 32 | 1 | 128 |
| 594 | 1 | — | >128 | 32 | >128 |
| 595 | 8 | — | >128 | 4 | >128 |
| 596 | 2 | — | 16 | 1 | 32 |
| 597 | 4 | — | 32 | 4 | 32 |
| 598 | 8 | — | 2 | 1 | 16 |
| 599 | 4 | — | 2 | 1 | 4 |

TABLE 1-continued

| | MIC of test compounds | | | | |
|---|---|---|---|---|---|
| | Pheno type- Organism | | | | |
| Example | MSSA S. aureus ATCC29213 | ESBL +ve (SHV-18) K. pneumoniae ATCC700603 | KPC-2 K. pneumoniae ATCC BAA-1705 | ESBL −ve E. coli ATCC25922 | Meropenem susceptible P. aeruginosa ATCC27853 |
| | | | MIC DATA (μg/mL) | | |
| 600 | 0.5 | — | 4 | 0.5 | 16 |
| 601 | 2 | — | 64 | 2 | 128 |

The invention claimed is:

1. A compound of formula (I):

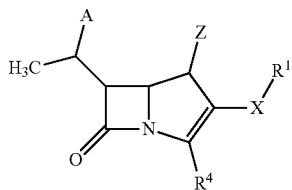

or a pharmaceutically acceptable salt, internal salt, stereoisomer, or N-oxide thereof,
wherein:

A is $NR^0R$;

$R^0$ is H or $C_{1-6}$alkyl, wherein the $C_{1-6}$ alkyl is optionally substituted with 1 or 2 substituents independently selected from the group consisting of halogen, CN, $C(O)NH_2$, OH, $OC_{1-6}$alkyl, and $S(O)_2NH_2$; and R is $C_{1-6}$alkyl, $(CH_2)_nC(O)R^2$, $(CH_2)_nC(S)R^2$, $(CH_2)_nS(O)_2R^2$, or C(NH)H, wherein the $C_{1-6}$ alkyl is optionally substituted with 1 or more independently selected $C_{3-6}$cycloalkyl substituents; or R and $R^0$, together with the nitrogen atom to which they are attached, form an optionally substituted 5- or 6-membered ring, wherein the 5- or 6-membered ring has 0, 1, 2, 3, or 4 additional ring heteroatoms independently selected from the group consisting of nitrogen, oxygen, and sulfur;

$R^1$ is $C_{2-6}$alkyl$NH_2$, $(CH_2)_{1-6}NHC(NH)NH_2$, $(CH_2)_{0-6}$AryC, or $(CH_2)_{0-6}$HetC;

wherein the $C_{2-6}$ alkyl$NH_2$ is optionally substituted with 1 or more substituents independently selected from the group consisting of $C(NR^x)R^x$, $C(O)OC_{1-6}$alkyl, $C(O)$Ophenyl, and C(O)pyrrolidinyl; and further wherein the C(O)pyrrolidinyl substituent is substituted with 1 or more independently selected $NR^xR^y$ substituents;

$R^2$ is H, $C_{1-6}$alkyl, $C_{1-6}$haloalkyl, $(CH_2)_{0-3}C(NOC_{1-6}$alkyl$)R^k$, $C(O)NR^xR^y$, C(O)OH, $C(O)OC_{1-6}$alkyl, $NR^xR^y$, OH, $OC_{1-6}$alkyl, $OC_{1-6}$haloalkyl, $C_{3-8}$cycloalkyl, Ary A, or HetA;

wherein the $C_{1-6}$ alkyl is optionally substituted with 1, 2, or 3 substituents independently selected from the group consisting of halogen, CN, $(CH_2)_{0-1}C(O)NR^xR^y$, C(O)OH, $C(O)OC_{1-6}$alkyl, $NR^aR^b$, OH, $OC_{1-6}$alkyl, $OC(O)C_{1-6}$alkyl, $P(O)(OC_{1-6}$alkyl$)_2$, $SCHF_2$, $S(O)C_{1-6}$haloalkyl, $S(O)_2C_{1-6}$alkyl, SAryA, $C_{3-8}$cycloalkyl, azetidinyl, azetidinonyl, HetA, and AryA; and further wherein the $(CH_2)_{0-3}C(NOC_{1-6}$alkyl$)R^k$ is optionally substituted with 1 or more independently selected $C(O)OR^x$ substituents;

wherein the $C_{3-8}$cycloalkyl of $R^2$ is optionally substituted with 1 or more substituents independently selected from the group consisting of $C_{1-6}$haloalkyl and $NR^xR^y$; and wherein the azetidinonyl substituent is optionally substituted with 1 or more independently selected $C_{1-6}$alkylOH substituents;

$R^4$ is $C(O)O^-$ or $C(O)OR^5$;

$R^5$ is H;

each $R^a$ is independently H, $C_{1-6}$alkyl, $CH_2C(O)N(R^x)_2$, $(CH_2)_{1-6}OR^x$, $C(NR^x)^x$, $C(NR^x)N(R^x)_2$, $S(O)_2C_{1-6}$alkyl, or $C_{3-8}$cycloalkyl;

each $R^b$ is independently H or $C_{1-3}$alkyl;

each $R^c$ is independently H, $C_{1-6}$alkyl, $(CH_2)_{1-3}C(O)NR^xR^y$, $(CH_2)_{1-3}C(O)NHCH_2CH_2OH$, $(CH_2)_{1-3}C(O)NHOCH_3$, $(CH_2)_{1-3}C(O)NHOCH_2$-phenyl, $(CH_2)_{1-3}C(O)$pyrrolidin-1-yl, $(CH_2)_{1-3}C(O)$diazepanyl, $(CH_2)_{1-3}$pyrrolidinyl, $(CH_2)_{1-3}$pyranyl, $(CH_2)_{1-3}$pyridinyl, C(NH)pyrrolidin-1-yl, $OC_{1-6}$alkyl, tetrahydro-2H-pyran-4-yl, phenyl-$(CH_2)_{1-3}NR^xR^y$, phenyl-C(O)pyrrolidinyl-$NR^xR^y$, phenyl-C(O)piperazinyl, or pyridinyl;

wherein each $C_{1-6}$alkyl of $R^c$ is optionally and independently substituted with 1 or more substituents independently selected from the group consisting of CN, $NR^hR^j$, and OH; and further wherein each $(CH_2)_{1-3}C(O)$pyrrolidin-1-yl is independently substituted with 1 or more independently selected $NR^xR^y$ substituents;

wherein each $(CH_2)_{1-3}$pyrrolidinyl is optionally and independently substituted with 1 or more independently selected $C(O)NR^xR^y$ substituents;

wherein each $(CH_2)_{1-3}$pyranyl is optionally and independently substituted with 1 or 2 substituents independently selected from the group consisting of oxo and $OCH_3$;

wherein each $(CH_2)_{1-3}$pyridinyl is optionally and independently substituted with 1 or more substituents independently selected from the group consisting of oxo, $CH_3$, and OH; and wherein each C(NH)pyrrolidin-1-yl is optionally and independently substituted with 1 or more independently selected $NR^xR^y$ substituents;

each $R^d$ is independently H, $C_{1-3}$alkyl, $C_{1-3}$alkylCN, or $C_{1-3}$alkylOH; or each $R^c$ and $R^d$, taken together with the nitrogen atom to which they are attached, independently forms an optionally substituted 4- to 12-membered heterocyclic ring or ring system;

wherein each 4- to 12-membered heterocyclic ring or ring system independently has 0, 1, or 2 additional ring heteroatoms independently selected from the group consisting of nitrogen, oxygen, and sulfur; and further wherein each 4- to 12-membered heterocyclic ring system is optionally and independently bridged, fused, or spirocyclic, or a combination thereof;

wherein any nitrogen ring heteroatom of each 4- to 12-membered heterocyclic ring or ring system is optionally and independently quaternized; and wherein each 4- to 12-membered heterocyclic ring or ring system is optionally and independently substituted with 1, 2, 3, or 4 substituents independently selected from the group consisting of oxo, $(CH_2)_{0-3}$halogen, $C_{1-6}$alkyl, $(CH_2)_{0-3}NR^hR^j$, $CH_2CH(F)CH_2NH_2$, $(CH_2)_{0-2}C(O)(CH_2)_{0-2}NR^hR^j$, $(CH_2)_{0-2}C(O)CH(NH_2)(CH_2)_{0-2}OH$, $(CH_2)_{0-1}C(O)$pyrrolidinyl, $(CH_2)_{0-1}NHCH_2CH_2NR^hR^j$, $(CH_2)_{0-1}NH(CH_2)_{0-1}C(O)(CH_2)_{0-1}NR^hR^j$, $(CH_2)_{0-3}NHC(NH)NH_2$, $(CH_2)_{0-2}NHS(O)_2CH_3$, $(CH_2)_{0-1}NHS(O)_2(CH_2)_{0-2}NR^hR^j$, $C(NH)NH_2$, $(CH_2)_{0-3}OH$, $CH_2CH(OH)CH_2NH_2$, $(CH_2)_{0-2}$azetidinyl, $(CH_2)_{0-2}$pyrrolidinyl, $(CH_2)_{0-2}$piperazinyl, $(CH_2)_{0-1}$phenyl, $(CH_2)_{0-2}$triazolyl, $(CH_2)_{0-2}$tetrazolyl, $C(O)(CH_2)_{1-3}NH_2$, $C(O)C_{1-6}$alkylNH$_2$, $C(O)(CH_2)_{0-3}NHC(NH)NH_2$, $C(O)NH(CH_2)_{1-3}NH_2$, C(O)NHpyridinyl, C(O)OH, C(O)piperazinyl, C(O)diazepinyl, NHCH$_2$CN, NHCH$_2$-pyridinyl, NHC(NH)H, NHC(O)R$^i$, NHC(O)CH$_2$NHC(NH)NH$_2$, =NH, NHpyrimidinyl, OC$_{1-6}$alkyl, ONH$_2$, and ONHC(O)CH$_2$NHCH$_3$;

wherein each C$_{1-6}$alkyl substituent is optionally and independently substituted with 1 or more substituents independently selected from the group consisting of halogen, CN, and OH; and further wherein each $(CH_2)_{0-2}C(O)(CH_2)_{0-2}NR^hR^j$ is optionally and independently substituted with 1 or more substituents independently selected from the group consisting of NH$_2$ and OH;

wherein each $(CH_2)_{0-1}C(O)$pyrrolidinyl is optionally and independently substituted with 1 or more NH$_2$ substituents;

wherein each $(CH_2)_{0-3}NR^hR^j$ is optionally and independently substituted with 1 or 2 substituents independently selected from the group consisting of halogen, CH$_3$, and NH$_2$;

wherein each $(CH_2)_{0-2}$azetidinyl is optionally and independently substituted with 1 or more substituents independently selected from the group consisting of CH$_2$NH$_2$, NH$_2$, and OH;

wherein each $(CH_2)_{0-2}$pyrrolidinyl is optionally and independently substituted with 1 or more NH$_2$ substituents;

wherein each $(CH_2)_{0-2}$triazolyl is optionally and independently substituted with 1 or more CH$_2$NH$_2$ substituents;

wherein each C(O)(CH$_2$)$_{1-3}$NH$_2$ is optionally and independently substituted with 1 or more NH$_2$ substituents;

wherein each C(O)C$_{1-6}$alkylNH$_2$ is optionally and independently substituted with 1 or more OH substituents;

wherein each C(O)NH(CH$_2$)$_{1-3}$NH$_2$ is optionally and independently substituted with—1 or more OH substituents;

wherein each C(O)diazepinyl is optionally and independently substituted with 1 or more C(NH)NH$_2$ substituents; and wherein each NHCH$_2$-pyridinyl is optionally and independently substituted with 1 or more substituents independently selected from the group consisting of oxo, CH$_3$, and OH;

each R$^f$ is independently H, C(O)N(C$_{1-6}$alkyl)$_2$, C(O)cyclopentyl-N(R$^x$)$_2$, C(O)pyrrolidinyl, C(O)thiazolidinyl, C(O)pyridinyl, S(O)$_2$C$_{1-6}$alkyl, S(O)$_2$N(R$^x$)$_2$, S(O)$_2$-pyrrolidinyl-N(R$^x$)$_2$, or S(O)$_2$-piperazinyl;

wherein each C(O)pyrrolidinyl is independently substituted with 1 or more substituents independently selected from the group consisting of halogen and NR$^a$R$^b$; and further wherein each C(O)pyridinyl is optionally and independently substituted with 1 or more substituents independently selected from the group consisting of oxo, C$_{1-3}$alkyl, and OH;

each R$^g$ is independently H or C$_{1-3}$alkyl; or each R$^f$ and R$^g$, taken together with the nitrogen atom to which they are attached, independently forms pyrrolidin-1-yl, piperidin-1-yl, piperazin-1-yl, morpholin-4-yl, thiomorpholin-4-yl, or triazolyl;

wherein each pyrrolidin-1-yl is optionally and independently substituted with 1 or more CH$_3$ substituents;

wherein each piperidin-1-yl and thiomorpholin-4-yl is optionally and independently substituted with 1 or more substituents independently selected from the group consisting of C$_{1-6}$ alkyl and N(R$^x$)$_2$; and further wherein each triazolyl is independently substituted with 1 or more CH$_2$NH$_2$ substituents;

each R$^h$ is independently H, C$_{1-6}$alkyl, or C$_{3-8}$cycloalkyl;

each R$^i$ is independently C$_{1-6}$haloalkyl, C$_{1-3}$alkylCN, C$_{1-5}$alkylNH$_2$, or OC$_{1-6}$alkyl, wherein each C$_{1-6}$haloalkyl is optionally and independently substituted with 1 or more independently selected NR$^x$R$^y$ substituents;

each R$^j$ is independently H, C$_{1-6}$alkyl, or C$_{3-8}$cycloalkyl;

R$^k$ is C$_{1-6}$alkyl or thiazolyl, wherein the thiazolyl is substituted with 1 or more NH$_2$ substituents;

each R$^x$ is independently H or C$_{1-3}$alkyl;

each R$^y$ is independently H or C$_{1-3}$alkyl;

each AryA is independently an optionally substituted 5- or 6-membered aromatic ring or an optionally substituted 9- or 10-membered bicyclic aromatic ring;

wherein each 5- or 6-membered aromatic ring independently has 0, 1, 2, 3, or 4 ring heteroatoms independently selected from the group consisting of nitrogen, oxygen, and sulfur; and further wherein each 9- or 10-membered bicyclic aromatic ring independently has 1, 2, 3, 4, 5, or 6 ring heteroatoms independently selected from the group consisting of nitrogen, oxygen, and sulfur;

AryC is an optionally substituted 5- or 6-membered aromatic ring or an optionally substituted 7- to 10-membered bicyclic aromatic ring;

wherein the 5- or 6-membered aromatic ring has 0, 1, 2, or 3 ring heteroatoms independently selected from the group consisting of nitrogen, oxygen, and sulfur;

wherein the 7- to 10-membered bicyclic aromatic ring has 0, 1, 2, or 3 ring heteroatoms independently selected from the group consisting of nitrogen, oxygen, and sulfur; and further wherein any nitrogen ring heteroatom of the 5- or 6-membered aromatic ring is optionally and independently quaternized with 1 CH$_3$ substituent;

each HetA is independently an optionally substituted 5- to 10-membered saturated ring;

wherein each 5- to 10-membered saturated ring independently has 1, 2, 3, or 4 ring heteroatoms independently selected from the group consisting of nitrogen, oxygen, and sulfur; and further wherein any sulfur ring heteroatom of each 5- to 10-membered saturated ring is optionally oxidized;

HetC is an optionally substituted 4- to 8-membered saturated ring, wherein the 4- to 8-membered saturated ring has 1 or 2 ring heteroatoms independently selected from the group consisting of nitrogen, oxygen, and sulfur;
n is 0, 1, 2, 3, 4, 5, or 6;
X is —S—; and
Z is H or $CH_3$;
wherein each AryA, AryC, each HetA, HetC, and the 5- or 6-membered ring formed by combining R and $R^o$ is optionally and independently substituted with 1, 2, 3, or 4 substituents independently selected from the group consisting of oxo, halogen, $C_{1-6}$ alkyl, $C_{1-6}$haloalkyl, $C_{1-6}$alkylOH, $(CH_2)_{0-3}C(NH)NH_2$, $(CH_2)_{1-3}C(O)NR^xR^y$, $(CH_2)_{1-3}C(O)$pyrrolidinyl, $(CH_2)_{0-3}NR^fR^g$, $(CH_2)_{0-1}NR^xR^y$, $(CH_2)_{0-3}NHC(NH)NH_2$, $(CH_2)_{0-1}NHS(O)_2NR^xR^y$, $(CH_2)_{0-3}OC_{1-3}$alkyl, $(CH_2)_{0-2}$pyrrolidinyl, $(CH_2)_{0-2}$piperidinyl, $(CH_2)_{0-2}$pyrazolyl, $(CH_2)_{0-2}$triazolyl, $(CH_2)_{0-2}$tetrazolyl, $(CH_2)_{0-2}$thiazolyl, $(CH_2)_{0-2}$thienyl, $(CH_2)_{0-2}$pyridinyl, C(NH)H, C(NH)pyrrolidinyl, $C(O)C_{1-6}$alkyl, $C(O)C_{1-6}$alkyl$NH_2$, $C(O)NR^cR^d$, C(O)OH, $C(O)OC_{1-6}$ alkyl, $NHCH_2CN$, $NHC(O)R^i$, OH, $OC_{1-6}$alkyl, $S(O)_2NR^cR^d$, $C_{3-8}$cycloalkyl, and 4,5-dihydrothiazol-2-yl;
wherein each $(CH_2)_{1-3}C(O)$pyrrolidinyl is optionally and independently substituted with 1 or more $NR^xR^y$ substituents;
wherein each $(CH_2)_{0-2}$pyrrolidinyl is optionally and independently substituted with 1 or more $NR^xR^y$ substituents;
wherein each $(CH_2)_{0-2}$piperidinyl is optionally and independently substituted with 1 or more $CH_3$ substituents and further optionally and independently quaternized with 1 substituent selected from the group consisting of $CH_3$ and $(CH_2)_{0-3}NH_2$;
wherein each $(CH_2)_{0-2}$pyrazolyl is optionally and independently substituted with 1 or more $(CH_2)_{0-3}NH_2$ substituents and further optionally and independently quaternized with 1 $CH_3$ substituent;
wherein each $(CH_2)_{0-2}$pyridinyl is optionally and independently substituted with 1 or more $CH_3$ substituents and further optionally and independently quaternized with 1 substituent selected from the group consisting of $CH_3$ and $CH_2C(O)NH_2$; and
wherein each C(NH)pyrrolidinyl is optionally and independently substituted with 1 or more $NR^xR^y$ substituents.

2. The compound of claim 1, or a stereoisomer thereof, wherein the stereoisomer of the compound is a compound of formula (Ia):

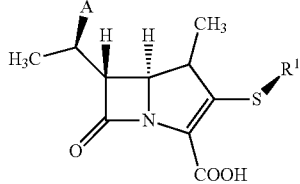

(Ia)

or a pharmaceutically acceptable salt, internal salt, or N-oxide thereof,
wherein:
A is $NR^oR$;
$R^o$ is H; and R is $C(O)CH_2$-tetrazolyl;
$R^1$ is $CH_2$-pyrrolidinyl or pyrrolidinyl;
wherein the pyrrolidinyl of the $CH_2$-pyrrolidinyl is optionally substituted with 1 $NH_2$ substituent; and
wherein the pyrrolidinyl is substituted with 1 $C(O)NR^cR^d$ substituent; and
$R^c$ and $R^d$, taken together with the nitrogen atom to which they are attached, forms azetidin-1-yl, pyrrolidin-1-yl, piperidin-1-yl, piperazin-1-yl, morpholin-4-yl, 1,4-diazepanyl, decahydro-1,6-naphthyridinyl, 2,6-diazaspiro[3.4]octanyl, 5-oxa-2-azaspiro[3.4]octanyl, 1,7-diazaspiro[3.5]nonanyl, 2,7-diazaspiro[3.5]nonanyl, 2,7-diazaspiro[4.4]nonanyl, 1,7-diazaspiro[4.5]decanyl, 1,8-diazaspiro[4.5]decanyl, 2,8-diazaspiro[4.5]decanyl, 1,9-diazaspiro[5.5]undecanyl, 3.6-diazabicyclo[3.2.0]heptanyl, octahydrocyclopenta[c]pyrrolyl, octahydropyrrolo[3,4-h]pyrrolyl, octahydropyrrolo[3,4-c]pyrrolyl, octahydropyrrolo[3,4-d]imidazolyl, octahydro-1H-pyrrolo[2,3-c]pyridinyl, octahydro-1H-pyrrolo[3,2-b]pyridinyl, octahydro-1H-pyrrolo[3,2-c]pyridinyl, 5,5-dimethyloctahydro-1H-pyrrolo[3,2-c]pyridinium, octahydro-1H-pyrrolo[3,4-b]pyridinyl, octahydro-1H-pyrrolo[3,4-c]pyridinyl, octahydropyrrolo[3,4-b][1,4]oxazinyl, 5,6,7,8-tetrahydroimidazo[1,5-a]pyrazinyl, 3,8-diazatricyclo[5.2.1.01,5]decanyl, and 8-azaspiro[bicyclo[3.2.1]octane-3,3'-pyrrolidinyl];
wherein each azetidin-1-yl is optionally and independently substituted with 1, 2, 3, or 4 $NHC(NH)NH_2$ substituents;
wherein each pyrrolidin-1-yl is independently substituted with 1 or 2 substituents independently selected from the group consisting of F, $CH_2F$, $CH_2NH_2$, $C(CH_3)_2NH_2$, $CH_2NHS(O)_2NH_2$, $CH_2OH$, C(O)OH, $NH_2$, $NHCH_3$, NHC(NH)H, $NHC(NH)NH_2$, $NHC(O)CH_2NH_2$, $NHC(O)CH_2CH_2NH_2$, $NHC(O)CH_2NHC(NH)NH_2$, OH, $OCH_3$, and triazolyl, wherein the triazolyl is substituted with 1 or more $CH_2NH_2$ substituents;
wherein each piperidin-1-yl is independently substituted with 1 or 2 substituents independently selected from the group consisting of F, $CH_3$, $(CH_2)_{0-2}NH_2$, $CH_2NHCH_2C(O)NH_2$, $CH_2OH$, $C(O)NHCH_2CH(OH)CH_2NH_2$, OH, and azetidinyl, wherein the azetidinyl is substituted with 1 or more OH substituents;
wherein each piperazin-1-yl is optionally and independently substituted with 1 or 2 substituents independently selected from the group consisting of $CH_3$, $CH_2NH_2$, $CH_2CH_2NH_2$, $CH_2CH_2NHC(NH)NH_2$, $CH_2CH(F)CH_2NH_2$, $CH_2CH(NH_2)CH_2NH_2$, $CH_2C(O)NH_2$, $C(NH)NH_2$, $C(O)(CH_2)_{1-2}NH_2$, $C(O)CH_2NHCH_3$, $C(O)CH(NH_2)NH_2$, and $C(O)CH(NH_2)CH_2OH$;
wherein each morpholin-4-yl is optionally and independently substituted with 1 $CH_2NH_2$ substituent;
wherein each 1.4-diazepanyl is optionally and independently substituted with 1 $C(NH)NH_2$ substituent;
wherein each 5-oxa-2-azaspiro[3.4]octanyl is optionally and independently substituted with 1 $NH_2$ substituent;
wherein each octahydrocyclopenta[c]pyrrolyl is optionally and independently substituted with 1 or 2 substituents independently selected from the group consisting of $CH_2NH_2$, $CH_2OH$, $NH_2$, and $NHC(NH)NH_2$;
wherein each octahydropyrrolo[3,4-b]pyrrolyl is optionally and independently substituted with 1 or 2 substituents independently selected from the group consisting of $CH_2OH$, $CH_2CH_2NH_2$, and $C(NH)NH_2$;

wherein each octahydropyrrolo[3,4-c]pyrrolyl is optionally and independently substituted with 1 CH$_2$OH substituent;

wherein each octahydropyrrolo[3,4-c]imidazolyl is optionally and independently substituted with 1 =NH substituent;

wherein each octahydro-1H-pyrrolo[3,2-c]pyridinyl is optionally and independently substituted with 1, 2, 3, or 4 substituents independently selected from the group consisting of CH$_2$CH$_2$NH$_2$, CH$_2$CH(OH)NH$_2$, CH$_2$CH(OH)CH$_2$NH$_2$, and C(NH)NH$_2$;

wherein each octahydro-1H-pyrrolo[3,4-b]pyridinyl is optionally and independently substituted with 1 CH$_2$OH substituent;

wherein each octahydro-1H-pyrrolo[3,4-c]pyridinyl is optionally and independently substituted with 1 or 2 substituents independently selected from the group consisting of CH$_2$OH and C(O)OH; and wherein each 5,6,7,8-tetrahydroimidazo[1,5-a]pyrazinyl is optionally and independently substituted with 1 NH$_2$ substituent.

3. The compound of claim 1, wherein the compound is of formula (Ib):

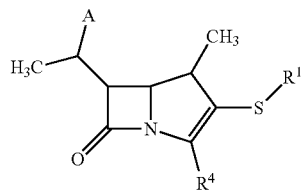

(Ib)

or a pharmaceutically acceptable salt, internal salt, stereoisomer, or N-oxide thereof,
wherein:
A is NR$^O$R;
R$^O$ is H or C$_{1-6}$alkyl, wherein the C$_{1-6}$ alkyl is optionally substituted with 1 or 2 substituents independently selected from the group consisting of halogen, CN, C(O)NH$_2$, OH, OC$_{1-6}$alkyl, and S(O)$_2$NH$_2$;
R is (CH$_2$)$_n$C(O)R$^2$, (CH$_2$)$_n$C(S)R$^2$, or (CH$_2$)$_n$S(O)$_2$R$^2$; or
R and R$^O$, together with the nitrogen atom to which they are attached, form an optionally substituted 5- or 6-membered ring, wherein the 5- or 6-membered ring has 0, 1, 2, 3, or 4 additional ring heteroatoms independently selected from the group consisting of nitrogen, oxygen, and sulfur;
R$^1$ is (CH$_2$)$_{0-6}$HetC;
R$^2$ is C$_{1-6}$alkyl or AryA, wherein the C$_{1-6}$ alkyl is optionally substituted with 1, 2, or 3 substituents independently selected from the group consisting of SAryA and AryA;
R$^4$ is C(O)O$^-$ or C(O)OR$^5$;
R$^5$ is H;
each R$^a$ is independently H, C$_{1-6}$alkyl, CH$_2$C(O)N(R$^x$)$_2$, C(NR$^x$)R$^x$, C(NR$^x$)N(R$^x$)$_2$, S(O)$_2$C$_{1-6}$alkyl, or C$_{3-8}$cycloalkyl;
each R$^b$ is independently H or C$_{1-3}$alkyl;
each R$^c$ is independently H, C$_{1-6}$alkyl, (CH$_2$)$_{1-3}$C(O)NR$^x$R$^y$, (CH$_2$)$_{1-3}$C(O)NHCH$_2$CH$_2$OH, (CH$_2$)$_{1-3}$C(O)NHOCH$_3$, (CH$_2$)$_{1-3}$C(O)NHOCH$_2$-phenyl, (CH$_2$)$_{1-3}$C(O)pyrrolidin-1-yl, (CH$_2$)$_{1-3}$C(O)diazepanyl, (CH$_2$)$_{1-3}$pyrrolidinyl, (CH$_2$)$_{1-3}$pyranyl, (CH$_2$)$_{1-3}$pyridinyl, C(NH)pyrrolidin-1-yl, OC$_{1-6}$alkyl, tetrahydro-2H-pyran-4-yl, phenyl-(CH$_2$)$_{1-3}$NR$^x$R$^y$, phenyl-C(O)pyrrolidinyl-NR$^x$R$^y$, phenyl-C(O)piperazinyl, or pyridinyl;

wherein each C$_{1-6}$alkyl of R$^c$ is optionally and independently substituted with 1 or more substituents independently selected from the group consisting of CN, NR$^h$R$^j$, and OH; and further wherein each (CH$_2$)$_{1-3}$C(O)pyrrolidin-1-yl is independently substituted with 1 or more independently selected NR$^x$R$^y$ substituents;

wherein each (CH$_2$)$_{1-3}$pyrrolidinyl is optionally and independently substituted with 1 or more independently selected C(O)NR$^x$R$^y$ substituents;

wherein each (CH$_2$)$_{1-3}$pyranyl is optionally and independently substituted with 1 or 2 substituents independently selected from the group consisting of oxo and OCH$_3$;

wherein each (CH$_2$)$_{1-3}$pyridinyl is optionally and independently substituted with 1 or more substituents independently selected from the group consisting of oxo, CH$_3$, and OH; and wherein each C(NH)pyrrolidin-1-yl is optionally and independently substituted with 1 or more independently selected NR$^x$R$^y$ substituents;

each R$^d$ is independently H, C$_{1-3}$alkyl, C$_{1-3}$alkylCN, or C$_{1-3}$alkylOH; or each R$^c$ and R$^d$, taken together with the nitrogen atom to which they are attached, independently forms an optionally substituted 4- to 12-membered heterocyclic ring or ring system;

wherein each 4- to 12-membered heterocyclic ring or ring system independently has 0, 1, or 2 additional ring heteroatoms independently selected from the group consisting of nitrogen, oxygen, and sulfur; and further wherein each 4- to 12-membered heterocyclic ring system is optionally and independently bridged, fused, or spirocyclic, or a combination thereof;

wherein any nitrogen ring heteroatom of each 4- to 12-membered heterocyclic ring or ring system is optionally and independently quaternized; and wherein each 4- to 12-membered heterocyclic ring or ring system is optionally and independently substituted with 1, 2, 3, or 4 substituents independently selected from the group consisting of oxo, (CH$_2$)$_{0-3}$halogen, C$_{1-6}$alkyl, (CH$_2$)$_{0-3}$NR$^h$R$^j$, CH$_2$CH(F)CH$_2$NH$_2$, (CH$_2$)$_{0-2}$C(O)(CH$_2$)$_{0-2}$NR$^h$R$^j$, (CH$_2$)$_{0-2}$C(O)CH(NH$_2$)(CH$_2$)$_{0-2}$OH, (CH$_2$)$_{0-1}$C(O)pyrrolidinyl, (CH$_2$)$_{0-1}$NHCH$_2$CH$_2$NR$^h$R$^j$, (CH$_2$)$_{0-1}$NH(CH$_2$)$_{0-1}$C(O)(CH$_2$)$_{0-1}$NR$^h$R$^j$, (CH$_2$)$_{0-3}$NHC(NH)NH$_2$, (CH$_2$)$_{0-2}$NHS(O)$_2$CH$_3$, (CH$_2$)$_{0-1}$NHS(O)$_2$(CH$_2$)$_{0-2}$NR$^h$R$^j$, C(NH)NH$_2$, (CH$_2$)$_{0-3}$OH, CH$_2$CH(OH)CH$_2$NH$_2$, (CH$_2$)$_{0-2}$azetidinyl, (CH$_2$)$_{0-2}$pyrrolidinyl, (CH$_2$)$_{0-2}$piperazinyl, (CH$_2$)$_{0-1}$phenyl, (CH$_2$)$_{0-2}$triazolyl, (CH$_2$)$_{0-2}$tetrazolyl, C(O)(CH$_2$)$_{1-3}$NH$_2$, C(O)C$_{1-6}$alkylNH$_2$, C(O)(CH$_2$)$_{0-3}$NHC(NH)NH$_2$, C(O)NH(CH$_2$)$_{1-3}$NH$_2$, C(O)NHpyridinyl, C(O)OH, C(O)piperazinyl, C(O)diazepinyl, NHCH$_2$CN, NHCH$_2$-pyridinyl, NHC(NH)H, NHC(O)R$^i$, NHC(O)CH$_2$NHC(NH)NH$_2$, =NH, NHpyrimidinyl, OC$_{1-6}$alkyl, ONH$_2$, and ONHC(O)CH$_2$NHCH$_3$;

wherein each C$_{1-6}$alkyl substituent is optionally and independently substituted with 1 or more substituents independently selected from the group consisting of halogen, CN, and OH; and further wherein each (CH$_2$)$_{0-2}$C(O)(CH$_2$)$_{0-2}$NR$^h$R$^j$ is optionally and independently substituted with 1 or more substituents independently selected from the group consisting of NH$_2$ and OH;

wherein each (CH$_2$)$_{0-1}$C(O)pyrrolidinyl is optionally and independently substituted with 1 or more NH$_2$ substituents;

wherein each (CH$_2$)$_{0-3}$NR$^h$R$^j$ is optionally and independently substituted with 1 or 2 substituents independently selected from the group consisting of halogen, CH$_3$, and NH$_2$;

wherein each (CH$_2$)$_{0-2}$azetidinyl is optionally and independently substituted with 1 or more substituents independently selected from the group consisting of CH$_2$NH$_2$, NH$_2$, and OH;

wherein each (CH$_2$)$_{0-2}$pyrrolidinyl is optionally and independently substituted with 1 or more NH$_2$ substituents;

wherein each (CH$_2$)$_{0-2}$triazolyl is optionally and independently substituted with 1 or more CH$_2$NH$_2$ substituents;

wherein each C(O)(CH$_2$)$_{1-3}$NH$_2$ is optionally and independently substituted with 1 or more NH$_2$ substituents;

wherein each C(O)C$_{1-6}$alkylNH$_2$ is optionally and independently substituted with 1 or more OH substituents;

wherein each C(O)NH(CH$_2$)$_{1-3}$NH$_2$ is optionally and independently substituted with—1 or more OH substituents;

wherein each C(O)diazepinyl is optionally and independently substituted with 1 or more C(NH)NH$_2$ substituents; and wherein each NHCH$_2$-pyridinyl is optionally and independently substituted with 1 or more substituents independently selected from the group consisting of oxo, CH$_3$, and OH;

each R$^f$ is independently H, C(O)N(C$_{1-6}$alkyl)$_2$, C(O)cyclopentyl-N(R$^x$)$_2$, C(O)pyrrolidinyl, C(O)thiazolidinyl, C(O)pyridinyl, S(O)$_2$C$_{1-6}$alkyl, S(O)$_2$N(R$^x$)$_2$, S(O)$_2$-pyrrolidinyl-N(R$^x$)$_2$, or S(O)$_2$-piperazinyl;

wherein each C(O)pyridinyl is optionally and independently substituted with 1 or more substituents independently selected from the group consisting of oxo, C$_{1-3}$alkyl, and OH, and further wherein each C(O)pyrrolidinyl is independently substituted with 1 or more substituents independently selected from the group consisting of halogen and NR$^a$R$^b$;

each R$^g$ is independently H or C$_{1-3}$alkyl; or each R$^f$ and R$^g$, taken together with the nitrogen atom to which they are attached, independently forms pyrrolidin-1-yl, piperidin-1-yl, piperazin-1-yl, morpholin-4-yl, thiomorpholin-4-yl, or triazolyl;

wherein each pyrrolidin-1-yl is optionally and independently substituted with 1 or more CH$_3$ substituents;

wherein each thiomorpholin-4-yl is optionally and independently substituted with 1 or more substituents independently selected from the group consisting of C$_{1-6}$alkyl and N(R$^x$)$_2$; and further wherein each triazolyl is independently substituted with 1 or more CH$_2$NH$_2$ substituents;

each R$^h$ is independently H, C$_{1-6}$alkyl, or C$_{3-8}$cycloalkyl;

each R$^j$ is independently C$_{1-6}$haloalkyl, C$_{1-3}$alkylCN, C$_{1-5}$alkylNH$_2$, or OC$_{1-6}$alkyl, wherein each C$_{1-6}$haloalkyl is optionally and independently substituted with 1 or more independently selected NR$^x$R$^y$ substituents;

each R$^j$ is independently H, C$_{1-6}$alkyl, or C$_{3-8}$cycloalkyl;

each R$^x$ is independently H or C$_{1-3}$alkyl;

each R$^y$ is independently H or C$_{1-3}$alkyl;

each AryA is independently an optionally substituted 5-membered aromatic ring, wherein each 5-membered aromatic ring independently has 3 or 4 nitrogen ring heteroatoms;

HetC is a substituted 4- to 8-membered saturated ring, wherein the 4- to 8-membered saturated ring has 1 nitrogen ring heteroatom; and n is 0, 1, 2, 3, 4, 5, or 6;

wherein each AryA, HetC, and the 5- or 6-membered ring formed by combining R and R$^o$ is optionally and independently substituted with 1, 2, 3, or 4 substituents independently selected from the group consisting of oxo, halogen, C$_{1-6}$ alkyl, C$_{1-6}$haloalkyl, C$_{1-6}$alkylOH, (CH$_2$)$_{0-3}$C(NH)NH$_2$, (CH$_2$)$_{1-3}$C(O)NR$^x$R$^y$, (CH$_2$)$_{1-3}$C(O)pyrrolidinyl, (CH$_2$)$_{0-3}$NR$^f$R$^g$, (CH$_2$)$_{0-1}$NR$^x$R$^y$, (CH$_2$)$_{0-3}$NHC(NH)NH$_2$, (CH$_2$)$_{0-1}$NHS(O)$_2$NR$^x$R$^y$, (CH$_2$)$_{0-3}$OC$_{1-3}$alkyl, (CH$_2$)$_{0-2}$pyrrolidinyl, (CH$_2$)$_{0-2}$piperidinyl, (CH$_2$)$_{0-2}$pyrazolyl, (CH$_2$)$_{0-2}$-triazolyl, (CH$_2$)$_{0-2}$tetrazolyl, (CH$_2$)$_{0-2}$thiazolyl, (CH$_2$)$_{0-2}$thienyl, (CH$_2$)$_{0-2}$pyridinyl, C(NH)H, C(NH)pyrrolidinyl, C(O)C$_{1-6}$alkyl, C(O)C$_{1-6}$alkylNH$_2$, C(O)NR$^c$R$^d$, C(O)OH, C(O)OC$_{1-6}$ alkyl, NHCH$_2$CN, NHC(O)R$^i$, OH, OC$_{1-6}$ alkyl, S(O)$_2$NR$^c$R$^d$, C$_{3-8}$cycloalkyl, and 4,5-dihydrothiazol-2-yl;

wherein each (CH$_2$)$_{1-3}$C(O)pyrrolidinyl is optionally and independently substituted with 1 or more NR$^x$R$^y$ substituents;

wherein each (CH$_2$)$_{0-2}$pyrrolidinyl is optionally and independently substituted with 1 or more NR$^x$R$^y$ substituents;

wherein each (CH$_2$)$_{0-2}$piperidinyl is optionally and independently substituted with 1 or more CH$_3$ substituents and further optionally and independently quaternized with 1 substituent selected from the group consisting of CH$_3$ and (CH$_2$)$_{0-3}$NH$_2$;

wherein each (CH$_2$)$_{0-2}$pyrazolyl is optionally and independently substituted with 1 or more (CH$_2$)$_{0-3}$NH$_2$ substituents and further optionally and independently quaternized with 1 CH$_3$ substituent;

wherein each (CH$_2$)$_{0-2}$pyridinyl is optionally and independently substituted with 1 or more CH$_3$ substituents and further optionally and independently quaternized with 1 substituent selected from the group consisting of CH$_3$ and CH$_2$C(O)NH$_2$; and wherein each C(NH)pyrrolidinyl is optionally and independently substituted with 1 or more NR$^x$R$^y$ substituents.

4. The compound of claim 1, or a pharmaceutically acceptable salt, internal salt, stereoisomer, or N-oxide thereof, wherein NR$^o$R is

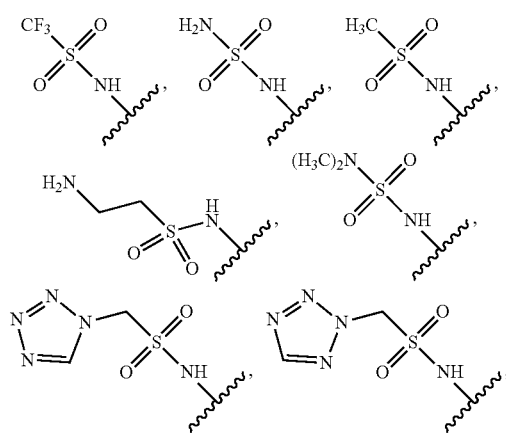

-continued

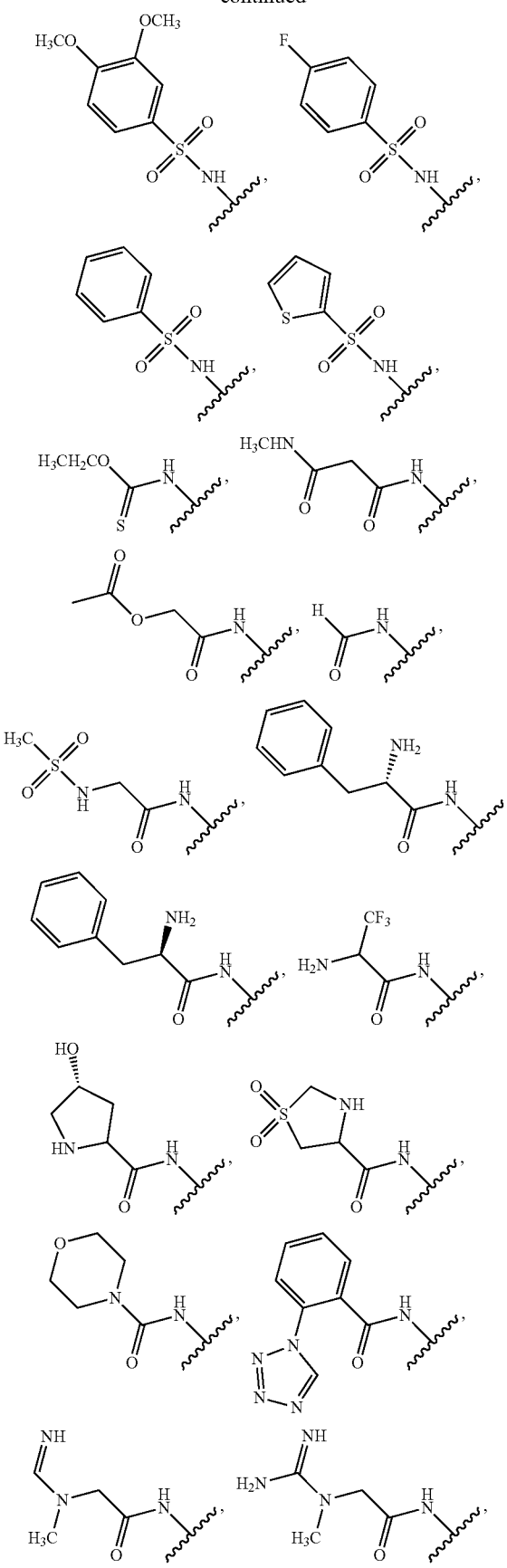

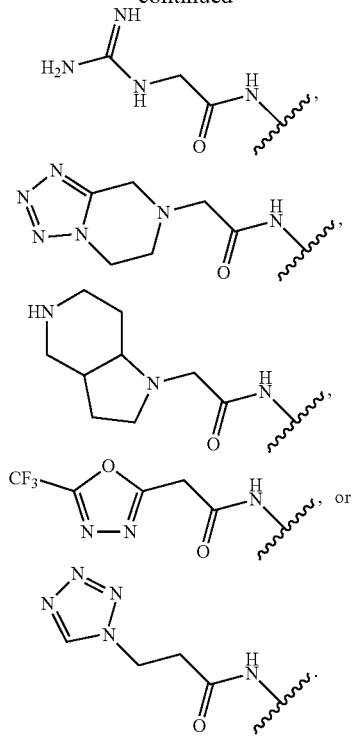

5. The compound of claim 1, or a pharmaceutically acceptable salt, internal salt, stereoisomer, or N-oxide thereof, wherein:

$R^0$ is H or $C_{1-6}$alkyl;

wherein the $C_{1-6}$ alkyl is optionally substituted with 1 or 2 substituents independently selected from the group consisting of halogen, CN, C(O)$NH_2$, OH, $OC_{1-6}$alkyl, and S(O)$_2NH_2$; and R is $(CH_2)_nC(O)R^2$, $(CH_2)_nC(S)R^2$, $(CH_2)_nS(O)_2R^2$, or C(NH)H; or R and $R^0$, together with the nitrogen atom to which they are attached, form an optionally substituted 5- or 6-membered ring, wherein the 5- or 6-membered ring has 0, 1, 2, 3, or 4 additional ring heteroatoms independently selected from the group consisting of nitrogen, oxygen, and sulfur;

with the provisos that:

1) when R is $(CH_2)_nC(O)R^2$, n is 0, and $R^0$ is H, then $R^2$ is not unsubstituted $C_{1-6}$alkyl;

2) when R is $(CH_2)_nC(O)R^2$ and n is 1, 2, 3, 4, 5, or 6, then $R^2$ is not $NH_2$ or OH;

3) when R is $(CH_2)_nS(O)_2R^2$ and n is 1, 2, 3, 4, 5, or 6, then $R^2$ is not OH; and 4) when R and $R^0$, together with the nitrogen atom to which they are attached, form triazolyl, then Z is not H.

6. The compound of claim 1, or a pharmaceutically acceptable salt, internal salt, stereoisomer, or N-oxide thereof, wherein:

$R^0$ is H or $CH_3$; and

R is $(CH_2)_nC(O)R^2$ or $(CH_2)_nS(O)_2R^2$; or

R and $R^0$, together with the nitrogen atom to which they are attached, form [1,2,3]triazolyl or tetrazolyl;

wherein the [1,2,3]triazolyl is substituted with 1 substituent selected from the group consisting of $C_{1-6}$haloalkyl, $C_{1-6}$alkylOH, $(CH_2)_{1-3}NR^fR^g$, $CH_2NR^xR^y$, and $OC_{1-3}$alkyl; and further wherein the tetrazolyl is optionally substituted with 1 substituent selected from the group consisting of $NR^fR^g$ and $NR^xR^y$.

7. The compound of claim 1, or a pharmaceutically acceptable salt, internal salt, stereoisomer, or N-oxide thereof, wherein:

$R^0$ is H; and

R is $C_{1-6}$alkyl, $C_{1-6}$alkyl$NR^aR^b$, $C_{1-6}$alkyl$C_{3-6}$cycloalkyl, C(NH)H $(CH_2)_{0-6}C(O)(CH_2)_{1-6}OH$, $(CH_2)_{0-6}C(O)(CH_2)_{1-6}OC_{1-6}$alkyl, $(CH_2)_{0-6}C(O)OH$, $(CH_2)_{0-6}C(O)OC_{1-6}$ alkyl, $C(O)C_{1-6}$alkyl, $C(O)C_{1-6}$alkyl$NR^aR^b$, $C(O)CHF_2$, $C(O)CF_2C_{1-5}$alkyl, $C(O)CF_3$, $C(O)CHFCH_3$, $C(O)CH_2CF_3$, $C(O)CH_2CN$, $C(O)(CH_2)_{1-6}C(O)NR^xR^y$, $C(O)CH(NH_2)C_{1-5}$alkyl, $C(O)CH(NH_2)CH_2$-pyrazolyl, $C(O)CH(NH_2)CH_2$-tetrazolyl, $C(O)C(NOCH_3)R^k$, $C(O)C(NOC(CH_3)_2C(O)OH)R^k$, $C(O)CH(OH)C_{1-5}$alkyl, $C(O)CH_2OH$, $C(O)CH_2OC(O)CH_3$, $C(O)CH_2P(O)(OCH_3)_2$, $C(O)CH_2SCHF_2$, $C(O)CH_2S(O)CHF_2$, $C(O)CH_2S(O)_2C_{1-6}$alkyl, $C(O)CH_2S$-tetrazolyl, $C(O)CH_2$-azetidinyl, $C(O)CH(CH_3)$-azetidinyl, $C(O)CH_2$-pyrrolidinyl, $C(O)(CH_2)_{0-1}$piperazinyl, $C(O)CH_2$-thienyl, $C(O)CF_2$-thienyl, $C(O)CH_2$-triazolyl, $C(O)CH_2$-oxadiazolyl, $C(O)CH_2$-tetrazolyl, $C(O)C(CH_3)_2$-tetrazolyl, $C(O)CH(F)C_{1-5}$alkyl, $C(O)CF_2CF_3$, $C(O)CF_2CH_2NH_2$, $C(O)CF_2CH_2OH$, $C(O)C(O)NR^xR^y$, $C(O)C(O)OH$, $C(O)C(O)OC_{1-6}$alkyl, $C(O)OCH_2CHF_2$, $C(O)OCH_2CF_3$, $C(O)C_{3-6}$cycloalkyl, C(O)pyrrolidinyl, C(O)tetrahydrofuranyl, C(O)thiazolidinyl, C(O)pyrazolyl, C(O)pyrazinyl, or $C(S)OC_{1-6}$alkyl;

wherein the $C(O)CH(NH_2)C_{1-5}$alkyl is optionally substituted with 1 or more substituents independently selected from the group consisting of OH and phenyl;

wherein the $C(O)CH_2S$-tetrazolyl is optionally substituted with 1 or more $CH_3$ substituents;

wherein the $C(O)CH_2$-pyrrolidinyl is optionally substituted with 1 or more substituents independently selected from the group consisting of F, $CH_3$ and $CH_2NHCH_3$;

wherein the $C(O)CH_2$-triazolyl is optionally substituted with 1 or more substituents independently selected from the group consisting of $CH_3$, $CF_3$, $CH_2NR^xR^y$, and $NH_2$;

wherein the $C(O)CH_2$-tetrazolyl is optionally substituted with 1 or more substituents independently selected from the group consisting of $CH_3$, $CHF_2$, $CF_3$, $CH_2NHCH_3$, $C(CH_3)_3$, $C(O)OCH_2CH_3$, $NH_2$, $NHC(O)OC_{1-6}$alkyl, and thienyl;

wherein the $C(O)CH(CH_3)$-azetidinyl is optionally substituted with 1 or more substituents independently selected from the group consisting of oxo, $CH_2CH_2OH$, and $CH(OH)CH_3$;

wherein the $C(O)C_{3-6}$cycloalkyl is substituted with 1 or more substituents independently selected from the group consisting of $CF_3$ and $NH_2$;

wherein the C(O)pyrrolidinyl is optionally substituted with 1 or more substituents independently selected from the group consisting of F and $NH_2$;

wherein the C(O)pyrazolyl is optionally substituted with 1 or more substituents independently selected from the group consisting of $CH_3$ and $CF_3$; and wherein the C(O)thiazolidinyl is optionally substituted with 1 or more oxo substituents; or R and $R^0$, together with the nitrogen atom to which they are attached, form [1,2,3]triazolyl or tetrazolyl;

wherein the [1,2,3]triazolyl is optionally substituted with 1 substituent selected from the group consisting of $CH_2F$, $CH_2NH_2$, $CH_2NHCH_3$, $CH_2OH$, $CH_2OCH_3$, and $C(O)OCH_3$; and wherein the tetrazolyl is optionally substituted with 1 $NH_2$ substituent.

8. The compound of claim 1, or a pharmaceutically acceptable salt, internal salt, stereoisomer, or N-oxide thereof, wherein:

$R^0$ is H; and

R is $C(O)CH_2$-triazolyl, $C(O)CH_2$-tetrazolyl, $C(O)C(CH_3)_2$-tetrazolyl, $C(O)CH(NH_2)CH_2$-tetrazolyl, or $C(O)CH_2S$-tetrazolyl;

wherein the triazolyl of $C(O)CH_2$-triazolyl is optionally substituted with 1, 2, 3, or 4 substituents independently selected from the group consisting of $CH_3$, $CF_3$, $CH_2NR^xR^y$, and $NH_2$;

wherein the tetrazolyl of $C(O)CH_2$-tetrazolyl is optionally substituted with 1, 2, 3, or 4 substituents independently selected from the group consisting of $CH_3$, $CHF_2$, $CF_3$, $C(CH_3)_3$, $CH_2NHCH_3$, $C(O)OCH_2CH_3$, $NH_2$, $NHC(O)OC_{1-6}$alkyl, and thienyl; and wherein the tetrazolyl of $C(O)CH_2S$-tetrazolyl is optionally substituted with 1 $CH_3$ substituent; or R and $R^0$, together with the nitrogen atom to which they are attached, form [1,2,3]triazolyl or tetrazolyl;

wherein the [1,2,3]triazolyl is optionally substituted with 1 substituent selected from the group consisting of $CH_2F$, $CH_2NH_2$, $CH_2NHCH_3$, $CH_2OH$, $CH_2OCH_3$, $C(O)OCH_3$, and tetrazolyl; and further wherein the tetrazolyl is optionally substituted with 1 $NH_2$ substituent.

9. The compound of claim 1, or a pharmaceutically acceptable salt, internal salt, stereoisomer, or N-oxide thereof, wherein:

$R^0$ is H; and

R is $C(O)CH_2$-tetrazolyl; or

R and $R^0$, together with the nitrogen atom to which they are attached, form triazolyl;

wherein the triazolyl is optionally substituted with 1 $CH_2OH$ substituent.

10. The compound of claim 1, or a pharmaceutically acceptable salt, internal salt, stereoisomer, or N-oxide thereof, wherein:

$R^1$ is $C_{2-6}$alkyl$NH_2$;

wherein the $C_{2-6}$ alkyl$NH_2$ is optionally substituted with 1 or more independently selected $C(NR^x)R^x$ substituents.

11. The compound of claim 1, or a pharmaceutically acceptable salt, internal salt, stereoisomer, or N-oxide thereof, wherein $R^1$ is $(CH_2)_{0-1}$HetC.

12. The compound of claim 1, or a pharmaceutically acceptable salt, internal salt, stereoisomer, or N-oxide thereof, wherein:

$R^1$ is $(CH_2)_2NHC(NH)NH_2$, $(CH_2)_2NHC(O)OC(CH_3)_3$, $CH_2$-pyrrolidinyl, $CH_2$-piperidinyl, $CH_2$-piperazinyl, $CH_2$-phenyl, $CH_2$-pyridinyl, $(CH_2)_2$-pyridinyl, azetidinyl, pyrrolidinyl, pyrazolyl, thiazolyl, 5-oxa-2-azaspiro[3.4]octan-7-yl, or 6,7-dihydro-5H-pyrazolo[1,2-a][1,2,4]triazol-4-ium-6-yl;

wherein the $CH_2$-pyrrolidinyl is substituted with 1 or more substituents independently selected from the group consisting of $C(O)CH_3$, $NH_2$, and $NHS(O)_2NH_2$;

wherein the $CH_2$-piperidinyl is optionally substituted with 1 or more $CH_3$ substituents and further optionally quaternized with 1 substituent selected from the group consisting of $CH_3$ and $(CH_2)_2NH_2$;

wherein the CH$_2$-phenyl is substituted with 1 pyrazolyl substituent, wherein the pyrazolyl is optionally substituted with 1 or more (CH$_2$)$_3$NH$_2$ substituents and further optionally quaternized with 1 CH$_3$ substituent;

wherein the (CH$_2$)$_2$-pyridinyl is substituted with 1 or more substituents independently selected from the group consisting of oxo, CH$_2$NH$_2$, and OH;

wherein the azetidinyl is substituted with 1 or more substituents independently selected from the group consisting of C(NH)NH$_2$, S(O)$_2$NH$_2$, 4,5-dihydrothiazol-2-yl, and thiazolyl;

wherein the pyrrolidinyl is substituted with 1 or 2 substituents independently selected from the group consisting of F, CH$_3$, CH$_2$NR$^f$R$^g$, (CH$_2$)$_{0-1}$NHC(NH)NH$_2$, C(NH)H, C(O)NR$^c$R$^d$, C(O)N(CH$_3$)—(CH$_2$)$_2$C(O)pyrrolidin-1-yl, and OH, wherein each (CH$_2$)$_2$C(O)pyrrolidin-1-yl is independently substituted with 1 or more NH$_2$ substituents;

wherein the pyrazolyl is optionally substituted with 1 or more CH$_2$NH$_2$ substituents and further optionally quaternized with 1 CH$_3$ substituent; and wherein the thiazolyl is substituted with 1 pyridinyl substituent, wherein the pyridinyl substituent is optionally substituted with 1 or more CH$_3$ substituents and further optionally quaternized with 1 substituent selected from the group consisting of CH$_3$ and CH$_2$C(O)NH$_2$.

13. The compound of claim 1, or a pharmaceutically acceptable salt, internal salt, stereoisomer, or N-oxide thereof, wherein:

R$^1$ is pyrrolidinyl;

wherein the pyrrolidinyl is substituted with 1, 2, 3, or 4 substituents independently selected from the group consisting of CH$_2$C(O)-pyrrolidinyl-NH$_2$, CH$_2$NHS(O)$_2$NH$_2$, CH$_2$-pyrrolidinyl-NH$_2$, and C(O)NR$^c$R$^d$;

each R$^c$ is independently CH$_3$; and each R$^d$ is independently CH$_3$; or each R$^c$ and R$^d$, taken together with the nitrogen atom to which they are attached, independently forms azetidin-1-yl, pyrrolidin-1-yl, piperidin-1-yl, piperazin-1-yl, morpholin-4-yl, 1,4-diazepanyl, decahydro-1,6-naphthyridinyl, 2,6-diazaspiro[3.4]octanyl, 5-oxa-2-azaspiro[3.4]octanyl, 1,7-diazaspiro[3.5]nonanyl, 2,7-diazaspiro[3.5]nonanyl, 2,7-diazaspiro[4.4]nonanyl, 1,7-diazaspiro[4.5]decanyl, 1,8-diazaspiro[4.5]decanyl, 2,8-diazaspiro[4.5]decanyl, 1,9-diazaspiro[5.5]undecanyl, 3,6-diazabicyclo[3.2.0]heptanyl, octahydrocyclopenta[c]pyrrolyl, octahydropyrrolo[3,4-h]pyrrolyl, octahydropyrrolo[3,4-c]pyrrolyl, octahydropyrrolo[3,4-d]imidazolyl, octahydro-1H-pyrrolo[2,3-c]pyridinyl, octahydro-1H-pyrrolo[3,2-b]pyridinyl, octahydro-1H-pyrrolo[3,2-c]pyridinyl, 5,5-dimethyloctahydro-1H-pyrrolo[3,2-c]pyridinium, octahydro-1H-pyrrolo[3,4-b]pyridinyl, octahydro-1H-pyrrolo[3,4-c]pyridinyl, octahydropyrrolo[3,4-b][1,4]oxazinyl, 5,6,7,8-tetrahydroimidazo[1,5-a]pyrazinyl, 3,8-diazatricyclo[5.2.1.01,5]decanyl, and 8-azaspiro[bicyclo[3.2.1]octane-3,3'-pyrrolidinyl];

wherein each azetidin-1-yl is optionally and independently substituted with 1, 2, 3, or 4 NHC(NH)NH$_2$ substituents;

wherein each pyrrolidin-1-yl is independently substituted with 1 or 2 substituents independently selected from the group consisting of F, CH$_2$F, CH$_2$NH$_2$, C(CH$_3$)$_2$NH$_2$, CH$_2$NHS(O)$_2$NH$_2$, CH$_2$OH, C(O)OH, NH$_2$, NHCH$_3$, NHC(NH)H, NHC(NH)NH$_2$, NHC(O)CH$_2$NH$_2$, NHC(O)CH$_2$CH$_2$NH$_2$, NHC(O)CH$_2$NHC(NH)NH$_2$, OH, OCH$_3$, and triazolyl, wherein the triazolyl is substituted with 1 or more CH$_2$NH$_2$ substituents;

wherein each piperidin-1-yl is independently substituted with 1 or 2 substituents independently selected from the group consisting of F, CH$_3$, (CH$_2$)$_{0-2}$NH$_2$, CH$_2$NHCH$_2$C(O)NH$_2$, CH$_2$OH, C(O)NHCH$_2$CH(OH)CH$_2$NH$_2$, OH, and azetidinyl, wherein the azetidinyl is substituted with 1 or more OH substituents;

wherein each piperazin-1-yl is optionally and independently substituted with 1 or 2 substituents independently selected from the group consisting of CH$_3$, CH$_2$NH$_2$, CH$_2$CH$_2$NH$_2$, CH$_2$CH$_2$NHC(NH)NH$_2$, CH$_2$CH(F)CH$_2$NH$_2$, CH$_2$CH(NH$_2$)CH$_2$NH$_2$, CH$_2$C(O)NH$_2$, C(NH)NH$_2$, C(O)(CH$_2$)$_{1-2}$NH$_2$, C(O)CH$_2$NHCH$_3$, C(O)CH(NH$_2$)NH$_2$, and C(O)CH(NH$_2$)CH$_2$OH;

wherein each morpholin-4-yl is optionally and independently substituted with 1 CH$_2$NH$_2$ substituent;

wherein each 1,4-diazepanyl is optionally and independently substituted with 1 C(NH)NH$_2$ substituent;

wherein each 5-oxa-2-azaspiro[3.4]octanyl is optionally and independently substituted with 1 NH$_2$ substituent;

wherein each octahydrocyclopenta[c]pyrrolyl is optionally and independently substituted with 1 or 2 substituents independently selected from the group consisting of CH$_2$NH$_2$, CH$_2$OH, NH$_2$, and NHC(NH)NH$_2$;

wherein each octahydropyrrolo[3,4-b]pyrrolyl is optionally and independently substituted with 1 or 2 substituents independently selected from the group consisting of CH$_2$OH, CH$_2$CH$_2$NH$_2$, and C(NH)NH$_2$;

wherein each octahydropyrrolo[3,4-c]pyrrolyl is optionally and independently substituted with 1 CH$_2$OH substituent;

wherein each octahydropyrrolo[3,4-d]imidazolyl is optionally and independently substituted with 1 =NH substituent;

wherein each octahydro-1H-pyrrolo[3,2-c]pyridinyl is optionally and independently substituted with 1, 2, 3, or 4 substituents independently selected from the group consisting of CH$_2$CH$_2$NH$_2$, CH$_2$CH(OH)NH$_2$, CH$_2$CH(OH)CH$_2$NH$_2$, and C(NH)NH$_2$;

wherein each octahydro-1H-pyrrolo[3,4-b]pyridinyl is optionally and independently substituted with 1 CH$_2$OH substituent;

wherein each octahydro-1H-pyrrolo[3,4-c]pyridinyl is optionally and independently substituted with 1 or 2 substituents independently selected from the group consisting of CH$_2$OH and C(O)OH; and wherein each 5,6,7,8-tetrahydroimidazo[1,5-a]pyrazinyl is optionally and independently substituted with 1 NH$_2$ substituent.

14. The compound of claim 1, or a pharmaceutically acceptable salt, internal salt, stereoisomer, or N-oxide thereof, wherein:

each R$^c$ is independently H, C$_{1-6}$alkyl, (CH$_2$)$_2$C(O)pyrrolidin-1-yl, (CH$_2$)$_{1-3}$pyrrolidinyl, C(NH)pyrrolidin-1-yl, phenyl-CH$_2$NR$^x$R$^y$, phenyl-C(O)pyrrolidinyl-NR$^x$R$^y$, phenyl-C(O)piperazinyl, or pyridinyl;

wherein each C$_{1-6}$alkyl of R$^c$ is optionally and independently substituted with 1 or more substituents independently selected from the group consisting of NR$^h$R$^j$, and OH; and further wherein each (CH$_2$)$_2$C(O)pyrrolidin-1-yl is independently substituted with 1 or more independently selected NR$^x$R$^y$ substituents;

wherein each $(CH_2)_{1-3}$pyrrolidinyl is optionally and independently substituted with 1 or more independently selected $C(O)NR^xR^y$ substituents; and wherein each C(NH)pyrrolidin-1-yl is optionally and independently substituted with 1 or more independently selected $NR^xR^y$ substituents; and each $R^d$ is independently H or $C_{1-3}$alkyl; or each $R^c$ and $R^d$, taken together with the nitrogen atom to which they are attached, independently forms an optionally substituted 4- to 8-membered heterocyclic ring or an optionally substituted, bicyclic or tricyclic 6- to 12-membered heterocyclic ring system;

wherein each 4- to 8-membered heterocyclic ring independently has 0, 1, or 2 additional ring heteroatoms independently selected from the group consisting of nitrogen, oxygen, and sulfur;

wherein each bicyclic or tricyclic 6- to 12-membered heterocyclic ring system independently has 0, 1, or 2 additional ring heteroatoms independently selected from the group consisting of nitrogen, oxygen, and sulfur; and further wherein each bicyclic 6- to 12-membered heterocyclic ring system is optionally and independently bridged, fused, or spirocyclic, or a combination thereof;

wherein any nitrogen ring heteroatom of each 4- to 8-membered heterocyclic ring is optionally and independently quaternized;

wherein any nitrogen ring heteroatom of each bicyclic or tricyclic 6- to 12-membered heterocyclic ring system is optionally and independently quaternized; and wherein each 4- to 8-membered heterocyclic ring and each bicyclic 6- to 12-membered heterocyclic ring system is optionally and independently substituted with 1, 2, or 3 substituents independently selected from the group consisting of oxo, halogen, $C_{1-6}$alkyl, $(CH_2)_{0-3}NR^hR^j$, $(CH_2)_{0-2}C(O)(CH_2)_{0-2}NR^hR^j$, $(CH_2)_{0-1}NHCH_2CH_2NR^hR^j$, $(CH_2)_{0-1}NH(CH_2)_{0-1}C(O)(CH_2)_{0-1}NR^hR^j$, $(CH_2)_{0-3}NHC(NH)NH_2$, $(CH_2)_{0-2}NHS(O)_2CH_3$, $(CH_2)_{0-1}NHS(O)_2(CH_2)_{0-2}NH_2$, $C(NH)NH_2$, $(CH_2)_{0-2}$piperazinyl, $(CH_2)_{0-1}$phenyl, $C(O)C_{1-6}$alkylNH$_2$, $C(O)(CH_2)_{0-3}NHC(NH)NH_2$, C(O)NHpyridinyl, C(O)OH, C(O)pyrrolidinyl, C(O)piperazinyl, NHCH$_2$CN, NHCH$_2$pyridinyl, NHC(NH)H, NHC(O)R$^i$, NHC(O)CH$_2$NHC(NH)NH$_2$, =NH, NHS(O)$_2$N(CH$_3$)$_2$, NHpyrimidinyl, OH, OC$_{1-6}$alkyl, ONH$_2$, ONHC(O)CH$_2$NHCH$_3$, azetidinyl, pyrrolidinyl, triazolyl, and tetrazolyl;

wherein each $C_{1-6}$alkyl substituent is optionally and independently substituted with 1 or 2 substituents independently selected from the group consisting of halogen, CN, and OH; and further wherein each $(CH_2)_{0-2}C(O)(CH_2)_{0-2}NR^hR^j$ is optionally and independently substituted with 1 or more substituents independently selected from the group consisting of NH$_2$ and OH;

wherein each C(O)pyrrolidinyl is optionally and independently substituted with 1 or more NH$_2$ substituents;

wherein each $(CH_2)_{0-3}NR^hR^j$ is optionally and independently substituted with 1 or 2 substituents independently selected from the group consisting of halogen and NH$_2$;

wherein each azetidinyl is optionally and independently substituted with 1 or more substituents independently selected from the group consisting of CH$_2$NH$_2$, NH$_2$, and OH;

wherein each pyrrolidinyl is optionally and independently substituted with 1 or more NH$_2$ substituents;

wherein each triazolyl is optionally and independently substituted with 1 or more CH$_2$NH$_2$ substituents;

wherein each $C(O)C_{1-6}$alkylNH$_2$ is optionally and independently substituted with 1 or more OH substituents; and wherein each NHCH$_2$-pyridinyl is optionally and independently substituted with 1 or more substituents independently selected from the group consisting of oxo, CH$_3$, and OH.

15. The compound of claim 1, or a pharmaceutically acceptable salt, internal salt, stereoisomer, or N-oxide thereof, wherein:

HetC is pyrrolidinyl;

wherein the pyrrolidinyl is substituted with 1 substituent selected from the group consisting of $(CH_2)_{0-3}C(NH)NH_2$, $(CH_2)_{1-3}C(O)$pyrrolidinyl, $(CH_2)_{0-3}NR^fR^g$, $(CH_2)_{0-3}NHC(NH)NH_2$, C(NH)pyrrolidinyl, $C(O)NR^cR^d$, and $S(O)_2NR^cR^d$; and further wherein the $(CH_2)_{1-3}C(O)$pyrrolidinyl is optionally substituted with 1 or more $NR^xR^y$ substituents, and the C(NH)pyrrolidinyl is optionally substituted with 1 or more $NR^xR^y$ substituents;

each $R^a$ is independently H, $C_{1-6}$alkyl, $CH_2C(O)N(R^x)_2$, $(CH_2)_{1-6}OR^x$, $C(NR^x)R^x$, $C(NR^x)N(R^x)_2$, or $S(O)_2C_{1-6}$alkyl;

each $R^b$ is independently H or $C_{1-3}$alkyl;

$R^f$ is C(O)pyrrolidinyl or $S(O)_2$-pyrrolidinyl-$N(R^x)_2$;

wherein the C(O)pyrrolidinyl is substituted with 1 or more substituents independently selected from the group consisting of halogen and $NR^aR^b$; and $R^g$ is H or $C_{1-3}$alkyl; or $R^f$ and $R^g$, taken together with the nitrogen atom to which they are attached, form pyrrolidin-1-yl, wherein the pyrrolidinyl is optionally substituted with 1 or more CH$_3$ substituents; and each $R^x$ is independently H or $C_{1-3}$alkyl.

16. The compound of claim 1, or a pharmaceutically acceptable salt, internal salt, stereoisomer, or N-oxide thereof, wherein:

A is $NR^0R$; and

HetC is pyrrolidinyl;

wherein the pyrrolidinyl is optionally substituted with 1, 2, 3, or 4 substituents independently selected from the group consisting of oxo, halogen, $C_{1-6}$ alkyl, $C_{1-6}$haloalkyl, $C_{1-6}$alkylOH, $(CH_2)_{1-3}NR^fR^g$, $(CH_2)_{0-1}NHS(O)_2NR^xR^y$, $(CH_2)_{0-3}OC_{1-3}$alkyl, $(CH_2)_{0-2}$triazolyl, $(CH_2)_{0-2}$tetrazolyl, $(CH_2)_{0-2}$thiazolyl, $(CH_2)_{0-2}$thienyl, $(CH_2)_{0-2}$pyridinyl, C(NH)H, $C(O)C_{1-6}$alkyl, $C(O)C_{1-6}$alkylNH$_2$, $C(O)NR^cR^d$, C(O)OH, $C(O)OC_{1-6}$ alkyl, NHCH$_2$CN, NHC(O)R$^i$, OH, OC$_{1-6}$alkyl, $S(O)_2NR^cR^d$, $C_{3-8}$cycloalkyl, and 4,5-dihydrothiazol-2-yl; and further wherein each $(CH_2)_{0-2}$pyridinyl is optionally and independently substituted with 1 or more CH$_3$ substituents and further optionally and independently quaternized with 1 CH$_3$ substituent.

17. The compound of claim 1, or a pharmaceutically acceptable salt, internal salt, stereoisomer, or N-oxide thereof, wherein n is 0 or 1.

18. The compound of claim 17, or a pharmaceutically acceptable salt, internal salt, stereoisomer, or N-oxide thereof, wherein n is 0.

19. The compound of claim 1, or a pharmaceutically acceptable salt, internal salt, stereoisomer, or N-oxide thereof, wherein:

Z is CH₃; and wherein each AryA, AryC, each HetA, HetC, and the 5- or 6-membered ring formed by combining R and R⁰ is optionally and independently substituted with 1, 2, 3, or 4 substituents independently selected from the group consisting of oxo, halogen, $C_{1-6}$ alkyl, $C_{1-6}$haloalkyl, $C_{1-6}$alkylOH, $(CH_2)_{0-3}C(NH)NH_2$, $(CH_2)_{1-3}C(O)NR^xR^y$, $(CH_2)_{1-3}C(O)$pyrrolidinyl, $(CH_2)_{0-3}NR^xR^y$, $(CH_2)_{0-1}NR^xR^y$, $(CH_2)_{0-3}NHC(NH)NH_2$, $(CH_2)_{0-1}NHS(O)_2NR^xR^y$, $(CH_2)_{0-3}OC_{1-3}$alkyl, $(CH_2)_{0-2}$pyrrolidinyl, $(CH_2)_{0-2}$piperidinyl, $(CH_2)_{0-2}$pyrazolyl, $(CH_2)_{0-2}$triazolyl, $(CH_2)_{0-2}$tetrazolyl, $(CH_2)_{0-2}$thiazolyl, $(CH_2)_{0-2}$thienyl, $(CH_2)_{0-2}$pyridinyl, C(NH)H, C(NH)pyrrolidinyl, $C(O)C_{1-6}$alkyl, $C(O)C_{1-6}$alkylNH₂, $C(O)NR^cR^d$, C(O)OH, $C(O)OC_{1-6}$ alkyl, NHCH₂CN, NHC(O)R^i, OH, $OC_{1-6}$alkyl, $S(O)_2NR^cR^d$, $C_{3-5}$cycloalkyl, and 4,5-dihydrothiazol-2-yl;

wherein each $(CH_2)_{1-3}C(O)$pyrrolidinyl is optionally and independently substituted with 1 or more NR^xR^y substituents;

wherein each $(CH_2)_{0-2}$pyrrolidinyl is optionally and independently substituted with 1 or more NR^xR^y substituents;

wherein each $(CH_2)_{0-2}$piperidinyl is optionally and independently substituted with 1 or more CH₃ substituents and further optionally and independently quaternized with 1 substituent selected from the group consisting of CH₃ and $(CH_2)_{0-3}NH_2$;

wherein each $(CH_2)_{0-2}$pyrazolyl is optionally and independently substituted with 1 or more $(CH_2)_{0-3}NH_2$ substituents and further optionally and independently quaternized with 1 CH₃ substituent;

wherein each $(CH_2)_{0-2}$pyridinyl is optionally and independently substituted with 1 or more CH₃ substituents and further optionally and independently quaternized with 1 substituent selected from the group consisting of CH₃ and CH₂C(O)NH₂; and wherein each C(NH)pyrrolidinyl is optionally and independently substituted with 1 or more NR^xR^y substituents.

20. The compound of claim 1, or a pharmaceutically acceptable salt, internal salt, stereoisomer, or N-oxide thereof, wherein the pharmaceutically acceptable salt is selected from the group consisting of a sodium salt, a potassium salt, a calcium salt, a magnesium salt, and an ammonium salt.

21. A pharmaceutical composition comprising a pharmaceutically acceptable carrier and the compound of claim 1, or a pharmaceutically acceptable salt, internal salt, stereoisomer, or N-oxide thereof.

22. A method for treating a bacterial infection in a subject, comprising administering to the subject in need of such treatment a therapeutically effective amount of the compound of claim 1, or a pharmaceutically acceptable salt, internal salt, stereoisomer, or N-oxide thereof.

23. The method of claim 22, wherein the bacterial infection is due to a gram-negative bacteria selected from the group consisting of *Pseudomonas* spp., *Klebsiella* spp., *Enterobacter* spp., *Escherichia* spp., *Morganella* spp., *Citrobacter* spp., *Serratia* spp., and *Acinetobacter* spp.

24. A method for treating a bacterial infection in a subject, comprising administering to the subject in need of such treatment a therapeutically effective amount of the pharmaceutical composition of claim 21.

25. The method of claim 24, wherein the bacterial infection is due to a gram-negative bacteria selected from the group consisting of *Pseudomonas* spp., *Klebsiella* spp., *Enterobacter* spp., *Escherichia* spp., *Morganella* spp., *Citrobacter* spp., *Serratia* spp., and *Acinetobacter* spp.

26. A compound, or a stereoisomer thereof, wherein the compound, or stereoisomer thereof, is selected from the group consisting of:

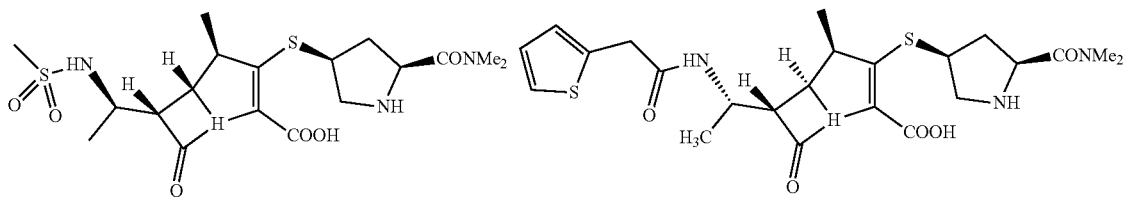

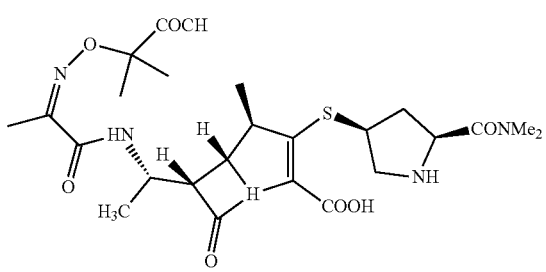

-continued
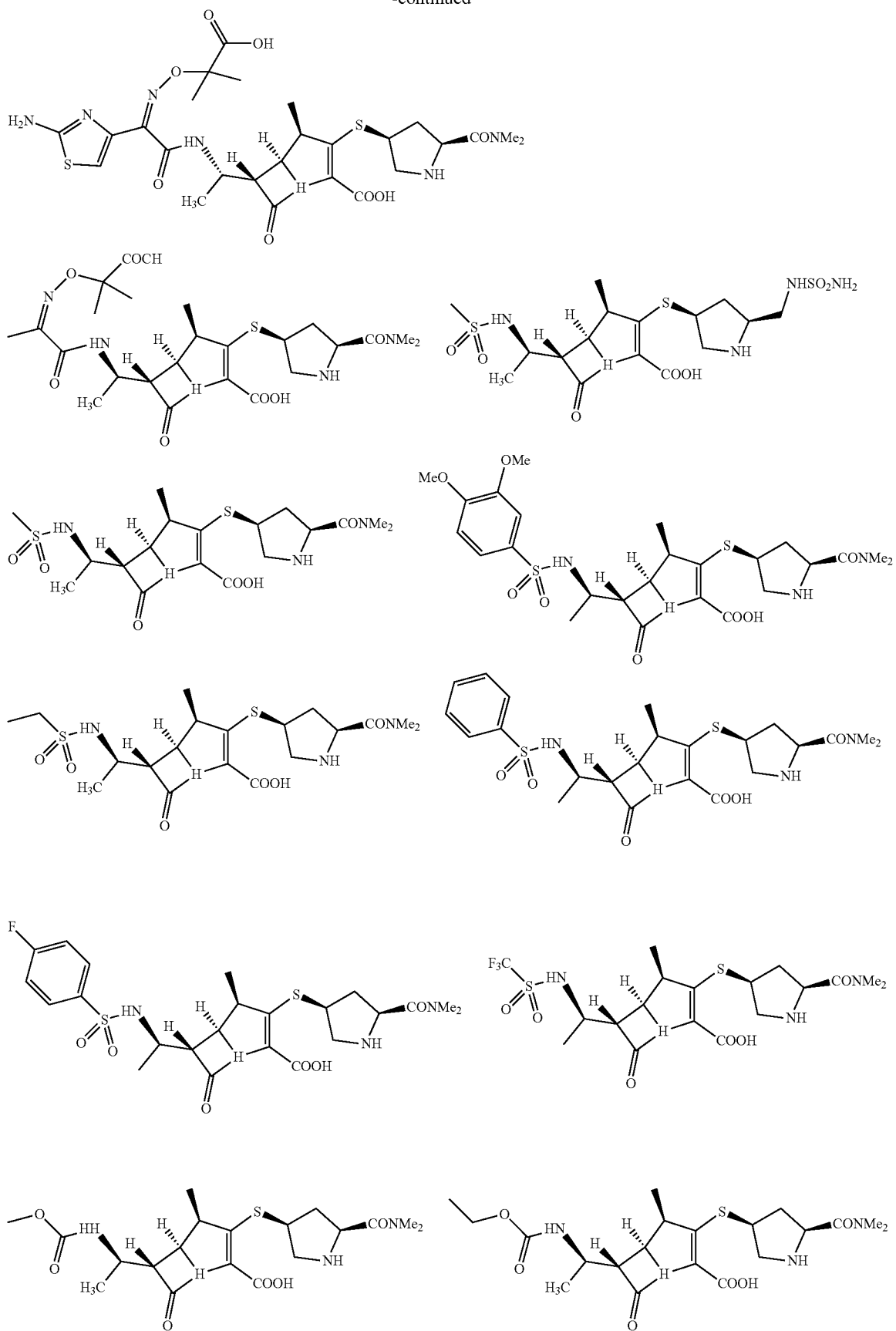

443 444
-continued
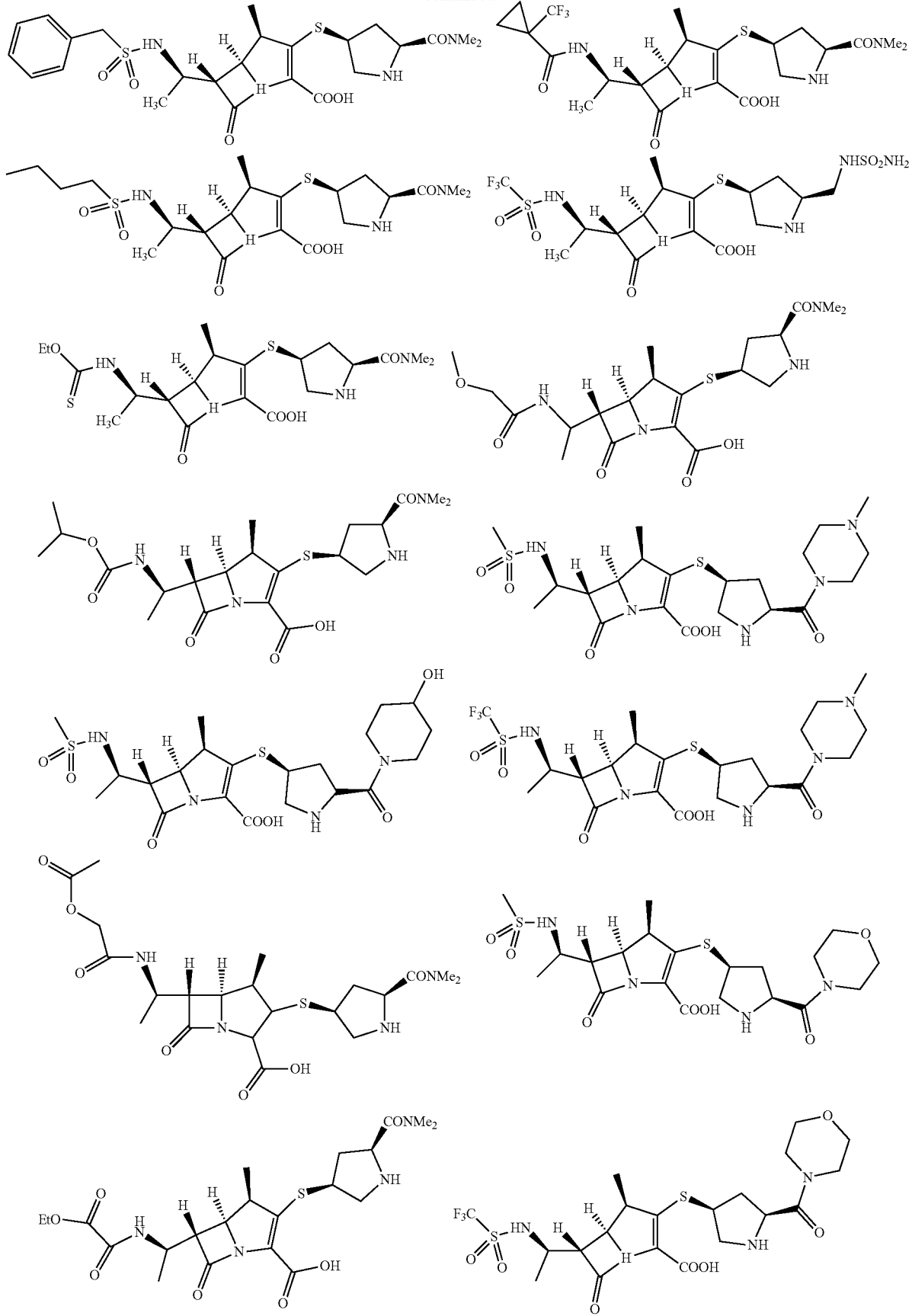

-continued
445
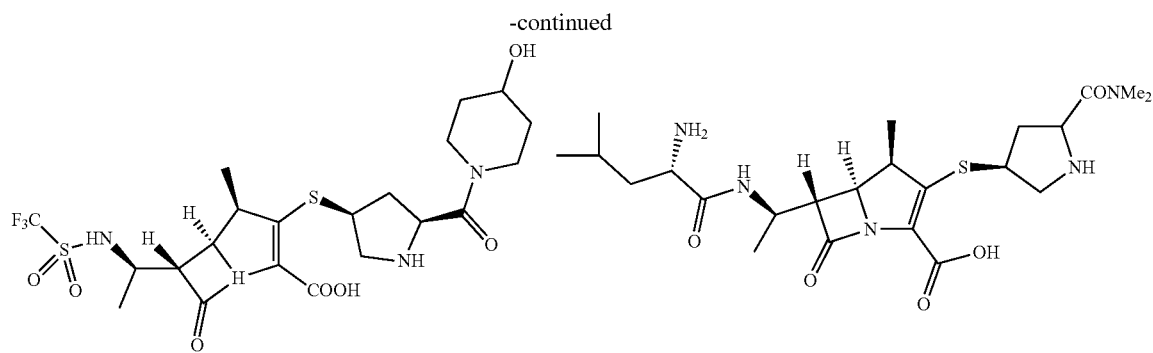
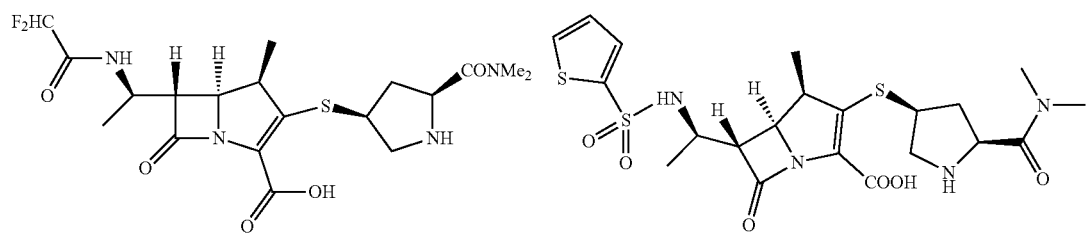
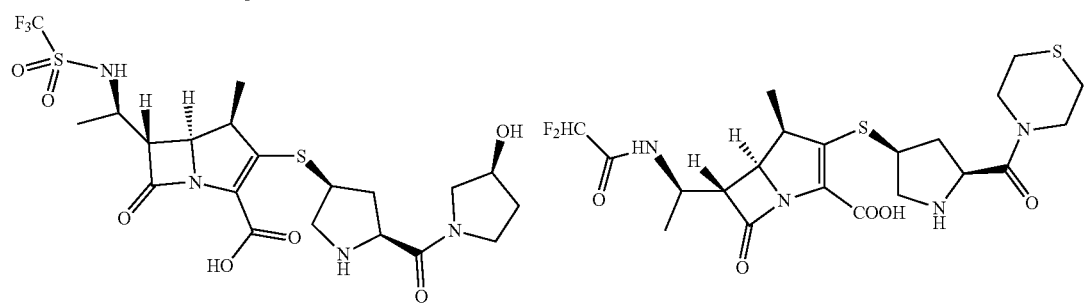
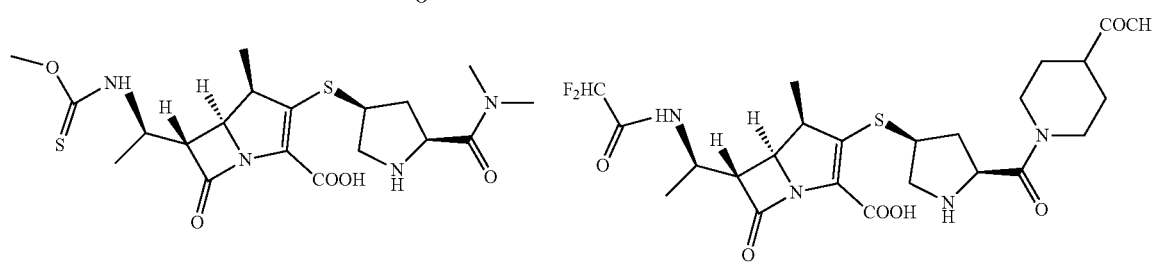
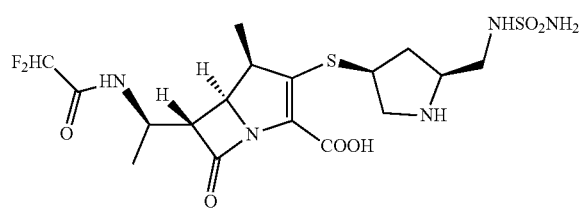
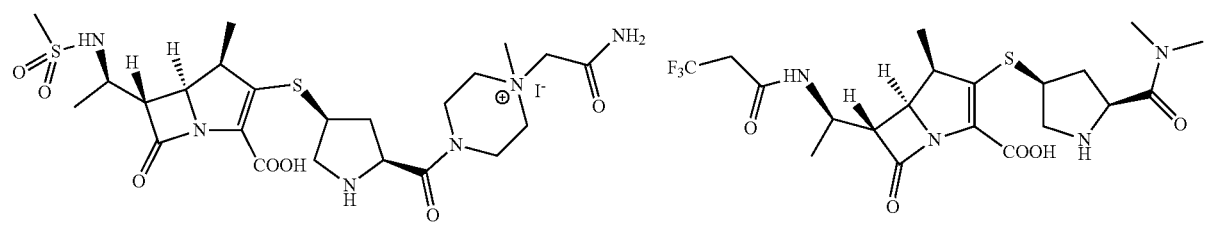

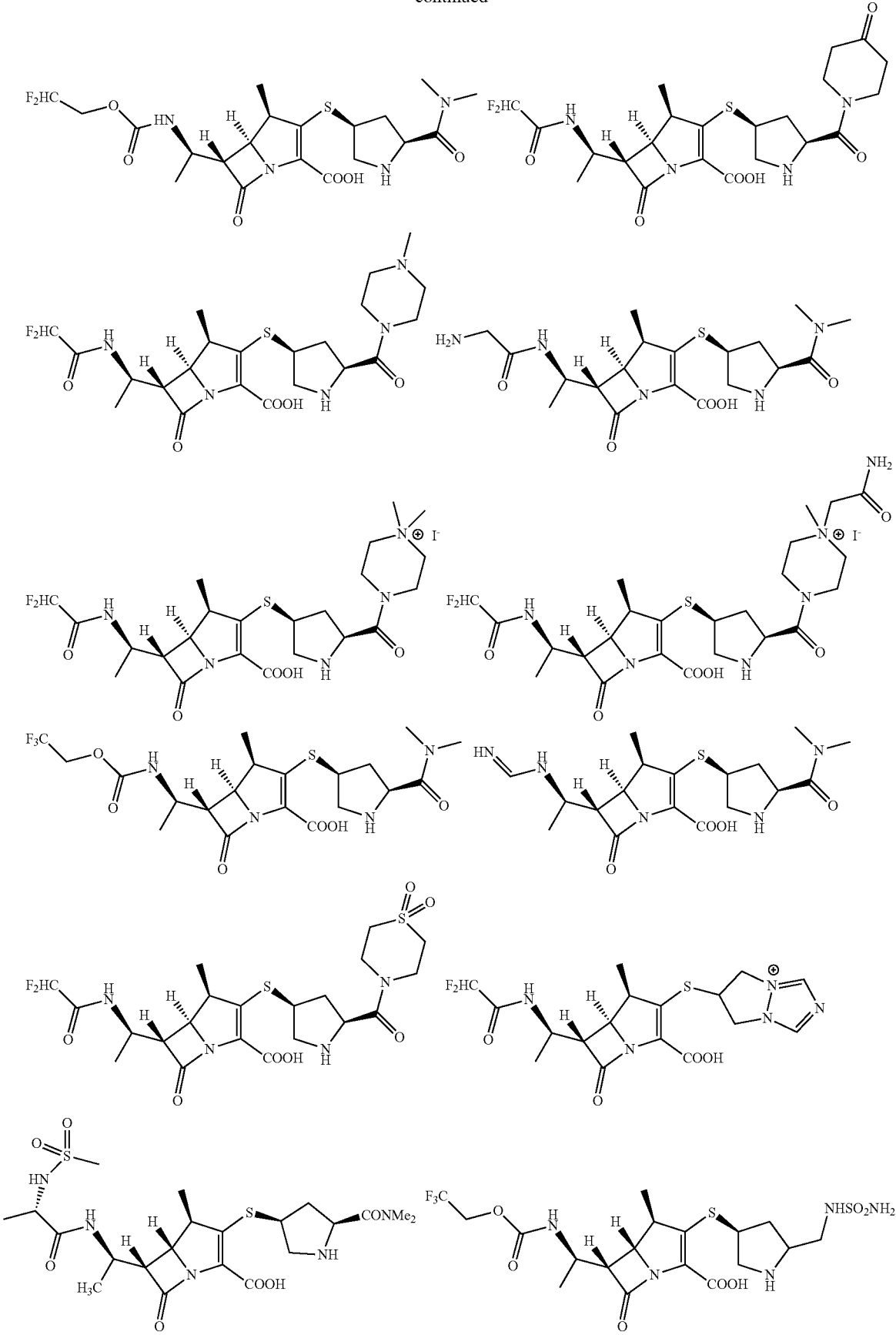

449 450
-continued
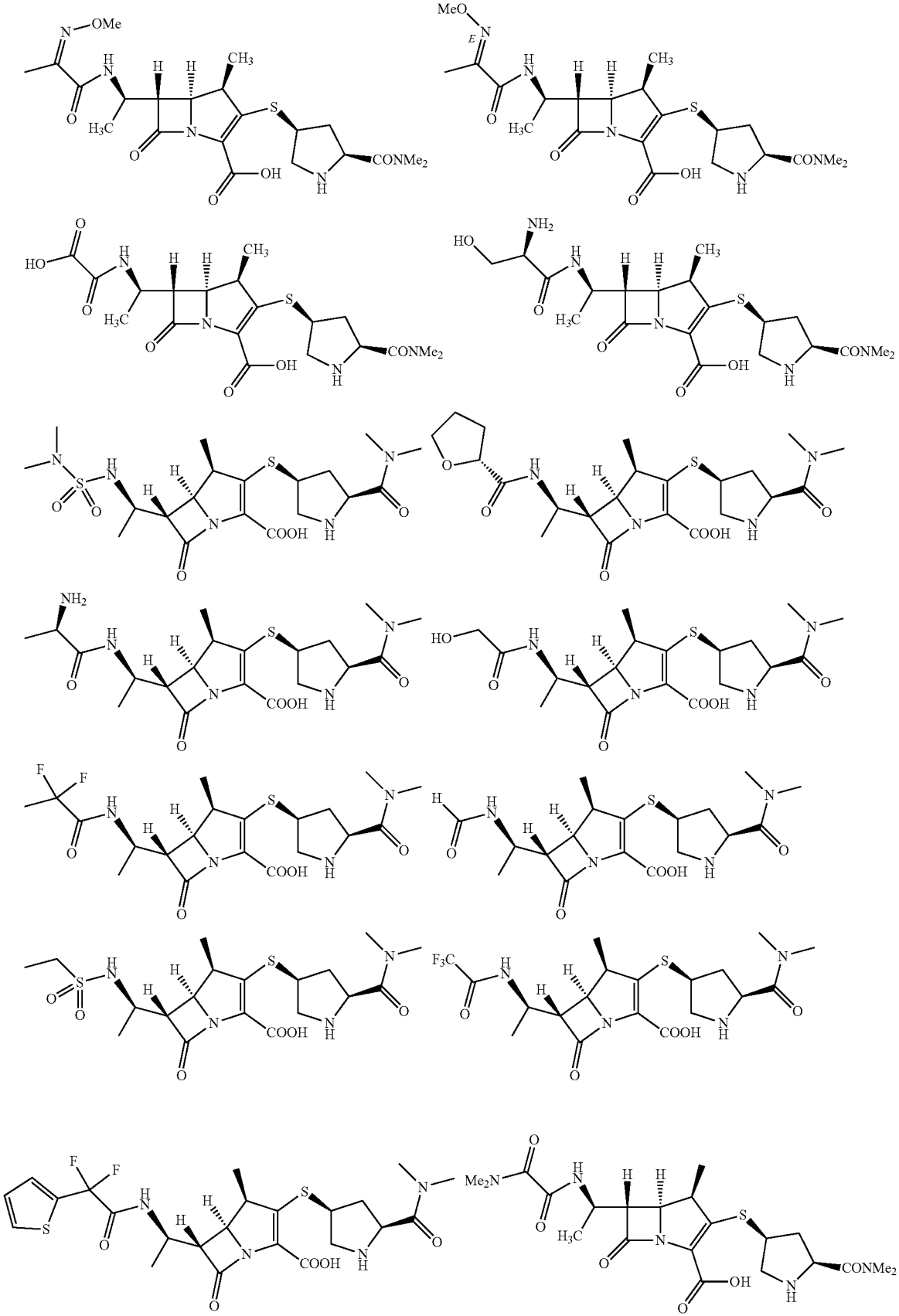

-continued
| 451 | 452 |
|---|---|
| 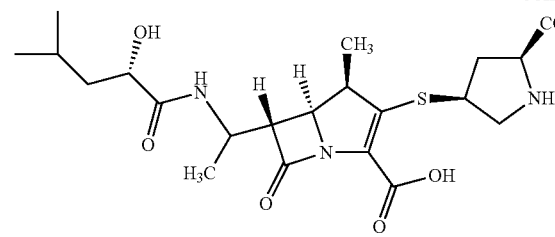 | 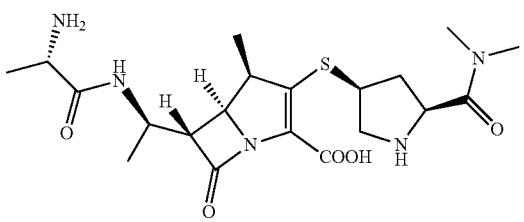 |
| 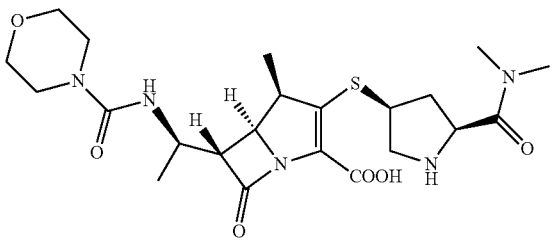 | 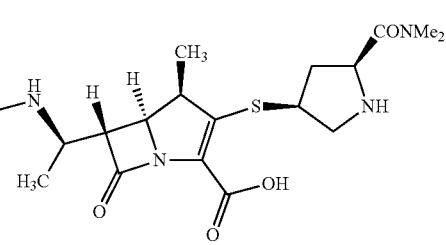 |
| 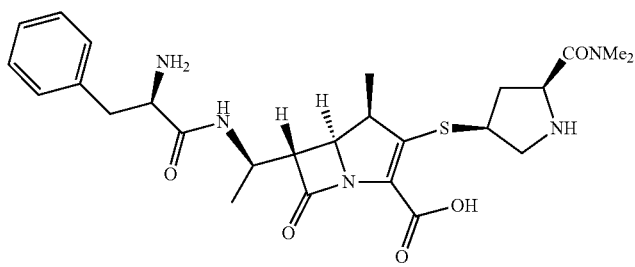 | |
| 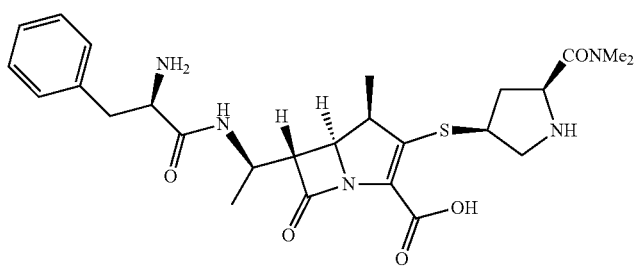 | |
| 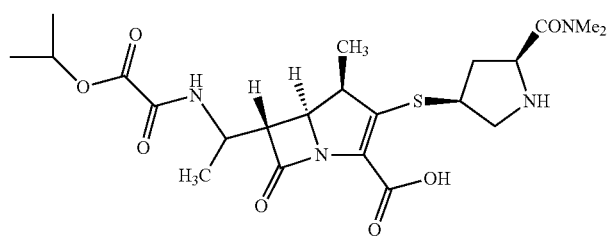 | 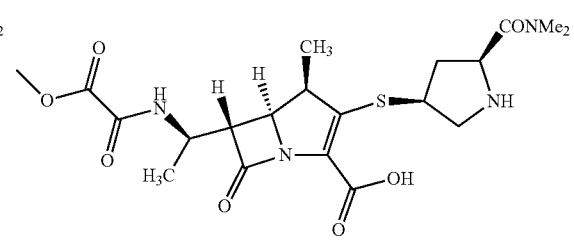 |
| 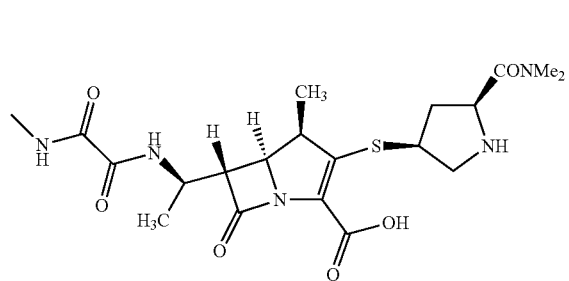 | 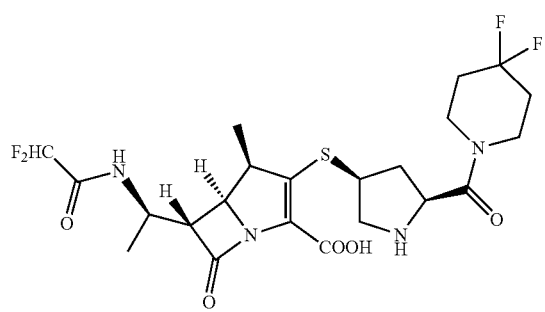 |

-continued
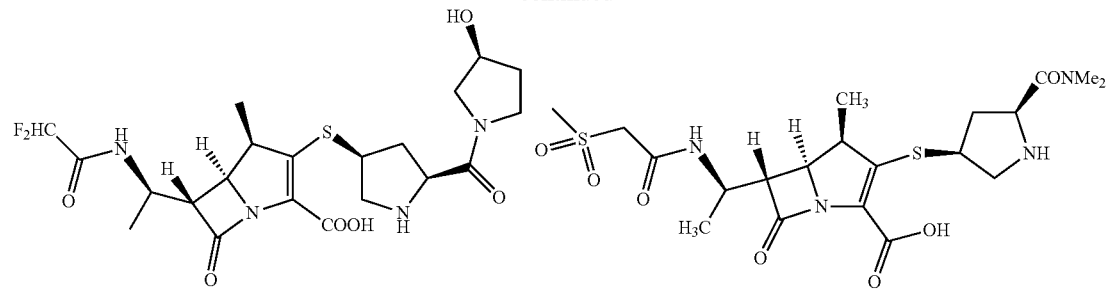
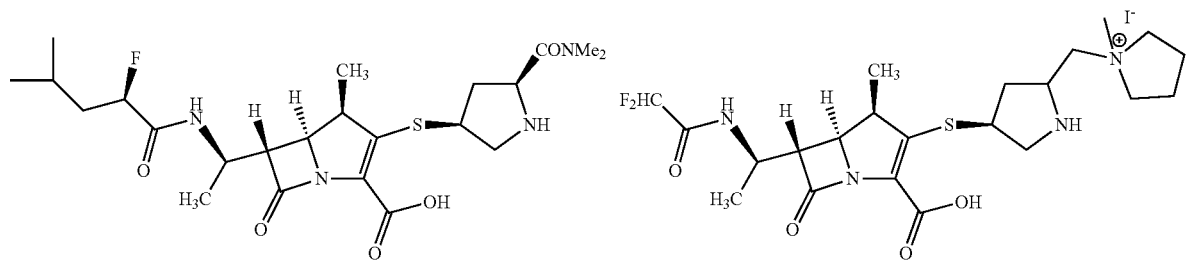
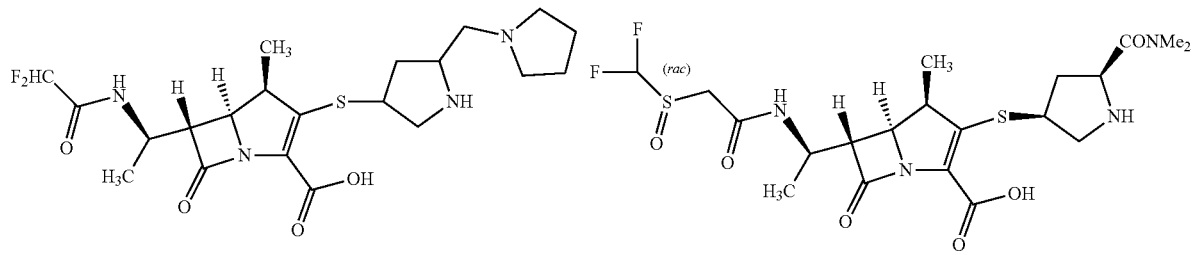
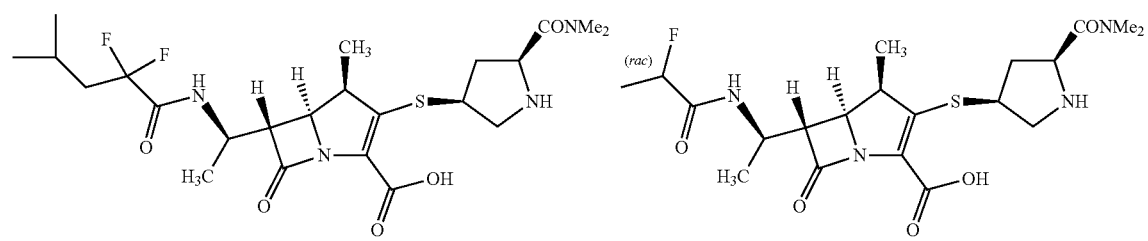
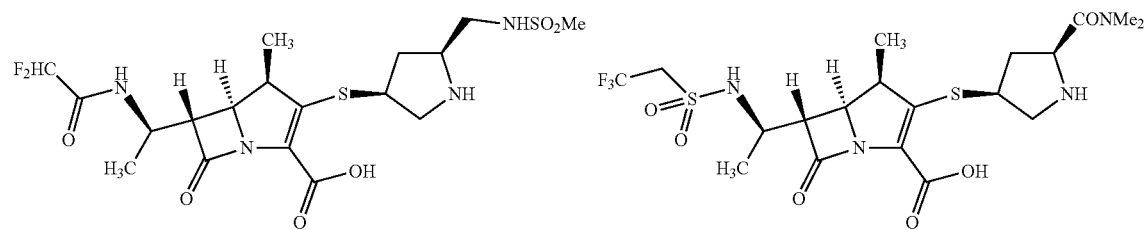
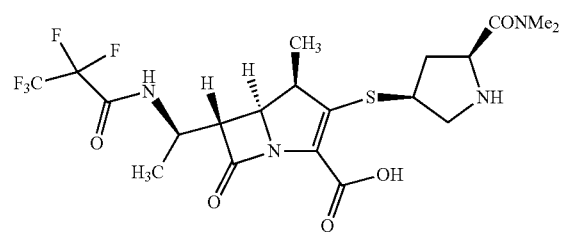

-continued
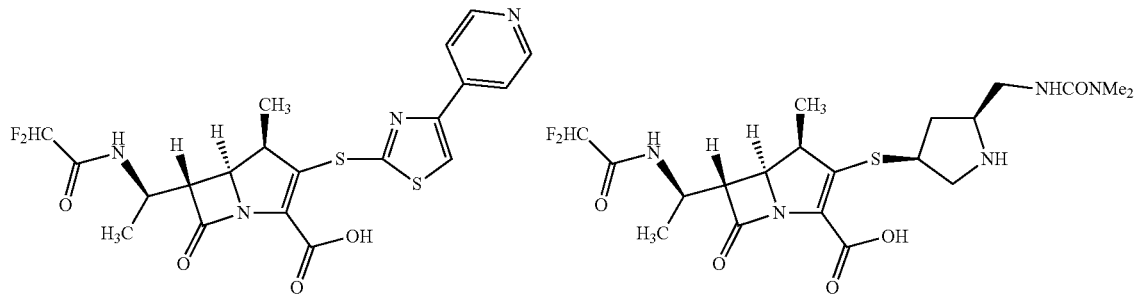
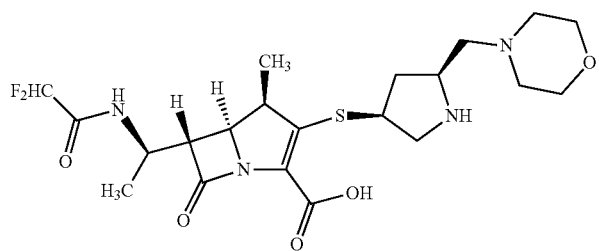
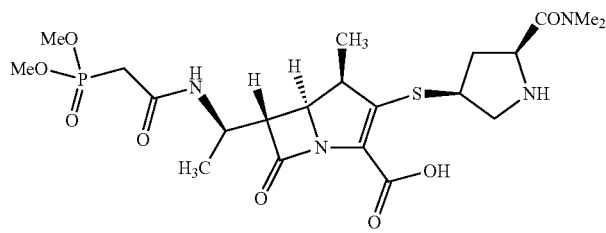
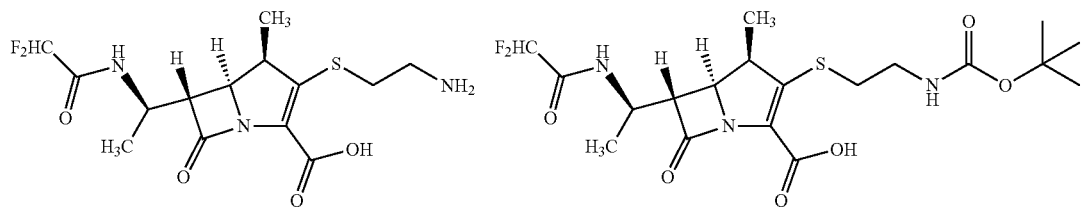
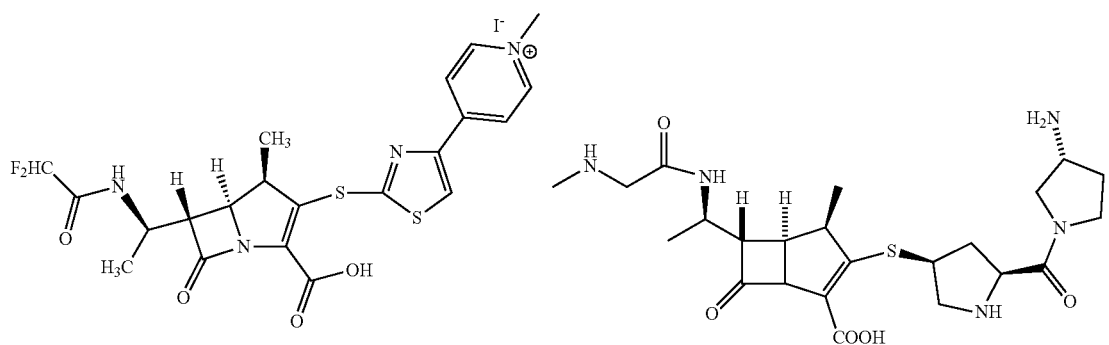
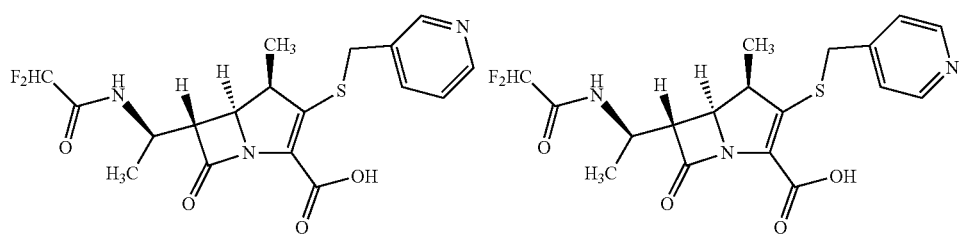

457 458
-continued
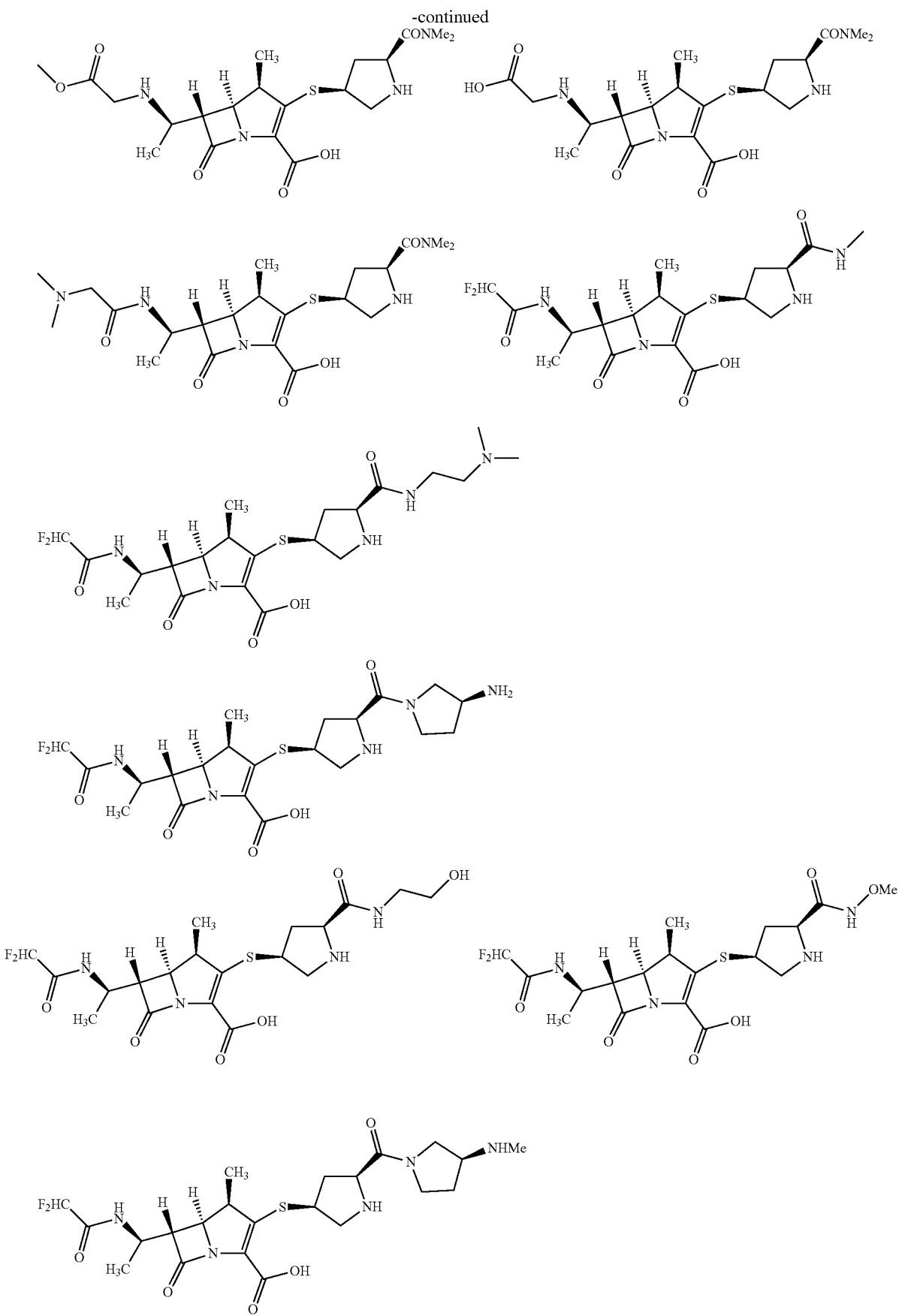

459 460
-continued
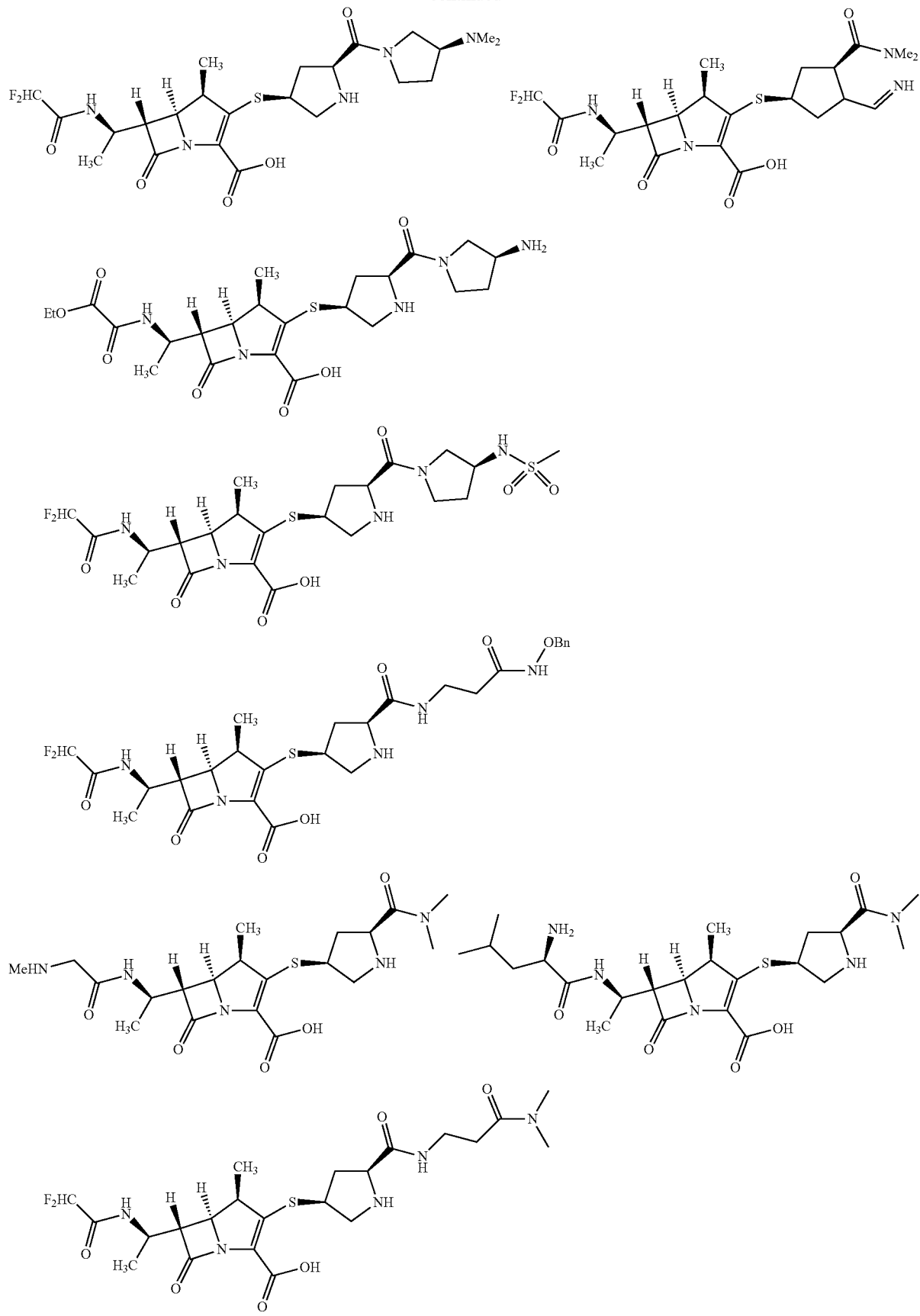

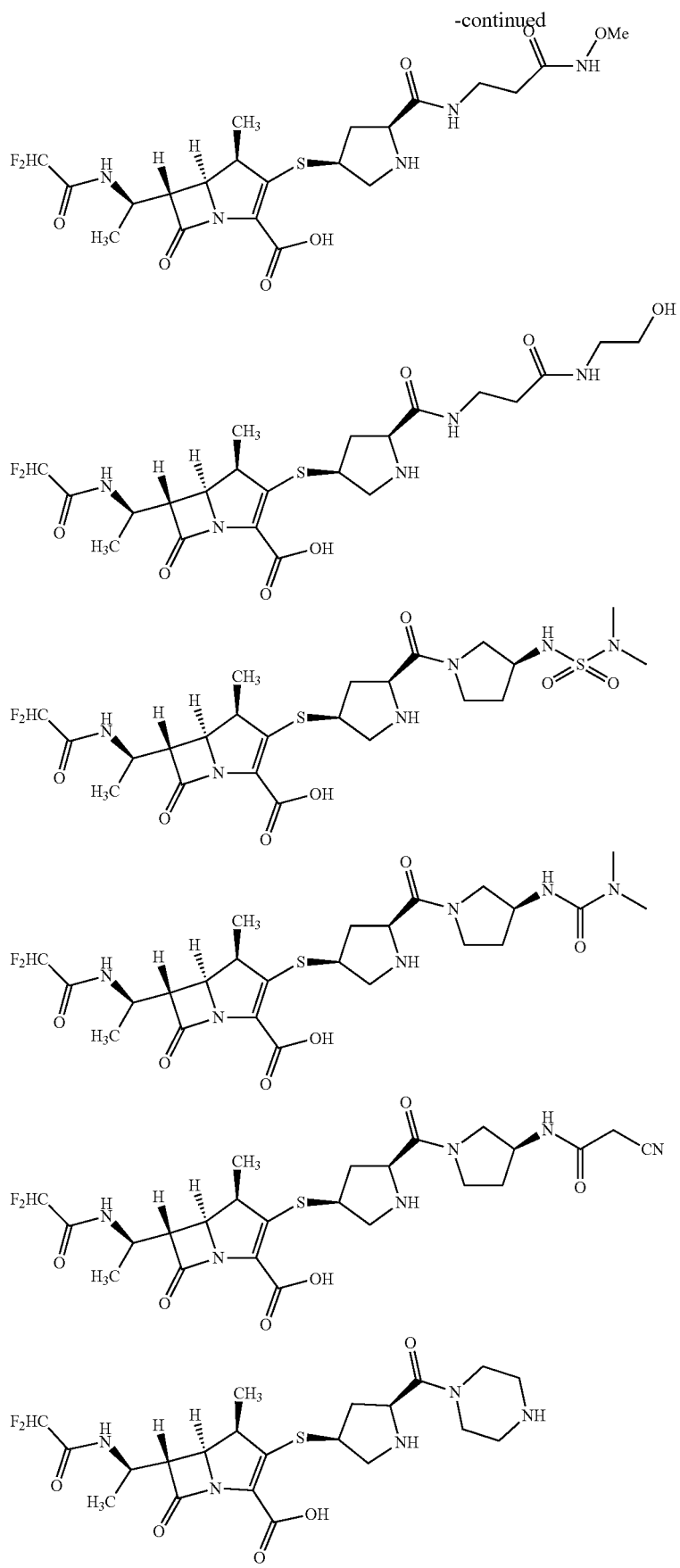

-continued
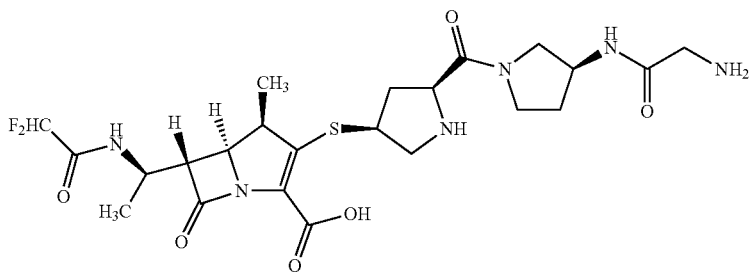
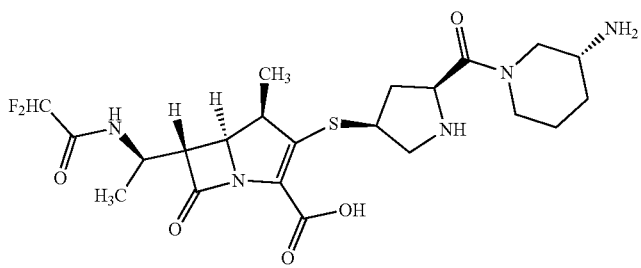
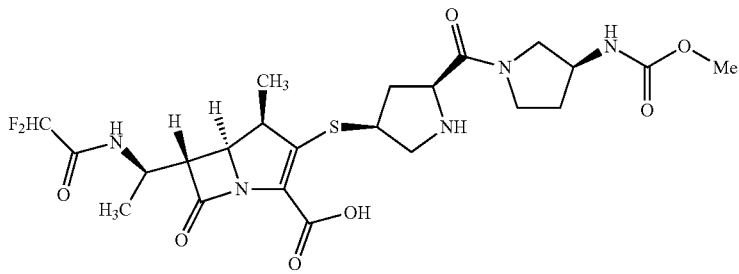
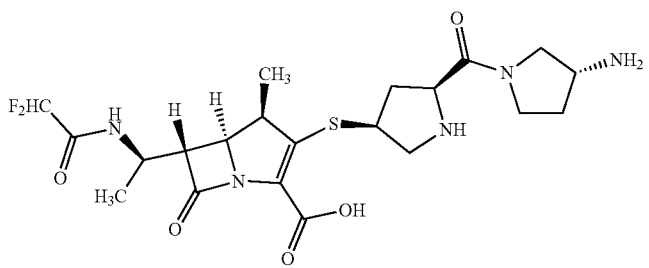
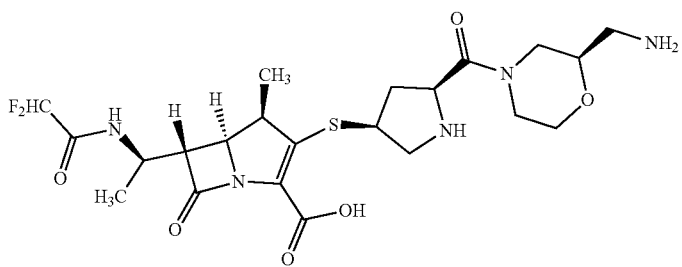

-continued
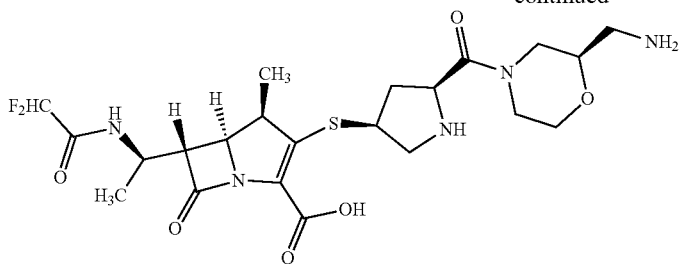
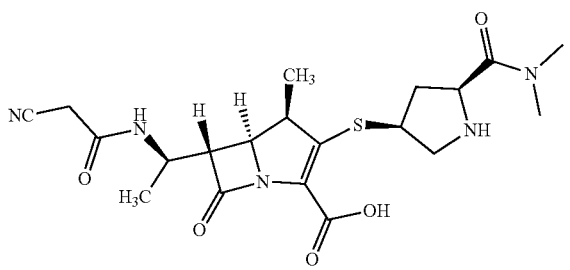
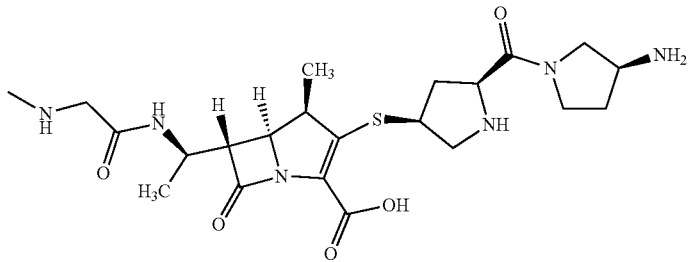
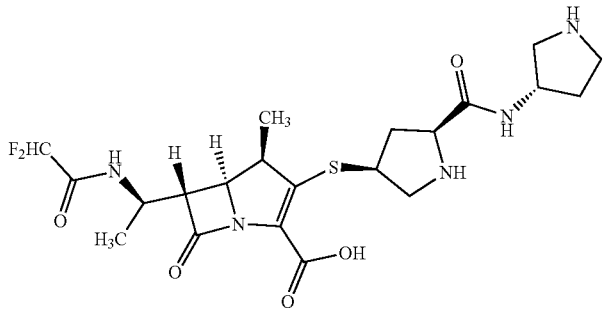
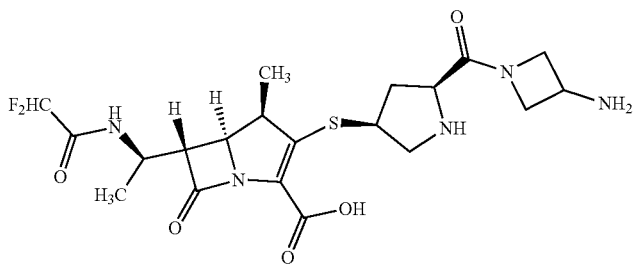
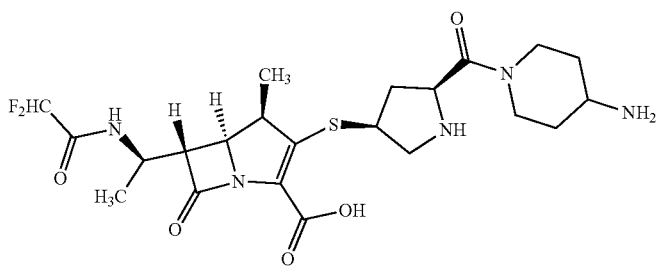

-continued
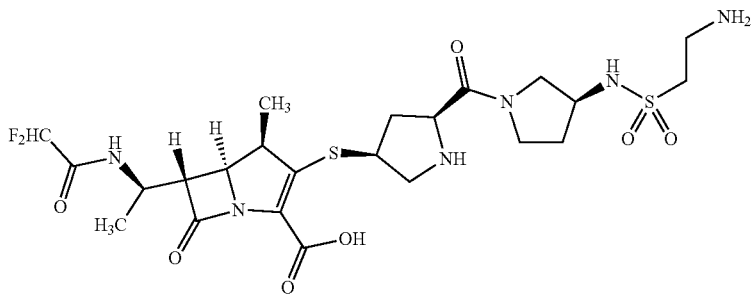
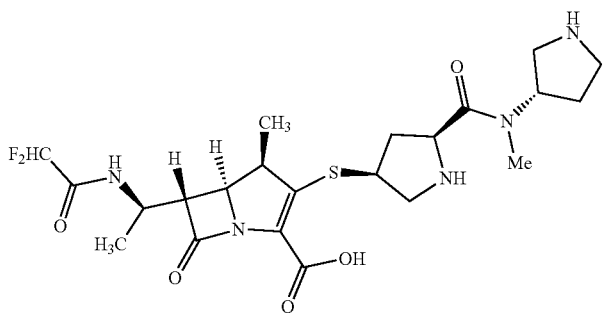
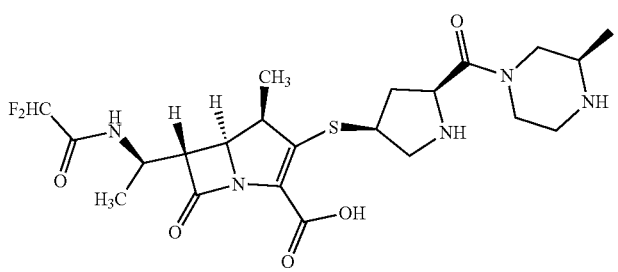
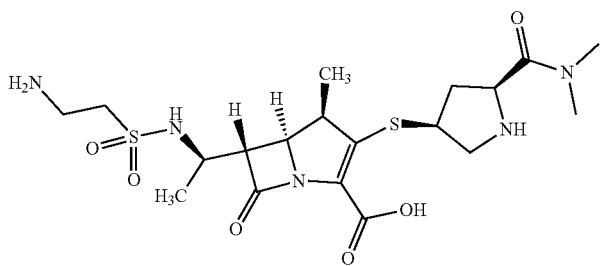
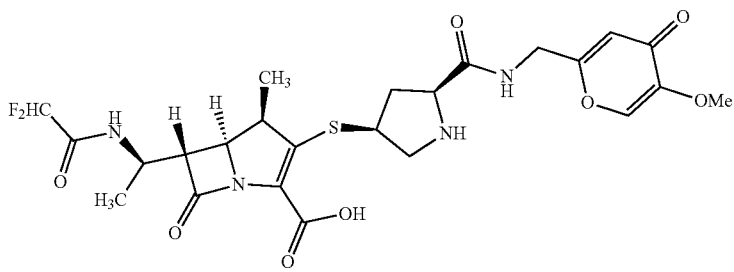
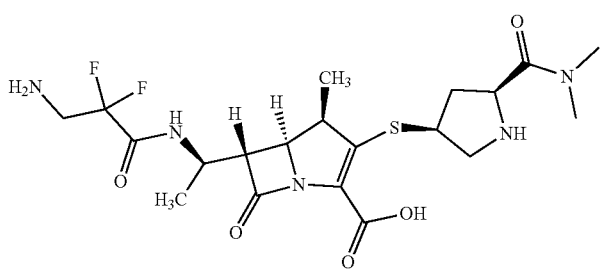

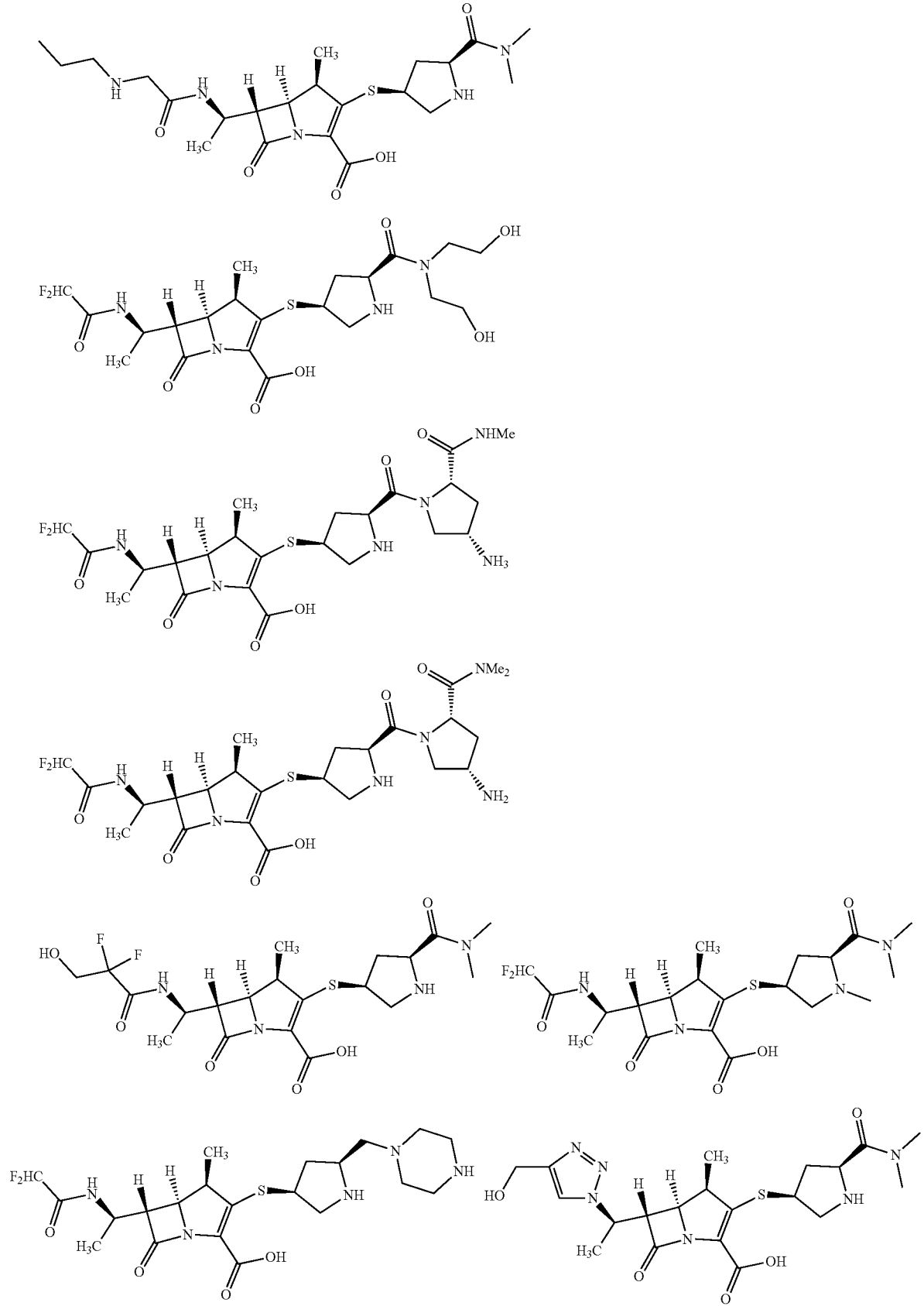

-continued
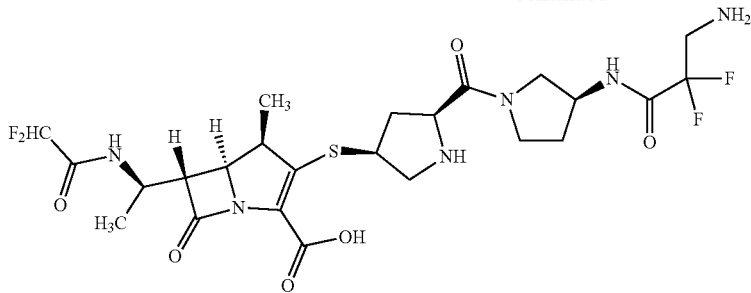
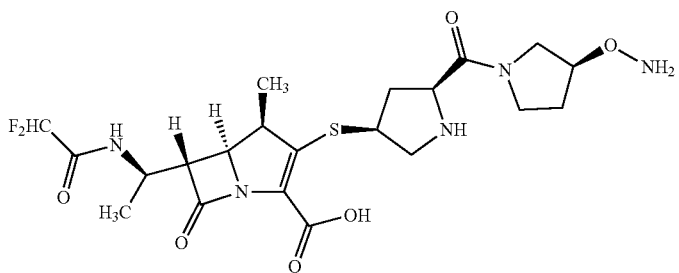
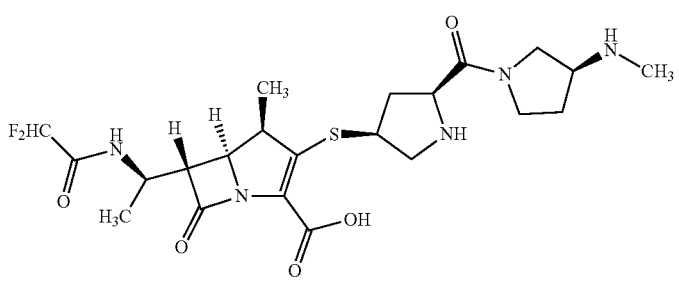
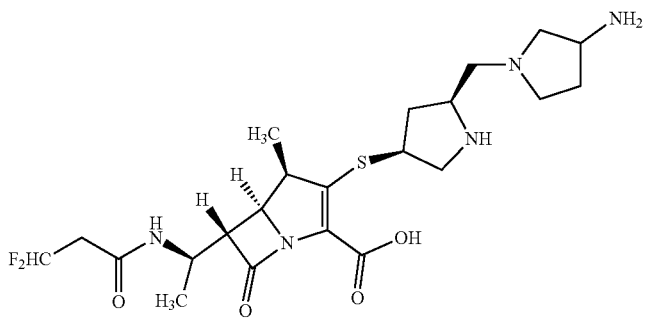
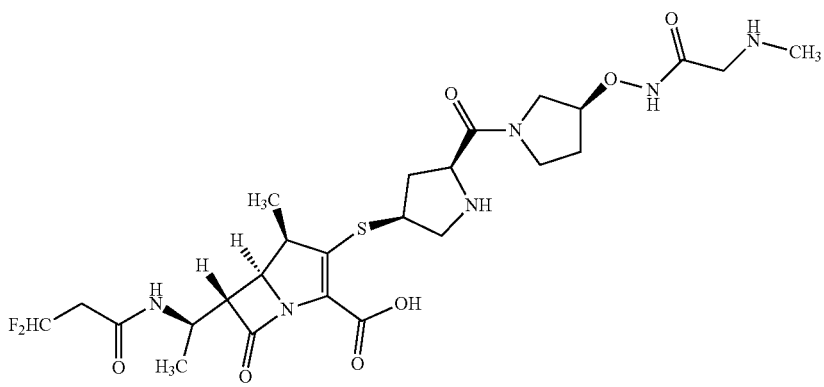

-continued
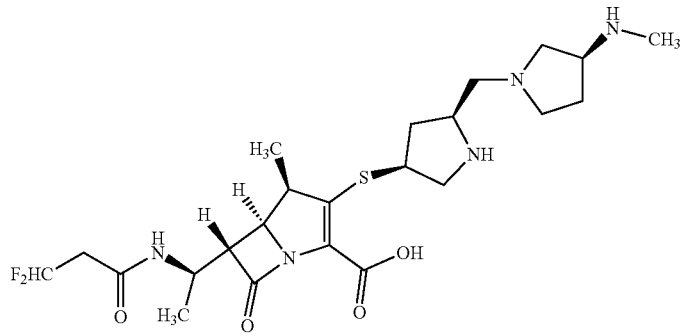
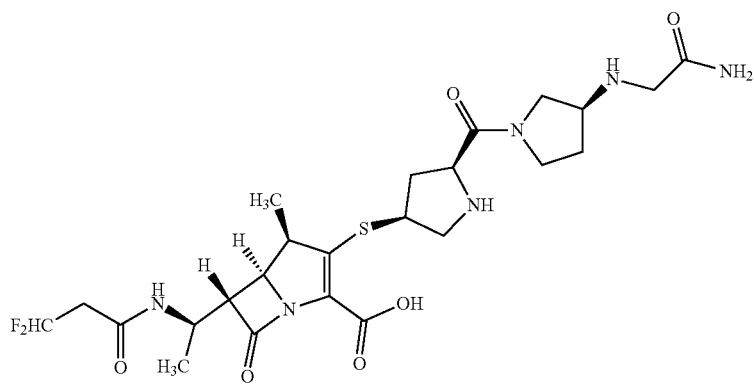
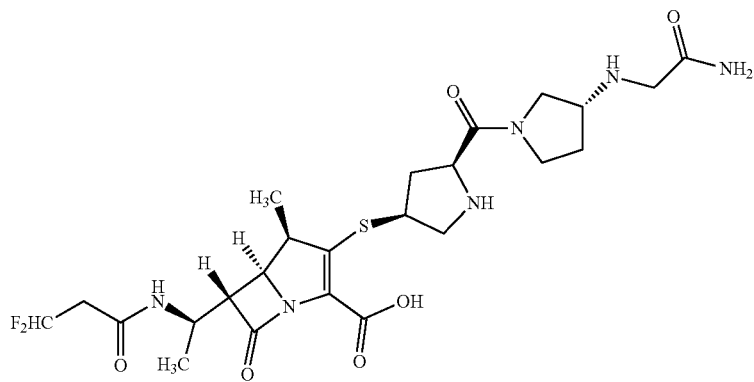
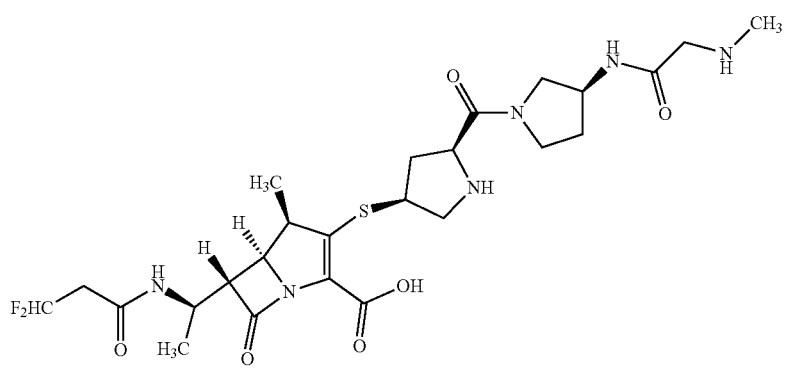

-continued
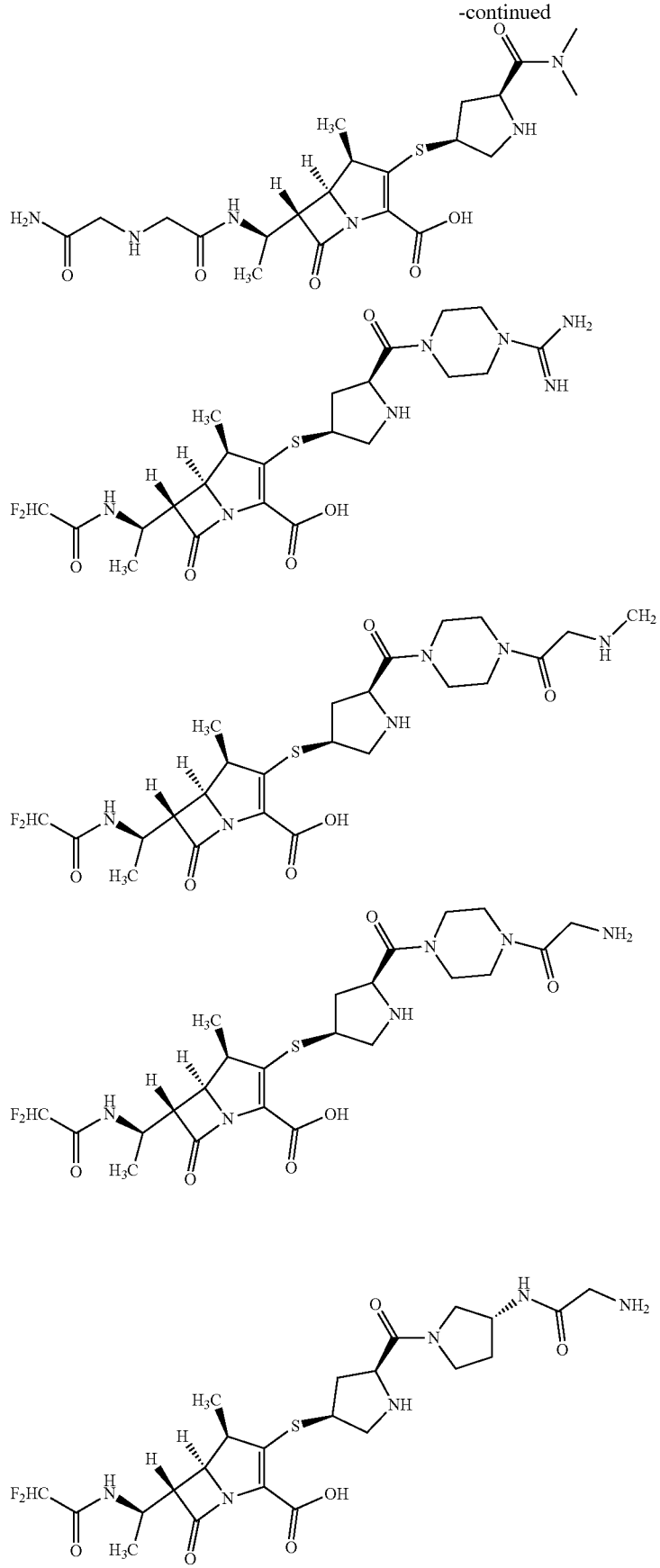

-continued
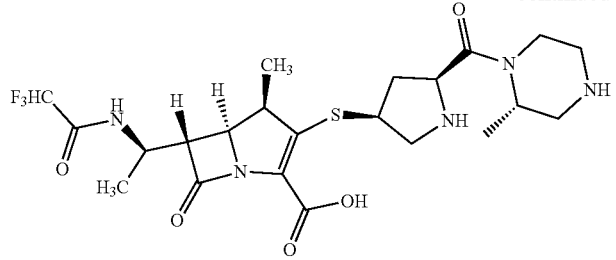
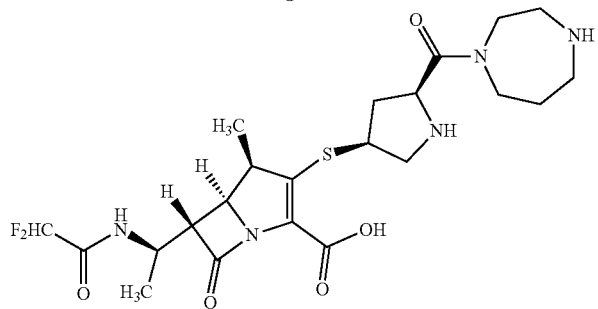
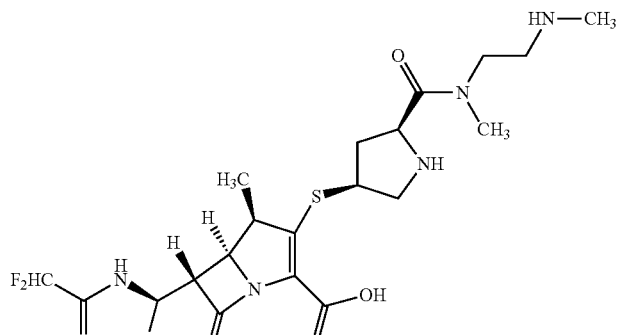
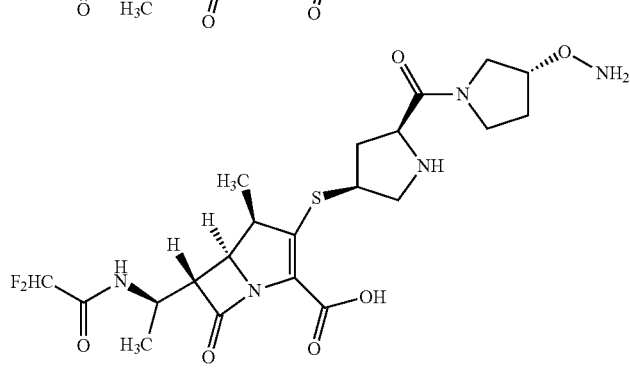
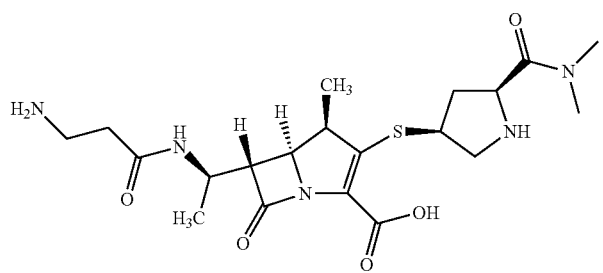

-continued
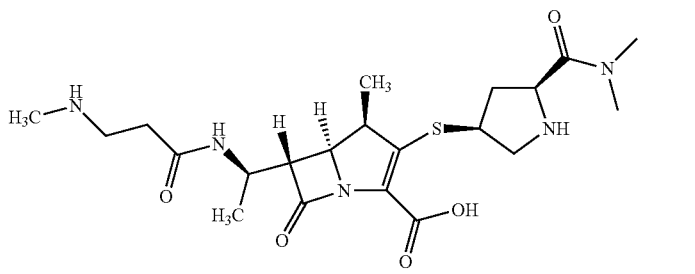
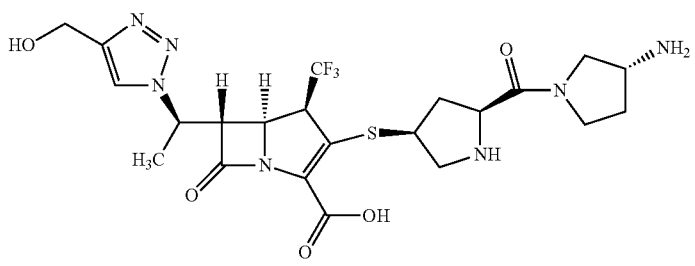
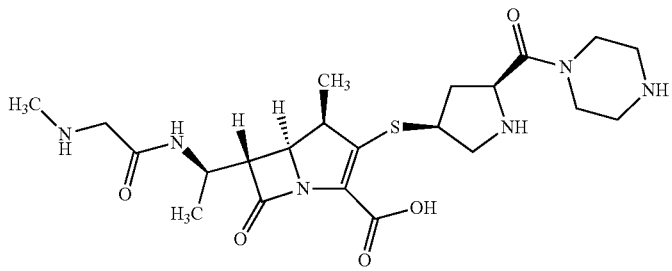
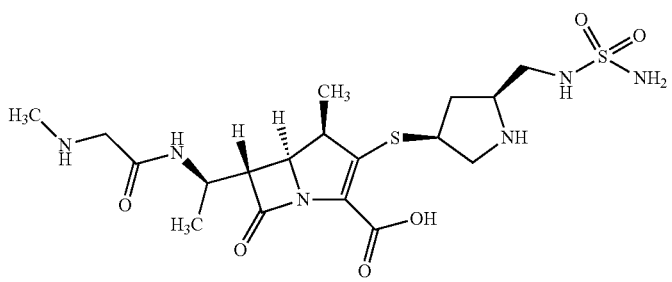
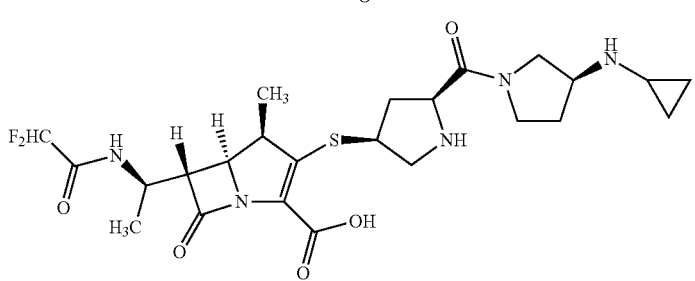
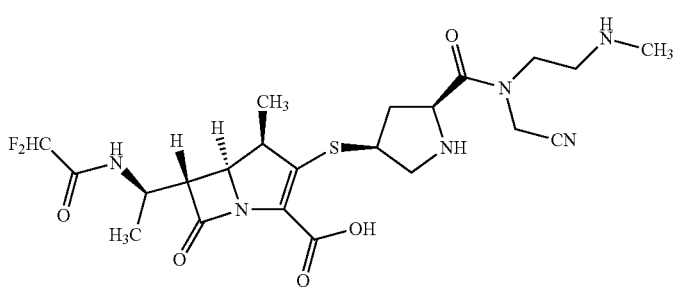

-continued
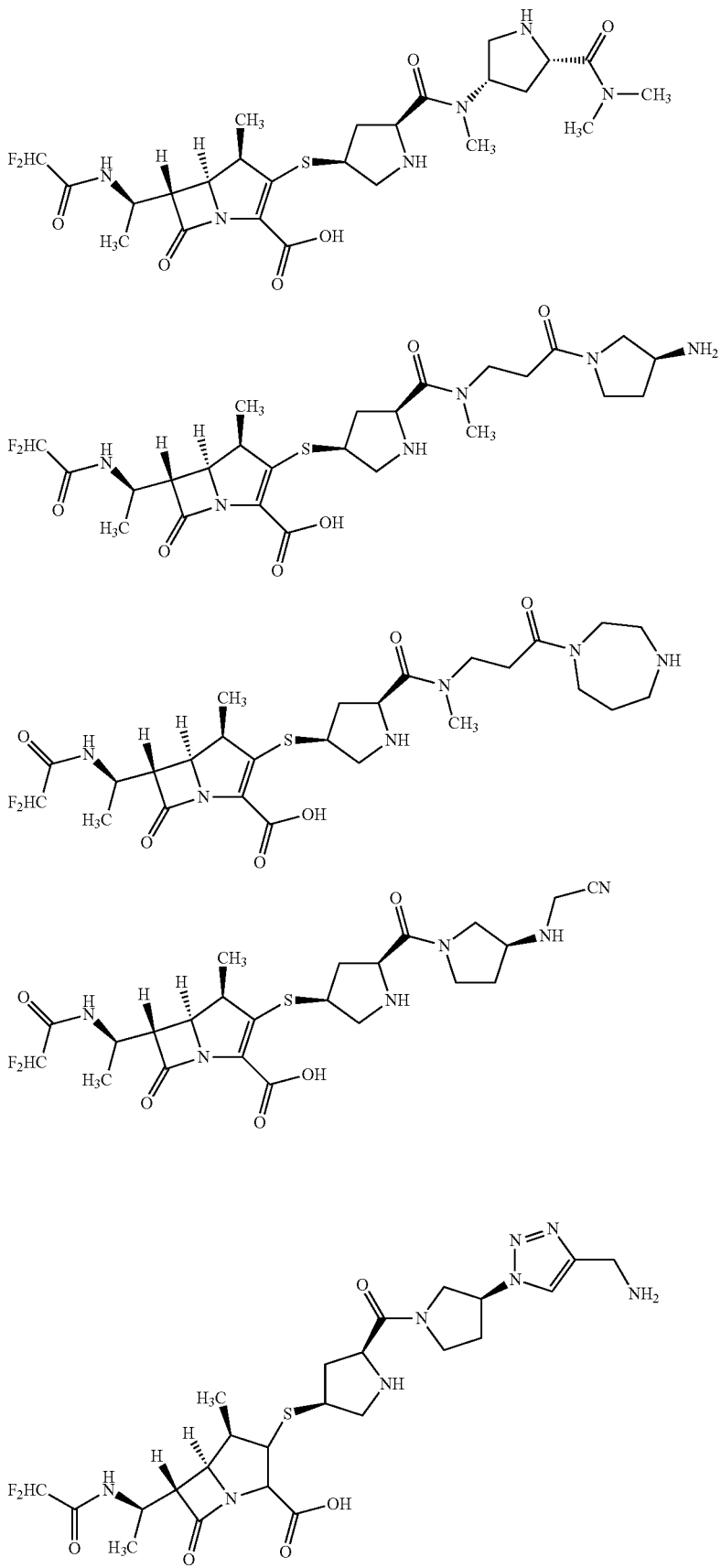

-continued
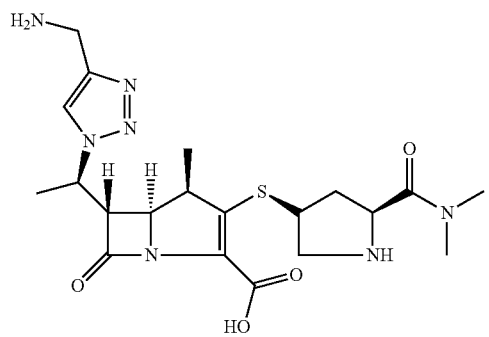
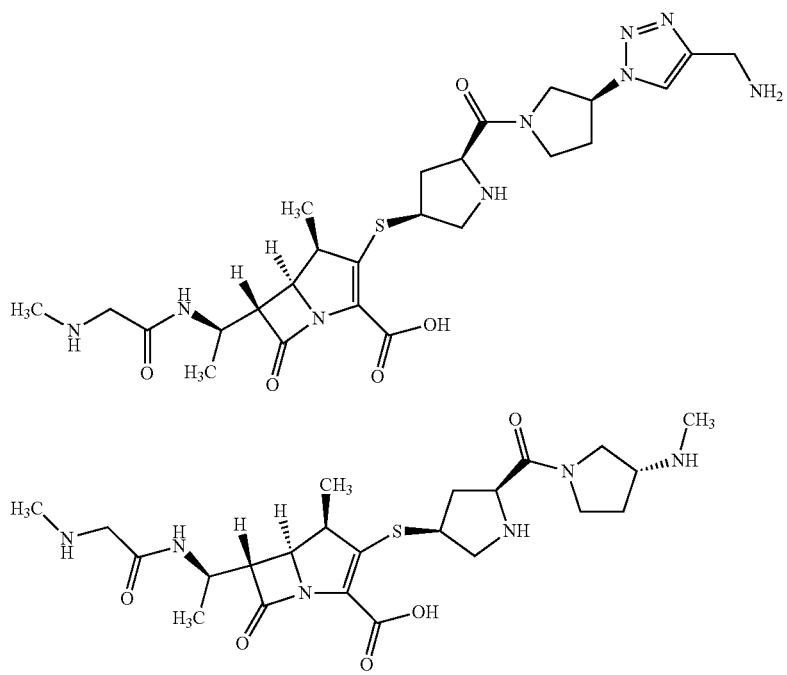
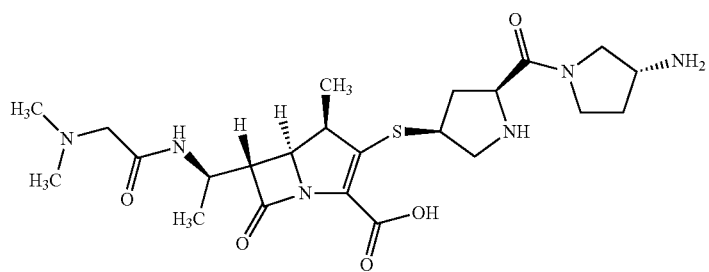
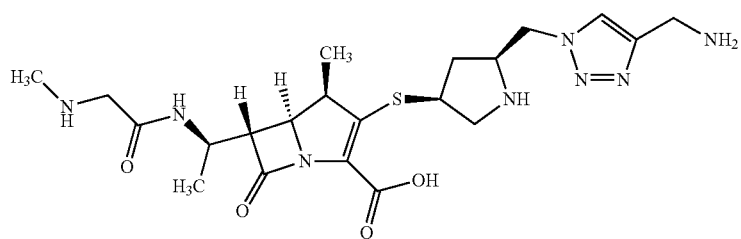

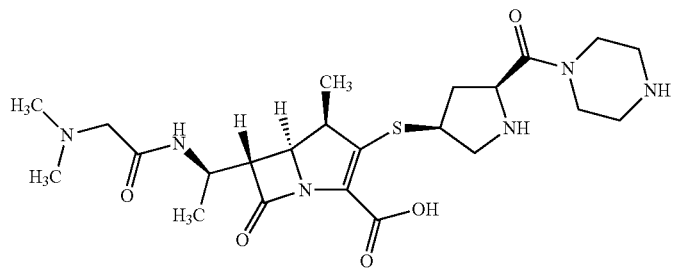
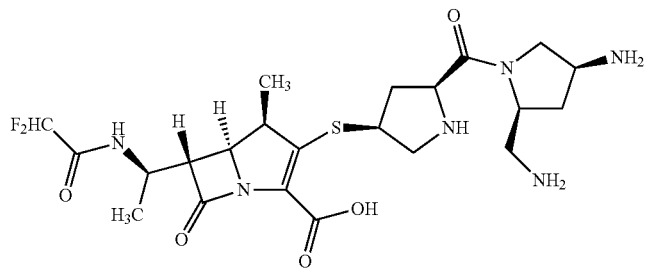
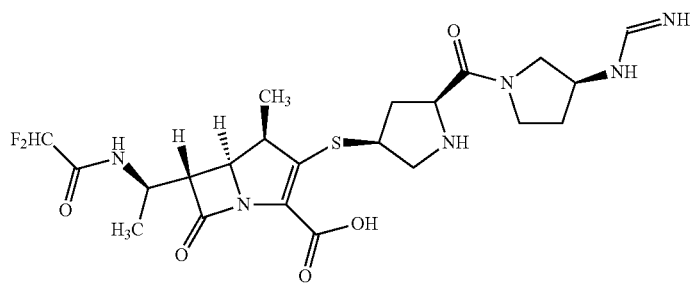
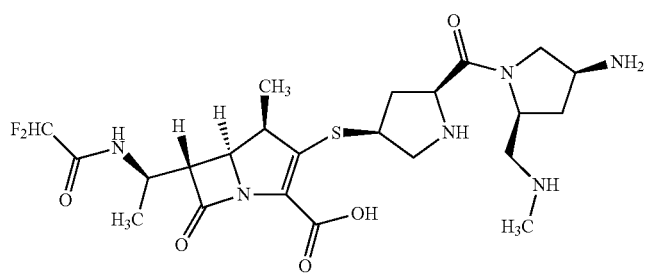
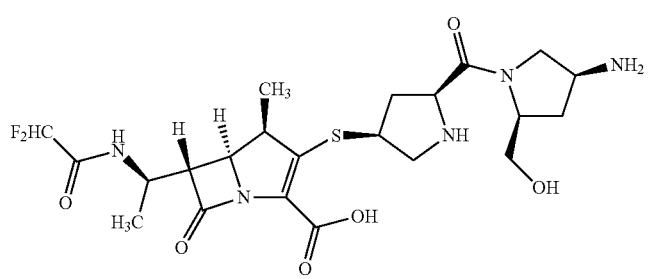
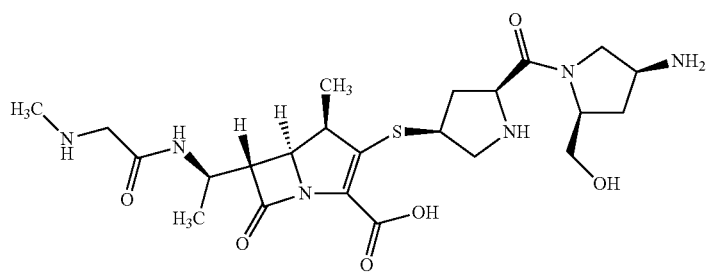

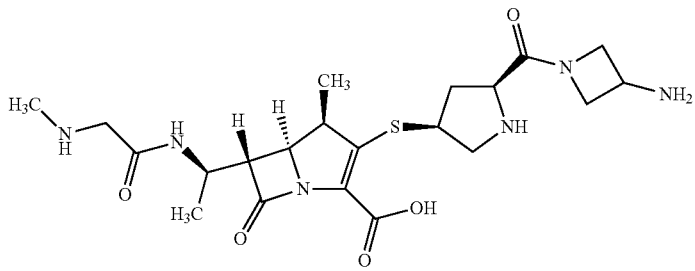
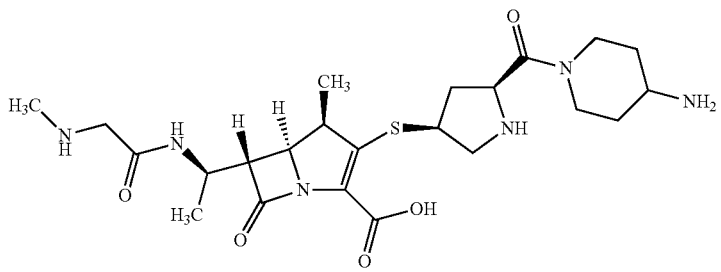
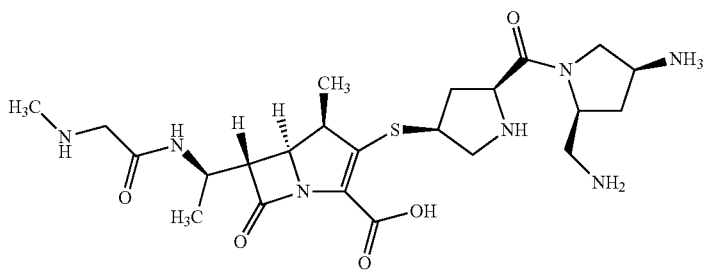
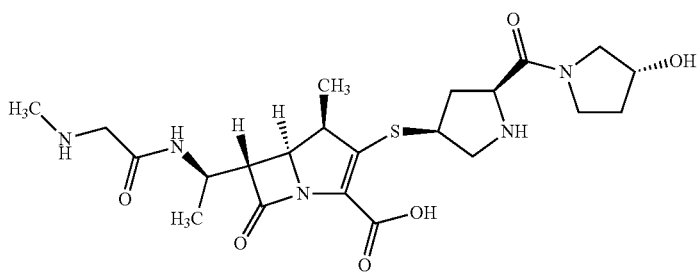
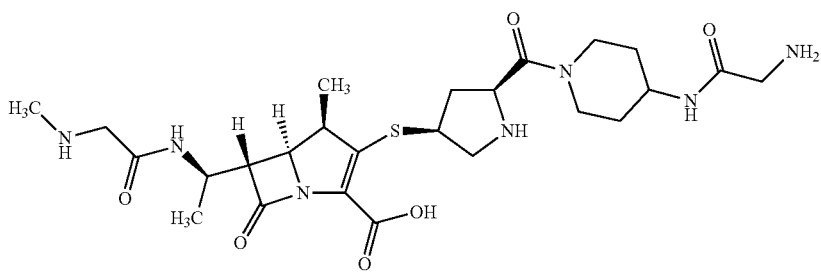
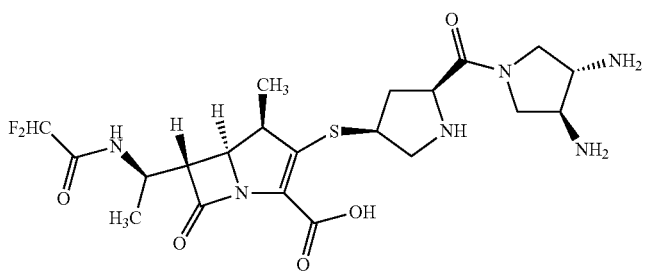

-continued
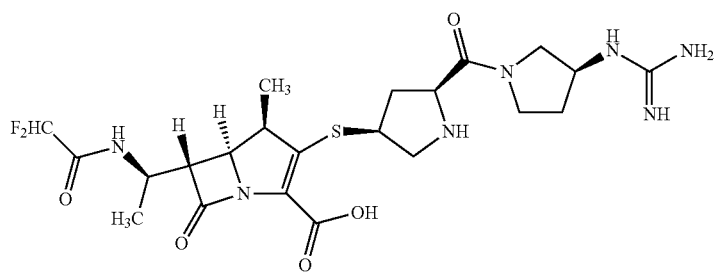
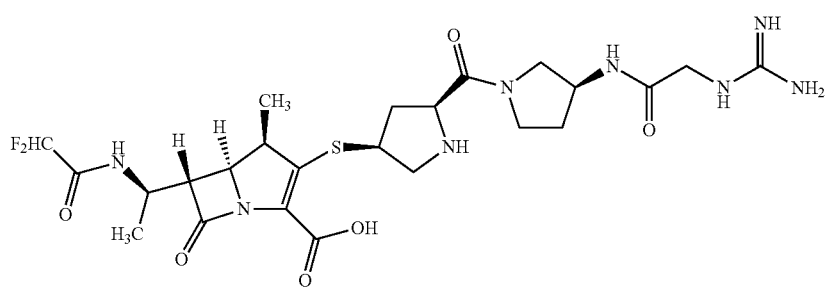
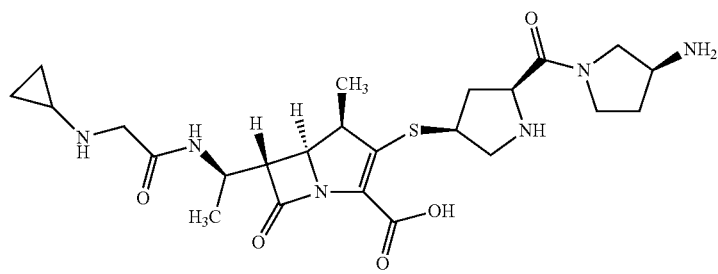
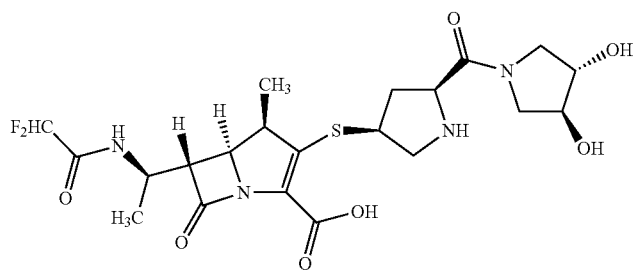
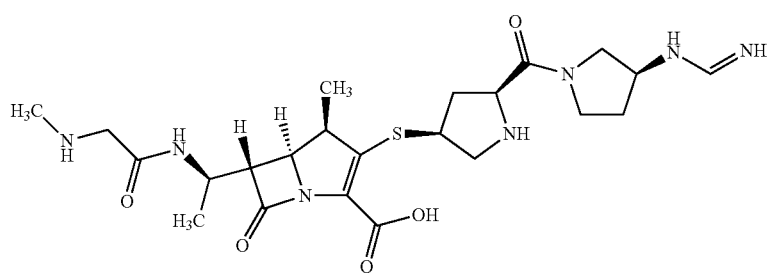
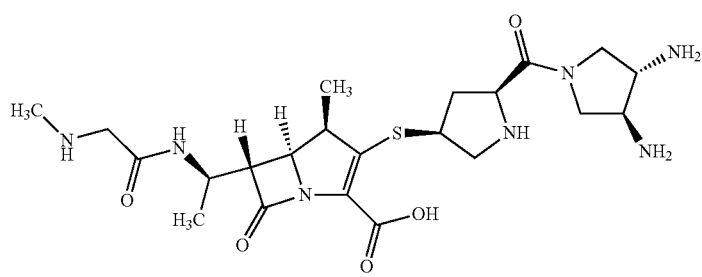

491                                     492
-continued
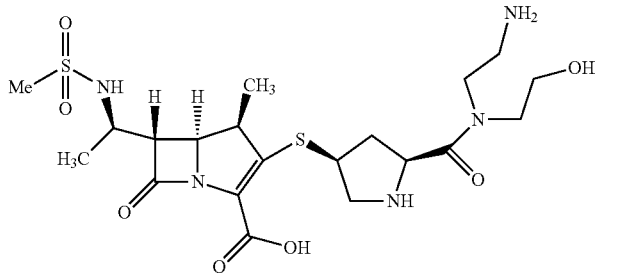
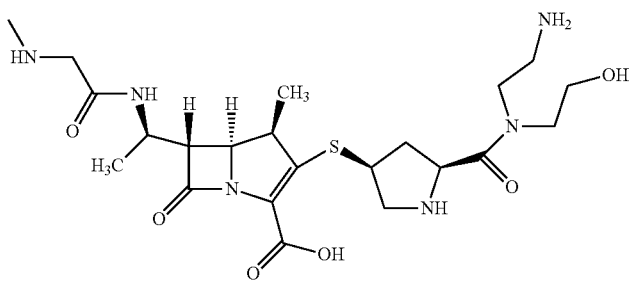
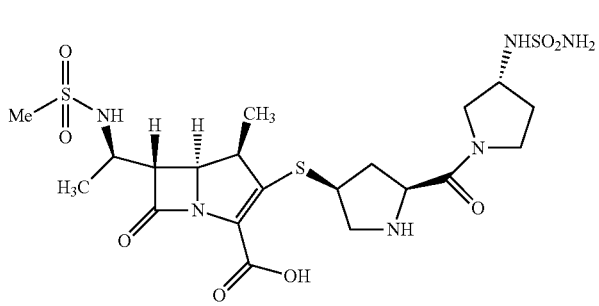    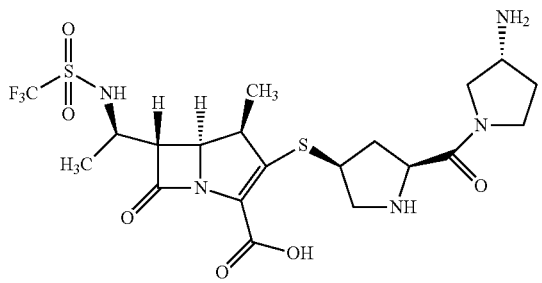
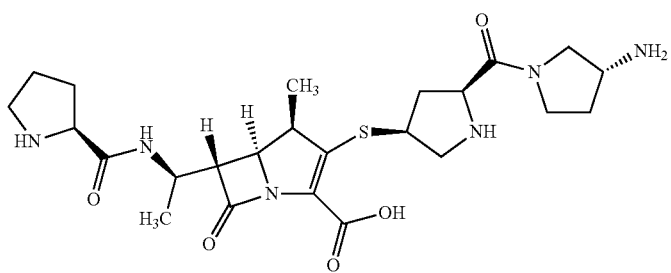
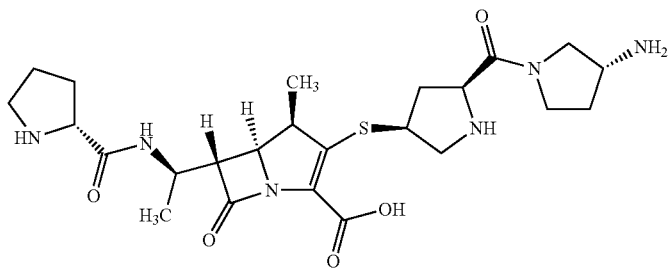
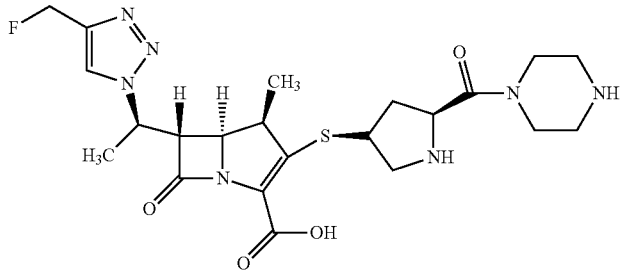

-continued
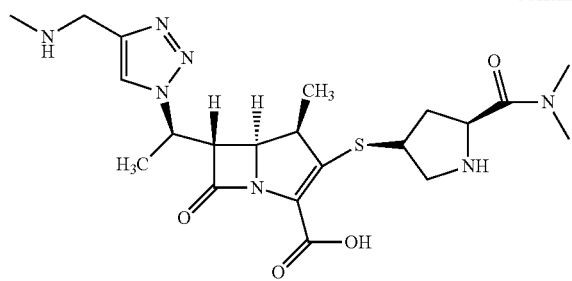
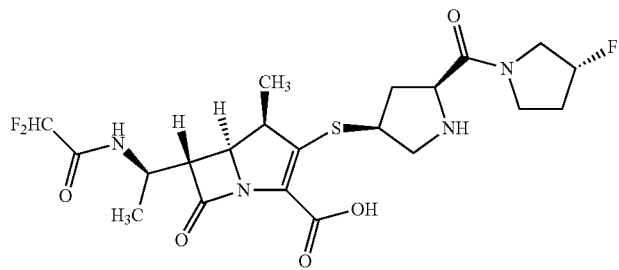
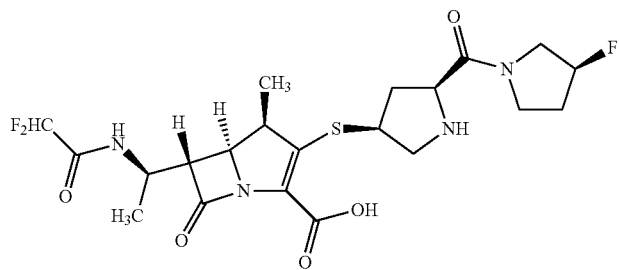
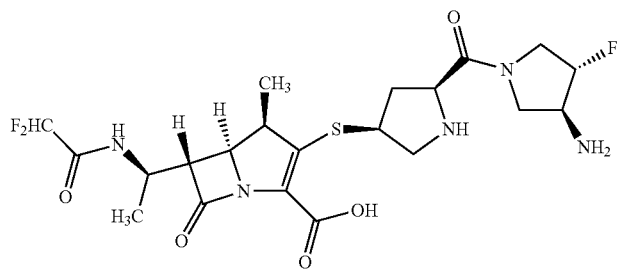
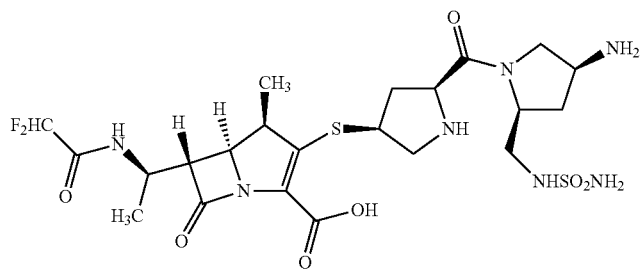
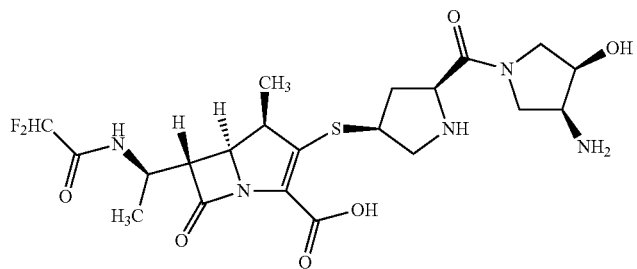

-continued
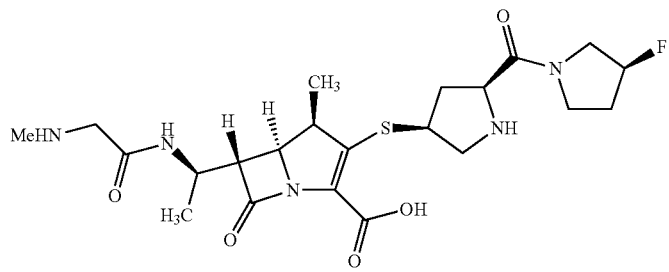
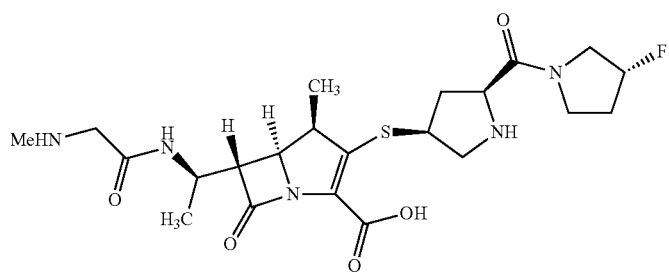
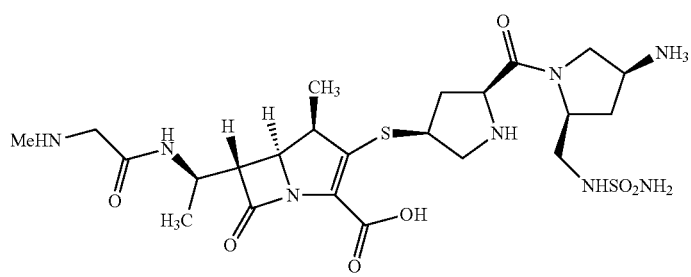
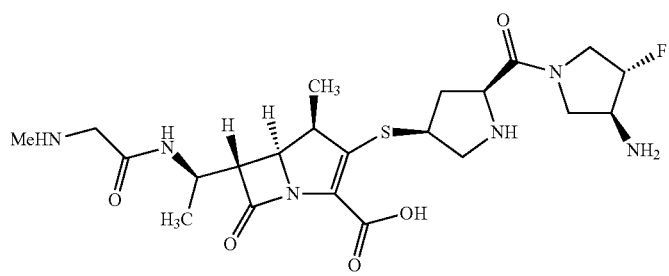
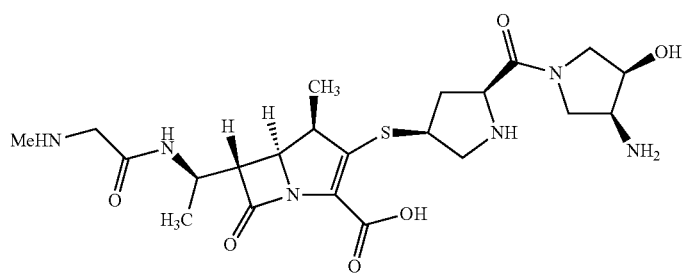
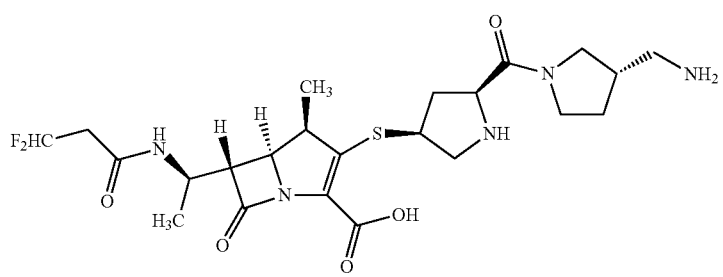

497 498
-continued
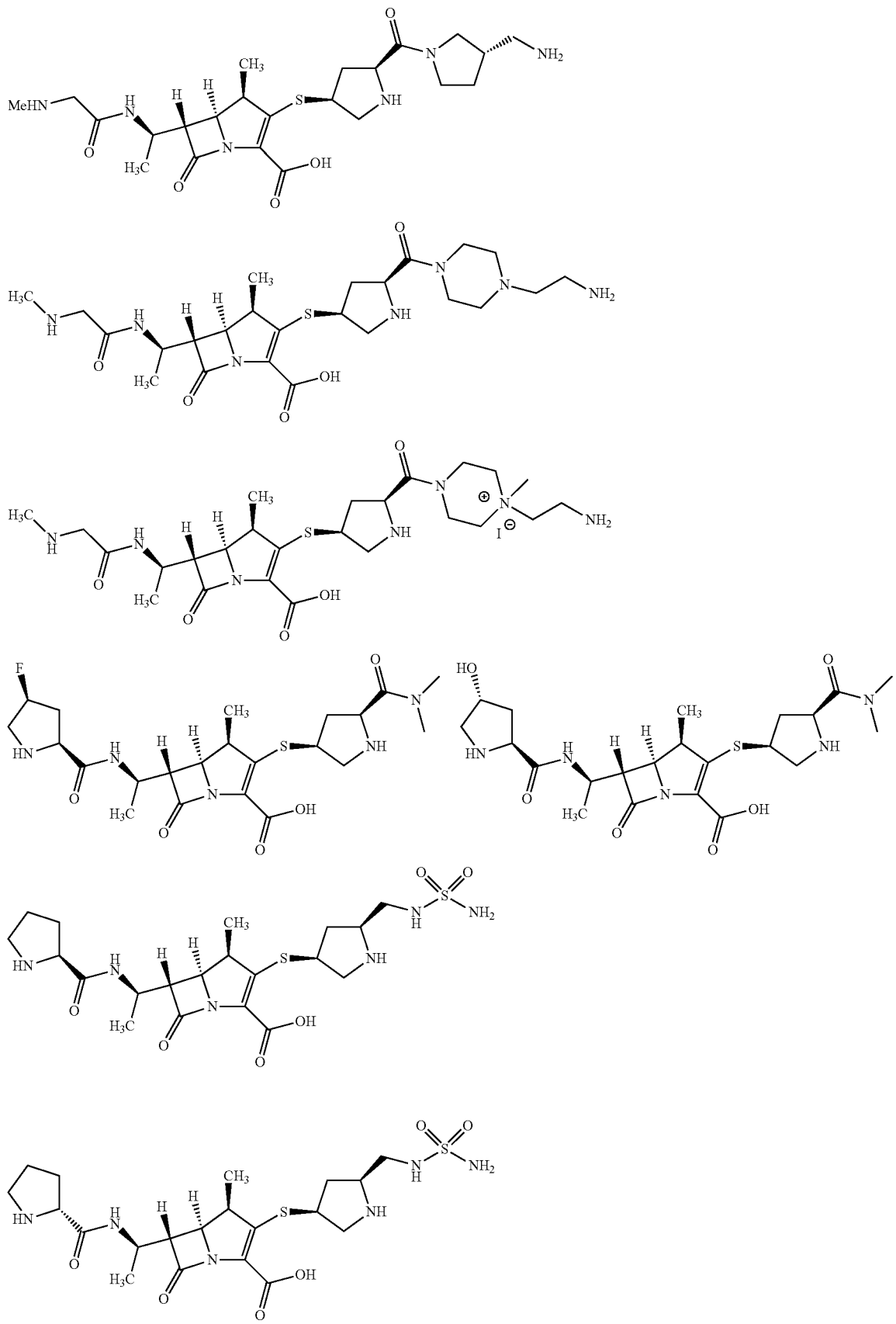

-continued
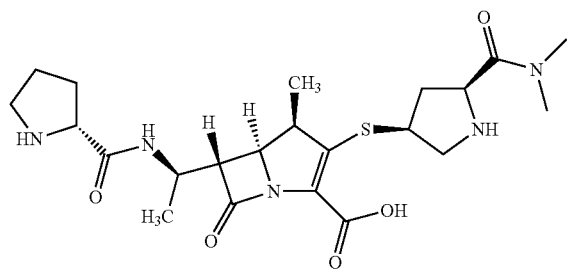
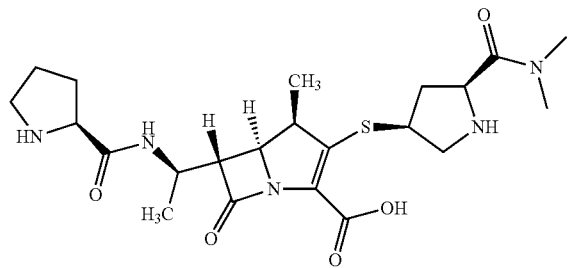
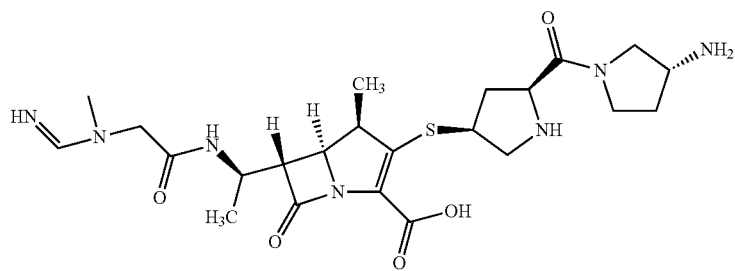
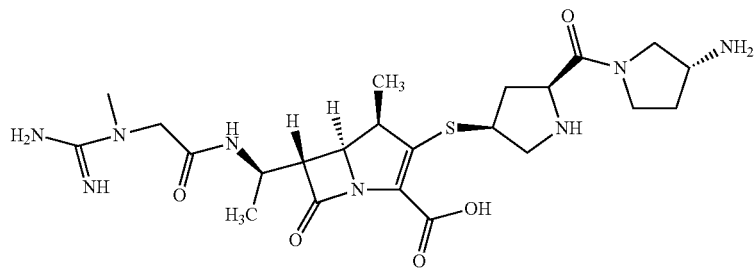
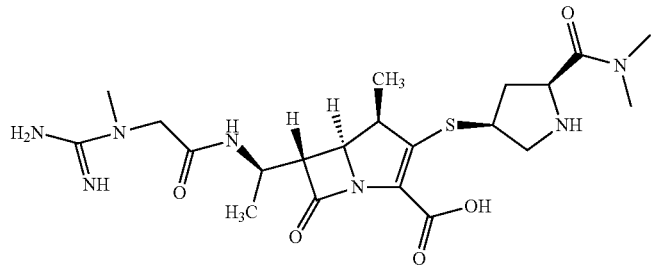
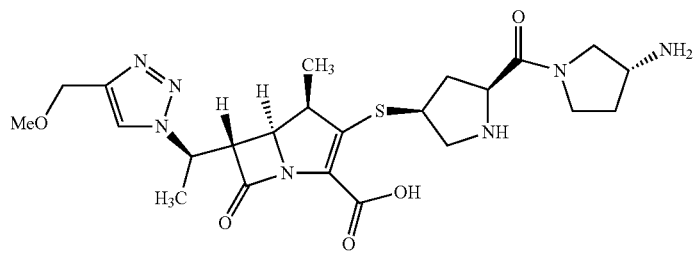

-continued
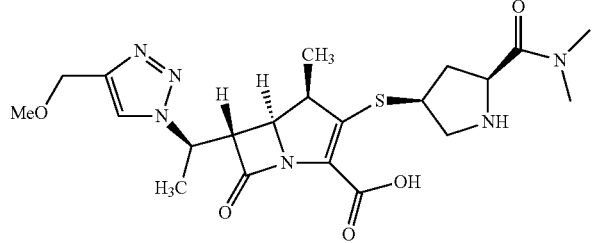
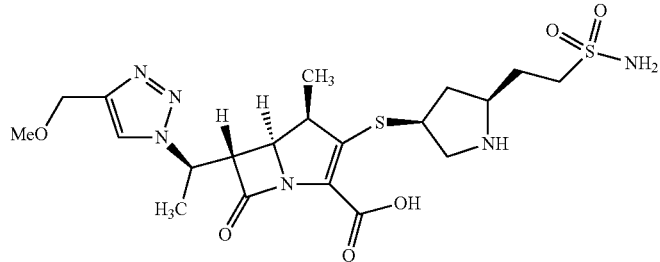
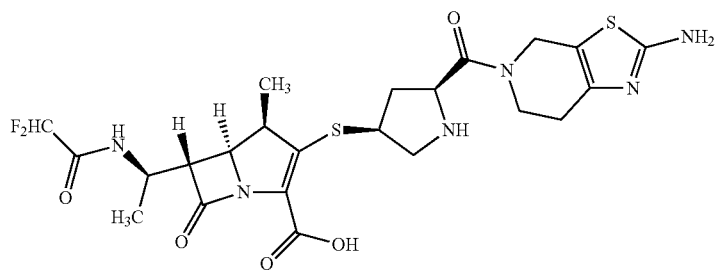
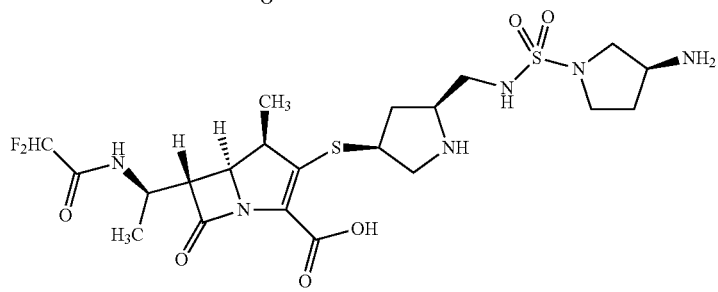
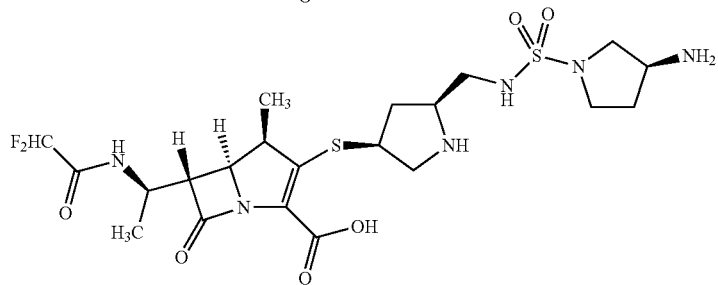
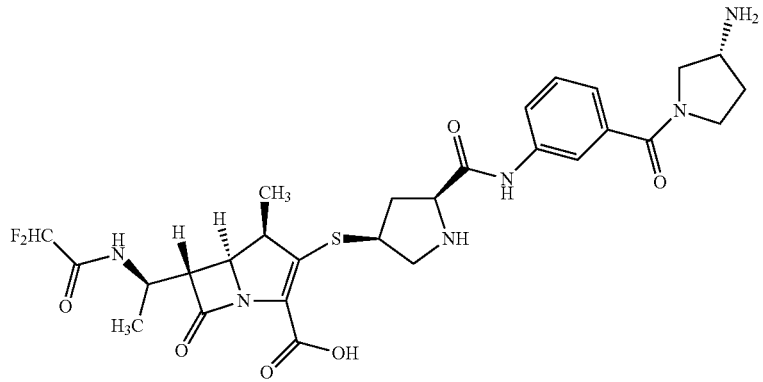

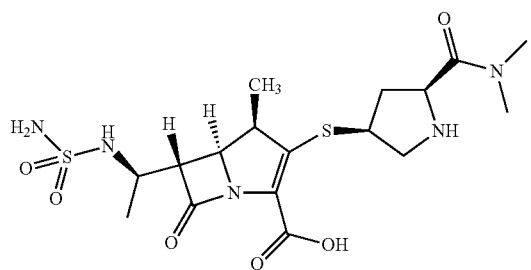
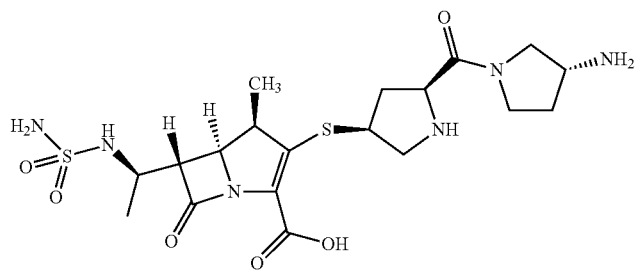
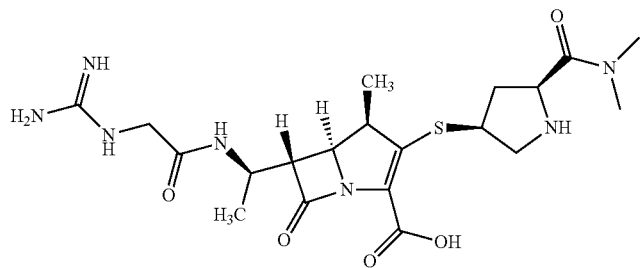
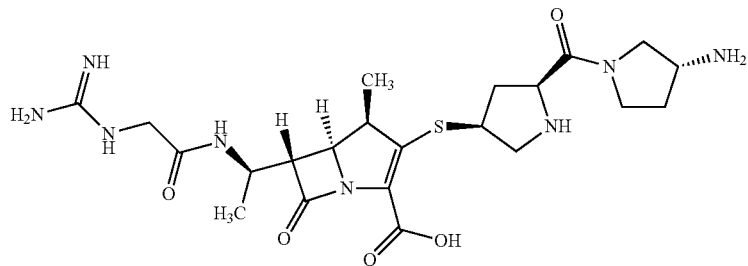
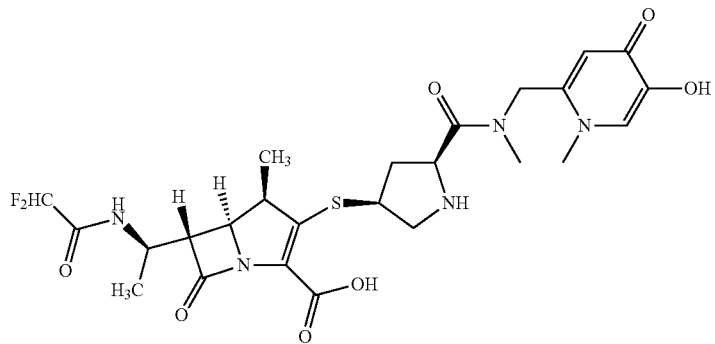

505 506
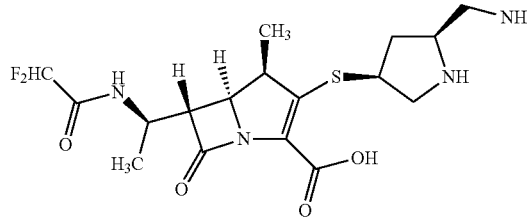
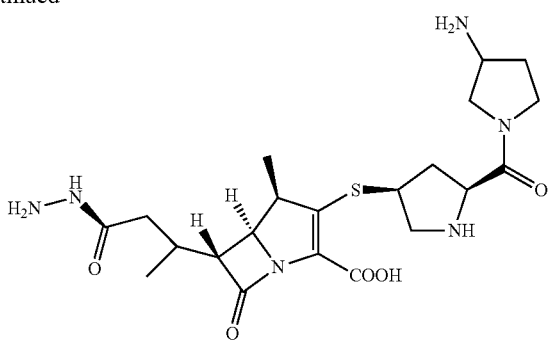
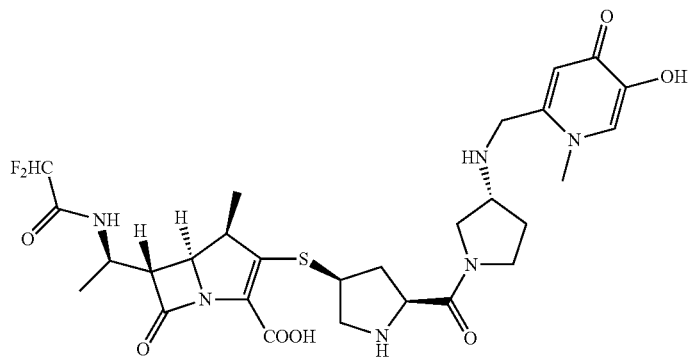
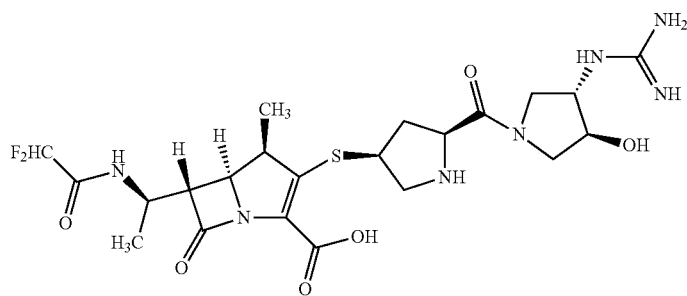
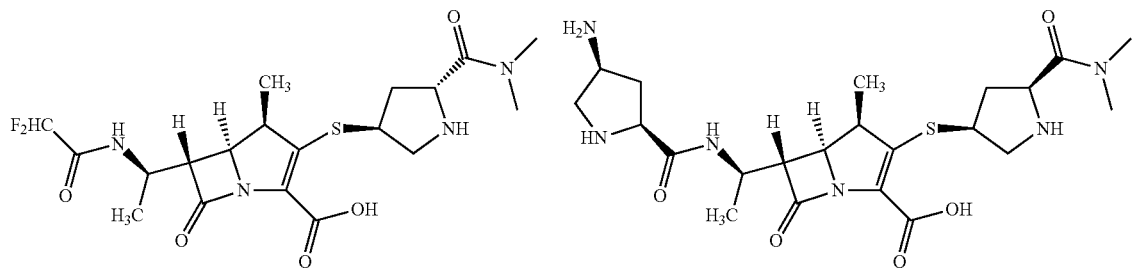
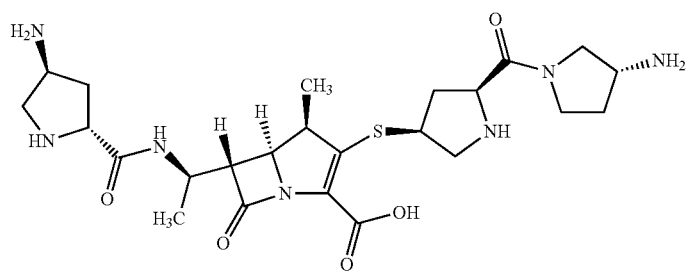

-continued
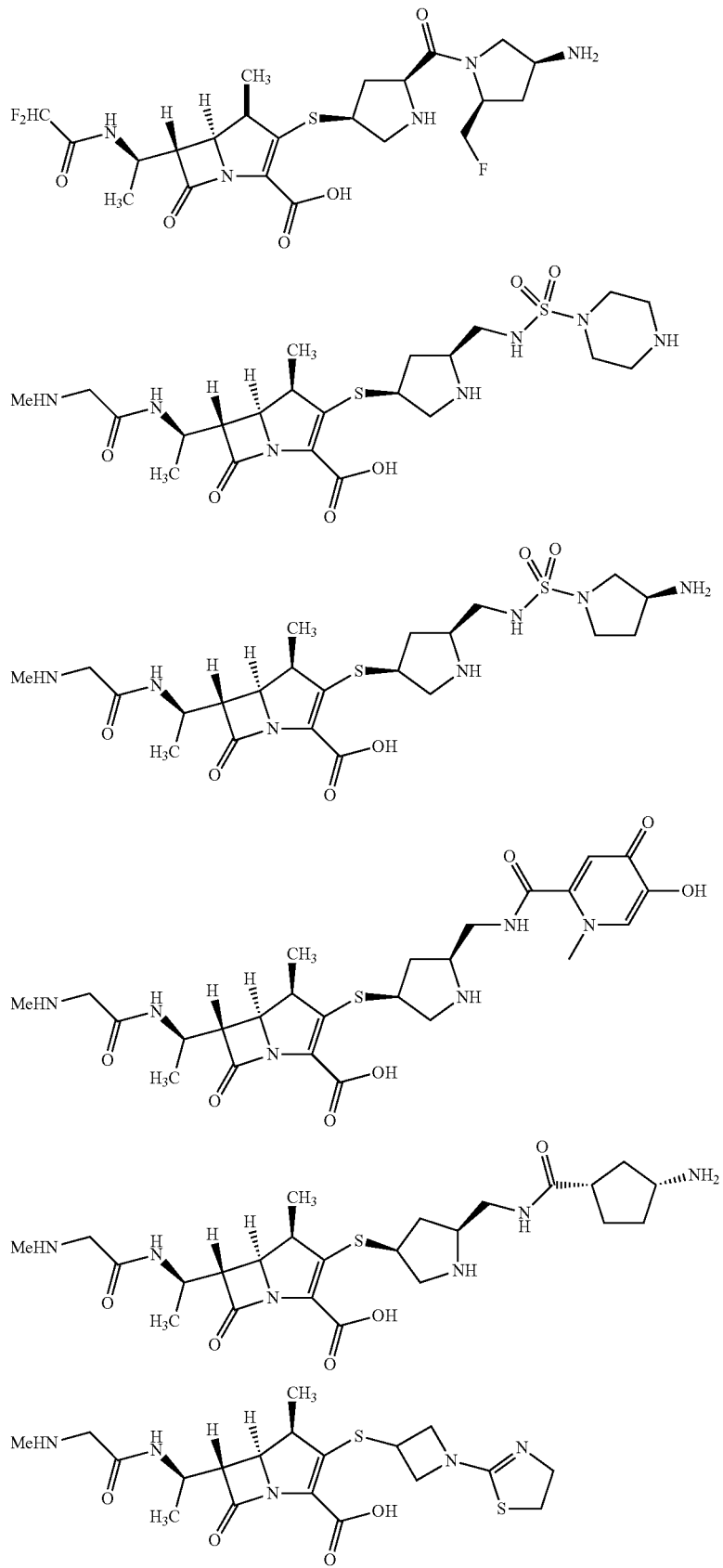

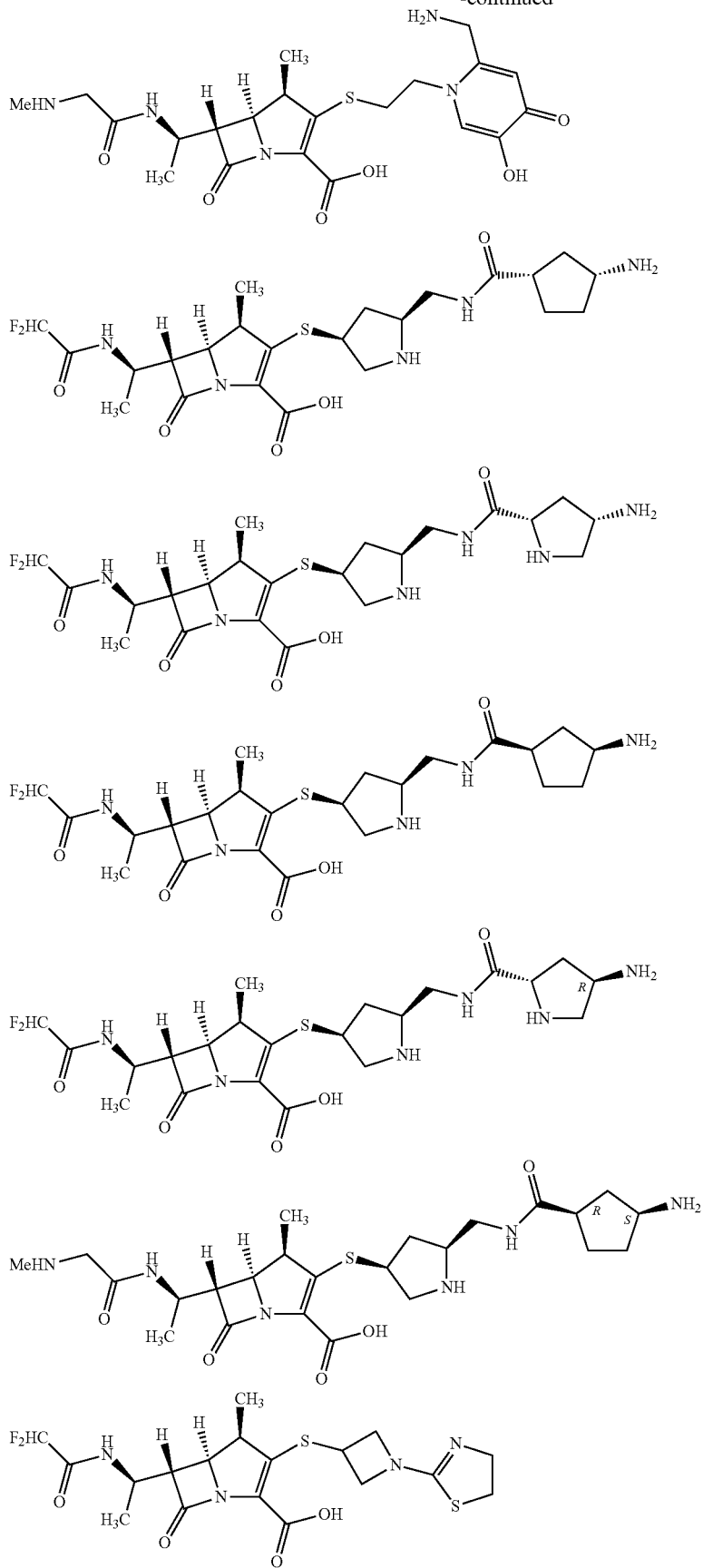

-continued
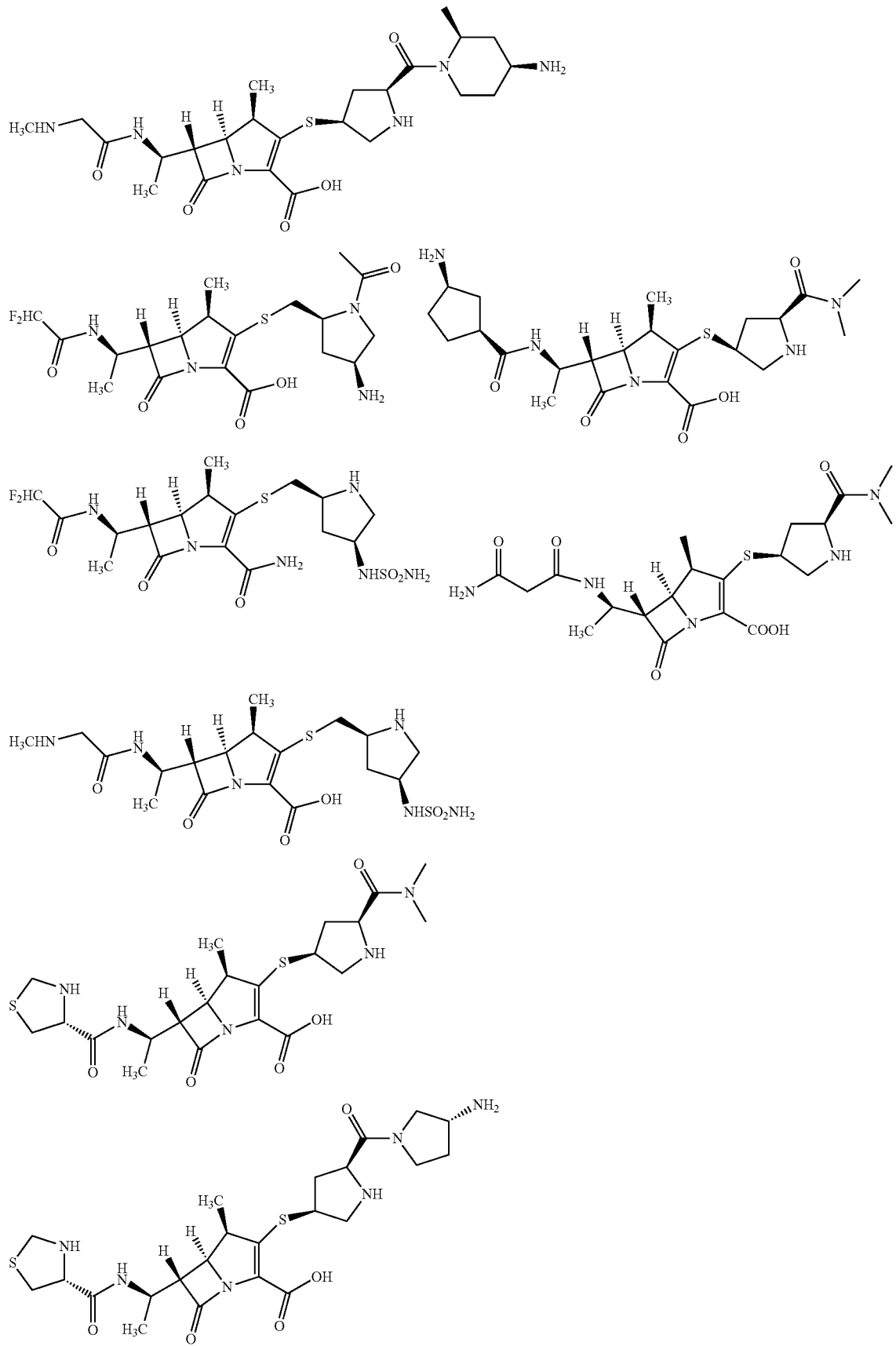

-continued
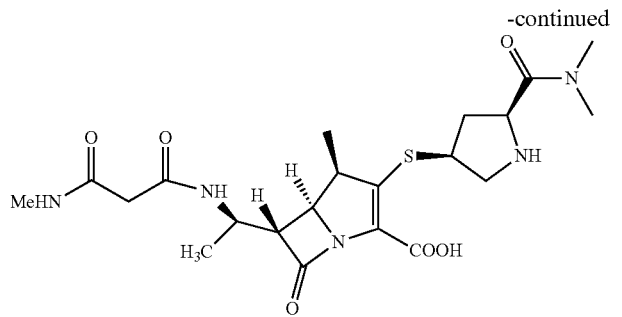
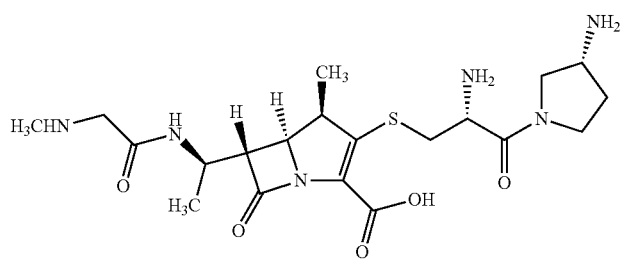
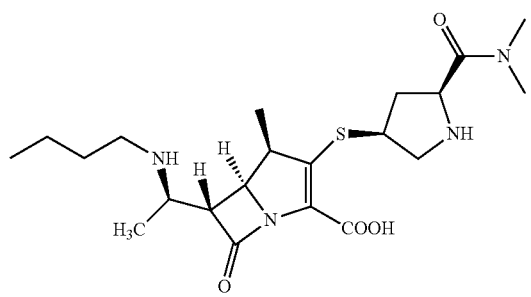
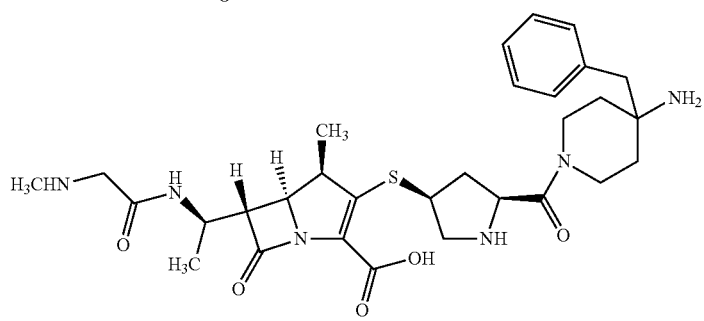
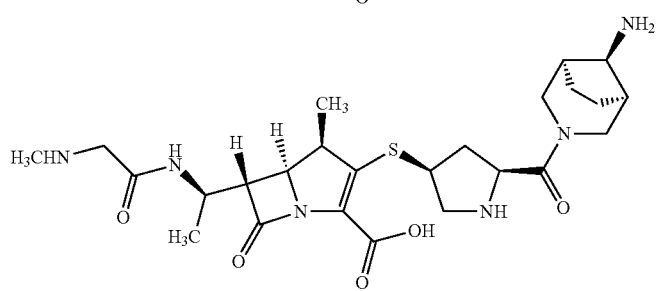
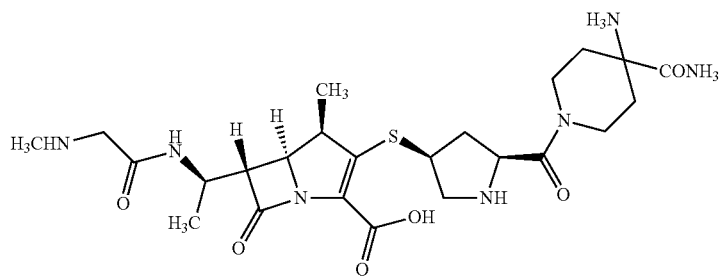

-continued
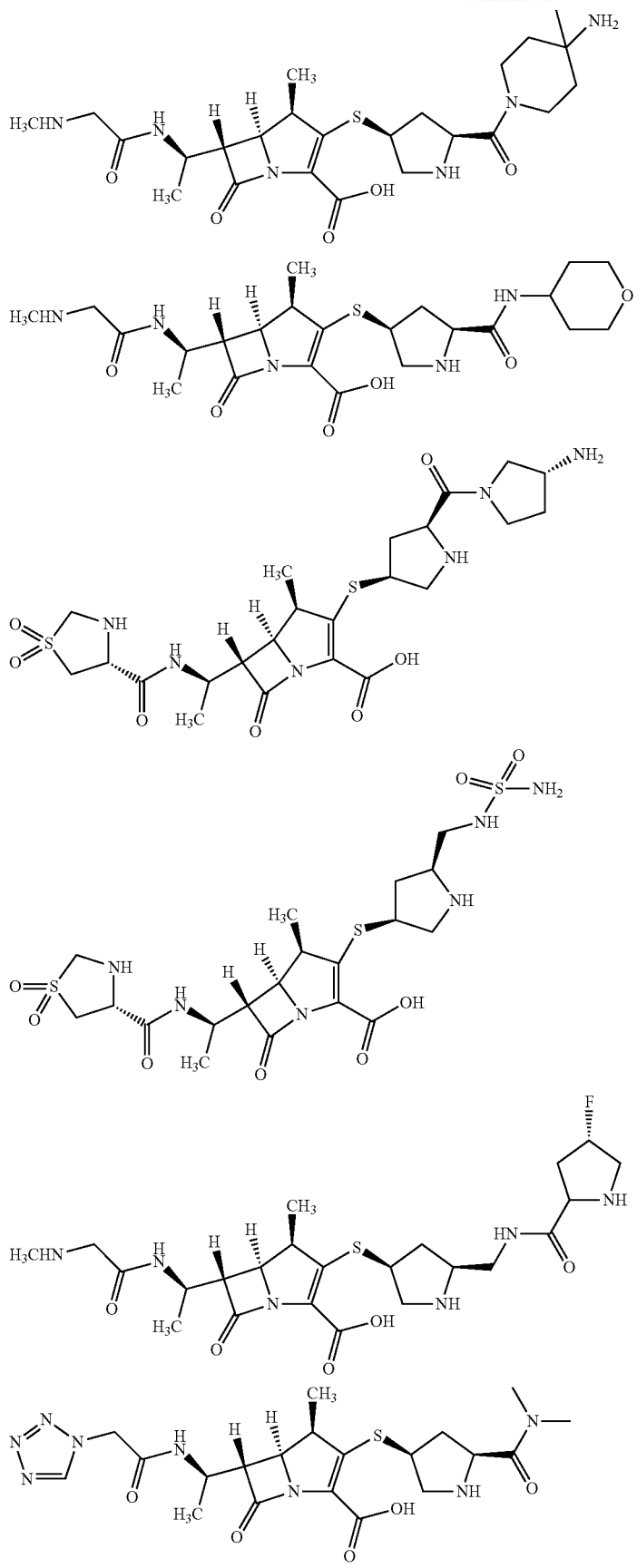

517 518
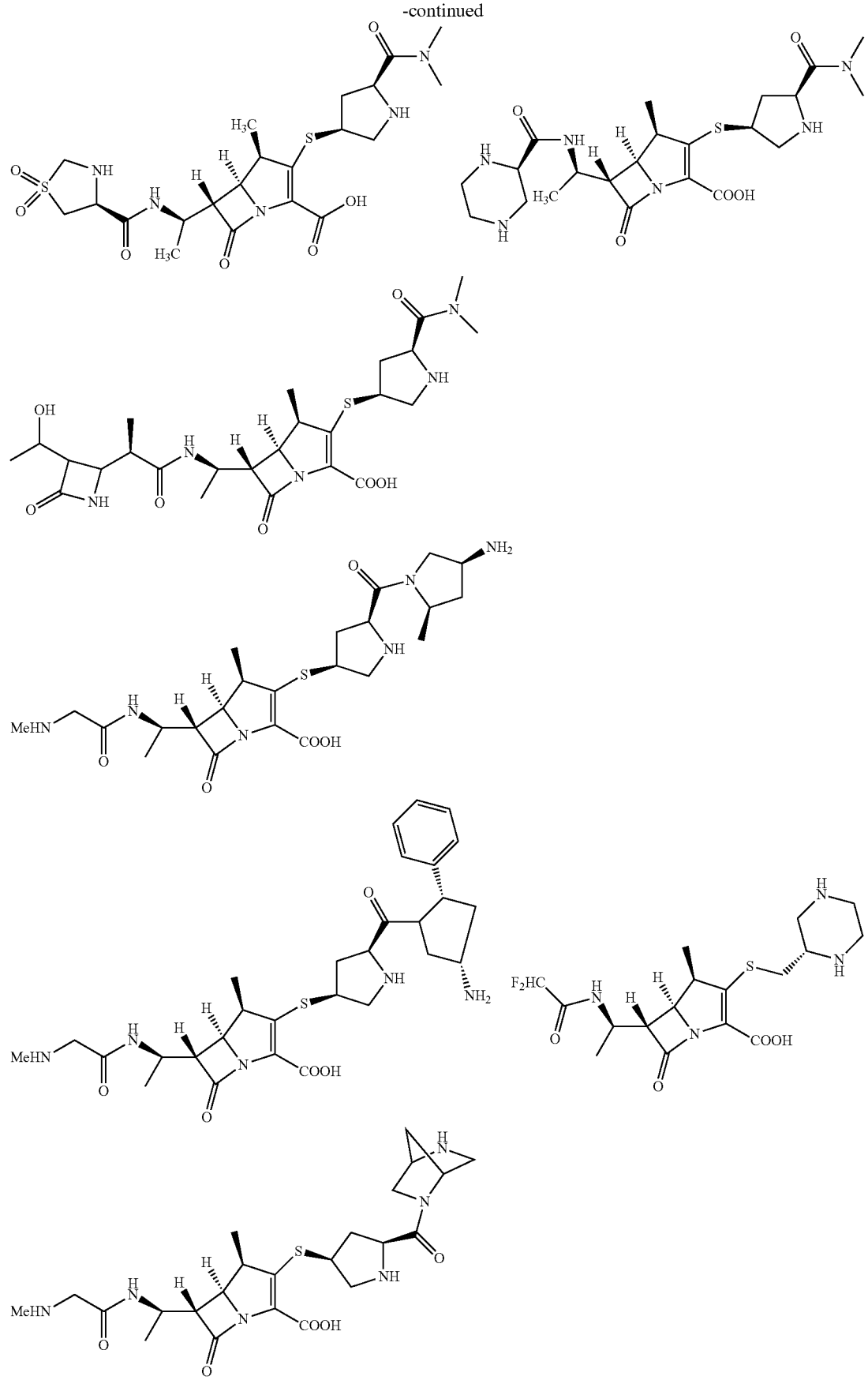

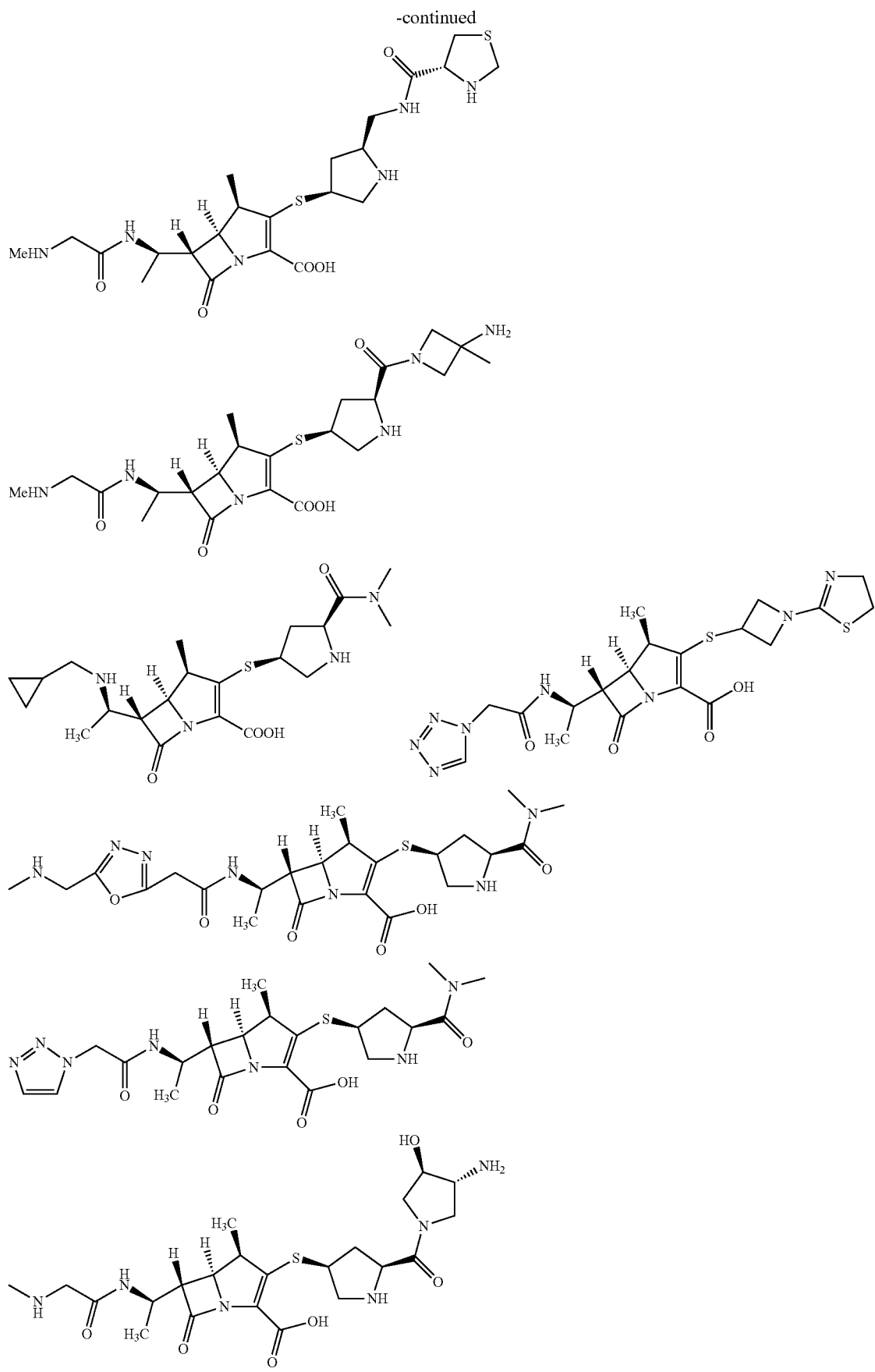

-continued
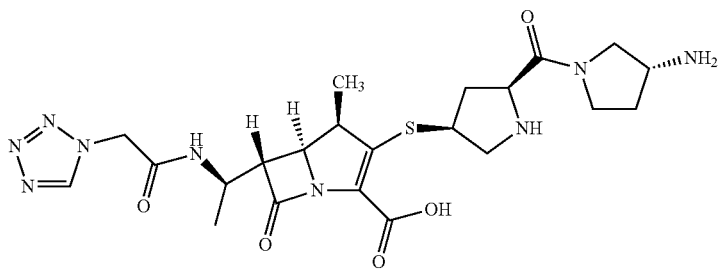
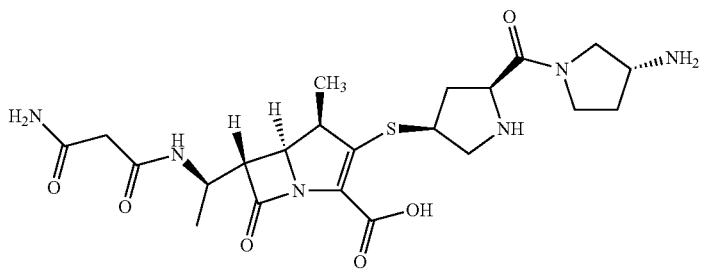
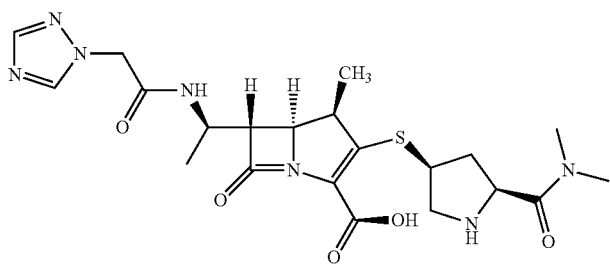
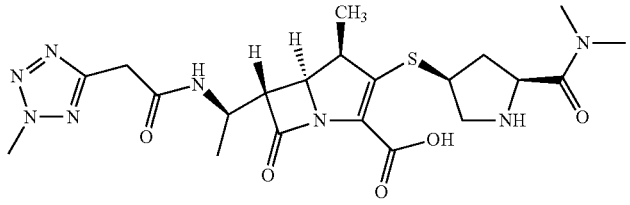
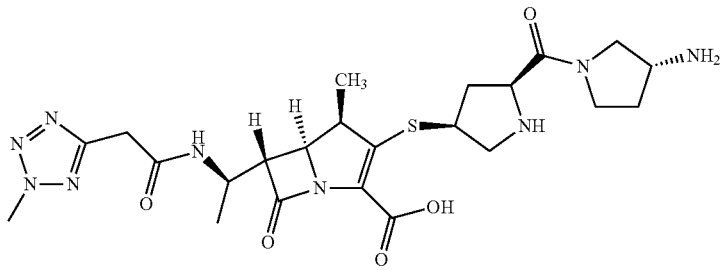
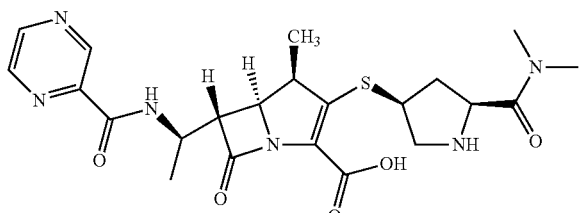
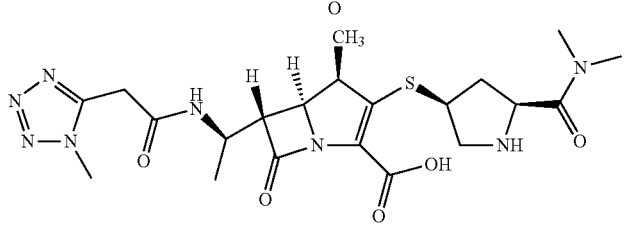

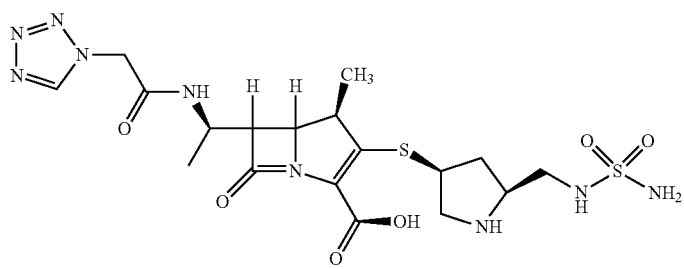
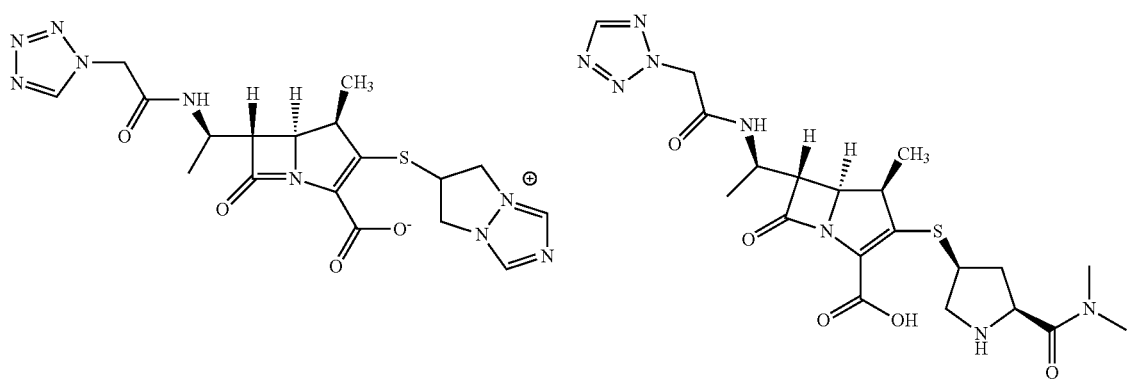
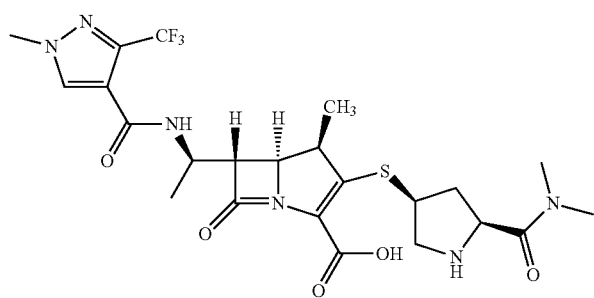
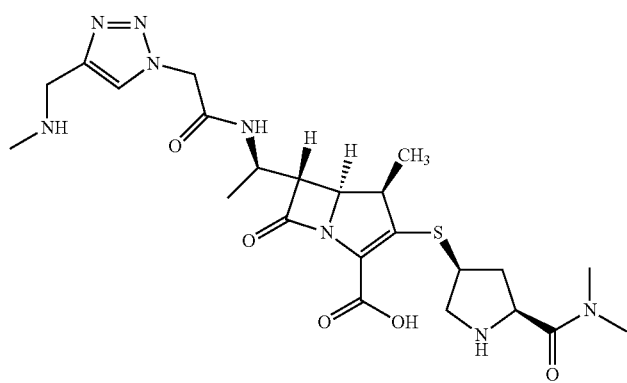

525 526
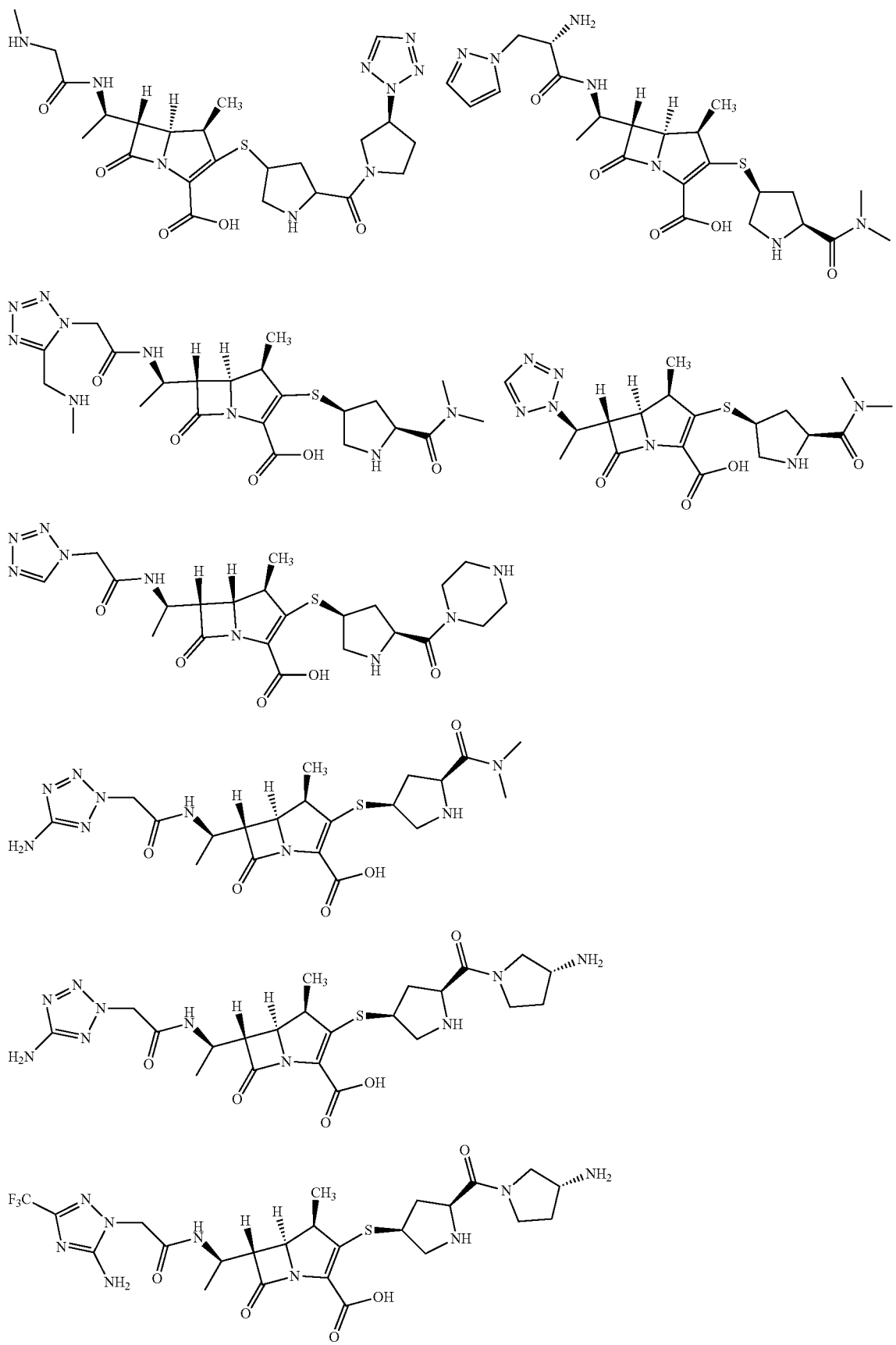

527
-continued
528
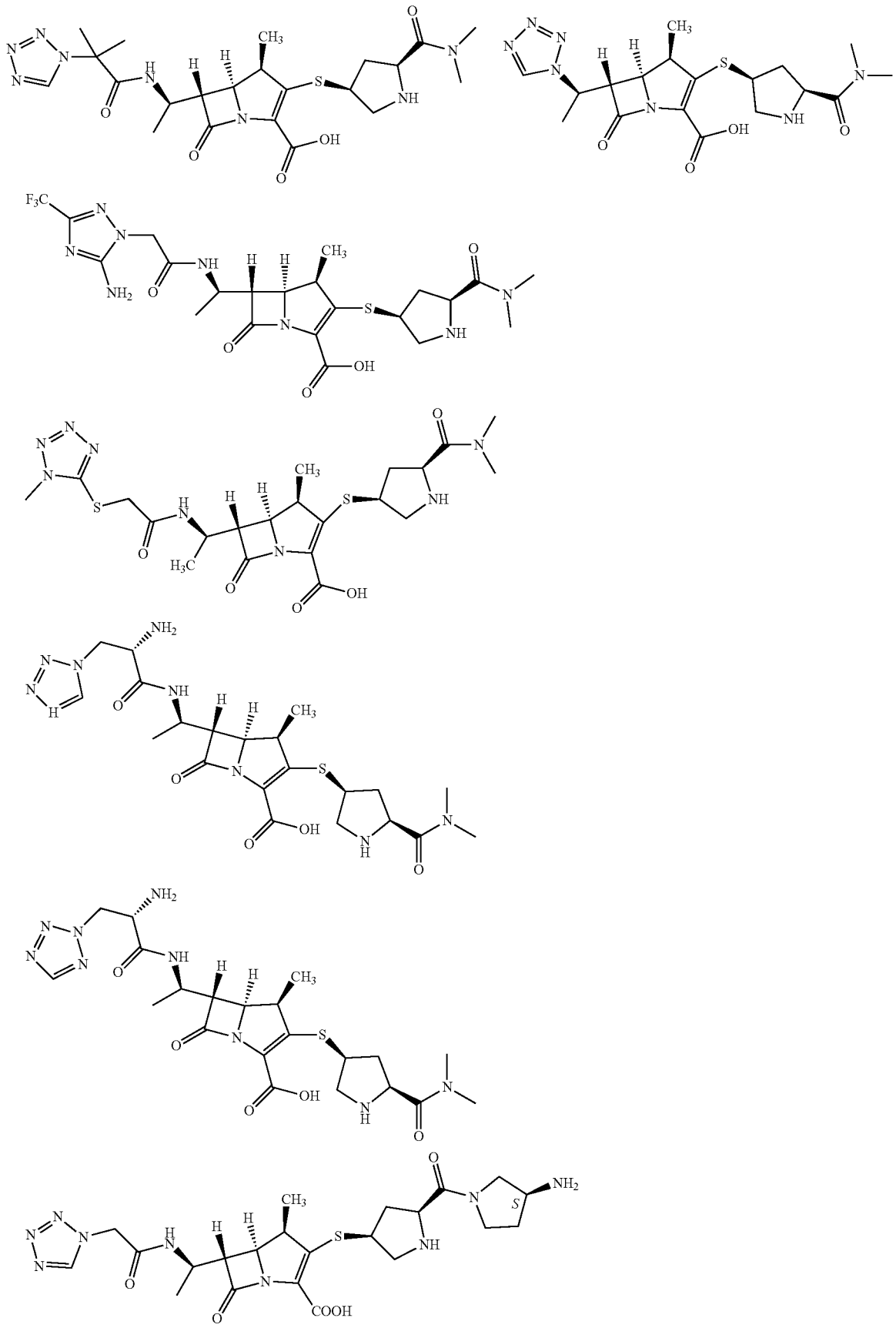

-continued
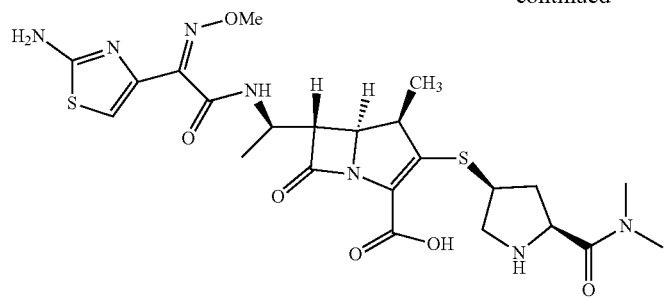
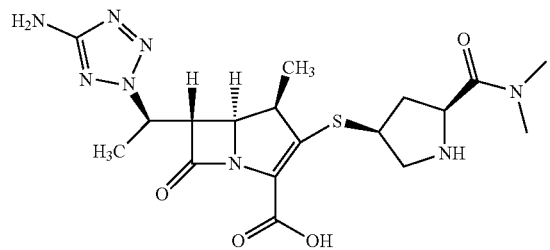
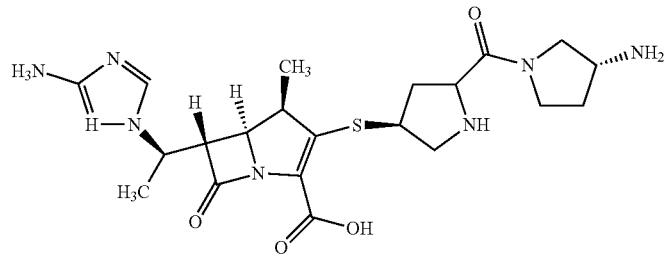
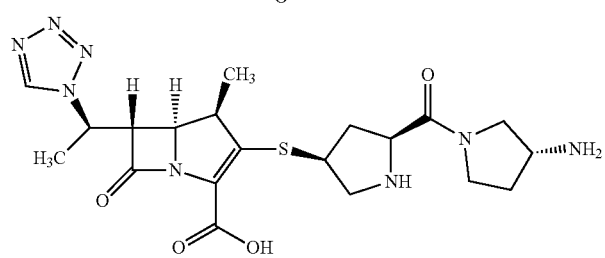
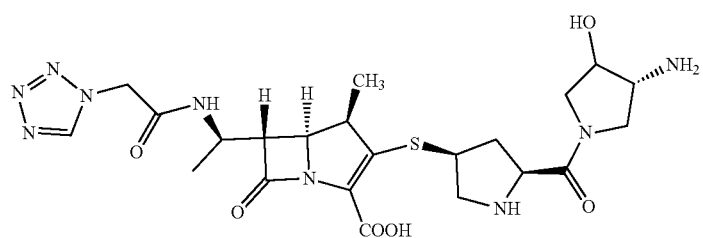
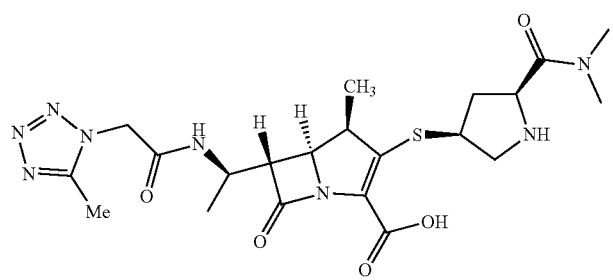

531
-continued
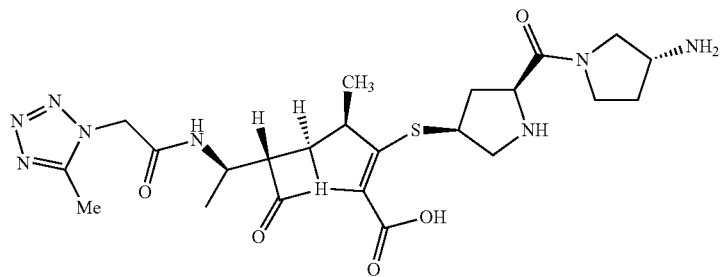
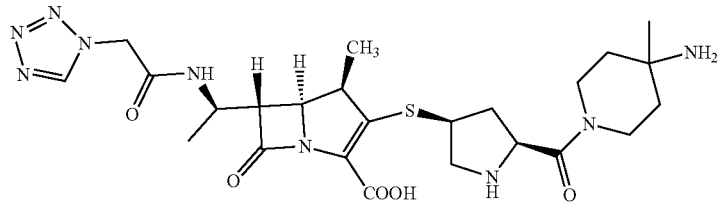
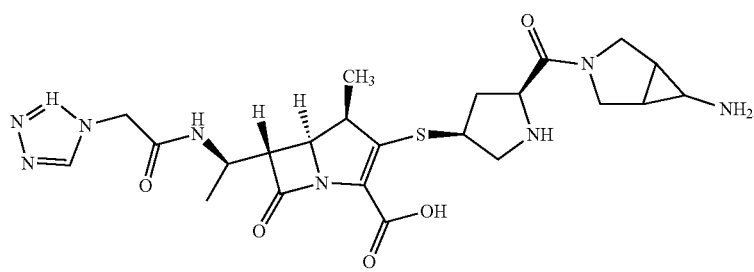
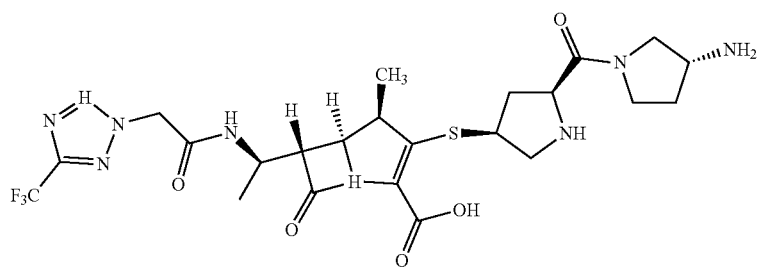
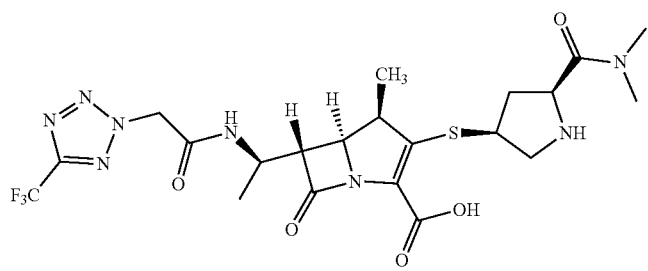
532
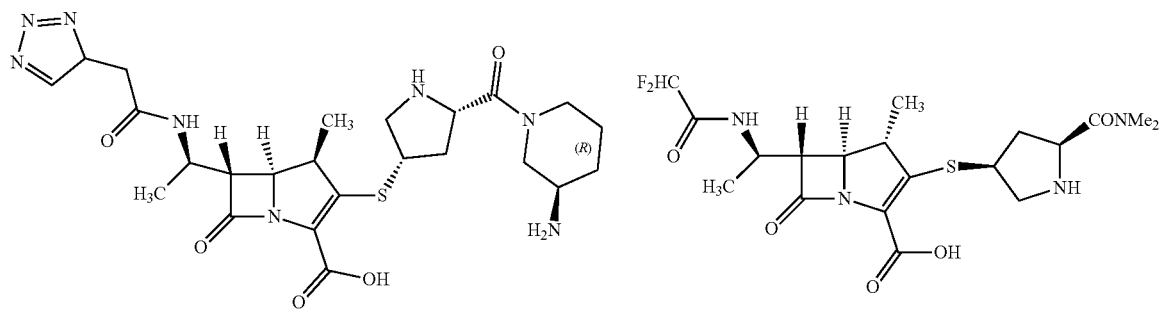

-continued
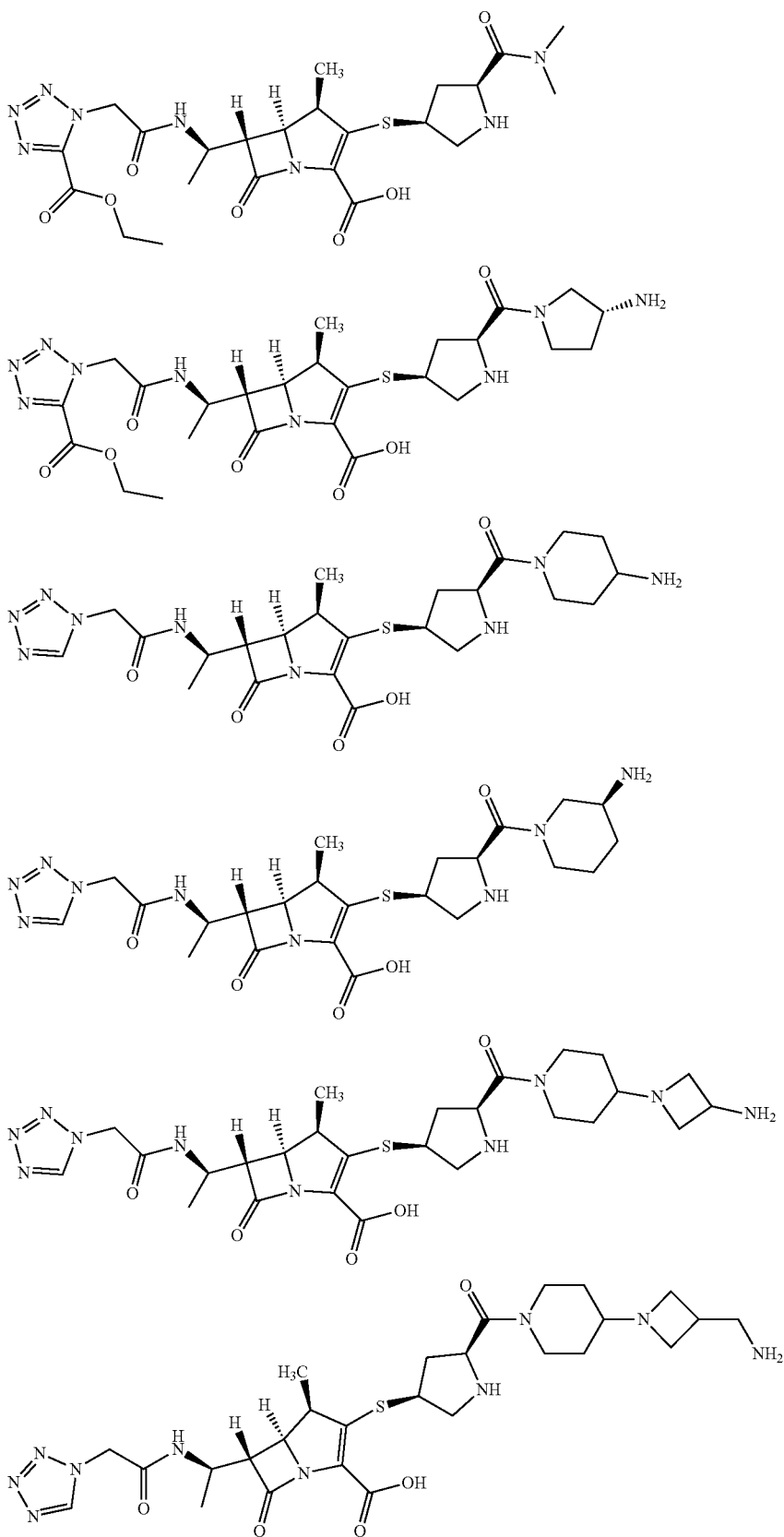

-continued
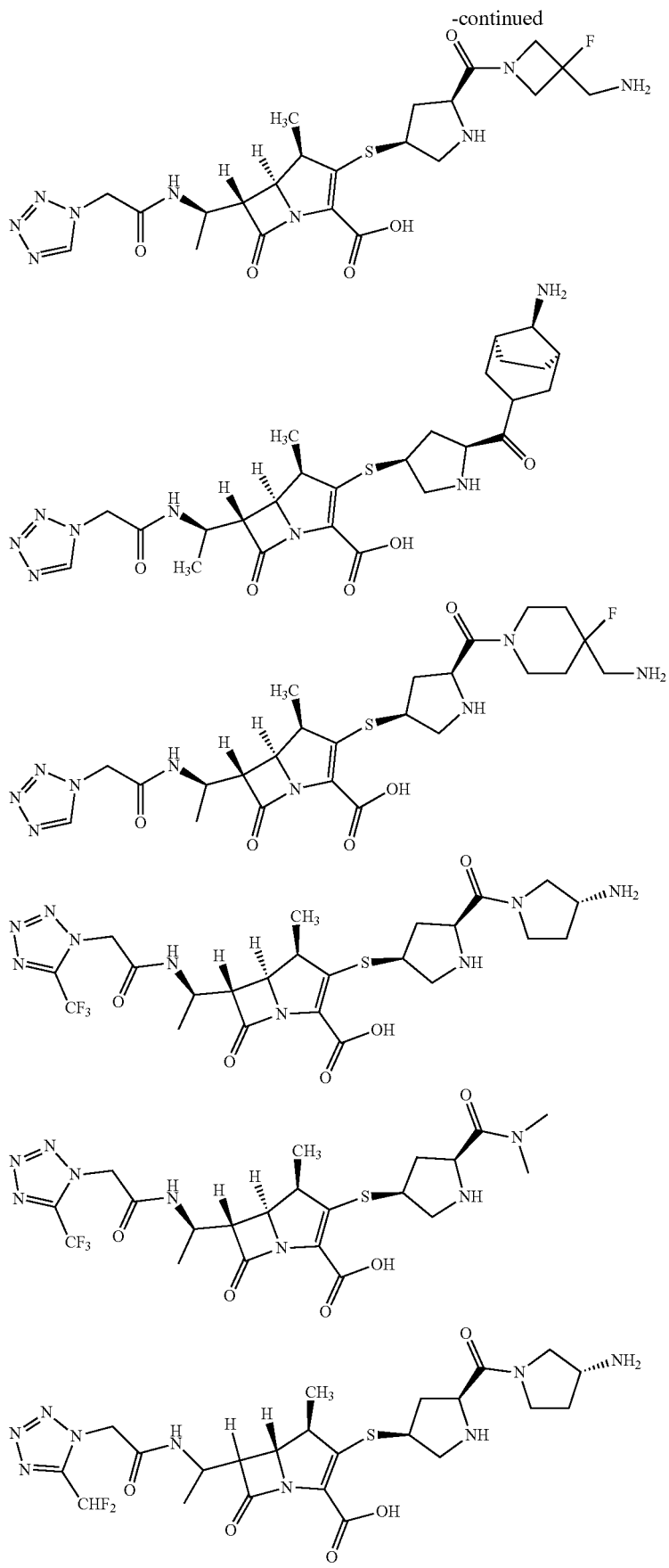

-continued
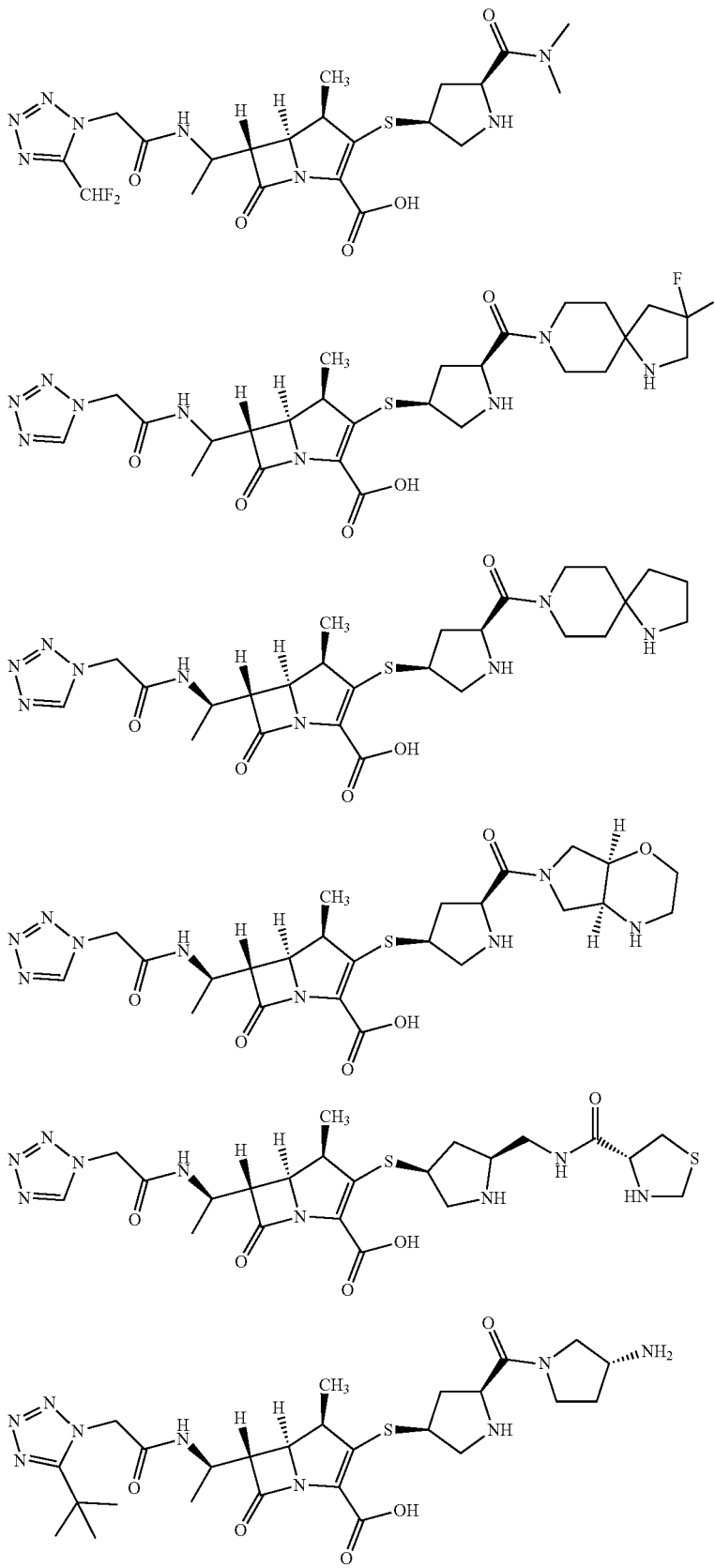

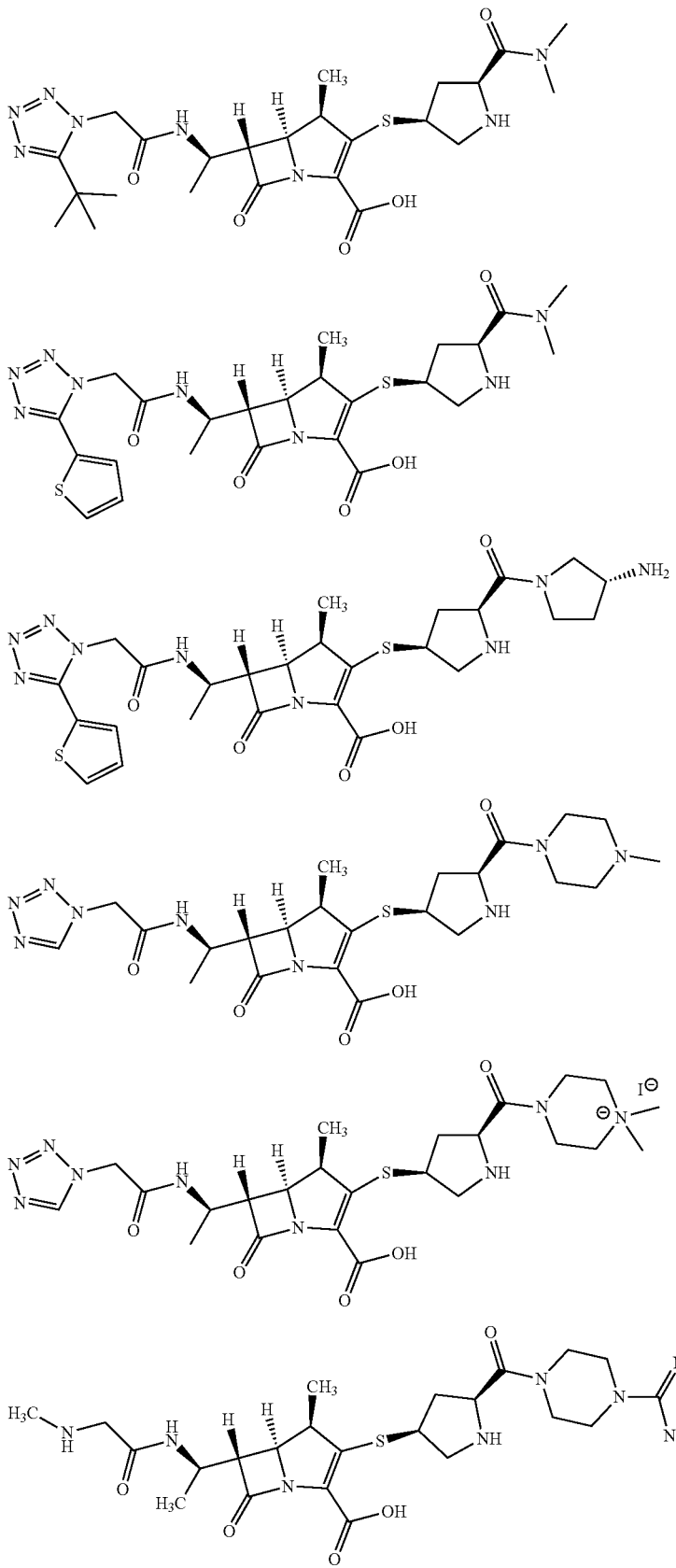

-continued
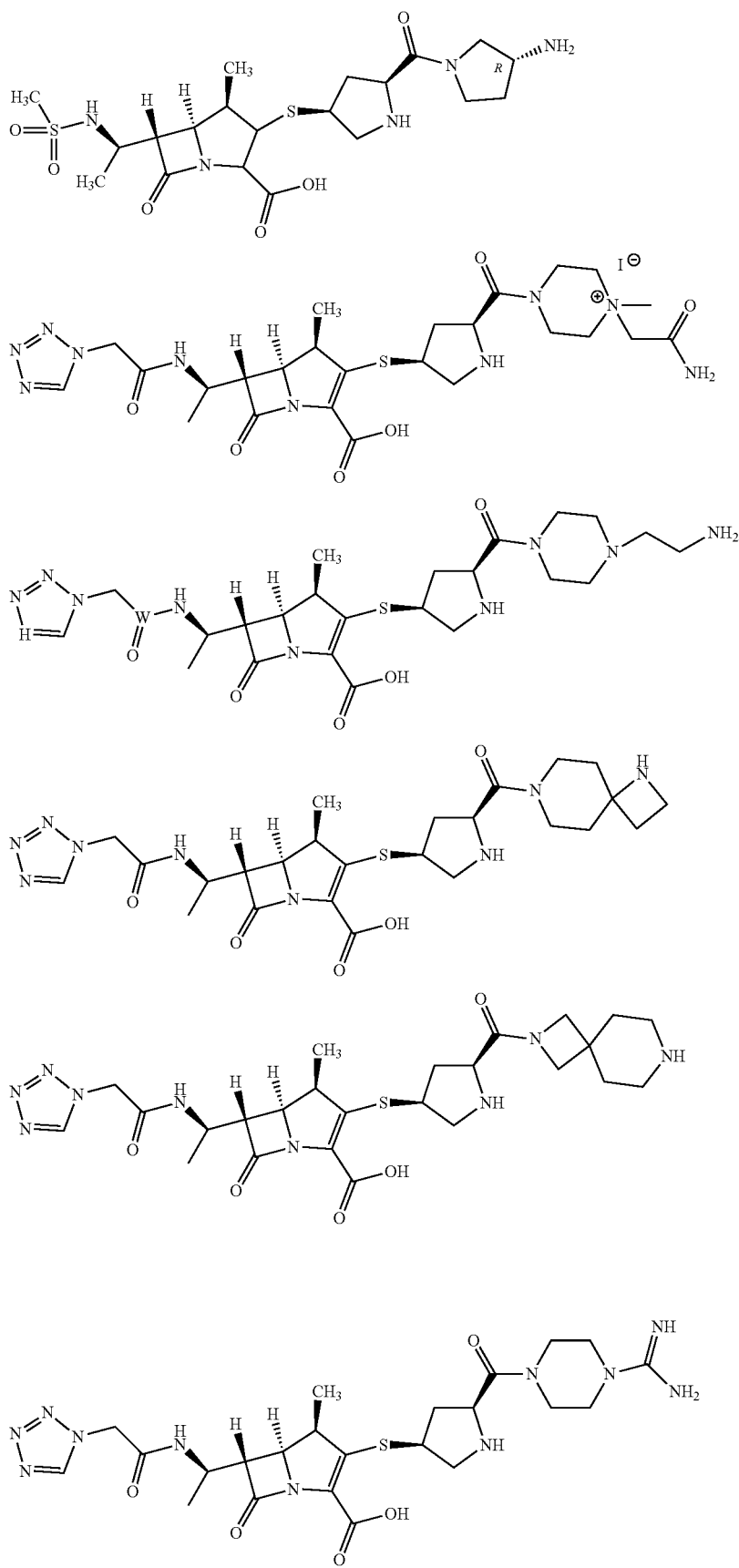

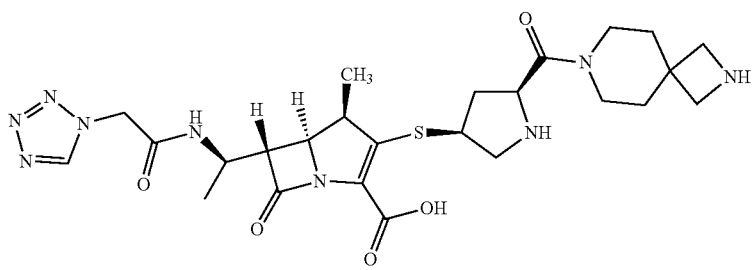
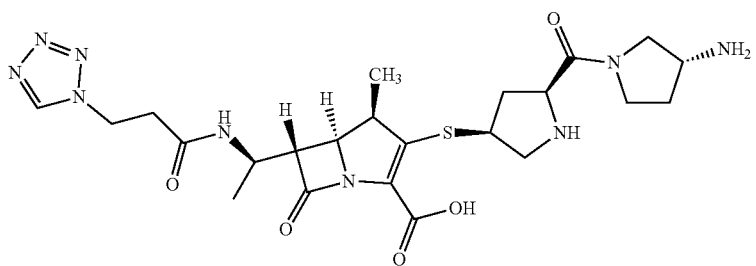
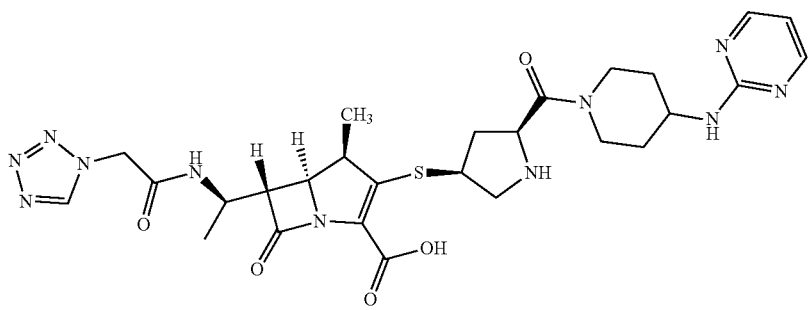
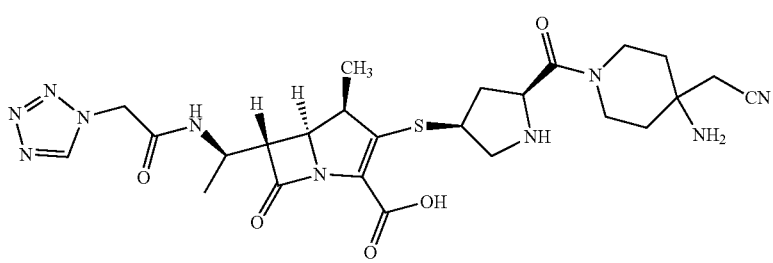
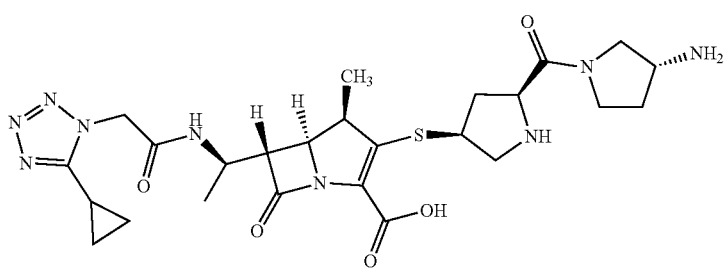
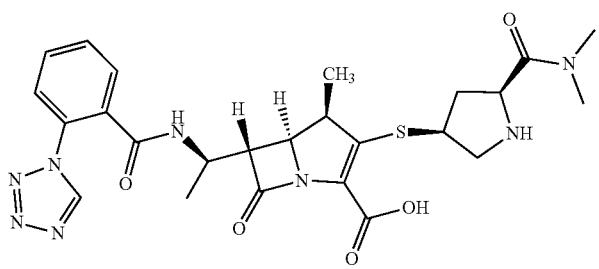

-continued
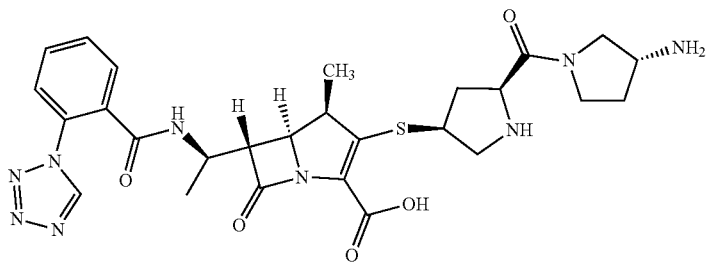
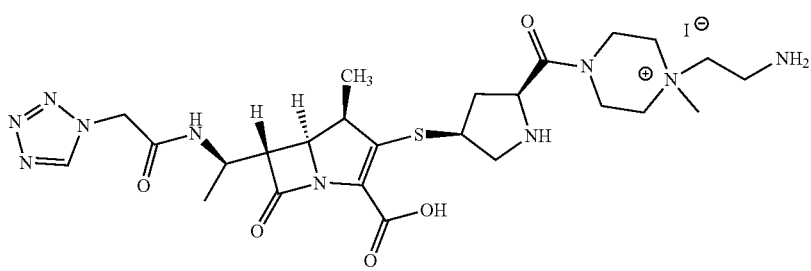
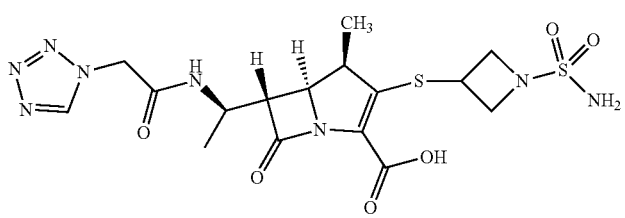
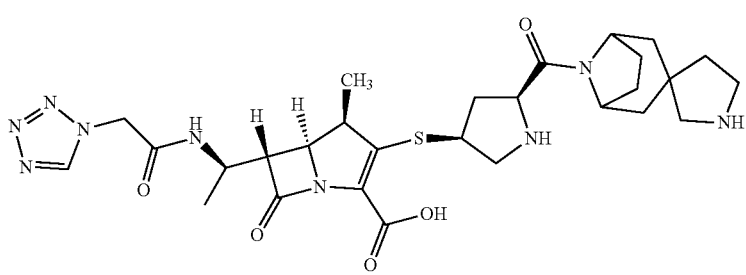
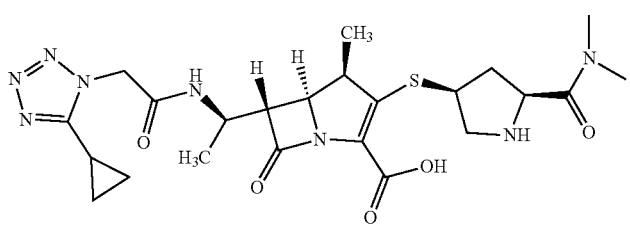
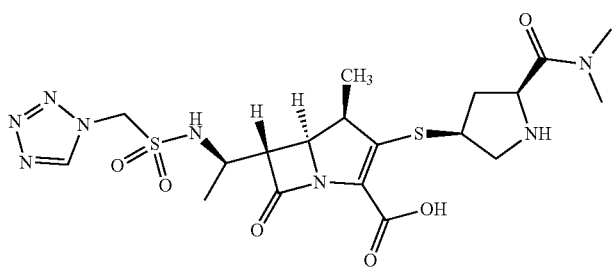

-continued
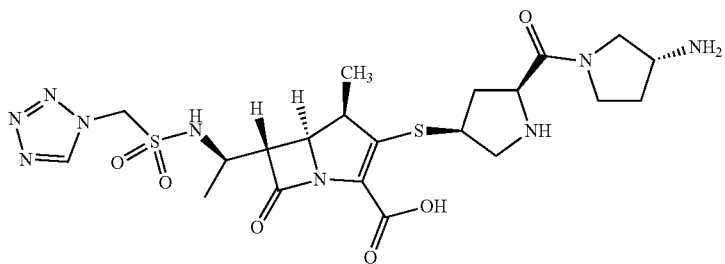
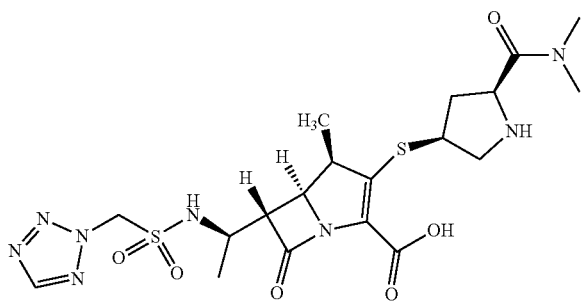
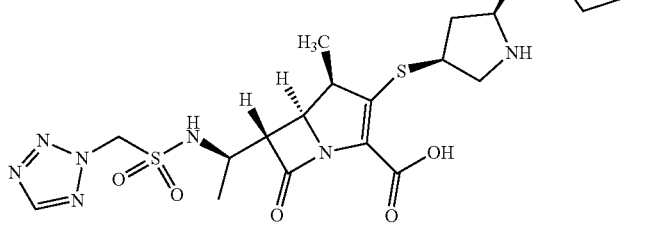
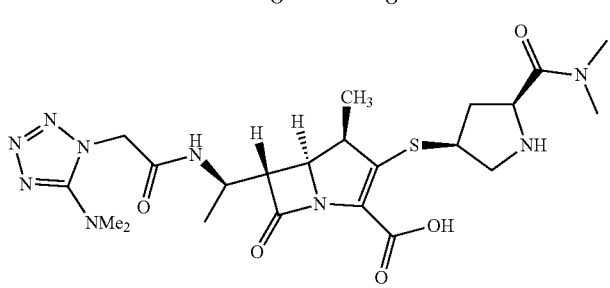
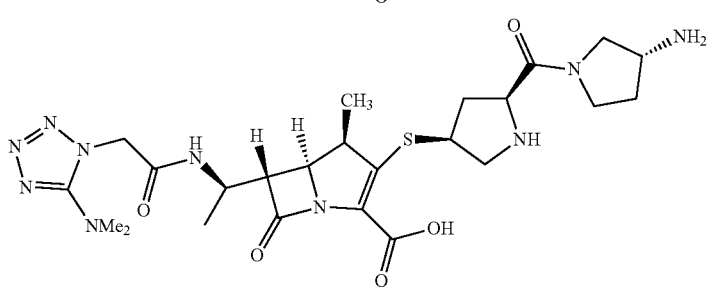
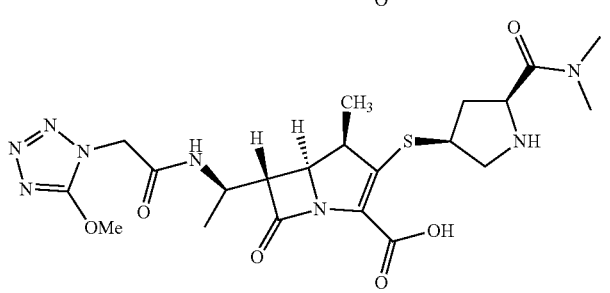

-continued
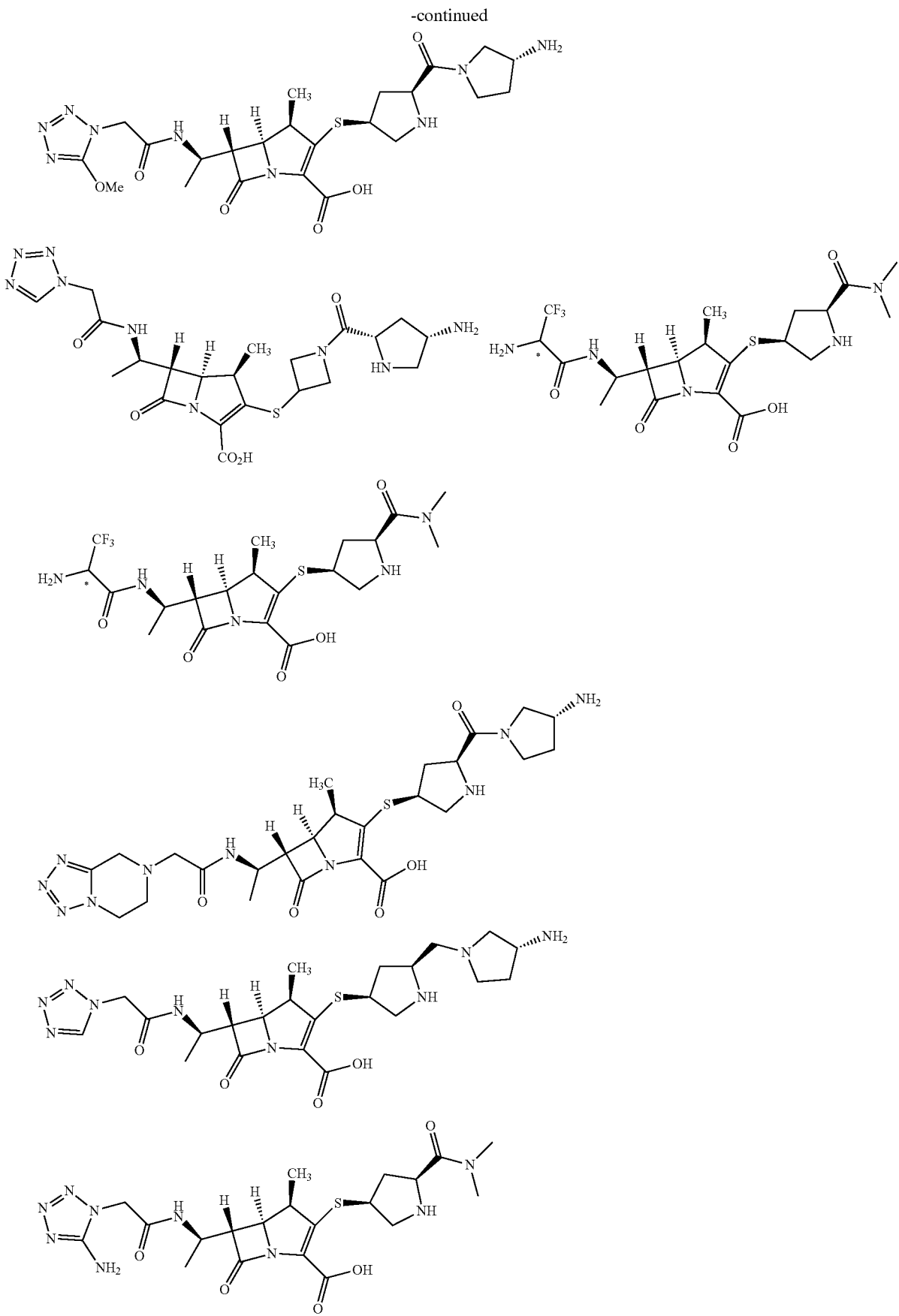

-continued
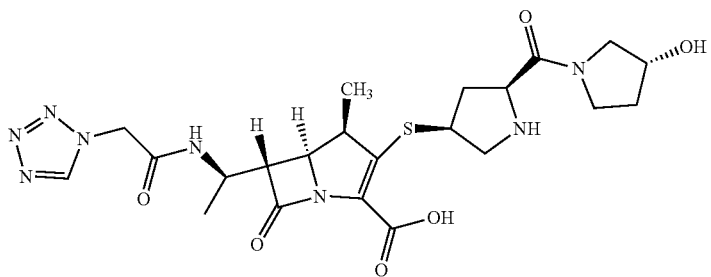
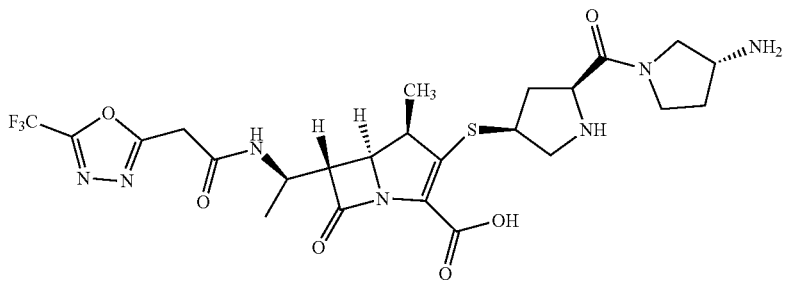
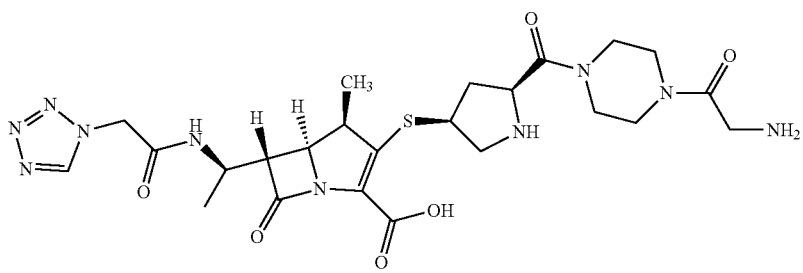
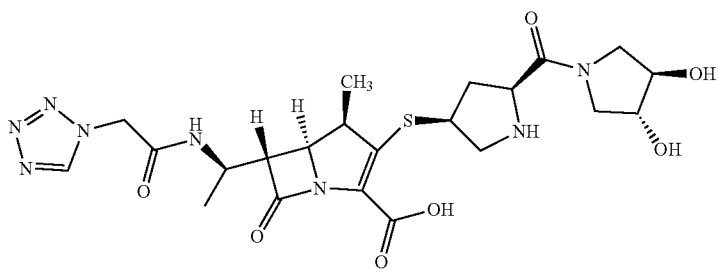
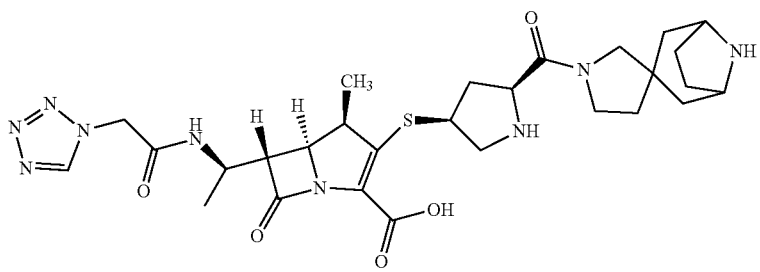
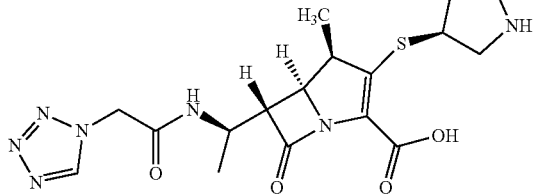

-continued
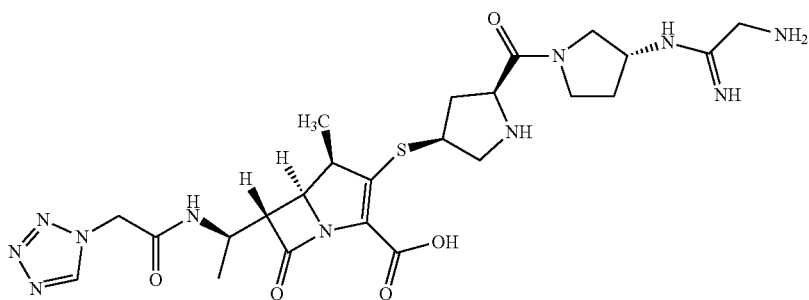
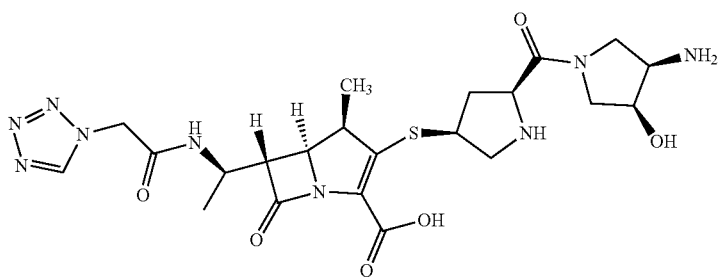
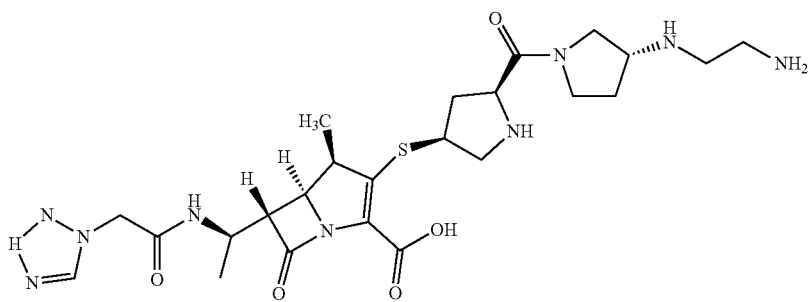
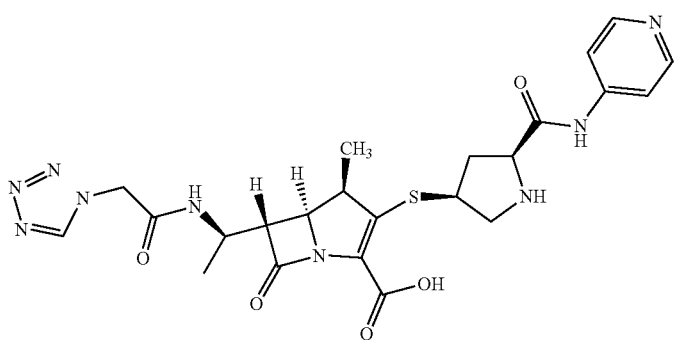
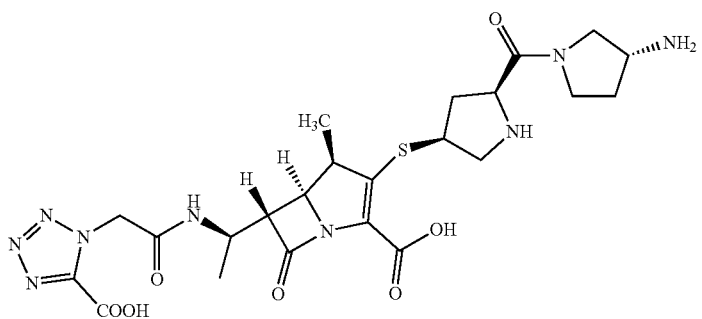

-continued
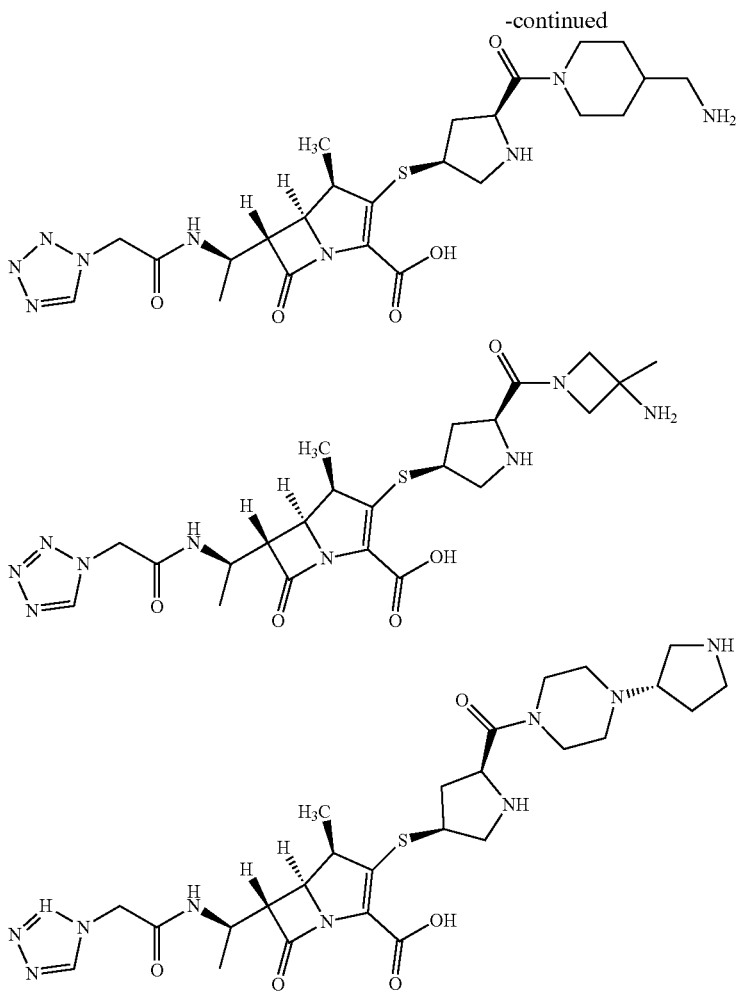
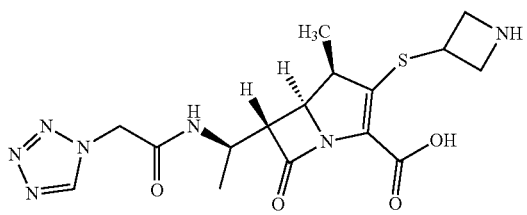
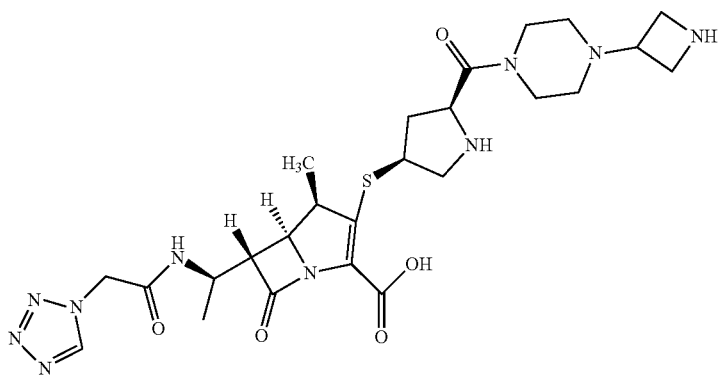

-continued
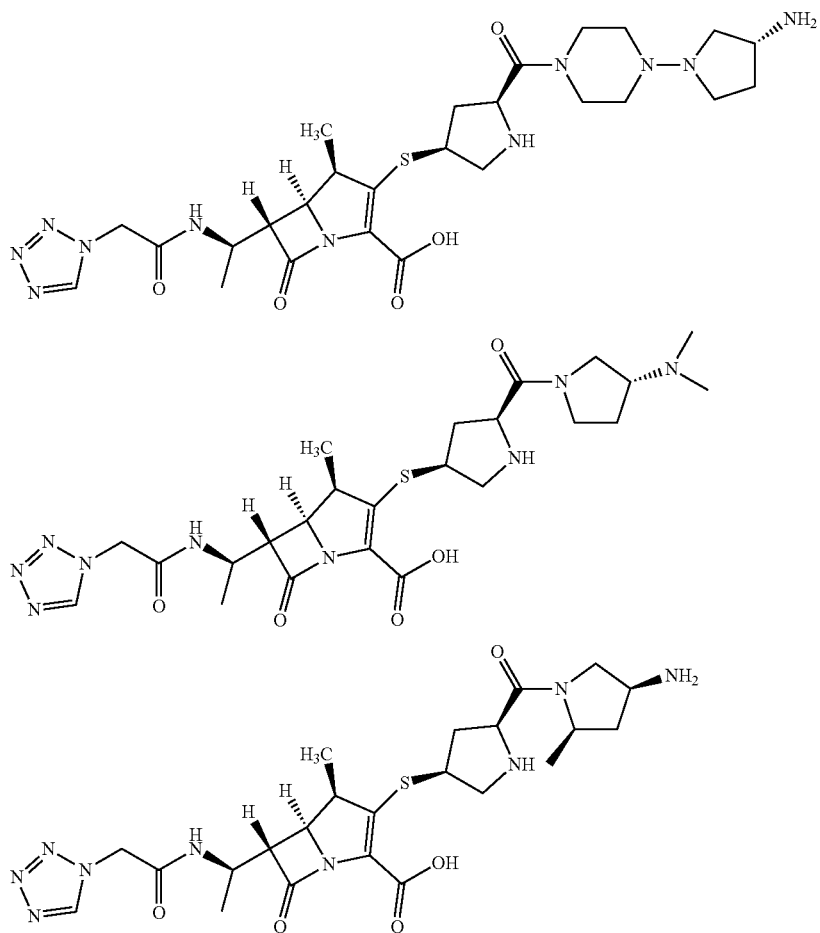
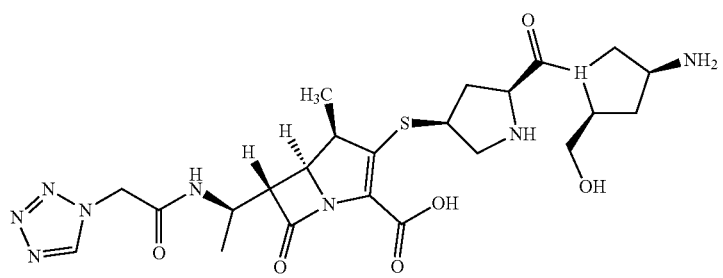
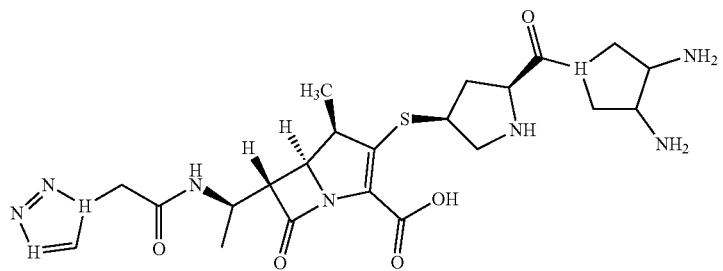

-continued
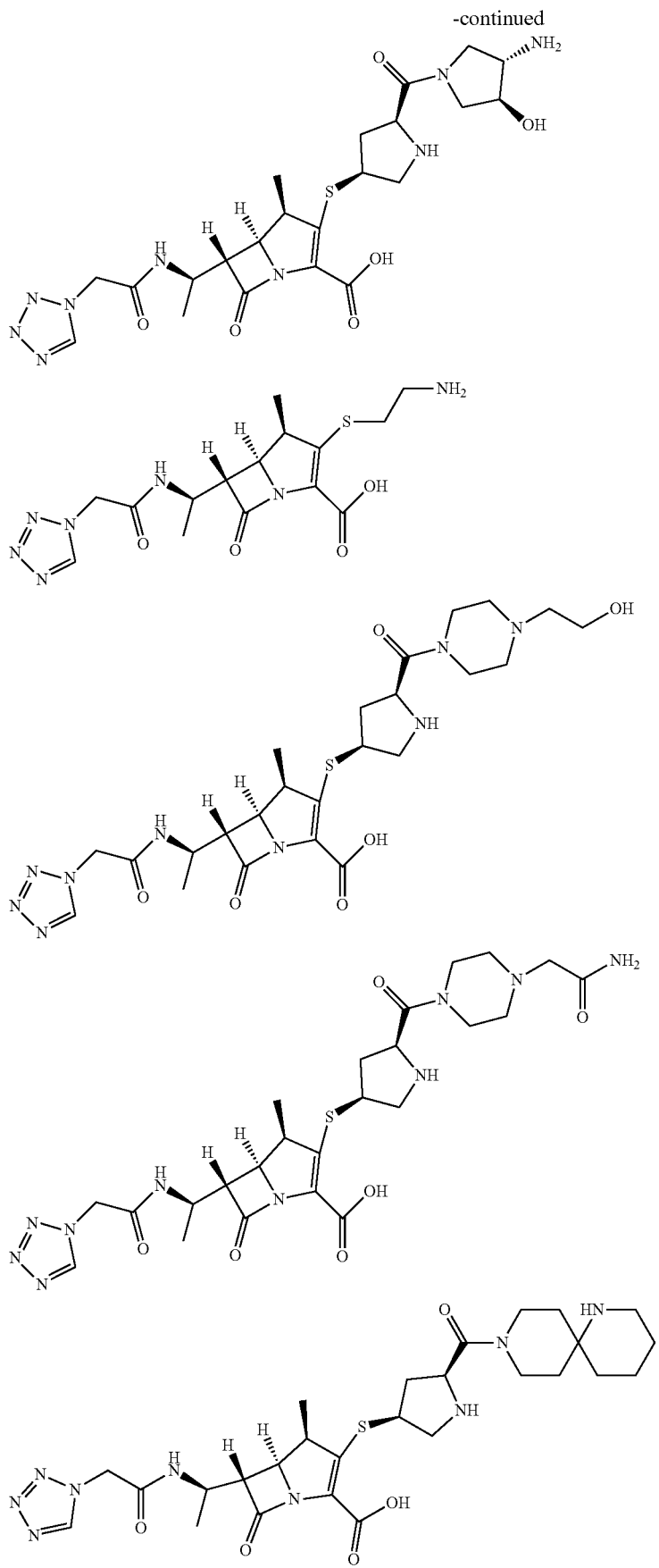

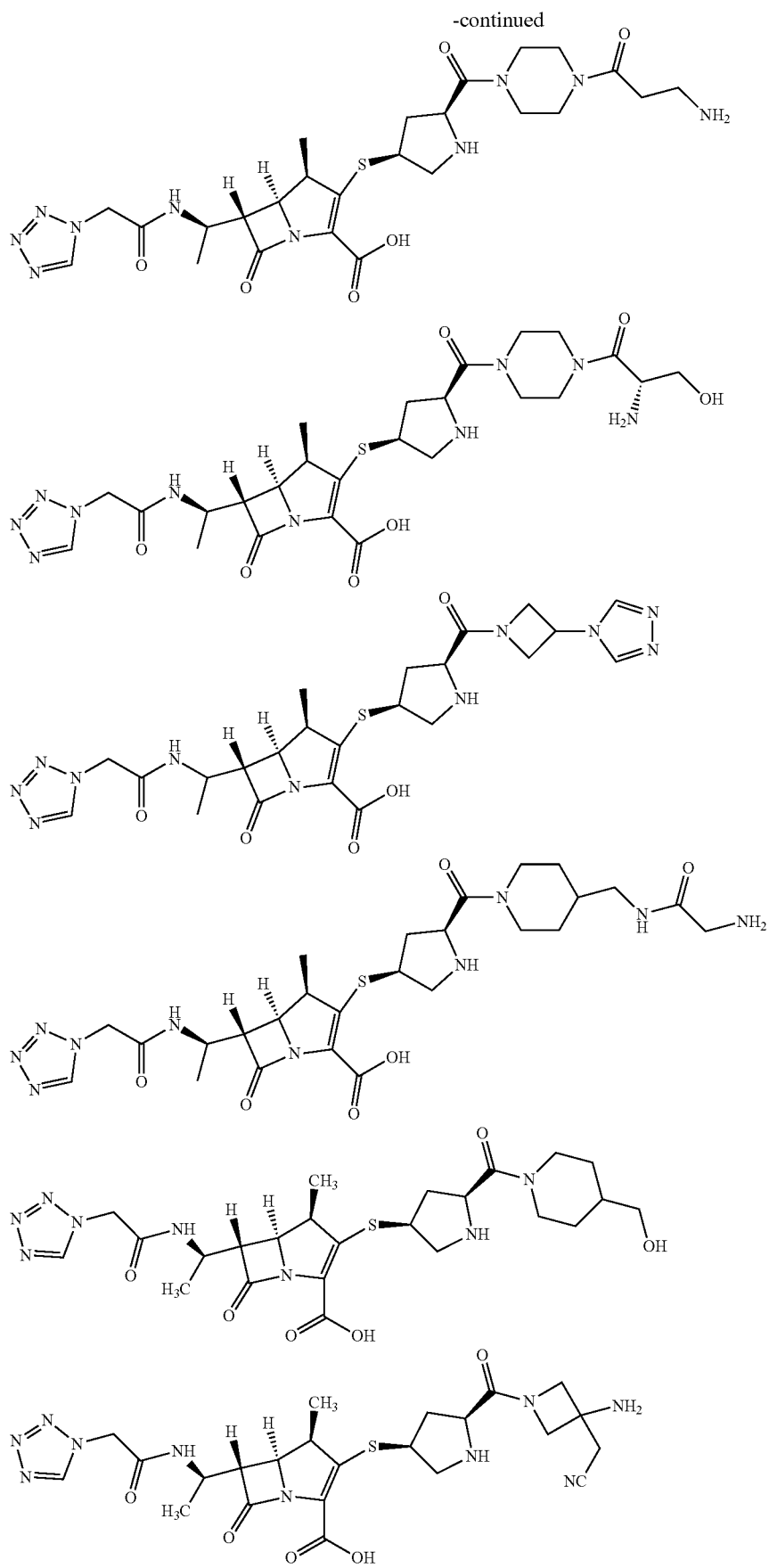

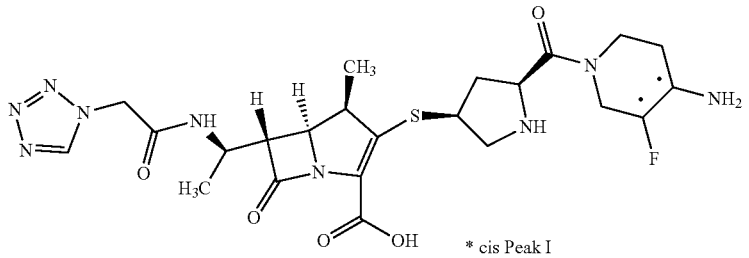
\* cis Peak I
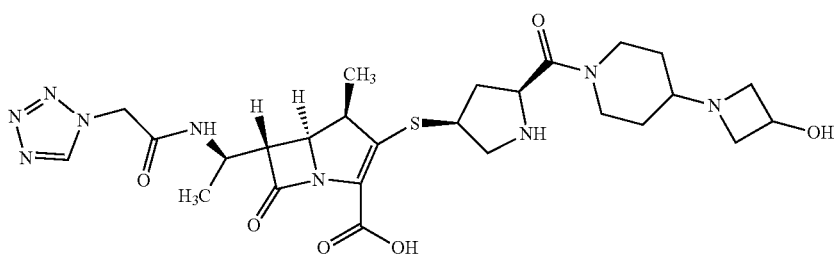
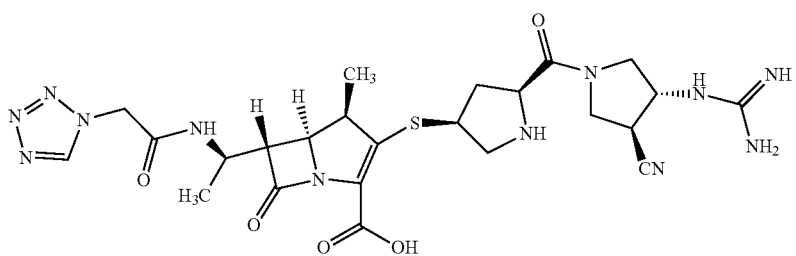
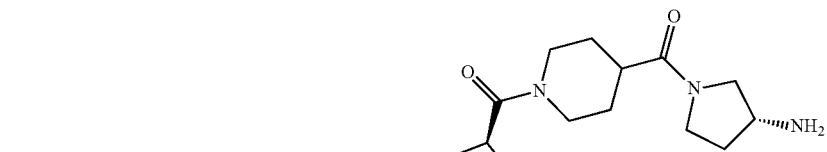
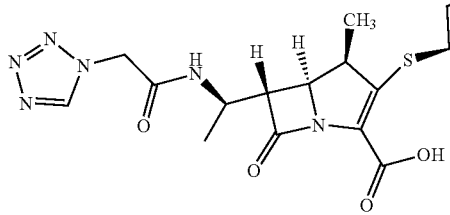
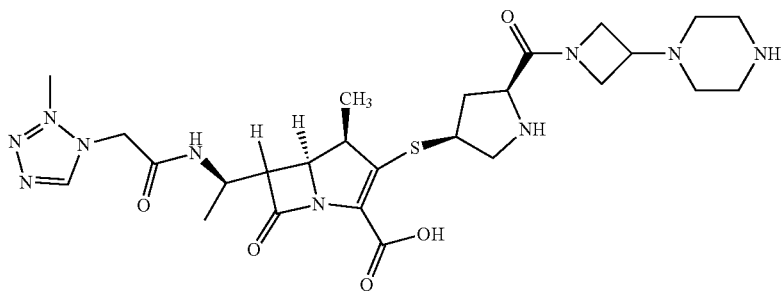
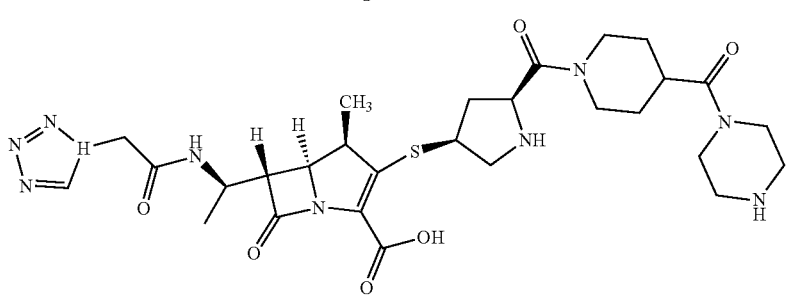

-continued
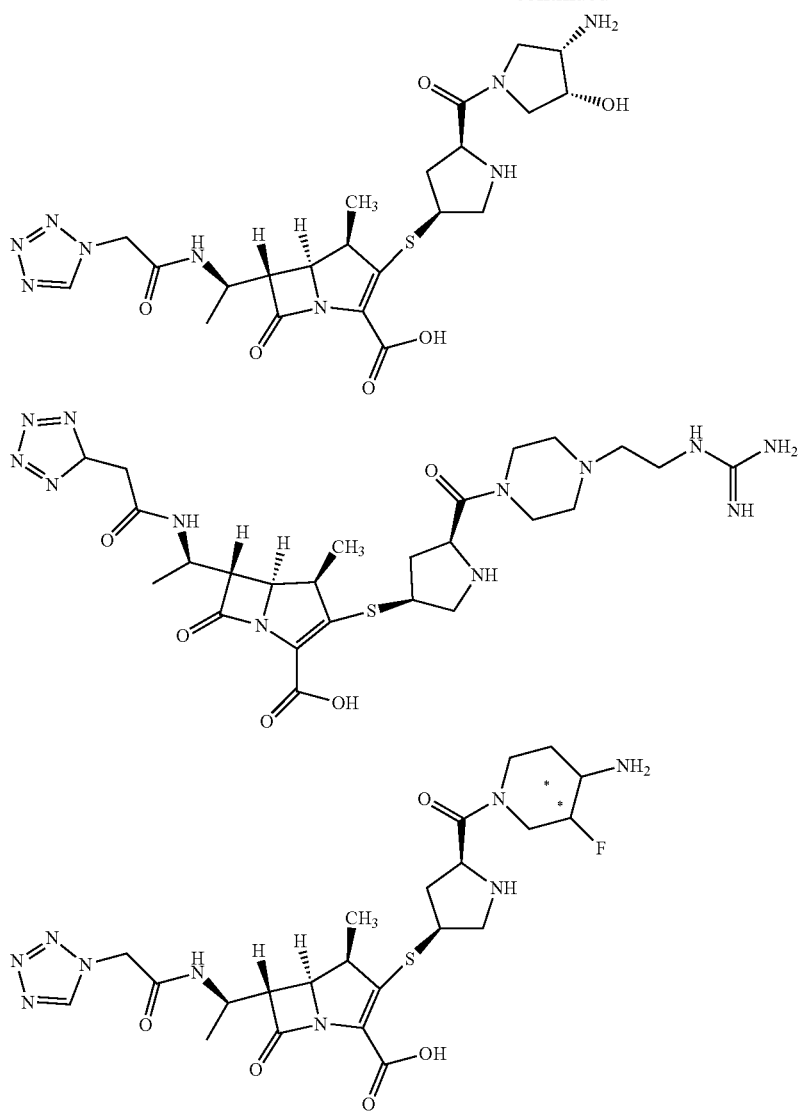
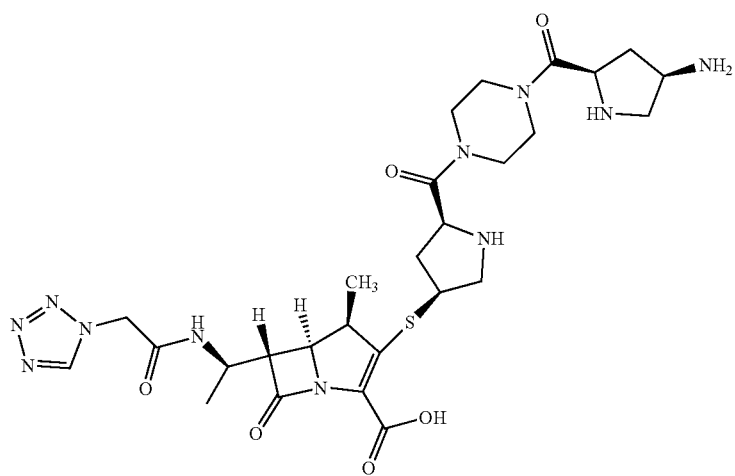

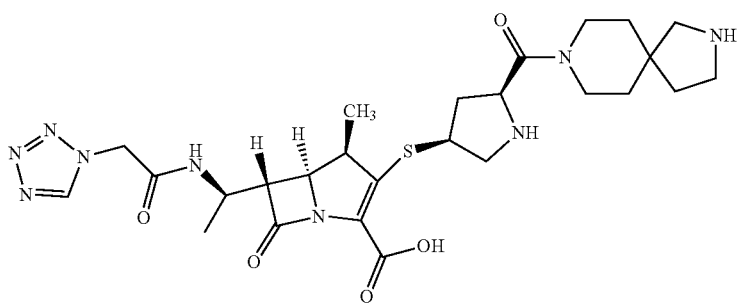
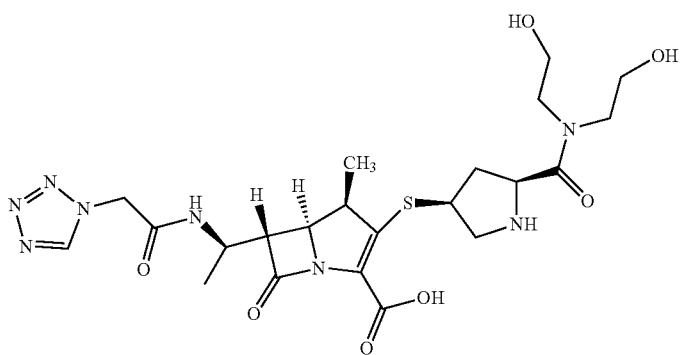
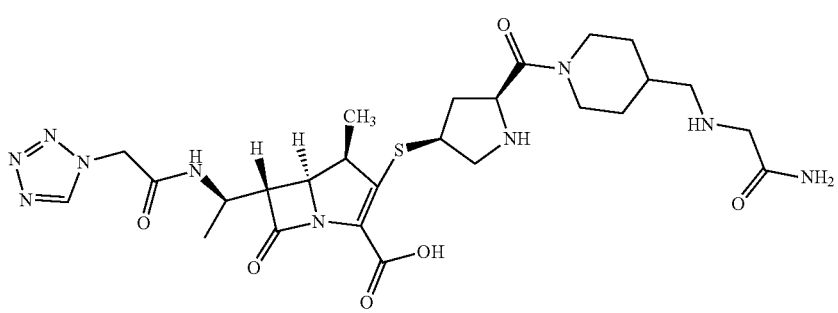
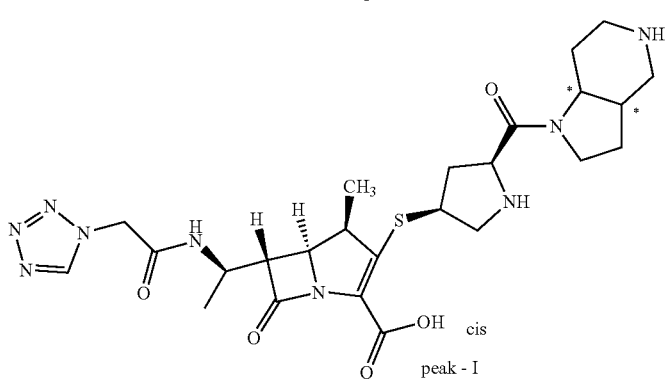
cis
peak - I
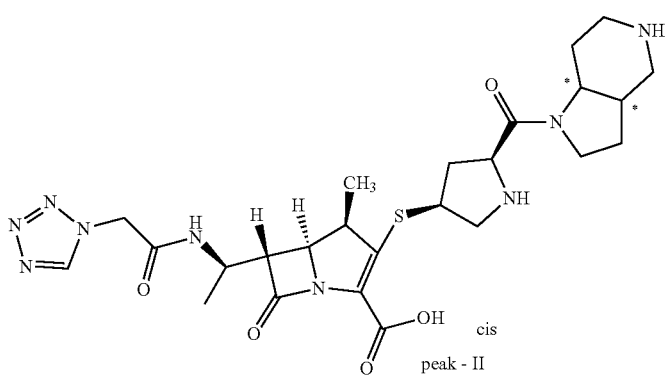
cis
peak - II -continued
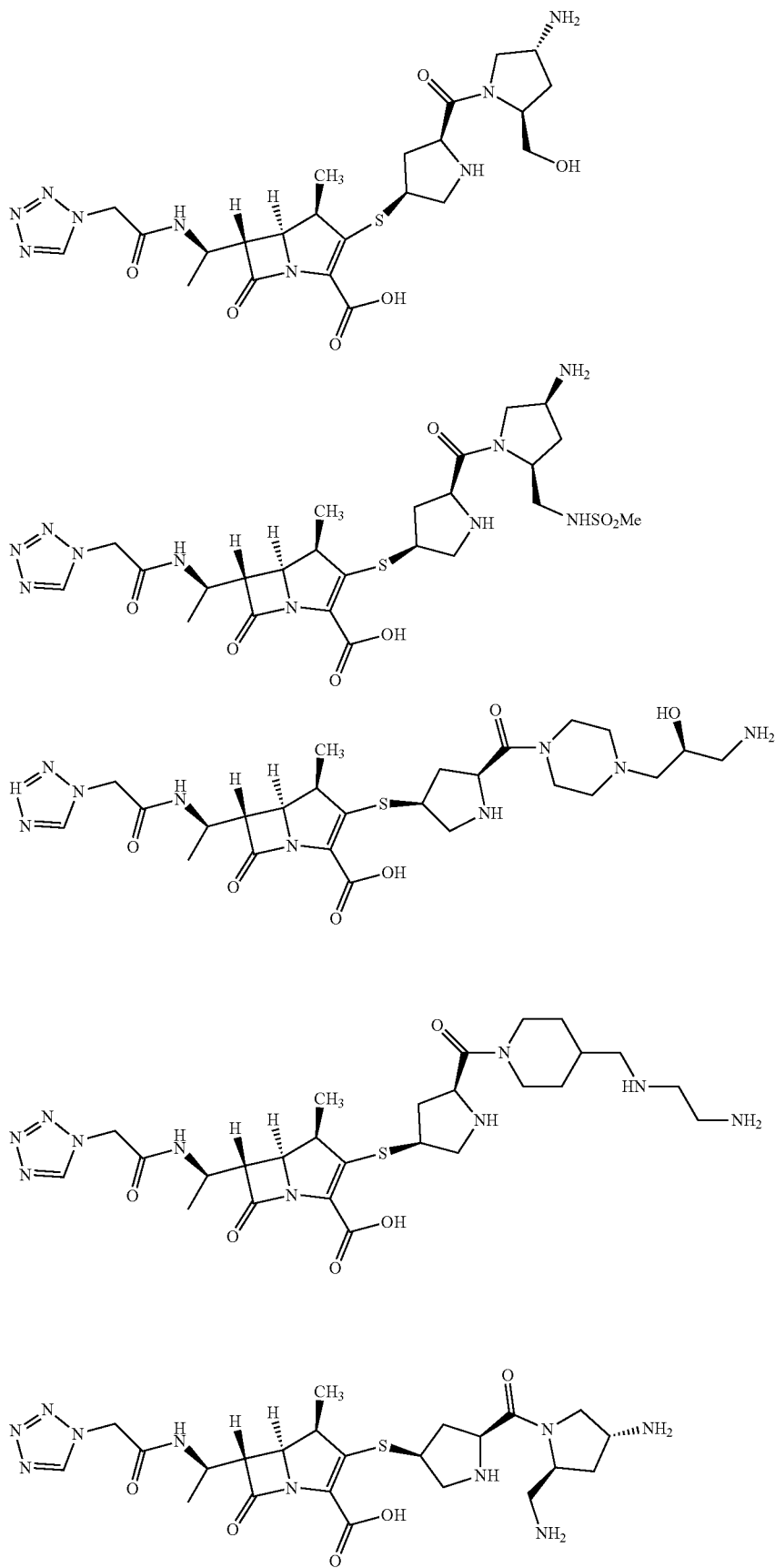

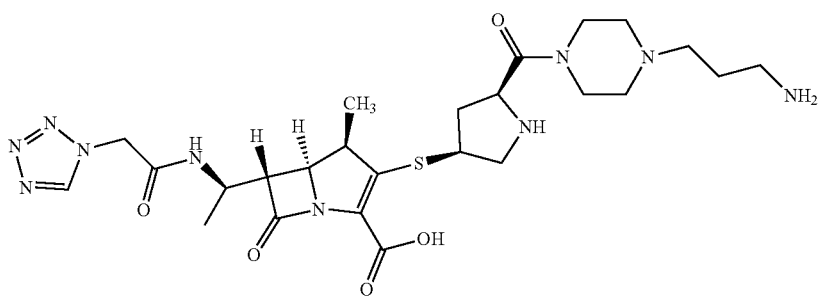
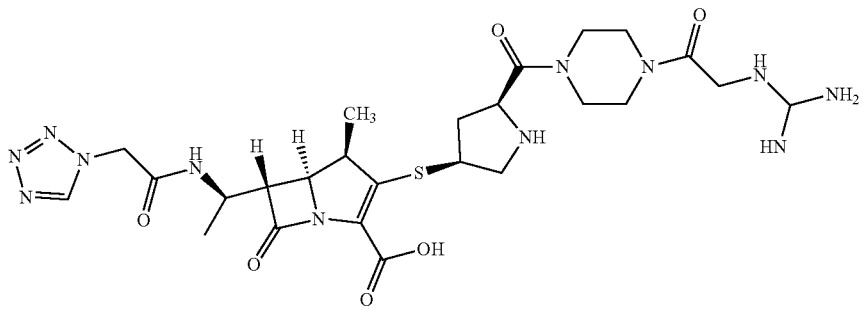
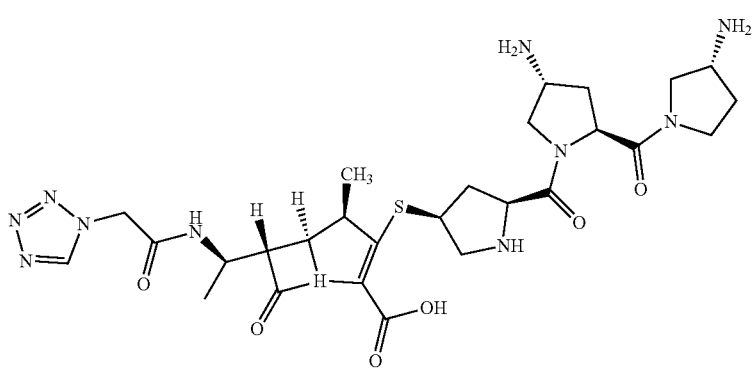
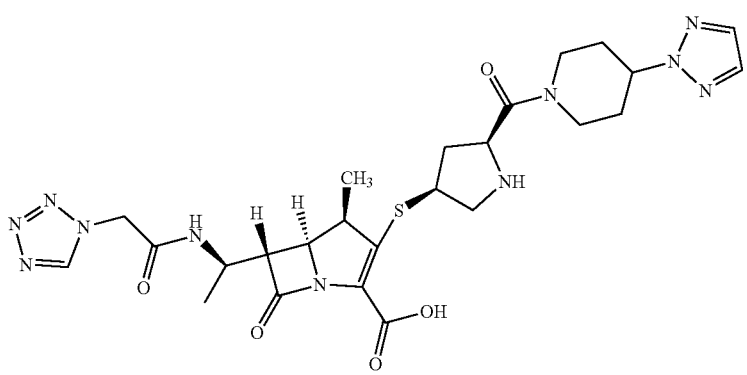
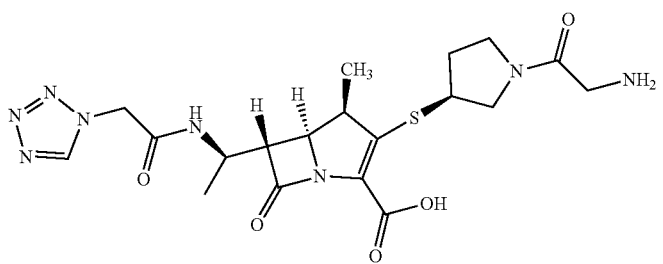

-continued
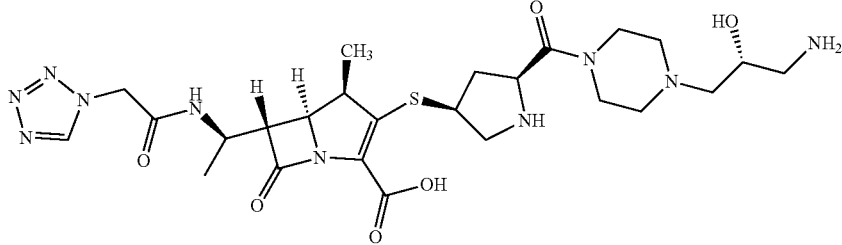
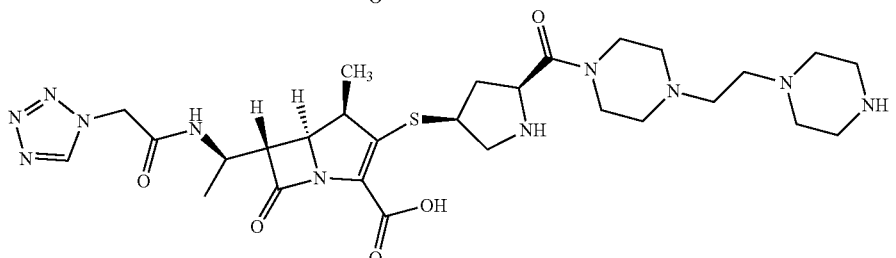
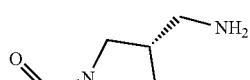
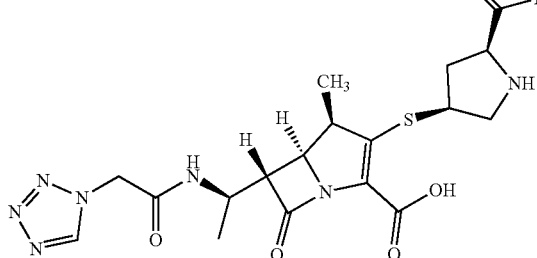
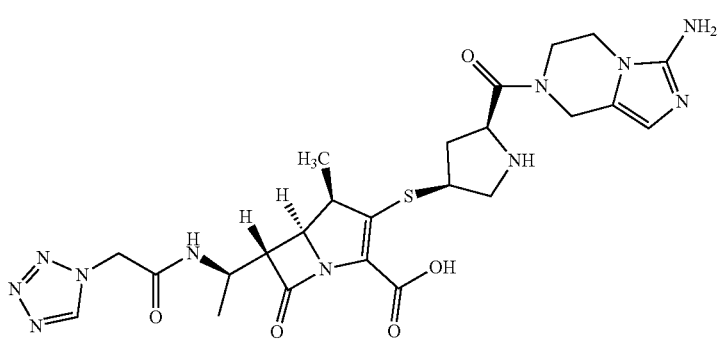
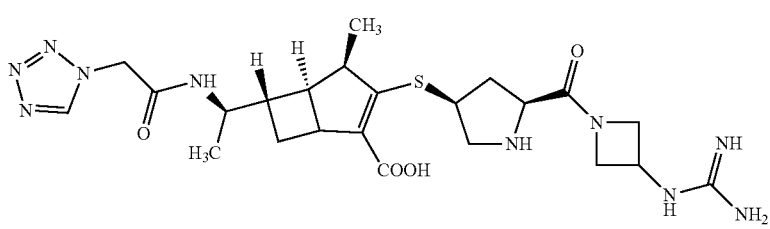
or a pharmaceutically acceptable salt, internal salt, or N-oxide thereof.

27. A compound, or a stereoisomer thereof, wherein the compound, or stereoisomer thereof, is selected from the group consisting of:
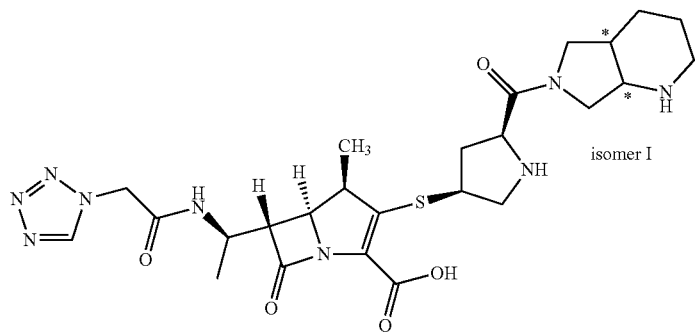
isomer I
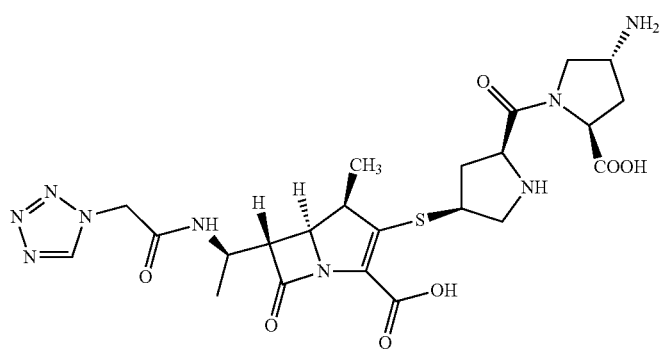
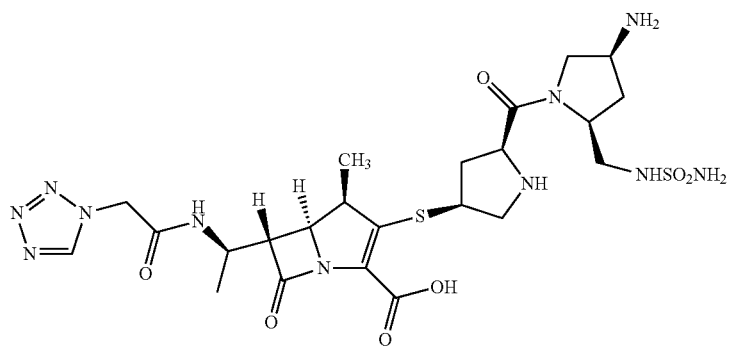
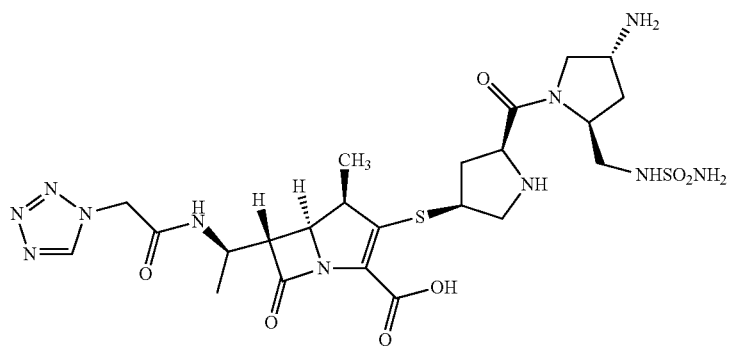

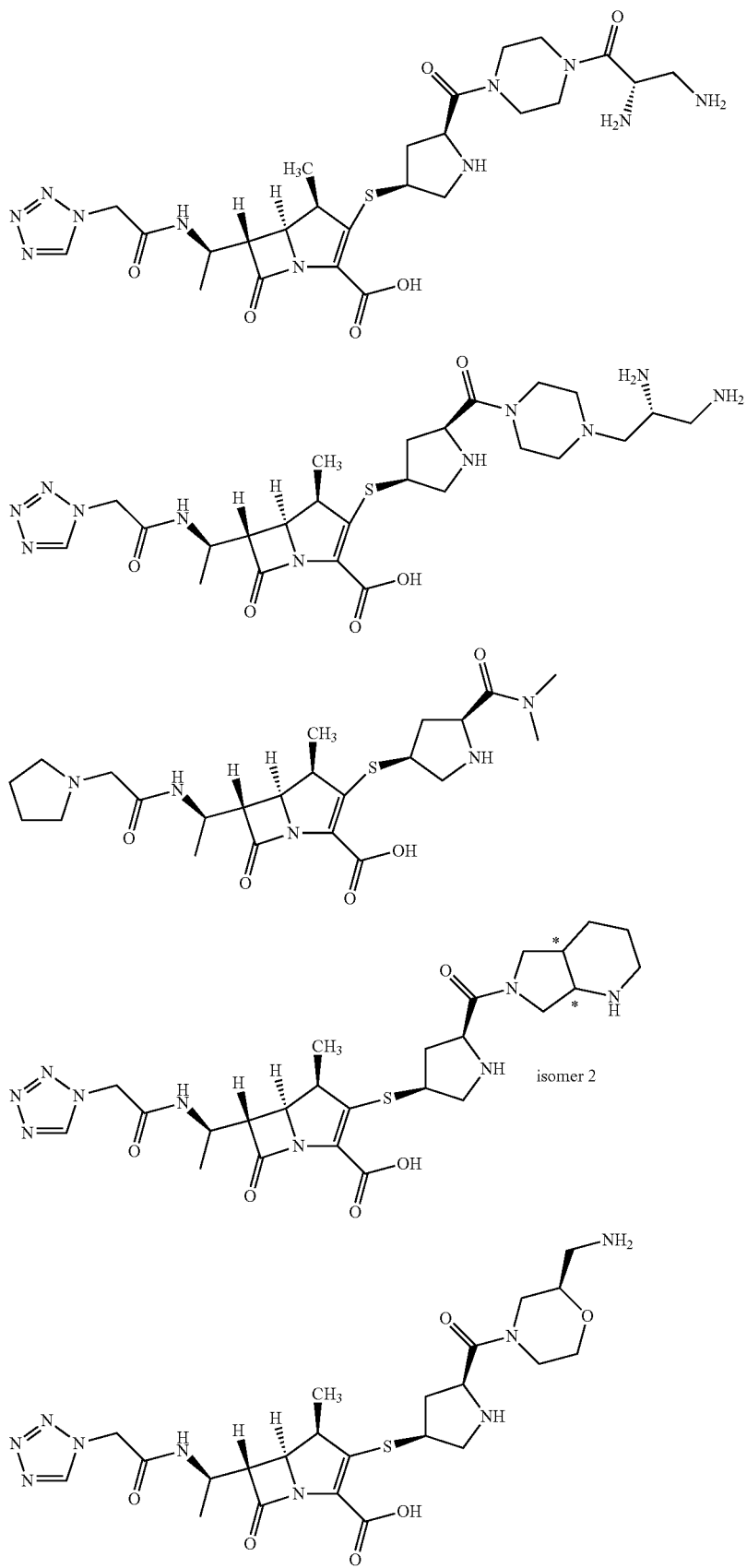

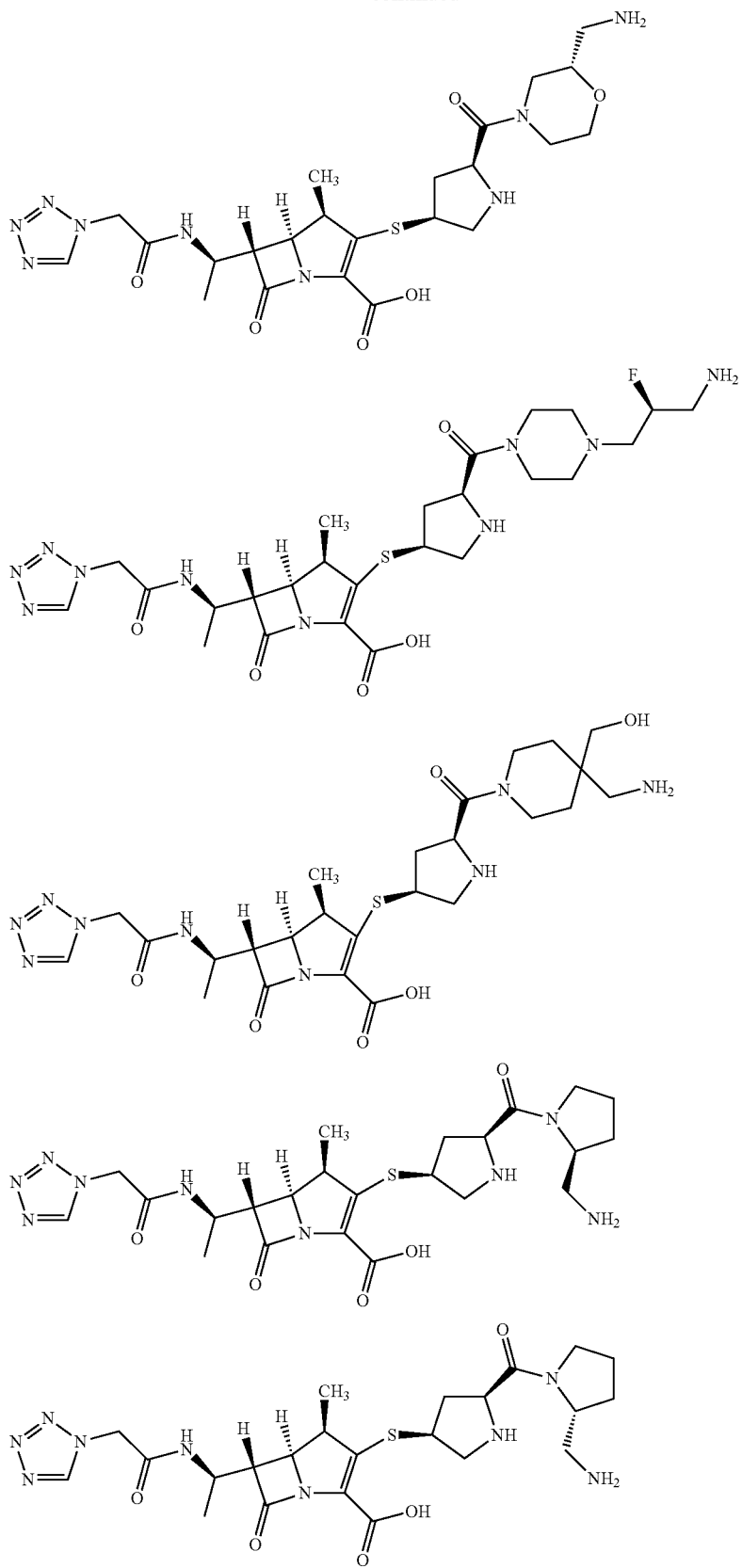

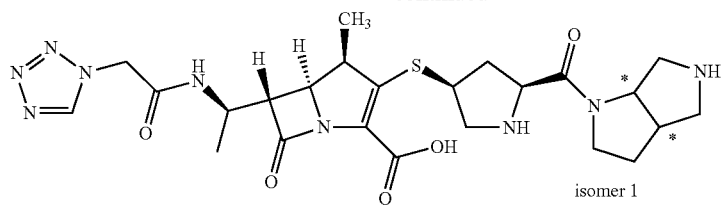
isomer 1
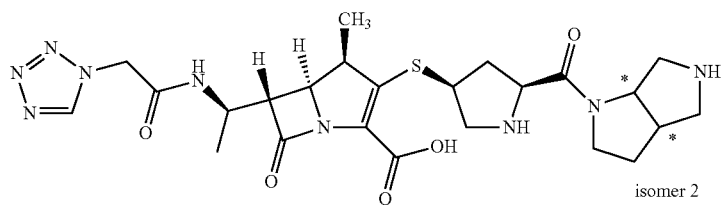
isomer 2
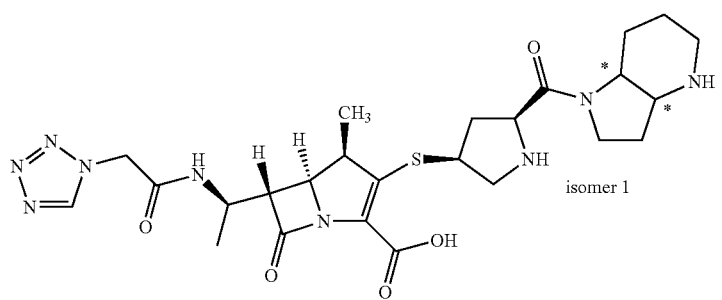
isomer 1
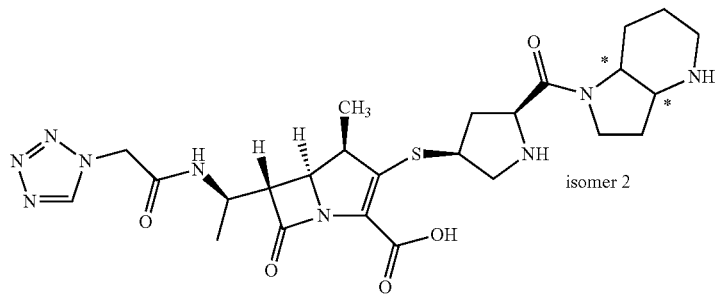
isomer 2
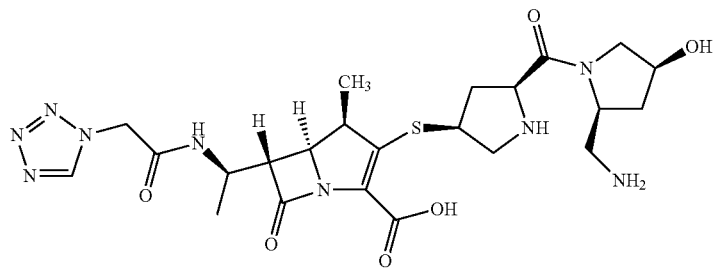
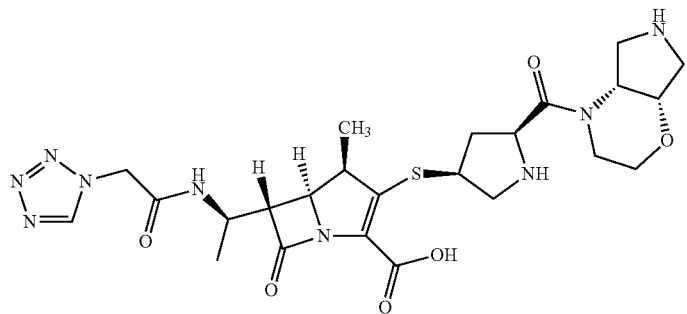

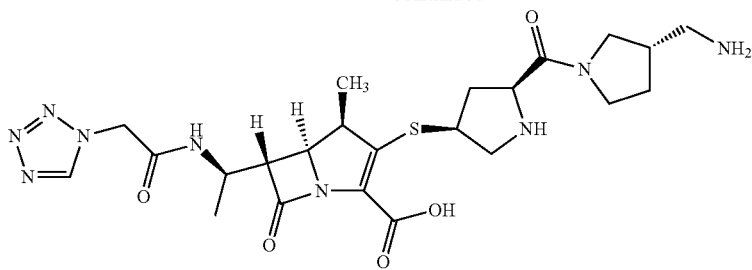
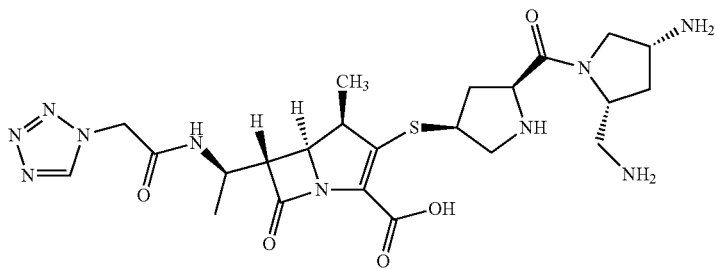
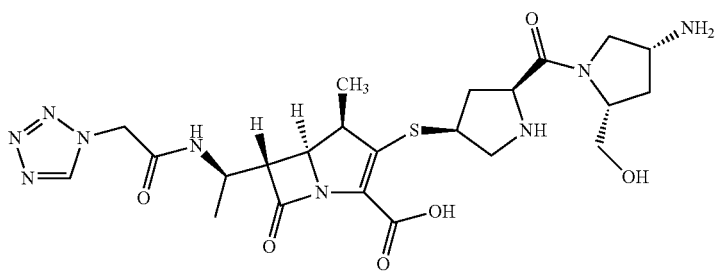
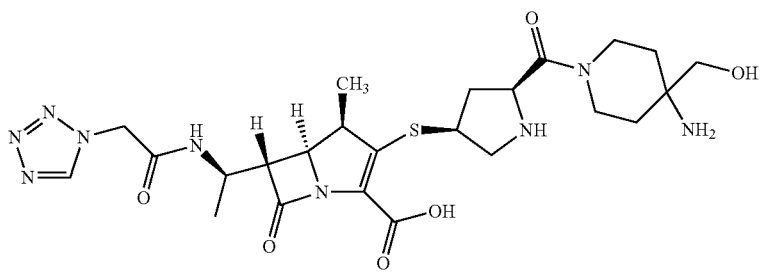
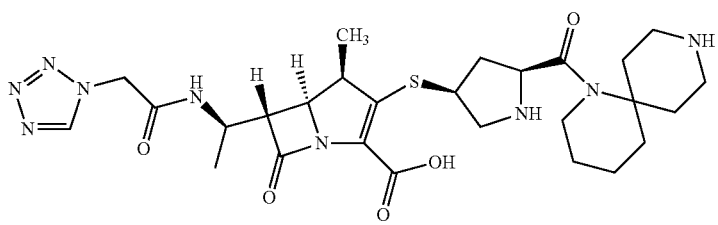
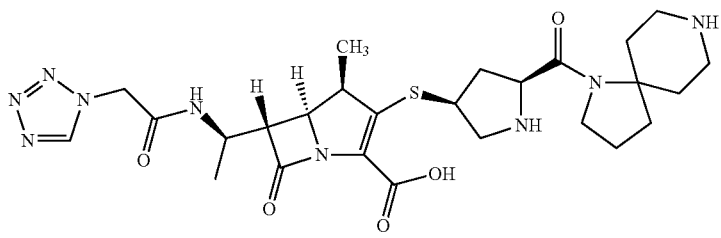

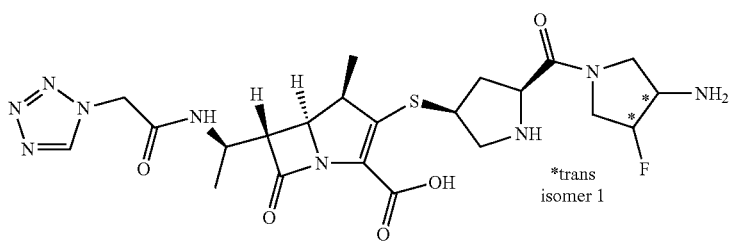
*trans isomer 1
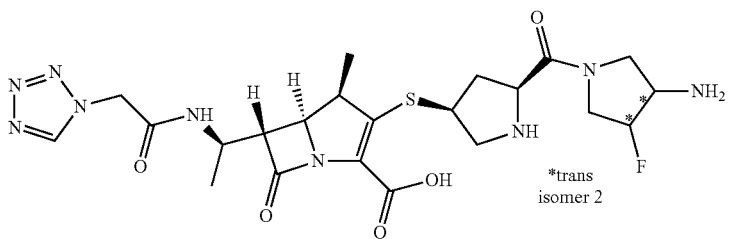
*trans isomer 2
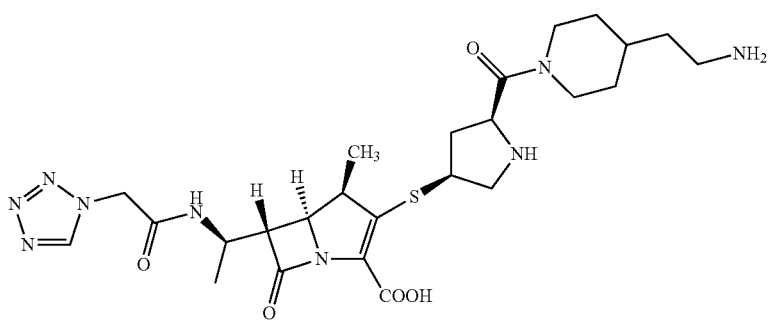
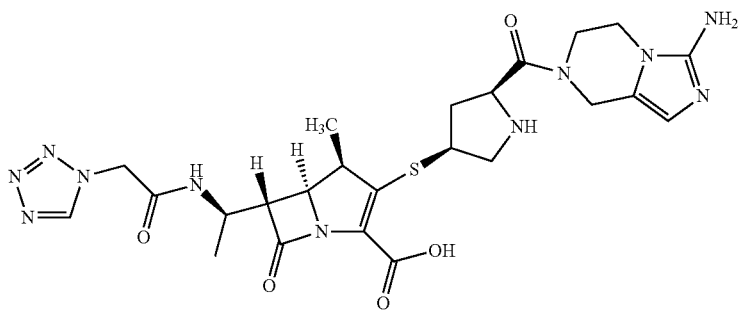
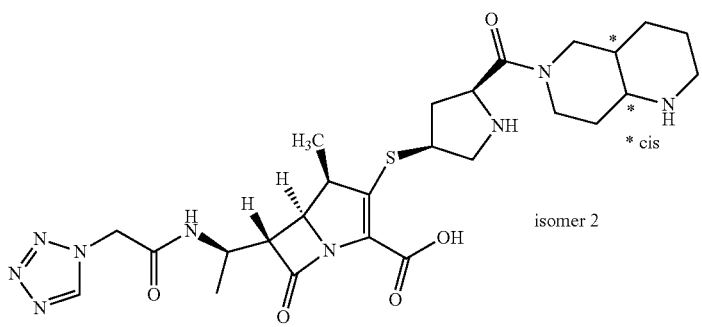
*cis isomer 2

-continued
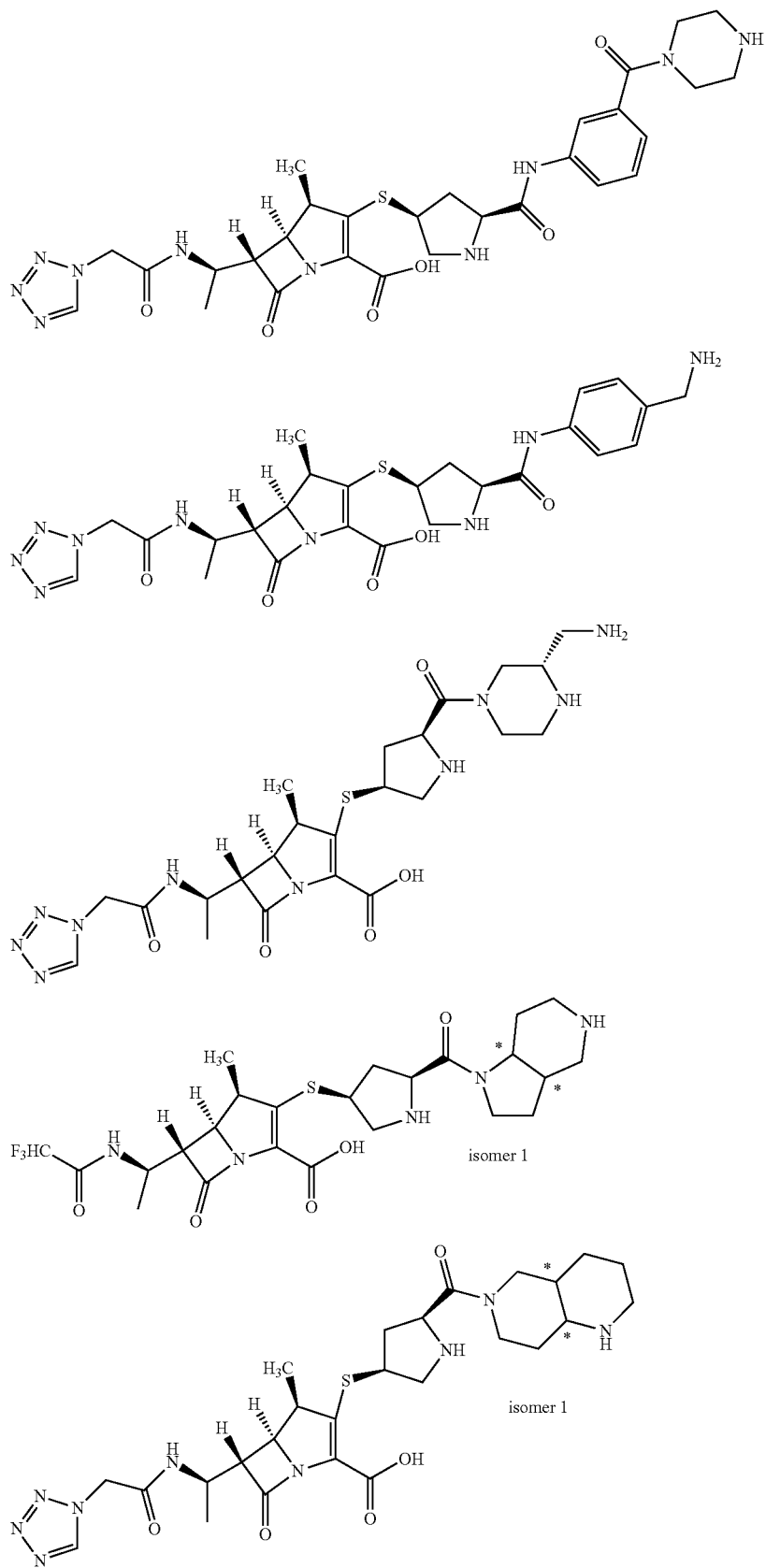

-continued
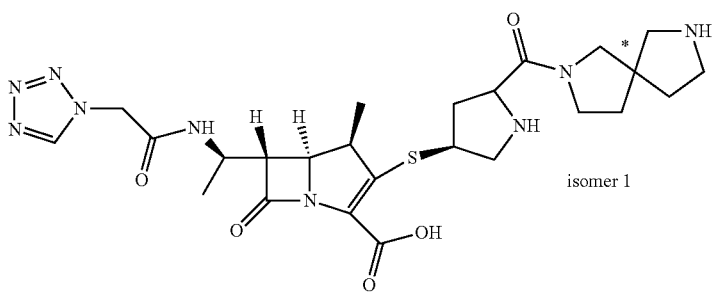
isomer 1
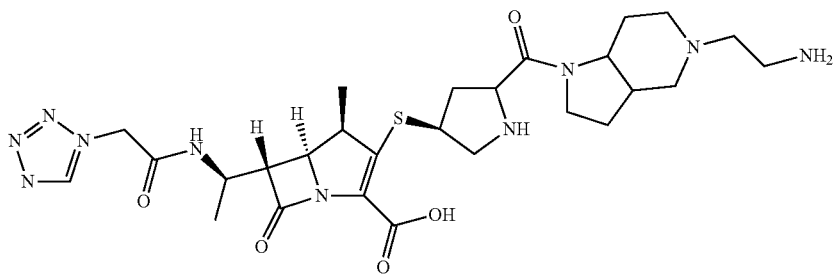
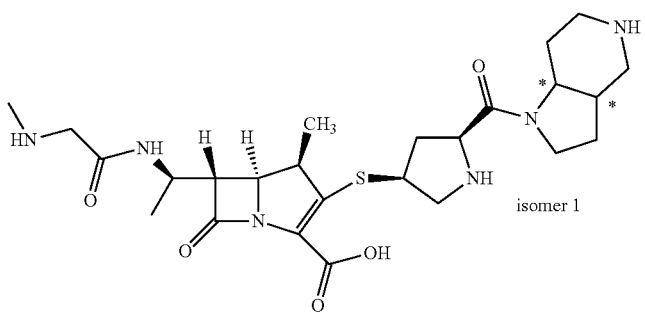
isomer 1
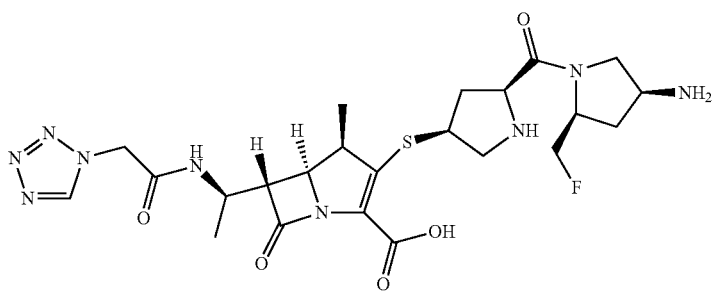
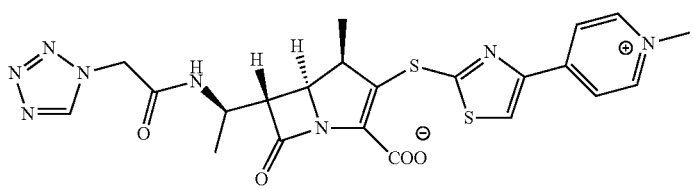
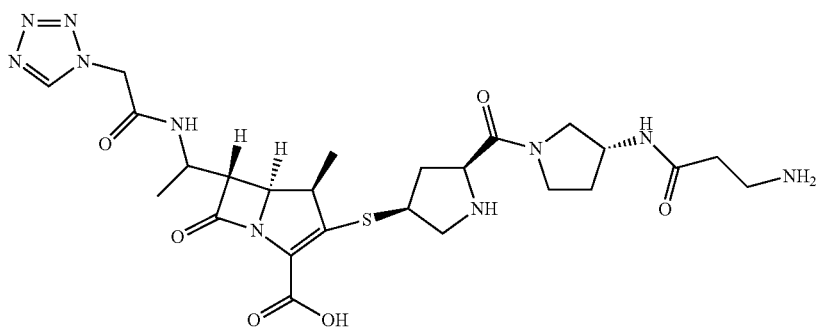

-continued
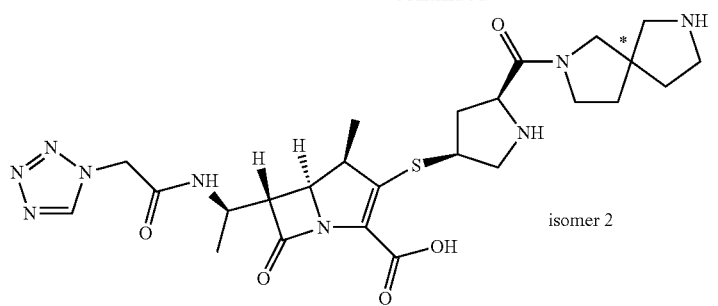
isomer 2
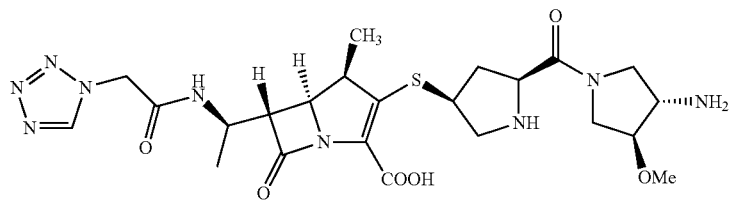
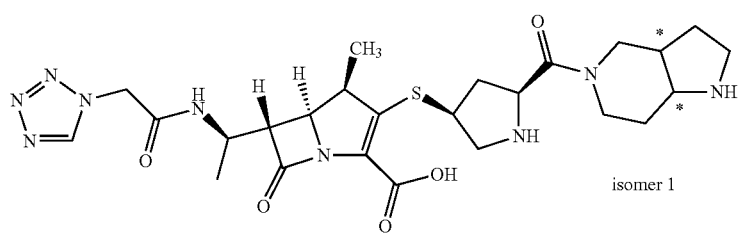
isomer 1
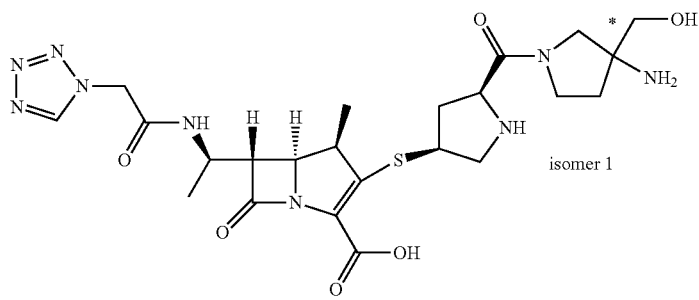
isomer 1
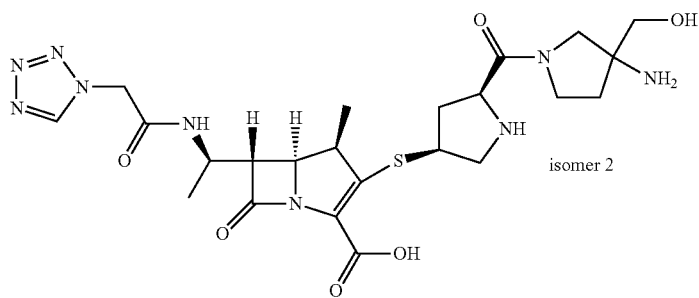
isomer 2
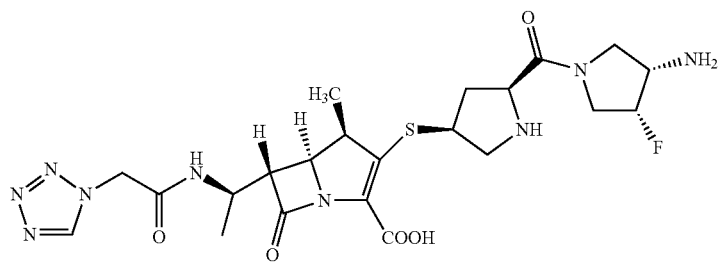

-continued
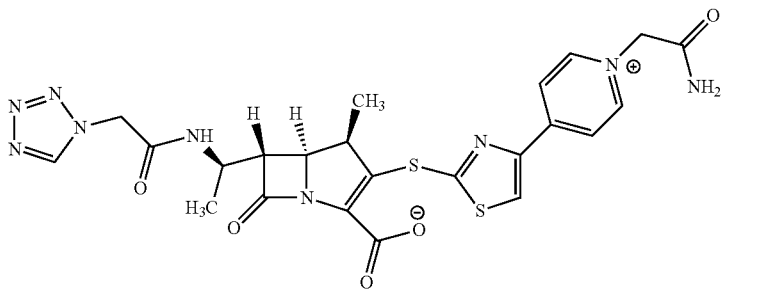
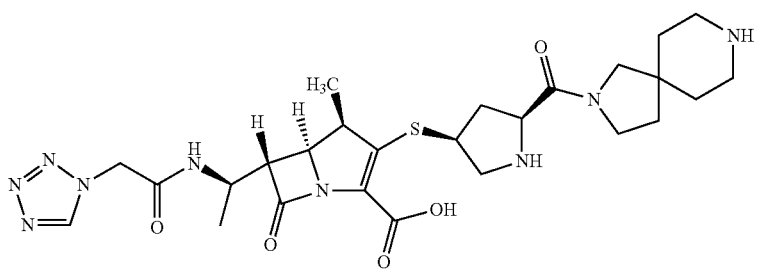
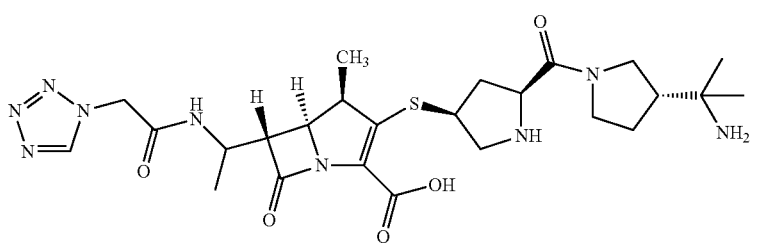
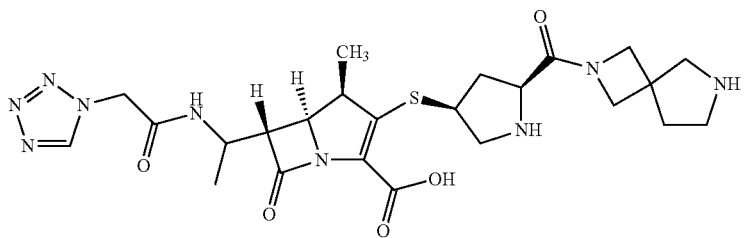
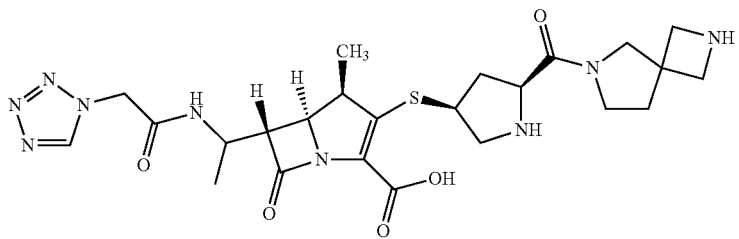
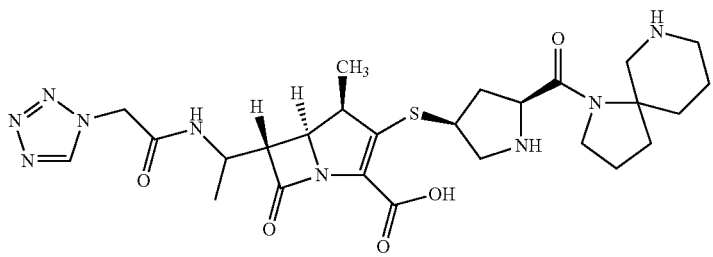

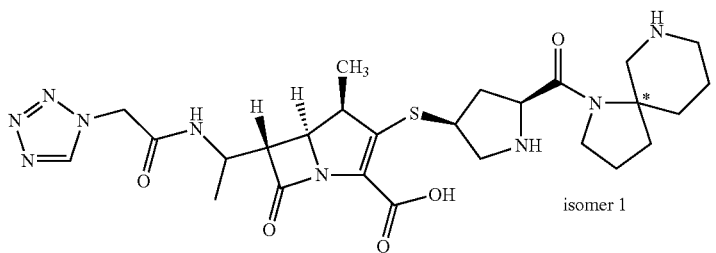
isomer 1
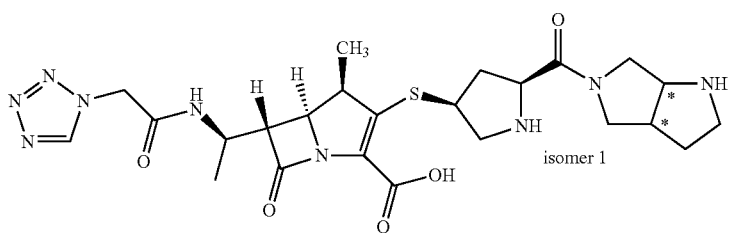
isomer 1
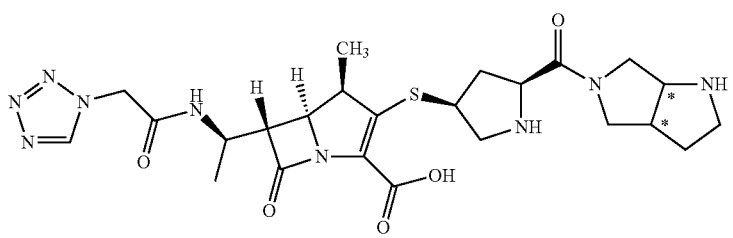
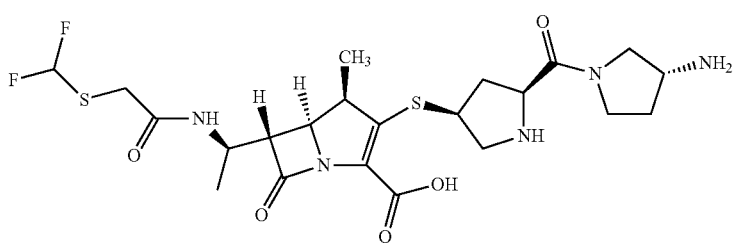
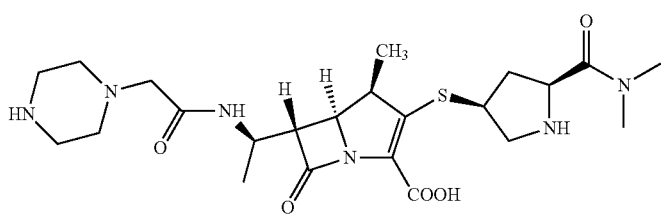
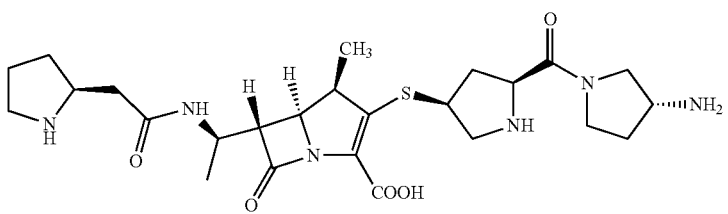
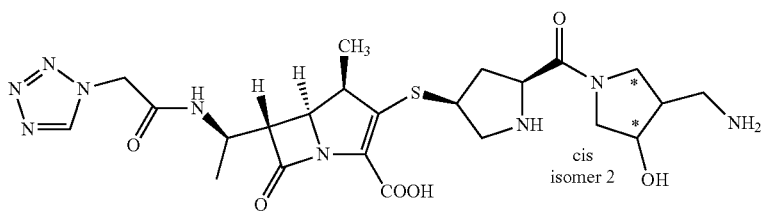
cis isomer 2

-continued
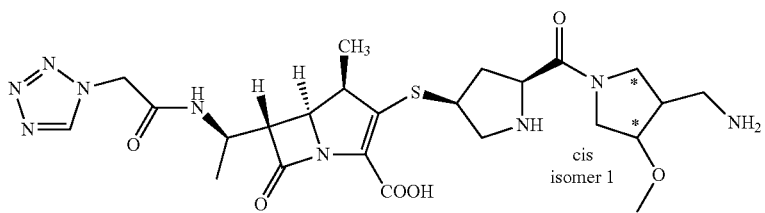
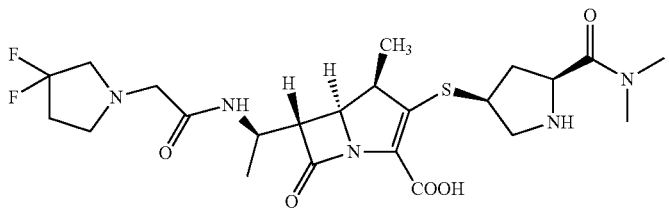
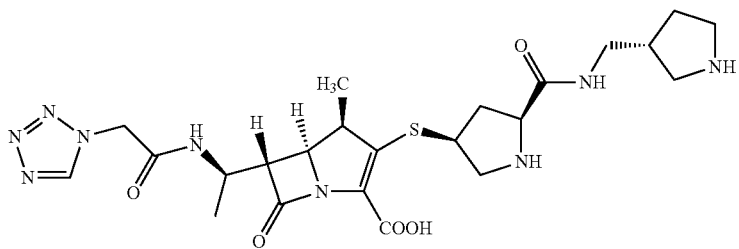
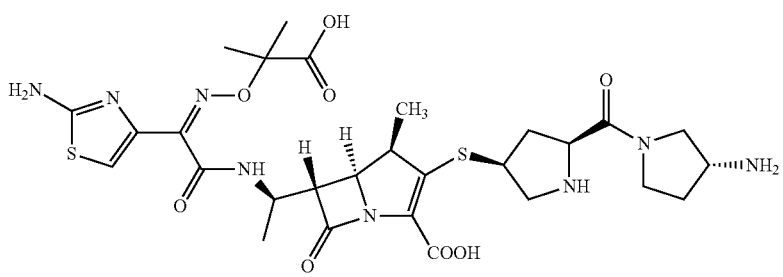
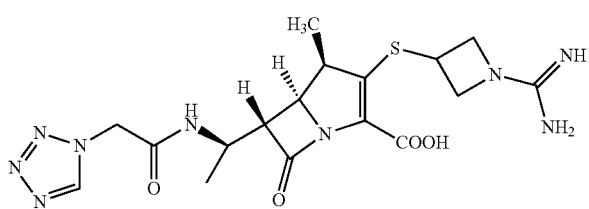
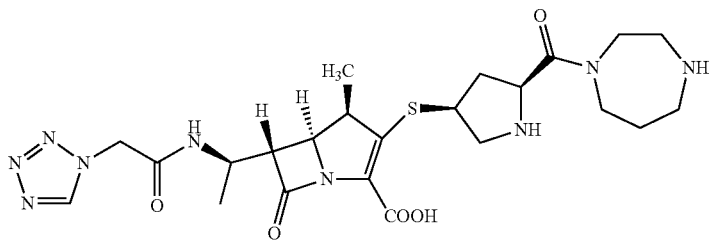
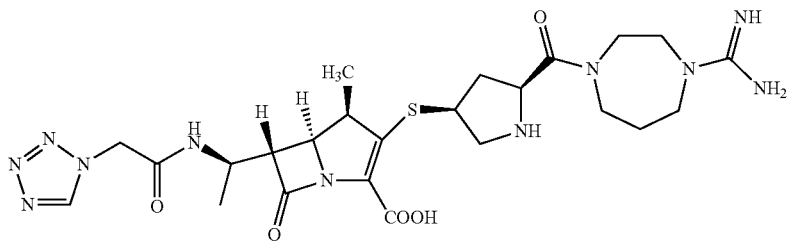

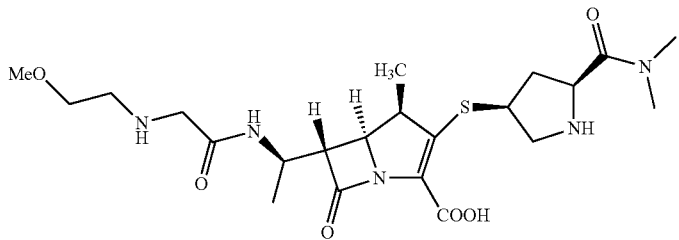
isomer 1
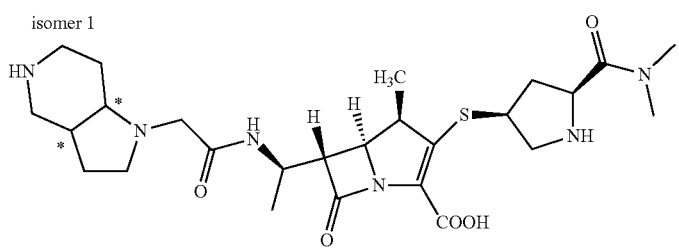
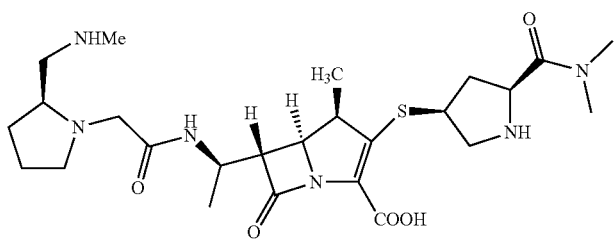
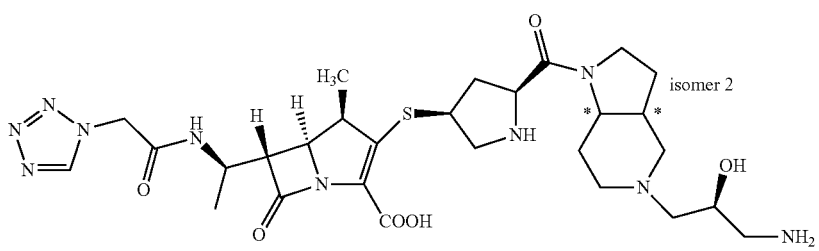
isomer 2
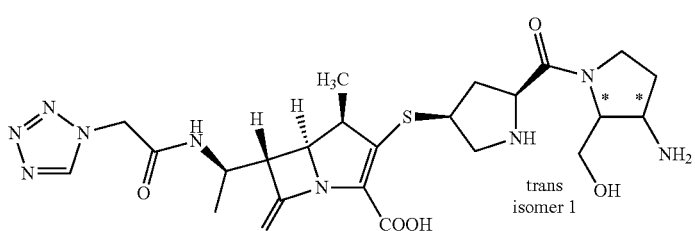
trans isomer 1
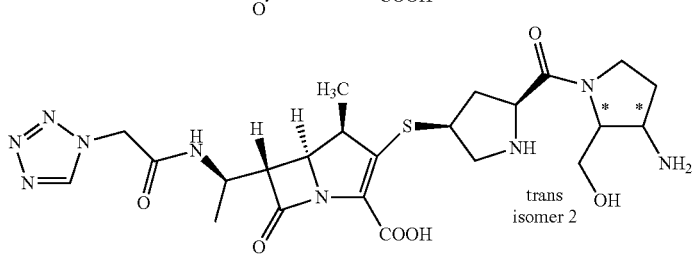
trans isomer 2
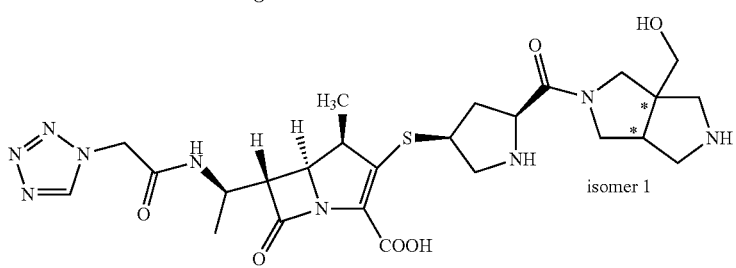
isomer 1

-continued
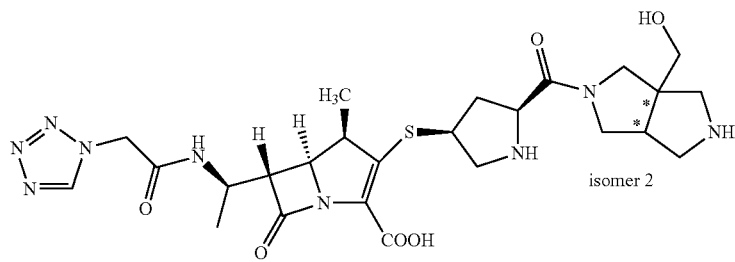
isomer 2
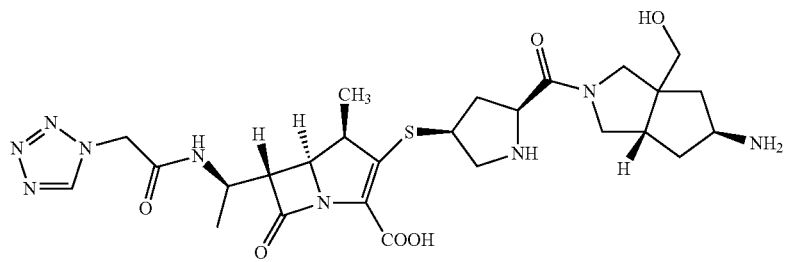
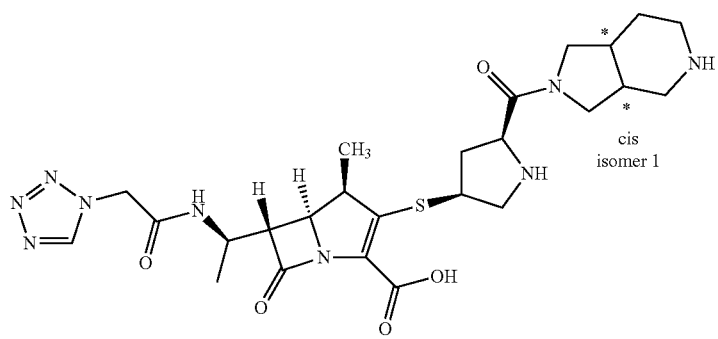
cis
isomer 1
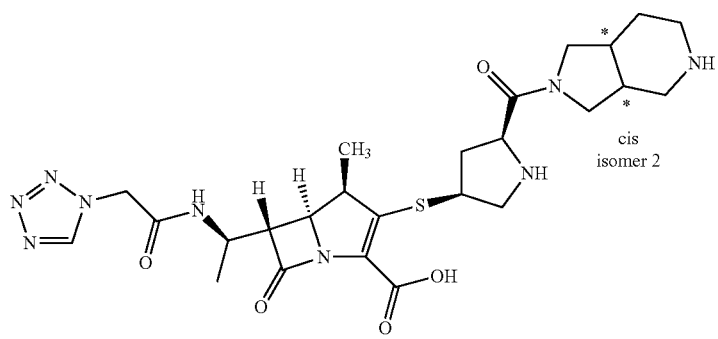
cis
isomer 2
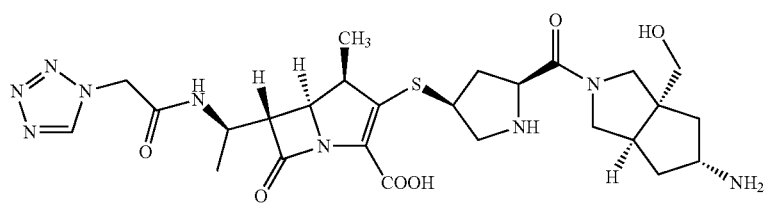
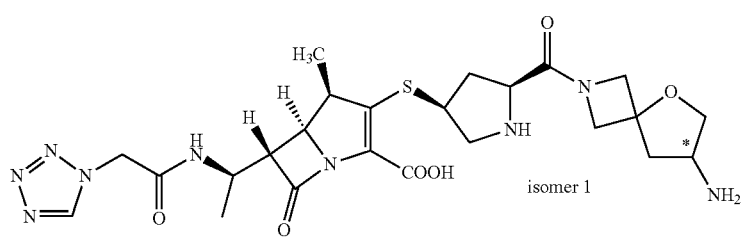
isomer 1

-continued
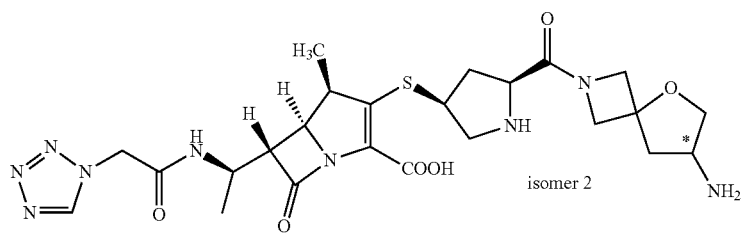
isomer 2
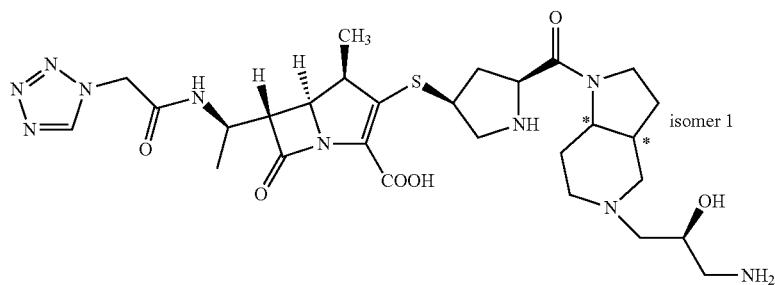
isomer 1
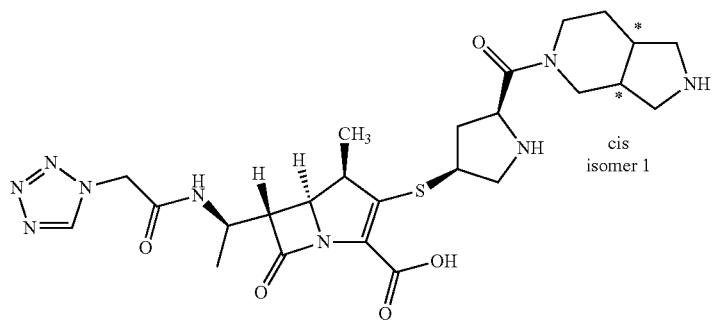
cis isomer 1
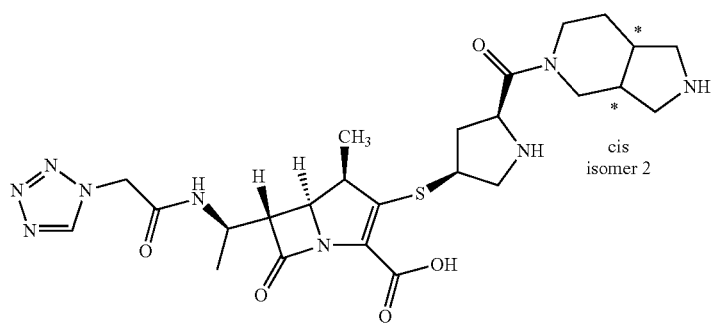 [SMILES: C[C@@H](NC(=O)Cn1cnnn1)[C@H]1C(=O)N2C(C(=O)O)=C(S[C@@H]3CN[C@H](C(=O)N4CCC5CNCC5C4)C3)[C@H](C)[C@H]12]
cis isomer 2
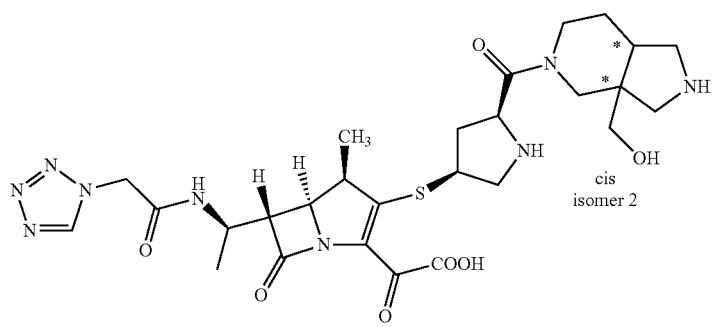
cis isomer 2

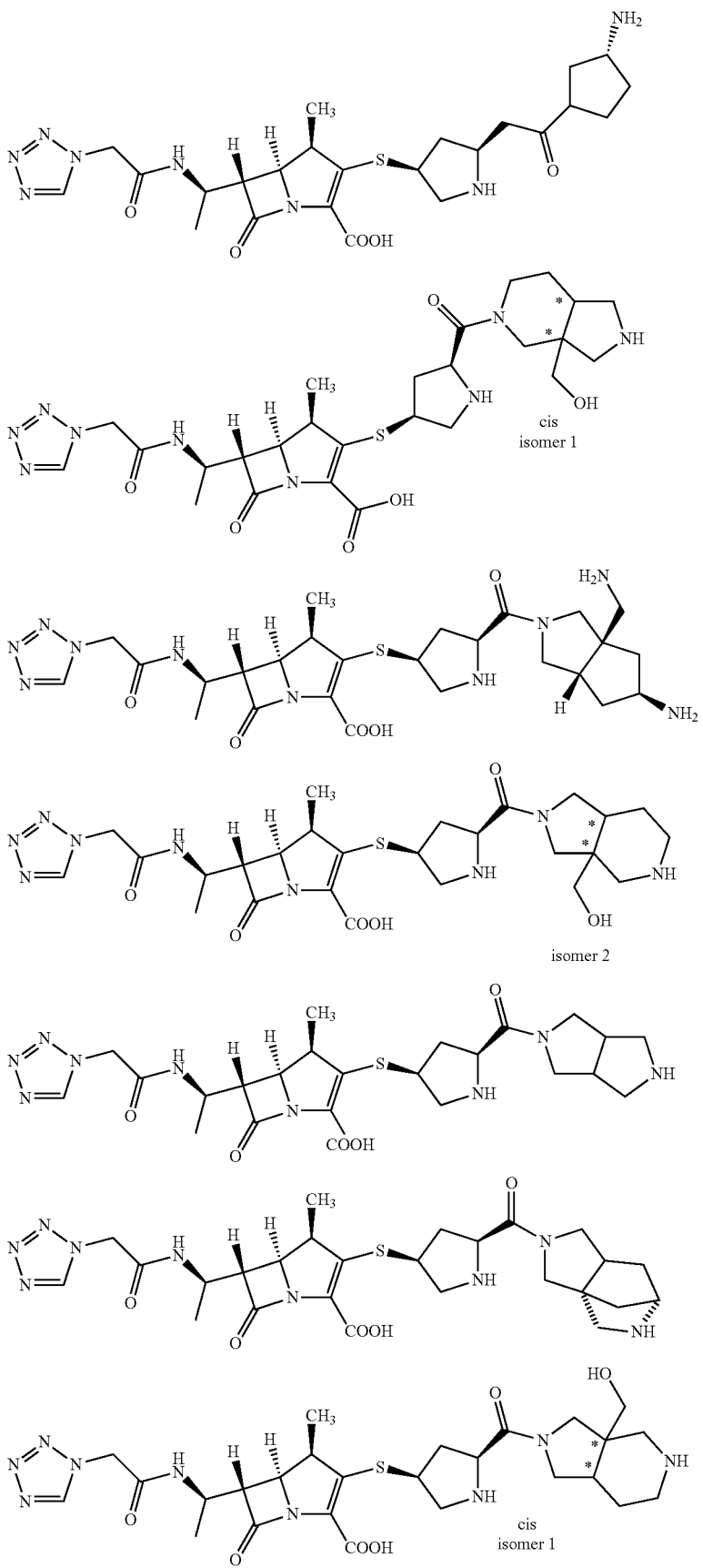

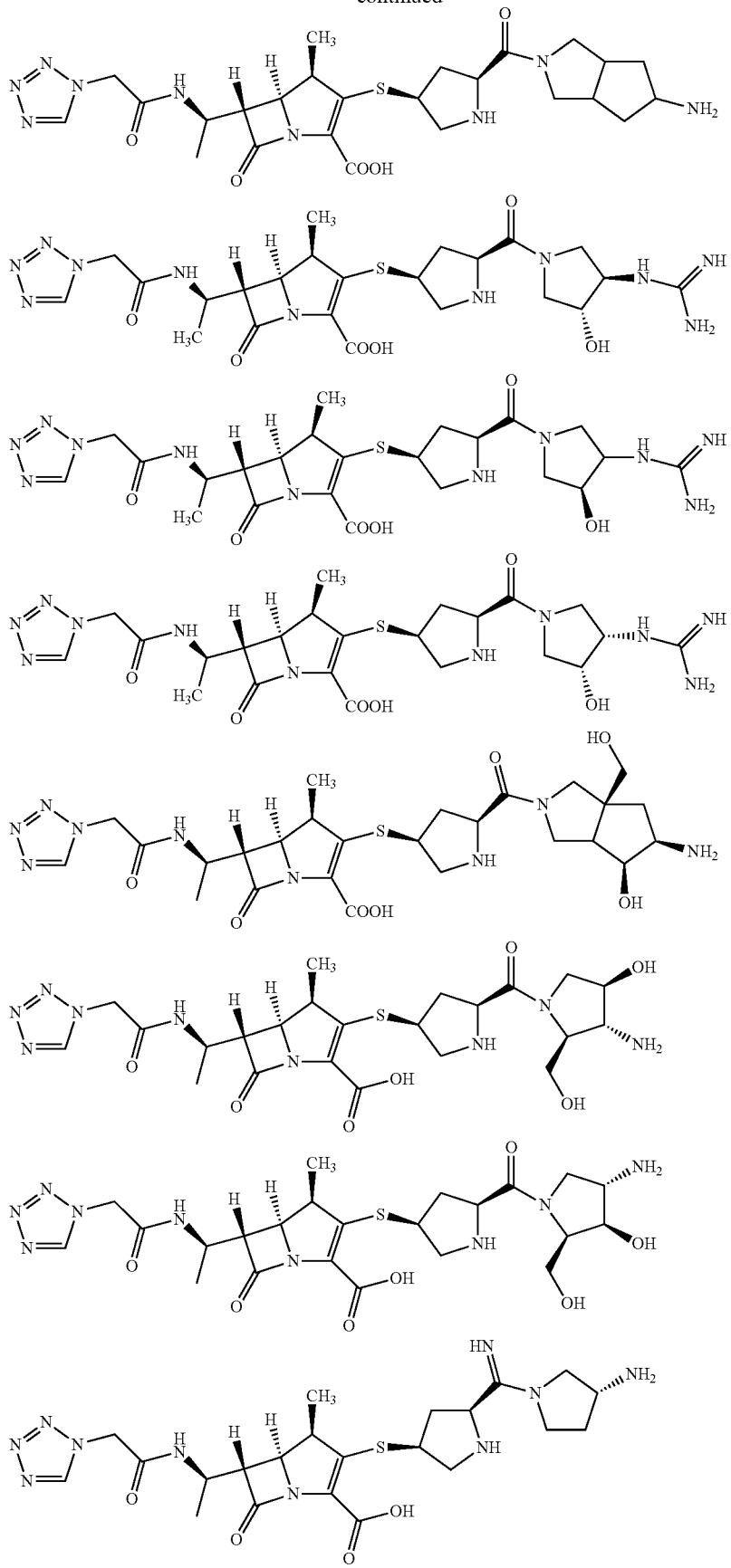

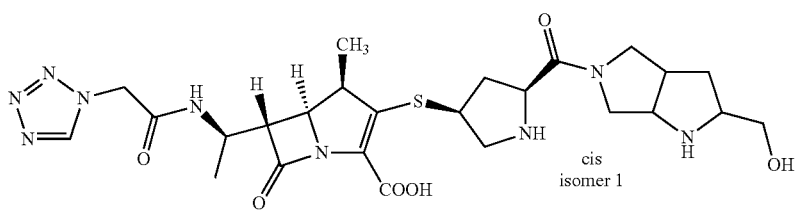
cis isomer 1
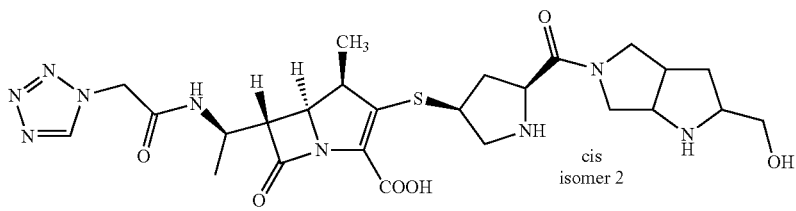
cis isomer 2
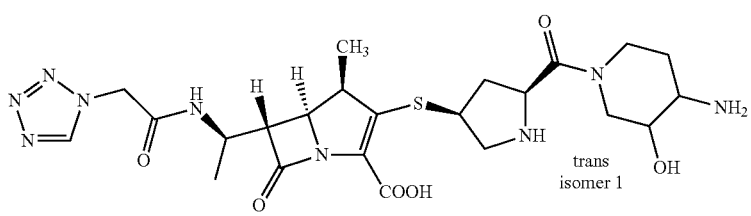
trans isomer 1
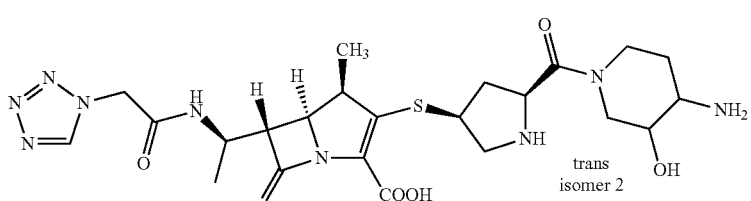
trans isomer 2
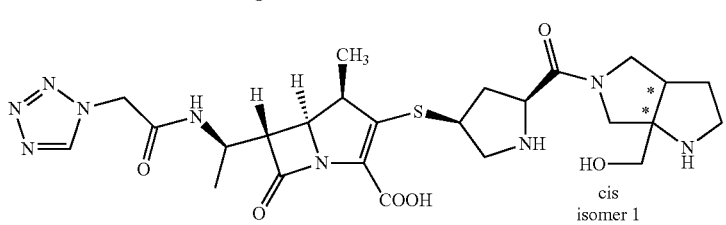
cis isomer 1
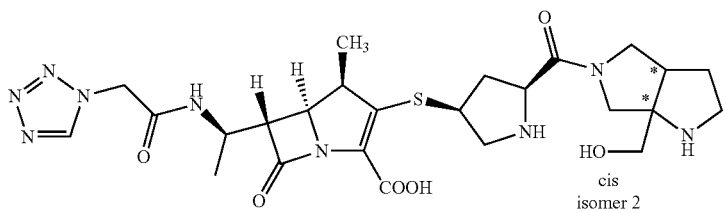
cis isomer 2
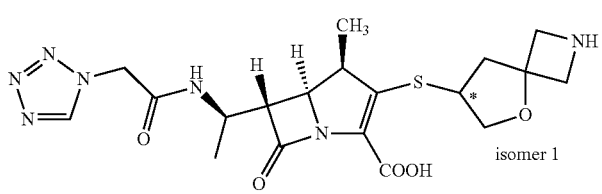
isomer 1
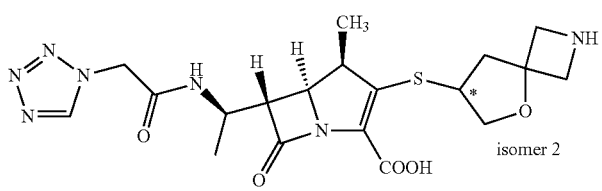
isomer 2

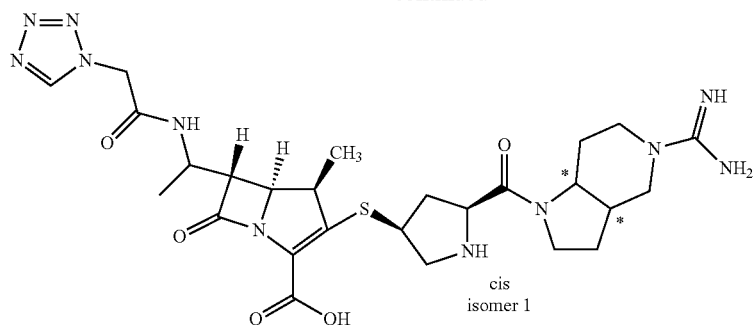
cis isomer 1
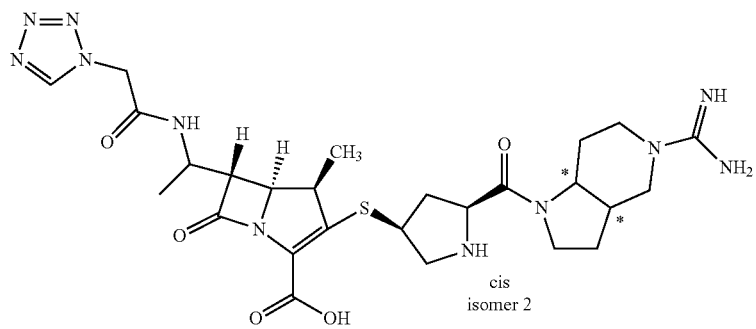
cis isomer 2
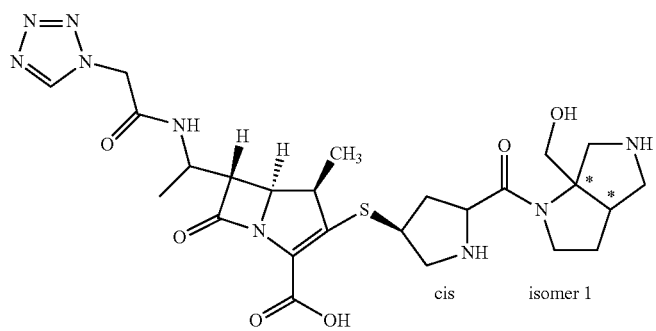
cis isomer 1
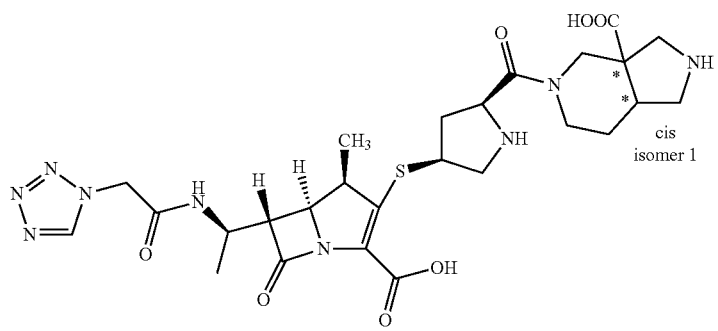
cis isomer 1
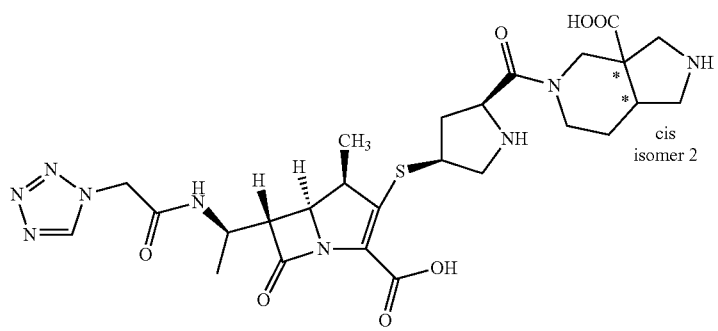
cis isomer 2

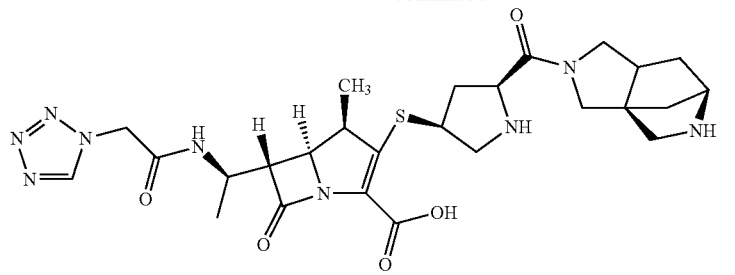
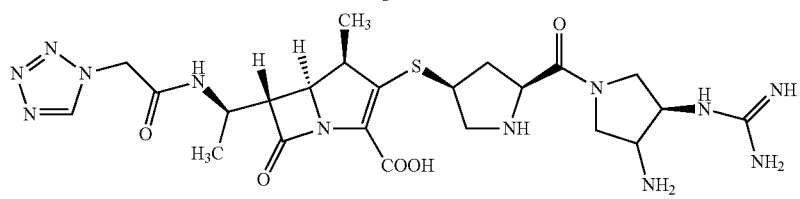
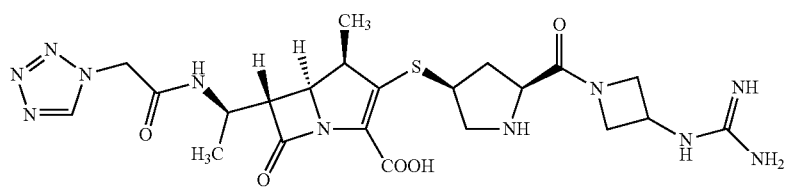
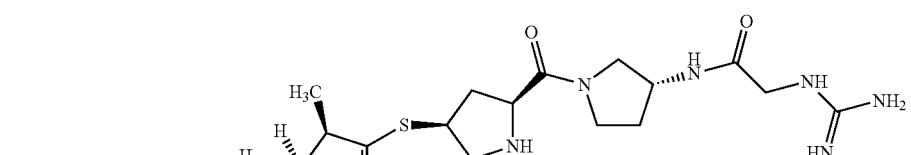
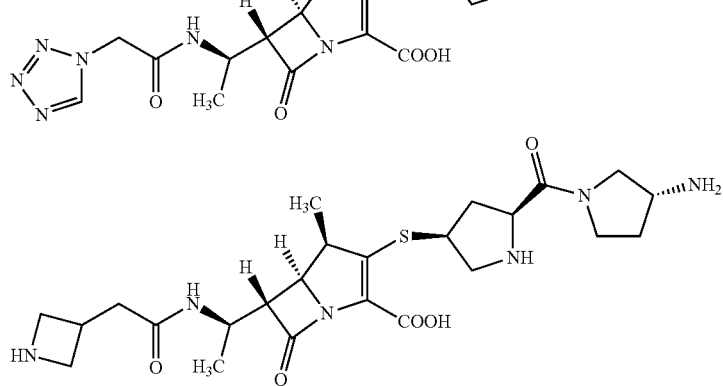
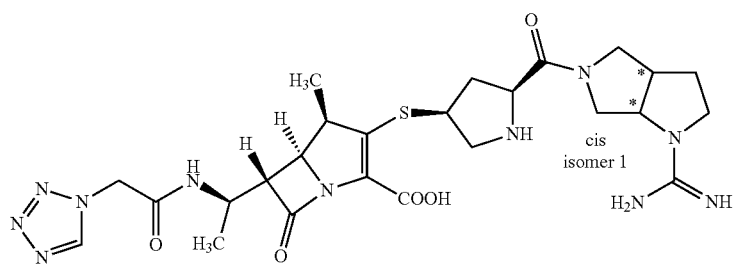
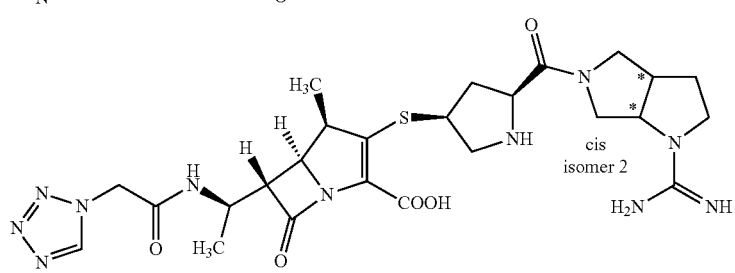

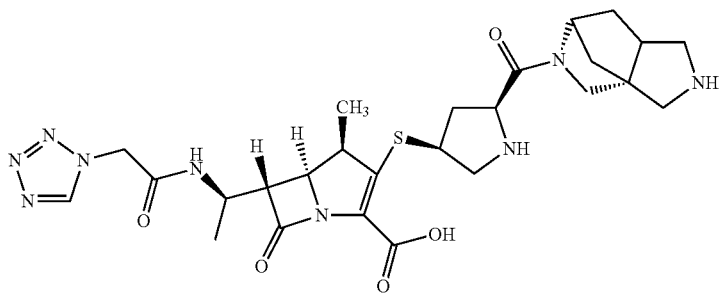
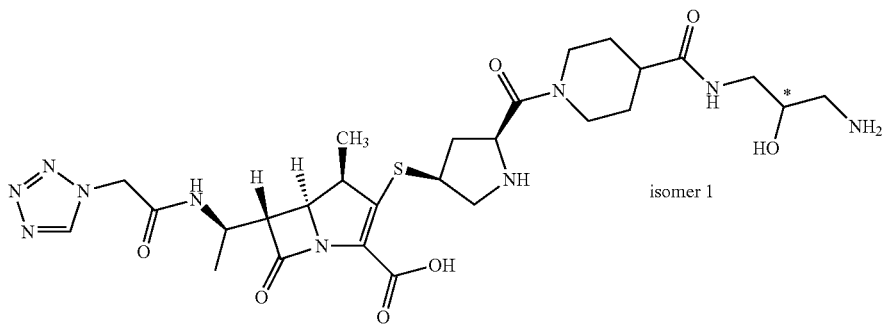
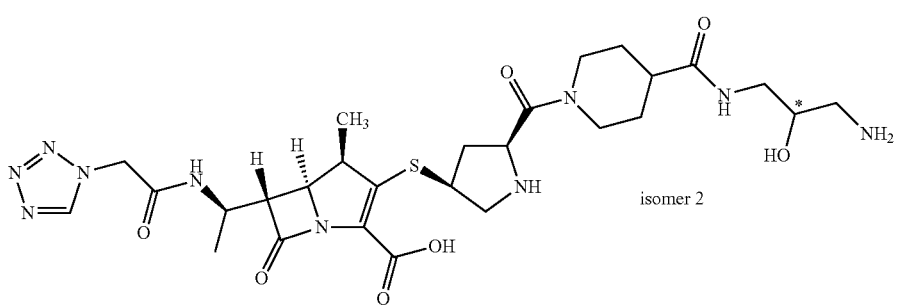
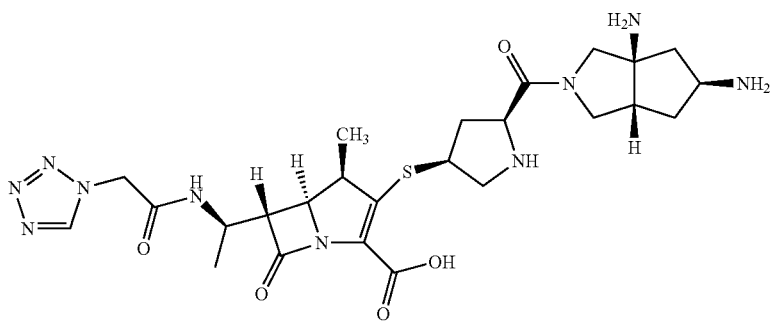
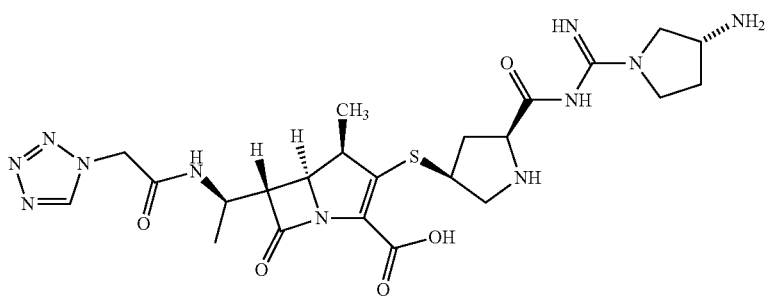

-continued
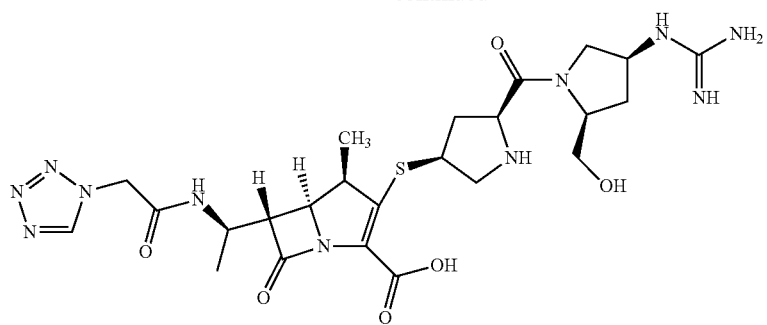
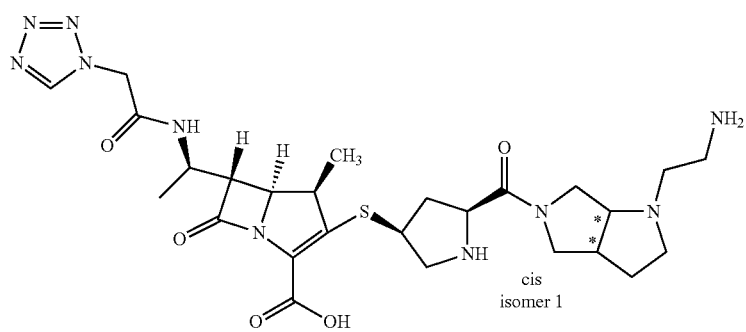
cis isomer 1
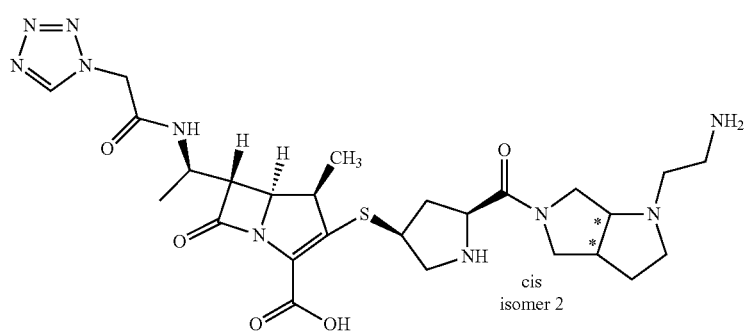
cis isomer 2
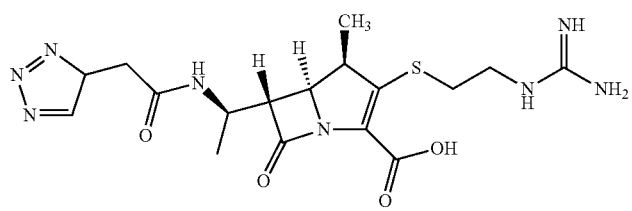
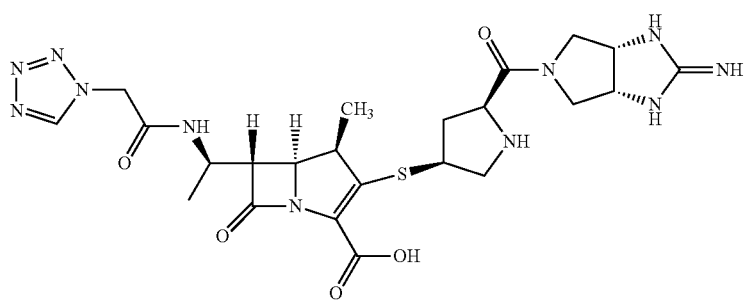

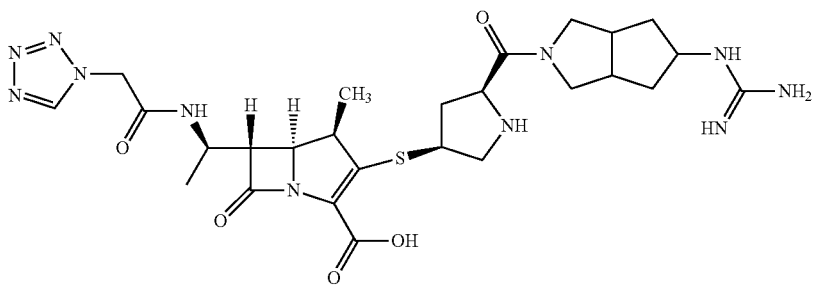
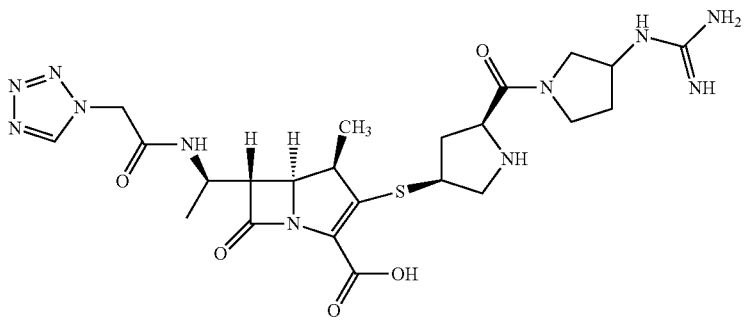
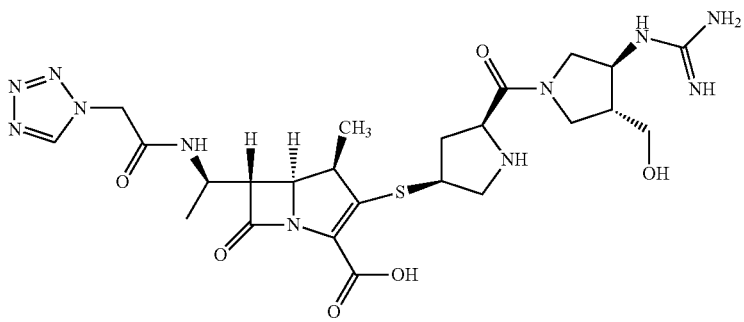
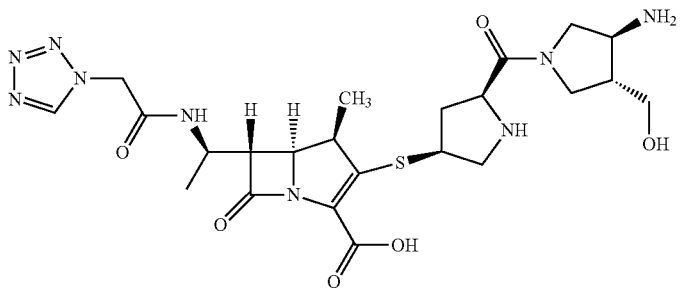
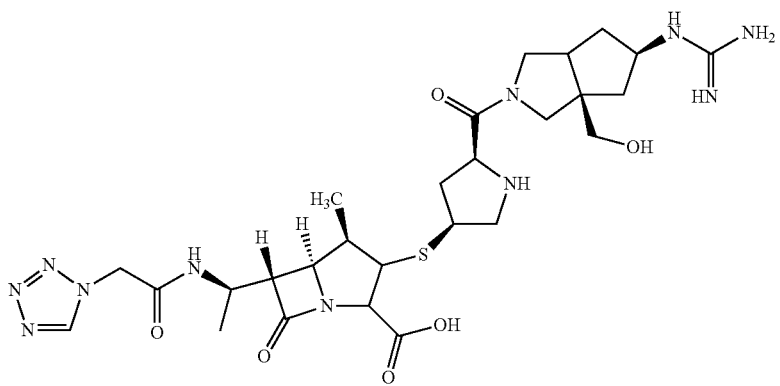

-continued
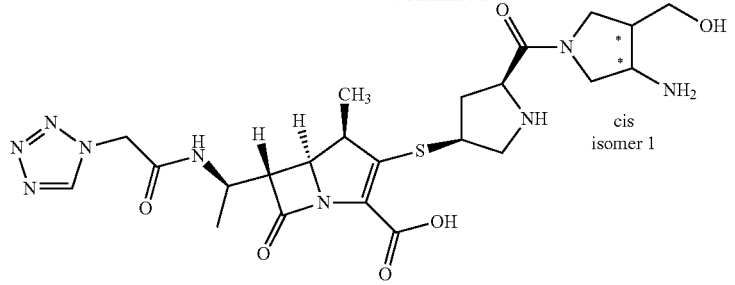
cis isomer 1
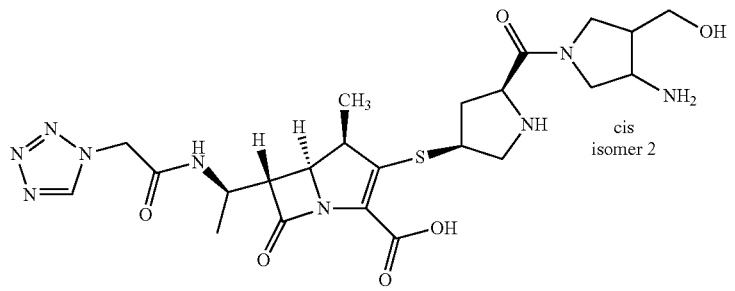
cis isomer 2
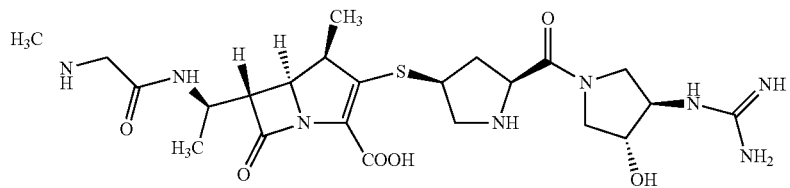
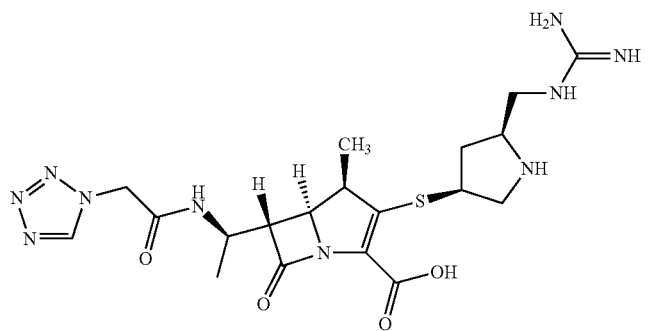
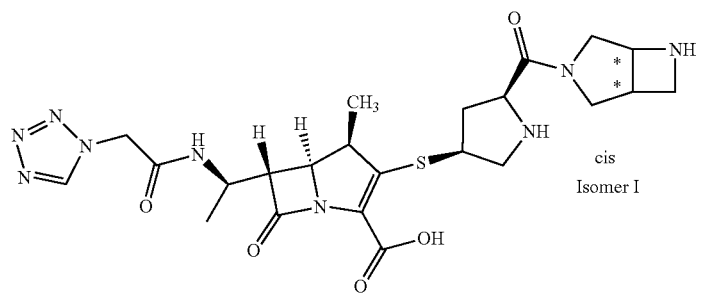
cis Isomer I -continued
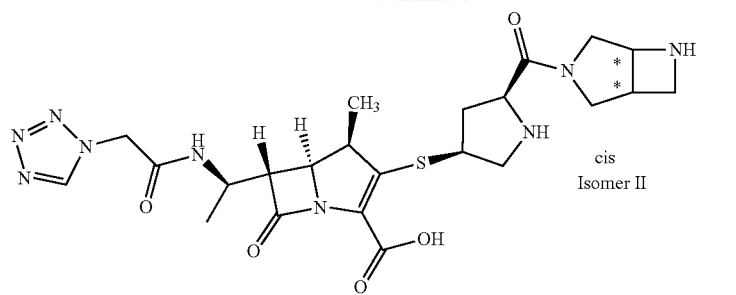
cis
Isomer II
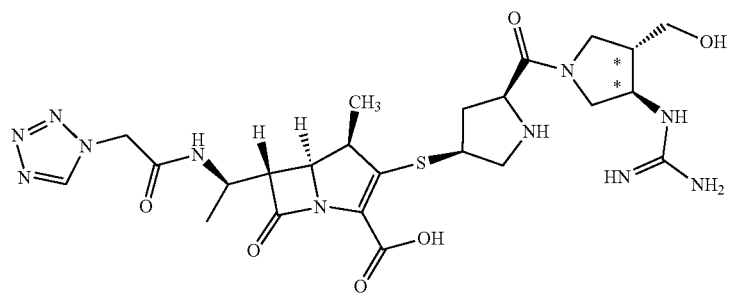
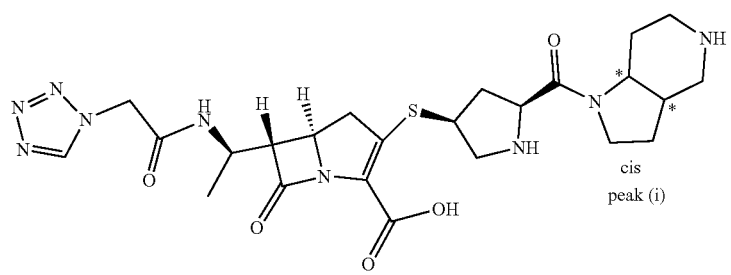
cis
peak (i)
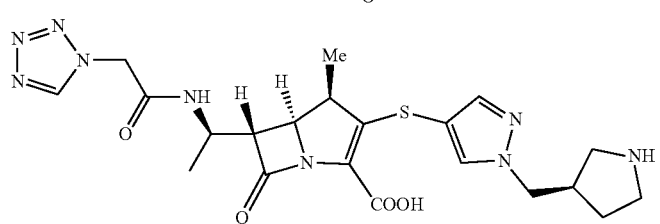
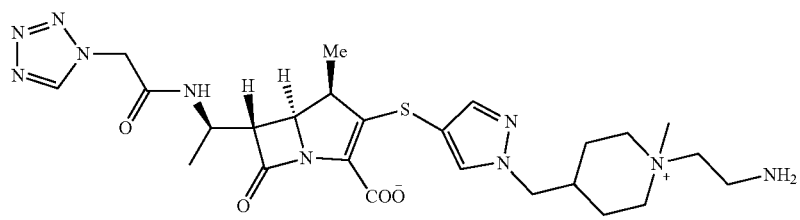
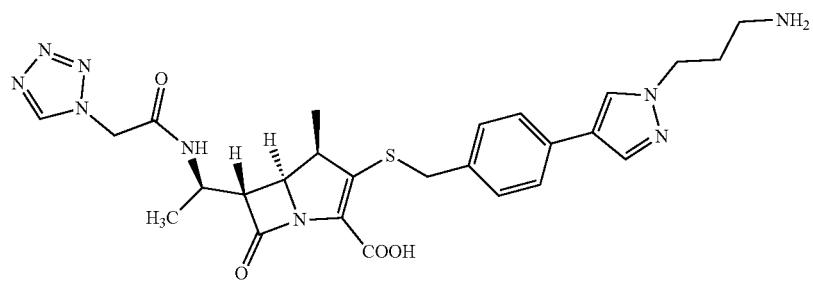

-continued
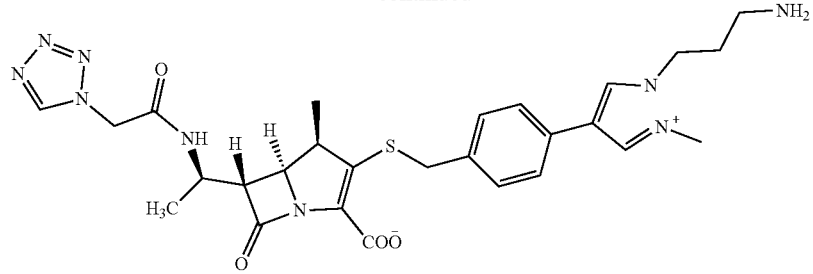
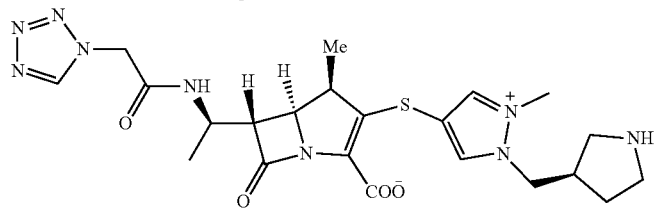
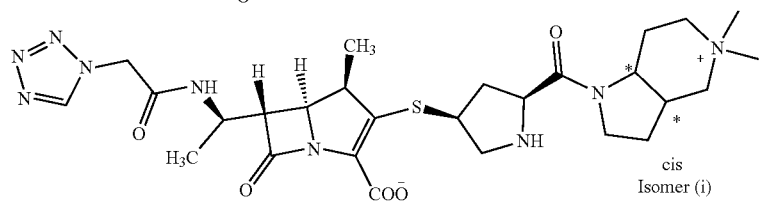
cis
Isomer (i)
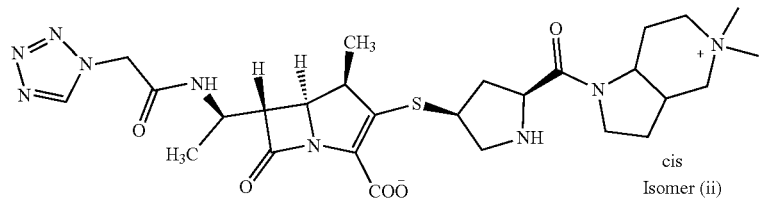
cis
Isomer (ii)
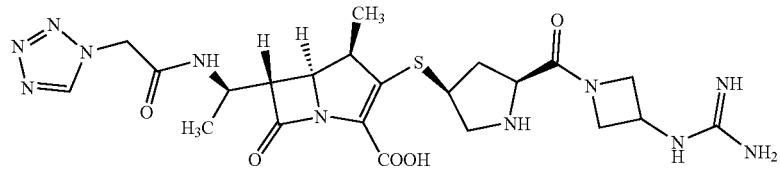 [SMILES: C[C@@H](NC(=O)Cn1cnnn1)[C@H]1C(=O)N2C(C(=O)O)=C(S[C@@H]3CN[C@H](C(=O)N4CC(NC(=N)N)C4)C3)[C@H](C)[C@H]12]
or a pharmaceutically acceptable salt, internal salt, or N-oxide thereof.
28. A compound, or a stereoisomer thereof, wherein the compound, or stereoisomer thereof, which is selected from the group consisting of:
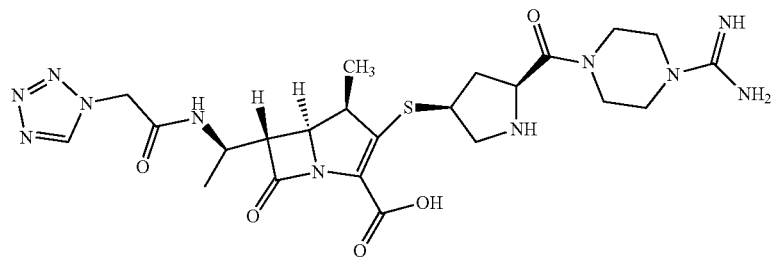

-continued
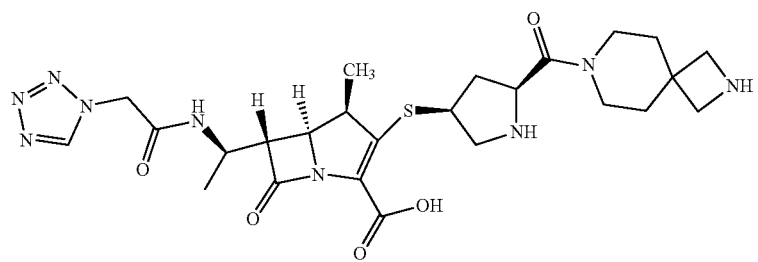
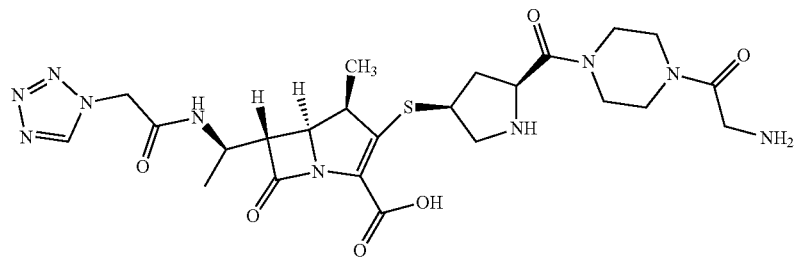
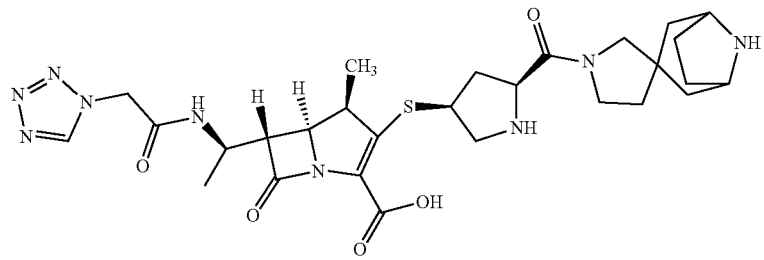
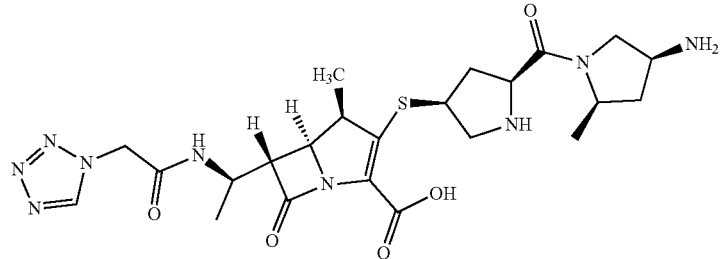
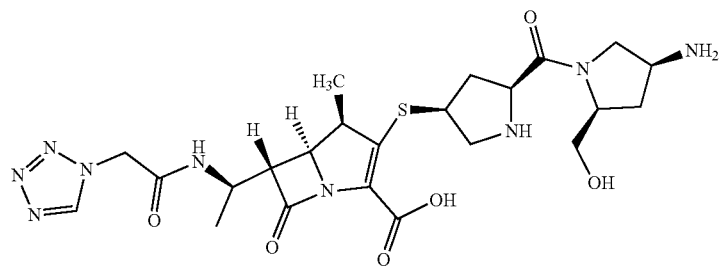
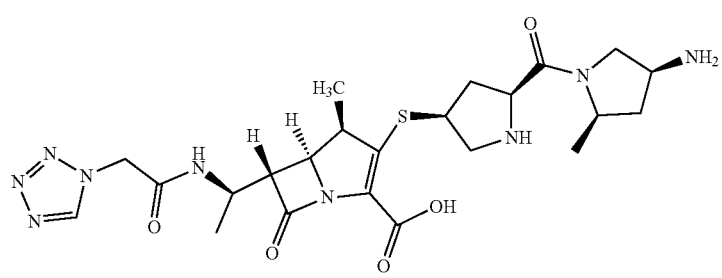

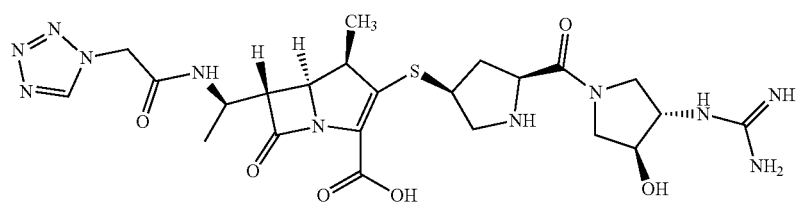
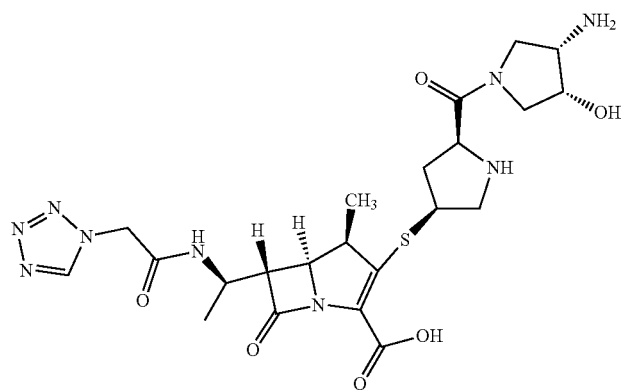
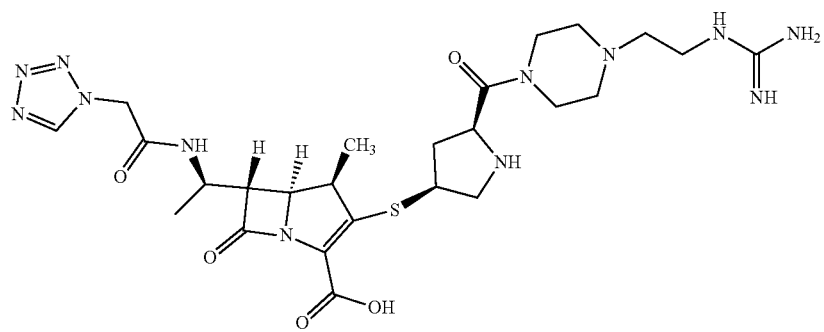
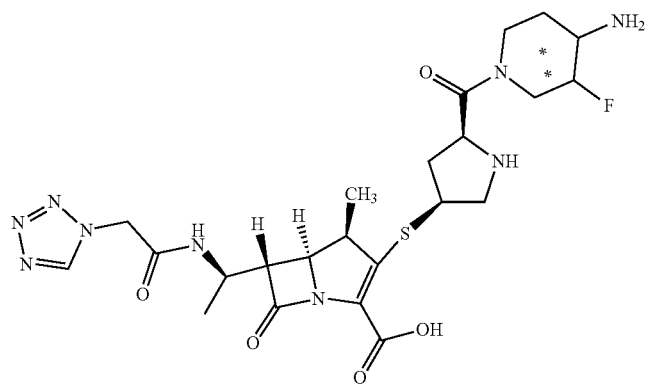

-continued
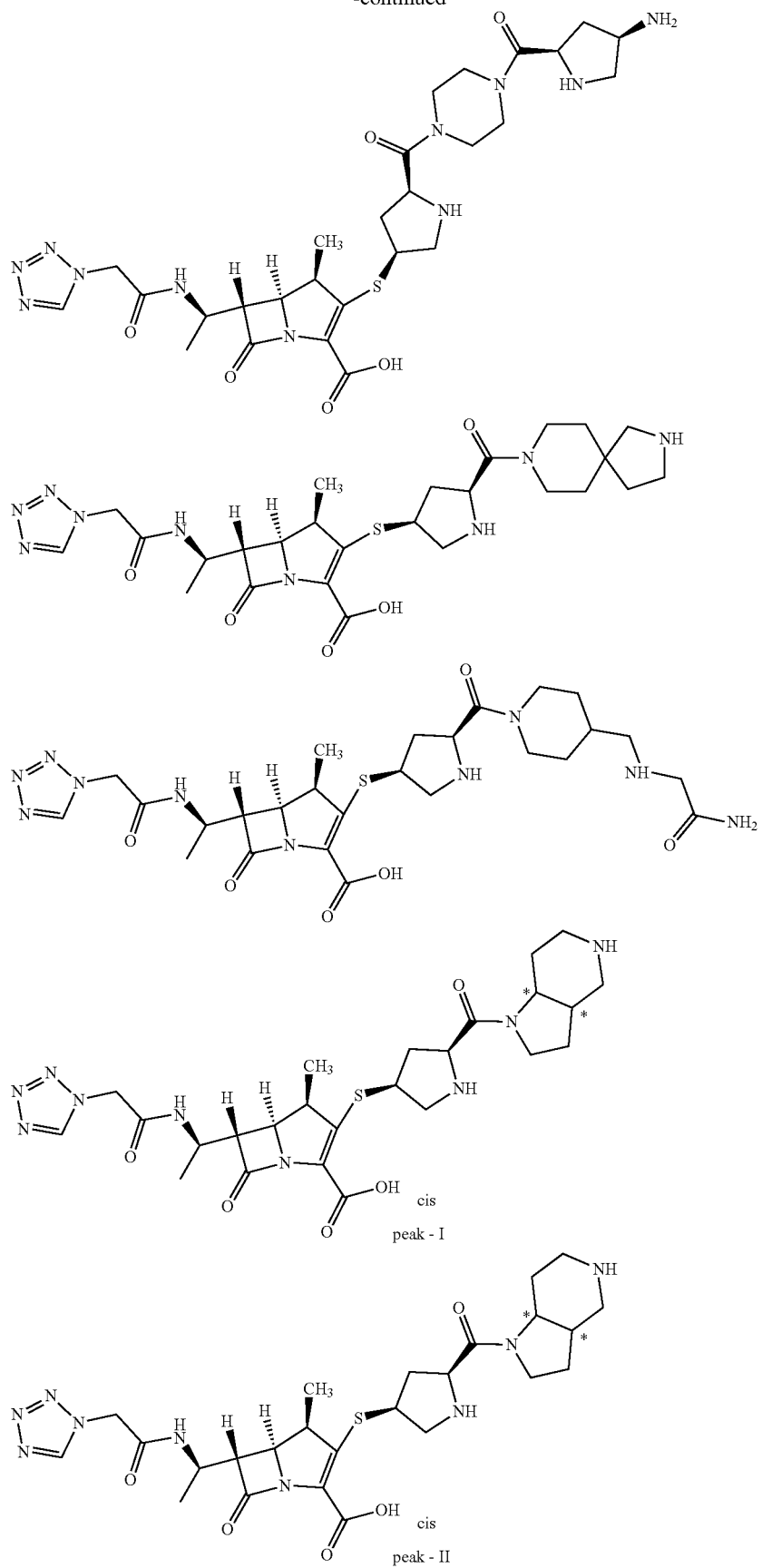

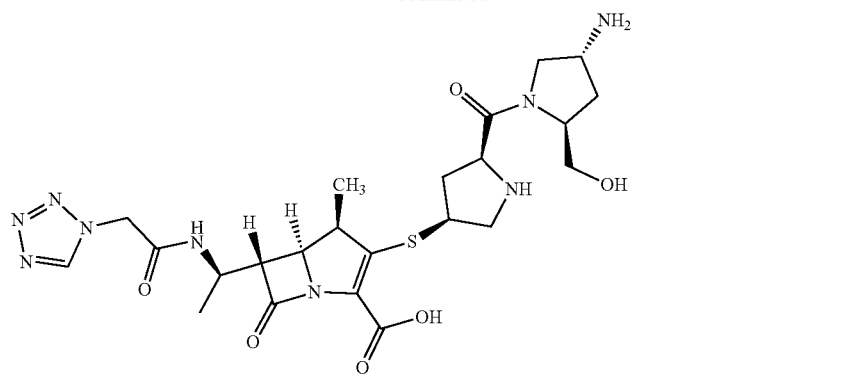
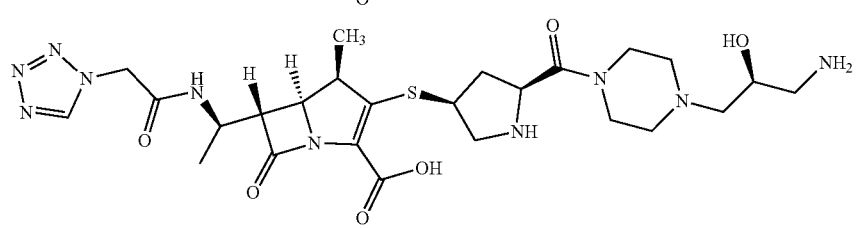
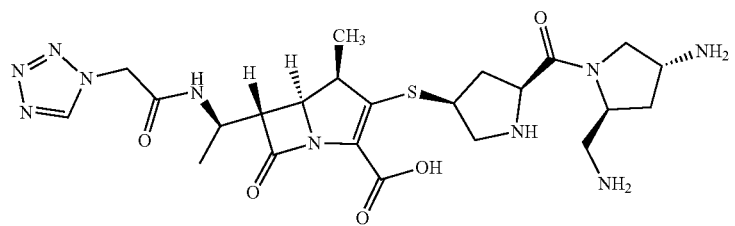
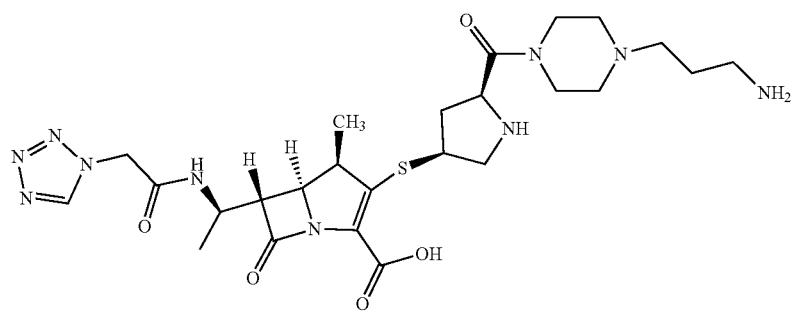
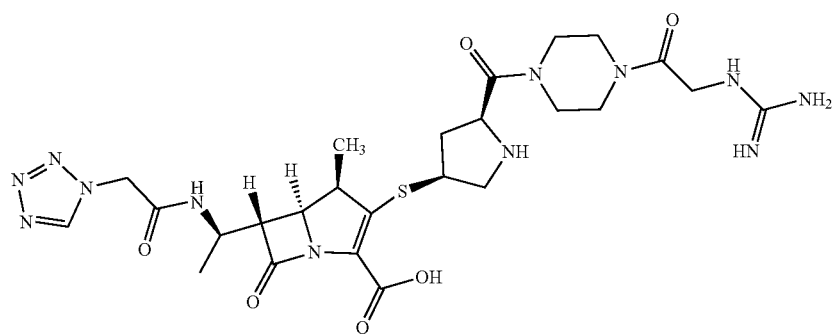

-continued
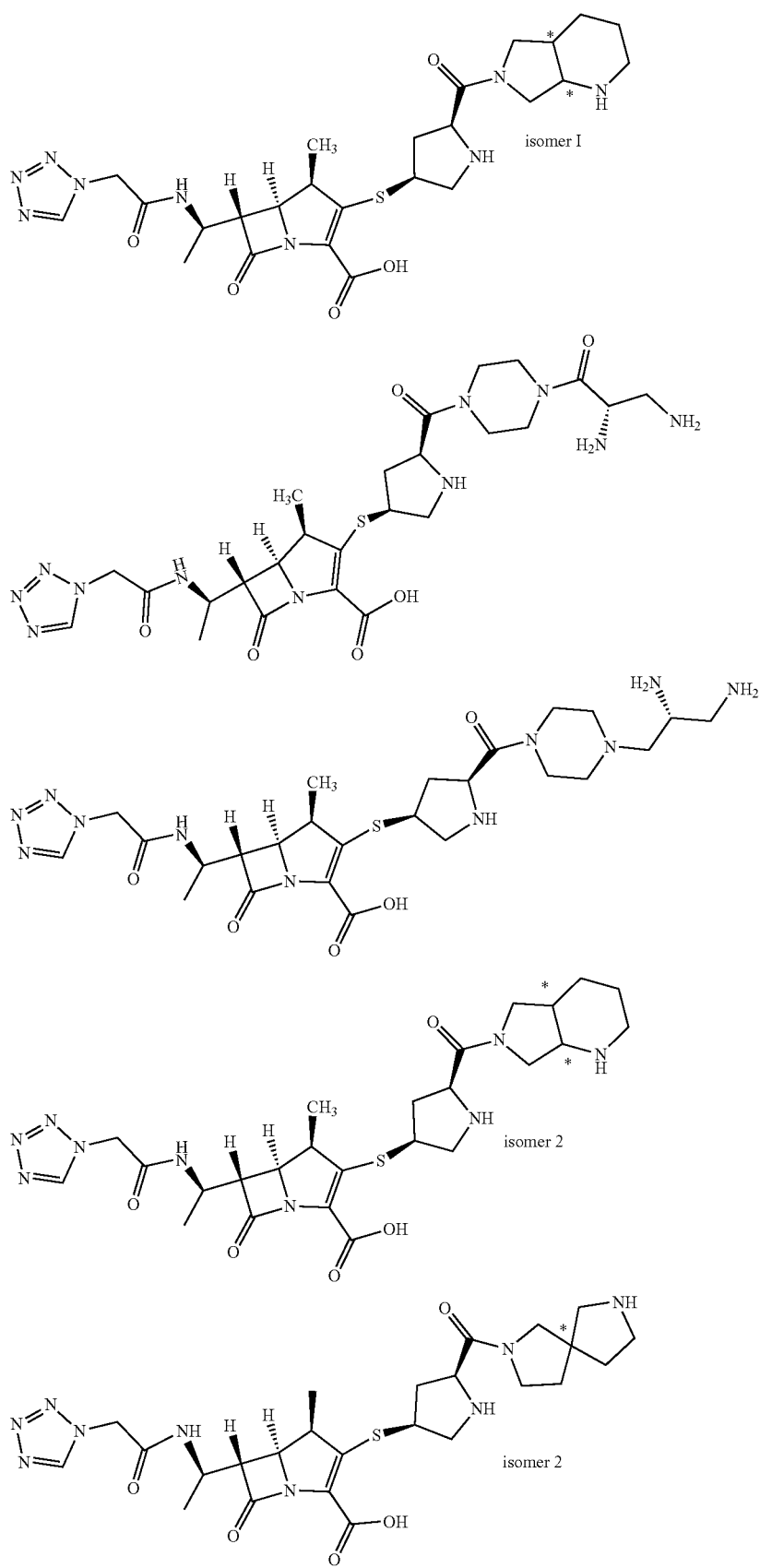

-continued
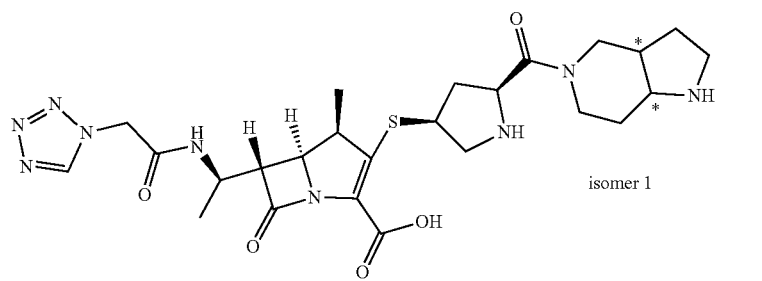
isomer 1
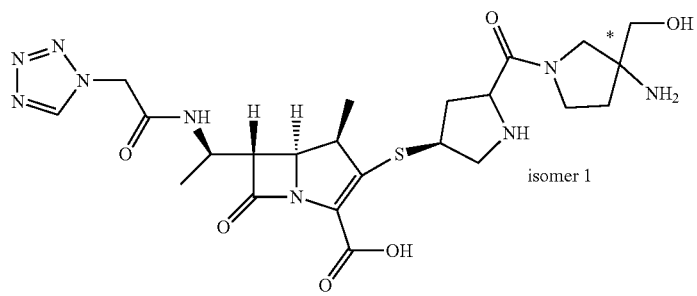
isomer 1
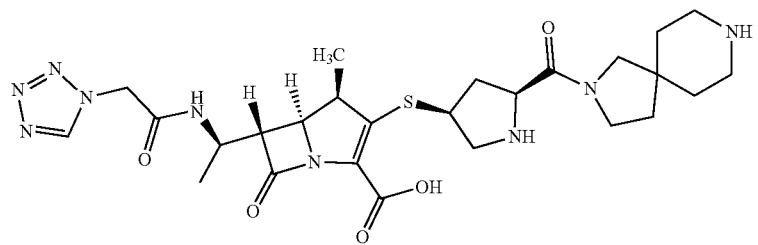
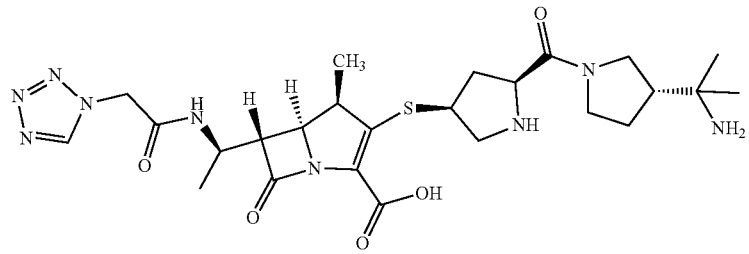
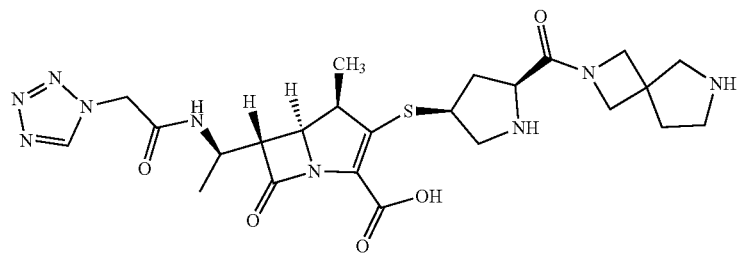
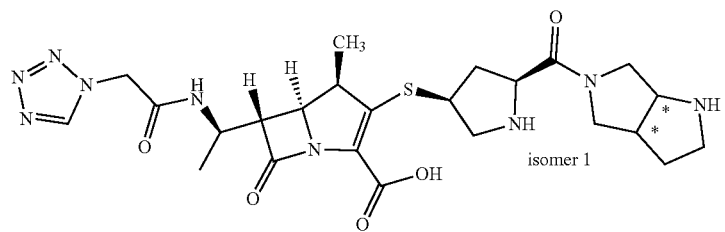
isomer 1

-continued
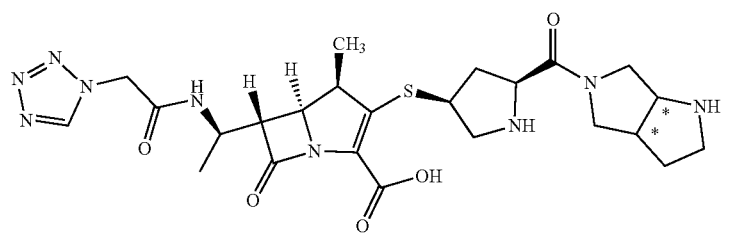
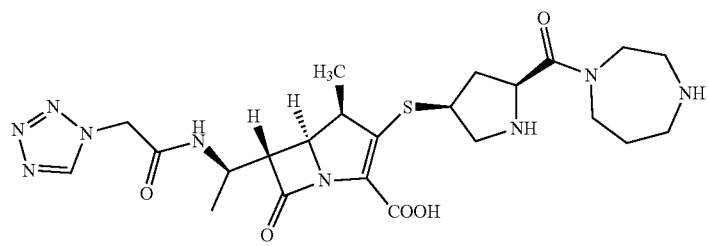
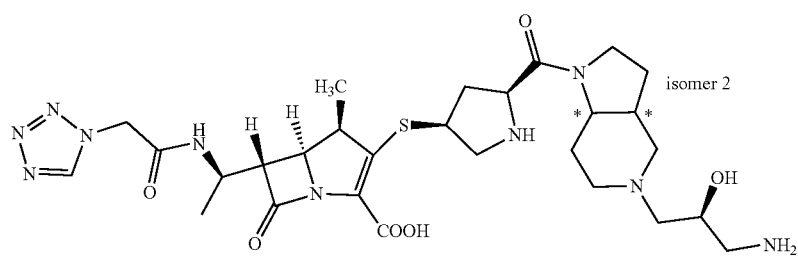
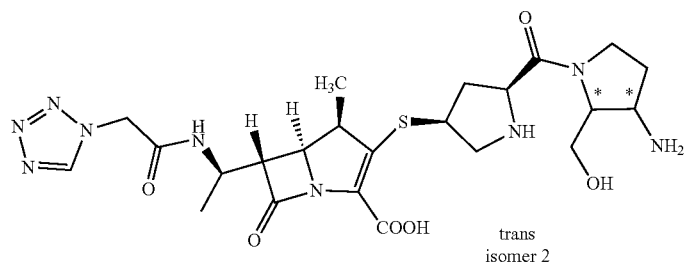
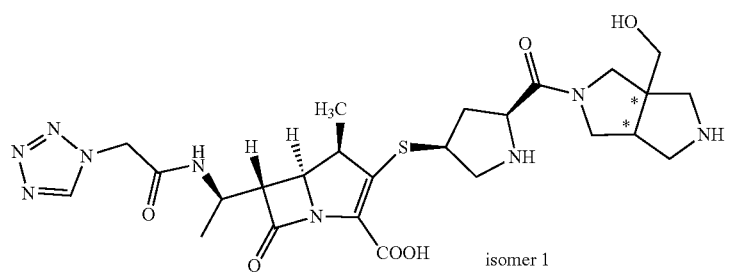
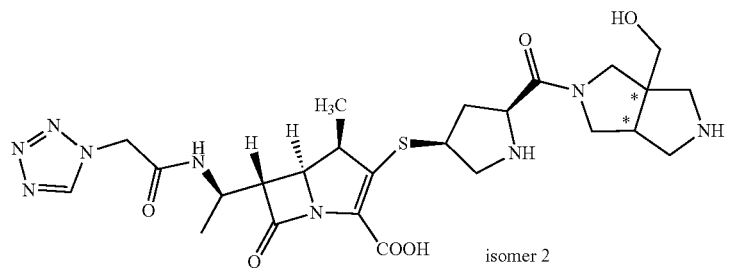

-continued
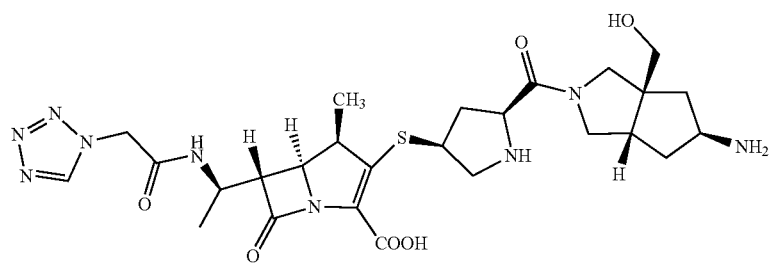
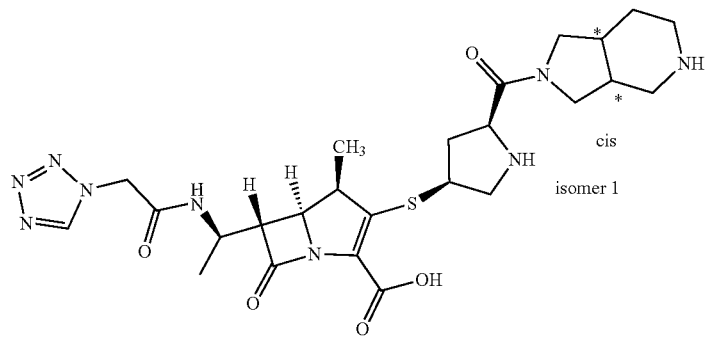
cis
isomer 1
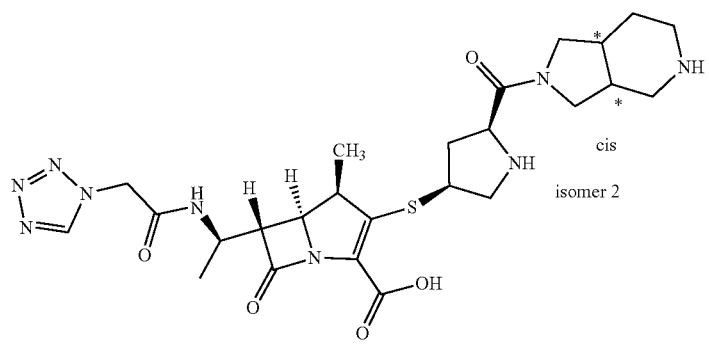
cis
isomer 2
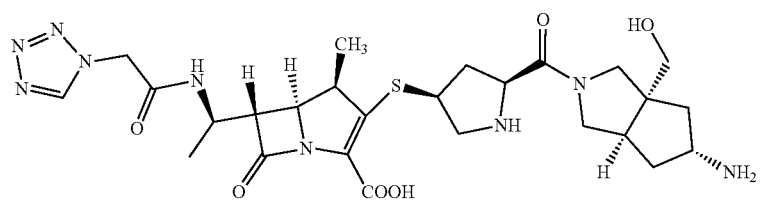
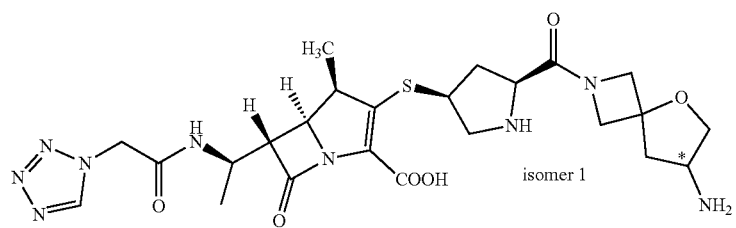
isomer 1
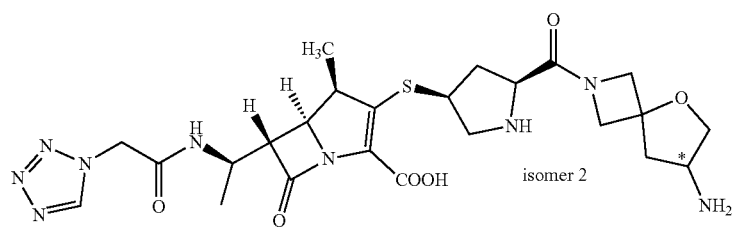
isomer 2

-continued
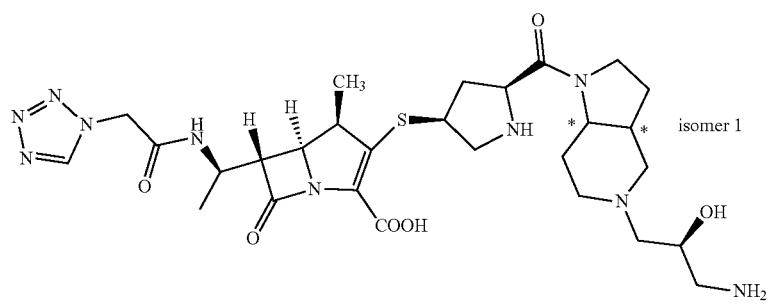
isomer 1
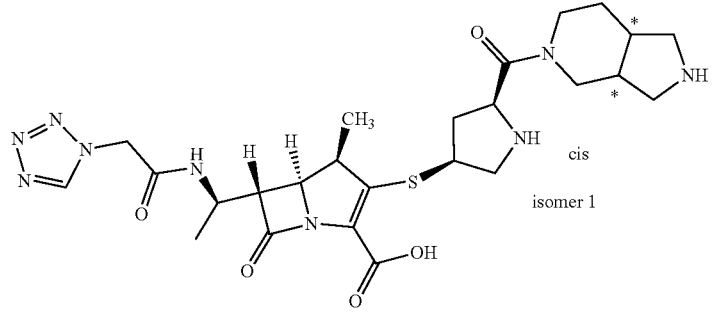
cis
isomer 1
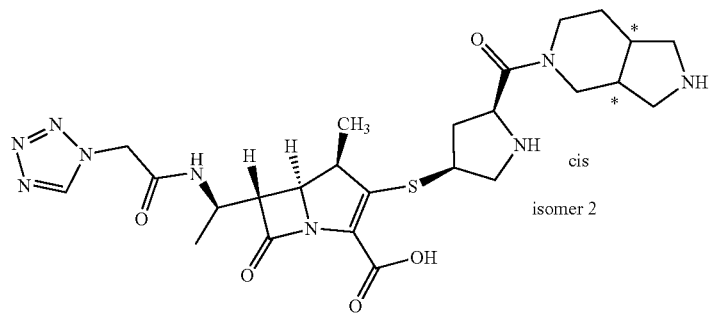
cis
isomer 2
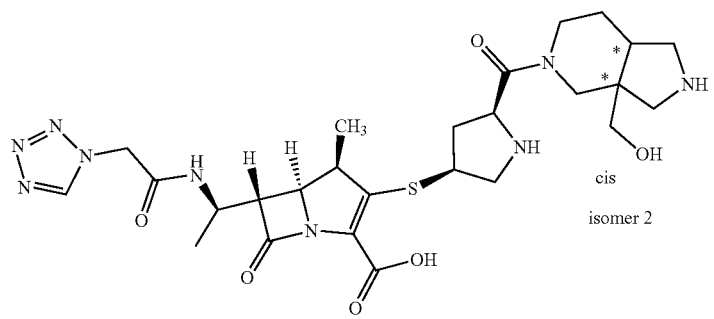
cis
isomer 2
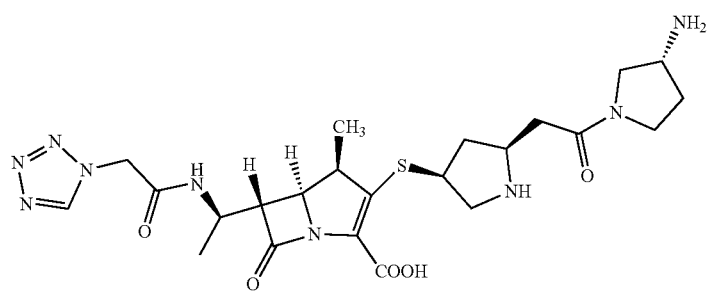

-continued
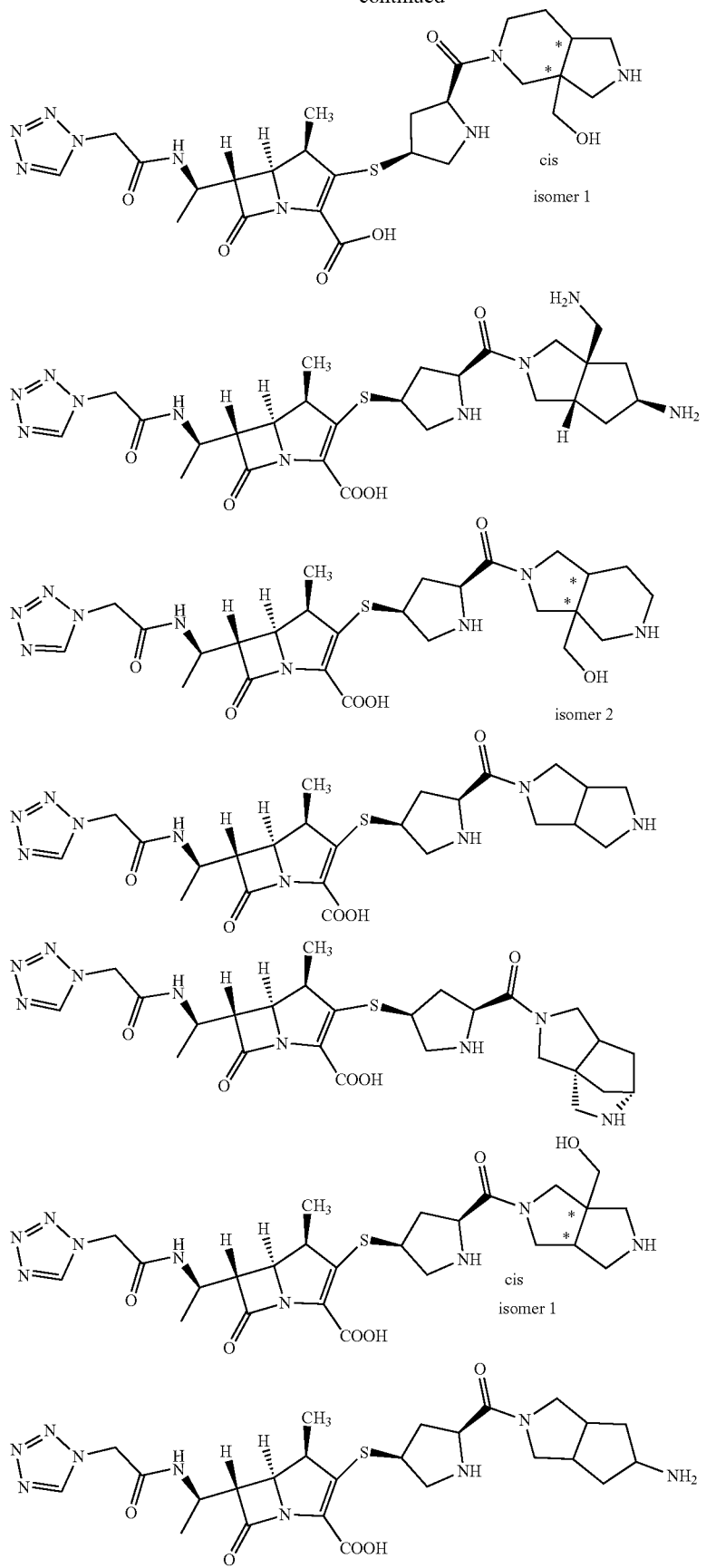

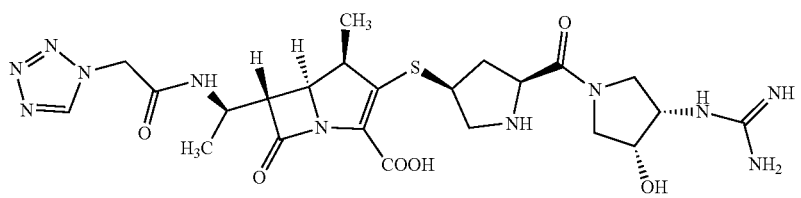
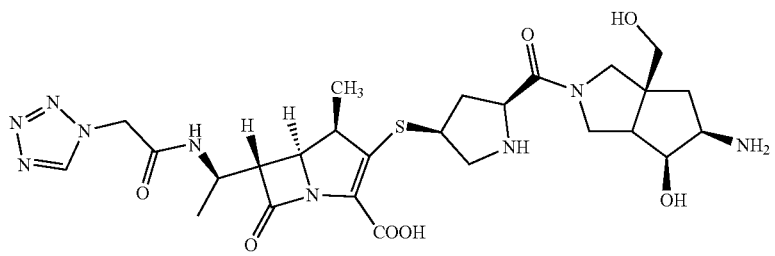
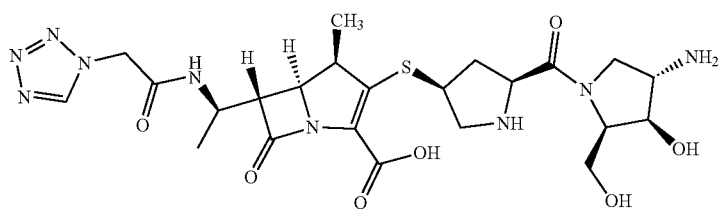
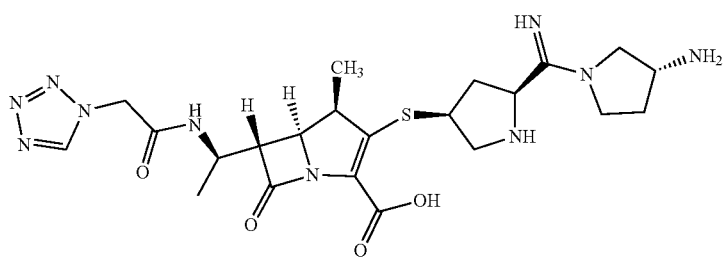
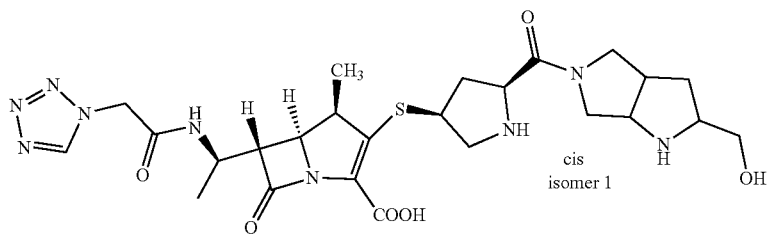
cis isomer 1
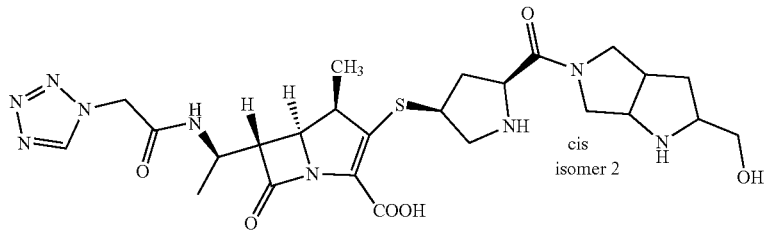
cis isomer 2
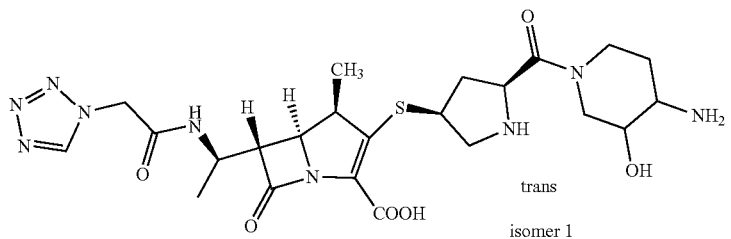
trans isomer 1

-continued
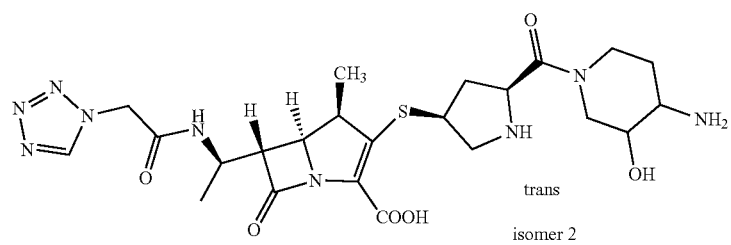
trans
isomer 2
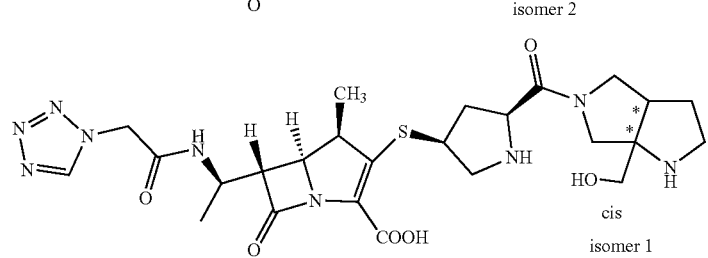
cis
isomer 1
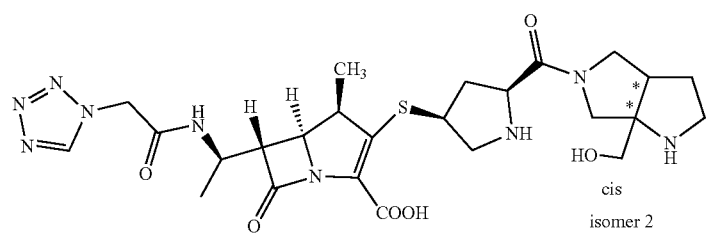
cis
isomer 2
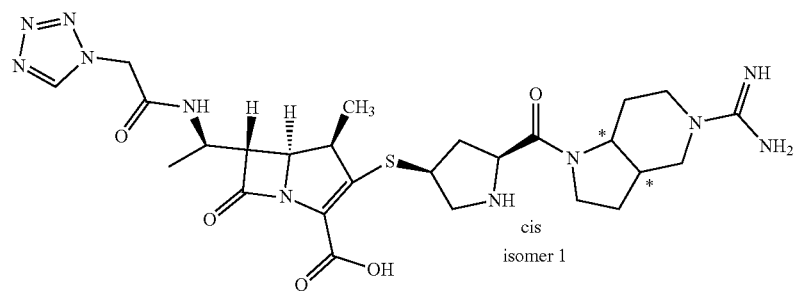
cis
isomer 1
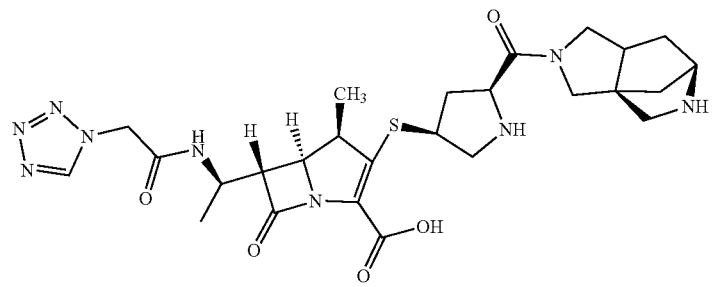
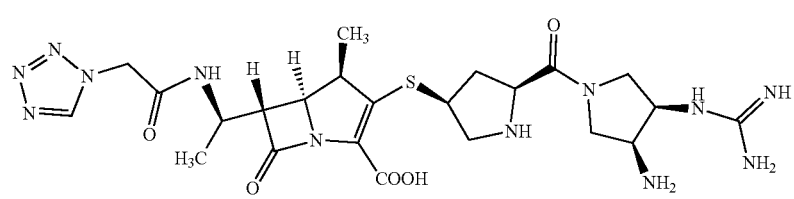
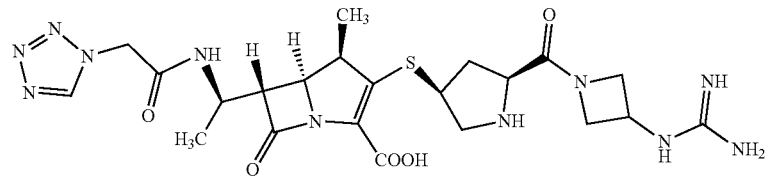

-continued
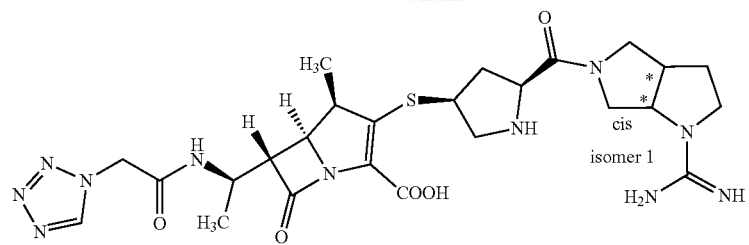
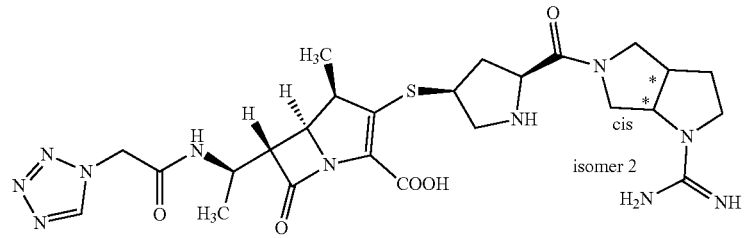
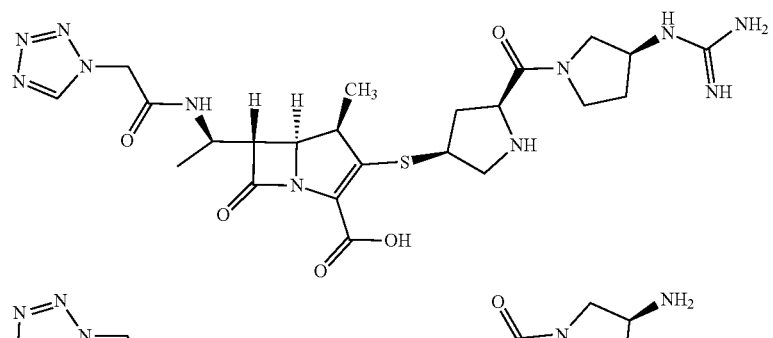
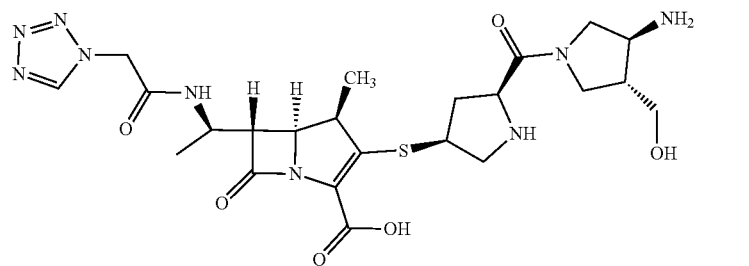
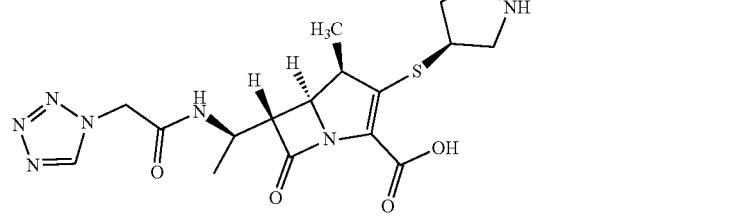
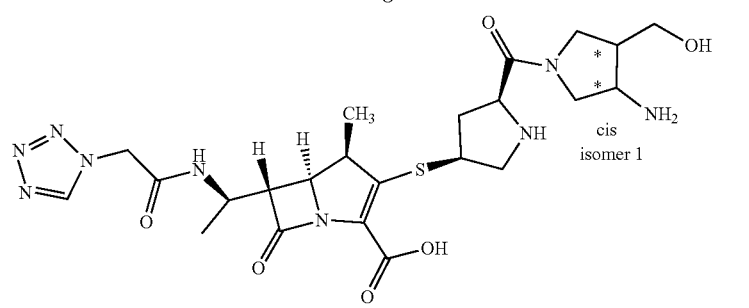

-continued
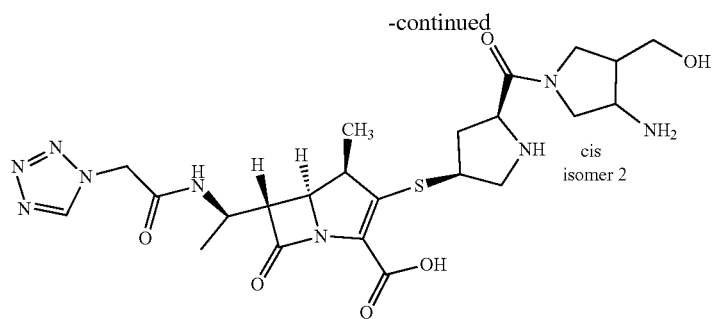
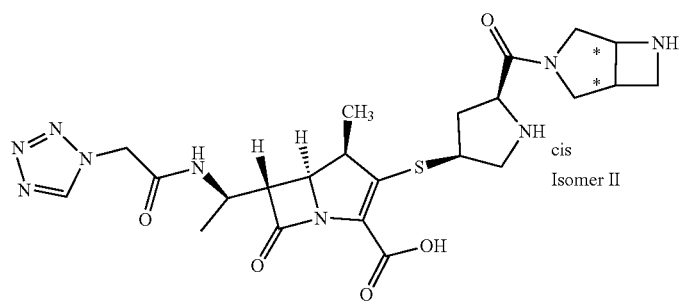 [SMILES: C[C@@H](NC(=O)Cn1cnnn1)[C@H]1C(=O)N2C(C(=O)O)=C(S[C@@H]3CN[C@H](C(=O)N4CC5CNC5C4)C3)[C@H](C)[C@H]12]
or a pharmaceutically acceptable salt, internal salt, or N-oxide thereof.
29. A compound, or a stereoisomer thereof, wherein the compound, or stereoisomer thereof, is selected from the group consisting of:
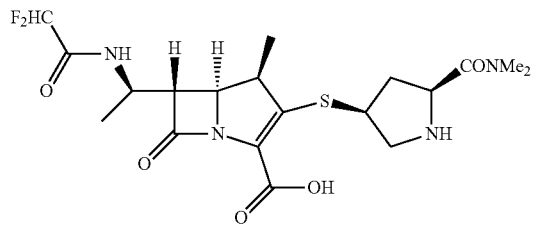
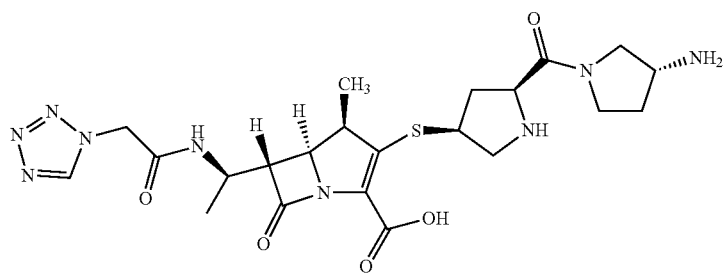

-continued
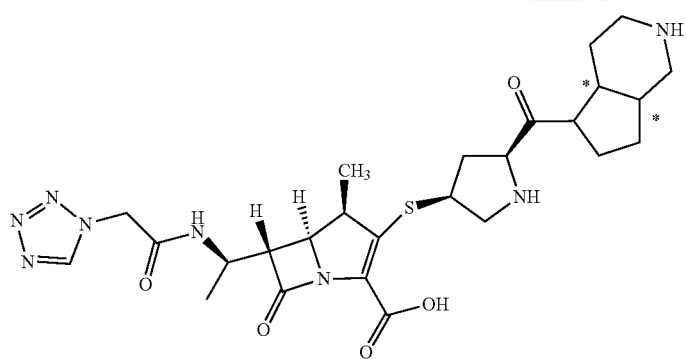
cis
peak-II
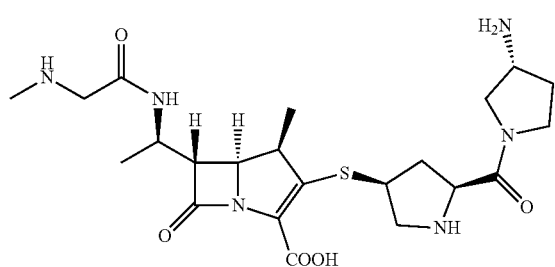
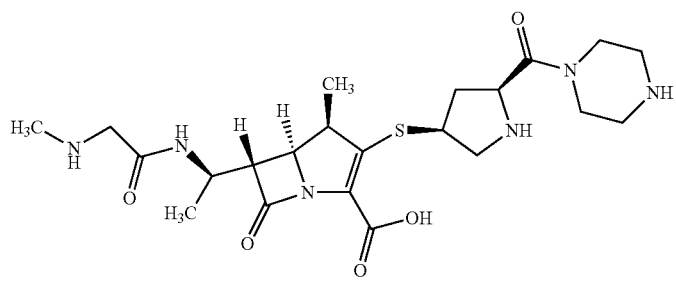
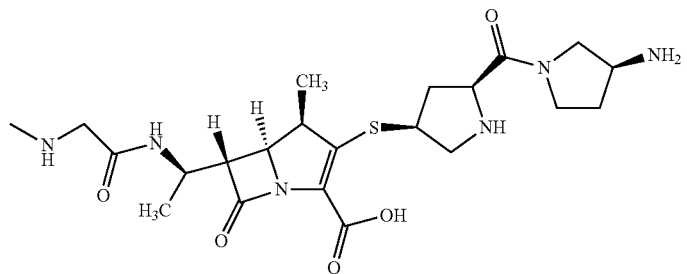
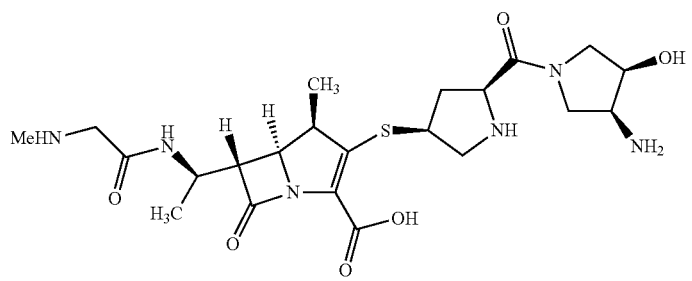

-continued
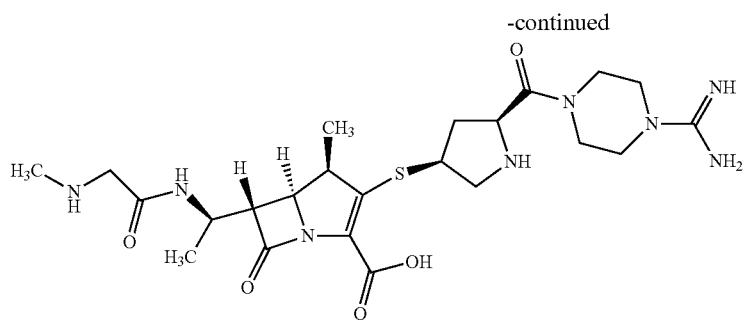
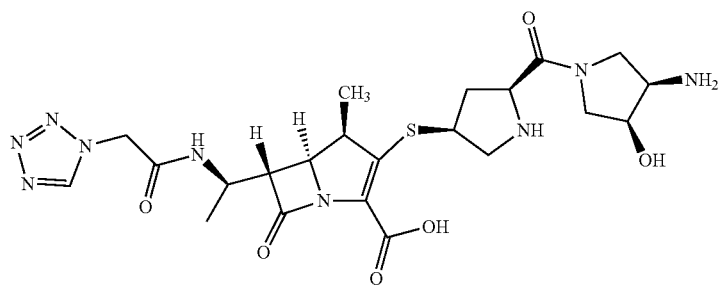
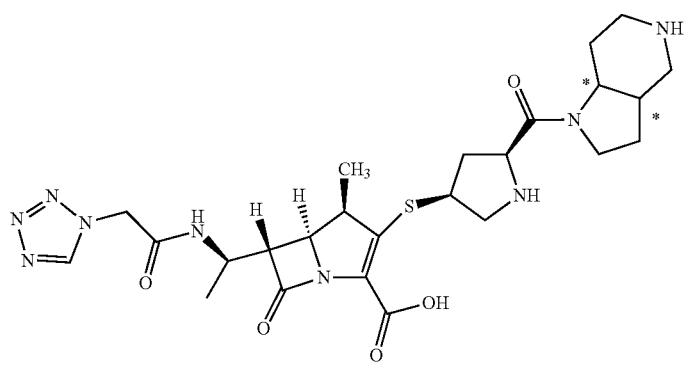
cis
peak-I
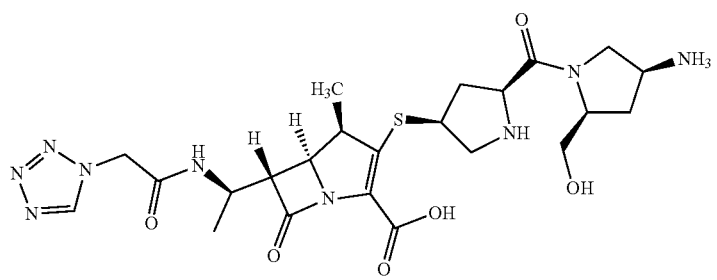
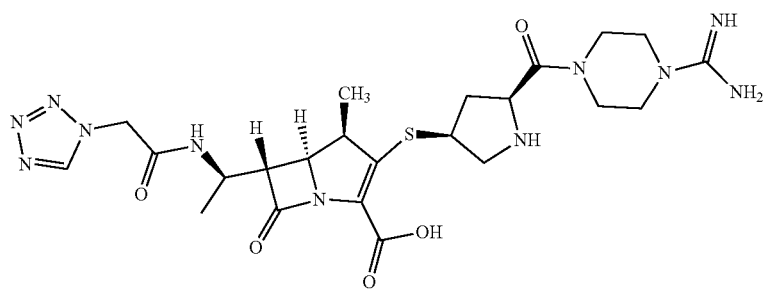

-continued
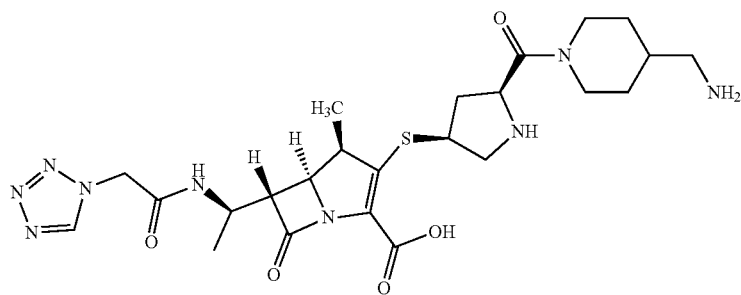
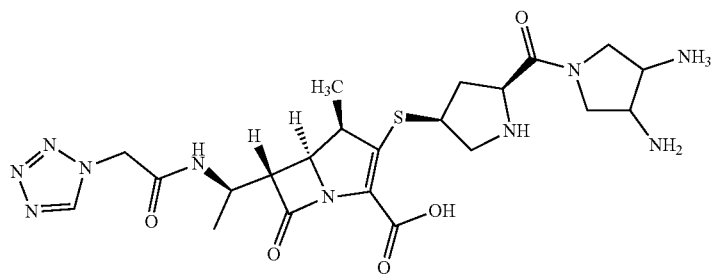 [SMILES: C[C@@H](NC(=O)Cn1cnnn1)[C@H]1C(=O)N2C(C(=O)O)=C(S[C@@H]3CN[C@H](C(=O)N4CC(N)C(N)C4)C3)[C@H](C)[C@H]12]
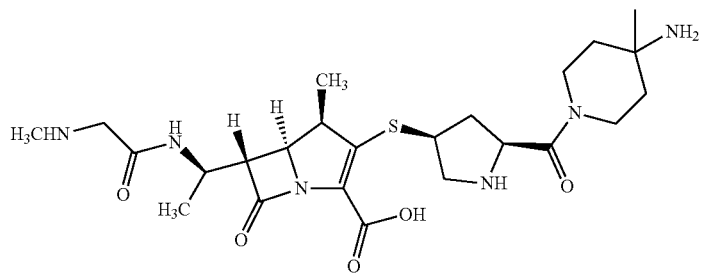
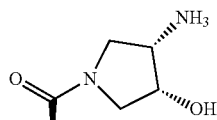
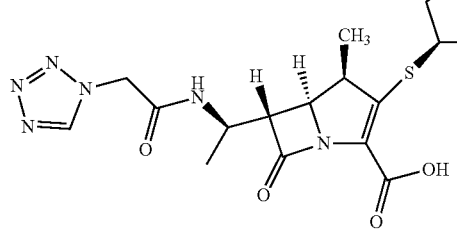
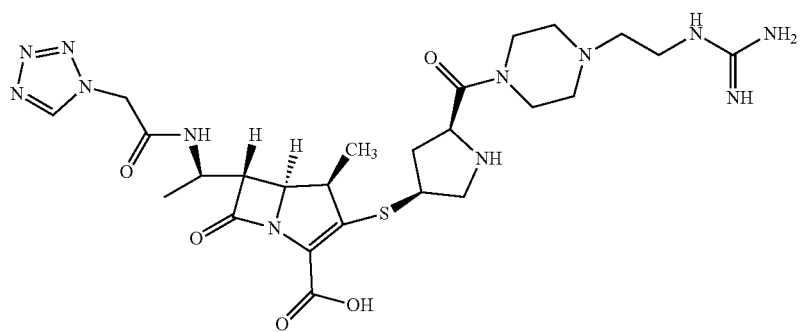

-continued
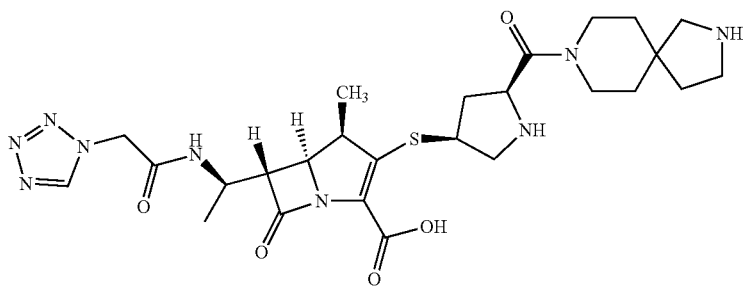
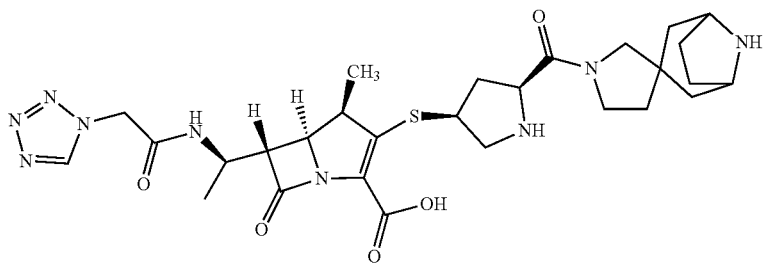
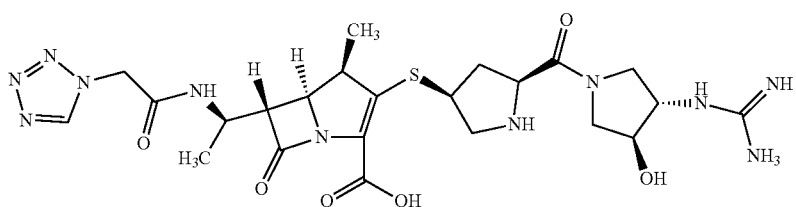
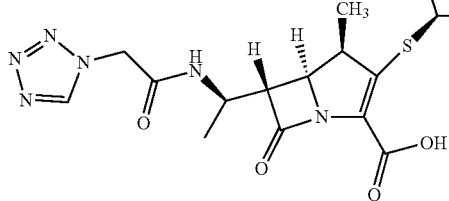
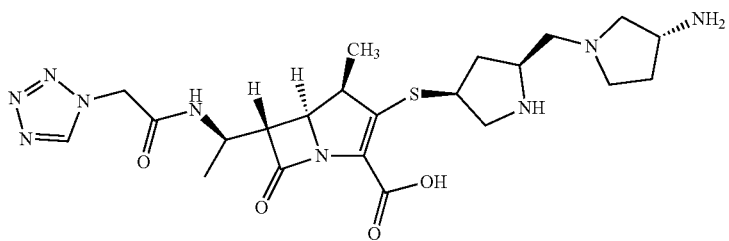
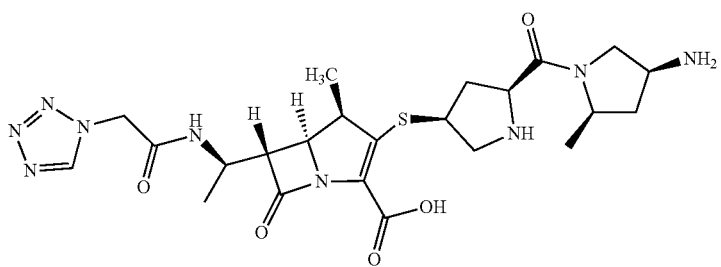

-continued
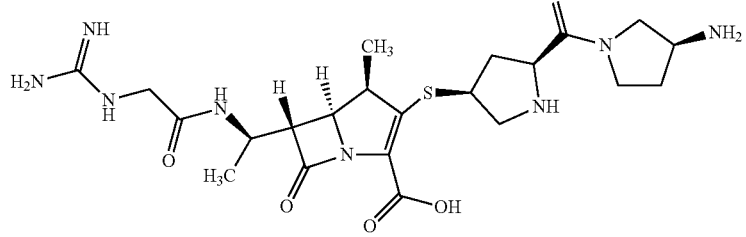
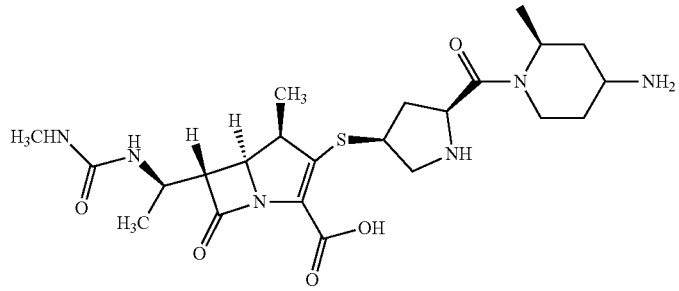
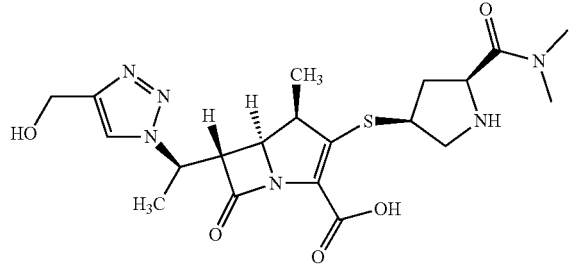
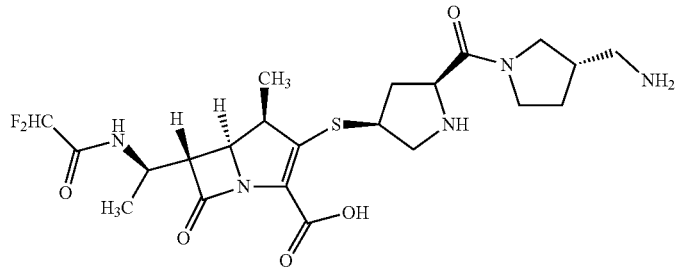
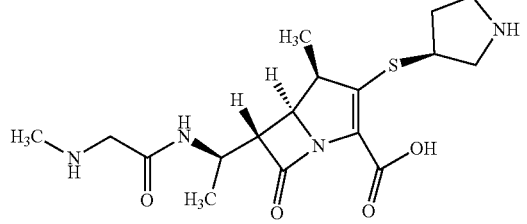
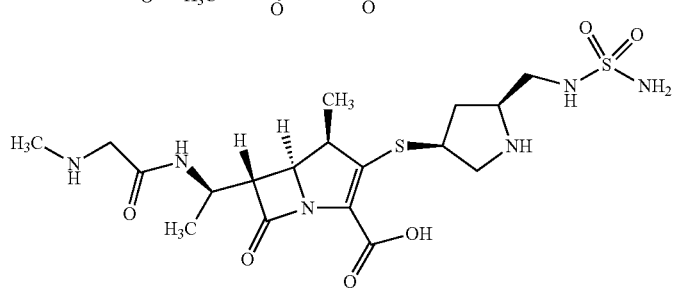

-continued
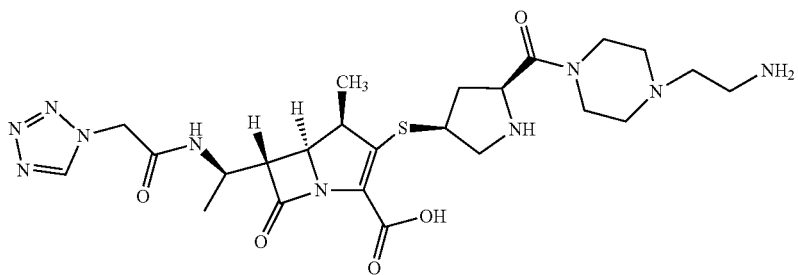
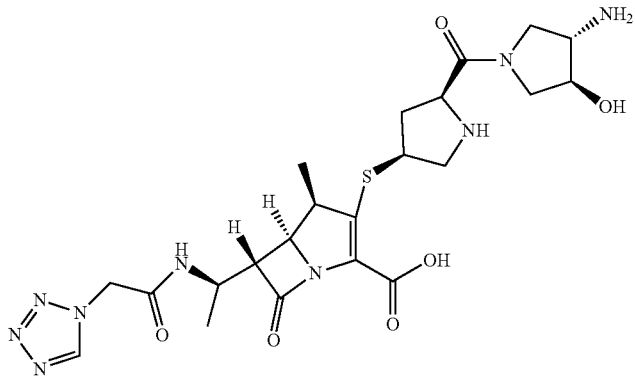
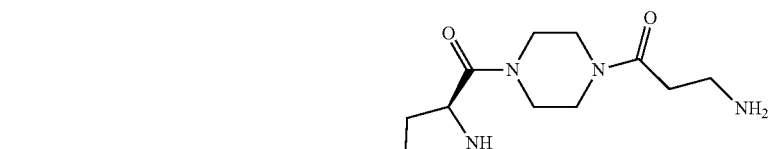
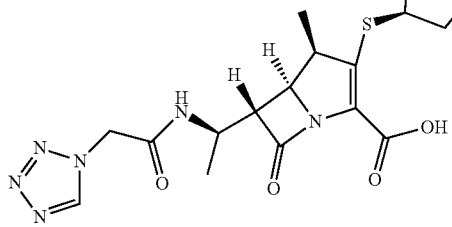
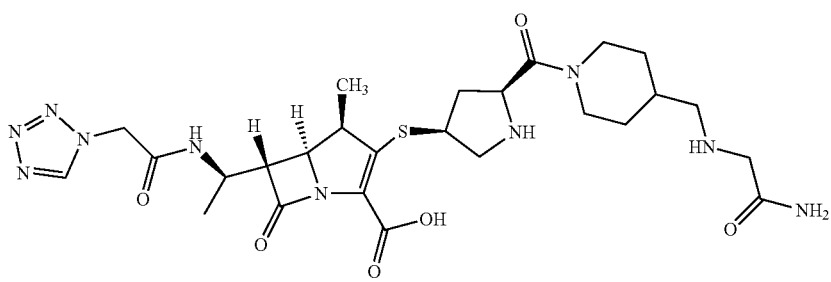
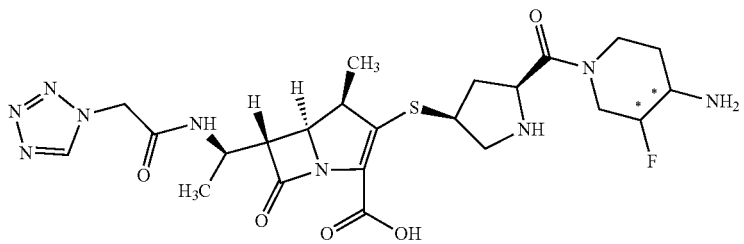
cis Peak I -continued
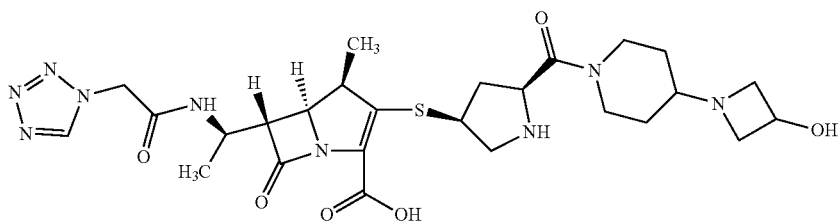
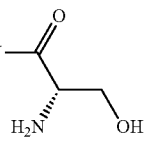
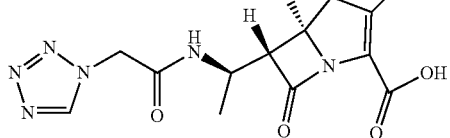
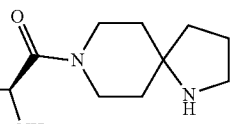
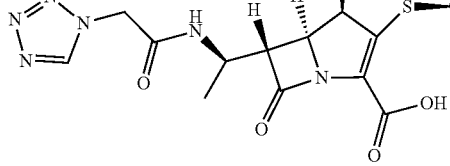
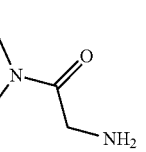
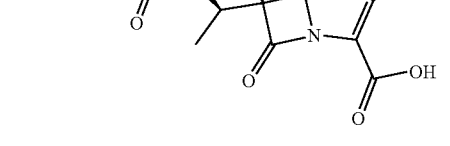
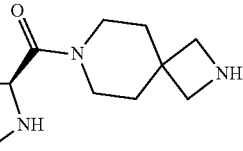
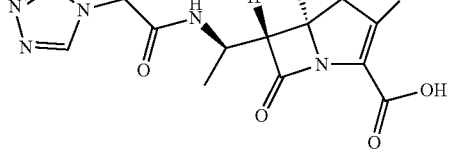
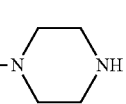
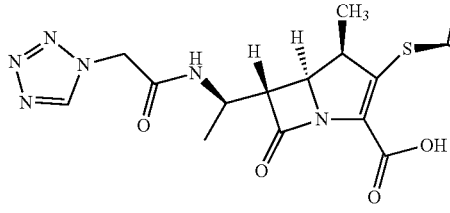

-continued
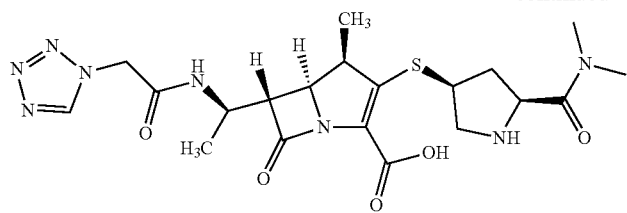
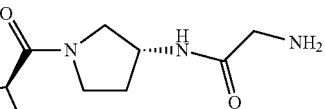
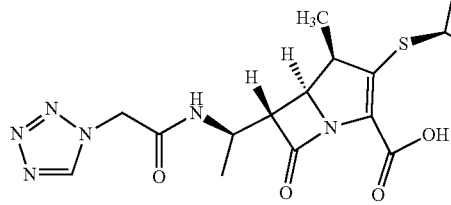
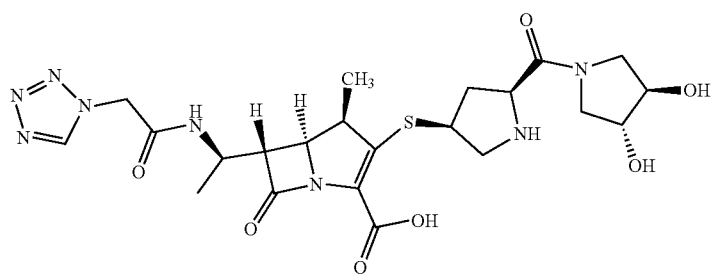
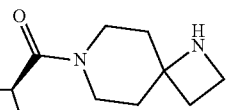
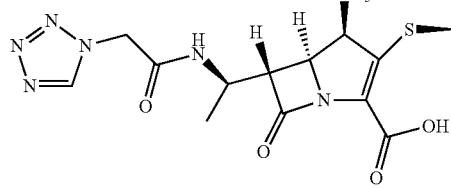
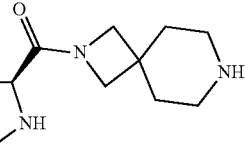
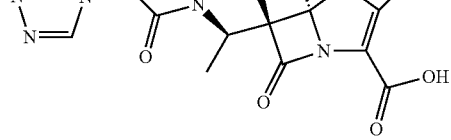
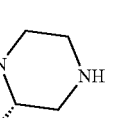
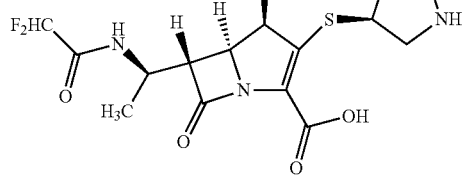

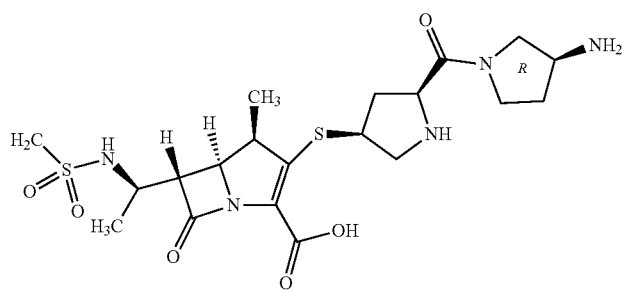
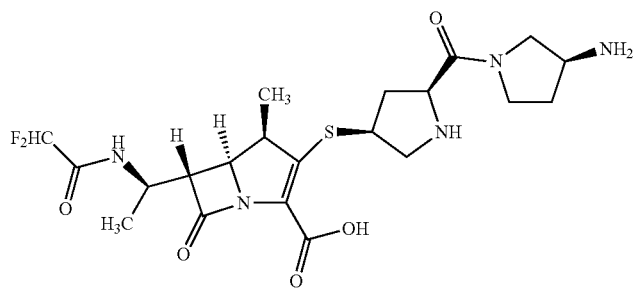
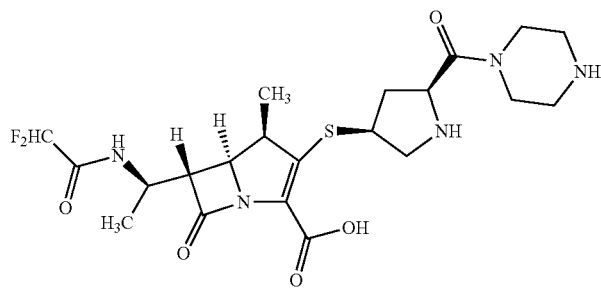
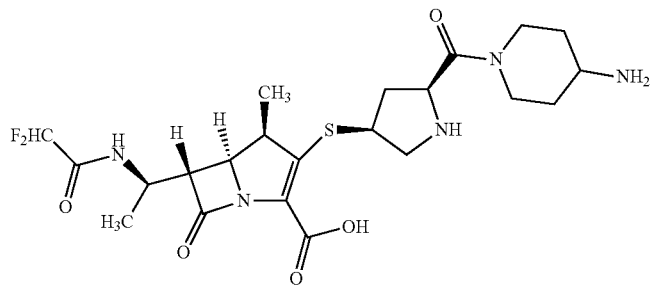
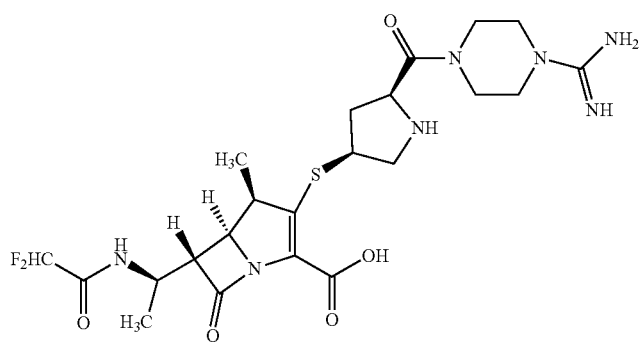

-continued
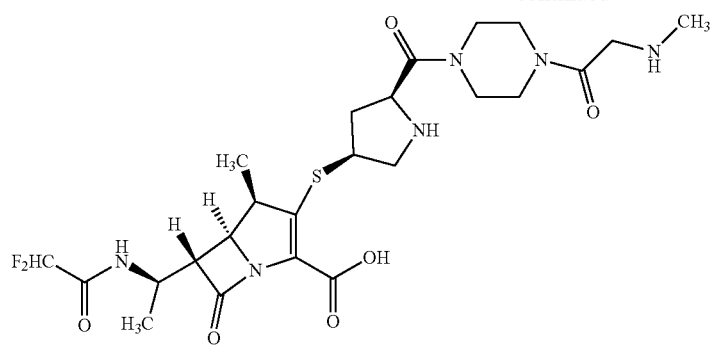
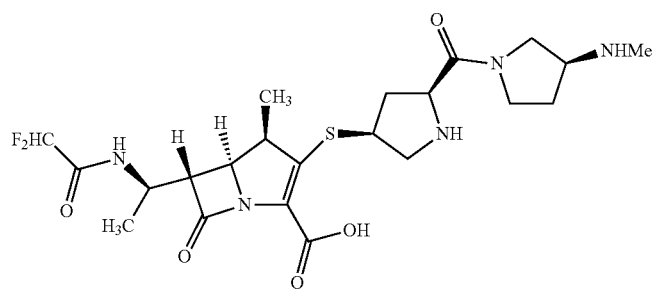
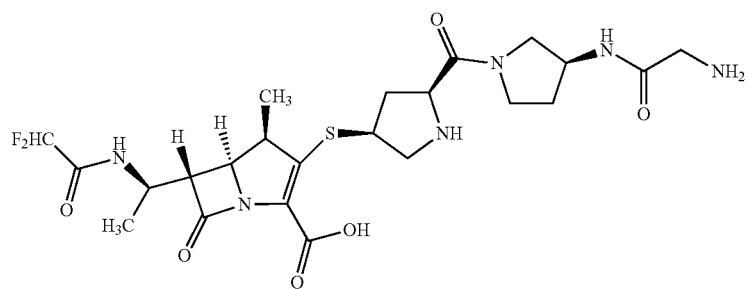
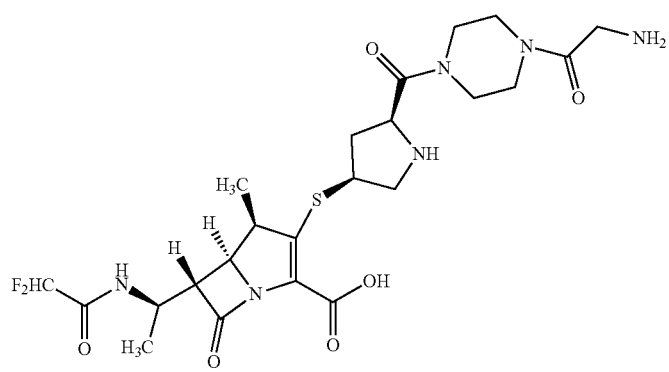
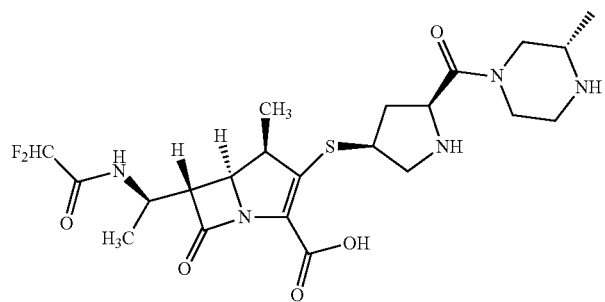

-continued
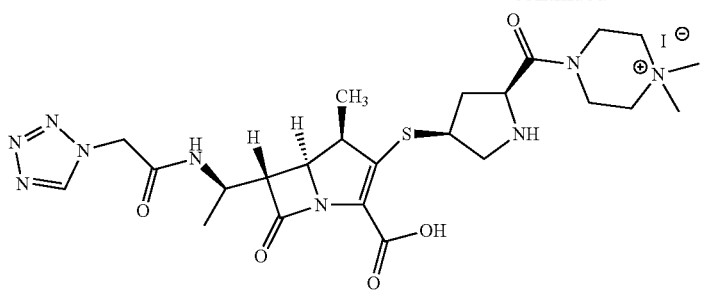
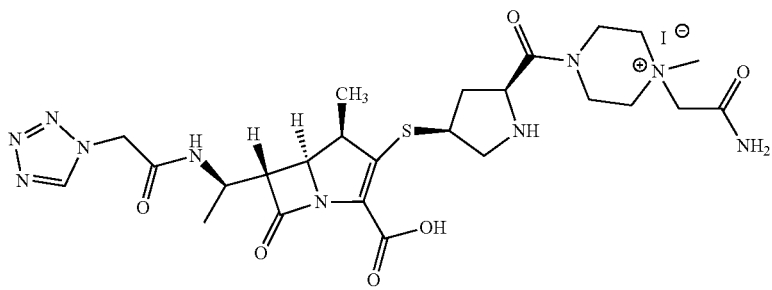
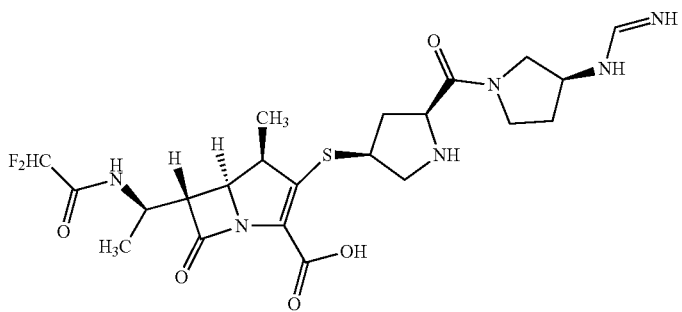
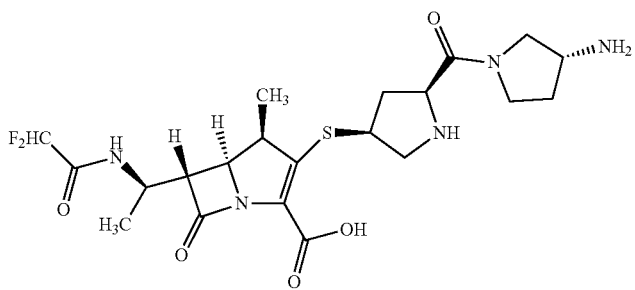
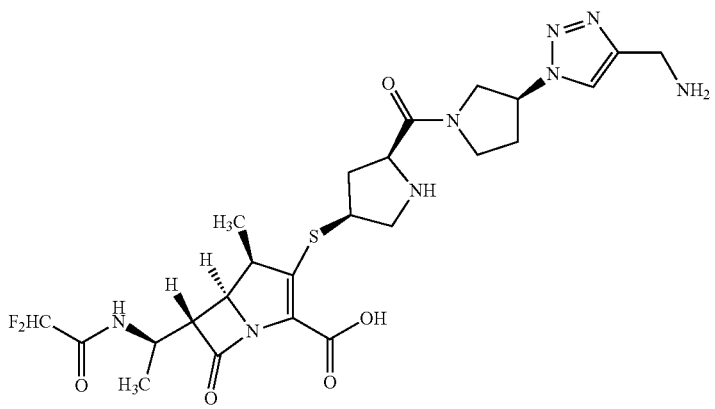

-continued
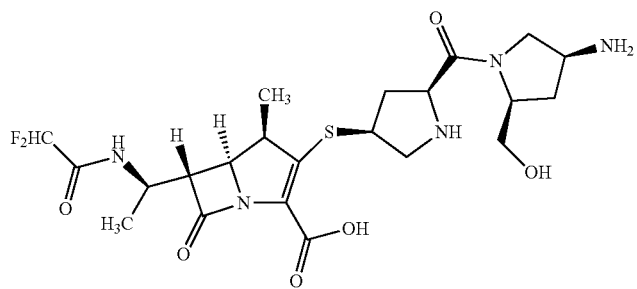
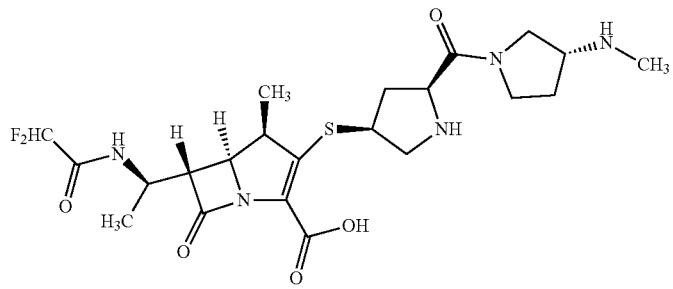
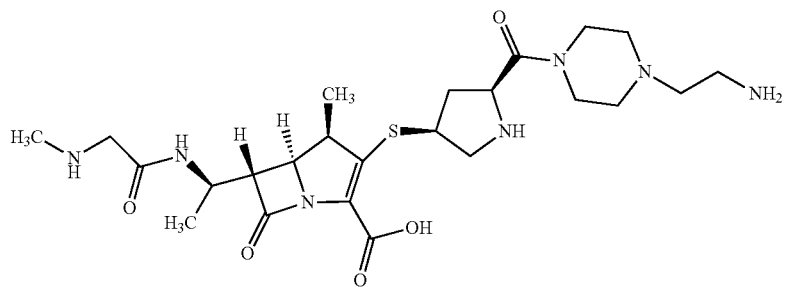
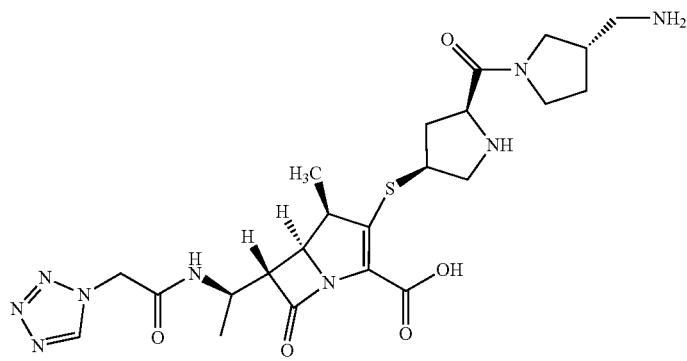
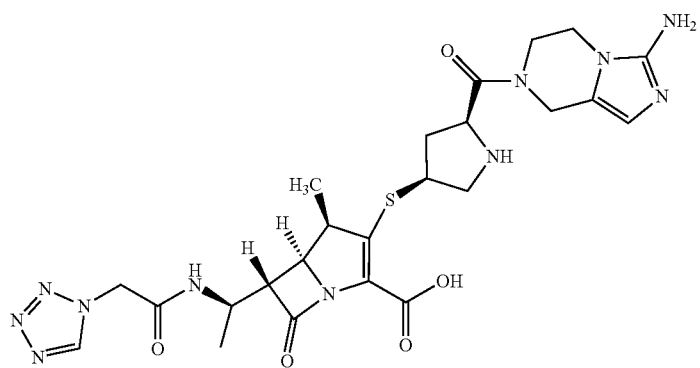

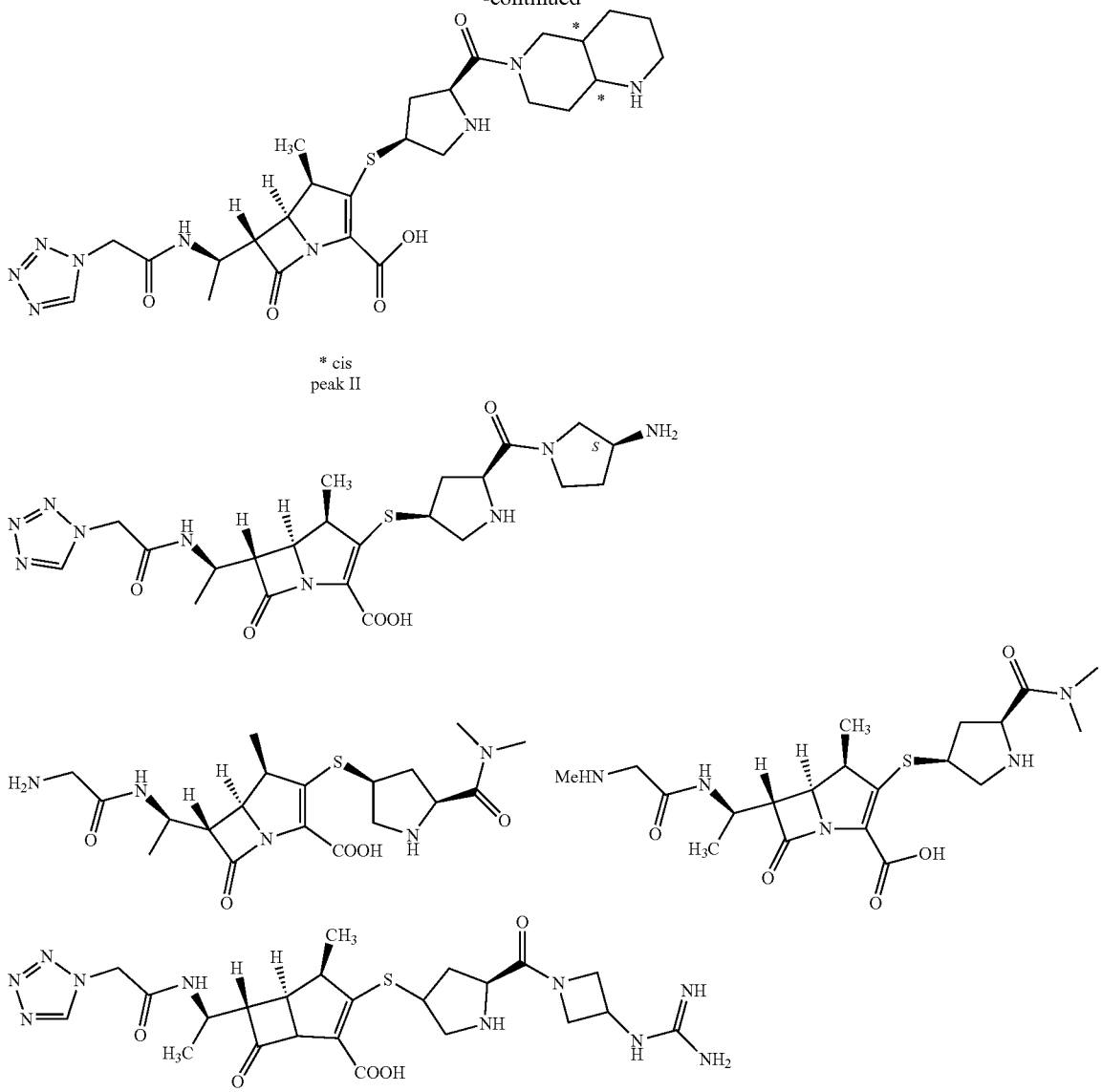
or a pharmaceutically acceptable salt, internal salt, or N-oxide thereof.
30. A compound, or a stereoisomer thereof, wherein the compound, or stereoisomer thereof, is selected from the group consisting of:
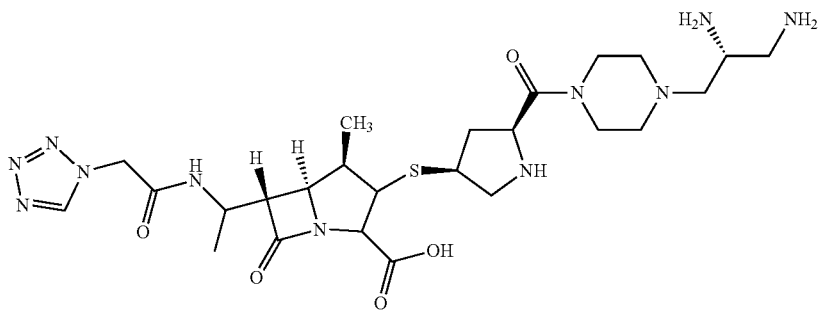

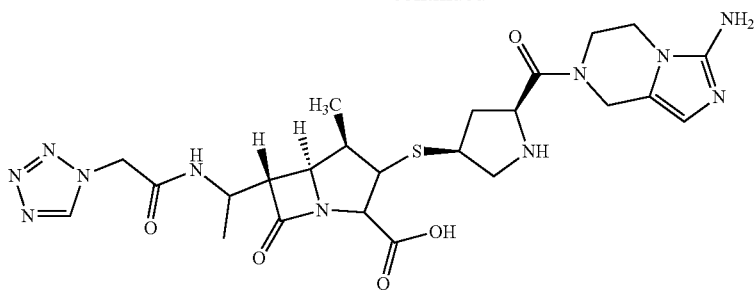
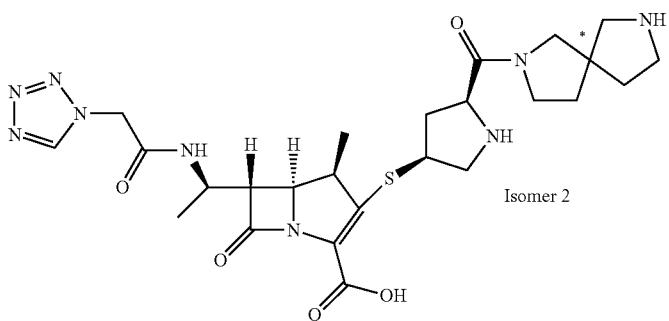
Isomer 2
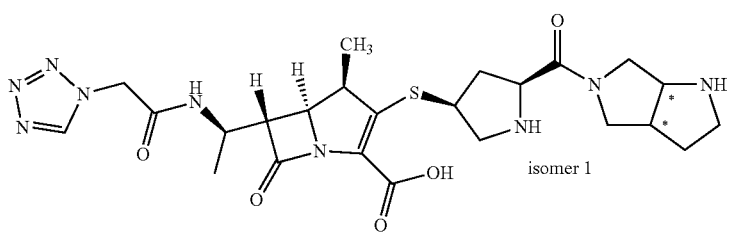
isomer 1
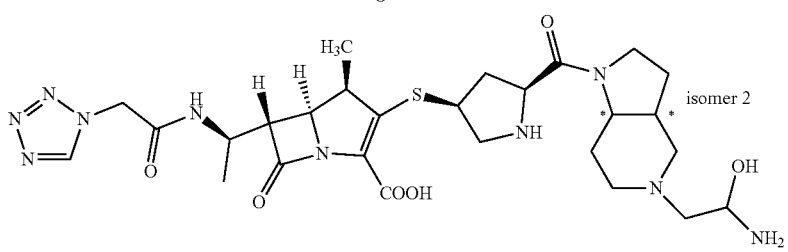
isomer 2
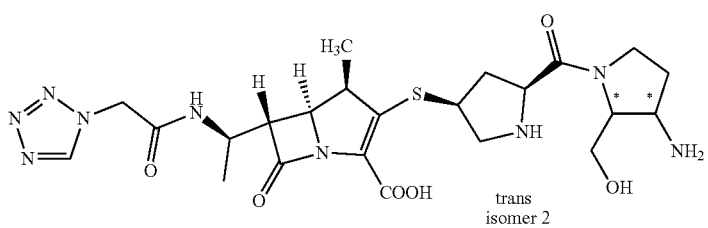
trans isomer 2
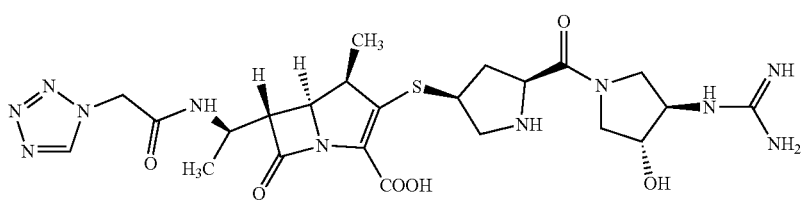
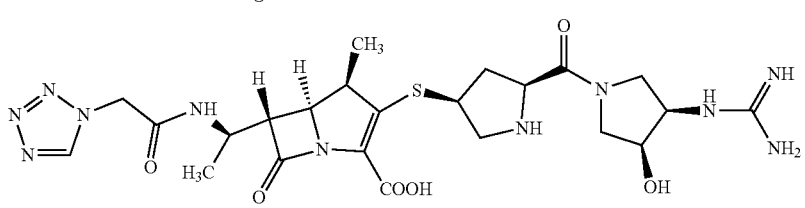

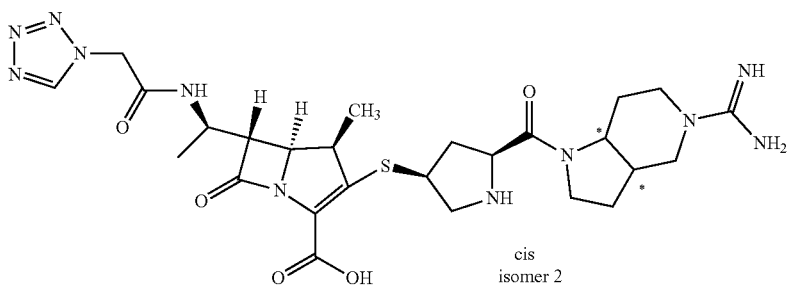
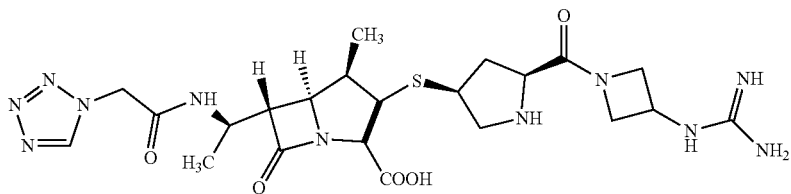
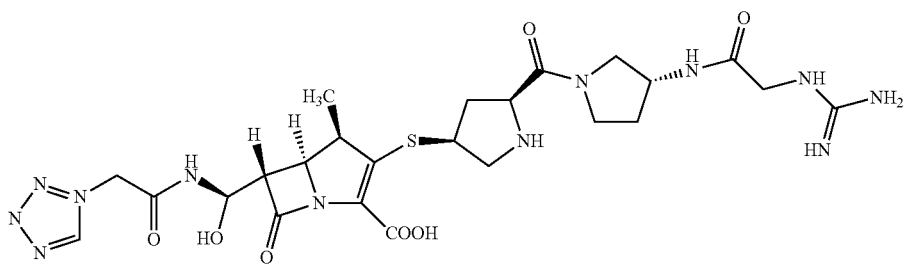
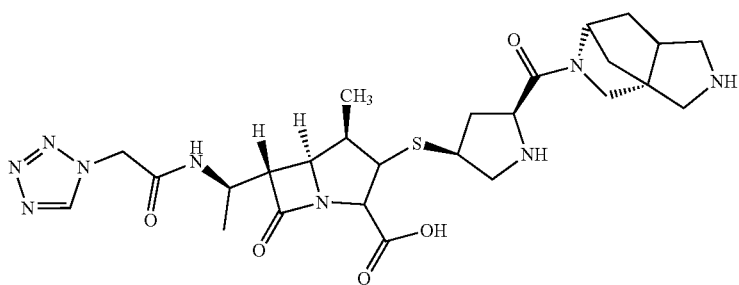
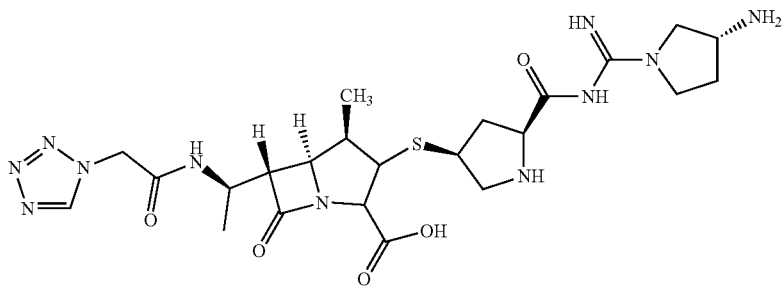
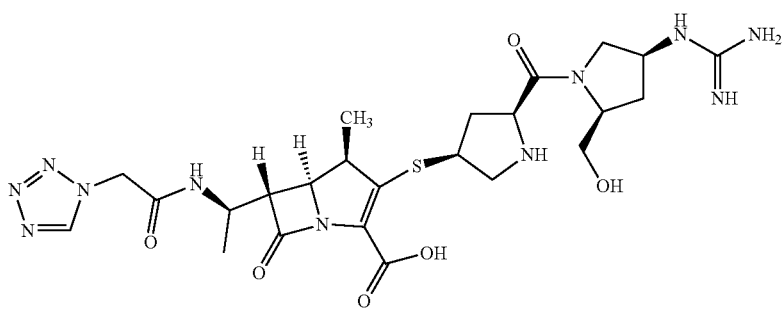

-continued
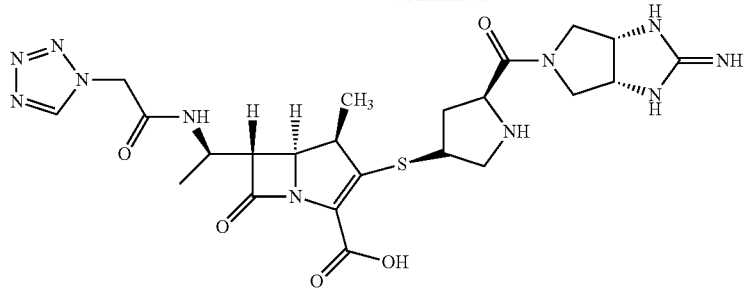
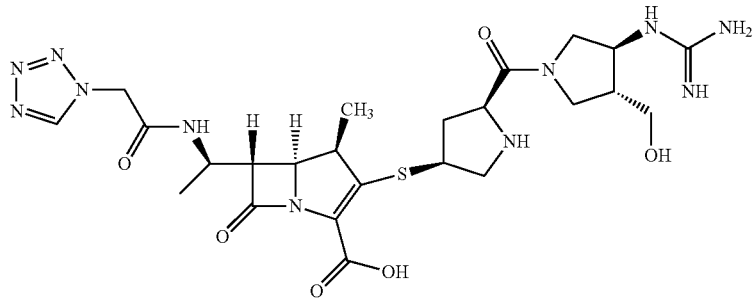
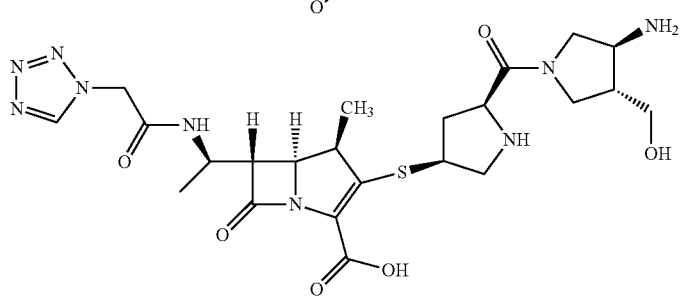
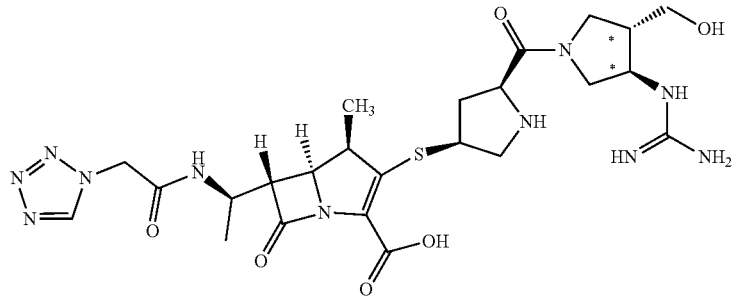
or a pharmaceutically acceptable salt, internal salt, or N-oxide thereof.
31. A compound, or a stereoisomer thereof, wherein the compound, or stereoisomer thereof, is selected from the group consisting of:
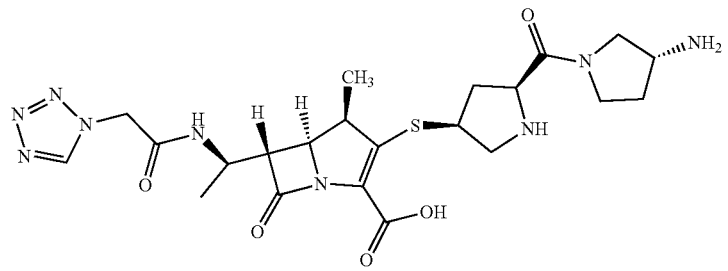

-continued
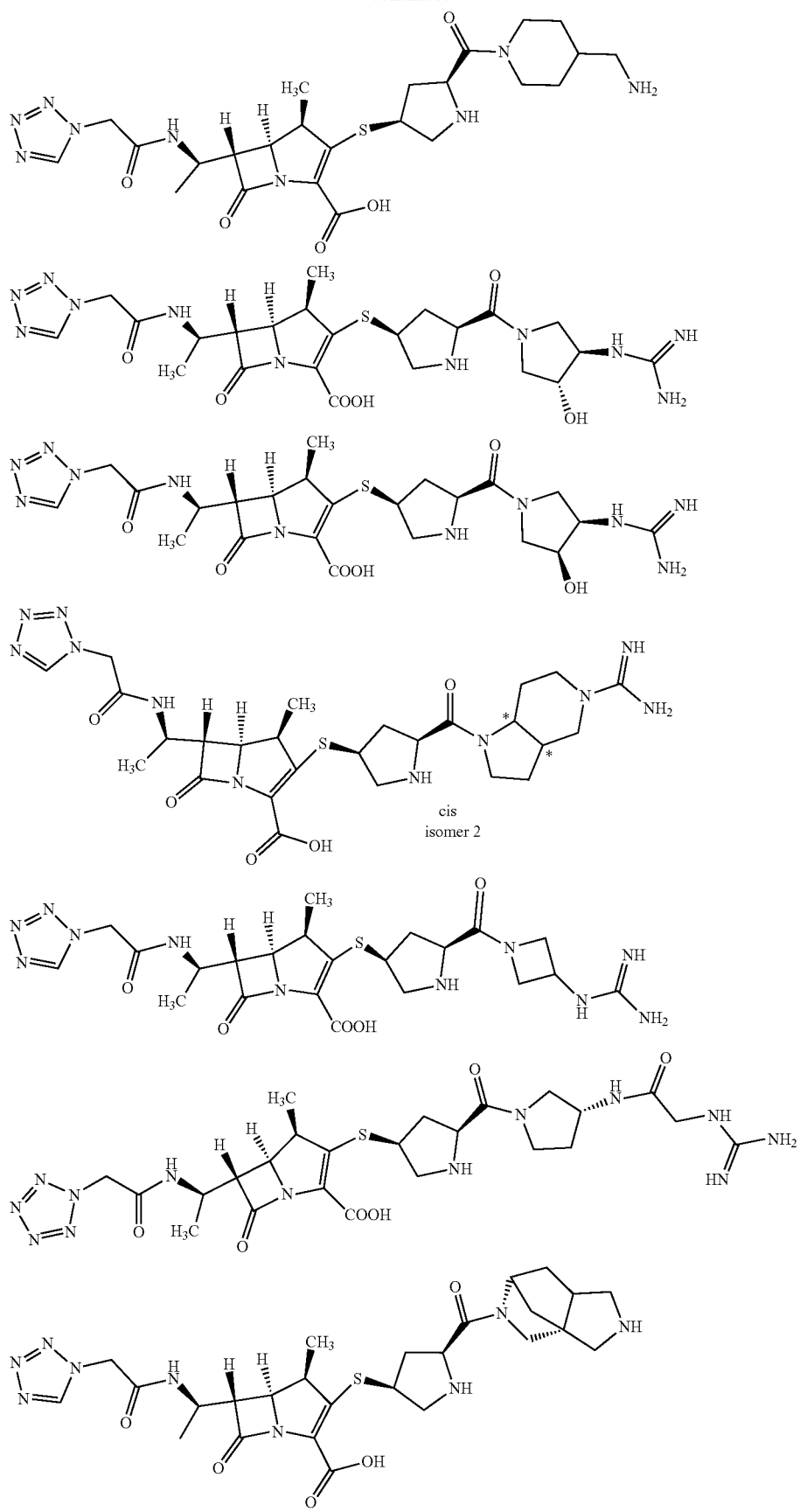

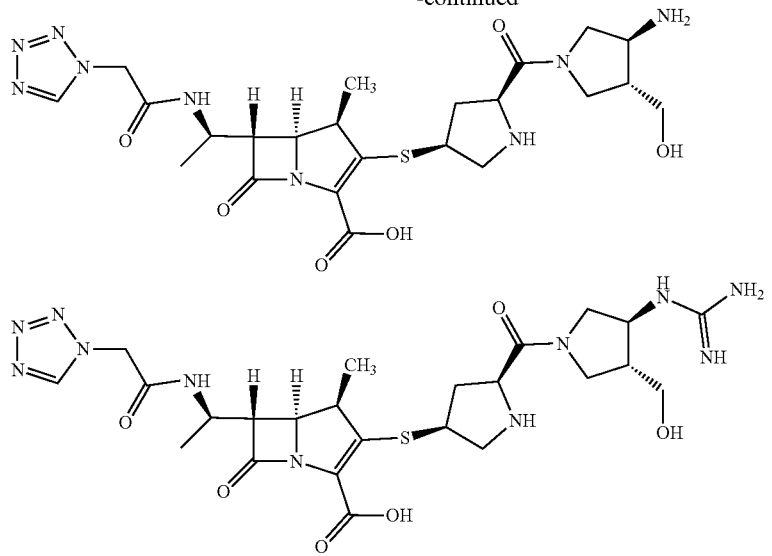
or a pharmaceutically acceptable salt, internal salt, or N-oxide thereof.
32. A compound, or a stereoisomer thereof, wherein the compound, or stereoisomer thereof, is
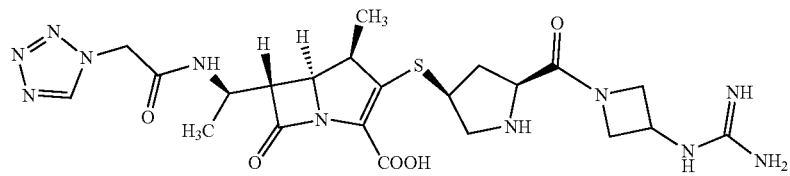 [SMILES: C[C@@H](NC(=O)Cn1cnnn1)[C@H]1C(=O)N2C(C(=O)O)=C(S[C@@H]3CN[C@H](C(=O)N4CC(NC(=N)N)C4)C3)[C@H](C)[C@H]12]
or a pharmaceutically acceptable salt, internal salt, or N-oxide thereof.
* * * * *

UNITED STATES PATENT AND TRADEMARK OFFICE
CERTIFICATE OF CORRECTION

PATENT NO. : 11,180,504 B2  
APPLICATION NO. : 16/083980  
DATED : November 23, 2021  
INVENTOR(S) : Gopalan Balasubramanian et al.

It is certified that error appears in the above-identified patent and that said Letters Patent is hereby corrected as shown below:

In the Claims

<u>Column 559:</u>
In Claim 26, Line 1—replace

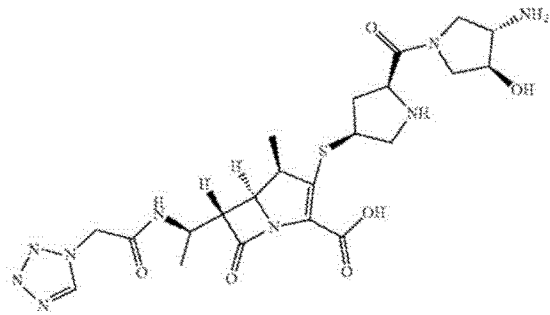 with 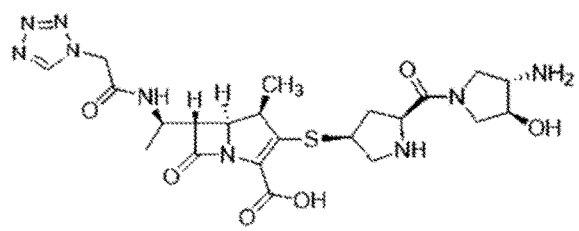

<u>Column 621:</u>
In Claim 27, Line 3—replace

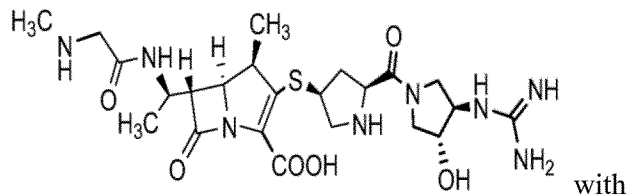 with 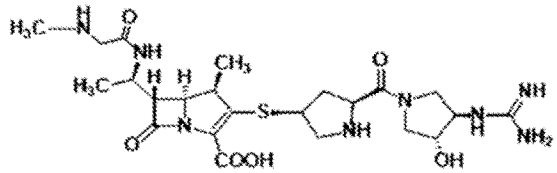

Signed and Sealed this  
First Day of November, 2022

Katherine Kelly Vidal  
*Director of the United States Patent and Trademark Office*

CERTIFICATE OF CORRECTION (continued)
U.S. Pat. No. 11,180,504 B2

Column 625:
In Claim 27, Line 1—replace

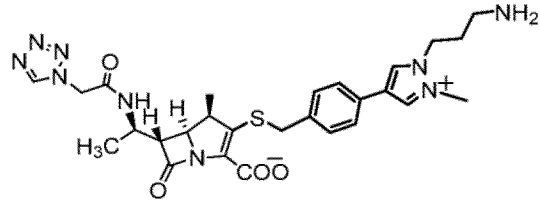

with

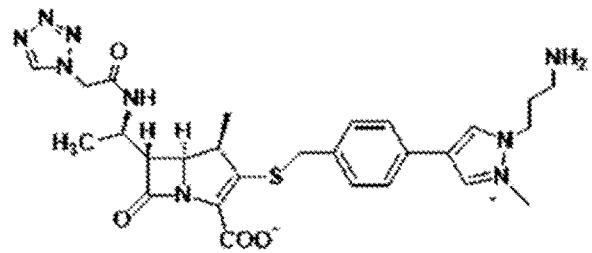

Column 671:
In Claim 29, Line 1—replace

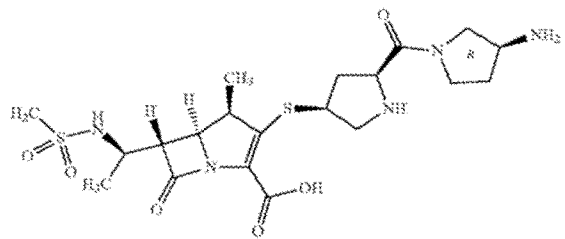

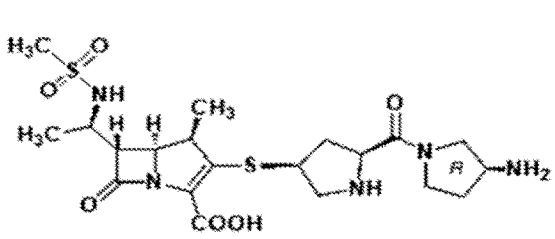

with